(12) United States Patent
Nakayama et al.

(10) Patent No.: US 8,309,546 B2
(45) Date of Patent: *Nov. 13, 2012

(54) MORPHOLINOPURINE DERIVATIVES

(75) Inventors: Kiyoshi Nakayama, Chiba (JP); Kazuyuki Sugita, Tokyo (JP); Masaki Setoguchi, Tokyo (JP); Yuichi Tominaga, Tokyo (JP); Masanori Saitou, Tokyo (JP); Takashi Odagiri, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,239

(22) Filed: Nov. 30, 2011

(65) Prior Publication Data

US 2012/0071476 A1 Mar. 22, 2012

Related U.S. Application Data

(63) Continuation of application No. 12/579,175, filed on Oct. 14, 2009, now Pat. No. 8,097,622.

(30) Foreign Application Priority Data

Oct. 14, 2008 (JP) ................. 2008-264797
May 20, 2009 (JP) ................. 2009-121690

(51) Int. Cl.
*A61K 31/535* (2006.01)
*C07D 413/14* (2006.01)

(52) U.S. Cl. ..................... 514/234.2; 544/118

(58) Field of Classification Search ............... 514/234.2; 544/118
See application file for complete search history.

(56) References Cited

U.S. PATENT DOCUMENTS

| | | | |
|---|---|---|---|
| 6,608,053 B2 | 8/2003 | Hayakawa | |
| 6,608,056 B1 | 8/2003 | Hayakawa | |
| 6,770,641 B2 | 8/2004 | Yamano | |
| 6,838,457 B2 | 1/2005 | Hayakawa | |
| 7,037,915 B2 | 5/2006 | Hayakawa | |
| 7,071,189 B2 | 7/2006 | Kawashima | |
| 7,153,853 B2 | 12/2006 | Kawashima | |
| 7,173,029 B2 | 2/2007 | Hayakawa | |
| 7,307,077 B2 | 12/2007 | Kawashima | |
| 8,097,622 B2 * | 1/2012 | Nakayama et al. | 514/234.2 |
| 2007/0037805 A1 | 2/2007 | Hayakawa | |
| 2008/0233127 A1 | 9/2008 | Bursavich | |

FOREIGN PATENT DOCUMENTS

| | | |
|---|---|---|
| EP | 1277738 A1 | 1/2003 |
| EP | 2050749 A1 | 4/2009 |
| GB | 864145 | 3/1961 |
| GB | 2431156 A | 4/2007 |
| JP | 2005-120102 A | 5/2005 |
| WO | 2004035740 A2 | 4/2004 |
| WO | 2004043913 A2 | 5/2004 |
| WO | 2004048365 A1 | 6/2004 |
| WO | 2006030031 A1 | 3/2006 |
| WO | 2006046031 A1 | 5/2006 |
| WO | 2006046035 A1 | 5/2006 |
| WO | 2006046040 A1 | 5/2006 |
| WO | 2006122806 A2 | 11/2006 |
| WO | 2006128129 A2 | 11/2006 |
| WO | 2007042806 A1 | 4/2007 |
| WO | 2007042810 A1 | 4/2007 |
| WO | 2007044698 A1 | 4/2007 |
| WO | 2007044813 A1 | 4/2007 |
| WO | 2007066103 A1 | 6/2007 |
| WO | 2007080382 A1 | 7/2007 |
| WO | 2007084786 A1 | 7/2007 |
| WO | 2007122410 A1 | 11/2007 |
| WO | 2007127175 A2 | 11/2007 |
| WO | 2007127183 A1 | 11/2007 |
| WO | 2007129161 A2 | 11/2007 |
| WO | 2007141504 A1 | 12/2007 |
| WO | 2008023159 A1 | 2/2008 |
| WO | 2008023161 A1 | 2/2008 |
| WO | 2008023180 A1 | 2/2008 |

(Continued)

OTHER PUBLICATIONS

Voskoglou-Nomikos et al., Clinical Cancer Research, vol. 9, 4227-4239.* ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Voskoglou-Nomikos et al., Clinical Cancer Research, vol. 9, 4227-4239, 2003.*
Abraham, R.T., and C.H. Eng, "Mammalian Target of Rapamycin as a Therapeutic Target in Oncology," Expert Opinion on Therapeutic Targets 12(2):209-222, Feb. 2008.
Bader, A.G., et al., "Oncogenic PI3K Deregulates Transcription and Translation," Nature Reviews/Cancer 5(12):921-929, Dec. 2005.
Engelman, J.A., et al., "The Evolution of Phosphatidylinositol 3-Kinases as Regulators of Growth and Metabolism," Nature Reviews/Genetics 7(8):606-619, Aug. 2006.
Foukas, L.C., et al., "Critical Role for the P110α Phosphoinositide-3-OH Kinase in Growth and Metabolic Regulation," Nature 441(7091):366-370, May 2006.

(Continued)

*Primary Examiner* — Rebecca Anderson
(74) *Attorney, Agent, or Firm* — Christensen O'Connor Johnson Kindness PLLC

(57) ABSTRACT

There is provided a novel compound that inhibits phosphatidylinositol 3-kinase (PI3K) and/or the mammalian target of rapamycin (mTOR) and exhibits anti-tumor activity. The present invention provides a compound represented by the following formula (1) having various substituents that inhibits PI3K and/or mTOR and exhibits anti-tumor activity:

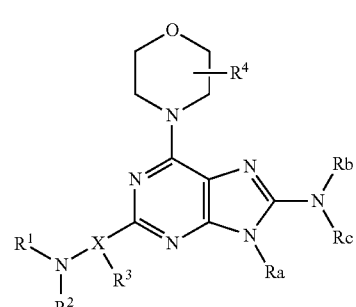

(1)

wherein $R^1$, $R^2$, $R^3$, $R^4$, $R^a$, $R^b$, $R^c$, and X each have the same meaning as defined in the specification.

16 Claims, No Drawings

FOREIGN PATENT DOCUMENTS

| | | |
|---|---|---|
| WO | 2008032028 A1 | 3/2008 |
| WO | 2008032033 A1 | 3/2008 |
| WO | 2008032036 A1 | 3/2008 |
| WO | 2008032060 A1 | 3/2008 |
| WO | 2008032072 A1 | 3/2008 |
| WO | 2008032086 A1 | 3/2008 |
| WO | 2008032089 A1 | 3/2008 |
| WO | 2008032091 A1 | 3/2008 |
| WO | 2008047109 A1 | 4/2008 |
| WO | 2008051493 A2 | 5/2008 |
| WO | 2008070447 A2 | 6/2008 |
| WO | 2008070740 A1 | 6/2008 |
| WO | 2008073785 A2 | 6/2008 |
| WO | 2008098058 A1 | 8/2008 |
| WO | 2008115974 A2 | 9/2008 |
| WO | 2008125833 A1 | 10/2008 |
| WO | 2008125835 A1 | 10/2008 |
| WO | 2008125839 A1 | 10/2008 |
| WO | 2008152387 A1 | 12/2008 |
| WO | 2008152390 A1 | 12/2008 |
| WO | 2008152394 A1 | 12/2008 |
| WO | 2009007748 A1 | 1/2009 |
| WO | 2009019656 A1 | 2/2009 |
| WO | 2009036082 A2 | 3/2009 |
| WO | 2009042607 A1 | 4/2009 |
| WO | 2009045145 A1 | 4/2009 |
| WO | 2009045174 A1 | 4/2009 |
| WO | 2009045175 A1 | 4/2009 |
| WO | 2009053715 A1 | 4/2009 |
| WO | 2009053716 A1 | 4/2009 |
| WO | 2009055730 A1 | 4/2009 |
| WO | 2009066084 A1 | 5/2009 |
| WO | 2009070524 A1 | 6/2009 |
| WO | 2009071888 A1 | 6/2009 |
| WO | 2009071890 A1 | 6/2009 |
| WO | 2009071895 A1 | 6/2009 |
| WO | 2009071901 A1 | 6/2009 |
| WO | 2009085230 A1 | 7/2009 |
| WO | 2009091788 A1 | 7/2009 |
| WO | 2009093972 A1 | 7/2009 |
| WO | 2009093981 A1 | 7/2009 |
| WO | 2009094224 A1 | 7/2009 |
| WO | 2009094560 A2 | 7/2009 |
| WO | 2009099163 A1 | 8/2009 |

OTHER PUBLICATIONS

Guertin, D.A., and D.M. Sabatini, "Defining the Role of mTOR in Cancer," Cancer Cell 12(1):9-22, Jul. 2007.

Knight, Z.A., et al., "A Pharmacological Map of the PI3-K Family Defines a Role for p110α in Insulin Signaling," Cell 125(4):733-747, May 2006.

Liu, P., et al., "Targeting the Phosphoinositide 3-Kinase Pathway in Cancer," Nature Reviews/Drug Discovery 8(8):627-644, Aug. 2009.

Maira, S.-M., et al., "Class IA Phosphatidylinositol 3-Kinase: From Their Biologic Implication in Human Cancers to Drug Discovery," Expert Opinion on Therapeutic Targets 12(2):223-238, Feb. 2008.

Maira, S.-M., et al., "Identification and Characterization of NVP-BEZ235, a New Orally Available Dual Phosphatidylinositol 3-Kinase/Mammalian Target of Rapamycin Inhibitor With Potent in Vivo Antitumor Activity," Molecular Cancer Therapeutics 7(7):1851-1863, Jul. 2008.

Maira, S.-M., et al., "PI3K Inhibitors for Cancer Treatment: Where Do We Stand?" Biochemical Society Transactions 37(Pt. 1):265-272, Feb. 2009.

Marone, R., et al., "Targeting Phosphoinositide 3-Kinase—Moving Towards Therapy," Biochimica et Biophysica Acta 1784(1):159-185, Jan. 2008.

Tsang, C.K., et al., "Targeting Mammalian Target of Rapamycin (mTOR) for Health and Diseases," Drug Discovery Today 12(3-4):112-124, Feb. 2007.

Wu, P., et al., "PI3K Inhibitors for Cancer Therapy: What Has Been Achieved So Far?" Current Medicinal Chemistry 16(8):916-930, Mar. 2009.

Yap, T.A., et al., "Targeting the PI3K-AKT-mTOR Pathway: Progress, Pitfalls, and Promises," Current Opinion in Pharmacology 8(4):393-412, Aug. 2008.

* cited by examiner

MORPHOLINOPURINE DERIVATIVES

CROSS-REFERENCES TO RELATED APPLICATIONS

This application is a continuation of U.S. application Ser. No. 12/579,175, filed Oct. 14, 2009, now U.S. Pat. No. 8,097,622, which claims benefit from Japanese Patent Application No. 2008-264797, filed Oct. 14, 2008, and Japanese Patent Application No. 2009-121690, filed May 20, 2009. Each application is incorporated herein by reference in its entirety.

BACKGROUND OF THE INVENTION

1. Field of the Invention

The present invention relates to a compound having a novel morpholinopurine derivative structure that inhibits phosphatidylinositol 3-kinase (PI3K) and/or the mammalian target of rapamycin (mTOR).

2. Description of the Related Art

PI3K is a lipid kinase known to play an important role in cellular growth, survival, motion, and the like. Class I PI3Ks (PI3K$\alpha$, PI3K$\beta$, PI3K$\delta$, PI3K$\gamma$) are known to be activated by a receptor tyrosine kinase or GPCR to generate phosphatidylinositol 3,4,5-trisphosphate (PIP3) to activate Akt. It has been reported that the activated Akt regulates cellular growth, survival, angiogenesis, and the like by phosphorylating TSC2, GSK3$\beta$, MDM2, FOXO, BAD, and the like (Non-Patent Document 1).

p110$\alpha$, a catalytic subunit of PI3K$\alpha$, is known to be activated in colon cancer, breast cancer, brain tumor, gastric cancer, liver cancer, ovary cancer, and the like due to mutation thereof. Furthermore, it is known that the PI3K-Akt pathway is also activated in cancers in which PTEN (phosphate and tensin homolog), which dephosphohrylates PIP3, is inactivated (for example, prostate cancer and melanoma) and cancers in which p110$\alpha$ is overexpressed (for example, ovary cancer and lung cancer). Therefore, it is suggested that a drug which exhibits PI3K inhibitory effect can inhibit cancer cell growth and survival, angiogenesis, and the like by suppressing the activation of Akt to block the PI3K-Akt pathway, and its usefulness as a cancer therapeutic agent is expected (Non-Patent Documents 2 and 3).

Compounds having PI3K inhibitory activity that have been reported include pyridinylfuranopyrimidine derivatives (Non-Patent Document 4 and Patent Document 1), thienopyrimidine derivatives, and furopyrimidine derivatives (Patent Documents 2 to 5), pyrimidine derivatives (Patent Documents 6 to 15), pyridopyrimidinone derivatives (Patent Documents 16 and 17), and imidazoquinoline derivatives (Non-Patent Document 5 and Patent Document 18). A compound having a hydrogen atom at Ra and at the 8th position of the purine ring and a 3-hydroxyphenyl group at the 2nd position in the general formula (I) described later has been reported as a PI3K inhibitor (Patent Document 19).

The mammalian target of rapamycin (mTOR) is a serine-threonine kinase activated by a signal from a growth factor (for example, insulin) via the PI3K-Akt pathway (Non-Patent Document 6). It is thought that mTOR activates translation of mRNA and the like by phosphorylating S6K1 and 4E-BP1 and promotes syntheses of proteins involved in cell growth, angiogenesis, and the like (for example, c-myc, cyclin D1, and HIF-1$\alpha$).

Rapamycin, a macrolide antibacterial agent, is known to inhibit the kinase activity of mTOR by forming a complex with FKBP12 and mTOR in the cell. Currently, clinical studies of rapamycin derivatives, such as CCI-779, as anti-cancer agents are ongoing.

Meanwhile, it has recently been revealed that some mTOR kinase activities are not inhibited by rapamycin (for example, the activity of phosphorylating Akt). It has been reported that mTOR forms at least two complexes, specifically, rapamycin-susceptible mTOR Complex 1 (mTORC1) (complex containing raptor and the like) and rapamycin-non-susceptible mTOR complex 2 (mTORC2) (complex containing rector and the like). Since a drug that exhibits inhibitory effect on mTOR kinase can inhibit both mTORC1 and mTORC2, it is expected to have broader therapeutic effect as an anti-cancer agent than rapamycin (Non-Patent Document 7).

As compounds having mTOR inhibitory activity, pyridopyrimidine derivatives (Patent Document 20), imidazopyrazine derivatives (Patent Document 21), and the like have been reported.

As compounds that inhibit both PI3K and mTOR, imidazolopyrimidine derivatives (Patent Document 22), 2-morpholinopurine derivatives (Patent Document 23) and 2-morpholinopurine derivatives substituted with pyrimidine moiety at 6-position (Patent Document 24) have been reported.

As compounds that inhibit PI3K$\delta$ more selectively than other subtypes of PI3K, morpholinopurine derivatives substituted with indole moiety at 2-position have been reported (Patent Document 25).

Patent Document 1: Japanese Patent Laid-Open No. 2005/120102
Patent Document 2: WO2008/070740
Patent Document 3: WO2007/127183
Patent Document 4: WO2007/129161
Patent Document 5: WO2007/122410
Patent Document 6: WO2007/084786
Patent Document 7: WO2008/098058
Patent Document 8: WO2008/032072
Patent Document 9: WO2008/032060
Patent Document 10: WO2008/032036
Patent Document 11: WO2008/032033
Patent Document 12: WO2008/032089
Patent Document 13: WO2008/032091
Patent Document 14: WO2008/032086
Patent Document 15: WO2008/032028
Patent Document 16: WO2007/044698
Patent Document 17: WO2007/044813
Patent Document 18: WO2006/122806
Patent Document 19: GB2431156
Patent Document 20: WO2008/023161
Patent Document 21: WO2008/051493
Patent Document 22: U.S. Patent application publication No. 2008/0233127
Patent Document 23: WO2009/045174
Patent Document 24: WO2009/045175
Patent Document 25: WO2009/053716
Non-Patent Document 1: Nature Rev. Cancer, 5, 921-929 (2005)
Non-Patent Document 2: Nature, 441, 366-370 (2006)
Non-Patent Document 3: Nature Rev. Genet., 7, 606-619 (2006)
Non-Patent Document 4: Cell, 125, 733-747 (2006)
Non-Patent Document 5: Mol. Cancer Ther., 7(7), 1851-1863 (2008)
Non-Patent Document 6: Cancer Cell, 12(1), 9-22 (2007)
Non-Patent Document 7: Drug Discov. Today, 12(3-4), 112-124 (2007)

An object of the present invention is to provide a novel orally bioavailable low molecular compound that exhibits potent and sustained PI3K inhibitory action and anti-tumor effect based thereon.

SUMMARY OF THE INVENTION

The present inventors have conducted various studies to achieve the foregoing object. As a result, they have revealed that a novel compound having a 6-morpholinopurine structure sustainably inhibits PI3K activity in tumor and exhibits potent anti-tumor effect in an in vivo mouse model after oral administration thereof, found that this compound group can be used as an active ingredient of an orally bioavailable anti-tumor agent, and thus accomplished the present invention.

Specifically, the present invention relates to the following [1] to [44].

[1] A compound represented by general formula (1) or a salt thereof:

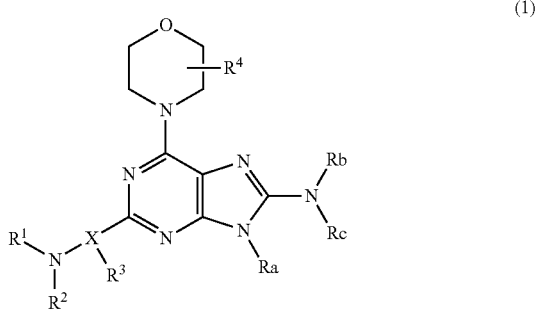

(1)

wherein $R^1$ and $R^2$ each independently represent a $C_1$-$C_6$ alkyl group that may have one or more substituents, a $C_1$-$C_6$ alkylsulfonyl group that may have one or more substituents, an aryl group that may have one or more substituents, or a hydrogen atom, X represents a 6-membered aromatic nitrogen-containing heterocyclic group, containing one or two nitrogen atoms, $R^3$ represents one or more substituents present on a carbon atom constituting X that each independently represent a $C_1$-$C_6$ alkyl group that may have one or more substituents, a $C_1$-$C_6$ alkoxy group that may have one or more substituents, a $C_1$-$C_6$ alkylamino group that may have one or more substituents, a di$C_1$-$C_6$ alkylamino group that may have one or more substituents, a $C_3$-$C_8$ cycloalkyl group that may have one or more substituents, an amino group, a halogen atom, or a hydroxyl group, $R^4$ represents a $C_1$-$C_6$ alkyl group that may have one or more substituents or a hydrogen atom, Ra represents a group represented by —Y—$R^5$, wherein Y represents a single bond or a $C_1$-$C_6$ alkylene group, and $R^5$ represents a $C_1$-$C_6$ alkyl group that may have one or more substituents, a tetrahydrofuranyl group that may have one or more substituents, a tetrahydropyranyl group that may have one or more substituents, a pyrrolidinyl group that may have one or more substituents, a piperidinyl group that may have one or more substituents, or a pyridinyl group that may have one or more substituents, and Rb and Rc each independently represent a $C_1$-$C_6$ alkyl group that may have one or more substituents or a hydrogen atom, or Rb and Rc, together with a nitrogen atom to which Rb and Rc are bonded, may form a 4- to 7-membered alicyclic nitrogen-containing heterocyclic group that may have one or more substituents.

[2] The compound according to [1] or a salt thereof, wherein $R^1$ and $R^2$ each independently represent a $C_1$-$C_6$ alkyl group that may have one or more substituents selected from the following Group A, a $C_1$-$C_6$ alkylsulfonyl group that may have one or more substituents selected from the following Group A, an aryl group that may have one or more substituents selected from the following Group B, or a hydrogen atom, X represents a 6-membered aromatic nitrogen-containing heterocyclic group that contains one or two nitrogen atoms, $R^3$ represents one or more substituents present on a carbon atom constituting X that each independently represent a $C_1$-$C_6$ alkyl group that may have one or more substituents selected from the following Group A, a $C_1$-$C_6$ alkoxy group that may have one or more substituents selected from the following Group A, a $C_1$-$C_6$ alkylamino group that may have one or more substituents selected from the following Group A, a di$C_1$-$C_6$ alkylamino group that may have one or more substituents selected from the following Group A, a $C_3$-$C_8$ cycloalkyl group that may have one or more substituents selected from the following Group A, an amino group, a halogen atom, or a hydroxyl group, $R^4$ represents a $C_1$-$C_6$ alkyl group that may have one or more substituents selected from the following Group A or a hydrogen atom, Ra represents a group represented by —Y—$R^5$, wherein Y represents a single bond or a $C_1$-$C_6$ alkylene group, $R^5$ represents a $C_1$-$C_6$ alkyl group that may have one or more substituents selected from the following Group A, a tetrahydrofuranyl group that may have one or more substituents selected from the following Group B, a tetrahydropyranyl group that may have one or more substituents selected from the following Group B, a pyrrolidinyl group that may have one or more substituents selected from the following Group D, a piperidinyl group that may have one or more substituents selected from the following Group B, or a pyridinyl group that may have one or more substituents selected from the following Group D, and Rb and Rc each independently represent a $C_1$-$C_6$ alkyl group that may have one or more substituents selected from the following Group E or a hydrogen atom, or Rb and Rc, together with a nitrogen atom to which Rb and Rc are bonded, form a 4- to 7-membered alicyclic nitrogen-containing heterocyclic group that may have one or more substituents selected from the following Group E:

Group A: a halogen atom, a hydroxy group, a $C_1$-$C_6$ alkyl group, a $C_3$-$C_8$ cycloalkyl group, a $C_1$-$C_6$ alkoxy group, an amino group, a $C_1$-$C_6$ alkylamino group, a di$C_1$-$C_6$ alkylamino group, a cyano group, a $C_1$-$C_6$ alkylamino $C_1$-$C_6$ alkyl group, and an oxo group;

Group B: a halogen atom, a hydroxy group, a $C_1$-$C_6$ alkyl group, a $C_1$-$C_6$ alkoxy group, an amino group, a $C_1$-$C_6$ alkylamino group, a di$C_1$-$C_6$ alkylamino group, a cyano group, a $C_1$-$C_6$ alkylamino $C_1$-$C_6$ alkyl group, and a $C_1$-$C_6$ alkylcarbonylamino group;

Group D: a halogen atom, a hydroxy group, a $C_1$-$C_6$ alkyl group, a $C_3$-$C_8$ cycloalkyl group, a $C_1$-$C_6$ alkylcarbonyl group, a $C_3$-$C_8$ cycloalkylcarbonyl group, a $C_3$-$C_8$ cycloalkyl $C_1$-$C_6$ alkylcarbonyl group, a $C_1$-$C_6$ alkylamino $C_1$-$C_6$ alkyl group, a $C_1$-$C_6$ alkylsulfonyl group, and an arylcarbonyl group that may have one or more substituents selected from said Group A; and Group E: a halogen atom, a hydroxy group, a formyl group, a $C_1$-$C_6$ alkyl group that may have one or more substituents selected from said Group A, a $C_3$-$C_8$ cycloalkyl group that may have one or more substituents selected from said Group A, a $C_1$-$C_6$ alkoxy group that may have one or more substituents selected from said Group A, an amino group, a $C_1$-$C_6$ alkylamino group that may have one or more substituents selected from said Group A, a $diC_1$-$C_6$ alkylamino group that may have one or more substituents selected from said Group A, a $C_1$-$C_6$ alkylsulfonylamino group that may have one or more substituents selected from said Group A, a $C_1$-$C_6$ alkylsulfonyl $C_1$-$C_6$ alkylamino group that may have one or more substituents selected from said Group A, an arylsulfonylamino group that may have one or more substituents selected from said Group A, an arylsulfonyl $C_1$-$C_6$ alkylamino group that may have one or more substituents selected from said Group A, a heteroarylsulfonylamino group that may have one or more substituents selected from said Group A, a heteroarylsulfonyl $C_1$-$C_6$ alkylamino group that may have one or more substituents selected from said Group A, a $C_1$-$C_6$ alkylsulfonylamino $C_1$-$C_6$ alkyl group that may have one or more substituents selected from said Group A, a $C_1$-$C_6$ alkylsulfonyl $C_1$-$C_6$ alkylamino $C_1$-$C_6$ alkyl group that may have one or more substituents selected from said Group A, an arylsulfonylamino $C_1$-$C_6$ alkyl group that may have one or more substituents selected from said Group A, an arylsulfonyl $C_1$-$C_6$ alkylamino $C_1$-$C_6$ alkyl group that may have one or more substituents selected from said Group A, a heteroarylsulfonylamino $C_1$-$C_6$ alkyl group that may have one or more substituents selected from said Group A, a heteroarylsulfonyl $C_1$-$C_6$ alkylamino $C_1$-$C_6$ alkyl group that may have one or more substituents selected from said Group A, a cyano group, a $C_1$-$C_6$ alkylamino $C_1$-$C_6$ alkyl group that may have one or more substituents selected from said Group A, an oxo group, a $C_1$-$C_6$ alkylcarbonyl group that may have one or more substituents selected from said Group A, a $C_3$-$C_8$ cycloalkylcarbonyl group that may have one or more substituents selected from said Group A, a $C_3$-$C_8$ cycloalkyl $C_1$-$C_6$ alkylcarbonyl group that may have one or more substituents selected from said Group A, a $C_1$-$C_6$ alkylsulfonyl group that may have one or more substituents selected from said Group A, a $C_1$-$C_6$ alkylamino $C_1$-$C_6$ alkylcarbonyl group that may have one or more substituents selected from said Group A, a $C_1$-$C_6$ alkylaminocarbonyl group that may have one or more substituents selected from said Group A, a $C_1$-$C_6$ alkylamino $C_1$-$C_6$ alkylsulfonyl group that may have one or more substituents selected from said Group A, a $diC_1$-$C_6$ alkylamino $C_1$-$C_6$ alkylsulfonyl group that may have one or more substituents selected from said Group A, a $C_1$-$C_6$ alkylaminosulfonyl group that may have one or more substituents selected from said Group A, a $diC_1$-$C_6$ alkylaminosulfonyl group that may have one or more substituents selected from said Group A, a $diC_1$-$C_6$ alkylamino $C_1$-$C_6$ alkylcarbonyl group that may have one or more substituents selected from said Group A, a $diC_1$-$C_6$ alkylaminocarbonyl group that may have one or more substituents selected from said Group A, an arylsulfonyl group that may have one or more substituents selected from said Group A, a heteroarylsulfonyl group that may have one or more substituents selected from said Group A, a heteroaryl $C_1$-$C_6$ alkylsulfonyl group that may have one or more substituents selected from said Group A, a heteroaryl $C_1$-$C_6$ alkylcarbonyl group that may have one or more substituents selected from said Group A, and a group represented by the following general formula (2):

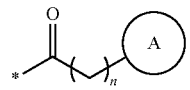

(2)

wherein n is any of 0 to 3, Ring A represents any of an azetidine ring, a pyrrolidine ring, a pyridine ring, a morpholine ring, and a piperazine ring, and a carbon atom constituting the ring may have one or more substituents selected from said Group A.

[3] A compound represented by a general formula (1a) or a salt thereof:

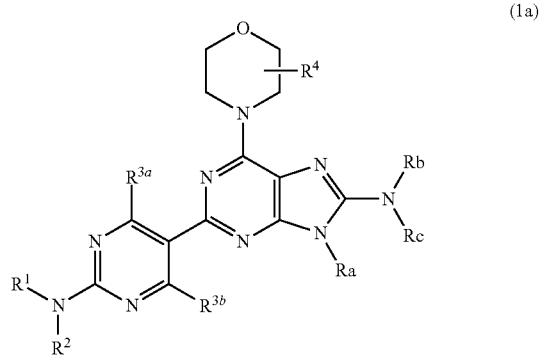

(1a)

wherein $R^1$, $R^2$, $R^4$, and Ra to Rc have the same meaning as defined in [2] and $R^{3a}$ and $R^{3b}$ each independently represent a $C_1$-$C_6$ alkyl group that may have one or more substituents selected from the following Group A, a $C_1$-$C_6$ alkoxy group that may have one or more substituents selected from the following Group A, a $C_1$-$C_6$ alkylamino group that may have one or more substituents selected from the following Group A, a $diC_1$-$C_6$ alkylamino group that may have one or more substituents selected from the following Group A, a $C_3$-$C_8$ cycloalkyl group that may have one or more substituents selected from the following Group A, an amino group, a halogen atom, a hydroxyl group, or a hydrogen atom:

Group A: a halogen atom, a hydroxy group, a $C_1$-$C_6$ alkyl group, a $C_3$-$C_8$ cycloalkyl group, a $C_1$-$C_6$ alkoxy group, an amino group, a $C_1$-$C_6$ alkylamino group, a $diC_1$-$C_6$ alkylamino group, a cyano group, a $C_1$-$C_6$ alkylamino $C_1$-$C_6$ alkyl group, and an oxo group; and

[4] The compound according to [3] or a salt thereof, wherein $R^{3a}$ and $R^{3b}$ each independently represent a $C_1$-$C_6$ alkyl group, a halo $C_1$-$C_6$ alkyl group, or a hydrogen atom.

[5] The compound according to any one of [1] to [4] or a salt thereof, wherein $R^1$ and $R^2$ are a combination of a $C_1$-$C_6$ alkyl group and a hydrogen atom or both represent a hydrogen atom.

[6] The compound according to any one of [1] to [5] or a salt thereof, wherein $R^4$ represents a $C_1$-$C_6$ alkyl group or a hydrogen atom.

[7] The compound according to any one of [1] to [6] or a salt thereof, wherein Ra represents any one selected from the following formulas $Ra_1$ to $Ra_{11}$:

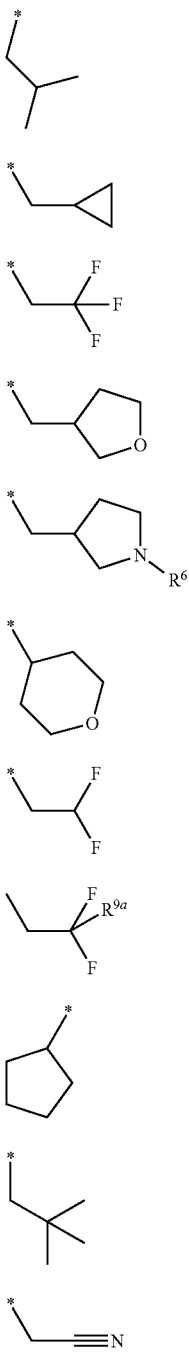

wherein, in Formula Ra$_5$, R$^6$ represents —SO$_2$R$^8$ or —COR$^8$, wherein R$^8$ represents a C$_1$-C$_6$ alkyl group or an aryl group, and, in Formula Ra$_8$, R$^{9a}$ represents a C$_1$-C$_6$ alkyl group, a C$_3$-C$_8$ cycloalkyl group, an amino C$_1$-C$_6$ alkyl group, a C$_1$-C$_6$ alkylamino C$_1$-C$_6$ alkyl group, a diC$_1$-C$_6$ alkylamino C$_1$-C$_6$ alkyl group, a hydroxy C$_1$-C$_6$ alkyl group, a carboxy C$_1$-C$_6$ alkyl group, an aryl group that may have one or more substituents selected from said Group A, or a heteroaryl group that may have one or more substituents selected from said Group A.

[8] The compound according to any one of [1] to [7] or a salt thereof, wherein, when Rb and Rc, together with a nitrogen atom to which Rb and Rc are bonded, forms a 4- to 7-membered alicyclic nitrogen-containing heterocyclic group that may have one or more substituents selected from said Group E, the 4- to 7-membered alicyclic nitrogen-containing heterocyclic group moiety is an azetidine ring, a pyrrolidine ring, a morpholine ring, a piperazine ring, or a piperidine ring.

[9] The compound according to any one of [1] to [8] or a salt thereof, wherein Rb, Rc, and a group formed by Rb and Rc together with a nitrogen atom to which Rb and Rc are bonded are any one selected from the following formulas Rbc1 to Rbc80:

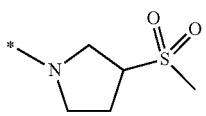

Rbc1

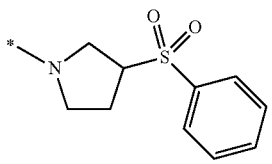

Rbc2

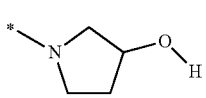

Rbc3

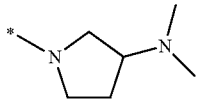

Rbc4

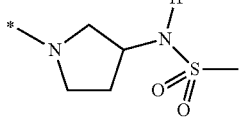

Rbc5

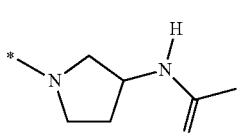

Rbc6

Rbc7

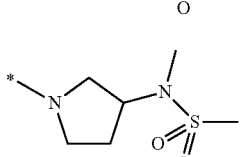

Rbc8

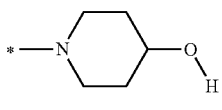

Rbc9

Rbc10

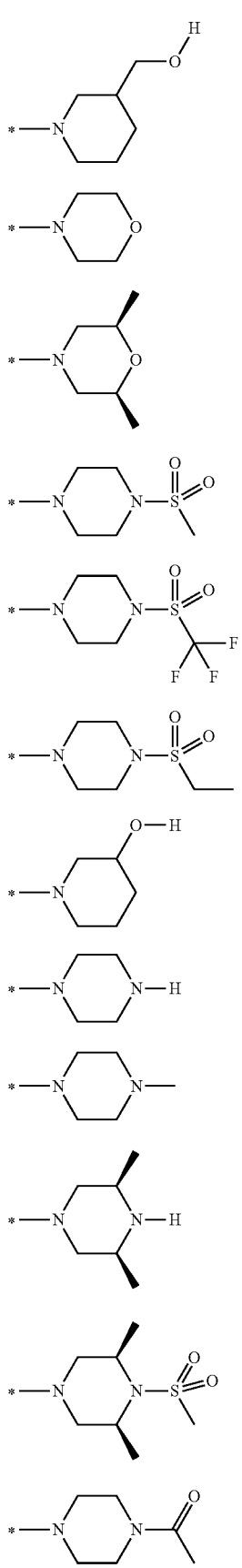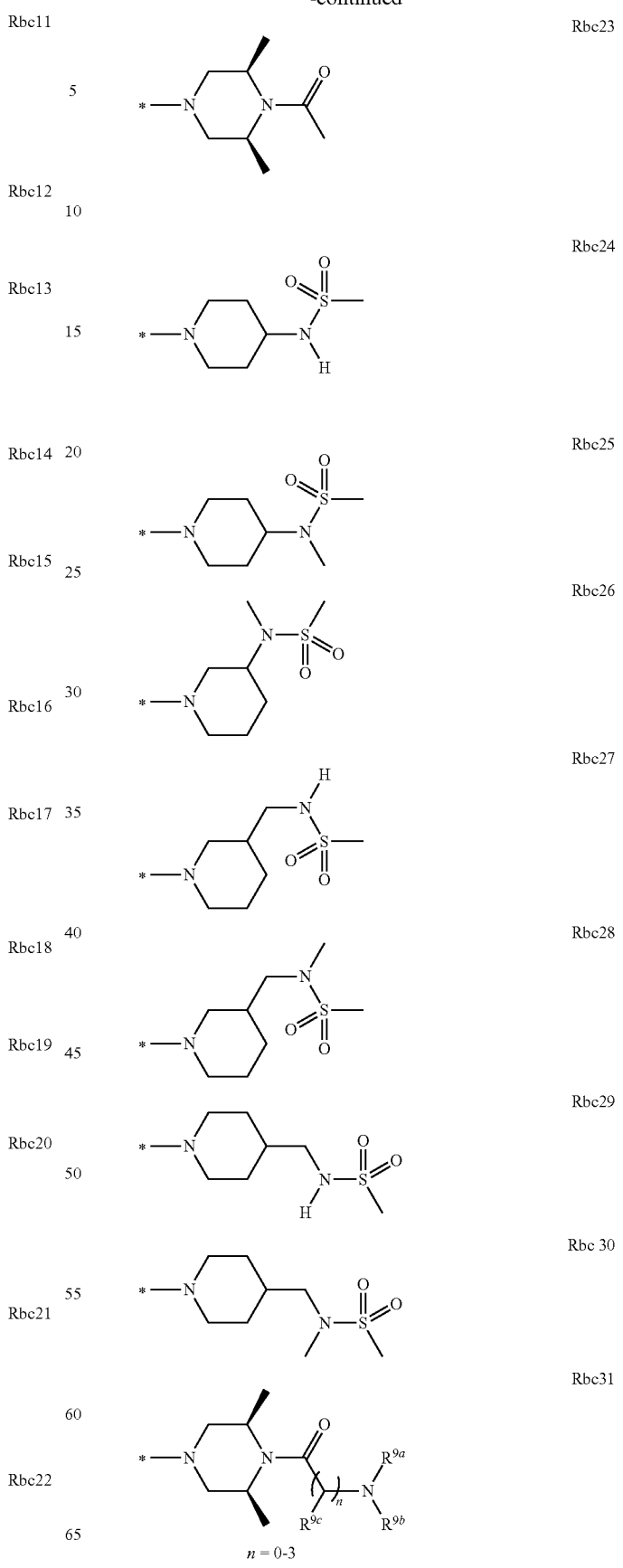

-continued
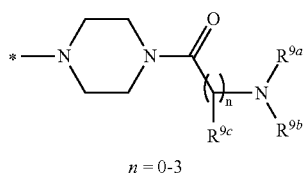
n = 0-3
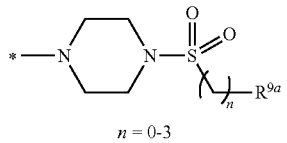
n = 0-3
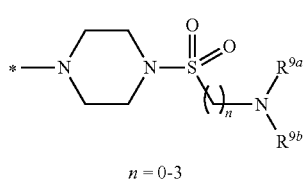
n = 0-3
Rbc35
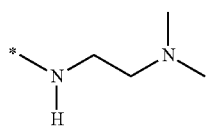
Rbc36
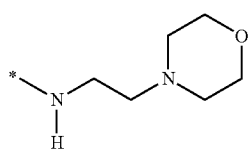
Rbc37
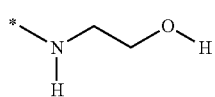
Rbc38
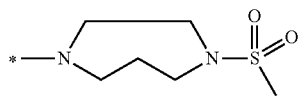
Rbc39
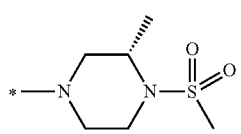
Rbc40
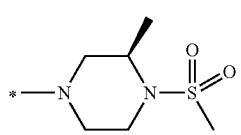
Rbc41
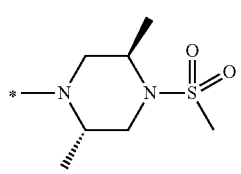
-continued
Rbc42
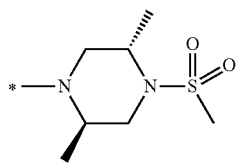
Rbc43
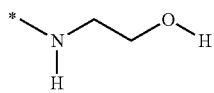
Rbc44
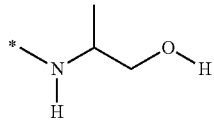
Rbc45
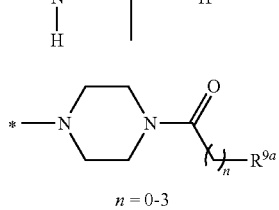
Rbc46
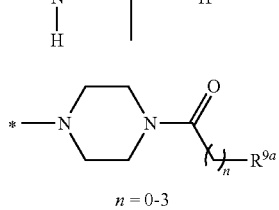
n = 0-3
Rbc47
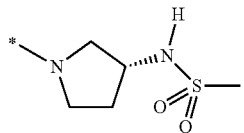
Rbc48
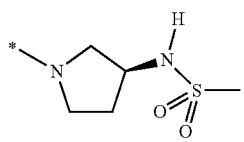
Rbc49
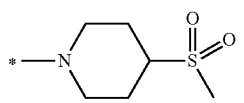
Rbc50
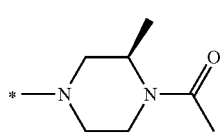
Rbc51
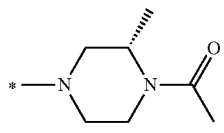
Rbc52
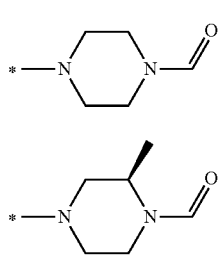
Rbc53

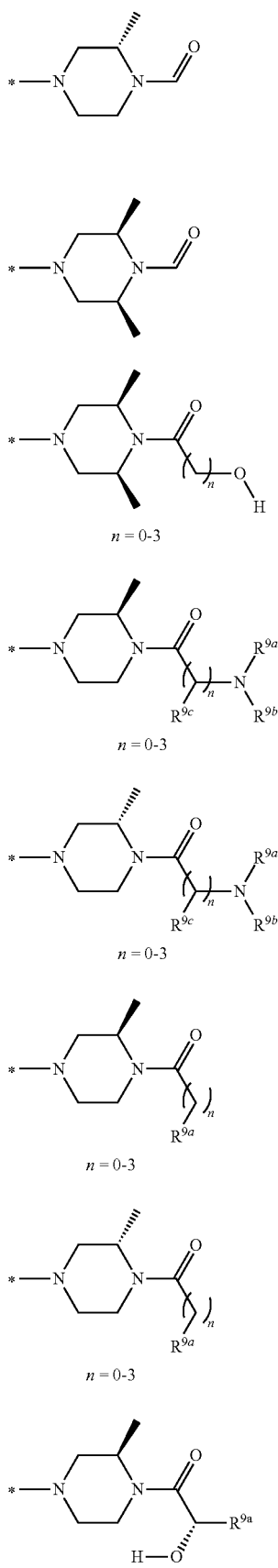
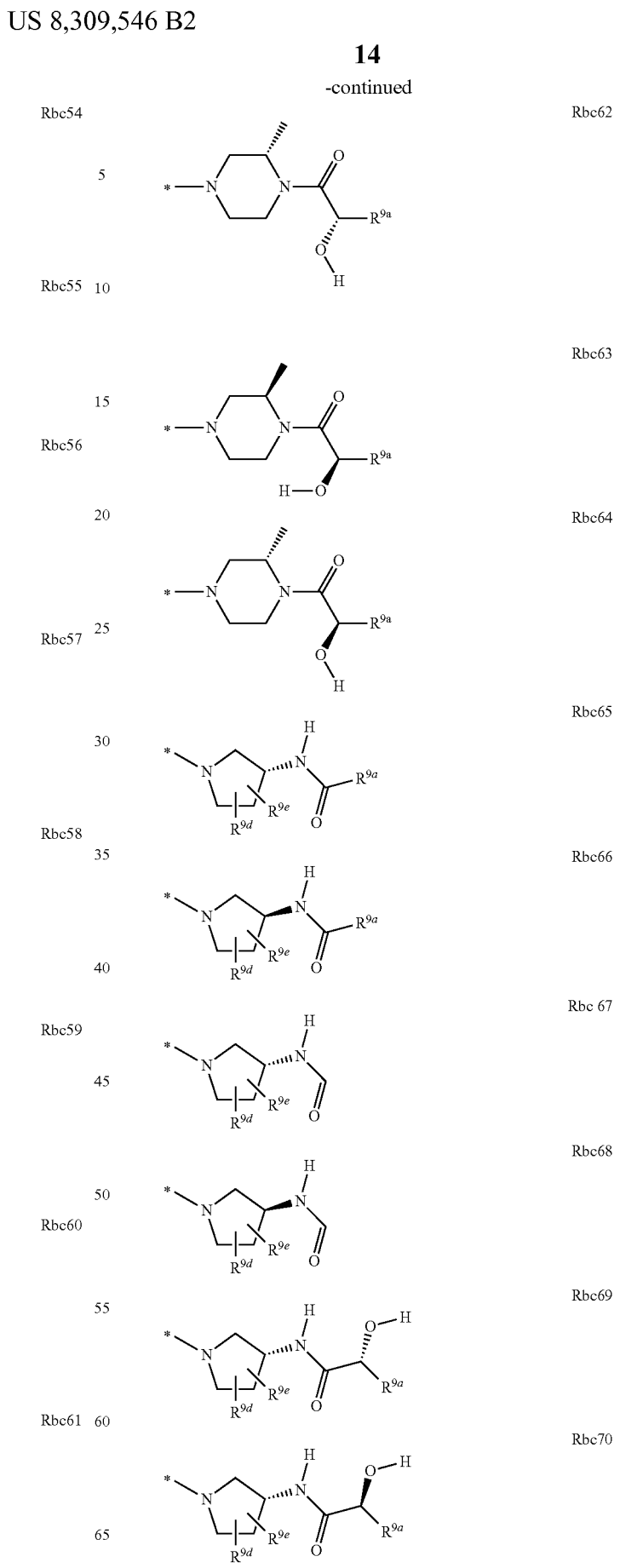

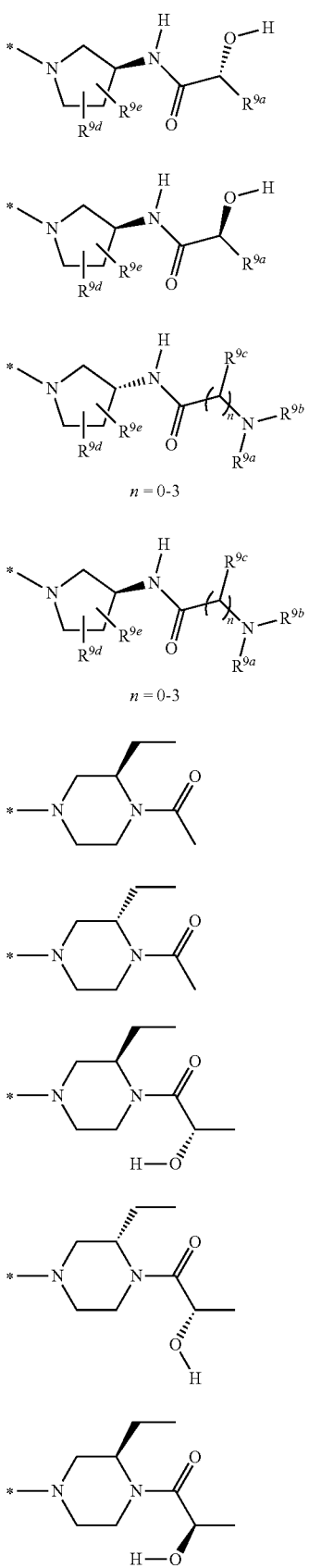

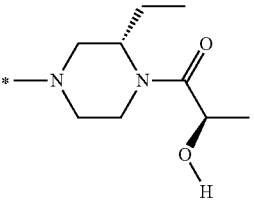

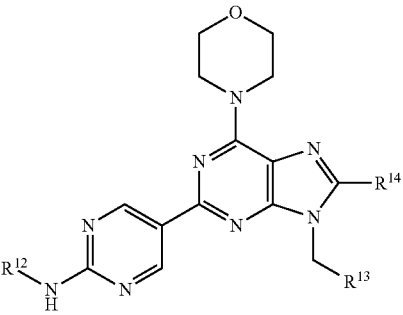

wherein, in Formulas Rbc1 to Rbc80, $R^{9a}$, $R^{9b}$, $R^{9c}$, $R^{10}$, and $R^{11}$ each independently represent a $C_1$-$C_6$ alkyl group, a $C_3$-$C_8$ cycloalkyl group, an amino $C_1$-$C_6$ alkyl group, a $C_1$-$C_6$ alkylamino $C_1$-$C_6$ alkyl group, a di$C_1$-$C_6$ alkylamino $C_1$-$C_6$ alkyl group, a hydroxy $C_1$-$C_6$ alkyl group, a carboxy $C_1$-$C_6$ alkyl group, an aryl group that may have one or more substituents selected from said Group A, or a heteroaryl group that may have one or more substituents selected from said Group A, and $R^{9d}$ and $R^{9e}$ each independently represent a $C_1$-$C_6$ alkyl group, a $C_3$-$C_8$ cycloalkyl group, an amino $C_1$-$C_6$ alkyl group, a $C_1$-$C_6$ alkylamino $C_1$-$C_6$ alkyl group, a di$C_1$-$C_6$ alkylamino $C_1$-$C_6$ alkyl group, a hydroxy $C_1$-$C_6$ alkyl group, a carboxy $C_1$-$C_6$ alkyl group, an aryl group that may have one or more substituents selected from said Group A, a heteroaryl group that may have one or more substituents selected from said Group A, a hydrogen atom, a hydroxyl group, an amino group, a group represented by NH—$R^{10}$, or a group represented by $NR^{10}R^{11}$.

[10] A compound represented by a general formula (1b) or a salt thereof:

(1b)

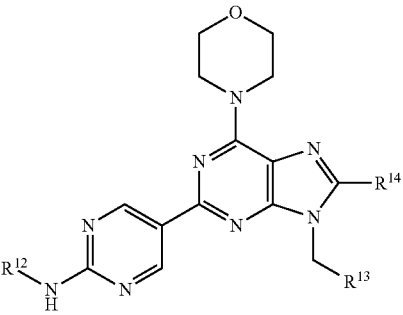

wherein $R^{12}$ represents methyl group or hydrogen, $R^{13}$ represents a $C_1$-$C_6$ alkyl group or a $C_3$-$C_8$ cycloalkyl group that may have one to three halogen atom(s), $R^{14}$ represents any one selected from the following formulas:

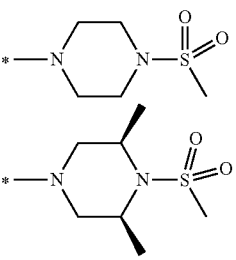

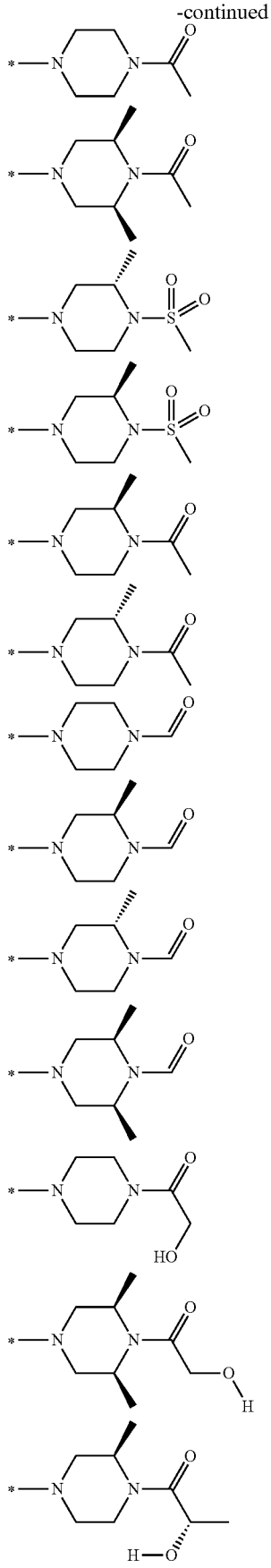
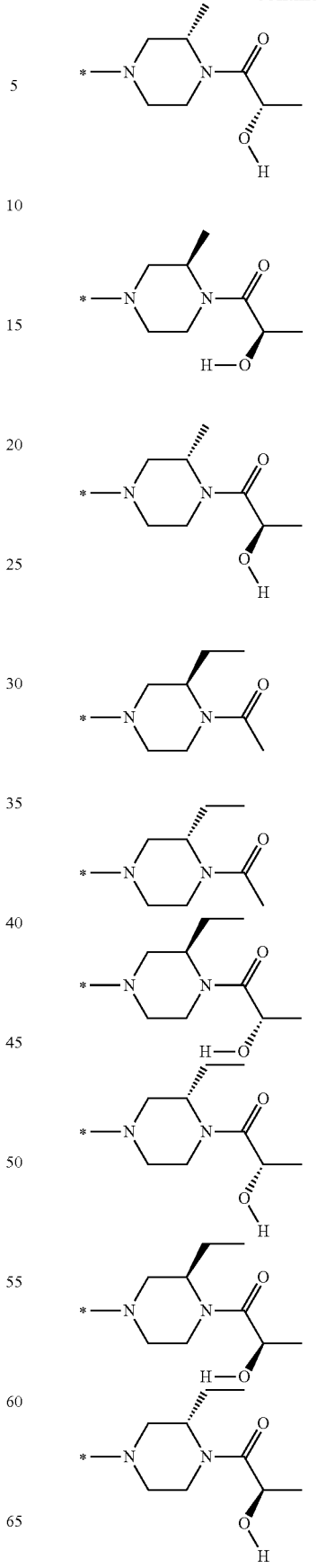

[11] A compound or a salt thereof, the compound being selected from the group consisting of:
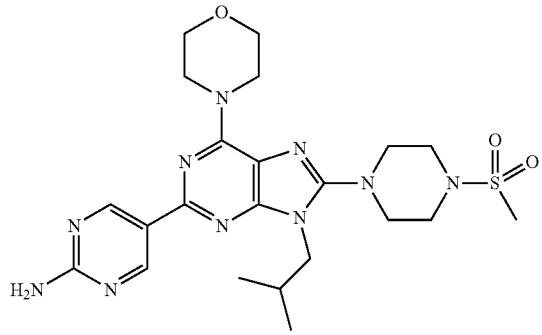
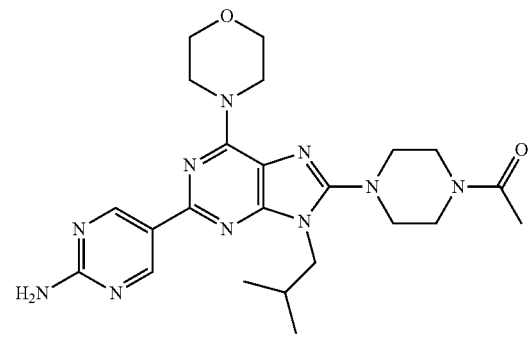
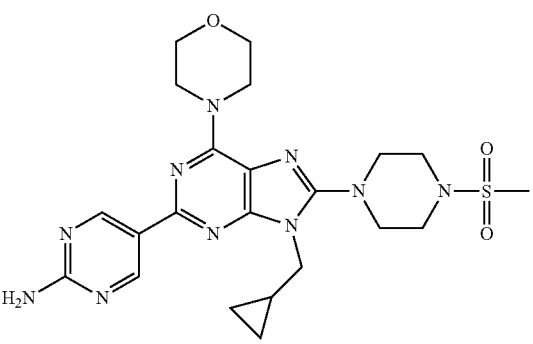
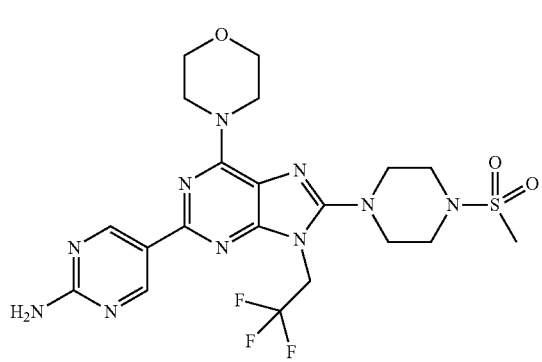
-continued
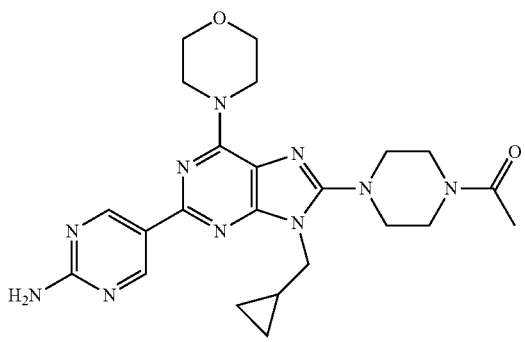
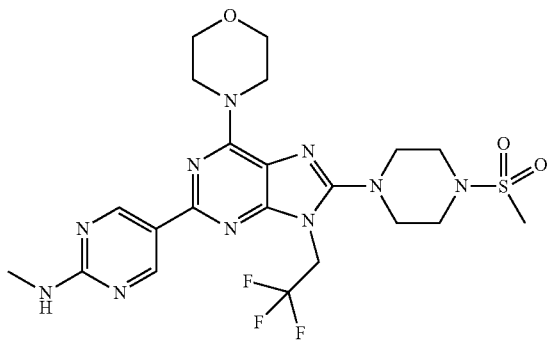
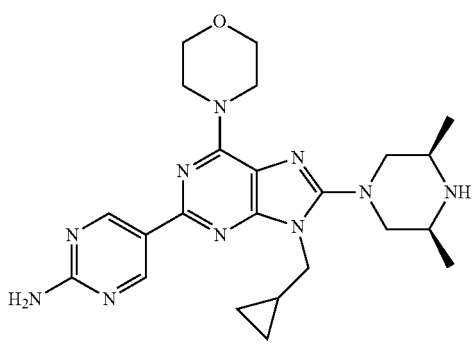
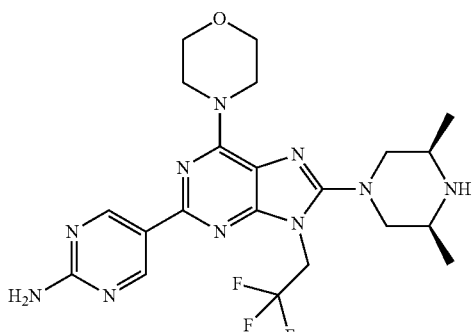
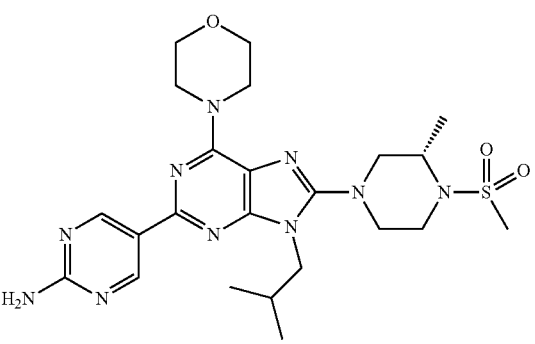

21
-continued
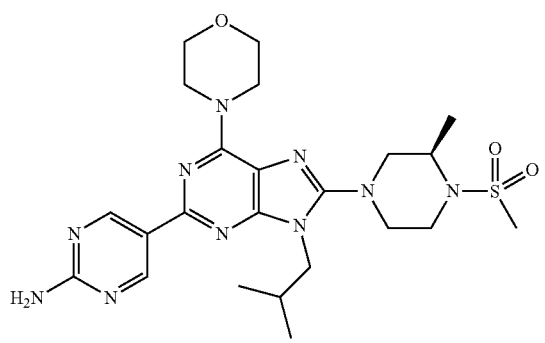
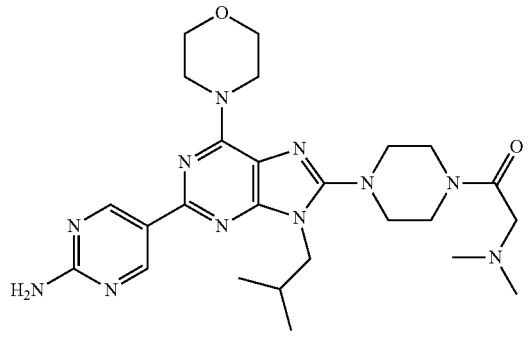
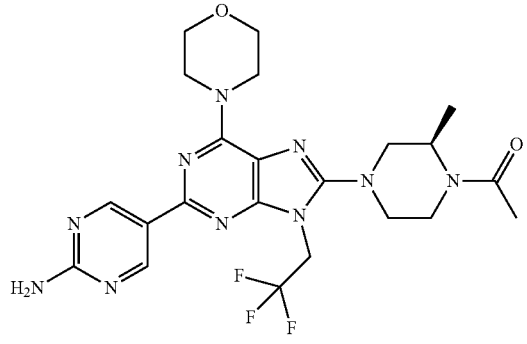
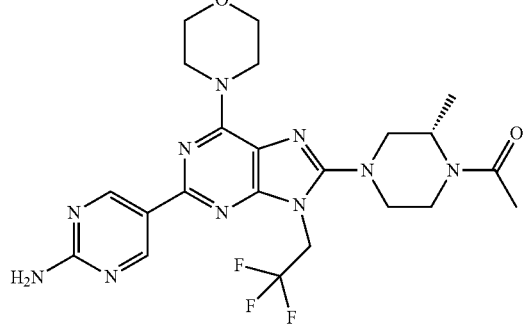
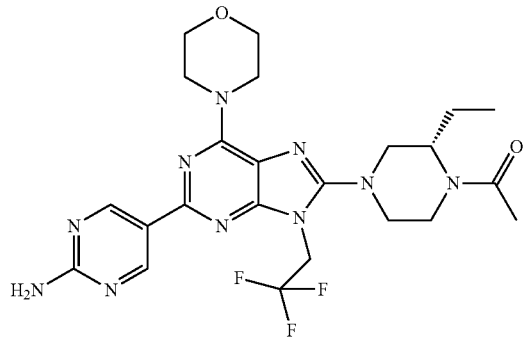
22
-continued
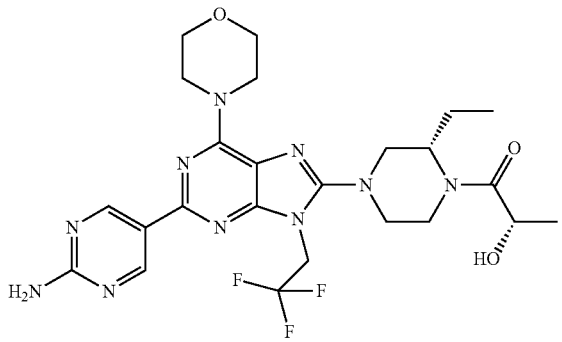
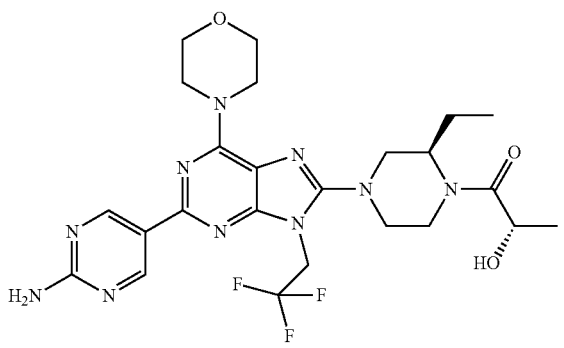
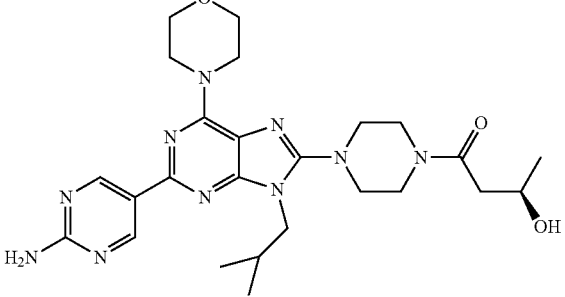
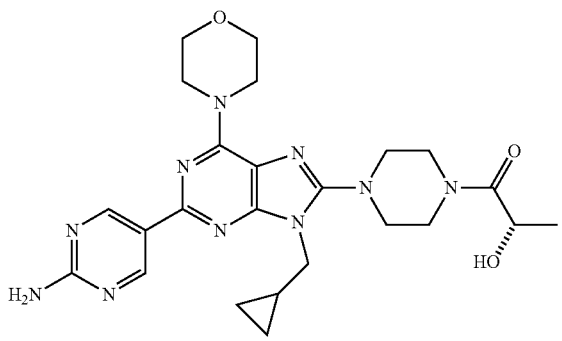
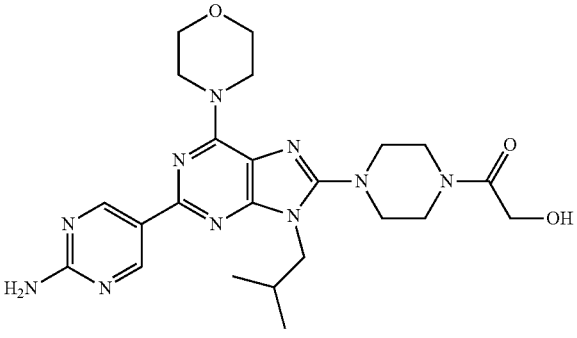

23
-continued
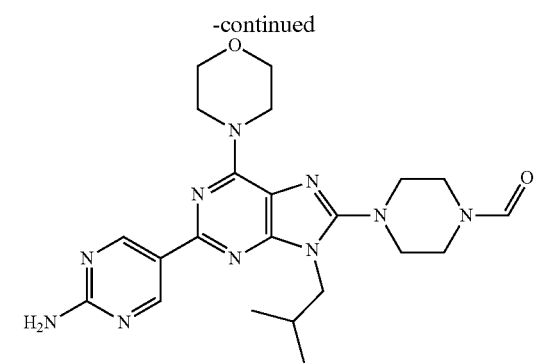
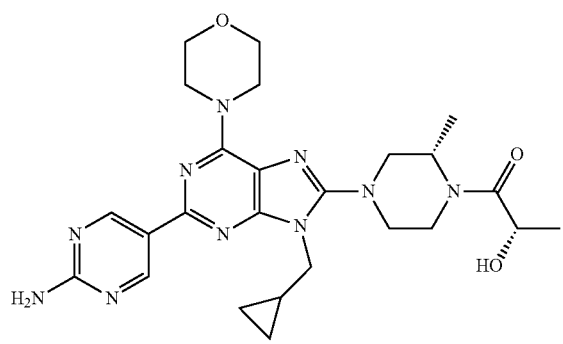
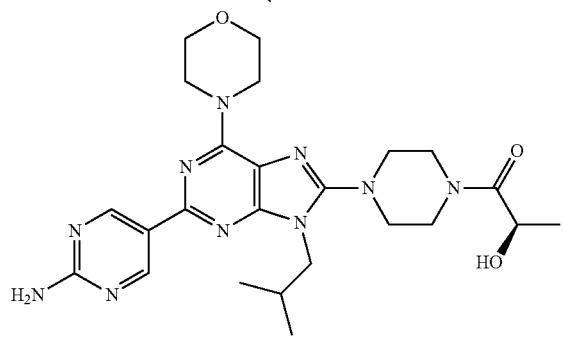
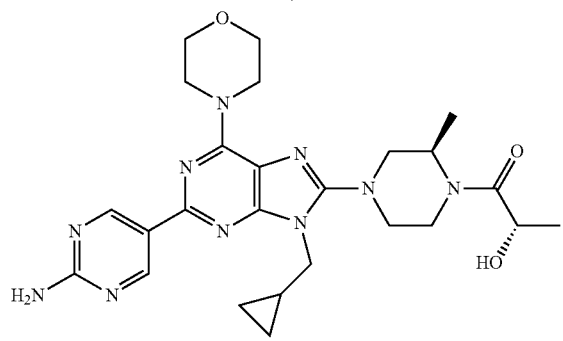
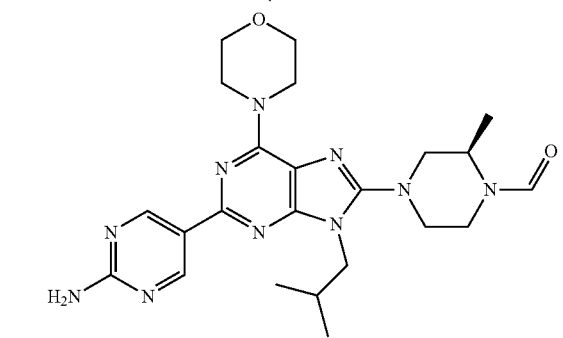
24
-continued
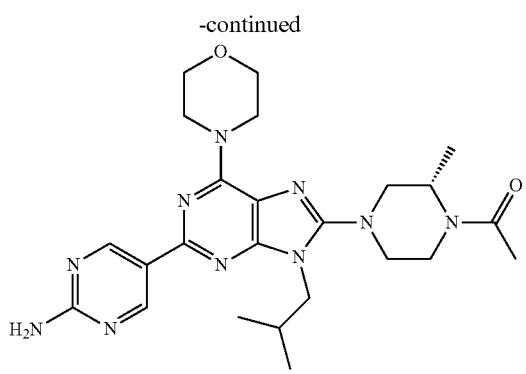
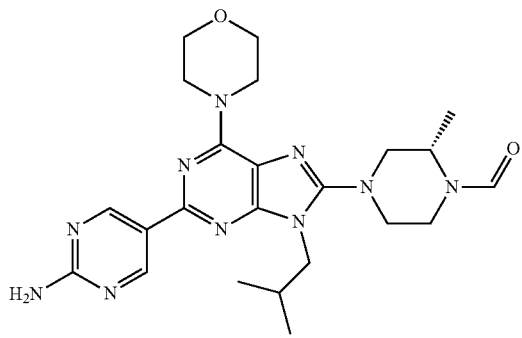
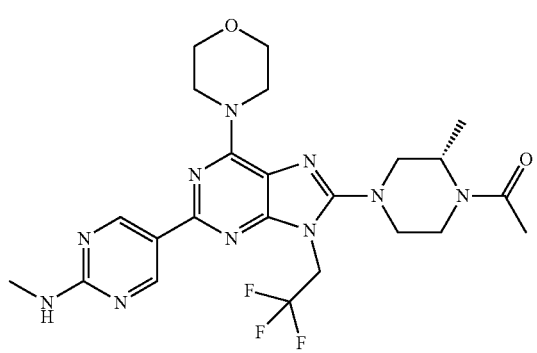
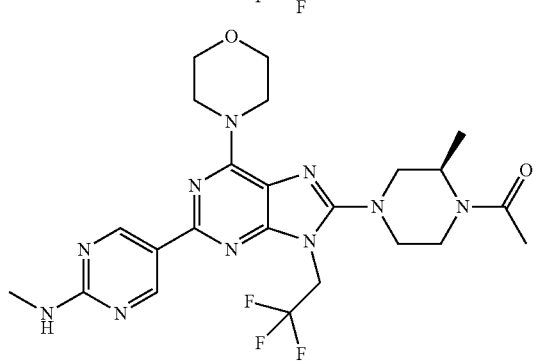
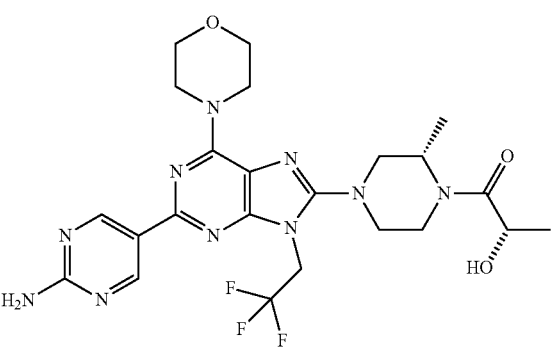

-continued
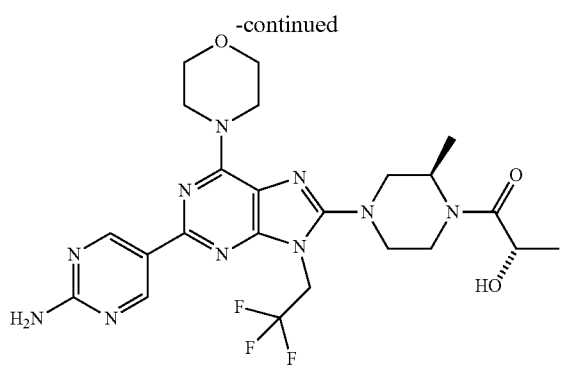
[12] A compound represented by the following formula:
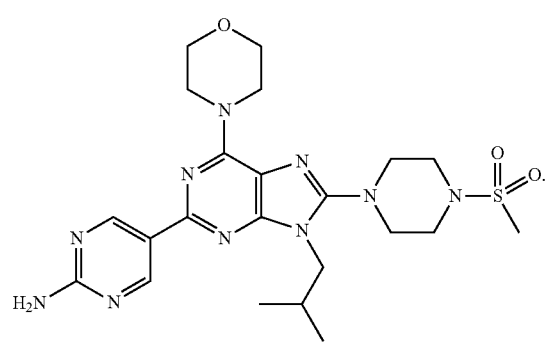
[13] A compound represented by the following formula:
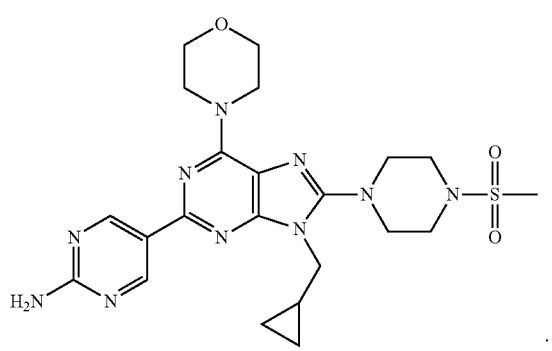
[14] A compound represented by the following formula:
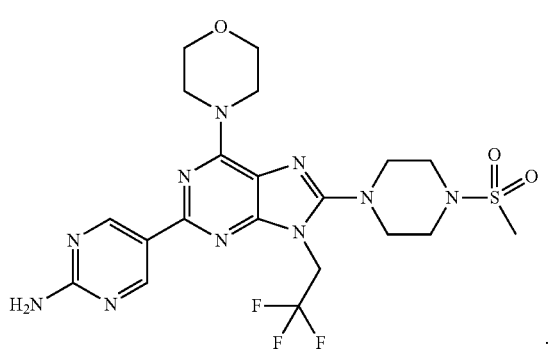
[15] A compound represented by the following formula:
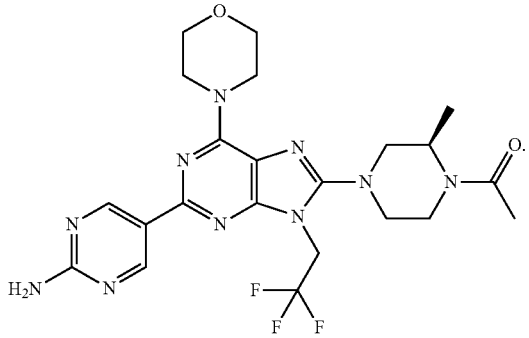
[16] A compound represented by the following formula:
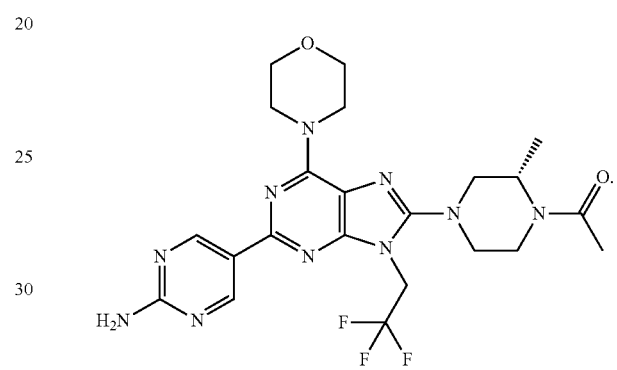
[17] A compound represented by the following formula:
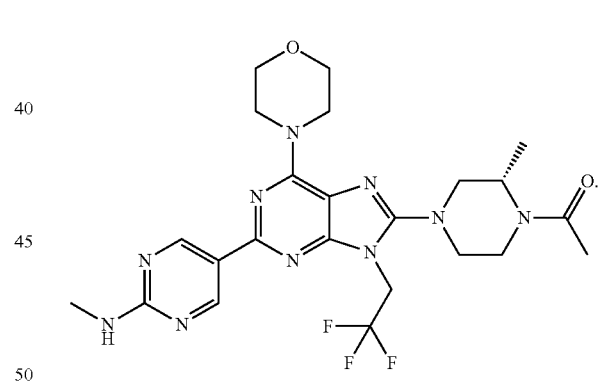
[18] A compound represented by the following formula:
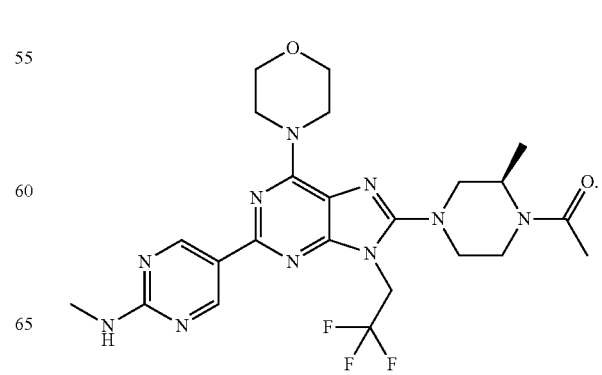

[19] A methanesulfonate of the compound represented by the following formula:

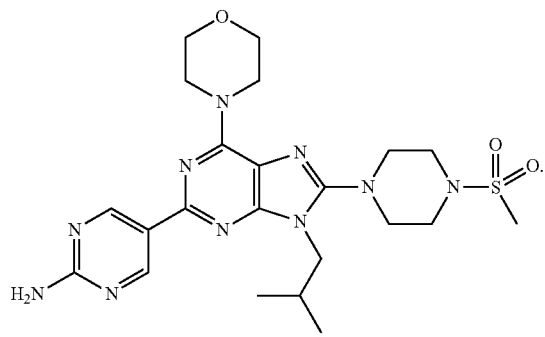

[20] A methanesulfonate of the compound represented by the following formula:

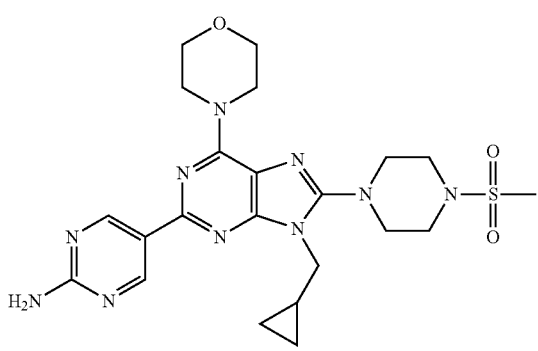

[21] A methanesulfonate of the compound represented by the following formula:

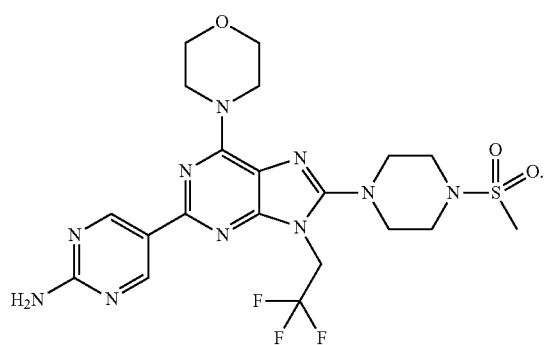

[22] A methanesulfonate of the compound represented by the following formula:

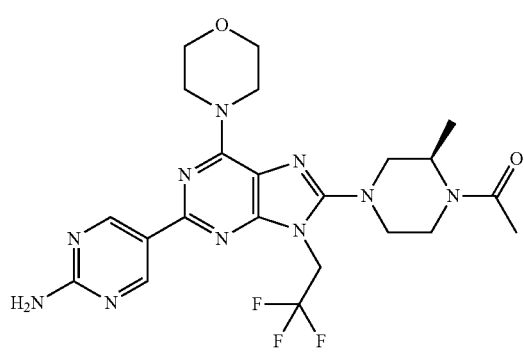

[23] A methanesulfonate of the compound represented by the following formula:

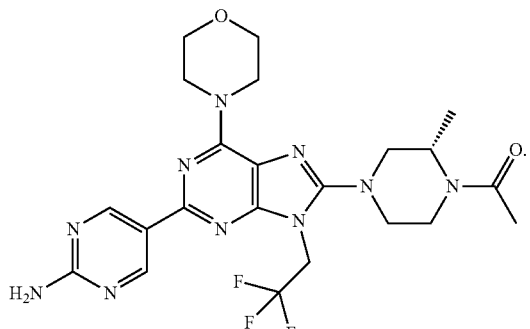

[24] A methanesulfonate of the compound represented by the following formula:

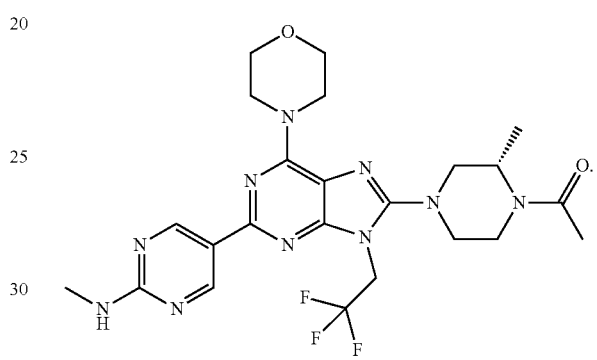

[25] A methanesulfonate of the compound represented by the following formula:

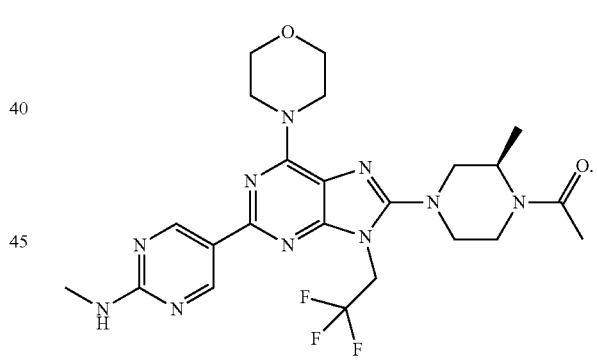

[26] A sulfate of the compound represented by the following formula:

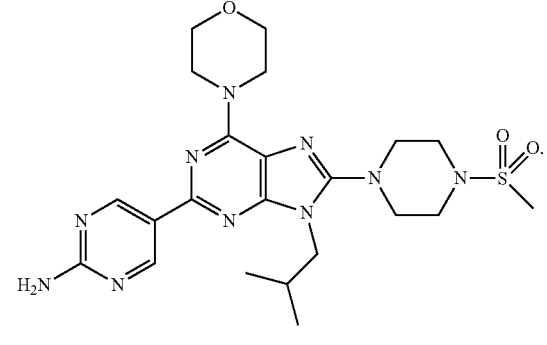

[27] A sulfate of the compound represented by the following formula:

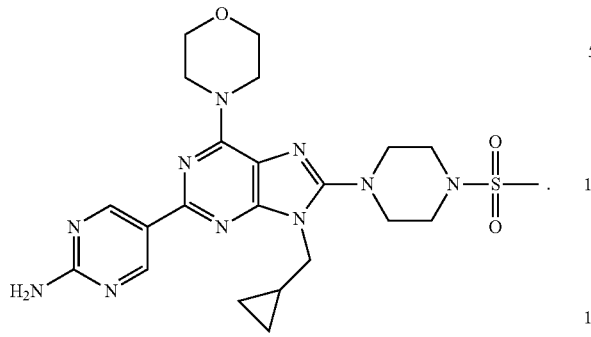

[28] A sulfate of the compound represented by the following formula:

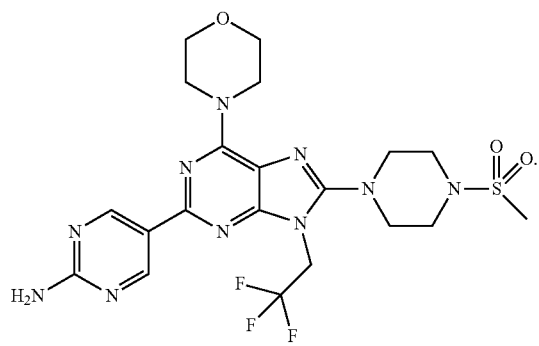

[29] A sulfate of the compound represented by the following formula:

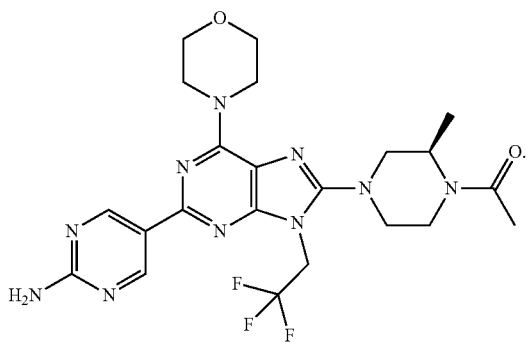

[30] A sulfate of the compound represented by the following formula:

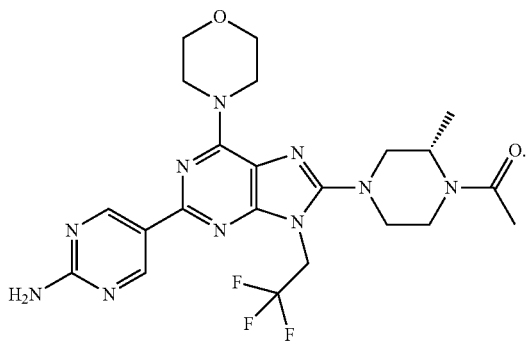

[31] A sulfate of the compound represented by the following formula:

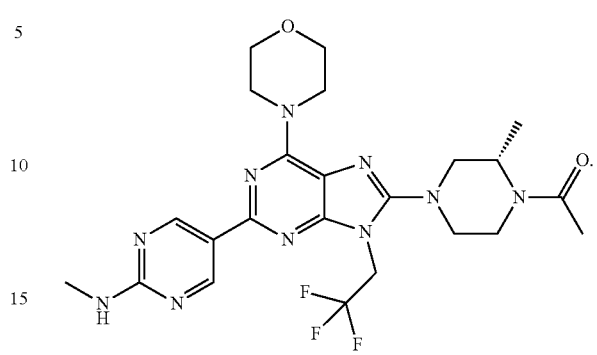

[32] A sulfate of the compound represented by the following formula:

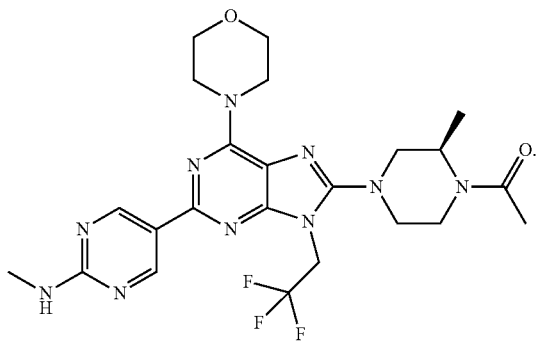

[33] A method for inhibiting phosphatidylinositol 3-kinase (PI3K) in a subject comprising administering to a subject in need thereof an effective amount of the compound according to any one of [1] to [18] or a salt thereof.

[34] A method for inhibiting the mammalian target of rapamycin (mTOR) in a subject comprising administering to a subject in need thereof an effective amount of the compound according to any one of [1] to [18] or a salt thereof.

[35] A method for inhibiting phosphatidylinositol 3-kinase (PI3K) and the mammalian target of rapamycin (mTOR) in a subject comprising administering to a subject in need thereof an effective amount of the compound according to any one of [1] to [18] or a salt thereof.

[36] A medicament comprising or consisting of the compound according to any one of [1] to [18] or a salt thereof as an active ingredient.

[37] An anti-tumor agent comprising the compound according to any one of [1] to [18] or a salt thereof as an active ingredient.

[38] The anti-tumor agent according to [37], wherein the tumor is selected from the following group: brain tumor, ovary cancer, lung cancer, breast cancer, colon cancer, gastrointestinal cancer, prostate cancer and melanoma.

[39] A pharmaceutical composition comprising the compound according to any one of [1] to [18] or a salt thereof and a pharmaceutically acceptable carrier.

[40] A method for treating a tumor comprising administering an effective amount of the compound according to any one of [1] to [18] or a salt thereof.

[41] The method for treating a tumor according to [40], wherein the tumor is selected from the following group: brain tumor, ovary cancer, lung cancer, breast cancer, colon cancer, gastrointestinal cancer, prostate cancer and melanoma.

[42] A method for treating a tumor possessing a mutation(s) of PTEN (phosphate and tensin homolog) comprising administering an effective amount of the compound according to any one of [1] to [18] or a salt thereof.

[43] A method for treating a tumor possessing a mutation(s) or over-expression in PI3K (phosphatidylinositol 3-kinase) comprising administering an effective amount of the compound according to any one of [1] to [18] or a salt thereof.

[44] A method of treating a tumor with the activated phospholilation level of Akt comprising administering an effective amount of the compound according to any one of [1] to [18] or a salt thereof.

The 6-morpholinopurine derivative of the present invention can be used as a potent anti-tumor agent because it exhibits PI3K inhibitory activity, mTOR inhibitory activity, and anti-tumor activity.

DETAILED DESCRIPTION OF THE PREFERRED EMBODIMENTS

Hereafter, each substituent in the present specification will be described.

In the present specification, "$C_1$-$C_6$ alkyl group" or the "$C_1$-$C_6$ alkyl group" moiety of a $C_1$-$C_6$ alkylamino group, a di$C_1$-$C_6$ alkylamino group, a $C_1$-$C_6$ alkylsulfonyl group, a $C_1$-$C_6$ alkylamino $C_1$-$C_6$ alkyl group, a $C_1$-$C_6$ alkylcarbonyl group, a $C_1$-$C_6$ alkylamino $C_1$-$C_6$ alkylcarbonyl group, a $C_1$-$C_6$ alkylamino $C_1$-$C_6$ alkylsulfonyl group, a di$C_1$-$C_6$ alkylamino $C_1$-$C_6$ alkylsulfonyl group, a di$C_1$-$C_6$ alkylamino $C_1$-$C_6$ alkylcarbonyl group, a $C_1$-$C_6$ alkylcarbonylamino group, a $C_1$-$C_6$ alkylaminocarbonyl group, a di$C_1$-$C_6$ alkylamino group, a $C_1$-$C_6$ alkylaminosulfonyl group, a dialkylaminosulfonyl group, a di$C_1$-$C_6$ alkylaminocarbonyl group, or the like means a straight or branched monovalent group comprising a saturated hydrocarbon having 1 to 6 carbon atoms, and examples thereof include a methyl group, an ethyl group, an n-propyl group, an isopropyl group, an n-butyl group, and a tert-butyl group.

In the present specification, "$C_1$-$C_6$ alkoxy group" means a $C_1$-$C_6$ alkyloxy group formed from the above-mentioned $C_1$-$C_6$ alkyl group, and examples thereof include a methoxy group, an ethoxy group, an n-propoxy group, and an isopropoxy group.

In the present specification, "$C_3$-$C_8$ cycloalkyl group" or the "$C_3$-$C_8$ cycloalkyl group" moiety of a $C_3$-$C_8$ cycloalkylcarbonyl group or the like means a group comprising a saturated cyclic hydrocarbon having 3 to 8 carbon atoms. Examples of the "$C_3$-$C_8$ cycloalkyl group" include a cyclopropyl group, a cyclobutyl group, and a cyclohexyl group.

In the present specification, "$C_1$-$C_6$ alkylene group" means a divalent group comprising a straight or branched saturated hydrocarbon having 1 to 6 carbon atoms. Examples of the "$C_1$-$C_6$ alkylene group" include a methylene group, an ethylene group, a trimethylene group, an isopropylene group, and a tetramethylene group.

In the present specification, "$C_1$-$C_6$ alkylsulfonyl group" or the "$C_1$-$C_6$ alkylsulfonyl group" moiety of a $C_1$-$C_6$ alkylamino $C_1$-$C_6$ alkylsulfonyl group or the like means a group comprising a sulfonyl group that is substituted with the above-mentioned $C_1$-$C_6$ alkyl group, and examples thereof include a methylsulfonyl group, an ethylsulfonyl group, and a propylsulfonyl group.

In the present specification, "$C_1$-$C_6$ alkylamino group" or the "$C_1$-$C_6$ alkylamino group" moiety of a di$C_1$-$C_6$ alkylamino group, a $C_1$-$C_6$ alkylaminocarbonyl group, a $C_1$-$C_6$ alkylamino $C_1$-$C_6$ alkylcarbonyl group, a $C_1$-$C_6$ alkylaminosulfonyl group, a di$C_1$-$C_6$ alkylaminosulfonyl group, a $C_1$-$C_6$ alkylamino $C_1$-$C_6$ alkylsulfonyl group, a di$C_1$-$C_6$ alkylamino $C_1$-$C_6$ alkylsulfonyl group, a di$C_1$-$C_6$ alkylaminocarbonyl group, a di$C_1$-$C_6$ alkylamino. $C_1$-$C_6$ alkylcarbonyl group, or the like means a group comprising an amino group substituted with the above-mentioned $C_1$-$C_6$ alkyl group. Of these, the "di$C_1$-$C_6$ alkylamino group" means an amino group substituted with two $C_1$-$C_6$ alkyl groups. When an amino group is substituted with two $C_1$-$C_6$ alkyl groups, these $C_1$-$C_6$ alkyl groups may be identical to or different from each other. Examples of the "$C_1$-$C_6$ alkylamino group" include a methylamino group and an ethylamino group. Examples of the "di$C_1$-$C_6$ alkylamino group" include a dimethylamino group, a diethylamino group, and a methylethylamino group.

In the present specification, "oxo group" means a group represented by "=O" unless otherwise specified.

In the present specification, "$C_1$-$C_6$ alkylcarbonyl group" or the "$C_1$-$C_6$ alkylcarbonyl group" of a $C_1$-$C_6$ alkylcarbonylamino group, a $C_3$-$C_8$ cycloalkyl $C_1$-$C_6$ alkylcarbonyl group, a $C_1$-$C_6$ alkylamino $C_1$-$C_6$ alkylcarbonyl group, a di$C_1$-$C_6$ alkylamino $C_1$-$C_6$ alkylcarbonyl group, a heteroaryl $C_1$-$C_6$ alkylcarbonyl group, or the like means a group comprising a carbonyl group (C=O) substituted with the above-mentioned $C_1$-$C_6$ alkyl group. Similarly, a "$C_3$-$C_8$ cycloalkylcarbonyl group" means a group comprising a carbonyl group (C=O) substituted with the above-mentioned $C_3$-$C_8$ cycloalkyl group.

In the present specification, "fluoro $C_1$-$C_6$ alkyl group" means the above-mentioned $C_1$-$C_6$ alkyl group substituted with one or more fluoro groups. Substitution with 1 to 3 fluoro groups is preferred. Examples of the "fluoro $C_1$-$C_6$ alkyl group" include a fluoromethyl group, a fluoroethyl group, a difluoromethyl group, a difluoroethyl group, a trifluoromethyl group, and a trifluoroethyl group.

In the present specification, "hydroxy $C_1$-$C_6$ alkyl group" means the above-mentioned $C_1$-$C_6$ alkyl group substituted with one or more hydroxy groups. Substitution with 1 to 3 hydroxy groups is preferred. Examples of the "hydroxy $C_1$-$C_6$ alkyl group" include a hydroxymethyl group and a hydroxyethyl group.

In the present specification, "$C_1$-$C_6$ alkylamino $C_1$-$C_6$ alkyl group" means the above-mentioned $C_1$-$C_6$ alkyl group substituted with the above-mentioned $C_1$-$C_6$ alkylamino group.

In the present specification, "$C_1$-$C_6$ alkylamino $C_1$-$C_6$ alkylcarbonyl group" means the above-mentioned "$C_1$-$C_6$ alkylcarbonyl group" substituted with the above-mentioned "$C_1$-$C_6$ alkylamino group."

In the present specification, "$C_1$-$C_6$ alkylamino $C_1$-$C_6$ alkylsulfonyl group" means the above-mentioned "$C_1$-$C_6$ alkylsulfonyl group" substituted with the above-mentioned "$C_1$-$C_6$ alkylamino group."

In the present specification, "di$C_1$-$C_6$ alkylamino $C_1$-$C_6$ alkylcarbonyl group" means the above-mentioned "$C_1$-$C_6$ alkylcarbonyl group" substituted with the above-mentioned "di$C_1$-$C_6$ alkylamino group."

In the present specification, "$C_3$-$C_8$ cycloalkyl $C_1$-$C_6$ alkylcarbonyl group" means the above-mentioned "$C_1$-$C_6$ alkylcarbonyl group" substituted with the above-mentioned "$C_3$-$C_8$ cycloalkyl group."

In the present specification, "$C_1$-$C_6$ alkylaminocarbonyl group" means a carbonyl group substituted with the above-mentioned $C_1$-$C_6$ alkylamino group.

In the present specification, "$C_1$-$C_6$ alkylaminosulfonyl group" means a sulfonyl group substituted with the above-mentioned $C_1$-$C_6$ alkylamino group.

In the present specification, "di$C_1$-$C_6$ alkylaminosulfonyl group" means a sulfonyl group substituted with the above-mentioned di$C_1$-$C_6$ alkylamino group.

In the present specification, "di$C_1$-$C_6$ alkylamino $C_1$-$C_6$ alkylsulfonyl group" means the above-mentioned $C_1$-$C_6$ alkylsulfonyl group substituted with the above-mentioned di$C_1$-$C_6$ alkylamino group.

In the present specification, "di$C_1$-$C_6$ alkylaminocarbonyl group" means a carbonyl group substituted with the above-mentioned di$C_1$-$C_6$ alkylamino group.

In the present specification, "$C_1$-$C_6$ alkylcarbonylamino group" means an amino group substituted with the above-mentioned $C_1$-$C_6$ alkylcarbonyl group.

In the present specification, "aryl group" or the "aryl group" moiety of an arylsulfonyl group or the like means an aromatic hydrocarbon ring group, and examples thereof include a phenyl group and a naphthyl group. This aryl group may be bonded at any position.

In the present specification, "heteroaryl group" or the "heteroaryl group" moiety of a heteroaryl $C_1$-$C_6$ alkylsulfonyl group, a heteroaryl $C_1$-$C_6$ alkylcarbonyl group, or the like means a 5- or 6-membered aromatic heterocyclic group containing one or more nitrogen atoms, sulfur atoms, or oxygen atoms as constituent atoms of the ring in addition to carbon atoms, and examples thereof include an imidazolyl group, a thiazolyl group, a pyrazolyl group, an oxazolyl group, a pyridyl group, a pyrimidinyl group, and a pyridazinyl group. These "heteroaryl groups" may be bonded to a sulfonyl group or the like at any position.

In the present specification, "6-membered aromatic nitrogen-containing heterocyclic group containing one or two nitrogen atoms" means a group derived from an unsaturated 6-membered heterocyclic ring compound containing at least one or two nitrogen atoms as constituent atoms of the ring structure. This 6-membered aromatic nitrogen-containing heterocyclic group may be bonded at any position. Examples of the 6-membered aromatic nitrogen-containing heterocyclic group containing one or two nitrogen atoms include groups derived from pyridine, pyridazine, and pyrimidine.

In the present specification, "4- to 7-membered alicyclic nitrogen-containing heterocyclic group" means a group derived from a saturated 4- to 7-membered heterocyclic ring compound containing at least one nitrogen atom as a constituent atom of the ring structure, and this group may be bonded at any position. Examples of the 4- to 7-membered alicyclic nitrogen-containing heterocyclic group include groups derived from azetidine, pyrrolidine, imidazolidine, triazolidine, oxazolidine, thiazolidine, piperidine, piperazine, morpholine, thiomorpholine, homomorpholine, and homopiperazine.

In the present specification, "arylsulfonyl group" means a sulfonyl group substituted with the above-mentioned "aryl group," and examples thereof include a benzenesulfonyl group.

In the present specification, "heteroarylsulfonyl group" means a sulfonyl group substituted with the above-mentioned heteroaryl group.

In the present specification, "heteroaryl $C_1$-$C_6$ alkylsulfonyl group" means the above-mentioned $C_1$-$C_6$ alkylsulfonyl substituted with the above-mentioned heteroaryl group.

In the present specification, "heteroaryl $C_1$-$C_6$ alkylcarbonyl group" means a group comprising the above-mentioned $C_1$-$C_6$ alkylcarbonyl group substituted with the above-mentioned heteroaryl group.

Hereafter, each substituent in the general formula (1) will be described.

$R^1$ and $R^2$ each independently represent a $C_1$-$C_6$ alkyl group that may have one or more substituents, a $C_1$-$C_6$ alkylsulfonyl group that may have one or more substituents, an aryl group that may have one or more substituents, or a hydrogen atom.

Here, the substituent(s) in the "$C_1$-$C_6$ alkyl group that may have one or more substituents" and the substituent(s) in the "$C_1$-$C_6$ alkylsulfonyl group that may have one or more substituents" are preferably one or more halogen atoms, hydroxy groups, $C_1$-$C_6$ alkyl groups, $C_3$-$C_8$ cycloalkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or oxo groups, and the substituent(s) in the "aryl group that may have one or more substituents" is preferably one or more halogen atoms, hydroxy groups, $C_1$-$C_6$ alkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or $C_1$-$C_6$ alkylcarbonylamino groups. Two or more substituents may be present on the same atom or different atoms.

$R^1$ and $R^2$ preferably each independently represent a $C_1$-$C_6$ alkyl group that may have one or more substituents or a hydrogen atom, more preferably a $C_1$-$C_6$ alkyl group or a hydrogen atom. Particularly preferably, one is a $C_1$-$C_6$ alkyl group, and the other is a hydrogen atom, or $R^1$ and $R^2$ are both a hydrogen atom.

X represents a 6-membered aromatic nitrogen-containing heterocyclic group containing one or two nitrogen atoms that may have one or more substituents. Examples of X include groups derived from pyridine, pyridazine, and pyrimidine. X may be bonded at any position on the imidazolopyrimidine ring in the general formula (1). X is preferably a group derived from pyrimidine and is particularly preferably bonded at the 2nd position on the imidazolopyrimidine ring.

X is preferably unsubstituted or has a substituent(s) represented by $R^3$ described later.

$R^3$ means one or more substituents present on a carbon atom constituting the above-mentioned X. $R^3$ may be a substituent(s) present on any carbon atom.

$R^3$ preferably each independently represents a $C_1$-$C_6$ alkyl group that may have one or more substituents, a $C_1$-$C_6$ alkoxy group that may have one or more substituents, a $C_1$-$C_6$ alkylamino group that may have one or more substituents, a di$C_1$-$C_6$ alkylamino group that may have one or more substituents, a $C_3$-$C_8$ cycloalkyl group, an amino group, a halogeno group, or a hydroxy group.

Here, the substituent(s) of the "$C_1$-$C_6$ alkyl group that may have one or more substituents," the "$C_1$-$C_6$ alkoxy group that may have one or more substituents," the "$C_1$-$C_6$ alkylamino group that may have one or more substituents," the "di$C_1$-$C_6$ alkylamino group that may have one or more substituents," and the "$C_3$-$C_8$ cycloalkyl group that may have one or more substituents" is preferably one or more halogen atoms, hydroxy groups, $C_1$-$C_6$ alkyl groups, $C_3$-$C_8$ cycloalkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or oxo groups.

$R^3$ more preferably each independently represents a $C_1$-$C_6$ alkyl group that may have one or more substituents.

$R^{3a}$ and $R^{3b}$ means a group present on a carbon atom constituting X when the above-mentioned X is a group derived from pyrimidine. $R^{3a}$ and $R^{3b}$ preferably each independently represent a substituent described as a preferred example of the above-mentioned $R^3$ or a hydrogen atom, more preferably a $C_1$-$C_6$ alkyl group, a halogeno $C_1$-$C_6$ alkyl group, or a hydrogen atom (namely, X is unsubstituted).

$R^4$ means a $C_1$-$C_6$ alkyl group that may have one or more substituents or a hydrogen atom. $R^4$ is a substituent present on a carbon atom constituting the morpholine ring in the general formula (1) and may be a substituent present on any carbon atom. Here, the one or more substituents of the "$C_1$-$C_6$ alkyl group that may have one or more substituents" is preferably one or more halogen atoms, hydroxy groups, $C_1$-$C_6$ alkyl groups, $C_3$-$C_8$ cycloalkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or oxo groups. $R^4$ is preferably a $C_1$-$C_6$ alkyl group or a hydrogen atom.

Ra represents a group represented by —Y—$R^5$, wherein Y represents a single bond or a $C_1$-$C_6$ alkylene group, $R^5$ represents a $C_1$-$C_6$ alkyl group that may have one or more substituents, a tetrahydrofuranyl group that may have one or more substituents, a tetrahydropyranyl group that may have one or more substituents, a pyrrolidinyl group that may have one or more substituents, a piperidinyl group that may have one or more substituents, or a pyridinyl group that may have one or more substituents.

Here, the one or more substituents of the "$C_1$-$C_6$ alkyl group that may have one or more substituents" is preferably one or more halogen atoms, hydroxy groups, $C_1$-$C_6$ alkyl groups, $C_3$-$C_8$ cycloalkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or oxo groups.

The substituent(s) of the "tetrahydrofuranyl group that may have one or more substituents," the "tetrahydropyranyl group that may have one or more substituents," and the "piperidinyl group that may have one or more substituents" is preferably one or more halogen atoms, hydroxy groups, $C_1$-$C_6$ alkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or $C_1$-$C_6$ alkylcarbonylamino groups. The substituent(s) of the "pyrrolidinyl group that may have one or more substituents" and the "pyridinyl group that may have one or more substituents" is preferably one or more halogen atoms, hydroxy groups, $C_1$-$C_6$ alkyl groups, $C_3$-$C_8$ cycloalkyl groups, $C_1$-$C_6$ alkylcarbonyl groups, $C_3$-$C_8$ cycloalkylcarbonyl groups, $C_3$-$C_8$ cycloalkyl $C_1$-$C_6$ alkylcarbonyl groups, $C_1$-$C_6$ alkylamino $C_1$-$C_6$ alkyl groups, $C_1$-$C_6$ alkylsulfonyl groups, or arylcarbonyl groups that may have one or more substituents.

Here, the substituent(s) of the "arylcarbonyl groups that may have one or more substituents" is preferably halogen atoms, hydroxy groups, $C_1$-$C_6$ alkyl groups, $C_3$-$C_8$ cycloalkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or oxo groups.

Ra is preferably a group in which Y is a single bond or a straight $C_1$-$C_3$ alkylene group and $R^5$ is a $C_1$-$C_6$ alkyl group, a $C_1$-$C_6$ alkyl group substituted with one or more halogen atoms, a $C_3$-$C_8$ cycloalkyl group, a tetrahydrofuranyl group, a pyrrolidinyl group that may have one or more substituents, or a tetrahydropyranyl group, and is preferably any one group selected from the following formulas $Ra_1$-$Ra_{11}$

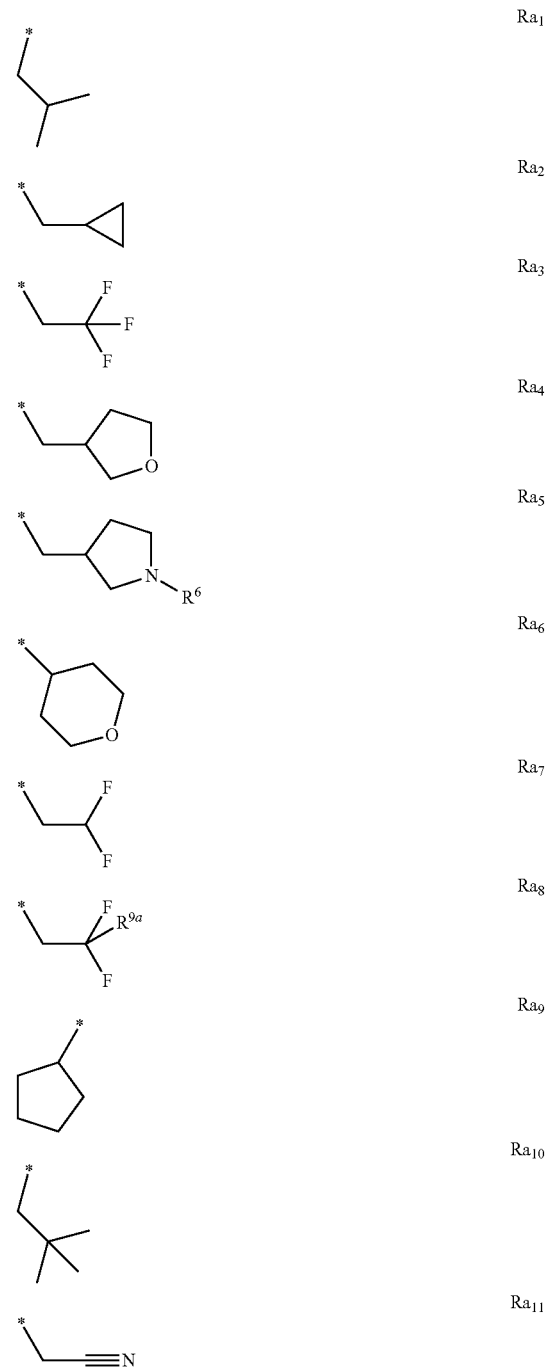

wherein, in the formula $Ra_5$, $R^6$ represents —$SO_2R^8$ or —$COR^8$, wherein $R^8$ represents a $C_1$-$C_6$ alkyl group that may have one or more substituents or an aryl group that may have one or more substituents, in the formula $Ra_8$, $R^{9a}$ represents a $C_1$-$C_6$ alkyl group, a $C_3$-$C_8$ cycloalkyl group, an amino $C_1$-$C_6$ alkyl group, a $C_1$-$C_6$ alkylamino $C_1$-$C_6$ alkyl group, a di$C_1$-$C_6$ alkylamino $C_1$-$C_6$ alkyl group, a hydroxy $C_1$-$C_6$ alkyl group, a carboxy $C_1$-$C_6$ alkyl group, an aryl group that may have one or more substituents selected from the above-mentioned Group A, or a heteroaryl group that may have one or more substituents selected from the above-mentioned Group A.

The substituent(s) of the "$C_1$-$C_6$ alkyl group that may have one or more substituents" and the "aryl group that may have one or more substituents" in $R^8$ is preferably one or more halogen atoms, hydroxy groups, $C_1$-$C_6$ alkyl groups, $C_3$-$C_8$ cycloalkyl groups, $C_1$-$C_6$ alkoxy groups, amino groups, $C_1$-$C_6$ alkylamino groups, di$C_1$-$C_6$ alkylamino groups, cyano groups, $C_1$-$C_6$ alkylamino $C_1$-$C_6$ alkyl groups, or oxo groups.

More preferably, Y in Ra represents a single bond, and $R^5$ in Ra represents a $C_1$-$C_6$ alkyl group, or a $C_1$-$C_6$ alkyl group substituted with halogen atom(s) or a $C_3$-$C_8$ cycloalkyl group.

$R^{9a}$ is preferably a methyl group, an ethyl group, a trifluoromethyl group, or a pentafluoroethyl group.

Rb and Rc each independently represent a $C_1$-$C_6$ alkyl group that may have one or more substituents or, a hydrogen atom, or Rb and Rc, together with a nitrogen atom to which Rb and Rc are bonded, may form a 4- to 7-membered alicyclic nitrogen-containing heterocyclic group that may have one or more substituents.

Here, the one or more substituents of the "$C_1$-$C_6$ alkyl group that may have one or more substituents" and the "when Rb and Rc, together with a nitrogen atom to which Rb and Rc are bonded, form a 4- to 7-membered alicyclic nitrogen-containing heterocyclic group that may have one or more substituents" are preferably one or more groups selected from halogen atoms, hydroxy groups, formyl groups, $C_1$-$C_6$ alkyl groups that may have one or more substituents selected from the above-mentioned Group A, $C_3$-$C_8$ cycloalkyl groups that may have one or more substituents selected from the above-mentioned Group A, $C_1$-$C_6$ alkoxy groups that may have one or more substituents selected from the above-mentioned Group A, amino groups, $C_1$-$C_6$ alkylamino groups that may have one or more substituents selected from the above-mentioned Group A, di$C_1$-$C_6$ alkylamino groups that may have one or more substituents selected from the above-mentioned Group A, $C_1$-$C_6$ alkylsulfonylamino groups that may have one or more substituents selected from the above-mentioned Group A, $C_1$-$C_6$ alkylsulfonyl $C_1$-$C_6$ alkylamino groups that may have one or more substituents selected from the above-mentioned Group A, arylsulfonylamino groups that may have one or more substituents selected from the above-mentioned Group A, arylsulfonyl $C_1$-$C_6$ alkylamino groups that may have one or more substituents selected from the above-mentioned Group A, heteroarylsulfonylamino groups that may have one or more substituents selected from the above-mentioned Group A, heteroarylsulfonyl $C_1$-$C_6$ alkylamino groups that may have one or more substituents selected from the above-mentioned Group A, a $C_1$-$C_6$ alkylsulfonylamino $C_1$-$C_6$ alkyl groups that may have one or more substituents selected from the above-mentioned Group A, $C_1$-$C_6$ alkylsulfonyl $C_1$-$C_6$ alkylamino $C_1$-$C_6$ alkyl groups that may have one or more substituents selected from the above-mentioned Group A, arylsulfonylamino $C_1$-$C_6$ alkyl groups that may have one or more substituents selected from the above-mentioned Group A, arylsulfonyl $C_1$-$C_6$ alkylamino $C_1$-$C_6$ alkyl groups that may have one or more substituents selected from the above-mentioned Group A, heteroarylsulfonylamino $C_1$-$C_6$ alkyl groups that may have one or more substituents selected from the above-mentioned Group A, heteroarylsulfonyl $C_1$-$C_6$ alkylamino $C_1$-$C_6$ alkyl groups that may have one or more substituents selected from the above-mentioned Group A, cyano groups, $C_1$-$C_6$ alkylamino $C_1$-$C_6$ alkyl group that may have one or more substituents selected from the above-mentioned Group A, oxo groups, $C_1$-$C_6$ alkylcarbonyl groups that may have one or more substituents selected from the above-mentioned Group A, $C_3$-$C_8$ cycloalkylcarbonyl groups that may have one or more substituents selected from the above-mentioned Group A, $C_3$-$C_8$ cycloalkyl $C_1$-$C_6$ alkylcarbonyl groups that may have one or more substituent selected from the above-mentioned Group A, $C_1$-$C_6$ alkylsulfonyl groups that may have one or more substituents selected from the above-mentioned Group A, $C_1$-$C_6$ alkylamino $C_1$-$C_6$ alkylcarbonyl groups that may have one or more substituents selected from the above-mentioned Group A, $C_1$-$C_6$ alkylaminocarbonyl groups that may have one or more substituents selected from the above-mentioned Group A, $C_1$-$C_6$ alkylamino $C_1$-$C_6$ alkylsulfonyl groups that may have one or more substituents selected from the above-mentioned Group A, di$C_1$-$C_6$ alkylamino $C_1$-$C_6$ alkylsulfonyl groups that may have one or more substituents selected from the above-mentioned Group A, $C_1$-$C_6$ alkylaminosulfonyl groups that may have one or more substituents selected from the above-mentioned Group A, di$C_1$-$C_6$ alkylaminosulfonyl groups that may have one or more substituents selected from the above-mentioned Group A, di$C_1$-$C_6$ alkylamino $C_1$-$C_6$ alkylcarbonyl groups that may have one or more substituents selected from the above-mentioned Group A, di$C_1$-$C_6$ alkylaminocarbonyl groups that may have one or more substituents selected from the above-mentioned Group A, arylsulfonyl group that may have one or more substituents selected from the above-mentioned Group A, heteroarylsulfonyl group that may have one or more substituents selected from the above-mentioned Group A, heteroaryl $C_1$-$C_6$ alkylsulfonyl group that may have one or more substituents selected from the above-mentioned Group A, heteroaryl $C_1$-$C_6$ alkylcarbonyl group that may have one or more substituents selected from the above-mentioned Group A, and groups represented by the following general formula (2):

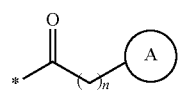

(2)

wherein n is any of 0 to 3, Ring A is any of an azetidine ring, a pyrrolidine ring, a pyridine ring, a morpholine ring, and a piperazine ring, and a carbon atom constituting the ring may have one or more substituents selected from the above-mentioned Group A.

When Rb and Rc, together with a nitrogen atom to which Rb and Rc are bonded, form a 4- to 7-membered alicyclic nitrogen-containing heterocyclic group that may have one or more substituents, the 4- to 7-membered alicyclic nitrogen-containing heterocyclic group moiety is preferably an azetidine ring, a pyrrolidine ring, a morpholine ring, a piperazine ring, or a piperidine ring.

Preferably, one of Rb and Rc is a $C_1$-$C_6$ alkyl group that may have one or more substituents and the other is a hydrogen atom, or Rb and Rc, together with a nitrogen atom to which Rb and Rc are bonded, form a 4- to 7-membered alicyclic nitrogen-containing heterocyclic group having one or more substituents, and Rb, Rc, and a group formed by Rb and Rc together with a nitrogen atom to which Rb and Rc are bonded are preferably any one selected from the following formulas Rbc1-Rbc80:

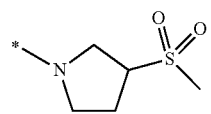

Rbc1

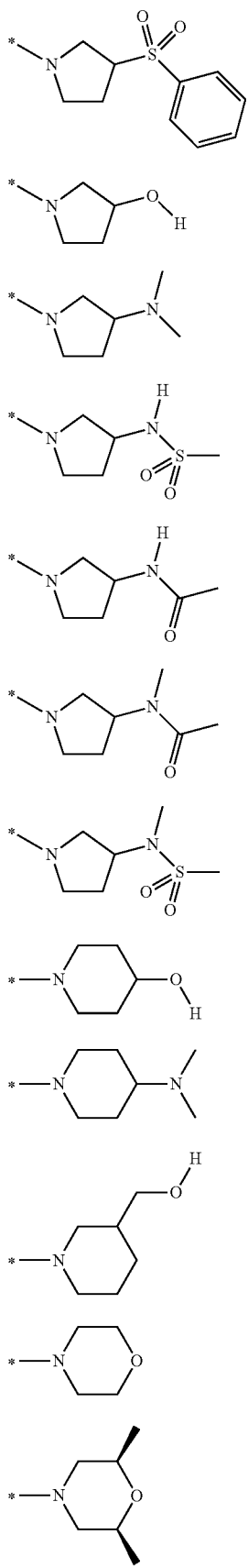
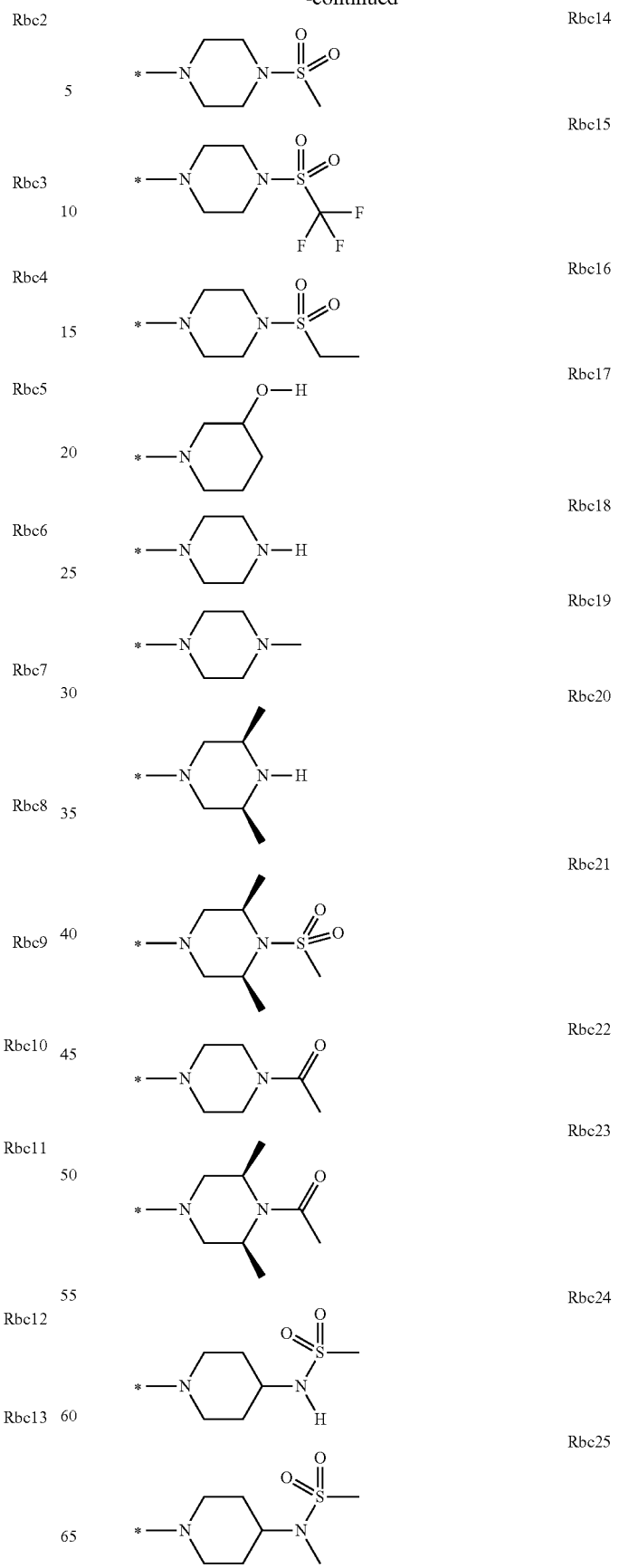

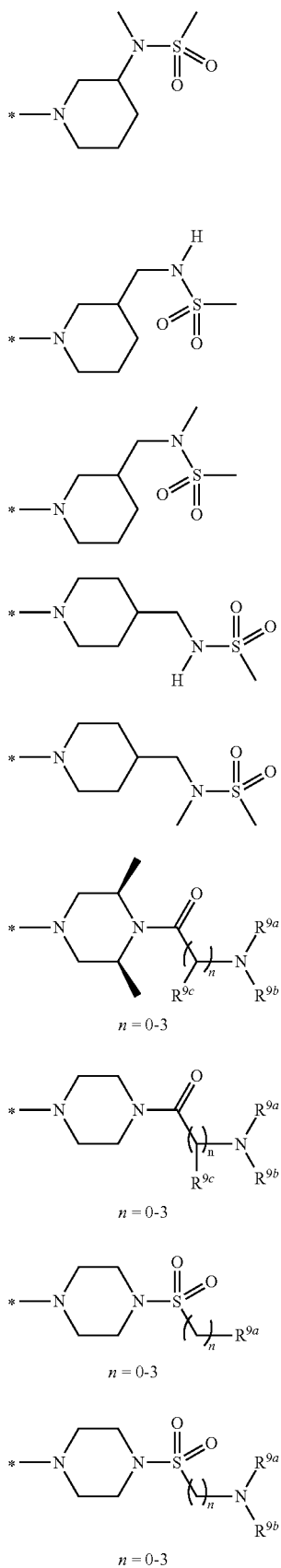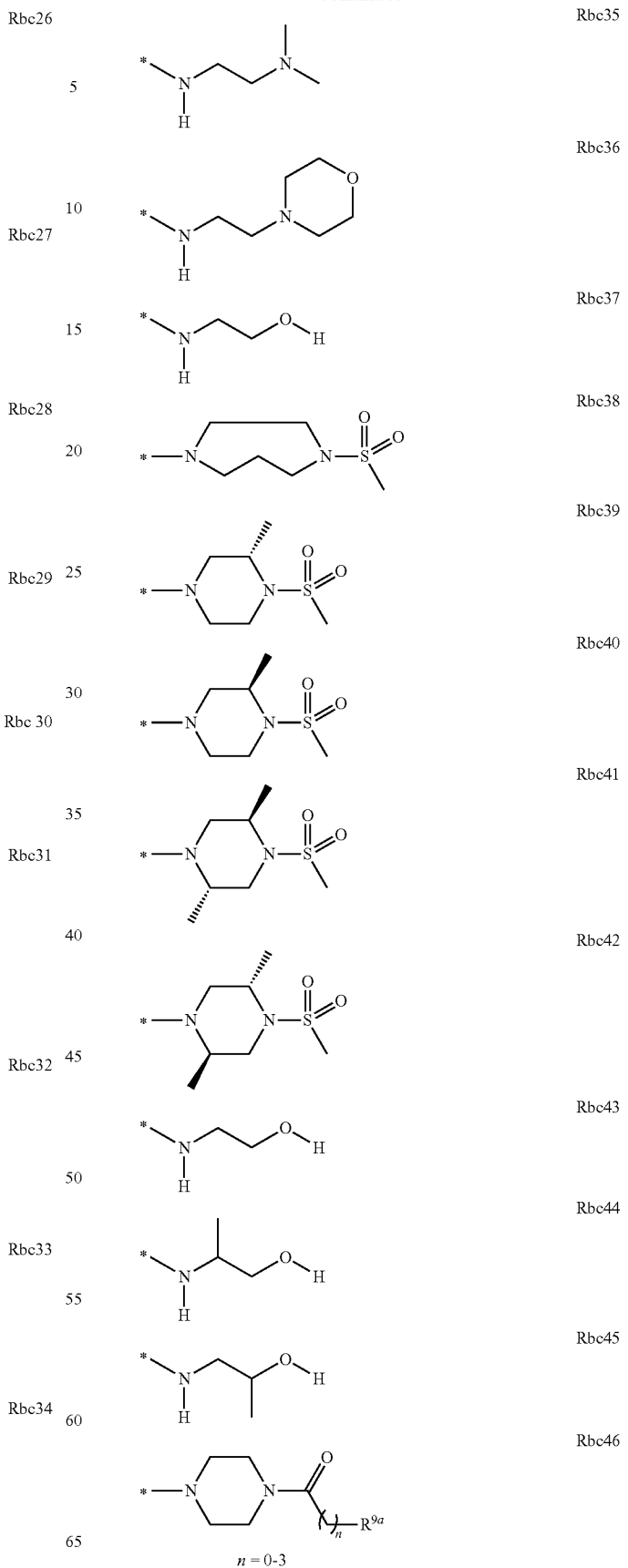

-continued
Rbc47 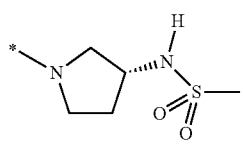
Rbc48 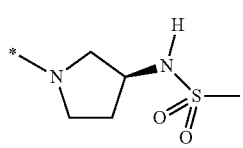
Rbc49 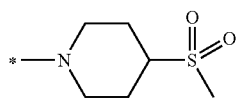
Rbc50 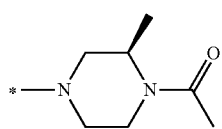
Rbc51 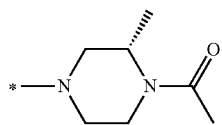
Rbc52 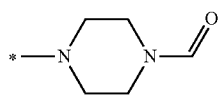
Rbc53 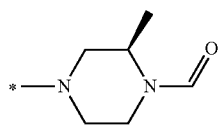
Rbc54 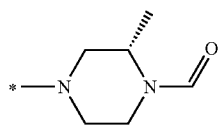
Rbc55 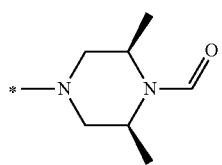
Rbc56 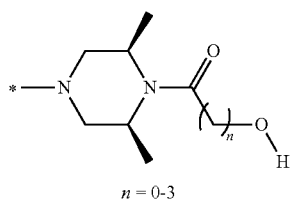
n = 0-3
-continued
Rbc57 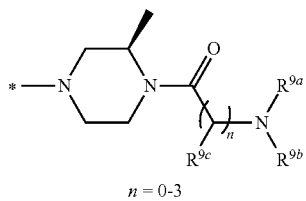
n = 0-3
Rbc58 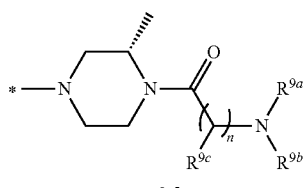
n = 0-3
Rbc59 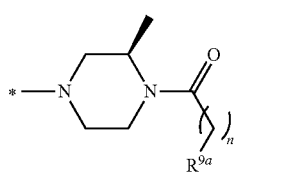
n = 0-3
Rbc60 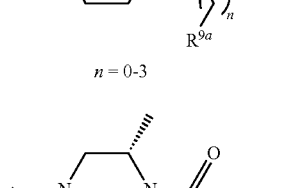
n = 0-3
Rbc61 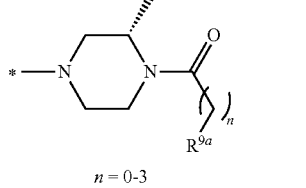
Rbc62 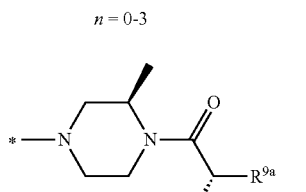
Rbc63 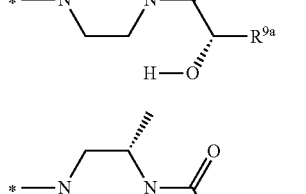
Rbc64 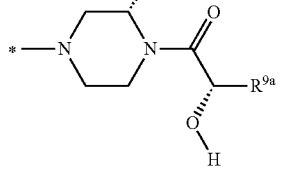

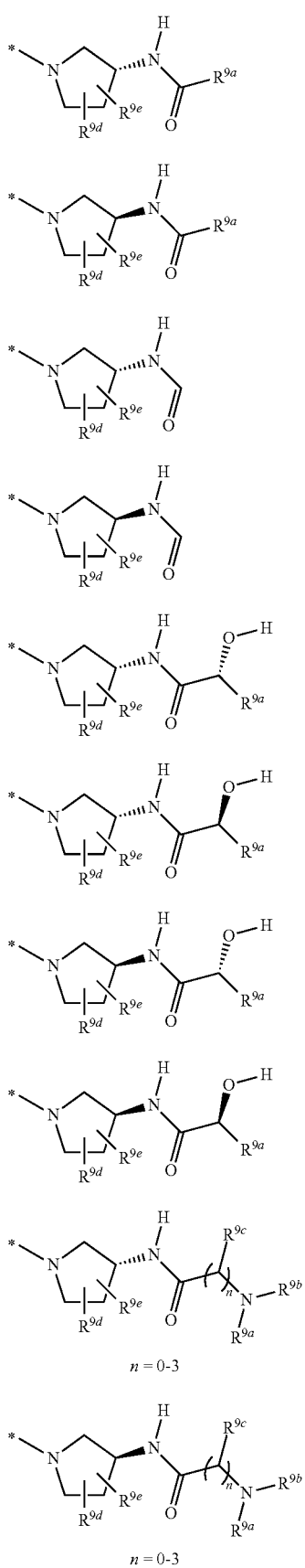
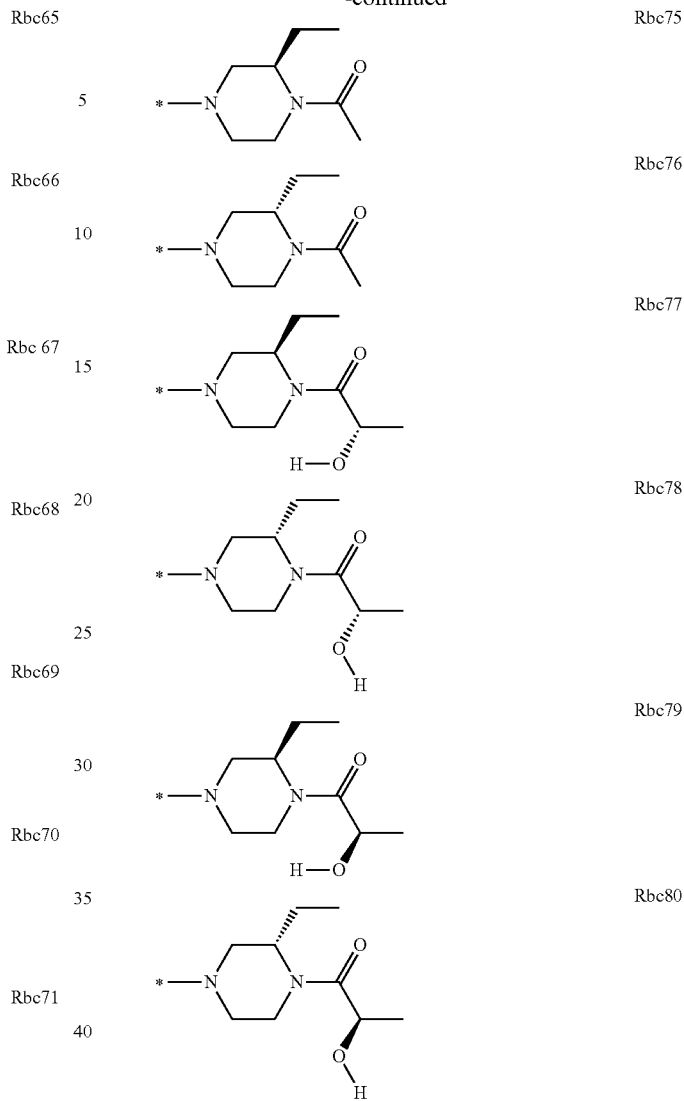

wherein, in the formula Rbc1 to Rbc80, $R^{9a}$, $R^{9b}$, $R^{9c}$, $R^{10}$, and $R^{11}$ each independently represent a $C_1$-$C_6$ alkyl group, a $C_3$-$C_8$ cycloalkyl group, an amino $C_1$-$C_6$ alkyl group, a $C_1$-$C_6$ alkylamino $C_1$-$C_6$ alkyl group, a di$C_1$-$C_6$ alkylamino $C_1$-$C_6$ alkyl group, a hydroxy $C_1$-$C_6$ alkyl group, a carboxy $C_1$-$C_6$ alkyl group, an aryl group that may have one or more substituents selected from the above-mentioned Group A, or a heteroaryl group that may have one or more substituents selected from the above-mentioned Group A, and $R^{9d}$ and $R^{9e}$ each independently represent a $C_1$-$C_6$ alkyl group, a $C_3$-$C_8$ cycloalkyl group, an amino $C_1$-$C_6$ alkyl group, a $C_1$-$C_6$ alkylamino $C_1$-$C_6$ alkyl group, a di$C_1$-$C_6$ alkylamino $C_1$-$C_6$ alkyl group, a hydroxy $C_1$-$C_6$ alkyl group, a carboxy $C_1$-$C_6$ alkyl group, an aryl group that may have one or more substituents selected from the above-mentioned Group A, a heteroaryl group that may have one or more substituents selected from the above-mentioned Group A, a hydrogen atom, a hydroxyl group, an amino group, a group represented by NH—$R^{10}$, or a group represented by $NR^{10}R^{11}$. Here, the substituent of the "aryl group that may have one or more substituents" and the "heteroaryl group that may have one or more substituents" is preferably a halogen atom, a hydroxy group, a $C_1$-$C_6$ alkyl group, a $C_3$-$C_8$ cycloalkyl group, a $C_1$-$C_6$ alkoxy group, an amino group, a $C_1$-$C_6$ alkylamino group, a di$C_1$-$C_6$ alkylamino group, a cyano group, a $C_1$-$C_6$ alkylamino$C_1$-$C_6$ alkyl group, or an oxo group.
More preferably, Rb and Rc form any one of an alicyclic nitrogen-containing heterocyclic group selected from the following formulas:
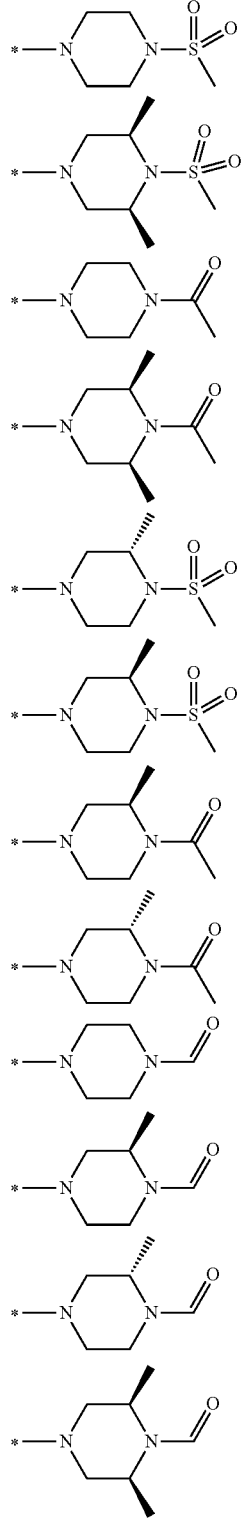
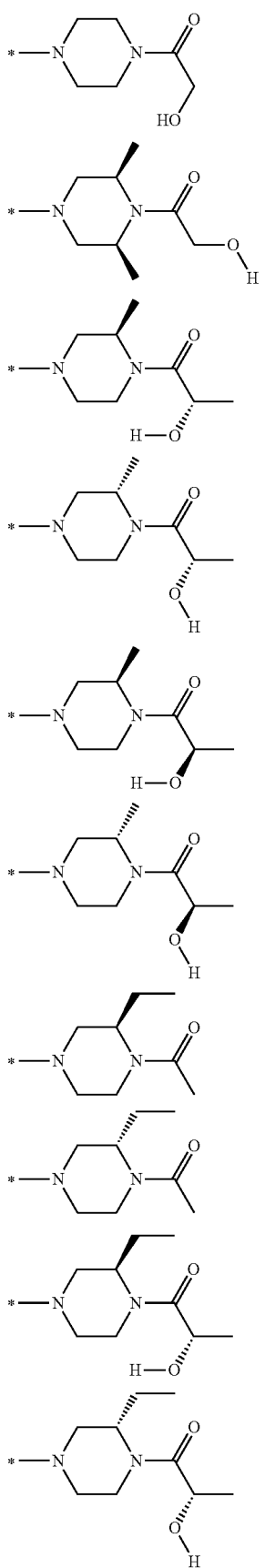

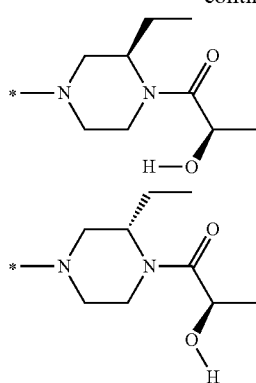
Furthermore, the compound of the general formula (1) is preferably any one of the compounds of Examples and/or Tables 1 to 18 described later or a salt thereof. Besides, the compound of the general formula (1) is preferably a compound being selected from the group consisting of:
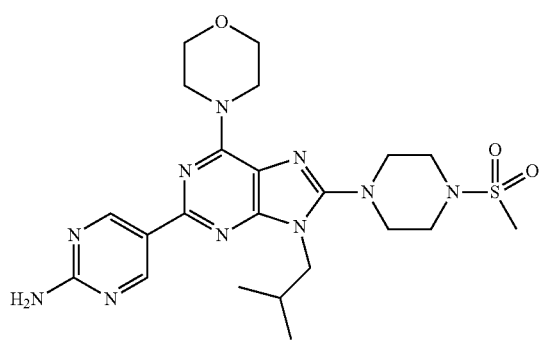
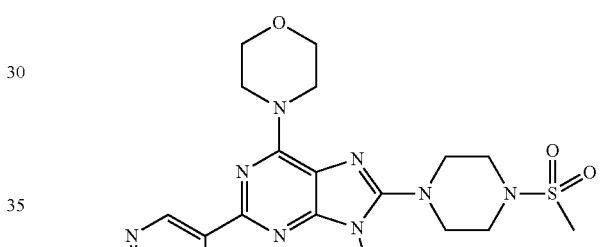
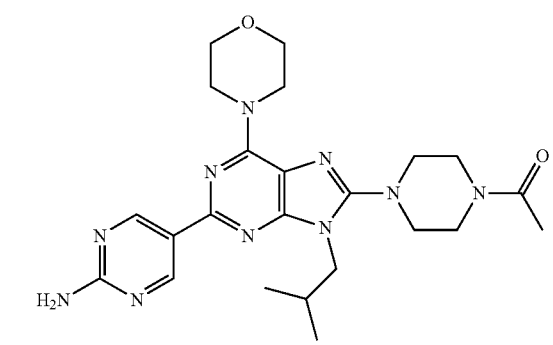
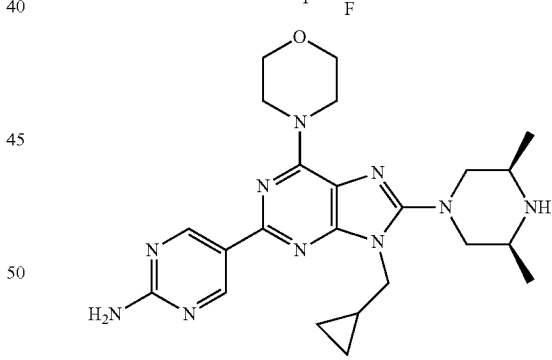
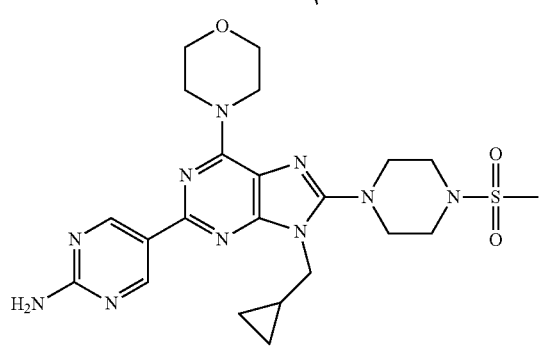

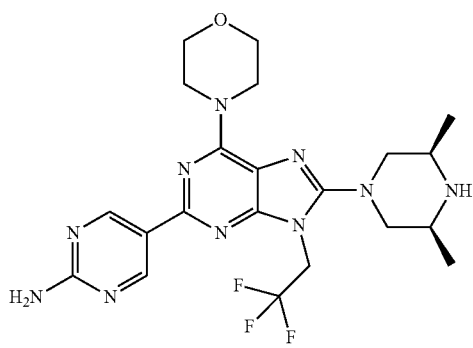
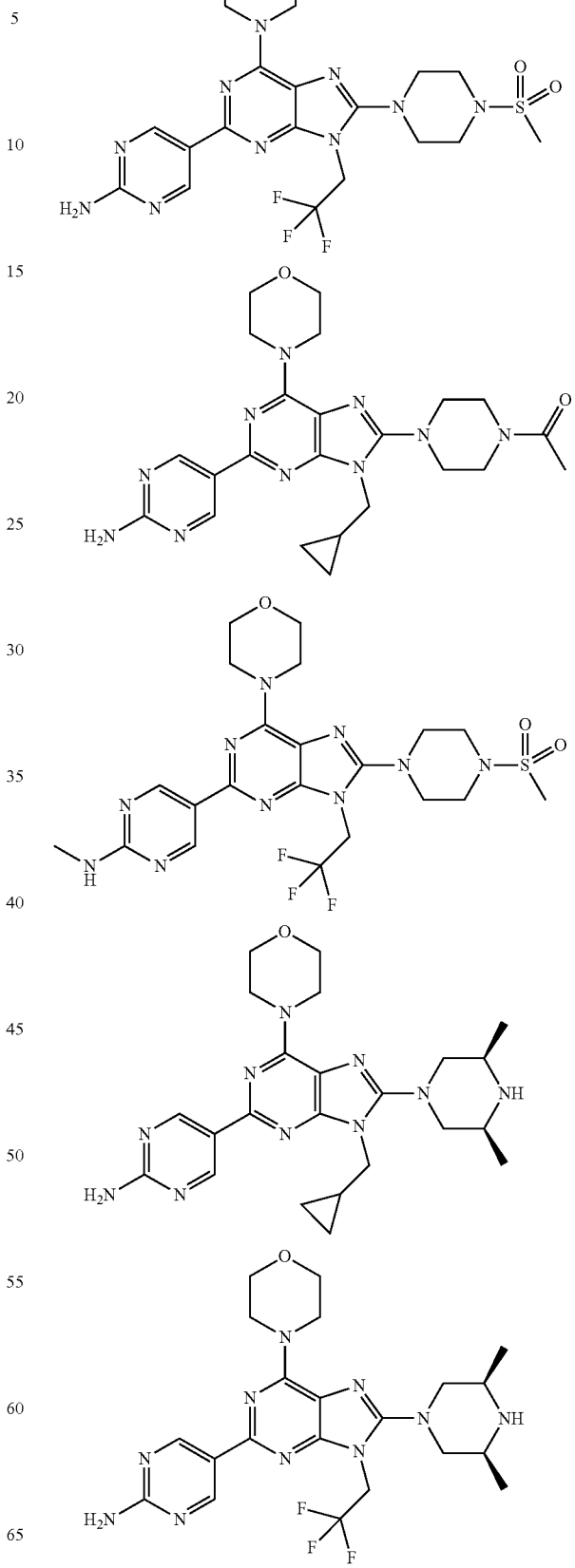

51
-continued
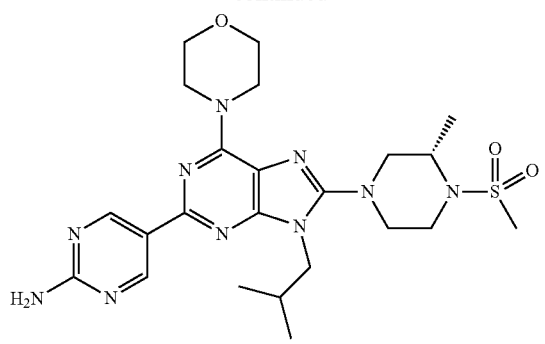
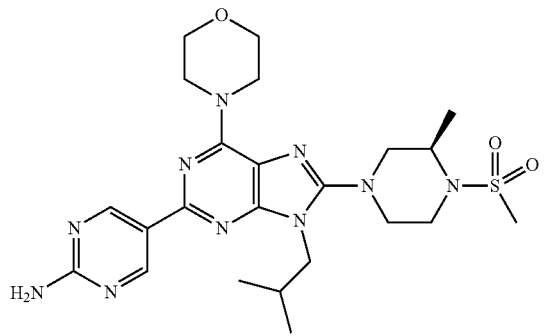
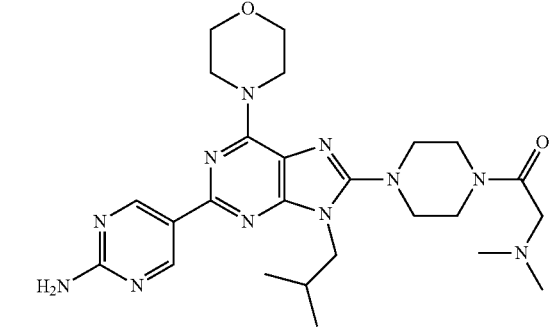
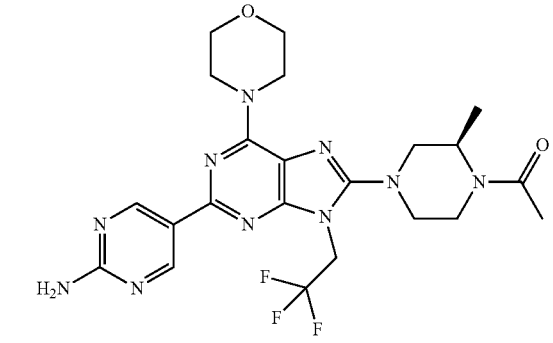
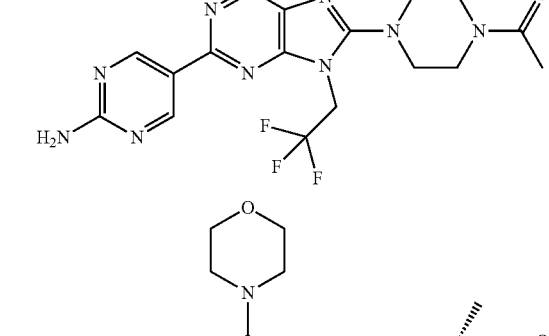
52
-continued
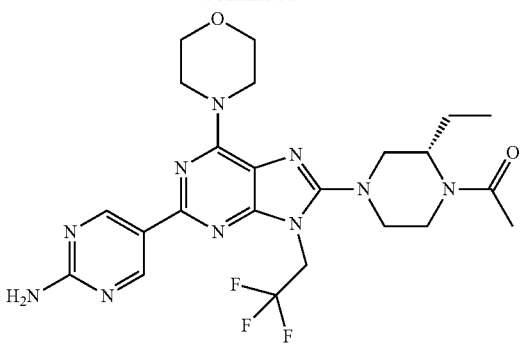
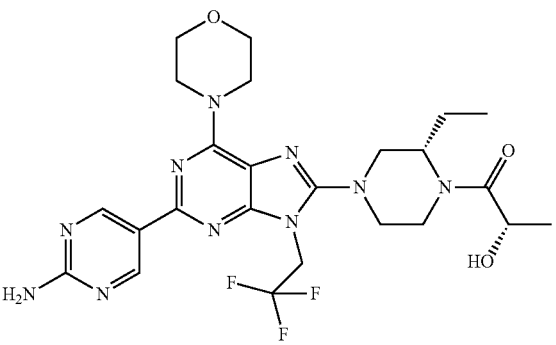
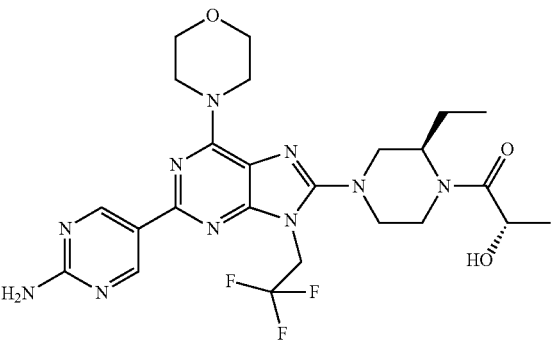
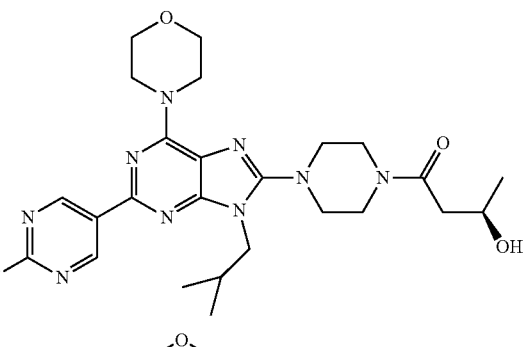
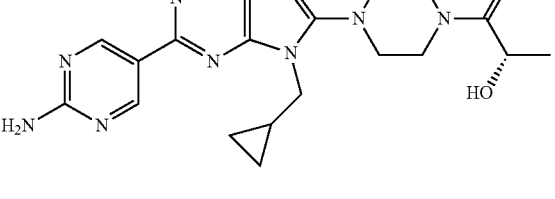

53 -continued
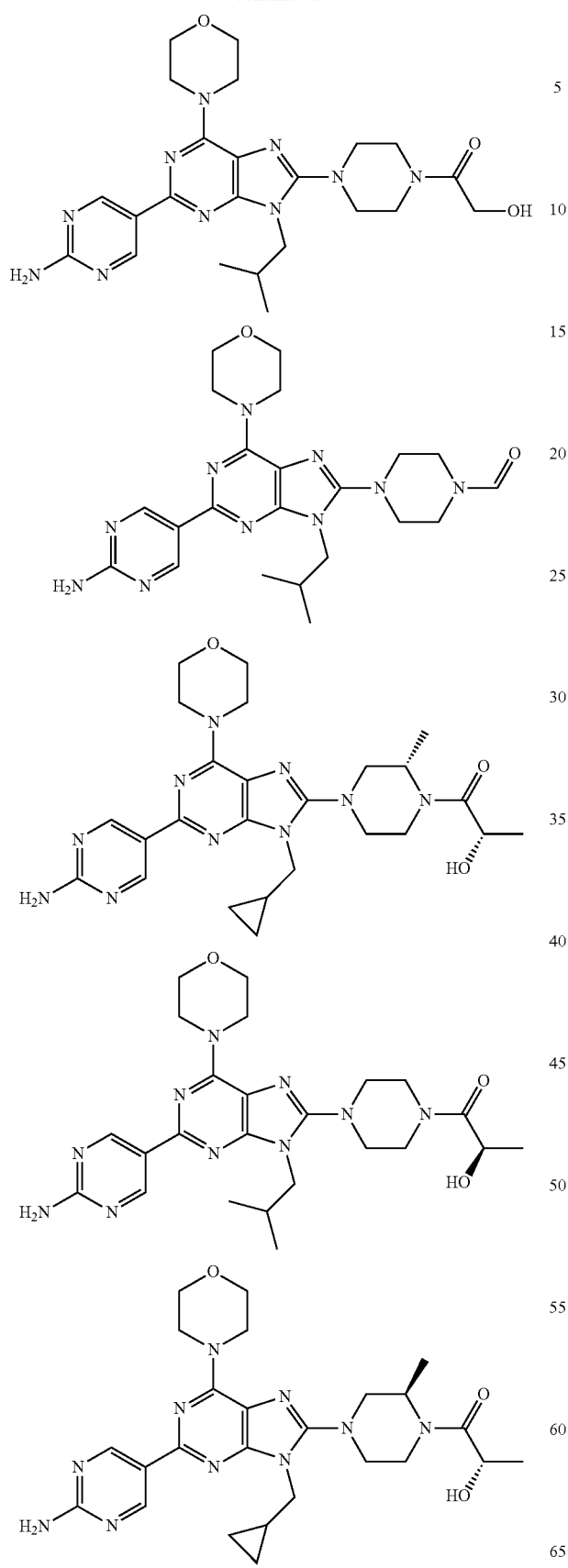
54 -continued
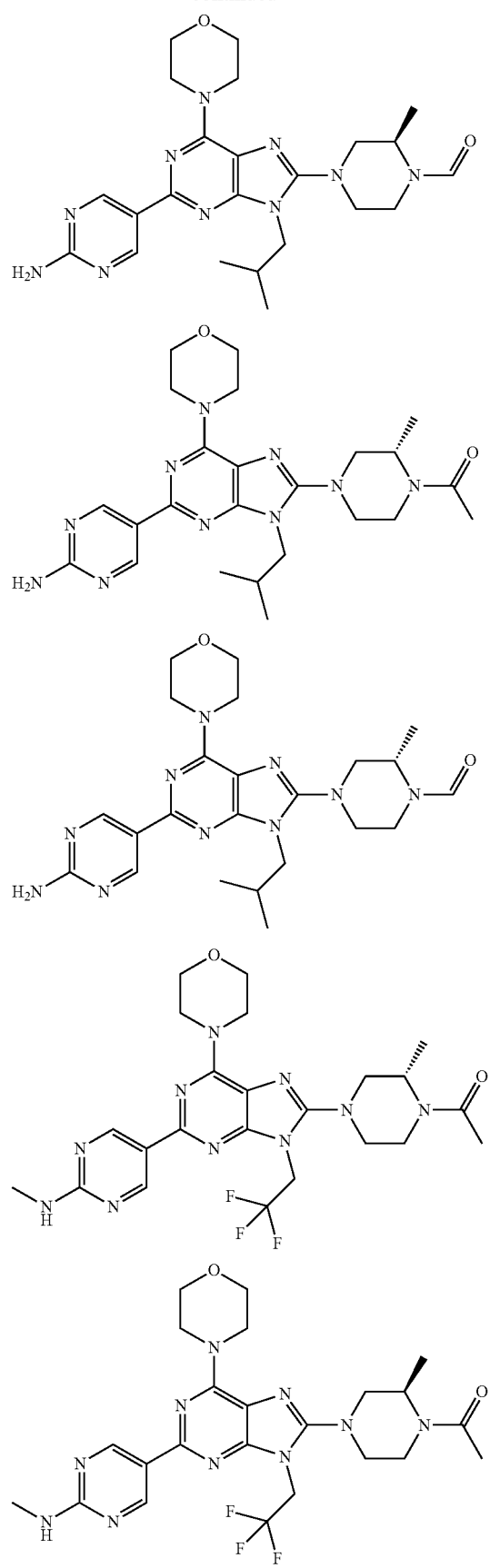

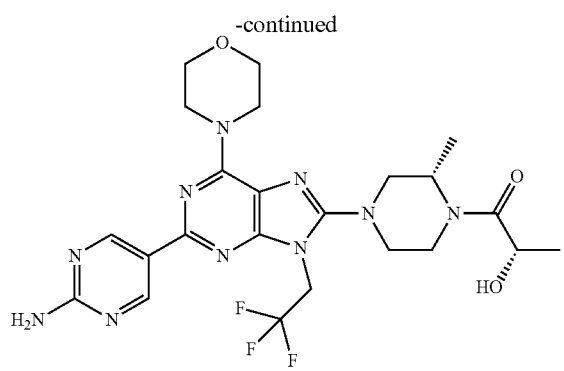
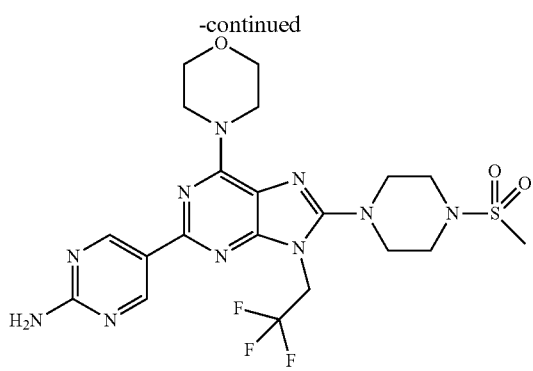
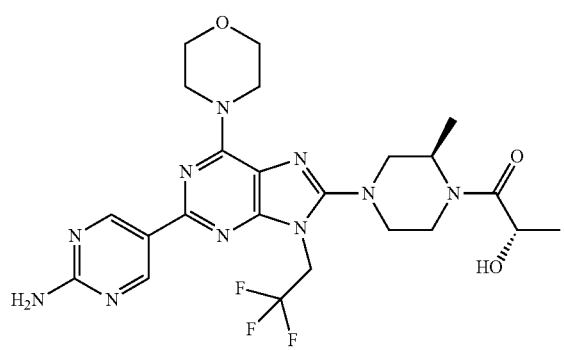
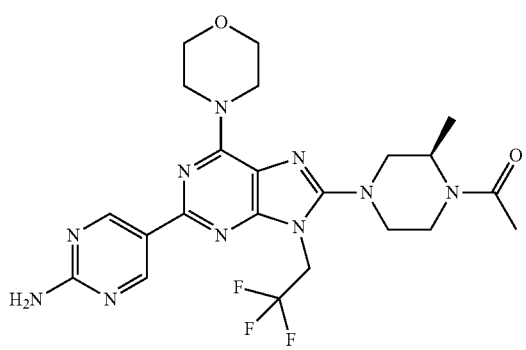
Furthermore, the compound of the general formula (1) is preferably a compound being selected from the group consisting of:
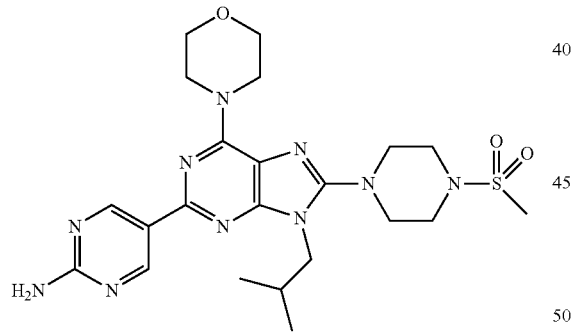
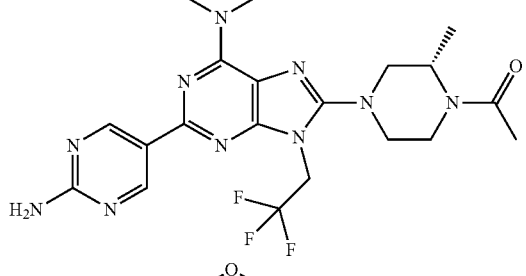
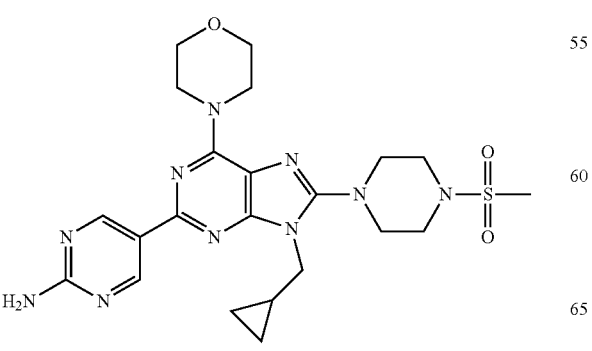
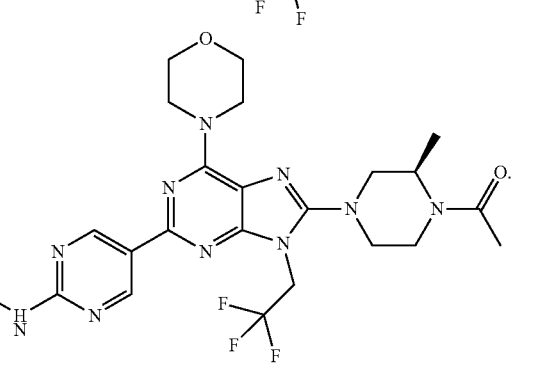

The compound represented by the general formula (1) of the present invention can be provided as a pharmaceutically acceptable salt as required. Examples of such a salt include hydrohalides such as hydrochlorides and hydroiodides, inorganic acid salts such as nitrates, perchlorates, sulfates, and phosphates, lower alkanesulfonates such as methanesulfonate, trifluoromethanesulfonates, and ethanesulfonates, arylsulfonates such as benzenesulfonates and p-toluenesulfonates, organic acid salts such as formates, acetates, malates, fumarates, succinates, citrates, tartrates, oxalates, and maleates, and amino acid salts such as ornithinates, glutamates, and aspartates. Of these, hydrohalides; lower alkanesulfonates such as methanesulfonate, trifruolo methanesulfonate and ethanesulfonate; arylsulfonates such as p-toluenesulfonate and benzenesulfonate; and sulfate are preferred.

Furthermore, when the compound represented by the general formula (1) of the present invention has an acidic group such as a carboxy group, a base addition salt can be formed in general. Examples of the pharmaceutically acceptable salt include alkali metal salts such as sodium salts, potassium salts, and lithium salts, alkaline earth metal salts such as calcium salts and magnesium salts, inorganic salts such as ammonium salts, and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts.

The compound represented by the general formula (1) of the present invention may exist as a free compound or a solvate. The solvate is not particularly limited so long as it is pharmaceutically acceptable, and specific preferred examples thereof include hydrates and ethanolates. Furthermore, when a nitrogen atom exists in the compound represented by the general formula (1) of the present invention, the solvate may be an N-oxide, and these solvates and N-oxides also fall within the scope of the present invention.

The compound represented by the general formula (1) of the present invention may have various isomers such as geometrical isomers having a cis or trans configuration and optical isomers such as tautomers and D- or L-isomers, depending on types and combinations of substituents. The compound of the present invention encompasses all these isomers, stereoisomers, and mixtures of these isomers and stereoisomers in any ratio unless otherwise specified.

The compound represented by the general formula (1) of the present invention may possess one or more isotope(s) on the atoms composing the general formula (1). The isotopes, for example, encompass deuterium ($^2$H), tritium ($^3$H), iodine-125 ($^{125}$I), carbon-14 ($^{14}$C), or carbon-13 ($^{13}$C). Those compounds are useful for the treatment of disease, the prevention of disease, the reagent such as an assay reagent for a research, and the diagnosis such as in vivo imaging. All the isotopic variations of the compound represented by the general formula (1) are included in this invention.

Furthermore, the present invention encompasses compounds converted to the compound (1), an active ingredient of the pharmaceutical composition of the present invention, by reactions mediated by enzymes, gastric acid, and the like under in vivo physiological conditions, specifically, compounds changed to the compound (1) due to enzymatic oxidation, reduction, hydrolysis, or the like and "pharmaceutically acceptable prodrug compounds" changed to compound (1) due to hydrolysis by gastric acid or the like.

When an amino group exists in the compound (1), examples of the above-mentioned prodrug include compounds containing the amino group subjected to acylation, alkylation, and phosphorylation (for example, compounds containing the amino group subjected to eicosanoylation, alanylation, pentylaminocarbonylation, (5 methyl-2-oxo-1,3-dioxolen-4-yl)methoxycarbonylation, tetrahydrofuranylation, pyrrolidylmethylation, and pivaloyloxymethylation, tert-butylation). When a hydroxyl group exists in the compound (1), examples thereof include compounds containing the hydroxyl group subjected to acylation, alkylation, phosphorylation, and boridation (for example, compounds containing the hydroxyl group subjected to acetylation, palmitoylation, propanoylation, pivaloylation, succinylation, fumarylation, alanylation, and dimethylaminomethylcarbonylation). Furthermore, when a carboxy group exists in the compound (1), examples the above-mentioned prodrug include compounds containing the carboxy group subjected to esterification and amidation (for example, compounds containing the carboxy group subjected to ethyl esterification, phenyl esterification, carboxymethyl esterification, dimethylaminomethyl esterification, pivaloyloxymethyl esterification, ethoxycarbonyloxyethyl esterification, amidation, and methylamidation).

The prodrug of the compound of the present invention can be produced from the compound (1) by a known method. Furthermore, the prodrug of the compound of the present invention also encompasses the compounds changed to the compound (1) under physiological conditions that are described in "Iyakuhin no Kaihatsu" (Development of Drugs) Vol. 7, Bunshi Sekkei (Molecular Design), pp. 163-198, 1990, Hirokawa Publishing Co.

Specific examples of the compound represented by the general formula (1) of the present invention include the compounds listed in the following Compound Tables 1 to 18. These compounds can be synthesized according to Production Method 1 or 2 described below or the methods described in the Examples. $R^1$, $R^2$, $R^{31}$, $R^{32}$, $R^4$, Ra, Rb, Rc, A, B, D, and E in Tables 1 to 18 mean groups represented in the following general formula (1b).

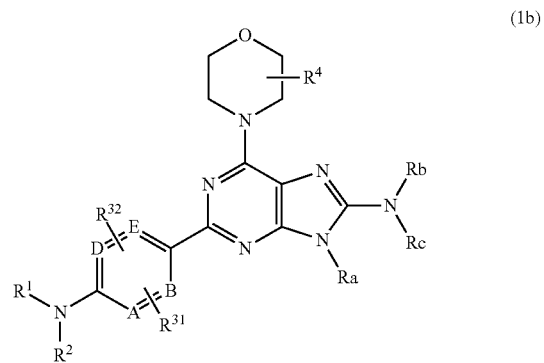

(1b)

TABLE 1
| | R¹ | R² | R³¹ | R³² | R⁴ | Ra | *—NRbRc | A | B | D | E |
|---|---|---|---|---|---|---|---|---|---|---|---|
| A1 | H | H | H | H | H | $CH_3$ | 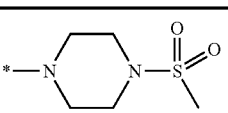 | N | C | N | C |
| A2 | H | H | H | H | H | $CH_2CH_3$ | 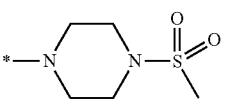 | N | C | N | C |
| A3 | H | H | H | H | H | $CH_2CH(CH_3)_2$ | 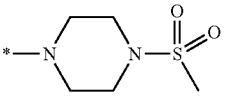 | N | C | N | C |
| A4 | H | H | H | H | H | $CH_2CH(CH_3)_2$ | 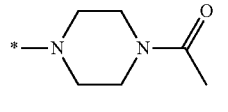 | N | C | N | C |
| A5 | H | H | H | H | H | $CH(CH_3)_2$ | 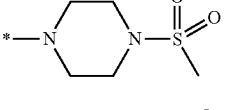 | N | C | N | C |
| A6 | H | H | H | H | H | $CH(CH_3)_2$ | 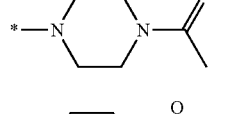 | N | C | N | C |
| A7 | H | H | H | H | H | 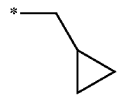 | 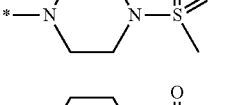 | N | C | N | C |
| A8 | $CH_3$ | H | H | H | H | 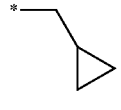 | 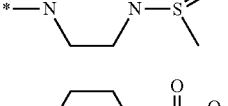 | N | C | N | C |
| A9 | H | H | H | H | H | 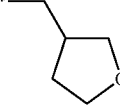 | 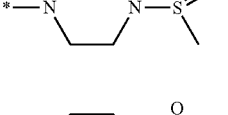 | N | C | N | C |
| A10 | H | H | 4-$CH_3$ | H | H | 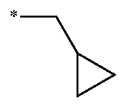 | 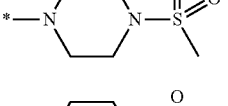 | N | C | N | C |
| A11 | H | H | 4-$CF_3$ | H | H | 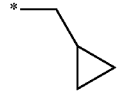 | 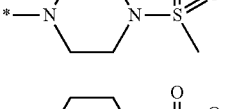 | N | C | N | C |
| A12 | H | H | H | H | 2-(R)—$CH_3$ | 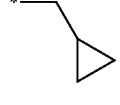 | 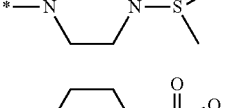 | N | C | N | C |
| A13 | H | H | H | H | 2-(S)—$CH_3$ | 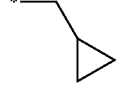 | 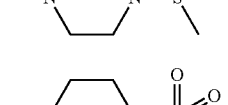 | N | C | N | C |
| A14 | H | H | H | H | H | $CH_2CF_3$ | 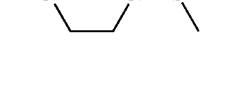 | N | C | N | C |

TABLE 1-continued

| | R¹ | R² | R³¹ | R³² | R⁴ | Ra | *—NRbRc | A | B | D | E |
|---|---|---|---|---|---|---|---|---|---|---|---|
| A15 | H | H | H | H | H | CH₂CF₃ | *-N(piperazine)N-C(=O)CH₃ | N | C | N | C |

TABLE 2

| | R¹ | R² | R³¹ | R³² | R⁴ | Ra | *—NRbRc | A | B | D | E |
|---|---|---|---|---|---|---|---|---|---|---|---|
| A16 | H | H | H | H | H | *-CH₂-cyclopropyl | *-N(piperazine)N-C(=O)CH₃ | N | C | N | C |
| A17 | CH₃ | H | H | H | H | CH₂CF₃ | *-N(piperazine)N-S(=O)₂CH₃ | N | C | N | C |
| A18 | H | H | H | H | 2-(R)—CH₃ | CH₂CF₃ | *-N(piperazine)N-S(=O)₂CH₃ | N | C | N | C |
| A19 | H | H | H | H | 2-(S)—CH₃ | CH₂CF₃ | *-N(piperazine)N-S(=O)₂CH₃ | N | C | N | C |
| A20 | CH₃ | H | H | H | H | CH₂CF₃ | *-N(piperazine)N-C(=O)CH₃ | N | C | N | C |
| A21 | H | H | 4-CH₃ | H | 2-(R)—CH₃ | *-CH₂-cyclopropyl | *-N(piperazine)N-S(=O)₂CH₃ | N | C | N | C |
| A22 | H | H | 4-CH₃ | H | 2-(S)—CH₃ | *-CH₂-cyclopropyl | *-N(piperazine)N-S(=O)₂CH₃ | N | C | N | C |
| A23 | H | H | H | H | H | *-CH₂-cyclopropyl | *-N(2,6-dimethylpiperazine)N—H | N | C | N | C |
| A24 | H | H | H | H | H | CH₂CF₃ | *-N(piperazine)N—CH₃ | N | C | N | C |
| A25 | H | H | H | H | H | CH₂CF₃ | *-N(2,6-dimethylpiperazine)N—H | N | C | N | C |

TABLE 2-continued

| | R¹ | R² | R³¹ | R³² | R⁴ | Ra | *—NRbRc | A | B | D | E |
|---|---|---|---|---|---|---|---|---|---|---|---|
| A26 | CH₃ | H | H | H | H | CH₂CF₃ | *—N⟨piperazine (2,6-dimethyl)⟩N—H | N | C | N | C |
| A27 | H | H | 4-CH₃ | H | H | *—CH₂-cyclopropyl | *—N⟨piperazine (2,6-dimethyl)⟩N—H | N | C | N | C |
| A28 | CH₃ | H | H | H | H | *—CH₂-cyclopropyl | *—N⟨piperazine (2,6-dimethyl)⟩N—H | N | C | N | C |
| A29 | H | H | H | H | H | *—CH₂-tetrahydrofuran-3-yl | *—N⟨piperazine (2,6-dimethyl)⟩N—H | N | C | N | C |
| A30 | CH₃ | H | H | H | H | *—CH₂-tetrahydrofuran-3-yl | *—N⟨piperazine (2,6-dimethyl)⟩N—H | N | C | N | C |

TABLE 3

| | R¹ | R² | R³¹ | R³² | R⁴ | Ra | *—NRbRc | A | B | D | E |
|---|---|---|---|---|---|---|---|---|---|---|---|
| A31 | H | H | 4-CH₃ | H | H | *—CH₂-tetrahydrofuran-3-yl | *—N⟨piperazine (2,6-dimethyl)⟩N—H | N | C | N | C |
| A32 | H | H | H | H | H | *—CH₂-cyclopropyl | *—N⟨piperazine⟩N—H | N | C | N | C |
| A33 | H | H | H | H | H | *—CH₂-cyclopropyl | *—N⟨morpholine⟩ | N | C | N | C |
| A34 | H | H | 4-CH₃ | H | H | *—CH₂-cyclopropyl | *—N(H)CH₂CH₂N(CH₃)₂ | N | C | N | C |

TABLE 3-continued

| | R¹ | R² | R³¹ | R³² | R⁴ | Ra | *—NRbRc | A | B | D | E |
|---|---|---|---|---|---|---|---|---|---|---|---|
| A35 | H | H | 4-CH₃ | H | H | *-CH₂-cyclopropyl | *-NH-CH₂CH₂-morpholine | N | C | N | C |
| A36 | CH₃ | H | 4-CH₃ | H | H | *-CH₂-cyclopropyl | *-N(piperazine)-S(O)₂CH₃ | N | C | N | C |
| A37 | CH₃ | CH₃ | 4-CH₃ | H | H | *-CH₂-cyclopropyl | *-N(piperazine)-S(O)₂CH₃ | N | C | N | C |
| A38 | H | H | H | H | H | *-CH₂-cyclopropyl | *-N(piperazine)-S(O)₂CH₃ | N | C | C | C |
| A39 | H | H | 4-CH₃ | H | H | *-CH₂-cyclopropyl | *-N(piperazine)-S(O)₂CH₃ | N | C | C | C |
| A40 | H | H | 4-CF₃ | H | H | *-CH₂-cyclopropyl | *-N(piperazine)-S(O)₂CH₃ | N | C | C | C |
| A41 | CH₃ | H | H | H | H | *-CH₂-cyclopropyl | *-N(piperazine)-S(O)₂CH₃ | N | C | C | C |
| A42 | H | H | 4-F | H | H | *-CH₂-cyclopropyl | *-N(piperazine)-S(O)₂CH₃ | N | C | N | C |
| A43 | H | H | 4-NH₂ | H | H | *-CH₂-cyclopropyl | *-N(piperazine)-S(O)₂CH₃ | N | C | N | C |
| A44 | H | H | 4-NHCH₃ | H | H | *-CH₂-cyclopropyl | *-N(piperazine)-S(O)₂CH₃ | N | C | N | C |
| A45 | H | H | 4-NCH₃CH₃ | H | H | *-CH₂-cyclopropyl | *-N(piperazine)-S(O)₂CH₃ | N | C | N | C |

TABLE 4
| | R¹ | R² | R³¹ | R³² | R⁴ | Ra | *—NRbRc | A | B | D | E |
|---|---|---|---|---|---|---|---|---|---|---|---|
| A46 | H | H | 4-OCH₃ | H | H |  | 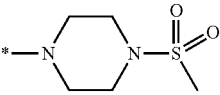 | N | C | N | C |
| A47 | H | H | H | H | H |  | 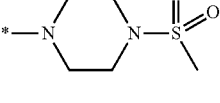 | N | N | C | C |
| A48 | H | H | H | H | H |  | 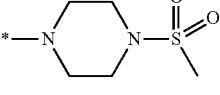 | N | C | C | N |
| A49 | H | H | H | H | H |  | 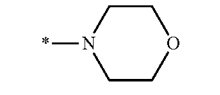 | N | C | C | C |
| A50 | H | H | H | H | H |  | 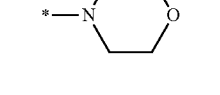 | N | C | N | C |
| A51 | CH₃ | H | H | H | H |  | 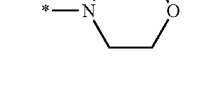 | N | C | N | C |
| A52 | CH₃ | H | H | H | H |  | 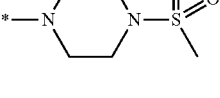 | N | C | N | C |
| A53 | H | H | H | H | H | 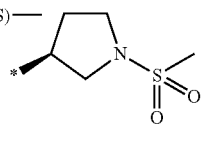 | 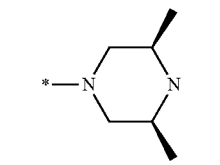 | N | C | N | C |
| A54 | H | H | H | H | H | 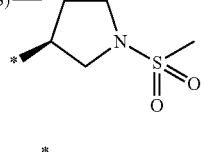 | 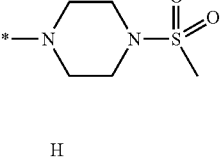 | N | C | N | C |
| A55 | H | H | H | H | H |  | 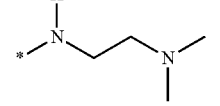 | N | C | N | C |
| A56 | | H | H | H | H |  | 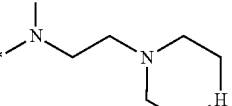 | N | C | N | C |
| A57 | H | H | H | H | H |  | 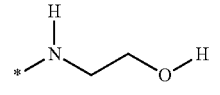 | N | C | N | C |

TABLE 4-continued
| | R¹ | R² | R³¹ | R³² | R⁴ | Ra | *—NRbRc | A | B | D | E |
|---|---|---|---|---|---|---|---|---|---|---|---|
| A58 | H | H | H | H | H | 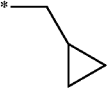 | 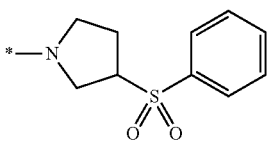 | N | C | N | C |
| A59 | H | H | 4-CH₃ | H | H |  | 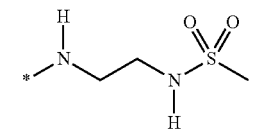 | N | C | N | C |
| A60 | H | H | 4-CH₃ | H | H |  | 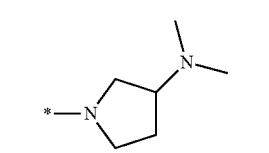 | N | C | N | C |
TABLE 5
| | R¹ | R² | R³¹ | R³² | R⁴ | Ra | *—NRbRc | A | B | D | E |
|---|---|---|---|---|---|---|---|---|---|---|---|
| A61 | H | H | 4-CH₃ | H | H |  | 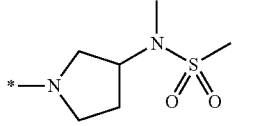 | N | C | N | C |
| A62 | H | H | 4-CH₃ | H | H |  | 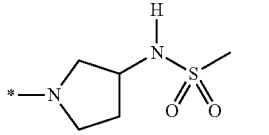 | N | C | N | C |
| A63 | H | H | 4-CH₃ | H | H |  | 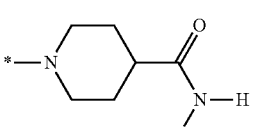 | N | C | N | C |
| A64 | H | H | 4-CH₃ | H | H |  | 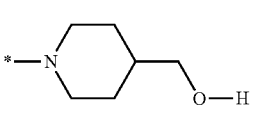 | N | C | N | C |
| A65 | H | H | H | H | H |  | 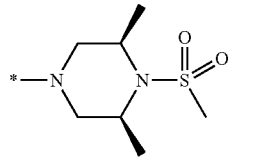 | N | C | N | C |
| A66 | CH₃ | H | H | H | H |  | 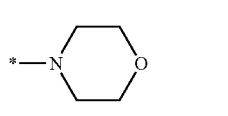 | N | C | N | C |
| A67 | H | H | H | H | H |  | 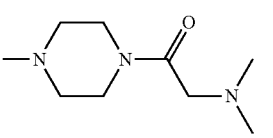 | N | C | N | C |

TABLE 5-continued
| | R¹ | R² | R³¹ | R³² | R⁴ | Ra | *—NRbRc | A | B | D | E |
|---|---|---|---|---|---|---|---|---|---|---|---|
| A68 | H | H | H | H | H | 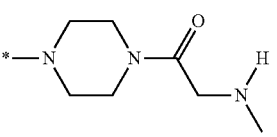 | 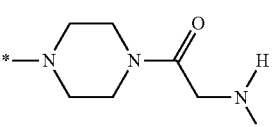 | N | C | N | C |
| A69 | H | H | H | H | H | 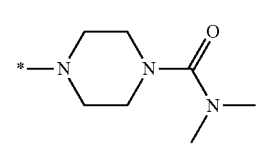 | 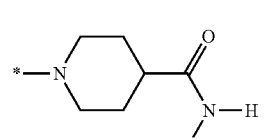 | N | C | N | C |
| A70 | H | H | H | H | H | 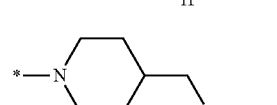 | 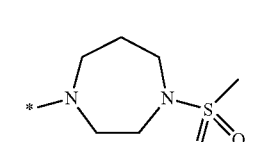 | N | C | N | C |
| A71 | H | H | 4-CH₃ | H | H | 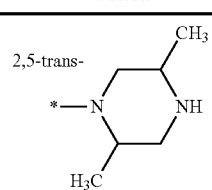 | 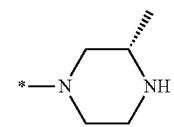 | N | C | N | C |
| A72 | H | H | 4-CH₃ | H | H | 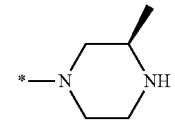 | 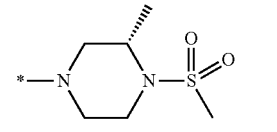 | N | C | N | C |
| A73 | H | H | H | H | H | CH₂CH(CH₃)₂ | | N | C | N | C |
TABLE 6
| | R¹ | R² | R³¹ | R³² | R⁴ | Ra | *—NRbRc | A | B | D | E |
|---|---|---|---|---|---|---|---|---|---|---|---|
| A74 | H | H | H | H | H | CH₂CH(CH₃)₂ | 2,5-trans- | N | C | N | C |
| A75 | H | H | H | H | H | CH₂CH(CH₃)₂ | | N | C | N | C |
| A76 | H | H | H | H | H | CH₂CH(CH₃)₂ | | N | C | N | C |
| A77 | H | H | H | H | H | CH₂CH(CH₃)₂ | | N | C | N | C |

TABLE 6-continued

| | R¹ | R² | R³¹ | R³² | R⁴ | Ra | *—NRbRc | A | B | D | E |
|---|---|---|---|---|---|---|---|---|---|---|---|
| A78 | H | H | H | H | H | CH₂CH(CH₃)₂ | (S)-3-methyl-4-(methylsulfonyl)piperazin-1-yl | N | C | N | C |
| A79 | H | H | H | H | H | CH₂CH(CH₃)₂ | 4-(2-(dimethylamino)acetyl)piperazin-1-yl | N | C | N | C |
| A80 | H | H | H | H | H | *—CH₂-cyclopropyl | 4-(2-(1H-imidazol-1-yl)acetyl)piperazin-1-yl | N | C | N | C |
| A81 | H | H | H | H | H | CH₂CH(CH₃)₂ | 4-((2-acetamido-4-methylthiazol-5-yl)sulfonyl)piperazin-1-yl | N | C | N | C |
| A82 | H | H | H | H | H | CH₂CF₃ | 4-((4-fluorophenyl)sulfonyl)piperazin-1-yl | N | C | N | C |
| A83 | H | H | H | H | H | *—CH₂-cyclopropyl | (S)-3-methyl-4-(methylsulfonyl)piperazin-1-yl | N | C | N | C |
| A84 | H | H | H | H | H | *—CH₂-cyclopropyl | (R)-3-methyl-4-(methylsulfonyl)piperazin-1-yl | N | C | N | C |

TABLE 7

| | R¹ | R² | R³¹ | R³² | R⁴ | Ra | *—NRbRc | A | B | D | E |
|---|---|---|---|---|---|---|---|---|---|---|---|
| A85 | H | H | H | H | 2-(R)—CH₃ | *—CH₂-cyclopropyl | (S)-3-methyl-4-(methylsulfonyl)piperazin-1-yl | N | C | N | C |

TABLE 7-continued

| | R¹ | R² | R³¹ | R³² | R⁴ | Ra | *—NRbRc | A | B | D | E |
|---|---|---|---|---|---|---|---|---|---|---|---|
| A86 | H | H | H | H | 2-(S)—CH₃ | *-cyclopropylmethyl | *-N(piperazinyl, 3-methyl)-N-S(O)₂CH₃ | N | C | N | C |
| A87 | H | H | H | H | 2-(R)—CH₃ | *-cyclopropylmethyl | *-N(piperazinyl, 3-methyl)-N-S(O)₂CH₃ | N | C | N | C |
| A88 | H | H | H | H | 2-(S)—CH₃ | *-cyclopropylmethyl | *-N(piperazinyl, 3-methyl)-N-S(O)₂CH₃ | N | C | N | C |
| A89 | H | H | H | H | H | CH₂CF₃ | *-N(CH₃)CH₂CH(CH₃)-N-S(O)₂CH₃ | N | C | N | C |
| A90 | H | H | H | H | H | CH₂CF₃ | *-N(piperazinyl, 3-methyl)-N-S(O)₂CH₃ | N | C | N | C |
| A91 | H | H | H | H | 2-(R)—CH₃ | CH₂CF₃ | *-N(piperazinyl, 3-methyl)-N-S(O)₂CH₃ | N | C | N | C |
| A92 | H | H | H | H | 2-(S)—CH₃ | CH₂CF₃ | *-N(piperazinyl, 3-methyl)-N-S(O)₂CH₃ | N | C | N | C |
| A93 | H | H | H | H | 2-(R)—CH₃ | CH₂CF₃ | *-N(piperazinyl, 3-methyl)-N-S(O)₂CH₃ | N | C | N | C |
| A94 | H | H | H | H | 2-(S)—CH₃ | CH₂CF₃ | *-N(piperazinyl, 3-methyl)-N-S(O)₂CH₃ | N | C | N | C |
| A95 | H | H | H | H | 2-(R)—CH₃ | CH₂CH(CH₃)₂ | *-N(piperazinyl, 3-methyl)-N-S(O)₂CH₃ | N | C | N | C |
| A96 | H | H | H | H | 2-(S)—CH₃ | CH₂CH(CH₃)₂ | *-N(piperazinyl, 3-methyl)-N-S(O)₂CH₃ | N | C | N | C |

TABLE 8

| | R¹ | R² | R³¹ | R³² | R⁴ | Ra | *—NRbRc | A | B | D | E |
|---|---|---|---|---|---|---|---|---|---|---|---|
| A97 | H | H | H | H | 2-(R)—CH₃ | CH₂CH(CH₃)₂ | | N | C | N | C |
| A98 | H | H | H | H | 2-(S)—CH₃ | CH₂CH(CH₃)₂ | | N | C | N | C |
| A99 | H | H | H | H | H | CH₂CF₂ | 2,5-trans- | N | C | N | C |
| A100 | H | H | H | H | H | CH₂CH(CH₃)₂ | 2,5-trans- | N | C | N | C |
| A101 | H | H | 4-CH₃ | H | H | * cyclopropyl-CH₂ | | N | C | N | C |
| A102 | H | H | 4-CH₃ | H | H | * cyclopropyl-CH₂ | | N | C | N | C |
| A103 | H | H | 4-CH₃ | H | 2-(R)—CH₃ | * cyclopropyl-CH₂ | | N | C | N | C |
| A104 | H | H | 4-CH₃ | H | 2-(S)—CH₃ | * cyclopropyl-CH₂ | | N | C | N | C |
| A105 | H | H | 4-CH₃ | H | 2-(R)—CH₃ | * cyclopropyl-CH₂ | | N | C | N | C |
| A106 | H | H | 4-CH₃ | H | 2-(S)—CH₃ | * cyclopropyl-CH₂ | | N | C | N | C |

TABLE 8-continued

| | $R^1$ | $R^2$ | $R^{31}$ | $R^{32}$ | $R^4$ | Ra | *—NRbRc | A | B | D | E |
|---|---|---|---|---|---|---|---|---|---|---|---|
| A107 | H | H | H | H | 2-(R)—CH$_3$ | CH$_2$CF$_3$ | 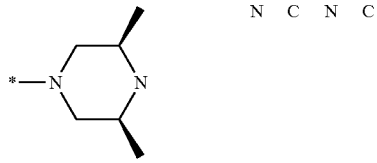 | N | C | N | C |

TABLE 9

| | $R^1$ | $R^2$ | $R^{31}$ | $R^{32}$ | $R^4$ | Ra | *—NRbRc | A | B | D | E |
|---|---|---|---|---|---|---|---|---|---|---|---|
| A108 | H | H | H | H | 2-(S)—CH$_3$ | CH$_2$CF$_3$ | | N | C | N | C |
| A109 | H | H | H | H | 2-(R)—CH$_3$ | CH$_2$CF$_3$ | | N | C | N | C |
| A110 | H | H | H | H | 2-(S)—CH$_3$ | CH$_2$CF$_3$ | | N | C | N | C |
| A111 | H | H | 4-CH$_3$ | H | H | CH$_2$CF$_3$ | | N | C | N | C |
| A112 | H | H | 4-CH$_3$ | H | H | CH$_2$CF$_3$ | | N | C | N | C |
| A113 | H | H | 4-CH$_3$ | H | H | CH$_2$CF$_3$ | | N | C | N | C |
| A114 | H | H | 4-CH$_3$ | H | H | CH$_2$CF$_3$ | | N | C | N | C |
| A115 | H | H | 4-CH$_3$ | H | H | CH$_2$CF$_3$ | | N | C | N | C |
| A116 | H | H | 4-CH$_3$ | H | H | CH$_2$CF$_3$ | | N | C | N | C |
| A117 | H | H | H | H | H | CH2cBu | | N | C | N | C |

TABLE 9-continued
| | R¹ | R² | R³¹ | R³² | R⁴ | Ra | *—NRbRc | A | B | D | E |
|---|---|---|---|---|---|---|---|---|---|---|---|
| A118 | CH₃ | H | H | H | H | CH2cBu | 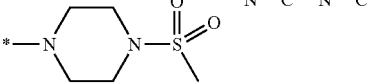 | N | C | N | C |
| A119 | H | H | H | H | H | CH2cBu |  | N | C | N | C |
| A120 | CH₃ | H | H | H | H | CH2cBu |  | N | C | N | C |
| A121 | H | H | H | H | H | CH2cBu | 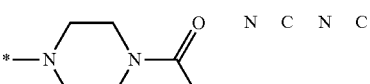 | N | C | N | C |
TABLE 10
| | R¹ | R² | R³¹ | R³² | R⁴ | Ra | *—NRbRc | A | B | D | E |
|---|---|---|---|---|---|---|---|---|---|---|---|
| A122 | CH3 | H | H | H | H | CH2cBu | 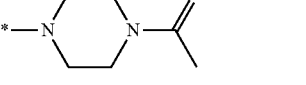 | N | C | N | C |
| A123 | H | H | 4-CH₃ | H | H | CH2cBu | 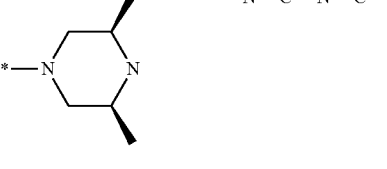 | N | C | N | C |
| A124 | H | H | 4-CH₃ | H | H | CH2cBu | 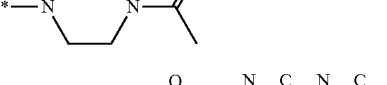 | N | C | N | C |
| A125 | H | H | 4-CH₃ | H | H | CH2cBu |  | N | C | N | C |
| A126 | H | H | 4-CH₃ | H | H | CH2cBu | 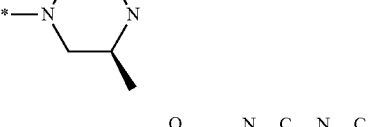 | N | C | N | C |
| A127 | CH3 | H | H | H | H | CH₂CH(CH₃)₂ | 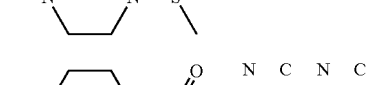 | N | C | N | C |
| A128 | CH3 | H | H | H | H | CH₂CH(CH₃)₂ | 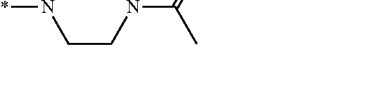 | N | C | N | C |

TABLE 10-continued
| | R¹ | R² | R³¹ | R³² | R⁴ | Ra | *—NRbRc | A | B | D | E |
|---|---|---|---|---|---|---|---|---|---|---|---|
| A129 | CH3 | H | H | H | H | CH₂CH(CH₃)₂ | 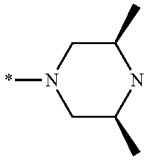 | N | C | N | C |
| A130 | H | H | 4-CH₃ | H | H | CH₂CH(CH₃)₂ | 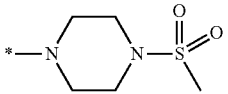 | N | C | N | C |
| A131 | H | H | 4-CH₃ | H | H | CH₂CH(CH₃)₂ | 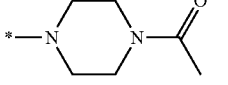 | N | C | N | C |
| A132 | H | H | 4-CH₃ | H | H | CH₂CH(CH₃)₂ | 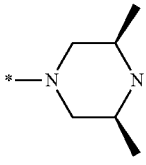 | N | C | N | C |
| A133 | H | H | H | H | H | CH₂C(CH₃)₂ | 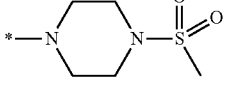 | N | C | N | C |
TABLE 11
| | R¹ | R² | R³¹ | R³² | R⁴ | Ra | *—NRbRc | A | B | D | E |
|---|---|---|---|---|---|---|---|---|---|---|---|
| A134 | H | H | H | H | H | CH₂C(CH₃)₂ | 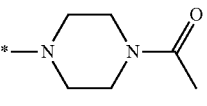 | N | C | N | C |
| A135 | H | H | H | H | H | CH₂C(CH₃)₂ | 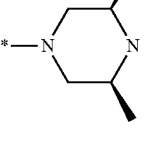 | N | C | N | C |
| A136 | H | H | H | H | H | * 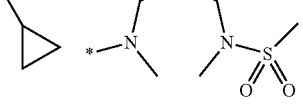 | 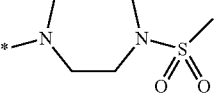 | N | C | N | C |
| A137 | H | H | H | H | H | CH₂C(CH₃)₂ | 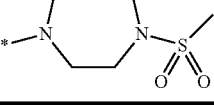 | N | C | N | C |
| A138 | H | H | H | H | H | CH₂CF₃ | | N | C | N | C |

TABLE 12

| | R¹ | R² | R³¹ | R³² | R⁴ | Ra | *—NRbRc | A | B | D | E |
|---|---|---|---|---|---|---|---|---|---|---|---|
| A139 | H | H | H | H | H | CH₂CF₃ | *-N(piperidine)-S(=O)₂-CH₃ | N | C | N | C |
| A140 | H | H | H | H | H | CH₂CF₃ | *-N(piperazine, 2-methyl)-NH | N | C | N | C |
| A141 | H | H | H | H | H | CH₂CF₃ | *-N(piperazine, 2-methyl)-NH | N | C | N | C |
| A142 | H | H | H | H | H | CH₂CF₃ | *-N(piperazine, 2-methyl)-N-C(=O)CH₃ | N | C | N | C |
| A143 | H | H | H | H | H | CH₂CF₃ | *-N(piperazine, 2-methyl)-N-S(=O)₂CH₃ | N | C | N | C |
| A144 | H | H | H | H | H | CH₂CF₃ | *-N(piperazine, 2-methyl)-N-S(=O)₂CH₃ | N | C | N | C |
| A145 | H | H | H | H | H | CH₂CF₃ | *-N(piperazine, 2-methyl)-N-C(=O)CH₃ | N | C | N | C |
| A146 | H | H | H | H | H | CH₂CHF₂ | *-N(piperazine)-N-S(=O)₂CH₃ | N | C | N | C |
| A147 | H | H | H | H | H | CH₂CF₃ | *-N(piperazine)-N-C(=O)C(=O)CH₃ | N | C | N | C |
| A148 | H | H | H | H | H | CH₂CF₃ | *-N(piperazine)-N-C(=O)C(=O)N(CH₃)₂ | N | C | N | C |
| A149 | H | H | H | H | H | CH₂CF₃ | *-N(piperazine)-N-C(=O)CH₂OH | N | C | N | C |

TABLE 12-continued

| | R¹ | R² | R³¹ | R³² | R⁴ | Ra | *—NRbRc | A | B | D | E |
|---|---|---|---|---|---|---|---|---|---|---|---|
| A150 | H | H | H | H | H | CH₂CF₃ | (piperazine-C(O)-CH(OH)CH₃) | N | C | N | C |

TABLE 13

| | R¹ | R² | R³¹ | R³² | R⁴ | Ra | *—NRbRc | A | B | D | E |
|---|---|---|---|---|---|---|---|---|---|---|---|
| A151 | H | H | H | H | H | CH₂CF₃ | (piperazine-C(O)-CH₂-CH(OH)CH₃) | N | C | N | C |
| A152 | H | H | H | H | H | CH₂CF₃ | (piperazine-C(O)-CH₂-CH(OH)CH₃) | N | C | N | C |
| A153 | H | H | H | H | H | CH₂CF₃ | (piperazine-CHO) | N | C | N | C |
| A154 | H | H | 4-CH₃ | H | H | *-CH₂-cyclopropyl | (pyrrolidine-NHSO₂CH₃) | N | C | N | C |
| A155 | H | H | H | H | H | *-CH₂-cyclopropyl | (pyrrolidine-NHSO₂CH₃) | N | C | N | C |
| A156 | H | H | H | H | H | CH₂CF₃ | (N(CH₃)-CH₂-CH(Et)-NHCH₃) | N | C | N | C |
| A157 | H | H | H | H | H | CH₂CF₃ | (2-Et-piperazine-C(O)CH₃) | N | C | N | C |
| A158 | H | H | H | H | H | CH₂CF₃ | (2-Et-piperazine-SO₂CH₃) | N | C | N | C |
| A159 | H | H | H | H | H | CH₂CF₃ | (2-Et-piperazine-C(O)-CH(OH)CH₃) | N | C | N | C |

TABLE 13-continued
| | R¹ | R² | R³¹ | R³² | R⁴ | Ra | *—NRbRc | A | B | D | E |
|---|---|---|---|---|---|---|---|---|---|---|---|
| A160 | H | H | H | H | H | CH₂CF₃ | 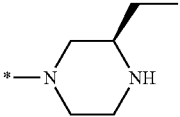 | N | C | N | C |
| A161 | H | H | H | H | H | CH₂CF₃ | 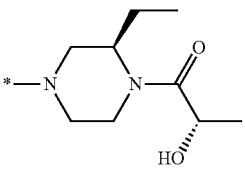 | N | C | N | C |
| A162 | H | H | H | H | H | CH₂CH(CH₃)₂ | 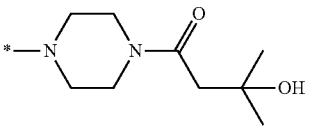 | N | C | N | C |
TABLE 14
| | R¹ | R² | R³¹ | R³² | R⁴ | Ra | *—NRbRc | A | B | D | E |
|---|---|---|---|---|---|---|---|---|---|---|---|
| A163 | H | H | H | H | H | CH₂CH(CH₃)₂ | 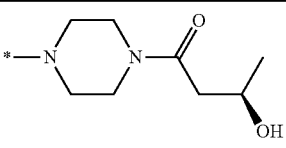 | N | C | N | C |
| A164 | H | H | H | H | H | CH₂CH(CH₃)₂ | 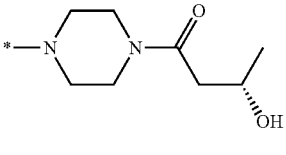 | N | C | N | C |
| A165 | H | H | H | H | H | CH₂CH(CH₃)₂ | 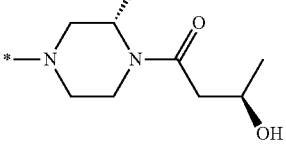 | N | C | N | C |
| A166 | H | H | H | H | H | CH₂CH(CH₃)₂ | 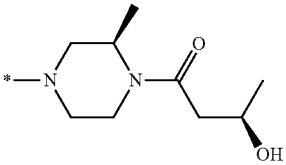 | N | C | N | C |
| A167 | H | H | H | H | H | CH₂CH(CH₃)₂ | 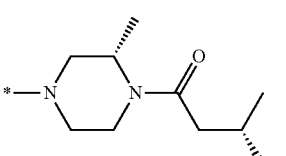 | N | C | N | C |
| A168 | H | H | H | H | H | CH₂CH(CH₃)₂ | 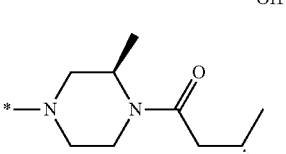 | N | C | N | C |

TABLE 14-continued
| | R¹ | R² | R³¹ | R³² | R⁴ | Ra | *—NRbRc | A | B | D | E |
|---|---|---|---|---|---|---|---|---|---|---|---|
| A169 | CH3 | H | H | H | H | CH₂CF₃ | 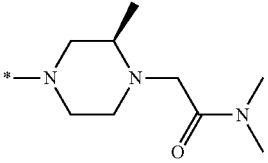 | N | C | N | C |
| A170 | H | H | H | H | H | 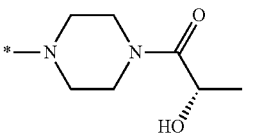 | 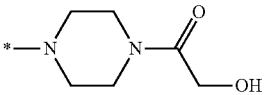 | N | C | N | C |
| A171 | H | H | H | H | H | CH₂CH(CH₃)₂ | 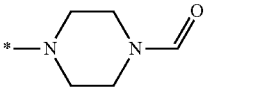 | N | C | N | C |
| A172 | H | H | H | H | H | CH₂CH(CH₃)₂ | 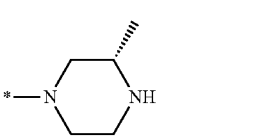 | N | C | N | C |
| A173 | H | H | H | H | H | 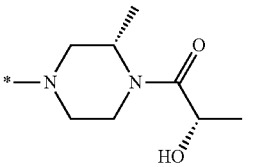 | 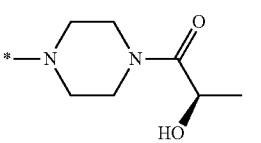 | N | C | N | C |
| A174 | H | H | H | H | H | 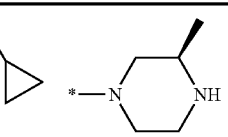 | 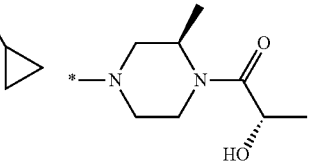 | N | C | N | C |
| A175 | H | H | H | H | H | CH₂CH(CH₃)₂ | 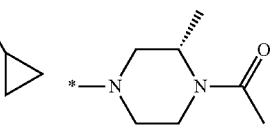 | N | C | N | C |
TABLE 15
| | R¹ | R² | R³¹ | R³² | R⁴ | Ra | *—NRbRc | A | B | D | E |
|---|---|---|---|---|---|---|---|---|---|---|---|
| A176 | H | H | H | H | H | * — △ | (piperazine with methyl, NH) | N | C | N | C |
| A177 | H | H | H | H | H | * — △ | (piperazine with methyl, N-C(O)-CH(OH)CH₃) | N | C | N | C |
| A178 | H | H | H | H | H | * — △ | (piperazine with methyl, N-acetyl) | N | C | N | C |

TABLE 15-continued

| | R[1] | R[2] | R[31] | R[32] | R[4] | Ra | *—NRbRc | A | B | D | E |
|---|---|---|---|---|---|---|---|---|---|---|---|
| A179 | H | H | H | H | H | *-CH2-cyclopropyl | (S)-2-methyl-4-acetylpiperazinyl | N | C | N | C |
| A180 | H | H | H | H | H | *-CH2-cyclopropyl | 2,6-dimethyl-4-acetylpiperazinyl | N | C | N | C |
| A181 | H | H | H | H | H | CH2CH(CH3)2 | (S)-2-methyl-4-acetylpiperazinyl | N | C | N | C |
| A182 | H | H | H | H | H | CH2CH(CH3)2 | (S)-2-methyl-4-formylpiperazinyl | N | C | N | C |
| A183 | H | H | H | H | H | CH2CH(CH3)2 | (R)-2-methyl-4-acetylpiperazinyl | N | C | N | C |
| A184 | H | H | H | H | H | CH2CH(CH3)2 | (R)-2-methyl-4-formylpiperazinyl | N | C | N | C |
| A185 | H | H | H | H | H | CH2CH(CH3)2 | (S)-2-methyl-4-((S)-2-hydroxypropanoyl)piperazinyl | N | C | N | C |
| A186 | H | H | H | H | H | CH2CH(CH3)2 | (S)-2-methyl-4-((R)-2-hydroxypropanoyl)piperazinyl | N | C | N | C |
| A187 | CH3 | H | H | H | H | CH2CF3 | (S)-2-methyl-4-methylsulfonylpiperazinyl | N | C | N | C |

TABLE 16

| | R¹ | R² | R³¹ | R³² | R⁴ | Ra | *—NRbRc | A | B | D | E |
|---|---|---|---|---|---|---|---|---|---|---|---|
| A188 | CH₃ | H | H | H | H | CH₂CF₃ | piperazine with methyl and sulfonyl | N | C | N | C |
| A189 | CH₃ | H | H | H | H | CH₂CF₃ | piperazine with methyl and acetyl | N | C | N | C |
| A190 | CH₃ | H | H | H | H | CH₂CF₃ | piperazine with methyl and acetyl | N | C | N | C |
| A191 | H | H | H | H | H | CH₂CF₃ | piperazine with methyl and 2-hydroxypropanoyl | N | C | N | C |
| A192 | H | H | H | H | H | CH₂CF₃ | piperazine with methyl and 2-hydroxypropanoyl | N | C | N | C |
| A193 | H | H | H | H | H | CH₂CF₃ | piperazine with methyl and formyl | N | C | N | C |
| A194 | H | H | H | H | H | CH₂CF₃ | piperazine with methyl and formyl | N | C | N | C |
| A195 | H | H | H | H | H | *—CH₂-cyclopropyl | piperazine with methyl and 2-hydroxypropanoyl | N | C | N | C |
| A196 | H | H | H | H | H | *—CH₂-cyclopropyl | piperazine with methyl and 2-hydroxypropanoyl | N | C | N | C |
| A197 | H | H | H | H | H | CH₂CF₃ | piperazine with two methyls and acetyl | N | C | N | C |

TABLE 16-continued
| | R¹ | R² | R³¹ | R³² | R⁴ | Ra | *—NRbRc | A | B | D | E |
|---|---|---|---|---|---|---|---|---|---|---|---|
| A198 | H | H | H | H | H | CH₂CF₃ | 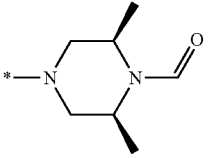 | N | C | N | C |
| A199 | H | H | H | H | H | CH₂CF₃ | 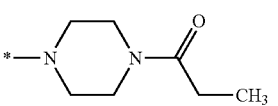 | N | C | N | C |
TABLE 17
| | R¹ | R² | R³¹ | R³² | R⁴ | Ra | *—NRbRc | A | B | D | E |
|---|---|---|---|---|---|---|---|---|---|---|---|
| A200 | H | H | H | H | H | CH₂CF₃ | 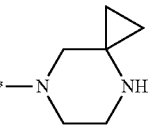 | N | C | N | C |
| A201 | H | H | H | H | H | CH₂CF₃ | 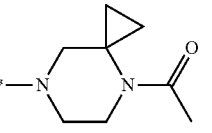 | N | C | N | C |
| A202 | H | H | H | H | H | CH₂CF₃ | 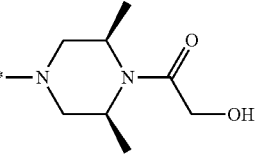 | N | C | N | C |
| A203 | H | H | H | H | H | CH₂CF₃ | 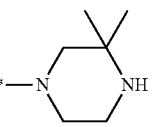 | N | C | N | C |
| A204 | H | H | H | H | H | CH₂CF₃ | 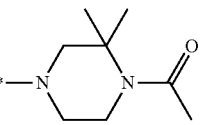 | N | C | N | C |
| A205 | H | H | H | H | H | CH₂CF₃ | 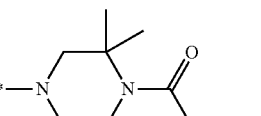 | N | C | N | C |
| A206 | H | H | H | H | H | CH₂CF₃ | 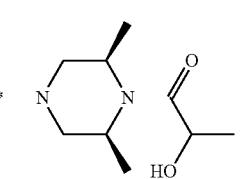 | N | C | N | C |

TABLE 17-continued

| | R$^1$ | R$^2$ | R$^{31}$ | R$^{32}$ | R$^4$ | Ra | *—NRbRc | A | B | D | E |
|---|---|---|---|---|---|---|---|---|---|---|---|
| A207 | H | H | H | H | H | CH$_2$CF$_3$ | (S)-2-methylpiperazinyl-N-CO-CH$_2$OH | N | C | N | C |
| A208 | H | H | H | H | H | CH$_2$CF$_3$ | (R)-2-methylpiperazinyl-N-CO-CH$_2$OH | N | C | N | C |
| A209 | H | H | H | H | 2-(S)—CH$_3$ | CH$_2$CF$_3$ | piperazinyl-N-SO$_2$CH$_3$ | N | C | N | C |
| A210 | H | H | 4-CH$_3$ | H | 2-(S)—CH$_3$ | *—CH$_2$-cyclopropyl | piperazinyl-N-COCH$_3$ | N | C | N | C |

TABLE 18

| | R$^1$ | R$^2$ | R$^{31}$ | R$^{32}$ | R$^4$ | Ra | *—NRbRc | A | B | D | E |
|---|---|---|---|---|---|---|---|---|---|---|---|
| A211 | H | H | H | H | 2-(S)—CH$_3$ | CH$_2$CH(CH$_3$)$_2$ | piperazinyl-N-COCH$_3$ | N | C | N | C |
| A212 | H | H | H | H | 2-(S)—CH$_3$ | CH$_2$CH(CH$_3$)$_2$ | piperazinyl-N-CO-CH$_2$OH | N | C | N | C |
| A213 | H | H | H | H | 2-(S)—CH$_3$ | CH$_2$CH(CH$_3$)$_2$ | piperazinyl-N-CO-CH(OH)CH$_3$ (R) | N | C | N | C |
| A214 | H | H | H | H | 2-(S)—CH$_3$ | CH$_2$CH(CH$_3$)$_2$ | piperazinyl-N-CHO | N | C | N | C |
| A215 | H | H | H | H | 2-(S)—CH$_3$ | CH$_2$CH(CH$_3$)$_2$ | piperazinyl-N-CO-CH$_2$-CH(OH)CH$_3$ | N | C | N | C |
| A216 | CH$_3$ | H | H | H | H | CH$_2$CF$_3$ | piperazinyl-N-COCH$_3$ | N | C | N | C |

Hereafter, methods for producing the compounds represented by the general formula (1) will be described. However, the methods for producing the compounds represented by the general formula (1) are not limited to the following methods.

The compound represented by the general formula (1) and intermediate products thereof can be produced utilizing various known reactions described below. At this time, at the stage of raw materials or intermediates, a functional group may be protected by a suitable protective group. Examples of such a functional group include a hydroxyl group, a carboxy group, and an amino group. Types of protective groups and conditions for introduction and removal of these protective groups can be determined with reference to, for example, those described in Protective Groups in Organic Synthesis (T. W. Greene and P. G. M. Wuts, John Wiley & Sons, Inc., New York, 2006).

The compound represented by the general formula (1) of the present invention (in the present specification, may be referred to as the compound (1)) (a compound in which either $R^1$ or $R^2$ is a hydrogen atom or $R^1$ and $R^2$ are both a hydrogen atom) can be produced by Production Method 1 described below. The raw materials used herein can be purchased as commercially available products or can be readily synthesized with reference to the Examples.

Production Method 1

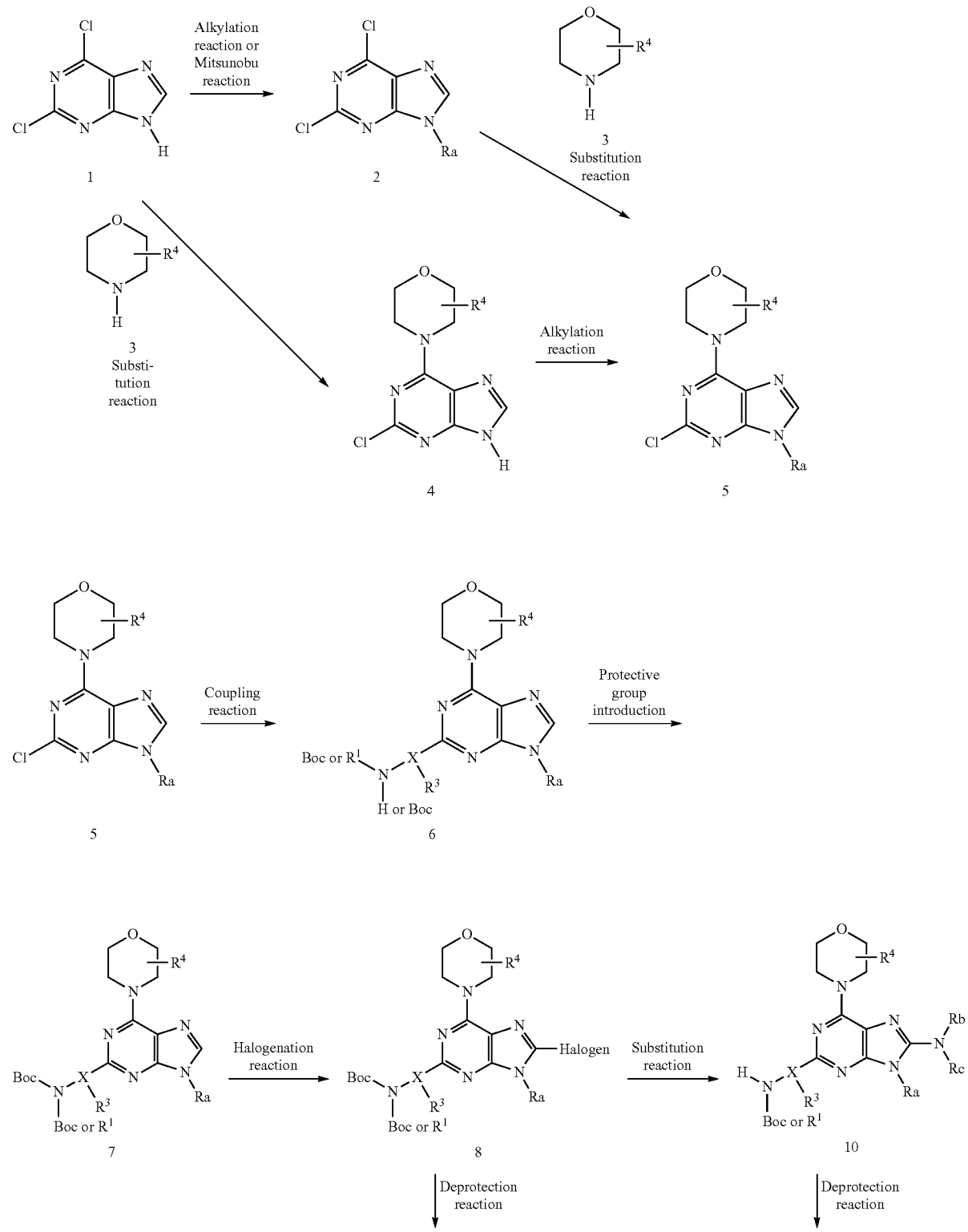

-continued

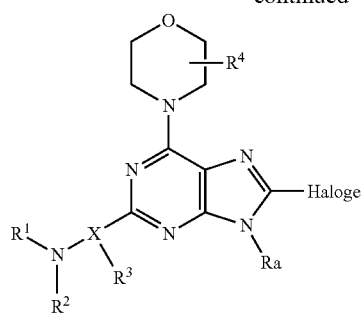

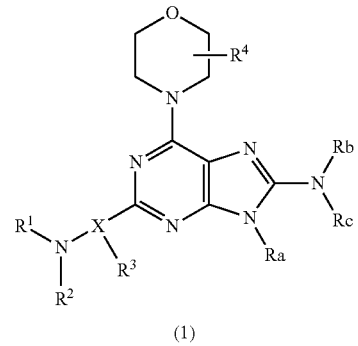

wherein R¹, R², R³, R⁴, Ra, Rb, Rc, and X have the same meaning as defined above.

Hereafter, each step in the above-mentioned scheme will be described.

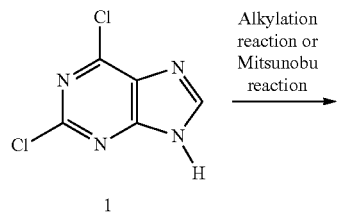

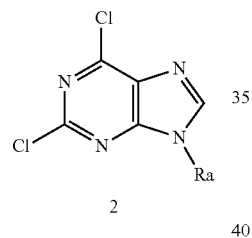

Compound 1 is converted to Compound 2 by treating the compound with an alkyl halide compound or a methanesulfonyloxyalkyl compound or a trifluoromethanesulfonyloxyalkyl compound at room temperature to 150° C. in a suitable solvent that does not adversely affect the reaction, such as, for example, N,N-dimethylformamide, dimethyl sulfoxide, 1,4-dioxane, or acetonitrile or a mixed solvent thereof in the presence of an organic base such as potassium carbonate, potassium t-butoxide, or triethylamine or an inorganic base with or without the addition of a suitable additive (for example, triethylbenzylammonium chloride). 1 to an excess mole, preferably 1 to 5 moles of an alkyl halide or a base per mole of Compound 1 is used. The reaction time is 30 minutes to 72 hours, preferably 30 minutes to 24 hours.

Furthermore, Compound 1 can also be converted to Compound 2 by a Mitsunobu reaction between Compound 1 and a corresponding alcohol (RaOH) thereof. For example, Compound 2 can be obtained by allowing a mixture of Compound 1 and a corresponding alcohol thereof to act on dialkyl azodicarboxylate or the like in an aprotic solvent such as methylene chloride or tetrahydrofuran in the presence of triphenylphosphine. 1 to an excess mole, preferably 1 to 1.5 mole of an alcohol per mole of Compound 1 is used. The reaction time is 30 minutes to 24 hours, preferably 30 minutes to 10 hours. The reaction temperature is preferably 0 to 80° C.

Compound 2 is converted to Compound 5 by heating the compound in a suitable solvent (may be protonic or aprotonic) in the coexistence of Compound 3. 1 to an excess mole, preferably 1 to 4 moles of Compound 3 per mole of Compound 2 is used. The reaction temperature is preferably about 60 to 100° C., more preferably 80 to 100° C. The reaction time is preferably about 1 to 10 hours.

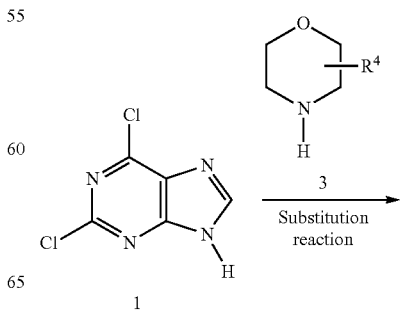

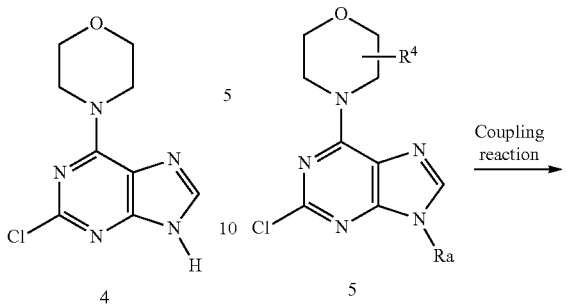

Compound 1 is converted to Compound 4 by heating the compound in a suitable solvent (may be protonic or aprotonic) in the coexistence of Compound 3. The reaction temperature is preferably about 60 to 100° C., more preferably 80 to 100° C. The reaction time is preferably about 1 to 10 hours.

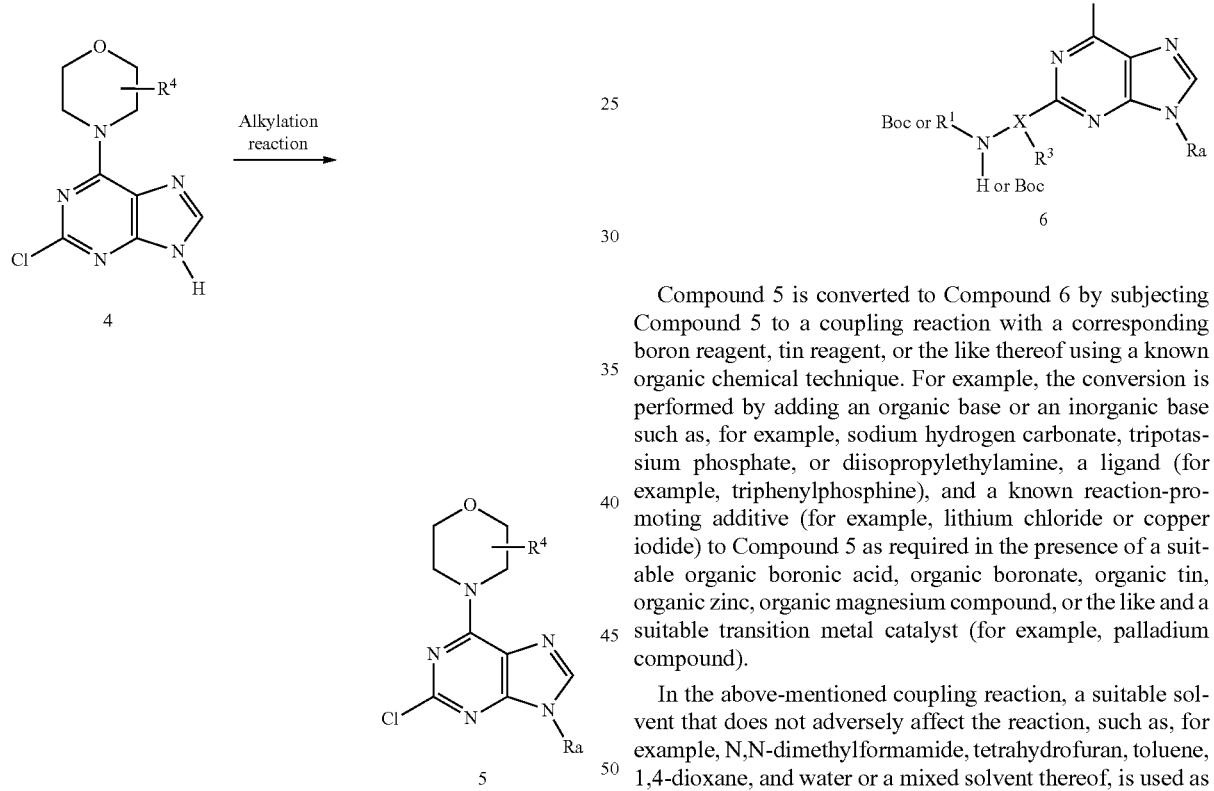

Compound 4 is converted to Compound 5 by treating Compound 4 with an alkyl halide compound or a methanesulfonyloxyalkyl compound or a trifluoromethanesulfonyloxyalkyl compound at room temperature to 150° C. in a suitable solvent that does not adversely affect the reaction, such as, for example, N,N-dimethylformamide, dimethyl sulfoxide, 1,4-dioxane, or acetonitrile or a mixed solvent thereof, in the presence of an organic base such as potassium carbonate, potassium t-butoxide, or triethylamine or an inorganic base with or without the addition of a suitable additive (for example, triethylbenzylammonium chloride). 1 to an excess mole, preferably 1 to 5 moles of an alkyl halide or a base per mole of Compound 4 is used. The reaction time is 30 minutes to 72 hours, preferably 30 minutes to 24 hours.

Compound 5 is converted to Compound 6 by subjecting Compound 5 to a coupling reaction with a corresponding boron reagent, tin reagent, or the like thereof using a known organic chemical technique. For example, the conversion is performed by adding an organic base or an inorganic base such as, for example, sodium hydrogen carbonate, tripotassium phosphate, or diisopropylethylamine, a ligand (for example, triphenylphosphine), and a known reaction-promoting additive (for example, lithium chloride or copper iodide) to Compound 5 as required in the presence of a suitable organic boronic acid, organic boronate, organic tin, organic zinc, organic magnesium compound, or the like and a suitable transition metal catalyst (for example, palladium compound).

In the above-mentioned coupling reaction, a suitable solvent that does not adversely affect the reaction, such as, for example, N,N-dimethylformamide, tetrahydrofuran, toluene, 1,4-dioxane, and water or a mixed solvent thereof, is used as the solvent, and the reaction temperature is 0 to 300° C., preferably room temperature to 200° C. 1 to an excess mole, preferably 1 to 5 moles of organic boronic acid, a boronic ester, and a base per mole of Compound 5 is used. The reaction time is preferably 1 minute to 60 hours, more preferably 5 minutes to 24 hours.

Furthermore, the coupling reaction can be also similarly performed by protecting an amino group of boronic acid, a boronic ester, or the like used by a suitable protective group such as a group that can be usually used as a protective group for an amino group of, for example, a tert-butoxycarbonyl group, a benzoyloxycarbonyl group, or an allyloxycarbonyl group. In this case, since a part of a protective group may be removed under a condition where a base is used as a catalyst, a coupling reaction can also be induced in Compound 7 with a technique similar to the condition shown in Formula 17.

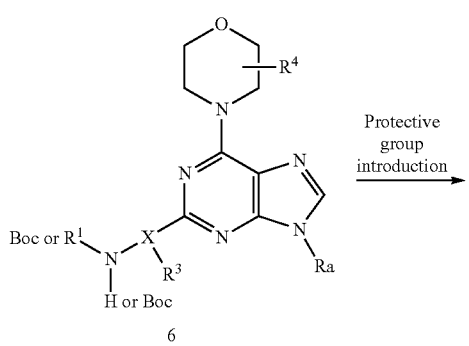

6

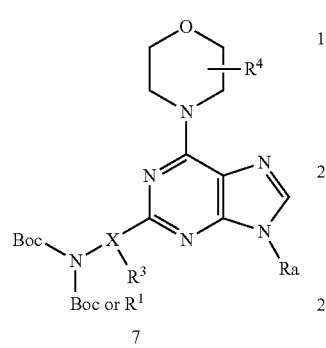

7

Compound 6 (when one or more substituents present on a nitrogen atom bonded to X are a hydrogen atom in the figure) is converted to Compound 7 by reacting an excess mole, preferably 2 to 5 moles of $Boc_2O$ per mole of Compound 6 in a suitable solvent that does not adversely affect the reaction, such as, for example, N-methylpyrolidone, N,N-dimethylformamide, tetrahydrofuran, or 1,4-dioxane, with the addition of a catalytic amount of a base such as 4-dimethylaminopyridine at room temperature to 80° C. for about 1 to 10 hours.

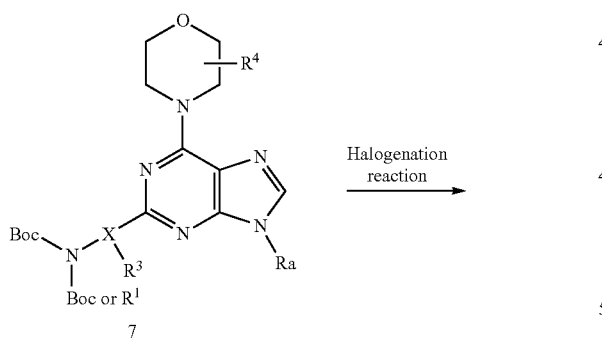

7

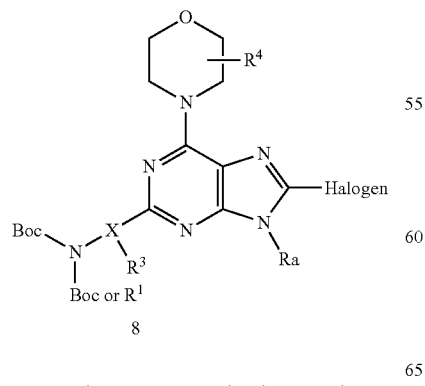

8

Compound 7 is converted to Compound 8 by reacting 1 mole to an excess mole, preferably 1 to 3 moles of a usually used halogenating agent such as, for example, N-chlorosuccinimide, N-bromosuccinimide, N-iodine succinimide, bromine, iodine, or BrI per mole of Compound 7 in a suitable solvent that does not adversely affect the reaction (for example, N,N-dimethylformamide, acetonitrile, chloroform, or methylene chloride) at room temperature to 80° C. for 1 to 24 hours. A radical reaction initiator may be added occasionally.

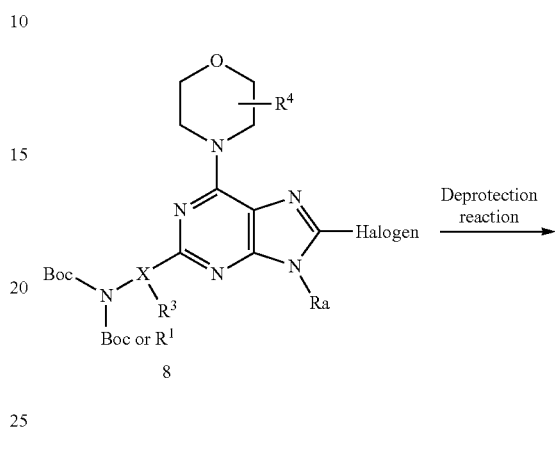

8

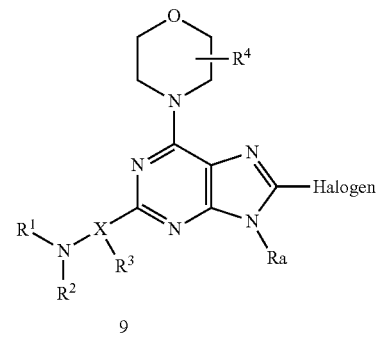

9

Compound 8 is converted to Compound 9 by allowing hydrochloric acid, trifluoroacetic acid, formic acid, or the like to act. The reaction temperature is 0 to 100° C., preferably 0° C. to room temperature. The conversion may be performed by adding a suitable solvent that does not adversely affect the reaction, such as, for example, N,N-dimethylformamide, acetonitrile, chloroform, methylene chloride, or 1,4-dioxane, at a suitable timing.

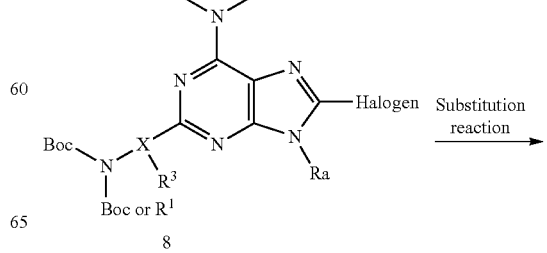

8

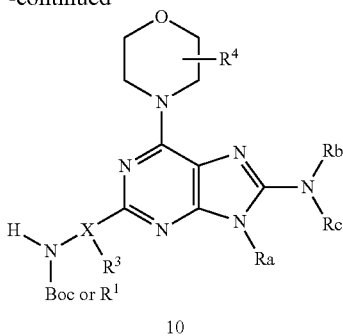

10

Compound 8 is converted to Compound 10 by using a solvent such as dimethyl sulfoxide, N,N-dimethylformamide, N,N-dimethyl acetamide, 1,3-dimethyl-2-imidazolidinone, 1,3-dimethyl-3,4,5,6-tetrahydro-2(1H)-pyrimidinone, N-methylpyrrolidone, or tert-butanol as the solvent and 1 mole to an excess mole, preferably 2 to 10 moles of a corresponding amine thereof in the range of 80 to 200° C.

When Rb and Rc have one or more substituents selected from the above-mentioned Group E, one or more substituents selected from Group E can be introduced into the corresponding amine beforehand. Furthermore, the substituent(s) (Group E) can be introduced by a known method after protecting the position on the amine into which the substituent(s) is to be introduced later as required, performing a substitution reaction with Compound 8, and then removing the protective group. When a protective group is not required, the substituent(s) can be introduced by a known method after a substitution reaction with Compound 8.

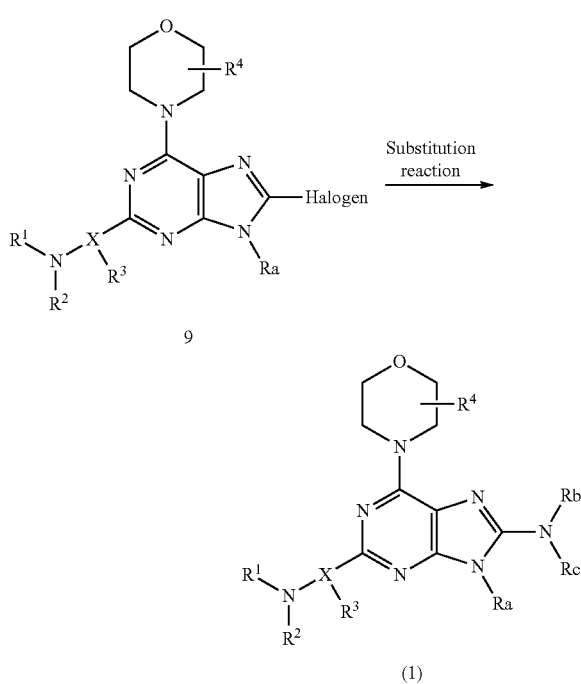

Compound 9 is converted to the Compound (1) using a solvent such as dimethyl sulfoxide, N,N-dimethylformamide, N,N-dimethyl acetamide, 1,3-dimethyl-2-imidazolidinone, 1,3-dimethyl-3,4,5,6-tetrahydro-2(1H)-pyrimidinone, N-methylpyrrolidone, or tert-butanol as the solvent and 1 to an excess mole, preferably 2 to 10 moles of the corresponding amine in the range of 80 to 200° C.

When Rb and Rc have one or more substituents selected from the above-mentioned Group E, the substituent(s) selected from Group E can be introduced into the corresponding amine beforehand. Furthermore, the substituent(s) (Group E) can be introduced by a known method after protecting the position on the amine into which the substituent(s) is to be introduced later as required, performing a substitution reaction with Compound 9, and then removing the protective group. When a protective group is not required, the substituent(s) can be introduced by a known method after a substitution reaction with Compound 9.

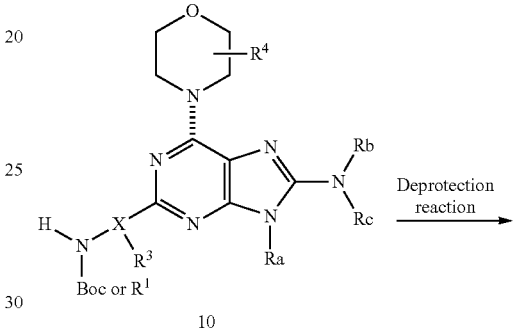

10

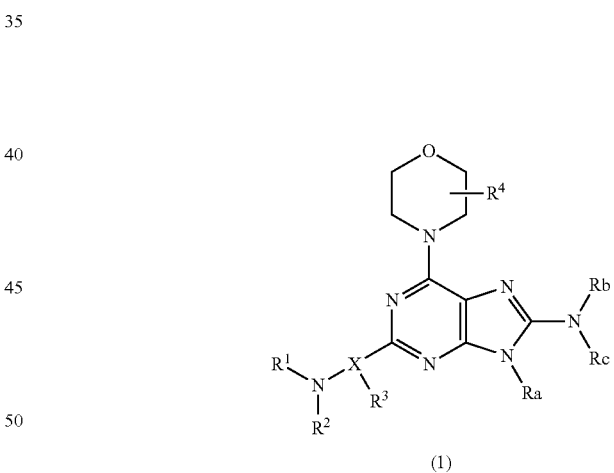

(1)

Compound 10 is converted to the Compound (1) by allowing hydrochloric acid, trifluoroacetic acid, formic acid, or the like to act. The reaction temperature is preferably 0 to 100° C., more preferably 0° C. to room temperature. The conversion may be performed by using a suitable solvent that does not adversely affect the reaction such as, for example, N,N-dimethylformamide, acetonitrile, chloroform, methylene chloride, or 1,4-dioxane, at a suitable timing.

Furthermore, the compound having the formula (1) of the present invention can also be readily produced according to the method described below.

Production Method 2
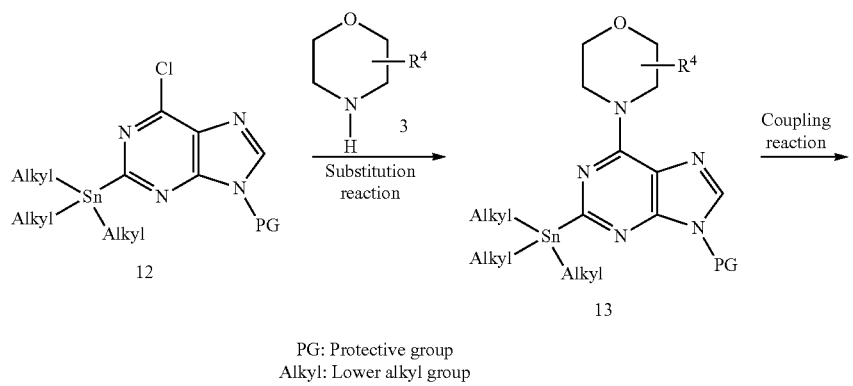
PG: Protective group
Alkyl: Lower alkyl group
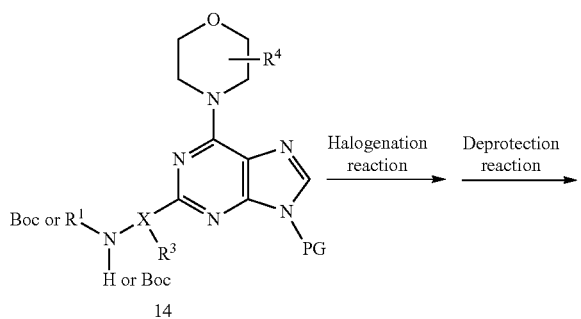
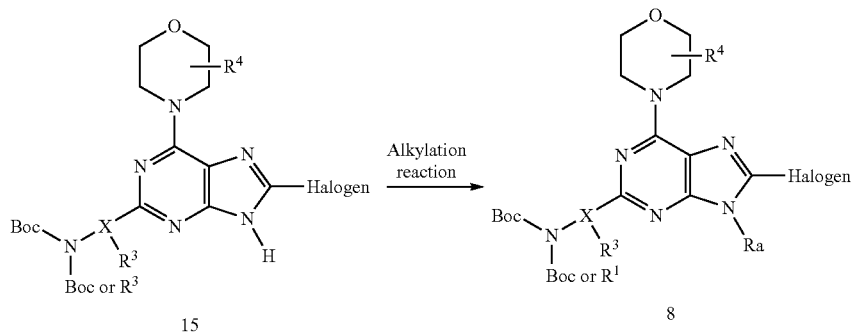
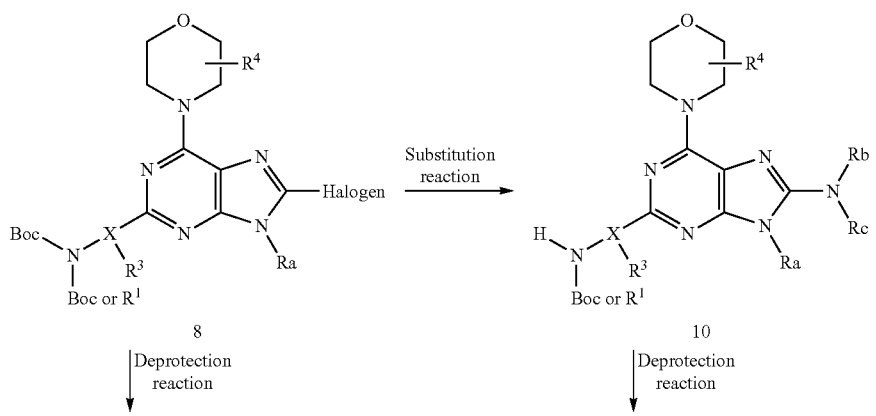

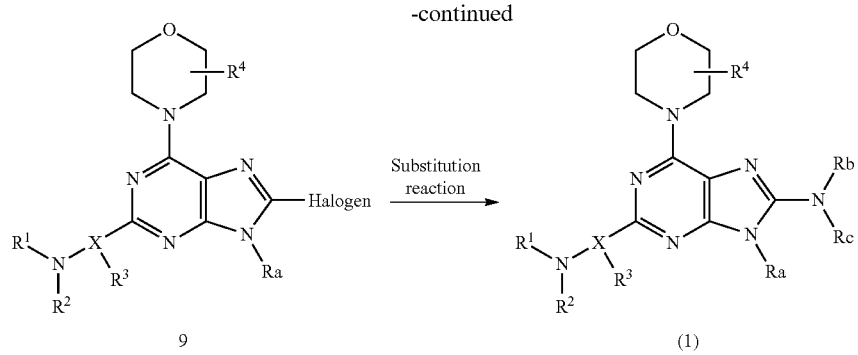

wherein $R^1$, $R^2$, $R^3$, $R^4$, Ra, Rb, Rc, and X have the same meaning as defined above, PG represents a usually used protective group, such as, for example, a tetrahydropyranyl group, an arylsulfonyl group, a benzyloxycarbonyl group, a tert-butoxycarbonyl group, a trialkylsilyl group, a tert-butyl-diphenylsilyl group, or a trimethylsilylethyl group, Halogen represents a halogeno group, and Alkyl represents a lower alkyl group.

Hereafter, each step of the above-mentioned scheme will be described.

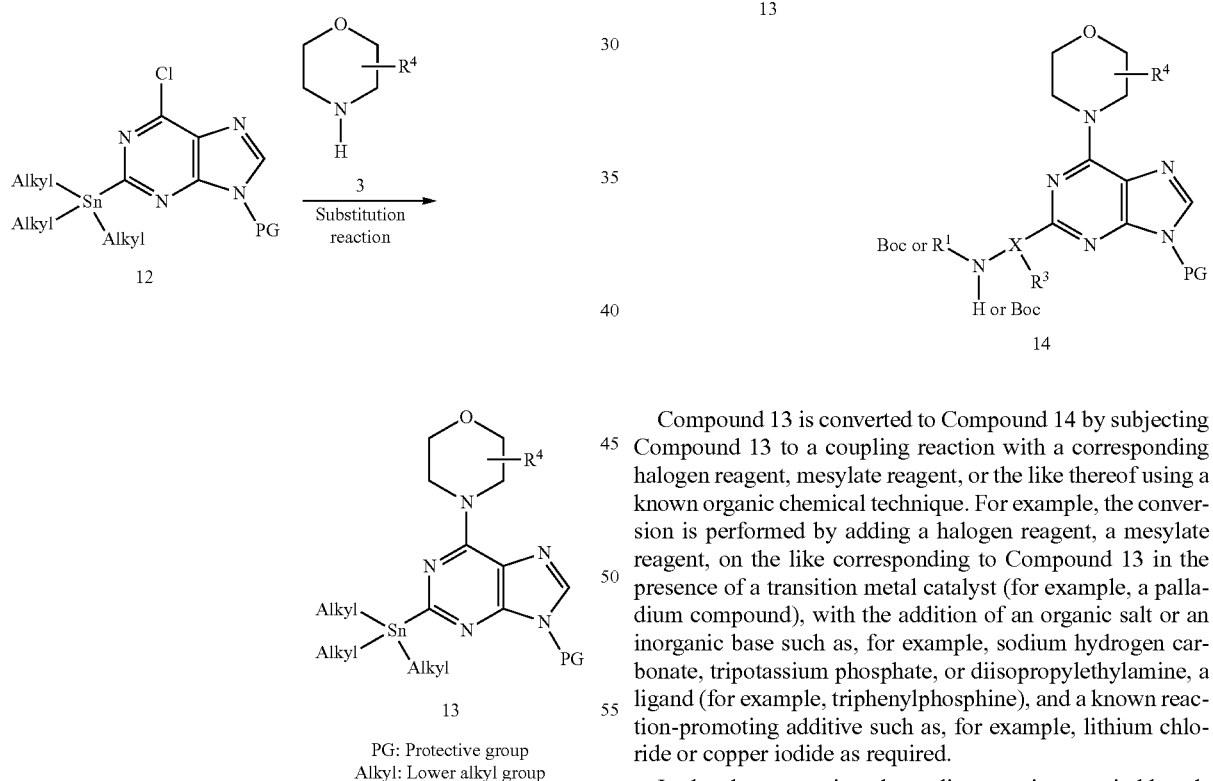

PG: Protective group
Alkyl: Lower alkyl group

Compound 12, which can be synthesized by a known method (for example, Brun, Virginie et al., Tetrahedron, 2002, 58, 7911-7924), is converted to Compound 13 by heating the compound in a suitable solvent (may be protonic or aprotonic) in the coexistence of Compound 3. The reaction temperature is preferably about 60 to 100° C., more preferably 80 to 100° C. The reaction time is preferably 1 to 10 hours.

Compound 13 is converted to Compound 14 by subjecting Compound 13 to a coupling reaction with a corresponding halogen reagent, mesylate reagent, or the like thereof using a known organic chemical technique. For example, the conversion is performed by adding a halogen reagent, a mesylate reagent, on the like corresponding to Compound 13 in the presence of a transition metal catalyst (for example, a palladium compound), with the addition of an organic salt or an inorganic base such as, for example, sodium hydrogen carbonate, tripotassium phosphate, or diisopropylethylamine, a ligand (for example, triphenylphosphine), and a known reaction-promoting additive such as, for example, lithium chloride or copper iodide as required.

In the above-mentioned coupling reaction, a suitable solvent that does not adversely affect the reaction, such as, for example, N,N-dimethylformamide, tetrahydrofuran, toluene, 1,4-dioxane, or water or a mixed solvent thereof, is used, and the reaction temperature is preferably 0 to 300° C., more preferably room temperature to 200° C. 1 to an excess mole, preferably 1 to 5 moles of a halogen reagent, a mesylate reagent, or the like and a base per mole of Compound 13 is used. The reaction time is preferably 1 minute to 60 hours, more preferably 5 minutes to 24 hours.

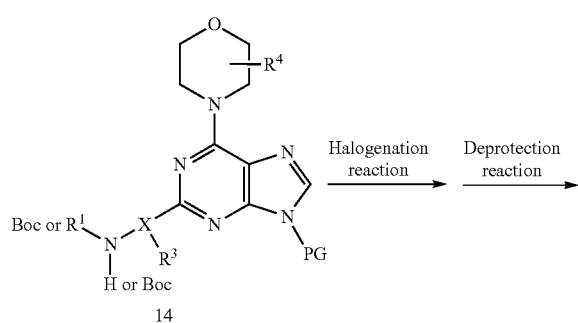

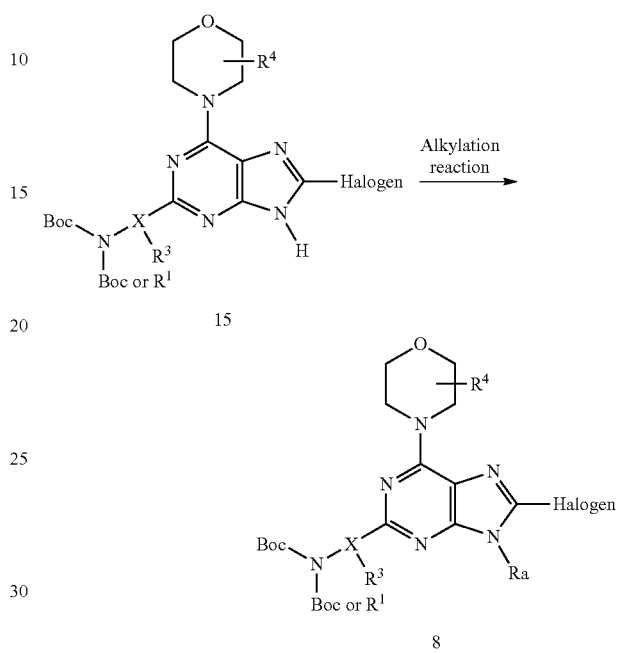

Halogenation at the 8th position of Compound 14 is performed by reacting 1 mole to an excess mole, preferably 1 to 3 moles of a usually used halogenating agent such as, for example, N-chlorosuccinimide, N-bromosuccinimide, N-iodine succinimide, bromine, iodine, or BrI in a suitable solvent that does not adversely affect the reaction, such as, for example, N,N-dimethylformamide, acetonitrile, chloroform, or methylene chloride, at room temperature to 80° C. for 1 to 24 hours. Depending on the reagent used, a protective group at the 9th position can be simultaneously removed in the halogenation step to obtain Compound 15 in one step. When a protective group is maintained at the 9th position in the halogenation step, the protective group (an arylsulfonyl group, a benzyloxycarbonyl group, a trialkylsilyl group, a tert-butyldiphenylsilyl group, or a trimethylsilylethyl group) can also be removed separately from a tert-butoxycarbonyl group by a known method to obtain Compound 15. Furthermore, when a tert-butoxycarbonyl group is present on a nitrogen atom bonded to X, the protective group at the 9th position can also be removed at the same time as the removal of a tert-butoxycarbonyl group by allowing a strong acidic reagent such as trifluoroacetic acid, hydrochloric acid, or formic acid to act in the deprotection step. At this time, a suitable solvent that does not adversely affect the reaction, such as, for example, N,N-dimethylformamide, acetonitrile, chloroform, methylene chloride, or 1,4-dioxane, may be used at a suitable timing.

Compound 15 is converted to Compound 8 by adding a suitable additive (for example, triethylbenzylammonium chloride) in a suitable solvent that does not adversely affect the reaction, such as, for example, N,N-dimethylformamide, dimethyl sulfoxide, 1,4-dioxane, or acetonitrile or a mixed solvent thereof, in the presence of an organic base or an inorganic base (for example, potassium carbonate, potassium t-butoxide, or triethylamine) and treating the resulting mixture with an alkyl halide compound, a methanesulfonyloxyalkyl compound, or the like at room temperature to 150° C. 1 to an excess mole, preferably 1 to 5 moles of an alkyl halide or a base per mole of Compound 15 is used. The reaction time is preferably 30 minutes to 72 hours, more preferably 30 minutes to 24 hours.

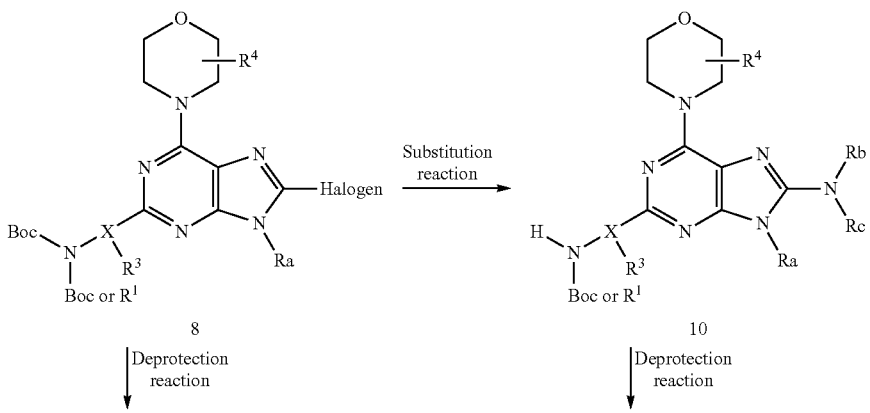

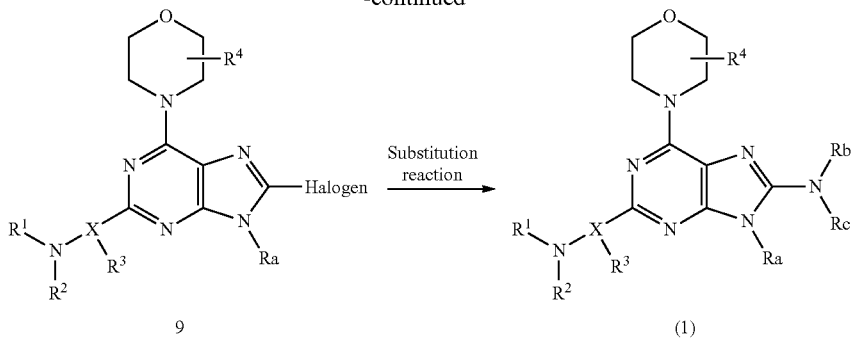

Compound 8 is converted to the Compound (1) by the method described in the above-mentioned Production Method 1.

When Rb and Rc have one or more substituents selected from the above-mentioned Group E, the substituent(s) selected from Group E can be introduced into the corresponding amine beforehand. Furthermore, the substituent(s) (Group E) can be introduced by a known method after protecting the position on the amine into which a substituent(s) is to be introduced later as required, performing a substitution reaction with Compound 8 or 9, and then removing the protective group. When a protective group is not required, the substituent(s) can be introduced by a known method after a substitution reaction with Compound 8 or 9.

The compound (1) of the present invention produced by the above-mentioned method can be isolated or purified by a known method such as, for example, extraction, precipitation, chromatography, fractional recrystallization, or recrystallization.

Furthermore, when the compound (1) of the present invention or an intermediate product thereof has an asymmetric carbon, optical isomers exist. Each of these optical isomers can be isolated or purified by a usual method such as a fractional recrystallization (salt fractionation) comprising recrystallization with an appropriate salt or column chromatography. Examples of references for a method for separating optical isomers from a racemate include "J. Jacques et al., Enantiomers, Racemates and Resolution, John Wiley and Sons, Inc."

As described above, PI3K inhibitors and mTOR inhibitors are useful as anti-tumor agents. The compound of the present invention is useful as an anti-tumor agents, because it shows P13K inhibitory activity and mTOR inhibitory activity.

In the present invention, "tumor" includes various kind of tumors, not limited to marignant tumor, for example, carcinoma, sarcoma, beginning tumor and the like. Specifically, marignant tumor is sometimes expressed as "cancer" in the present invention.

PI3K inhibitory activity, mTOR inhibitory activity, and anti-tumor activity can be determined by the methods described in the Examples, but the methods are not limited to these Examples, and any method can be used.

PI3K inhibitory activity can be determined by, for example, the method described in Cell, 125, 733-747 (2006). Furthermore, since it is known that Akt is activated by activation of PI3K, activation of Akt can be determined by examining phosphorylation of Akt (Cell, 125, 733-747 [2006]). Furthermore, mTORC1 inhibitory activity can be indirectly determined by examining phosphorylation of S6 (Cell, 125, 733-747 [2006]).

The compound of the present invention can be used for the treatment of tumor or cancer, such as, for example, lung cancer, digestive system cancer such as colon cancer and gastrointestinal cancer, ovary cancer, uterus cancer, breast cancer, liver cancer, head/neck region cancer such as brain cancer, blood cancer, kidney cancer, prostate cancer, skin cancer such as melanoma and testicle tumor.

As described above, it is suggested that the PI3K-Akt pathway play an important role in growth, survival and angiogenesis of cancer cells. The compound of the present invention is preferred to be used for the treatment of tumors with activated PI3K-Akt pathway. For the examples of the tumors with the activation of the PI3K-Akt pathway, tumors with over-expression of gene and/or protein of PI3K, the tumors possess mutations in gene(s) of PI3K and/or PTEN and tumors with the activated phospholilation level of Akt.

Activation of the PI3K-Akt pathway can be determined by examining over-expression and/or mutation in PI3K and/or PTEN, and/or phosphorylation of Akt, in patient's tissue samples (Patient's tissue samples can be obtained by blood sampling, biopsy etc.) by using well-known methods such as Southern blotting, Northern blottinng, Western blotting, ELISA, DNA microarrays, pathological methods and the like.

The pharmaceutical composition of the present invention comprises the compound of the present invention and a pharmaceutically acceptable carrier and can be administered by various injections such as intravenous injection, intramuscular injection, and subcutaneous injection or by various methods such as oral administration and percutaneous administration. The pharmaceutically acceptable carrier means a pharmacologically acceptable material (for example, excipient, diluent, additive, or solvent) involved in transport of the compound of the present invention or a composition containing the compound of the present invention from one organ to another organ.

A formulation can be prepared by selecting a suitable formulation (for example, an oral formulation or an injection) depending on the administration method and using usually used methods for preparing various formulations. Examples of the oral formulation include tablet, powder, granule, capsule, pill, lozenge, solution, syrup, elixir, emulsion, and oily or aqueous suspension. In oral administration, a free compound or a salt form may be used. An aqueous formulation can be prepared by forming an acid adduct with a pharmacologically acceptable acid or by forming an alkali metal salt such as sodium. As an injection, a stabilizer, a preservative, a dissolving aid, and the like can be used in the formulation. After filling a solution that may contain these aids and the like in a vessel, a formulation for use may be prepared as a solid formulation by lyophilization or the like to be prepared immediately before use. Furthermore, one dose may be filled in one vessel, or two or more doses may be filled in a vessel.

Examples of a solid formulation include tablet, powder, granule, capsule, pill, and lozenge. These solid formulations may contain pharmaceutically acceptable additives together with the compound of the present invention. Examples of the additives include filler, extender, binder, disintegrating agent, dissolution promoting agent, skin wetting agent, and lubricant, and these additives can be selected and mixed as required to prepare a formulation.

Examples of a liquid formulation include solution, syrup, elixir, emulsion, and suspension. These liquid formulations may contain pharmaceutically acceptable additives together with the compound of the present invention. Examples of the additives include suspending agents and emulsifiers, and these additives can be selected and mixed as required to prepare a formulation.

The compound of the present invention can be used in cancer treatment of mammals, in particular, humans. The dose and the administration interval can be suitably selected according to a physician's judgment depending on the site of a disease, the patient's height, body weight, sex, or medical history. When the compound of the present invention is administered to a human, the dose range is approx. 0.01 to 500 mg/kg body weight per day, preferably approx. 0.1 to 100 mg/kg body weight per day. Preferably, the compound of the present invention is administered to a human once a day, or the dose is divided into two to four times, and administration is repeated at an appropriate interval. Furthermore, the daily dose may exceed the above-mentioned dose at a physician's discretion, if necessary.

The compound present invention may be used in combination with other anti-tumor agents. Examples of the other anti-tumor agents include anti-tumor antibiotics, anti-tumor plant components, biological response modifiers (BRMs), hormones, vitamins, anti-tumor antibodies, molecular targeted drugs, and other anti-tumor agents.

More specifically, examples of alkylating agents include alkylating agents such as nitrogen mustard, nitrogen mustard N-oxide, and chlorambucil, aziridine alkylating agents such as carboquone and thiotepa, epoxide alkylating agents such as dibromomannitol and dibromodulcitol, nitrosourea alkylating agents such as carmustine, lomustine, semustine, nimustine hydrochloride, streptozocin, chlorozotocin, and ranimustine, busulfan, improsulfan tosylate, and dacarbazine.

Examples of anti-metabolites include purine anti-metabolites such as 6-mercaptopurine, 6-thioguanine, and thioinosine, pyrimidine anti-metabolites such as fluorouracil, tegafur, tegafur-uracil, carmofur, doxifluridine, broxuridine, cytarabine, and enocitabine, and anti-folates such as methotrexate and trimetrexate.

Examples of anti-tumor antibiotics include anthracycline antibiotic anti-tumor agents such as mytomycin C, bleomycin, peplomycin, daunorubicin, aclarubicin, doxorubicin, pirarubicin, THP-adriamycin, 4'-epidoxorubicin, and epirubicin, chromomycin A 3, and actinomycin D.

Examples of anti-tumor plant components include vinca alkaloids such as vindesine, vincristine, and vinblastine, taxanes such as paclitaxel and docetaxel, and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethynylestradiol, chlormadinone, and medroxyprogesterone.

Examples of vitamins include vitamin C and vitamin A.

Examples of anti-tumor antibodies and molecular targeted drugs include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other anti-tumor agents include cisplatin, carboplatin, oxaliplatin, tamoxifen, camptothecin derivatives, ifosfamide, cyclophosphamide, melphalan, L-asparaginase, acecratone, schizophyllan, picibanil, procarbazine, pipobroman, neocarzinostatin, hydroxyurea, ubenimex, and krestin.

The present invention encompasses methods for prophylactic and/or therapeutic treatment of cancer comprising administration of the present invention compound or a salt thereof.

Furthermore, the present invention encompasses use of the compound of the present invention or a salt thereof or a solvate of the compound or the salt for production of the above-mentioned medicaments.

EXAMPLES

Example 1

5-{9-Isobutyl-8-[4-(methylsulfonyl)piperazin-1-yl]-6-morpholin-4-yl-9H-purin-2-yl}pyrimidin-2-amine

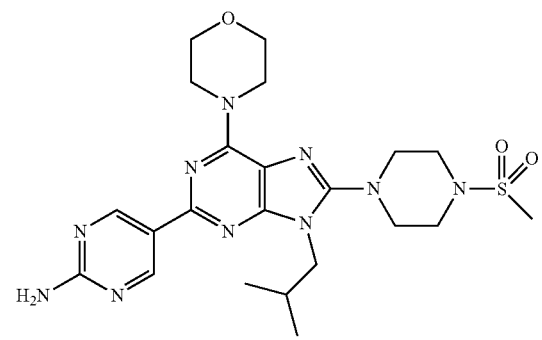

Step 1:
2-Chloro-9-isobutyl-6-morpholin-4-yl-9H-purine

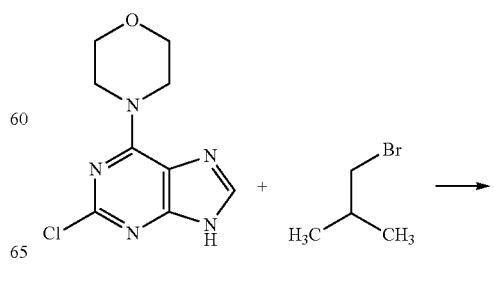

-continued

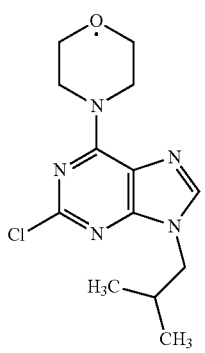

N,N-Dimethylformamide (60 ml), isobutyl bromide (2 ml, 18 mmol), and potassium carbonate (3 g) were added to 2-chloro-6-morpholin-4-yl-9H-purine (5 g, 17 mmol) and the resulting mixture was stirred at 80° C. for 5 hours. The reaction mixture was cooled and partitioned with ethyl acetate and water and the organic layer was dried over magnesium sulfate. The solvent was evaporated under reduced pressure to give the title compound (5.2 g, 100%) as a pale yellow oil.

$^1$H-NMR (CDCl$_3$) δ: 0.94 (6H, d, J=6.30 Hz), 2.20-2.29 (1H, m), 3.82-3.84 (4H, m), 3.96 (2H, d, J=7.45 Hz), 4.30 (4H, brs), 7.66 (1H, s).

Step 2: Di-tert-butyl [5-(9-isobutyl-6-morpholin-4-yl-9H-purin-2-yl)pyrimidin-2-yl]imide dicarbonate 1,4-Dioxane (50 ml) and water (25 ml) were added to 2-chloro-9-isobutyl-6-morpholin-4-yl-9H-purine (3.0 g, 10.1 mmol), di-tert-butyl [5-(4,4,5,5-tetramethyl-1,3,2-dioxaborolan-2-yl)pyrimidin-2-yl]imide dicarbonate (4.3 g, 10.1 mmol), and sodium carbonate (3.2 g) and the atmosphere in the reaction vessel was substituted with nitrogen under stirring. Tetrakis triphenylphosphine palladium (0.6 g, 0.51 mmol) was added and the resulting mixture was heated to reflux for 3 hours after the atmosphere in the reaction vessel was substituted with nitrogen again. The reaction mixture was partitioned with ethyl acetate and water, the organic layer was dried over magnesium sulfate, and then the solvent was evaporated under reduced pressure. The residue was dissolved in tetrahydrofuran (50 ml) followed by the addition of 4-dimethylaminopyridine (120 mg) and di-tert-butyl dicarbonate (4.4 g, 20.3 mmol) and the resulting mixture was stirred at 50° C. for 1 hour. The solvent was evaporated under reduced pressure and the residue was purified by silica gel chromatography (hexane:ethyl acetate=8:2 to 6:4) to give the title compound (4.7 g, 84%) as a colorless amorphous substance.

$^1$H-NMR (CDCl$_3$) δ: 0.98 (6H, d, J=6.87 Hz), 1.48 (18H, s), 2.29-2.34 (1H, m), 3.87-3.89 (4H, m), 4.06 (2H, d, J=7.45 Hz), 4.39 (4H, brs), 7.75 (1H, s), 9.67 (2H, s).

Step 3: Di-tert-butyl [5-(8-chloro-9-isobutyl-6-morpholin-4-yl-9H-purin-2-yl)pyrimidin-2-yl]imide dicarbonate

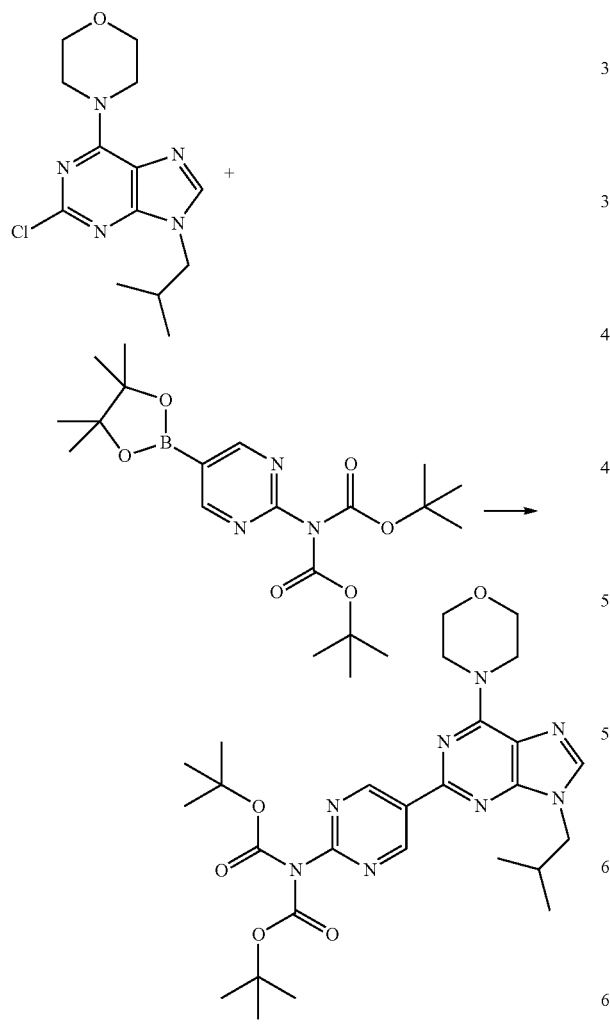

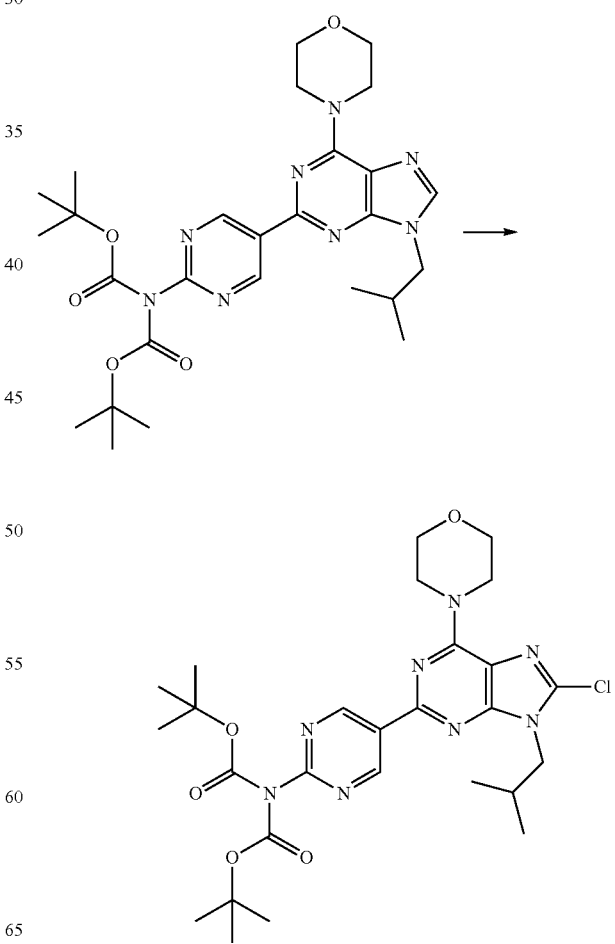

Di-tert-butyl [5-(9-isobutyl-6-morpholin-4-yl-9H-purin-2-yl)pyrimidin-2-yl]imide dicarbonate (4.7 g, 8.47 mmol) was dissolved in N,N-dimethylformamide (50 ml) followed by the addition of N-chlorosuccinimide (1.7 g, 12.7 mmol) and the resulting mixture was stirred for 3 hours. The reaction mixture was partitioned with ethyl acetate and water, the organic layer was dried over magnesium sulfate, and the solvent was evaporated under reduced pressure. The residue was purified by silica gel chromatography (hexane:ethyl acetate=9:1 to 6:4) to give the title compound (4.6 g, 92%) as a colorless amorphous substance.

$^1$H-NMR (CDCl$_3$) δ: 0.99 (6H, d, J=6.87 Hz), 1.48 (18H, s), 2.32-2.39 (1H, m), 3.85-3.87 (4H, m), 4.06 (2H, d, J=7.45 Hz), 4.31 (4H, brs), 9.63 (2H, d, J=5.15 Hz).

Step 4: 5-(8-Chloro-9-isobutyl-6-morpholin-4-yl-9H-purin-2-yl)pyrimidin-2-amine

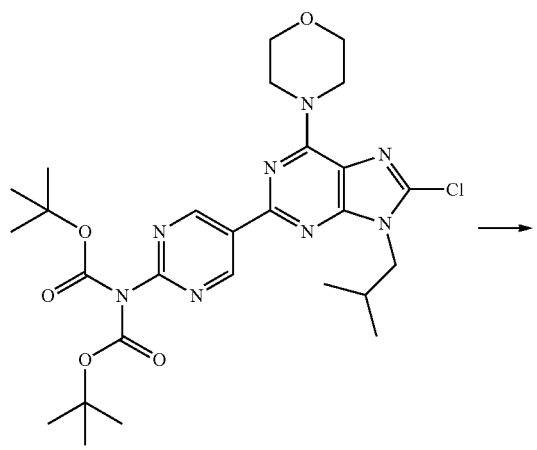

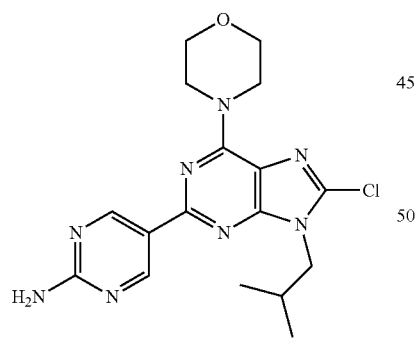

Di-tert-butyl [5-(8-chloro-9-isobutyl-6-morpholin-4-yl-9H-purin-2-yl)pyrimidin-2-yl]imide dicarbonate (4.5 g, 7.6 mmol) was dissolved in methylene chloride (20 ml) followed by the addition of trifluoroacetic acid (60 ml) and the resulting mixture was stirred for 2 hours. The solvent was evaporated under reduced pressure, toluene was added to the residue, and the solvent was evaporated again. The residue was partitioned with ethyl acetate and saturated aqueous sodium bicarbonate solution, the organic layer was dried over magnesium sulfate, and the solvent was evaporated under reduced pressure to give the title compound (2.9 g, 98%) as a white solid.

$^1$H-NMR (DMSO-d$_6$) δ: 0.92 (6H, d, J=6.30 Hz), 2.23-2.28 (1H, m), 3.74-3.76 (4H, m), 4.02 (2H, d, J=7.45 Hz), 4.19 (4H, brs), 7.09 (2H, s), 9.09 (2H, s).

Step 5: 5-(9-Isobutyl-6-morpholin-4-yl-8-piperazin-1-yl-9H-purin-2-yl)pyrimidin-2-amine

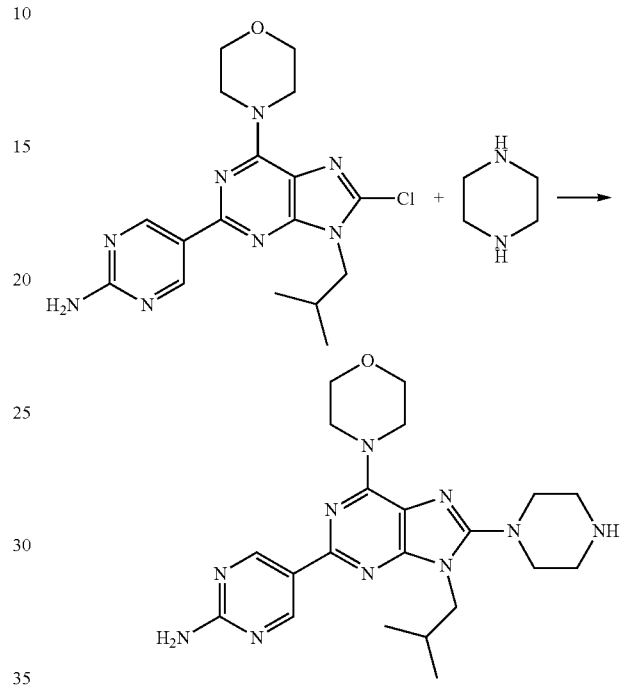

Piperazine (2.0 g, 23 mmol) and N-methylpyrrolidone (10 ml) were added to 5-(8-chloro-9-isobutyl-6-morpholin-4-yl-9H-purin-2-yl)pyrimidin-2-amine (1.0 g, 2.6 mmol) and the resulting mixture was stirred at 130° C. for 4 hours. The reaction mixture was cooled and partitioned with methylene chloride and water, the organic layer was dried over magnesium sulfate, and the solvent was concentrated under reduced pressure. This compound (10 ml in liquid) was stored with N-methylpyrrolidone remaining and used for next step.

Step 6: 5-{9-Isobutyl-8-[4-(methylsulfonyl)piper-azin-1-yl]-6-morpholin-4-yl-9H-purin-2-yl}pyrimidin-2-amine

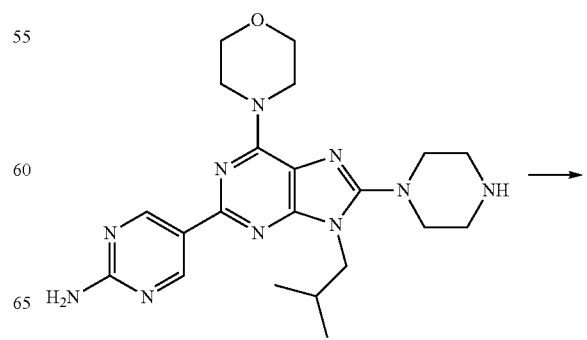

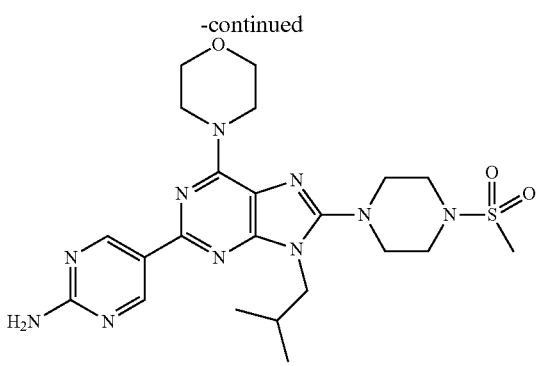

Triethylamine (143 μl) and mesyl chloride (50 μl, 0.63 mmol) were added to 5-(9-isobutyl-6-morpholin-4-yl-8-piperazin-1-yl-9H-purin-2-yl)pyrimidin-2-amine (2 ml of solution of 100 mg of this compound in 1 ml of NMP) and the resulting mixture was stirred for 1 hour. Mesyl chloride (50 μl, 0.63 mmol) was further added, the resulting mixture was stirred for 1 hour, then the reaction mixture was partitioned with ethyl acetate and water, and the organic layer was dried over magnesium sulfate. The solvent was evaporated under reduced pressure and the residue was purified by preparative HPLC (column, NOMURA Develosil Combi-RP-5; mobile phase, acetonitrile/water/formic acid) to give the title compound (135 mg, 51%) as a pale yellow solid.

$^1$H-NMR (DMSO-d$_6$) δ: 0.83 (6H, d, J=6.30 Hz), 2.37-2.42 (1H, m), 2.96 (3H, s), 3.30 (8H, brs), 3.73-3.75 (4H, m), 3.95 (2H, d, J=7.45 Hz), 4.18 (4H, brs), 7.00 (2H, s), 9.06 (2H, s).

Example 2

5-[8-(4-Acetylpiperazin-1-yl)-9-isobutyl-6-morpholin-4-yl-9H-purin-2-yl]pyrimidin-2-amine

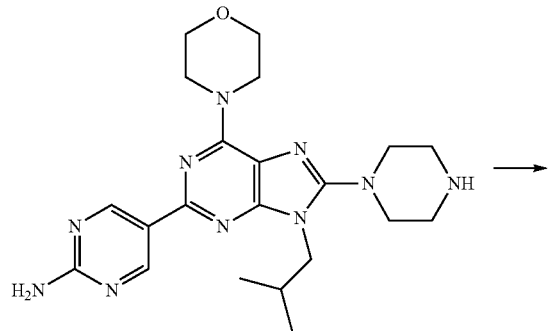

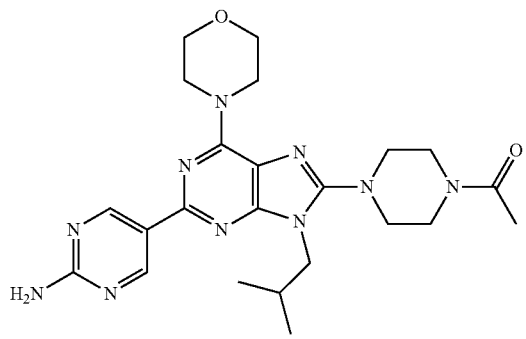

Triethylamine (143 μl) and acetyl chloride (50 μl, 0.72 mmol) were added to 5-(9-isobutyl-6-morpholin-4-yl-8-piperazin-1-yl-9H-purin-2-yl)pyrimidin-2-amine (2 ml of solution of 100 mg of this compound in 1 ml of N-methylpyrrolidone) and the resulting mixture was stirred for 1 hour. The resulting mixture was partitioned with ethyl acetate and water and the organic layer was dried over magnesium sulfate. The solvent was evaporated under reduced pressure, the residue was dissolved in methanol (2 ml) followed by the addition of 25% sodium methoxide-methanol solution (1 ml), and the resulting mixture was stirred for 3 hours. The reaction mixture was partitioned with ethyl acetate and water, the organic layer was dried over magnesium sulfate, and the solvent was evaporated under reduced pressure. Dimethyl sulfoxide (3 ml) was added to the residue, then the resulting mixture was partitioned with ethyl acetate and water, the organic layer was similarly dried, and then the solvent was evaporated to give the title compound (150 mg, 61%) as a pale yellow solid.

$^1$H-NMR (DMSO-d$_6$) δ: 0.83 (6H, d, J=6.87 Hz), 2.05 (3H, s), 2.38-2.43 (1H, m), 3.12-3.15 (2H, m), 3.21-3.22 (2H, m), 3.59-3.62 (4H, m), 3.73-3.75 (5H, m), 3.96 (2H, d, J=7.45 Hz), 4.18 (4H, brs), 6.99 (2H, s), 9.06 (2H, s).

Example 3

5-{9-(Cyclopropylmethyl)-8-[4-(methylsulfonyl)piperazin-1-yl]-6-morpholin-4-yl-9H-purin-2-yl}pyrimidin-2-amine

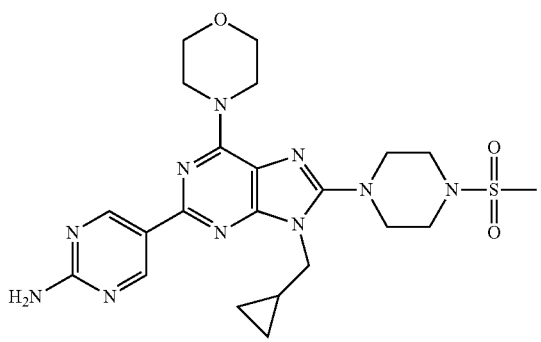

Step 1: 2-Chloro-6-morpholin-4-yl-9H-purine

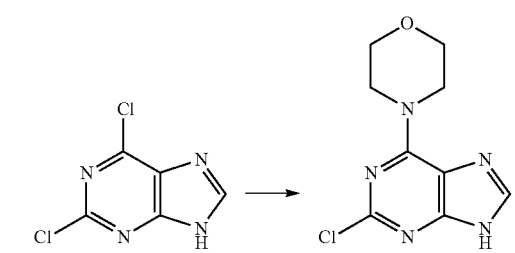

Morpholine (46.9 ml, 538.2 mmol) was added to an ethanol solution (1.2 l) of 2,6-dichloropurine (50.9 g, 269.1 mmol) at room temperature and the resulting mixture was stirred and heated to reflux for 2.5 hours. The reaction mixture was left standing to cool and then concentrated until the solvent was reduced nearly by half in volume and the solid was collected by filtration. The solid was washed with ethanol and dried at 50° C. under reduced pressure to give a mixture (63.3 g, 95%) of the title compound and morpholine hydrochloride (approx. 13:1) as a white solid.

$^1$H-NMR (DMSO-d$_6$) δ: 3.67-3.77 (4H, m), 3.84-4.56 (4H, brm), 8.16 (1H, s).

Step 2: 2-Chloro-9-(cyclopropylmethyl)-6-morpholin-4-yl-9H-purine

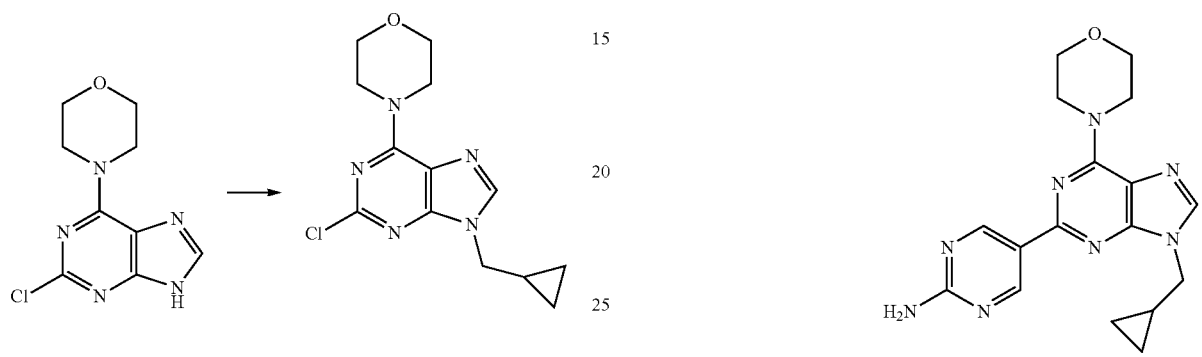

Potassium carbonate (36.0 g, 260.5 mmol) and cyclopropylmethyl bromide (20.2 g, 143.3 mmol) were added to an N,N-dimethylformamide suspension (400 ml) of 2-chloro-6-morpholin-4-yl-9H-purine (32.4 g; purity, approx. 96%; 130.2 mmol) at room temperature and the resulting mixture was stirred at 80° C. for 3 hours in a nitrogen atmosphere. The reaction mixture was left standing to cool, then poured into ethyl acetate, washed with saturated aqueous sodium hydrogen carbonate solution, and dried over anhydrous sodium sulfate. After filtration, the filtrate was concentrated under reduced pressure and the resulting solid was washed with diethyl ether and collected by filtration to give the title compound (26.9 g, 70%) as a colorless acicular crystal. The mother liquor was further concentrated by the same procedure to give the secondary crystal of the title compound (7.68 g, 20%) as a white solid.

$^1$H-NMR (CDCl$_3$) δ: 0.41-0.46 (2H, m), 0.64-0.69 (2H, m), 1.26-1.35 (1H, m), 3.81-3.85 (4H, m), 4.00 (2H, d, J=6.87 Hz), 4.05-4.55 (4H, brm), 7.81 (1H, s).

Step 3: 5-[9-(Cyclopropylmethyl)-6-morpholin-4-yl-9H-purin-2-yl]pyrimidin-2-amine

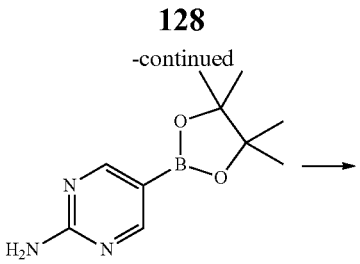

Sodium carbonate (3.25 g, 30.6 mmol) and tetrakis triphenylphosphine palladium (0.59 g, 0.51 mmol) were added to a 1,4-dioxane (60.0 ml)-water (30.0 ml) mixture solution of 2-chloro-9-(cyclopropylmethyl)-6-morpholin-4-yl-9H-purine (3.0 g, 10.2 mmol) and 5-(4,4,5,5-tetramethyl-1,3,2-dioxaborolan-2-yl)pyrimidin-2-amine (2.5 g, 11.2 mmol) at room temperature and the resulting mixture was heated to reflux for 3 hours in an argon atmosphere. The reaction mixture was left standing to cool and then poured into water, and ethyl acetate was added to separate the layers. The solid precipitated in the aqueous layer was collected by filtration, washed with water, and dried at 50° C. under reduced pressure to give the title compound (3.63 g, 100%) as a white solid.

$^1$H-NMR (CDCl$_3$) δ: 0.46-0.52 (2H, m), 0.64-0.70 (2H, m), 1.28-1.39 (1H, m), 3.84-3.90 (4H, m), 4.08 (2H, d, J=7.08 Hz), 4.28-4.46 (4H, m), 5.22 (2H, brs), 7.84 (1H, s), 9.27 (2H, s).

Step 4: Di-tert-butyl {5-[9-(cyclopropylmethyl)-6-morpholin-4-yl-9H-purin-2-yl]pyrimidin-2-yl}imide dicarbonate

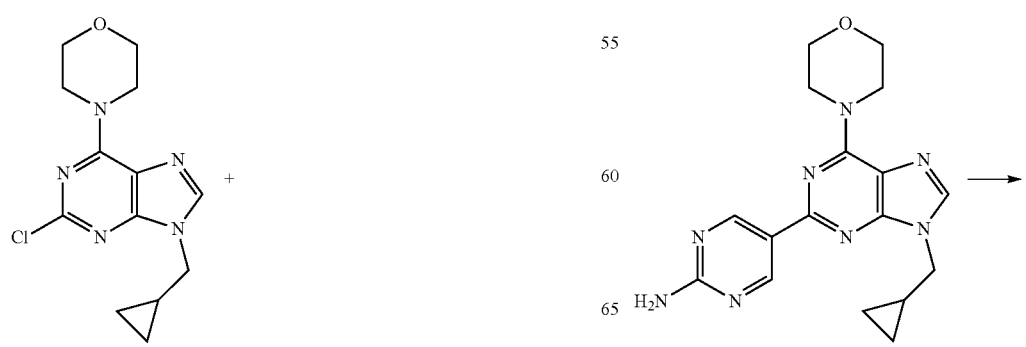

-continued

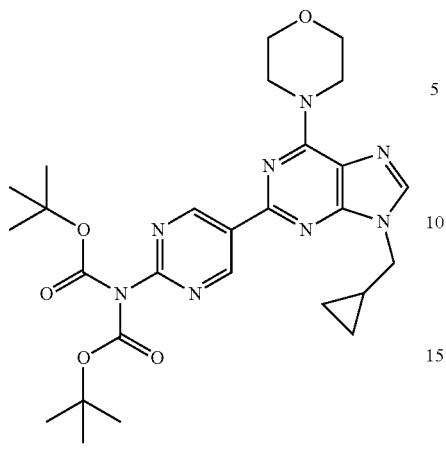

Di-tert-butyl dicarbonate (35.6 g, 163.2 mmol) and 4-dimethylaminopyridine (0.80 g, 6.53 mmol) were added to an N,N-dimethylformamide suspension (350 ml) of 5-[9-(cyclopropylmethyl)-6-morpholin-4-yl-9H-purin-2-yl]pyrimidin-2-amine (11.5 g, 32.6 mmol) at room temperature. The pale orange color reaction mixture solution was stirred for 22 hours and then the reaction mixture was poured into ethyl acetate, washed successively with 10% aqueous citric acid solution and saturated aqueous sodium hydrogen carbonate solution, and dried over anhydrous sodium sulfate. After filtration, the filtrate was concentrated under reduced pressure and the resulting residue was purified by medium pressure liquid chromatography (hexane:ethyl acetate=7:3 to 3:2) to give the title compound (17.4 g, 96%) as a colorless amorphous substance.

$^1$H-NMR (CDCl$_3$) δ: 0.48-0.55 (2H, m), 0.65-0.74 (2H, m), 1.30-1.41 (1H, m), 1.48 (18H, s), 3.85-3.93 (4H, m), 4.08-4.16 (2H, m), 4.29-4.50 (4H, m), 7.90 (1H, s), 9.67 (2H, s)

Step 5: Di-tert-butyl {5-[8-chloro-9-(cyclopropylmethyl)-6-morpholin-4-yl-9H-purin-2-yl]pyrimidin-2-yl}imide dicarbonate -continued N-Chlorosuccinimide (4.6 g, 34.5 mmol) was added to an N,N-dimethylformamide solution (350 ml) of di-tert-butyl {5-[9-(cyclopropylmethyl)-6-morpholin-4-yl-9H-purin-2-yl]pyrimidin-2-yl}imide dicarbonate (17.3 g, 31.3 mmol) at room temperature. The resulting mixture was stirred for 14 hours followed by the addition of N-chlorosuccinimide (2.09 g, 15.7 mmol), N-chlorosuccinimide (1.05 g, 7.83 mmol) was further added 3.5 hours later, and the resulting mixture was stirred for 2 hours. The reaction mixture was poured into ethyl acetate, washed with water, and dried over anhydrous sodium sulfate. After filtration, the filtrate was concentrated under reduced pressure and the resulting residue was purified by silica gel column chromatography (hexane:ethyl acetate=17:3 to hexane:ethyl acetate:dichloromethane=16:4:0.3) to give the title compound (15.31 g, 83%) as a white solid.

$^1$H-NMR (CDCl$_3$) δ: 0.52-0.63 (4H, m), 1.31-1.42 (1H, m), 1.49 (18H, s), 3.83-3.90 (4H, m), 4.13 (2H, d, J=6.88 Hz), 4.19-4.44 (4H, brm), 9.64 (2H, s).

Step 6: 5-[8-Chloro-9-(cyclopropylmethyl)-6-morpholin-4-yl-9H-purin-2-yl]pyrimidin-2-amine

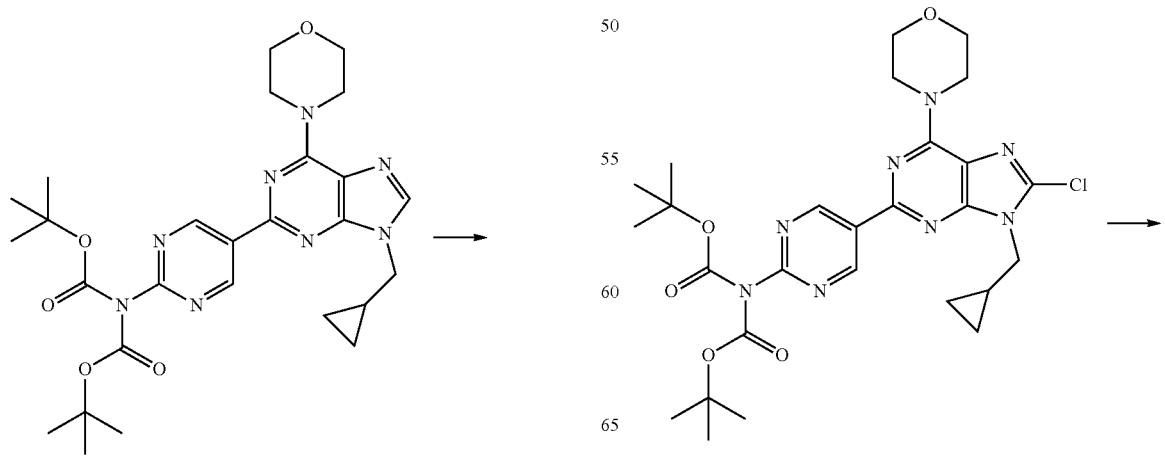

-continued

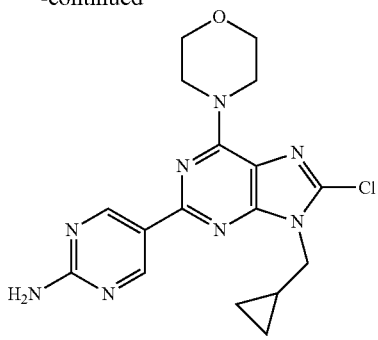

Trifluoroacetic acid (150 ml) was added to a dichloromethane solution (300 ml) of di-tert-butyl {5-[8-chloro-9-(cyclopropylmethyl)-6-morpholin-4-yl-9H-purin-2-yl]pyrimidin-2-yl}imide dicarbonate (15.3 g, 26.1 mmol) with ice cooling and the resulting mixture was stirred at room temperature for 2 hours. The reaction mixture was concentrated, then neutralized with saturated aqueous sodium hydrogen carbonate solution, and extracted with a chloroform-ethyl acetate (5:1) mixed solvent. The organic layer was dried over anhydrous sodium sulfate and, after the reaction mixture was filtered, the filtrate was concentrated under reduced pressure and evaporated to dryness to give the title compound (10.2 g, 100%) as a white solid.

$^1$H-NMR (CDCl$_3$) δ: 0.51-0.60 (4H, m), 1.30-1.42 (1H, m), 3.82-3.89 (4H, m), 4.11 (2H, d, J=7.34 Hz), 4.22-4.36 (4H, brm), 5.16-5.28 (2H, m), 9.24 (2H, s).

Step 7: 5-{9-(Cyclopropylmethyl)-8-[4-(methylsulfonyl)piperazin-1-yl]-6-morpholin-4-yl-9H-purin-2-yl}pyrimidin-2-amine

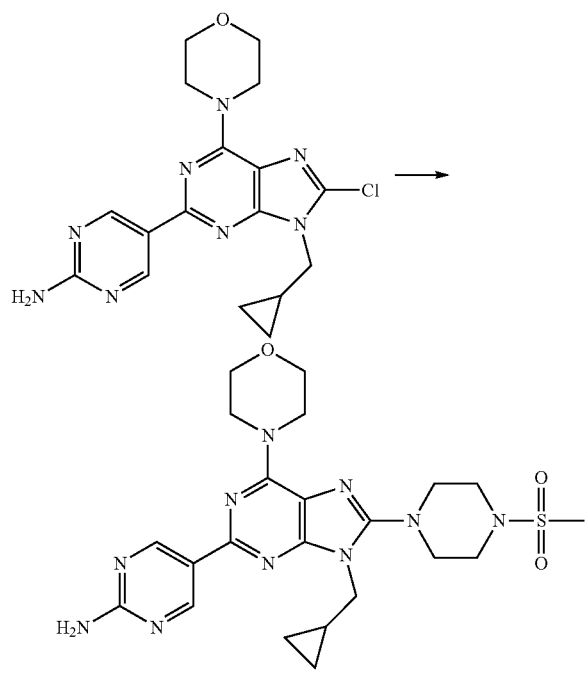

A dimethyl sulfoxide solution (1.0 ml) of 5-[8-chloro-9-(cyclopropylmethyl)-6-morpholin-4-yl-9H-purin-2-yl]pyrimidin-2-amine (101.9 mg, 0.26 mmol) and N-mesylpiperazine (125.8 mg, 0.77 mmol) was heated at 140° C. and stirred for 4 hours followed by the addition of N-mesylpiperazine (83.8 mg, 0.51 mmol) and the resulting mixture was further stirred at 140° C. for 3 hours. The reaction mixture was left standing to cool followed by the addition of dichloromethane-methanol (10:1) and washed with saturated aqueous sodium hydrogen carbonate solution. The organic layer was dried over anhydrous sodium sulfate, the reaction mixture was filtrated, then the filtrate was concentrated under reduced pressure, and the resulting residue was purified by preparative thin layer silica gel chromatography (dichloromethane:methanol=15:1) to give the title compound (89.2 mg, 68%) as a white solid.

$^1$H-NMR (CDCl$_3$) δ: 0.49-0.59 (4H, m), 1.31-1.32 (1H, m), 2.87 (3H, s), 3.36-3.49 (8H, m), 3.82-3.88 (4H, m), 3.96 (2H, d, J=6.87 Hz), 4.18-4.38 (4H, brm), 5.29 (2H, s), 9.23 (2H, s).

Step 8: 5-{9-(Cyclopropylmethyl)-8-[4-(methylsulfonyl)piperazin-1-yl]-6-morpholin-4-yl-9H-purin-2-yl}pyrimidin-2-amine methanesulfonate

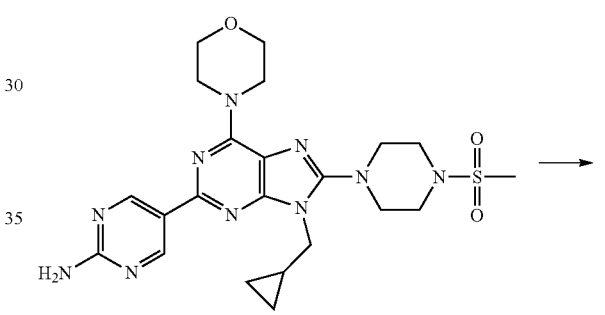

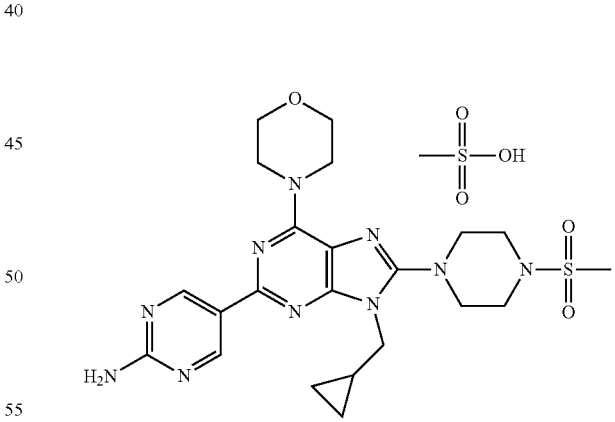

5-{9-(Cyclopropylmethyl)-8-[4-(methylsulfonyl)piperazin-1-yl]-6-morpholin-4-yl-9H-purin-2-yl}pyrimidin-2-amine (149.4 mg, 0.29 mmol) was stirred in a dichloromethane-methanol (3:2) mixed solvent followed by the addition of methanesulfonic acid (18.7 μl, 0.29 mmol) at room temperature and the resulting mixture was stirred for 10 minutes. The reaction mixture was concentrated under reduced pressure and the resulting residue was dried at 60° C. under reduced pressure to give the title compound (176.7 mg, 100%) as a yellow solid.

133

¹H-NMR (CDCl₃) δ: 0.45-0.50 (2H, m), 0.57-0.62 (2H, m), 1.28-1.37 (1H, m), 2.89 (3H, s), 2.94 (3H, s), 3.47 (8H, brs), 3.84-3.90 (4H, m), 3.99 (2H, d, J=6.87 Hz), 4.16-4.37 (4H, brm), 9.32 (2H, brs).

Example 4

5-{9-(Cyclopropylmethyl)-8-[4-(methylsulfonyl)piperazin-1-yl]-6-morpholin-4-yl-9H-purin-2-yl}-N-methylpyrimidin-2-amine

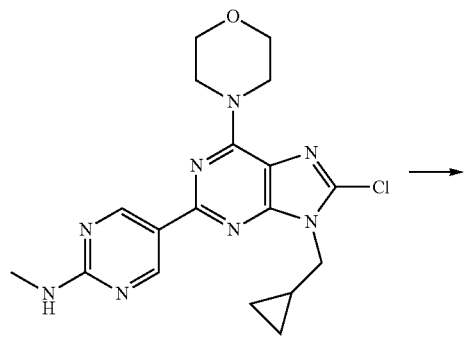

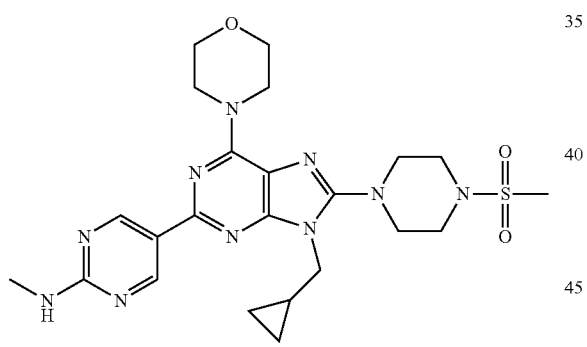

A dimethyl sulfoxide solution (1.0 ml) of 5-[8-chloro-9-(cyclopropylmethyl)-6-morpholin-4-yl-9H-purin-2-yl]-N-methylpyrimidin-2-amine (140.5 mg, 0.29 mmol) and N-mesylpiperazine (190.2 mg, 1.16 mmol) was heated at 140° C. and stirred for 3 hours. N-Mesylpiperazine (190.2 mg, 1.16 mmol) was added, the resulting mixture was further stirred for 5.5 hours and left standing to cool followed by the addition of dichloromethane-methanol (10:1), and the resulting mixture was washed with saturated aqueous sodium hydrogen carbonate solution. The organic layer was dried over anhydrous sodium sulfate, the reaction mixture was filtrated, then the filtrate was concentrated under reduced pressure, and the resulting residue was purified by preparative thin layer silica gel chromatography (dichloromethane:methanol=20:1) to give the title compound (120.5 mg, 79%) as a pale yellow solid.

134

¹H-NMR (CDCl₃) δ: 0.51-0.58 (4H, m), 1.24-1.37 (1H, m), 2.87 (3H, s), 3.08 (3H, d, J=5.04 Hz), 3.37-3.48 (8H, m), 3.82-3.88 (4H, m), 3.95 (2H, d, J=7.34 Hz), 4.19-4.35 (4H, brm), 5.38 (1H, brs), 9.25 (2H, s).

Example 5

5-{8-[4-(Methylsulfonyl)piperazin-1-yl]-6-morpholin-4'-yl-9-(tetrahydrofuran-3-ylmethyl)-9H-purin-2-yl}pyrimidin-2-amine

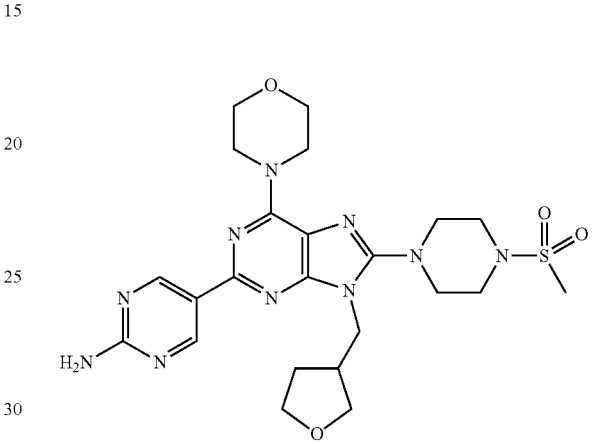

Step 1: 2,6-Dichloro-9-(tetrahydrofuran-3-ylmethyl)-9H-purine

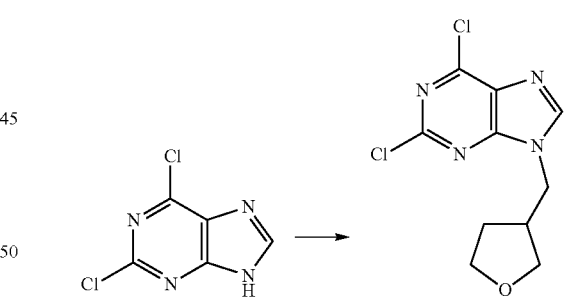

2,6-Dichloropurine (21 g, 113 mmol) and (tetrahydrofuran-3-yl)methanol (11.5 g, 113 mmol) were dissolved in tetrahydrofuran (250 ml) followed by the dropwise addition of triphenylphosphine (33 g, 125 mmol) and a diisopropyl azodicarboxylate (24.5 ml, 125 mmol)-tetrahydrofuran (50 ml) solution with ice cooling and the resulting mixture was stirred at room temperature for 2 hours. The solvent was concentrated under reduced pressure and then the residue was purified by silica gel chromatography (hexane:ethyl acetate=5:1 to 1:1 to 0:1) to give the title compound (44 g) as a pale yellow oil.

Step 2: 2-Chloro-6-morpholin-4-yl-9-(tetrahydrofuran-3-ylmethyl)-9H-purine

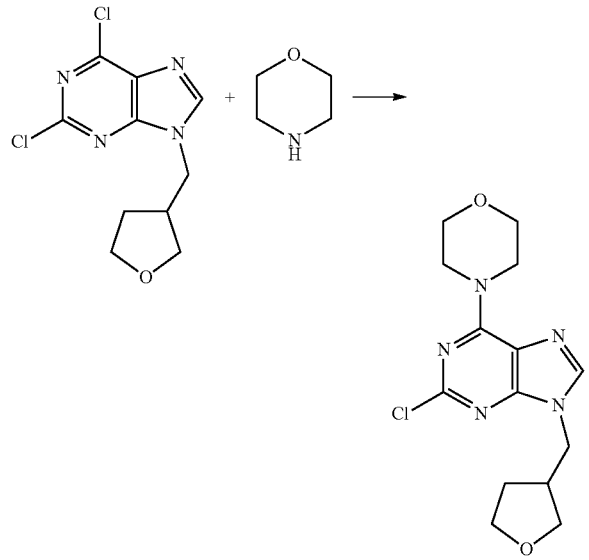

2,6-Dichloro-9-(tetrahydrofuran-3-ylmethyl)-9H-purine (41 g) was dissolved in ethanol (200 ml) followed by the addition of morpholine (20 ml) and the resulting mixture was heated to reflux for 2 hours. The solvent was evaporated under reduced pressure, the residue was partitioned with ethyl acetate and saturated aqueous sodium bicarbonate solution, and the organic layer was washed with water and dried over magnesium sulfate. The solvent was evaporated under reduced pressure, and the residue was purified by silica gel chromatography (hexane:ethyl acetate, 5:5 to 2:8 to 0:10) to give the title compound (41 g) as a white solid.

Step 3: 5-[6-Morpholin-4-yl-9-(tetrahydrofuran-3-ylmethyl)-9H-purin-2-yl]pyrimidin-2-amine

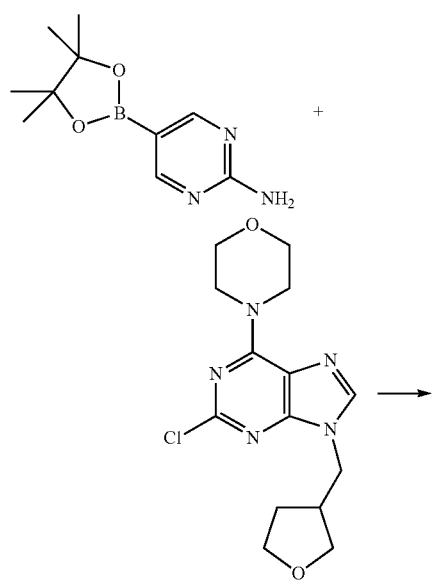

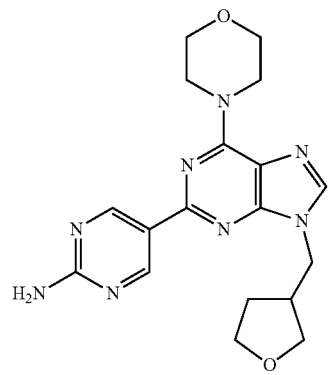

1,4-Dioxane (40 ml), water (20 ml), and sodium carbonate (3.6 g, 33.9 mmol) were added to 5-(4,4,5,5-tetramethyl-1,3,2-dioxaborolan-2-yl)pyrimidin-2-amine (2.5 g, 11.3 mmol) and 2-chloro-6-morpholin-4-yl-9-(tetrahydrofuran-3-ylmethyl)-9H-purine (3.7 g, 11.3 mmol) and the atmosphere in the reaction vessel was substituted with nitrogen. Tetrakis triphenylphosphine palladium (0.65 g, 0.57 mmol) was added, then the atmosphere in the reaction vessel was substituted with nitrogen again, and the resulting mixture was heated to reflux for 2 hours. The reaction mixture was cooled followed by the addition of ethyl acetate and water and the insoluble matter was collected by filtration, then washed with ethyl acetate and water, and dried to give the title compound (2.6 g, 59%) as a pale orange solid.

$^1$H-NMR (DMSO-$d_6$) δ: 1.61-1.69 (1H, m), 1.88-1.96 (1H, m), 2.83-2.90 (1H, m), 3.55 (1H, dd, J=8.78, 5.37 Hz), 3.63-3.70 (2H, m), 3.74-3.82 (5H, m), 4.21 (2H, d, J=7.56 Hz), 4.27 (4H, brs), 7.05 (2H, s), 8.22 (1H, s), 9.10 (2H, s).

Step 4: Di-tert-butyl {5-[6-morpholin-4-yl-9-(tetrahydrofuran-3-ylmethyl)-9H-purin-2-yl]pyrimidin-2-yl}imide dicarbonate

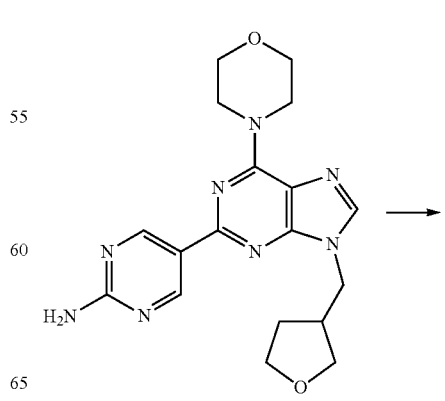

137

-continued

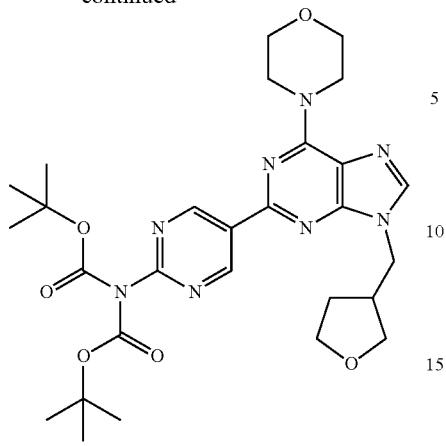

5-[6-Morpholin-4-yl-9-(tetrahydrofuran-3-ylmethyl)-9H-purin-2-yl]pyrimidin-2-amine (2.6 g, 6.8 mmol) was suspended in N,N-dimethylformamide (30 ml) followed by the addition of dimethylaminopyridine (0.17 g, 20.4 mmol) and di-tert-butyl dicarbonate (4.45 g, 20.4 mmol) and the resulting mixture was stirred at 60° C. for 0.5 hours. The reaction mixture was cooled and then partitioned with ethyl acetate and water and the organic layer was washed twice with saturated brine and dried over magnesium sulfate. The solvent was evaporated under reduced pressure and then the residue was purified by silica gel chromatography (hexane:ethyl acetate=2:8 to 4:6 to 5:5) to give the title compound (3.5 g, 88%) as a white solid.

$^1$H-NMR (CDCl$_3$) δ: 1.48 (18H, s), 1.71-1.79 (1H, m), 2.06-2.11 (1H, m), 2.96-3.00 (1H, m), 3.67 (1H, dd, J=9.16, 4.58 Hz), 3.77-3.82 (2H, m), 3.87-3.89 (4H, m), 3.96-4.00 (1H, m), 4.19-4.29 (2H, m), 4.39 (4H, brs), 7.78 (1H, s), 9.66 (2H, s).

Step 5: Di-tert-butyl {5-[8-chloro-6-morpholin-4-yl-9-(tetrahydrofuran-3-ylmethyl)-9H-purin-2-yl]pyrimidin-2-yl}imide dicarbonate

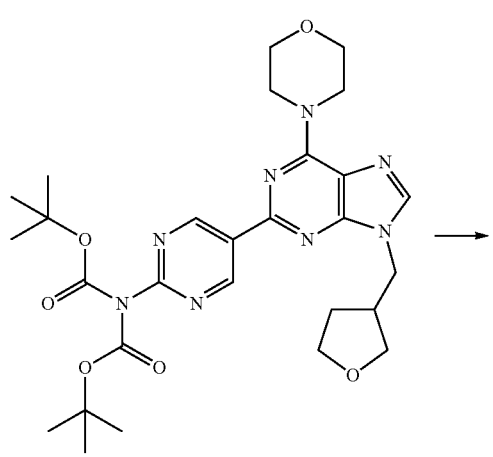

138

-continued

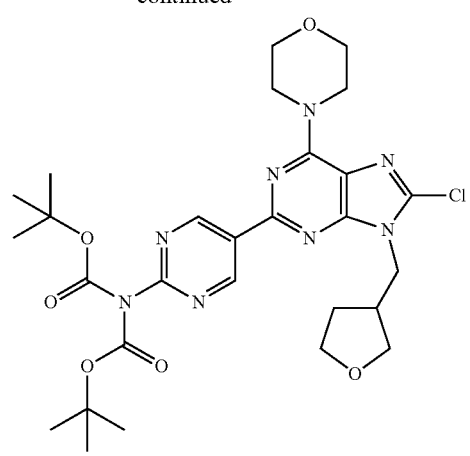

Di-tert-butyl {5-[6-morpholin-4-yl-9-(tetrahydrofuran-3-ylmethyl)-9H-purin-2-yl]pyrimidin-2-yl}imide dicarbonate (3.5 g, 6.01 mmol) was dissolved in N,N-dimethylformamide (30 ml) followed by the addition of N-chlorosuccinimide (1.2 g, 9.01 mmol) and the resulting mixture was stirred for 15 hours. The reaction mixture was partitioned with ethyl acetate and water, the organic layer was dried over magnesium sulfate, and then the solvent was evaporated under reduced pressure. The residue was purified by silica gel chromatography (hexane:ethyl acetate, 8:2 to 4:6) to give the title compound (3.35 g, 96%) as a white solid.

$^1$H-NMR (CDCl$_3$) δ: 1.49 (18H, s), 1.75-1.83 (1H, m), 1.98-2.06 (1H, m), 2.94-3.01 (1H, m), 3.72 (1H, dd, J=9.02, 5.12 Hz), 3.78-3.82 (2H, m), 3.85-3.88 (4H, m), 3.99-4.04 (1H, m), 4.22-4.34 (6H, m), 9.63 (2H, s).

Step 6: 5-[8-Chloro-6-morpholin-4-yl-9-(tetrahydrofuran-3-ylmethyl)-9H-purin-2-yl]pyrimidin-2-amine

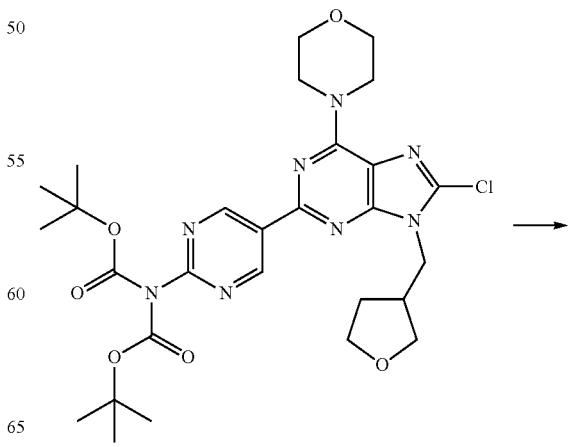

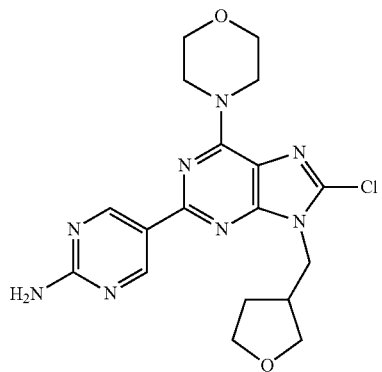

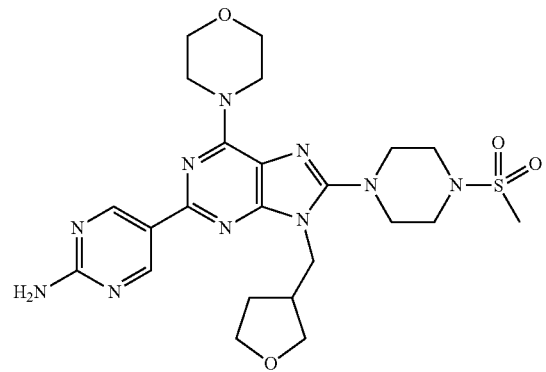

Di-tert-butyl {5-[8-chloro-6-morpholin-4-yl-9-(tetrahydrofuran-3-ylmethyl)-9H-purin-2-yl]pyrimidin-2-yl}imide dicarbonate (2.79 g, 4.52 mmol) was dissolved in methylene chloride (10 ml) followed by the addition of trifluoroacetic acid (20 ml) with ice cooling and the resulting mixture was stirred at room temperature for 1.5 hours. The solvent was evaporated under reduced pressure, the residue was partitioned with chloroform and saturated aqueous sodium bicarbonate solution, the organic layer was dried over magnesium sulfate, and then the solvent was evaporated under reduced pressure to give the title compound (2.1 g, 93%) as a white solid.

$^1$H-NMR (DMSO-$d_6$) δ: 1.65-1.72 (1H, m), 1.89-1.96 (1H, m), 2.81-2.86 (1H, m), 3.59 (1H, dd, J=8.59, 5.15 Hz), 3.63-3.68 (2H, m), 3.74-3.76 (4H, m), 3.83-3.88 (1H, m), 4.17-4.21 (6H, m), 7.12 (2H, s), 9.09 (2H, s).

Step 7: 5-{8-[4-(Methylsulfonyl)piperazin-1-yl]-6-morpholin-4-yl-9-(tetrahydrofuran-3-ylmethyl)-9H-purin-2-yl}pyrimidin-2-amine

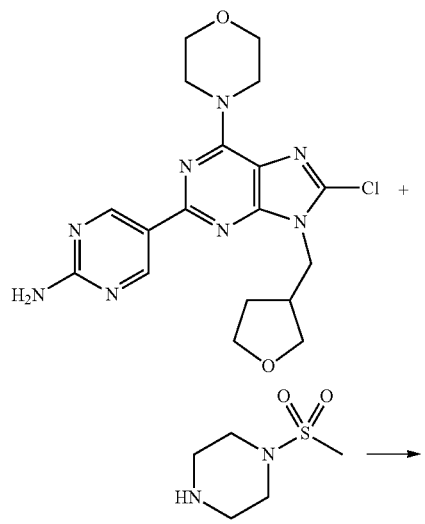

Dimethyl sulfoxide (1 ml) was added to a mixture of 5-[8-chloro-6-morpholin-4-yl-9-(tetrahydrofuran-3-ylmethyl)-9H-purin-2-yl]pyrimidin-2-amine (100 mg, 0.24 mmol) and N-mesylpiperazine (118 mg, 0.72 mmol) and the resulting mixture was stirred at 150° C. for 3 hours. The reaction mixture was cooled and then partitioned with chloroform and water, and the organic layer was washed with water again and then dried over magnesium sulfate. The solvent was evaporated under reduced pressure and then the residue was purified by silica gel chromatography (chloroform:methanol=10:0 to 25:1 to 20:1) to give the title compound (50 mg, 45%) as a pale yellow solid.

$^1$H-NMR (CDCl$_3$) δ: 1.65-1.69 (1H, m), 1.94-2.00 (1H, m), 2.87 (3H, s), 3.07-3.12 (1H, m), 3.35-3.36 (4H, m), 3.43-3.45 (4H, m), 3.63 (1H, dd, J=8.59, 4.58 Hz), 3.70 (1H, dd, J=8.88, 6.59 Hz), 3.74-3.78 (1H, m), 3.85-3.87 (4H, m), 3.93-3.97 (1H, m), 4.05 (1H, dd, J=13.75, 8.02 Hz), 4.12 (1H, dd, J=13.75, 7.45 Hz), 4.28 (4H, brs), 5.23 (2H, s), 9.23 (2H, s).

Example 6

5-{9-(Cyclopropylmethyl)-8-[4-(methylsulfonyl)piperazin-1-yl]-6-morpholin-4-yl-9H-purin-2-yl}-4-methylpyrimidin-2-amine

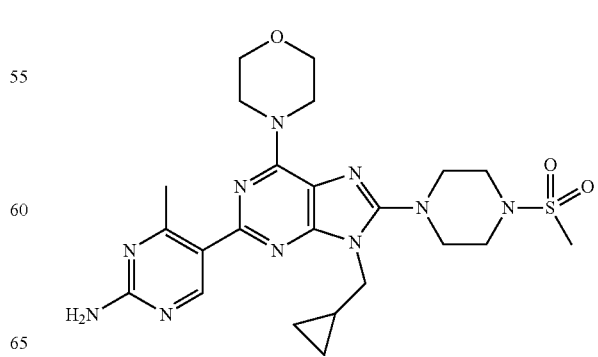

Step 1: Di-tert-butyl {5-[9-(cyclopropylmethyl)-6-morpholin-4-yl-9H-purin-2-yl]-4-methylpyrimidin-2-yl}imide dicarbonate

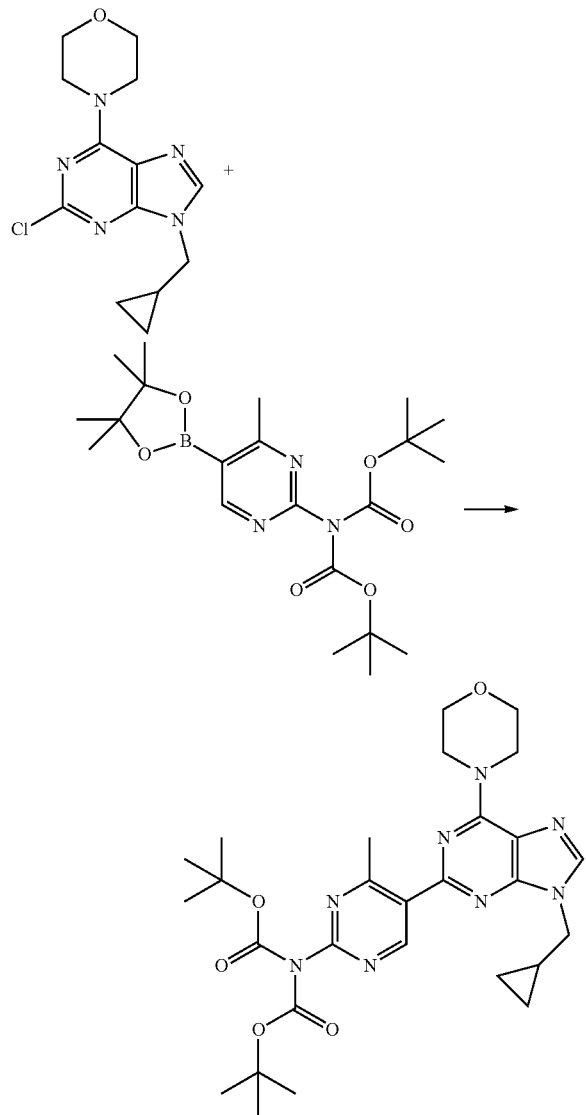

1,4-Dioxane (50 ml) and water (25 ml) were added to 2-chloro-9-cyclopropylmethyl-6-morpholin-4-yl-9H-purine (2.1 g, 7.15 mmol), di-tert-butyl [4-methyl-5-(4,4,5,5-tetramethyl-1,3,2-dioxaborolan-2-yl)pyrimidin-2-yl]imide dicarbonate (3.11 g, 7.15 mmol), and sodium carbonate (2.3 g) and the atmosphere in the reaction vessel was substituted with nitrogen under stirring. Tetrakis triphenylphosphine palladium (0.4 g, 0.36 mmol) was added, the atmosphere in the reaction vessel was substituted with nitrogen again, and then the resulting mixture was heated to reflux for 3 hours. The reaction mixture was partitioned with ethyl acetate and water, the organic layer was dried over magnesium sulfate, and then the solvent was evaporated under reduced pressure. The residue was dissolved in tetrahydrofuran (5 ml) followed by the addition of 4-dimethylaminopyridine (50 mg) and di-tert-butyl dicarbonate (1.0 g, 4.5 mmol) and the resulting mixture was stirred at 50° C. for 1 hour. The solvent was evaporated under reduced pressure and the residue was purified by silica gel chromatography (hexane:ethyl acetate=8:2 to 5:5) to give the title compound (3.25 g, 80%) as a colorless amorphous substance.

$^1$H-NMR (CDCl$_3$) δ: 0.45-0.49 (2H, m), 0.66-0.70 (2H, m), 1.32-1.37 (1H, m), 1.49 (18H, s), 2.91 (3H, s), 3.86-3.88 (4H, m), 4.08 (2H, d, J=7.45 Hz), 4.36 (4H, brs), 7.90 (1H, s), 9.32 (1H, s).

Step 2: Di-tert-butyl {5-[8-chloro-9-(cyclopropylmethyl)-6-morpholin-4-yl-9H-purin-2-yl]-4-methylpyrimidin-2-yl}imide dicarbonate

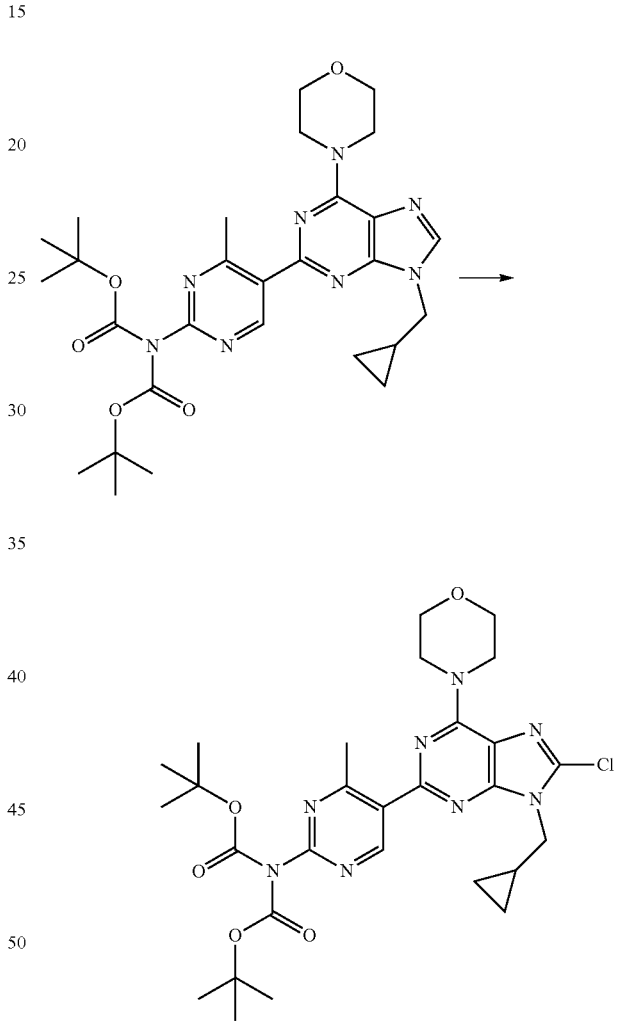

Di-tert-butyl {5-[9-(cyclopropylmethyl)-6-morpholin-4-yl-9H-purin-2-yl]-4-methylpyrimidin-2-yl}imide dicarbonate (3.2 g, 5.65 mmol) was dissolved in N,N-dimethylformamide (20 ml) followed by the addition of N-chlorosuccinimide (1.6 g) and the resulting mixture was stirred for 2 hours. The reaction mixture was partitioned with ethyl acetate and water, the organic layer was washed twice with water and then dried over magnesium sulfate, the solvent was evaporated under reduced pressure, and the residue was purified by silica gel chromatography (hexane:ethyl acetate=9:1 to 6:4) to give the title compound (2.73 g, 80%) as a colorless oil.

$^1$H-NMR (CDCl$_3$) δ: 0.51-0.59 (4H, m), 1.34-1.40 (1H, m), 1.50 (18H, s), 2.89 (3H, s), 3.84-3.86 (4H, m), 4.11 (2H, d, J=7.32 Hz), 4.28 (4H, brs), 9.30 (1H, s).

Step 3: 5-[8-Chloro-9-(cyclopropylmethyl)-6-morpholin-4-yl-9H-purin-2-yl]-4-methylpyrimidin-2-amine

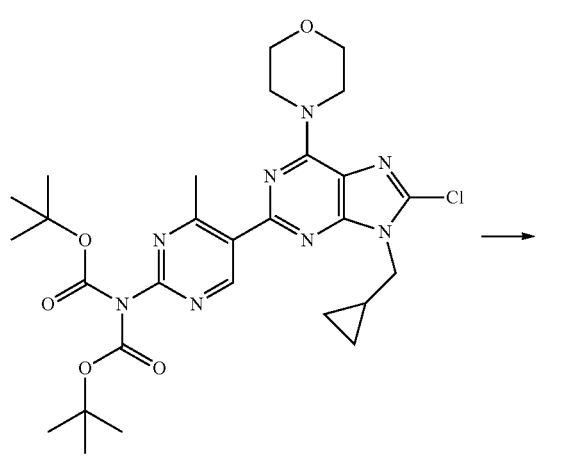

Di-tert-butyl {5-[8-chloro-9-(cyclopropylmethyl)-6-morpholin-4-yl-9H-purin-2-yl]-4-methylpyrimidin-2-yl}imide dicarbonate (2.7 g, 4.5 mmol) was dissolved in methylene chloride (5 ml) followed by the addition of trifluorbacetic acid (15 ml) and the resulting mixture was stirred for 1 hour. The solvent was evaporated under reduced pressure, then the residue was partitioned with chloroform and saturated aqueous sodium bicarbonate solution, the organic layer was dried over magnesium sulfate, and then the solvent was evaporated under reduced pressure to give the title compound (1.67 g, 93%) as a white solid.

$^1$H-NMR (DMSO-d$_6$) δ: 0.46-0.55 (4H, m), 1.28-1.33 (1H, m), 2.64 (3H, s), 3.73-3.75 (4H, m), 4.08 (2H, d, J=7.07 Hz), 4.16 (4H, brs), 6.84 (2H, s), 8.83 (1H, s).

Step 4: 5-{9-(Cyclopropylmethyl)-8-[4-(methylsulfonyl)piperazin-1-yl]-6-morpholin-4-yl-9H-purin-2-yl}-4-methylpyrimidin-2-amine

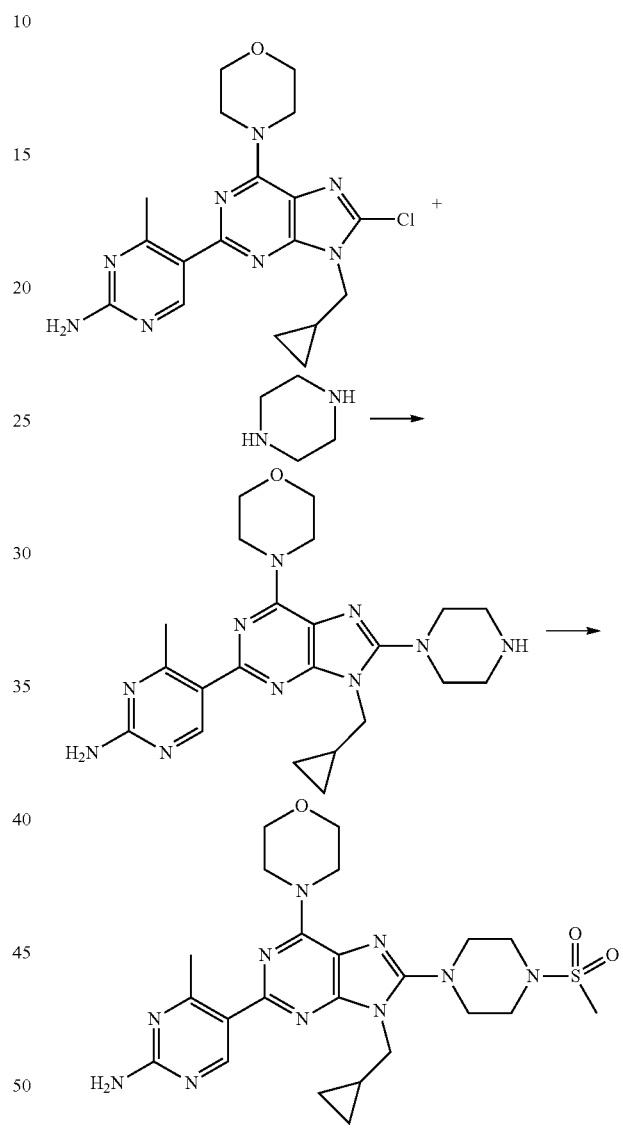

N-Methylpyrrolidone (2 ml) was added to 5-[8-chloro-9-(cyclopropylmethyl)-6-morpholin-4-yl-9H-purin-2-yl]-4-methylpyrimidin-2-amine (200 mg, 0.50 mmol) and piperazine (430 mg, 5.0 mmol) and the resulting mixture was stirred at 120° C. for 2 hours. The reaction mixture was partitioned with ethyl acetate and water and the organic layer was washed with saturated brine and dried over magnesium sulfate. The solvent was evaporated under reduced pressure, the residue was dissolved in tetrahydrofuran (2 ml) followed by the addition of triethylamine (140 μl, 1.0 mmol) and mesyl chloride (50 μl, 0.65 mmol) and the resulting mixture was stirred for 1 hour. The reaction mixture was partitioned with ethyl acetate and water and the organic layer was washed with saturated brine and dried over magnesium sulfate. The solvent was evaporated under reduced pressure and then the residue was purified by preparative HPLC (column, NOMURA Develosil Combi-RP-5; mobile phase, acetonitrile/water/formic acid) to give the title compound (135 mg, 51%) as a white solid.

$^1$H-NMR (DMSO-d$_6$) δ: 0.43-0.50 (4H, m), 1.35-1.39 (1H, m), 2.63 (3H, s), 2.96 (3H, s), 3.73-3.75 (4H, m), 3.97 (2H, d, J=6.87 Hz), 4.15 (4H, brs), 6.77 (2H, s), 8.79 (1H, s).

Example 7

5-{9-(Cyclopropylmethyl)-8-[4-(methylsulfonyl)piperazin-1-yl]-6-morpholin-4-yl-9H-purin-2-yl}-4-(trifluoromethyl)pyrimidin-2-amine

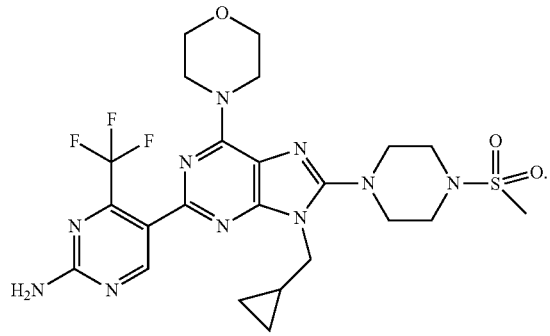

Step 1:
5-Bromo-4-(trifluoromethyl)pyrimidin-2-amine

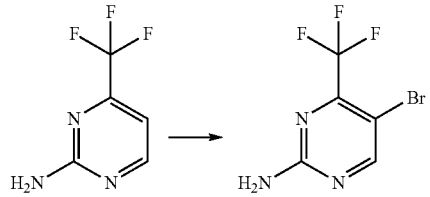

4-(Trifluoromethyl)pyrimidin-2-ylamine (2 g, 12.3 mmol) was suspended in chloroform (70 ml) followed by the addition of N-bromosuccinimide (3.3 g, 18.4 mmol) and the resulting mixture was stirred at 50° C. for 5 hours and then at room temperature for 15 hours. A mixture of methylene chloride (50 ml) and 1 M sodium hydroxide (50 ml) was added, the resulting mixture was stirred, and then the organic layer was fractionated and dried over magnesium sulfate. The solvent was evaporated under reduced pressure to give the title compound (2.2 g, 75%) as a pale orange solid.

$^1$H-NMR (CDCl$_3$) δ: 5.37 (2H, brs), 8.52 (1H, s).

Step 2: Di-tert-butyl [5-bromo-4-(trifluoromethyl)pyrimidin-2-yl]imide dicarbonate

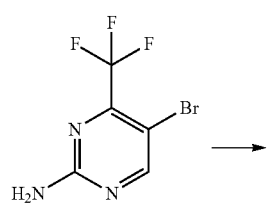

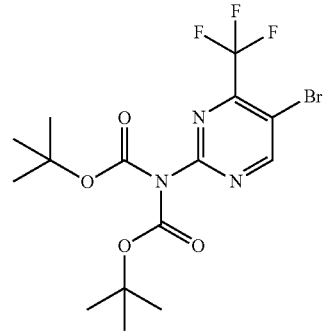

5-Bromo-4-(trifluoromethyl)pyrimidin-2-amine (2.2 g, 9.1 mmol) was dissolved in tetrahydrofuran (50 ml) followed by the addition of di-tert-butyl dicarbonate (9.9 g, 46 mmol) and 4-dimethylaminopyridine (110 mg, 0.91 mmol) and the resulting mixture was stirred at 50° C. for 2 hours. The solvent was evaporated under reduced pressure and the residue was purified by silica gel chromatography (hexane:ethyl acetate=9:1) to give the title compound (5.3 g) as a pale yellow oil.

Step 3: 6-Chloro-9-(tetrahydro-2H-pyran-2-yl)-9H-purine

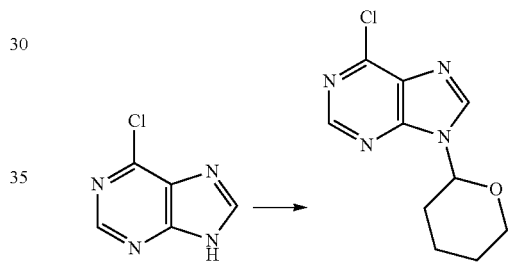

Ethyl acetate (300 ml) was added to 6-chloropurine (25 g, 162 mmol) and tosylic acid monohydrate (460 mg, 2.43 mmol) and the resulting mixture was heated at 60° C. Dihydropyrane (16 ml, 178 mmol) was added and the resulting mixture was stirred at the same temperature for 30 minutes. The reaction mixture was cooled to room temperature followed by the addition of 28% aqueous ammonia solution (15 ml) and the organic layer was fractionated, washed with water, and dried over magnesium sulfate. The solvent was evaporated under reduced pressure to give the title compound (35 g, 91%) as a pale yellow solid.

Step 4: 6-Chloro-9-(tetrahydro-2H-pyran-2-yl)-2-(tributylstannyl)-9H-purine

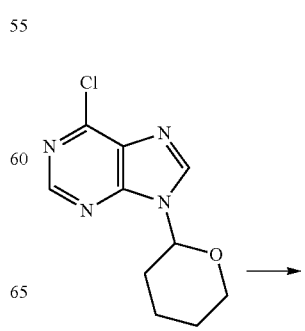

-continued

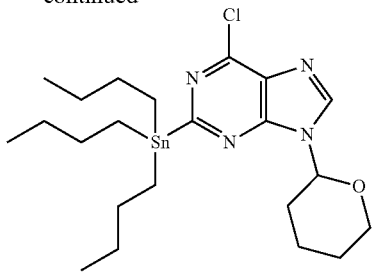

2,2,6,6-Tetramethylpiperidine (26.5 ml, 157 mmol) was dissolved in tetrahydrofuran (200 ml) in an argon atmosphere and n-butyl lithium (2.6 M hexane solution, 54 ml) was added dropwise at room temperature. After the completion of dropwise addition, the resulting mixture was stirred for 15 minutes. The reaction mixture was cooled to −78° C. followed by the dropwise addition of a tetrahydrofuran (30 ml) solution of 6-chloro-9-(tetrahydro-2H-pyran-2-yl)-9H-purine (7.5 g, 31.4 mmol) and the resulting mixture was stirred at the same temperature for 40 minutes. Tetrabutyltin chloride (26 ml, 94.3 mmol) was added dropwise to this solution and the resulting mixture was stirred for 30 minutes. An aqueous ammonium chloride solution was added, the resulting mixture was heated to room temperature followed by the addition of ethyl acetate, and the organic layer was fractionated. The organic layer was washed with water and saturated brine and dried over magnesium sulfate and the solvent was evaporated under reduced pressure. The residue was purified by silica gel chromatography (hexane:ethyl acetate=9:1 to 8:2 to 7:3 to 6:4 to 5:5) to give the title compound (13.3 g, 80%) as a pale yellow oil.

$^1$H-NMR (CDCl$_3$) δ: 0.90 (9H, t, J=7.32 Hz), 1.18-1.40 (14H, m), 1.60-1.80 (9H, m), 2.07-2.20 (3H, m), 3.75-3.81 (1H, m), 4.17-4.21 (1H, m), 5.78 (1H, dd, J=10.12, 2.56 Hz), 8.21 (1H, s).

Step 5: 6-Morpholin-4-yl-9-(tetrahydro-2H-pyran-2-yl)-2-(tributylstannyl)-9H-purine 6-Chloro-9-(tetrahydro-2H-pyran-2-yl)-2-(tributylstannyl)-9H-purine (3.3 g, 6.25 mmol) was dissolved in acetonitrile (30 ml) followed by the addition of morpholine (2.2 ml, 25 mmol) and the resulting mixture was heated to reflux for 1 hour. The reaction mixture was partitioned with ethyl acetate and saturated aqueous sodium bicarbonate solution, the organic layer was dried over magnesium sulfate, and then the solvent was evaporated under reduced pressure. The residue was purified by silica gel chromatography (hexane:ethyl acetate=9:1 to 8:2) to give the title compound (3.3 g, 91%) as a pale yellow oil.

$^1$H-NMR (CDCl$_3$) δ: 0.87-0.91 (9H, m), 1.04-1.17 (6H, m), 1.32-1.41 (6H, m), 1.58-1.68 (8H, m), 1.72-1.80 (2H, m), 1.95-2.12 (3H, m), 3.74-3.79 (1H, m), 3.81-3.82 (4H, m), 4.15-4.17 (1H, m), 4.28 (4H, brs), 5.76 (1H, dd, J=10.31, 2.29 Hz), 7.87 (1H, s).

Step 6: Di-tert-butyl {5-[6-morpholin-4-yl-9-(tetrahydro-2H-pyran-2-yl)-9H-purin-2-yl]-4-(trifluoromethyl)pyrimidin-2-yl}imide dicarbonate

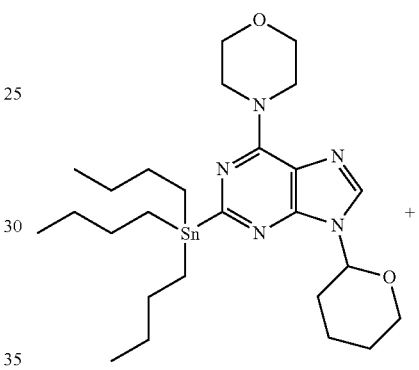

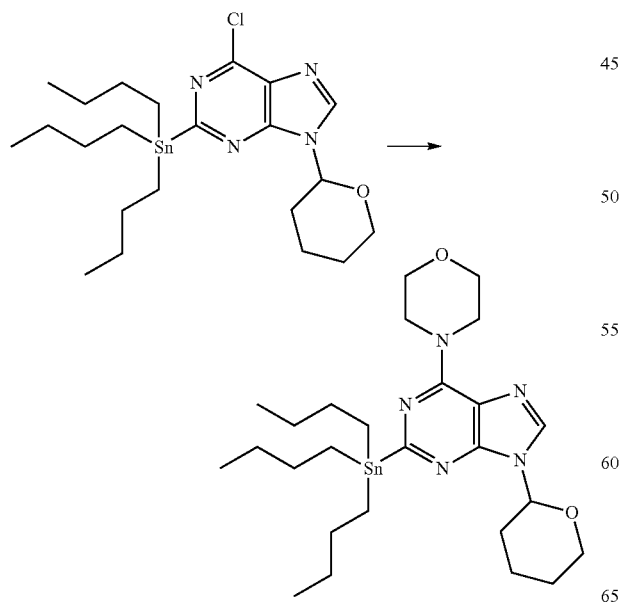

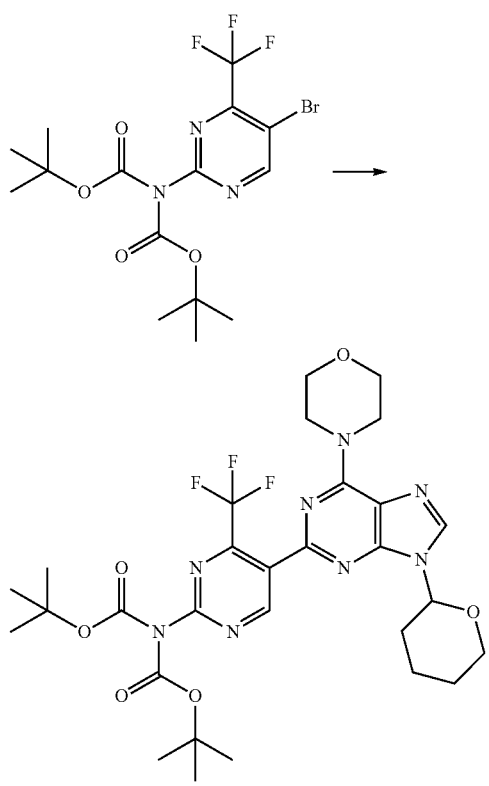

Bistriphenylphosphinopalladium dichloride (120 mg, 0.17 mmol) and di-tert-butyl-p-cresol (catalytic amount) were added to a 1,4-dioxane (20 ml) solution of 6-morpholin-4-yl-9-(tetrahydro-2H-pyran-2-yl)-2-(tributylstannyl)-9H-purine (1.0 g, 1.73 mmol) and di-tert-butyl [5-bromo-4-(trifluoromethyl)pyrimidin-2-yl]imide dicarbonate (0.76 g, 1.73 mmol) and the resulting mixture was heated to reflux for 7 hours in a nitrogen atmosphere. The reaction mixture was cooled and partitioned with ethyl acetate and water, the organic layer was dried over magnesium sulfate, and then the solvent was evaporated under reduced pressure. The residue was purified by silica gel chromatography (hexane:ethyl acetate=9:1 to 8:2 to 7:3) to give the title compound (0.64 g, 57%) as a colorless oil.

$^1$H-NMR (CDCl$_3$) δ: 1.51 (19H, s), 1.63-1.67 (1H, m), 1.73-1.80 (1H, m), 1.99-2.09 (2H, m), 2.12-2.16 (1H, m), 3.75-3.80 (1H, m), 3.83-3.84 (4H, m), 4.17-4.20 (1H, m), 4.34 (4H, brs), 5.73 (1H, dd, J=10.31, 2.29 Hz), 8.02 (1H, s), 9.39 (1H, s).

Step 7: Di-tert-butyl [5-(8-chloro-6-morpholin-4-yl-9H-purin-2-yl)-4-(trifluoromethyl)pyrimidin-2-yl]imide dicarbonate

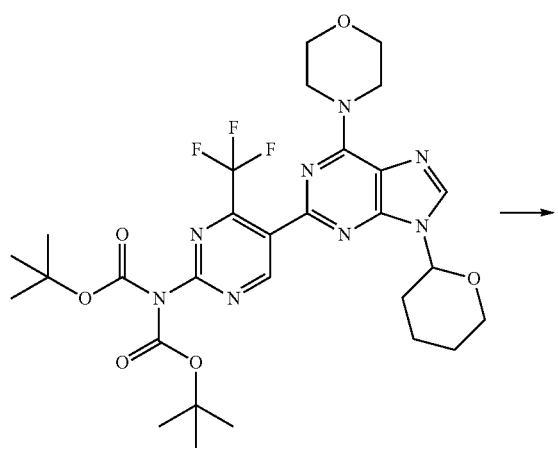

Di-tert-butyl {5-[6-morpholin-4-yl-9-(tetrahydro-2H-pyran-2-yl)-9H-purin-2-yl]-4-(trifluoromethyl)pyrimidin-2-yl}imide dicarbonate (600 mg, 1.04 mmol) was dissolved in N,N-dimethylformamide (5 ml) followed by the addition of N-chlorosuccinimide (208 mg, 1.56 mmol) and the resulting mixture was stirred for 5 hours. The reaction mixture was partitioned with ethyl acetate and water, the organic layer was dried over magnesium sulfate, and the solvent was evaporated under reduced pressure. The residue was purified by silica gel chromatography (hexane:ethyl acetate=9:1 to 6:4) to give the title compound (136 mg, 22%) as a white solid.

$^1$H-NMR (CDCl$_3$) δ: 1.53 (20H, s), 3.80-3.83 (4H, m), 4.27 (4H, s), 9.29 (1H, s).

Step 8: 5-[8-Chloro-9-(cyclopropylmethyl)-6-morpholin-4-yl-9H-purin-2-yl]-4-(trifluoromethyl)pyrimidin-2-amine

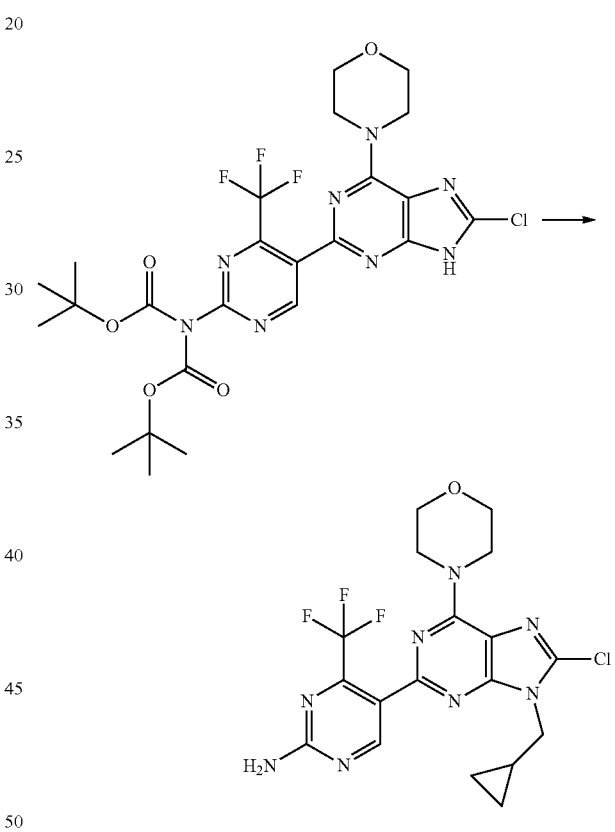

Di-tert-butyl [5-(8-chloro-6-morpholin-4-yl-9H-purin-2-yl)-4-(trifluoromethyl)pyrimidin-2-yl]imide dicarbonate (136 mg, 0.23 mmol) was dissolved in N,N-dimethylformamide (2 ml) followed by the addition of cesium carbonate (150 mg, 0.45 mmol) and cyclopropylmethyl bromide (45 μl, 0.45 mmol) and the resulting mixture was stirred at 60° C. for 8 hours. The reaction mixture was partitioned with ethyl acetate and water, the organic layer was washed with saturated brine and dried over magnesium sulfate, and the solvent was evaporated under reduced pressure. Trifluoroacetic acid (1 ml) was added to the residue, the resulting mixture was stirred for 2 hours, and the solvent was evaporated under reduced pressure. The residue was partitioned with methylene chloride and saturated aqueous sodium bicarbonate solution, the organic layer was dried over magnesium sulfate, and then the solvent was evaporated under reduced pressure. The residue was purified by silica gel chromatography (methylene chloride:methanol=10:0 to 20:1) to give the title compound (75 mg, 73%) as a white solid.

$^1$H-NMR (CDCl$_3$) δ: 0.48-0.59 (4H, m), 1.34-1.40 (1H, m), 3.82-3.84 (4H, m), 4.08 (2H, d, J=7.32 Hz), 4.26 (4H, brs), 5.40 (2H, brs), 8.93 (1H, s).

Step 9: 5-{9-(Cyclopropylmethyl)-8-[4-(methylsulfonyl)piperazin-1-yl]-6-morpholin-4-yl-9H-purin-2-yl}-4-(trifluoromethyl)pyrimidin-2-amine

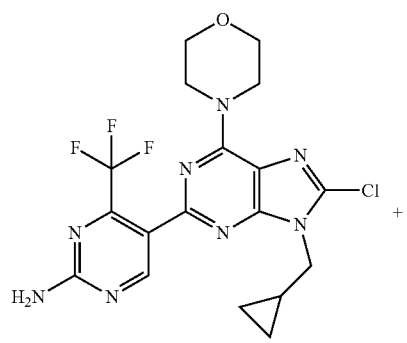

+

N-Methylpyrrolidone (1 ml) was added to 5-[8-chloro-9-(cyclopropylmethyl)-6-morpholin-4-yl-9H-purin-2-yl]-4-(trifluoromethyl)pyrimidin-2-amine (75 mg, 0.16 mmol) and N-methanesulfonylpiperazine (135 mg, 0.8 mmol) and the resulting mixture was stirred at 150° C. for 7 hours. The reaction mixture was partitioned with ethyl acetate and water and the organic layer was washed with saturated brine and dried over magnesium sulfate. The solvent was evaporated under reduced pressure and then the residue was purified by preparative HPLC (column; NOMURA Develosil Combi-RP-5; mobile phase, acetonitrile/water/formic acid) to give the title compound (45 mg, 47%) as a white solid.

$^1$H-NMR (DMSO-d$_6$) δ: 0.40-0.48 (4H, m), 1.35-1.40 (1H, m), 2.96 (3H, s), 3.32-3.34 (16H, m), 3.71-3.73 (4H, m), 3.96 (2H, d, J=6.87 Hz), 4.15 (4H, brs), 7.49 (2H, brs), 8.84 (1H, s).

Example 8

5-{8-[4-(Methylsulfonyl)piperazin-1-yl]-6-morpholin-4-yl-9-(2,2,2-trifluoroethyl)-9H-purin-2-yl}pyrimidin-2-amine

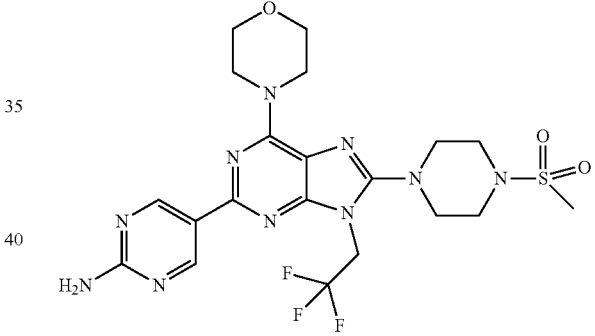

Step 1: 2-Chloro-6-morpholin-4-yl-9-(2,2,2-trifluoroethyl)-9H-purine

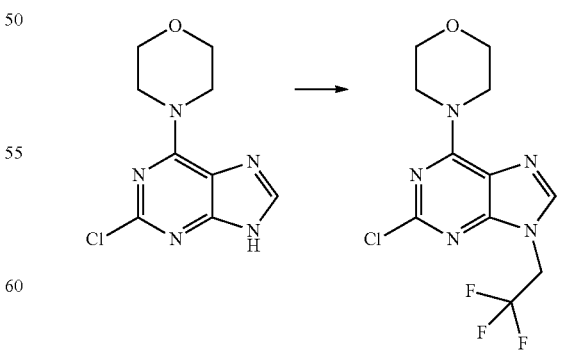

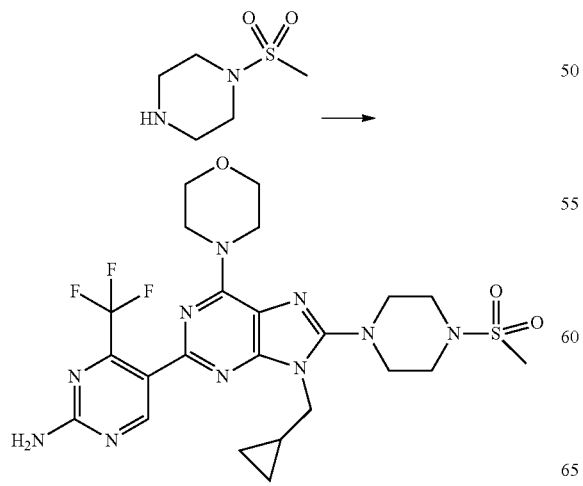

The title compound was synthesized by using 2,2,2-trifluoroethyl trifluoromethanesulfonate as an alkylating agent in the same way as in Step 1 of Example 1.

¹H-NMR (CDCl₃) δ: 3.80-3.86 (4H, m), 4.62-3.95 (4H, m), 4.77 (2H, q, J=8.5 Hz), 7.78 (1H, s).

Step 2: 5-[6-Morpholin-4-yl-9-(2,2,2-trifluoroethyl)-9H-purin-2-yl]pyrimidin-2-amine

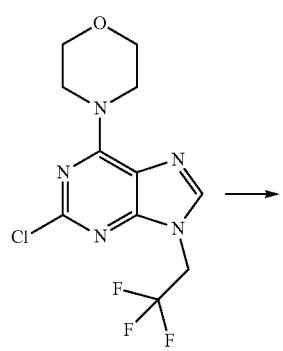

The title compound was synthesized in the same way as in Step 3 of Example 3.
¹H-NMR (DMSO-d₆) δ: 3.69-3.78 (4H, m), 4.17-4.37 (4H, m), 5.13-5.26 (2H, m), 7.05 (2H, brs), 8.21 (1H, s), 9.11 (2H, s).

Step 3: Di-tert-butyl {5-[6-morpholin-4-yl-9-(2,2,2-trifluoroethyl)-9H-purin-2-yl]pyrimidin-2-yl}imide dicarbonate

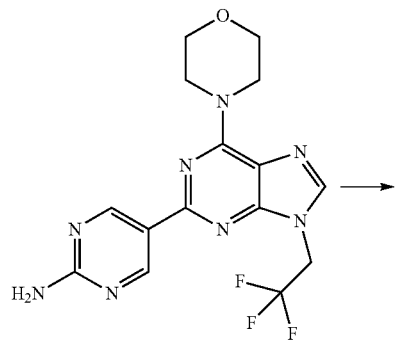

-continued

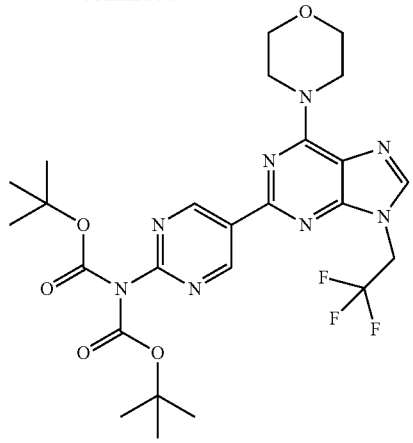

The title compound was synthesized in the same way as in Step 4 of Example 3.
¹H-NMR (CDCl₃) δ: 1.46 (18H, s), 3.85-3.91 (4H, m), 4.26-4.52 (4H, m), 4.88 (2H, q, J=8.2 Hz), 7.87 (1H, s), 9.65 (2H, s).

Step 4: Di-tert-butyl {5-[8-chloro-6-morpholin-4-yl-9-(2,2,2-trifluoroethyl)-9H-purin-2-yl]pyrimidin-2-yl}imide dicarbonate

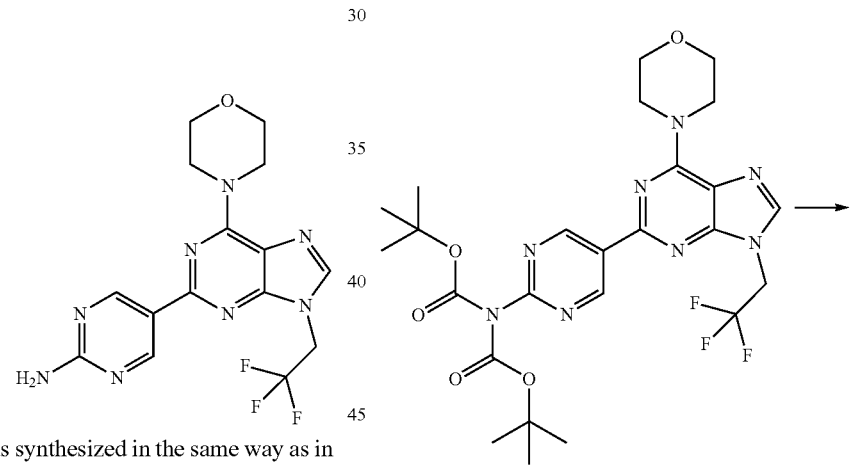

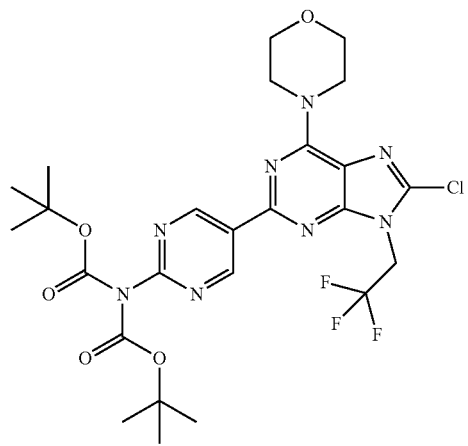

The title compound was synthesized in the same way as in Step 5 of Example 3.

¹H-NMR (CDCl₃) δ: 1.48 (18H, s), 3.84-3.90 (4H, m), 4.20-4.44 (4H, m), 4.86 (2H, q, J=8.2 Hz), 9.62 (2H, s).

Step 5: tert-Butyl {5-[6-morpholin-4-yl-8-piperazin-1-yl-9-(2,2,2-trifluoroethyl)-9H-purin-2-yl]pyrimidin-2-yl}carbamate

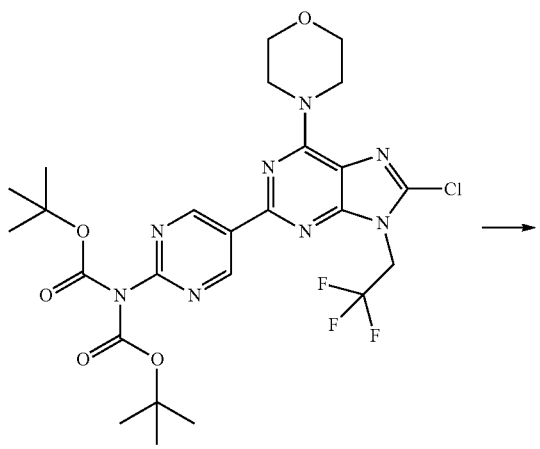

The title compound was synthesized in the same way as in Step 4 of Example 6.

¹H-NMR (CDCl₃) δ: 1.57 (9H, s), 2.62 (1H, s), 3.05-3.12 (4H, m), 3.20-3.26 (4H, m), 3.82-3.89 (4H, m), 4.24-4.35 (4H, m), 4.72 (2H, q, J=8.2 Hz), 8.55 (1H, brs), 9.50 (2H, s).

Step 6: tert-Butyl (5-{8-[4-(methylsulfonyl)piperazin-1-yl]-6-morpholin-4-yl-9-(2,2,2-trifluoroethyl)-9H-purin-2-yl}pyrimidin-2-yl)carbamate

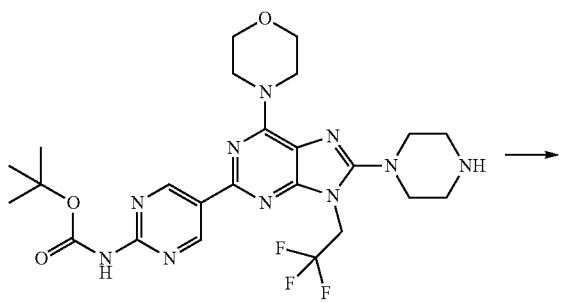

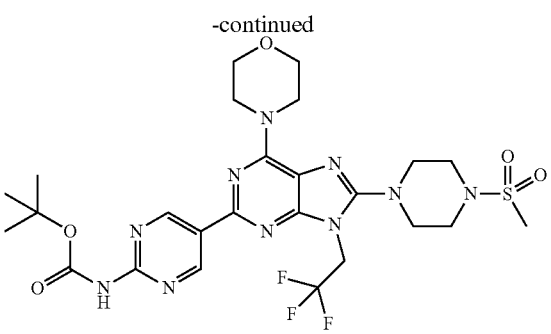

The title compound was synthesized in the same way as in Step 4 of Example 6.

¹H-NMR (CDCl₃) δ: 1.58 (9H, s), 2.87 (3H, s), 3.30-3.36 (4H, m), 3.42-3.47 (4H, m), 3.82-3.88 (4H, m), 4.23-4.34 (4H, m), 4.72 (2H, q, J=8.2 Hz), 7.68 (1H, brs), 9.47 (2H, s).

Step 7: 5-{8-[4-(Methylsulfonyl)piperazin-1-yl]-6-morpholin-4-yl-9-(2,2,2-trifluoroethyl)-9H-purin-2-yl}pyrimidin-2-amine

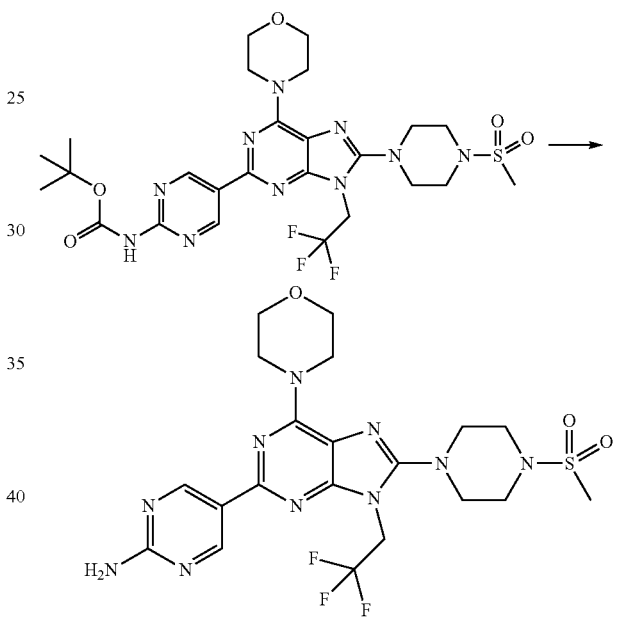

The title compound was synthesized in the same way as in Step 3 of Example 6.

¹H-NMR (CDCl₃) δ: 2.87 (3H, s), 3.29-3.35 (4H, m), 3.42-3.47 (4H, m), 3.82-3.88 (4H, m), 4.23-4.32 (4H, m), 4.71 (2H, q, J=8.2 Hz), 5.22 (2H, brs), 9.23 (1H, s).

Step 8: 5-{8-[4-(Methylsulfonyl)piperazin-1-yl]-6-morpholin-4-yl-9-(2,2,2-trifluoroethyl)-9H-purin-2-yl}pyrimidin-2-amine methanesulfonate

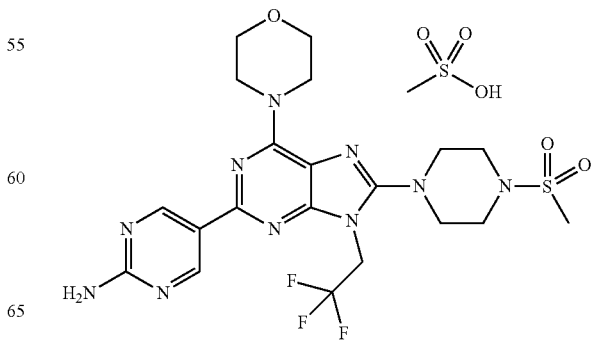

The title compound was synthesized in the same way as in Step 8 of Example 3.

¹H-NMR (CDCl₃) δ: 2.89 (3H, s), 2.91 (3H, s), 3.30-3.37 (4H, m), 3.42-3.48 (4H, m), 3.84-3.89 (4H, m), 4.23-4.34 (4H, m), 4.73 (2H, q, J=8.2 Hz), 8.25 (2H, brs), 9.33 (2H, s).

Example 9

5-[8-(4-Acetylpiperazin-1-yl)-6-morpholin-4-yl-9-(2,2,2-trifluoroethyl)-9H-purin-2-yl]pyrimidin-2-amine

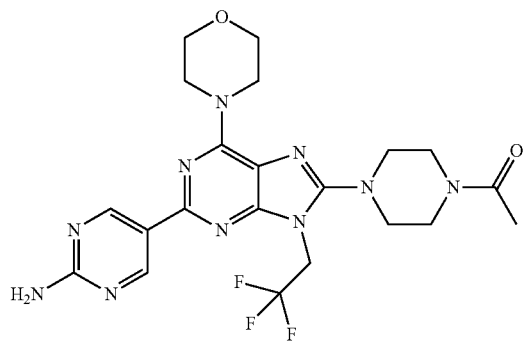

Step 1: tert-Butyl {5-[8-(4-acetylpiperazin-1-yl)-6-morpholin-4-yl-9-(2,2,2-trifluoroethyl)-9H-purin-2-yl]pyrimidin-2-yl}carbamate

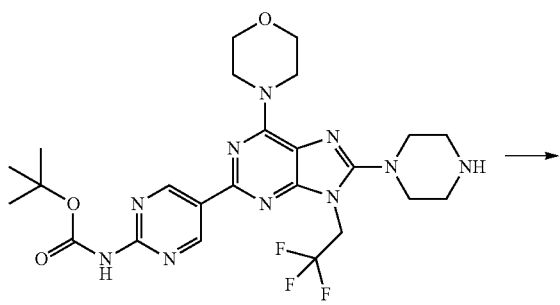

The title compound was synthesized by a known acetylating method using acetic anhydride and pyridine.

¹H-NMR (CDCl₃) δ: 1.56 (9H, s), 2.16 (3H, s), 3.15-3.21 (2H, m), 3.22-3.27 (2H, m), 3.63-3.69 (2H, m), 3.78-3.88 (6H, m), 4.22-4.34 (4H, m), 4.73 (2H, q, J=8.4 Hz), 7.94 (1H, s), 9.48 (2H, s).

Step 2: 5-[8-(4-Acetylpiperazin-1-yl)-6-morpholin-4-yl-9-(2,2,2-trifluoroethyl)-9H-purin-2-yl]pyrimidin-2-amine

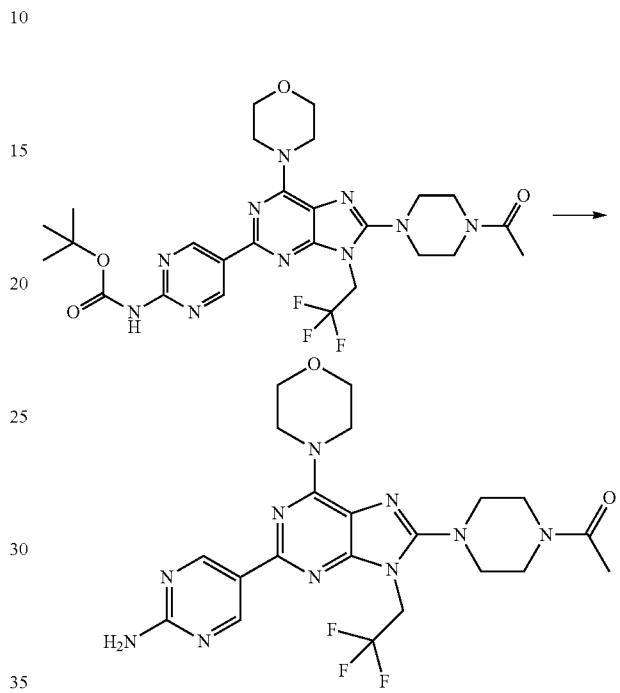

A tert-butoxycarbonyl group was removed in the same way as in Step 3 of Example 6 to give the title compound.

¹H-NMR (CDCl₃) δ: 2.16 (3H, s), 3.14-3.20 (2H, m), 3.21-3.26 (2H, m), 3.62-3.69 (2H, m), 3.78-3.88 (6H, m), 4.21-4.33 (4H, m), 4.73 (2H, q, J=8.3 Hz), 5.25 (2H, s), 9.23 (2H, s).

Example 10

5-[8-(4-Acetylpiperazin-1-yl)-9-(cyclopropylmethyl)-6-morpholin-4-yl-9H-purin-2-yl]pyrimidin-2-amine

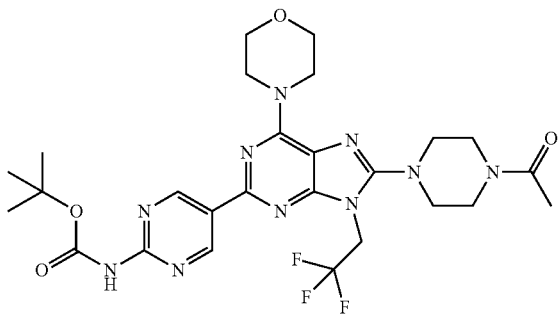

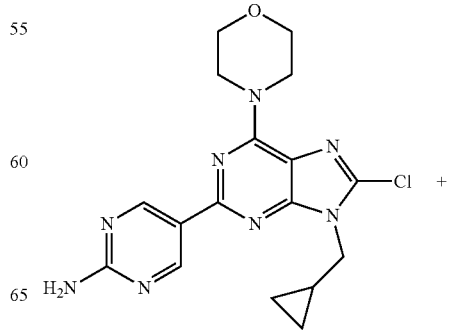

-continued

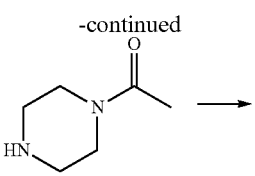

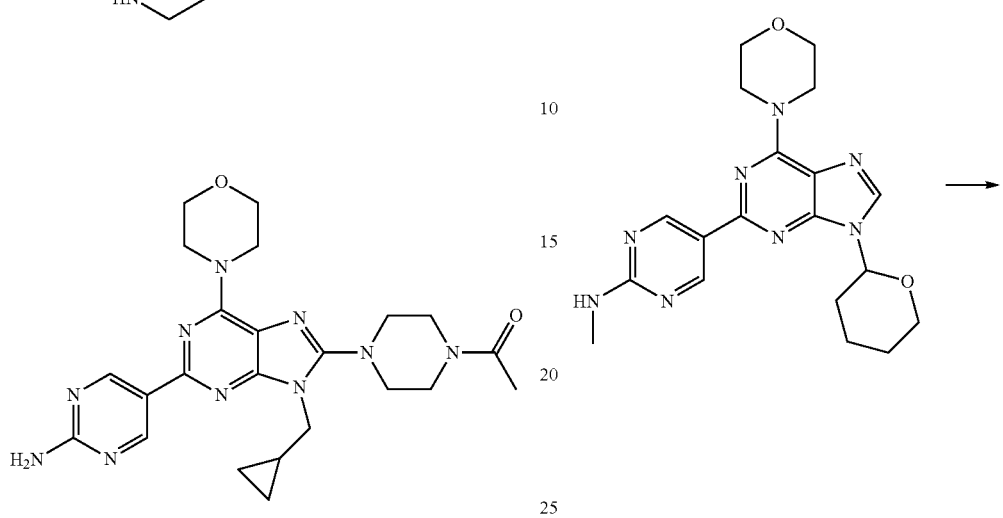

N-Methylpyrrolidone (1 ml) was added to 5-[8-chloro-9-(cyclopropylmethyl)-6-morpholin-4-yl-9H-purin-2-yl]pyrimidin-2-amine (100 mg, 0.26 mmol) and N-acetylpiperazine (166 mg, 1.3 mmol) and the resulting mixture was stirred at 150° C. for 7 hours. The reaction mixture was partitioned with ethyl acetate and water and the organic layer was washed with saturated brine and dried over magnesium sulfate. The solvent was evaporated under reduced pressure and the residue was purified by preparative HPLC (column, NOMURA Develosil Combi-RP-5; mobile phase, acetonitrile/water/formic acid) to give the title compound (105 mg, 85%) as a white solid.

$^1$H-NMR (DMSO-d$_6$) δ: 0.48-0.50 (4H, m), 1.32-1.38 (1H, m), 2.05 (3H, s), 3.15-3.17 (2H, m), 3.23-3.25 (2H, m), 3.60-3.64 (4H, m), 3.73-3.75 (4H, m), 3.99 (2H, d, J=7.45 Hz), 4.18 (4H, s), 7.00 (2H, s), 9.07 (2H, s).

Example 11

N-Methyl-5-{8-[4-(methylsulfonyl)piperazin-1-yl]-6-morpholin-4-yl-9-(2,2,2-trifluoroethyl)-9H-purin-2-yl}pyrimidin-2-amine

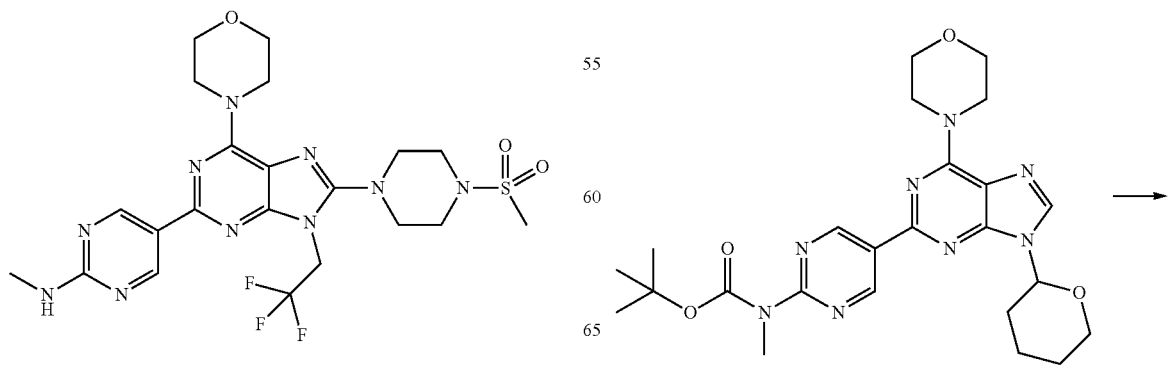

Step 1: tert-Butylmethyl {5-[6-morpholin-4-yl-9-(tetrahydro-2H-pyran-2-yl)-9H-purin-2-yl]pyrimidin-2-yl}carbamate The title compound was obtained in the same way as in Step 4 of Example 3.

$^1$H-NMR (CDCl$_3$) δ: 1.52-1.87 (3H, m), 1.57 (9H, s), 2.03-2.15 (3H, m), 3.51 (3H, s), 3.74-3.88 (5H, m), 4.15-4.22 (1H, m), 4.28-4.44 (4H, m), 5.73-5.81 (1H, m), 7.98 (1H, s), 9.56 (2H, s).

Step 2: tert-Butyl [5-(8-chloro-6-morpholin-4-yl-9H-purin-2-yl)pyrimidin-2-yl]methylcarbamate

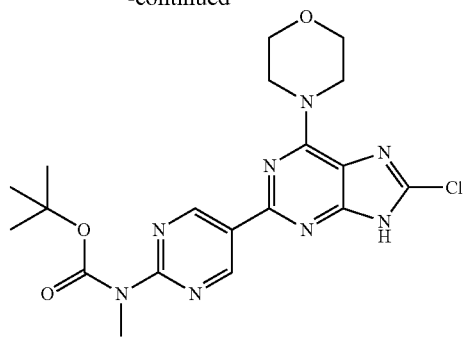

The title compound was synthesized in the same way as in Step 7 of Example 7.

$^1$H-NMR (CDCl$_3$) δ: 1.55 (9H, s), 2.74 (3H, s), 3.48-3.53 (4H, m), 3.83-3.90 (4H, m), 4.30 (1H, br s), 9.57 (2H, br s).

Step 3: tert-Butyl {5-[8-chloro-6-morpholin-4-yl-9-(2,2,2-trifluoroethyl)-9H-purin-2-yl]pyrimidin-2-yl}methylcarbamate

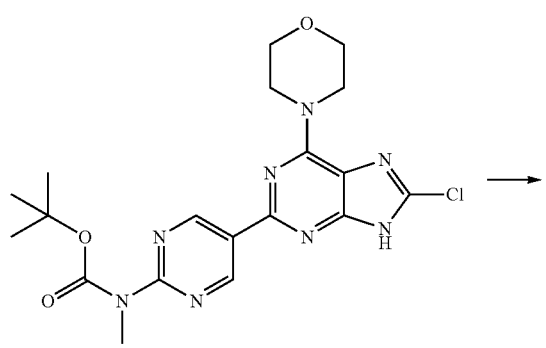

The title compound was synthesized in the same way as the alkylation described in Step 8 of Example 7.

$^1$H-NMR (CDCl$_3$) δ: 1.56 (9H, s), 3.48 (3H, s), 3.82-3.88 (4H, m), 4.20-4.38 (4H, m), 4.84 (2H, q, J=8.1 Hz), 9.52 (2H, s).

Step 4: tert-Butylmethyl {5-[6-morpholin-4-yl-8-piperazin-1-yl-9-(2,2,2-trifluoroethyl)-9H-purin-2-yl]pyrimidin-2-yl}carbamate

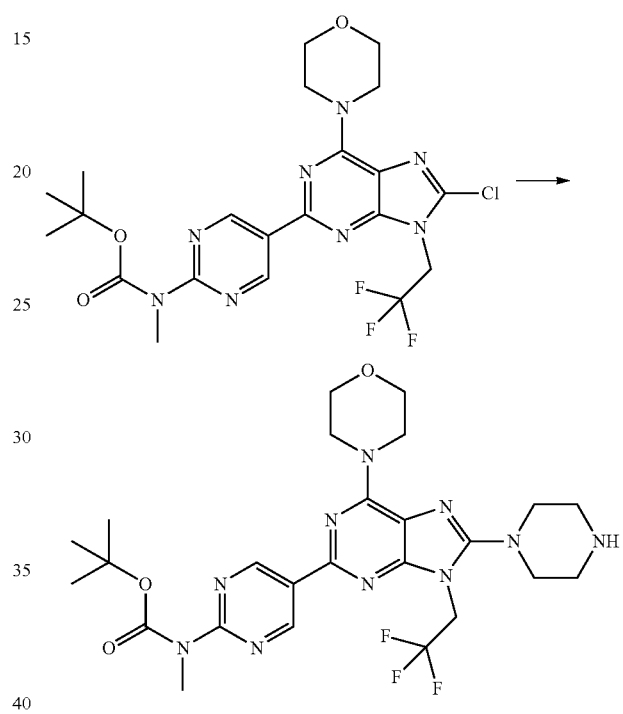

The title compound was synthesized in the same way as in Step 4 of Example 6.

$^1$H-NMR (CDCl$_3$) δ: 1.56 (9H, s), 2.83 (1H, s), 3.03-3.09 (4H, m), 3.16-3.23 (4H, m), 3.49 (3H, s), 3.82-3.88 (4H, m), 4.23-4.37 (4H, m), 4.71 (2H, q, J=8.5 Hz), 9.53 (2H, s).

Step 5: tert-Butylmethyl (5-{8-[4-(methylsulfonyl)piperazin-1-yl]-6-morpholin-4-yl-9-(2,2,2-trifluoroethyl)-9H-purin-2-yl}pyrimidin-2-yl)carbamate

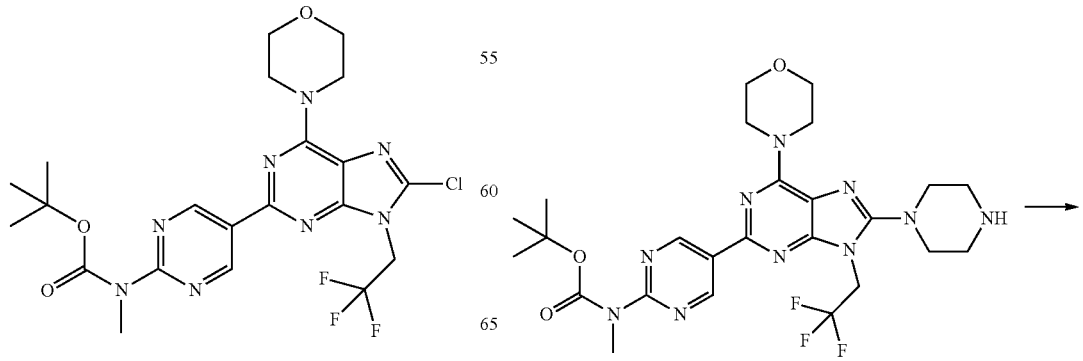

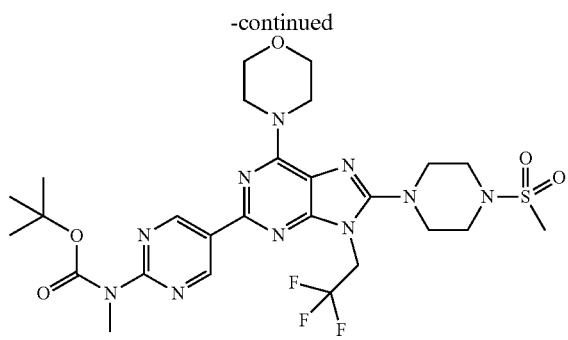

The title compound was synthesized in the same way as in Step 4 of Example 6.

¹H-NMR (CDCl₃) δ: 1.56 (9H, s), 2.87 (3H, s), 3.31-3.36 (4H, m), 3.42-3.47 (4H, m), 3.49 (3H, s), 3.82-3.88 (4H, m), 4.21-4.38 (4H, m), 4.72 (2H, q, J=8.3 Hz), 9.5 (2H, s).

Step 6: N-Methyl-5-{8-[4-(methylsulfonyl)piperazin-1-yl]-6-morpholin-4-yl-9-(2,2,2-trifluoroethyl)-9H-purin-2-yl}pyrimidin-2-amine

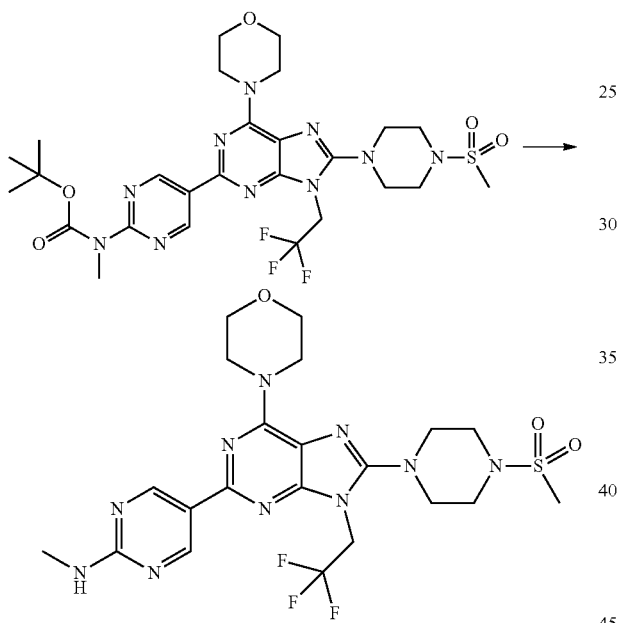

The title compound was synthesized in the same way as in Step 3 of Example 6.

¹H-NMR (CDCl₃) δ: 2.87 (3H, s), 3.08 (3H, d, J=5.1 Hz), 3.28-3.34 (4H, m), 3.41-3.48 (4H, m), 3.82-3.88 (4H, m), 4.32-4.21 (4H, m), 4.70 (2H, q, J=8.3 Hz), 5.32 (1H, d, J=5.1 Hz), 9.25 (1H, s).

Step 7: N-Methyl-5-{8-[4-(methylsulfonyl)piperazin-1-yl]-6-morpholin-4-yl-9-(2,2,2-trifluoroethyl)-9H-purin-2-yl}pyrimidin-2-amine methanesulfonate

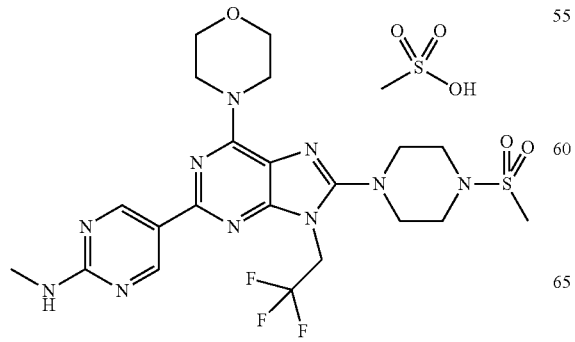

The title compound was synthesized in the same way as in Step 8 of Example 3.

¹H-NMR (CDCl₃) δ: 2.88 (3H, s), 2.93 (3H, s), 3.16-3.19 (3H, m), 3.30-3.36 (4H, m), 3.42-3.48 (4H, m), 3.82-3.88 (4H, m), 4.14-4.38 (4H, m), 4.69 (2H, q, J=8.3 Hz), 8.93 (1H, br s), 9.46 (1H, br s), 9.67 (1H, s).

Example 12

5-{9-(Cyclopropylmethyl)-8-(cis-3,5-dimethylpiperazin-1-yl)-6-morpholin-4-yl-9H-purin-2-yl}pyrimidin-2-amine

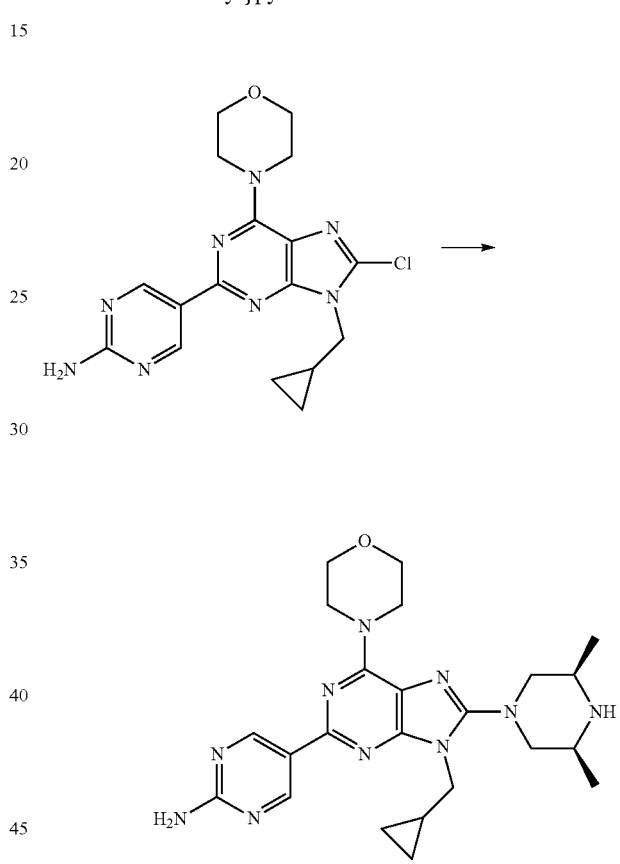

A dimethyl sulfoxide solution (0.8 ml) of 5-[8-chloro-9-(cyclopropylmethyl)-6-morpholin-4-yl-9H-purin-2-yl]pyrimidin-2-amine (76.5 mg, 0.19 mmol) and cis-2,6-dimethylpiperazine (87.5 mg, 0.77 mmol) was heated at 140° C. and stirred for 2.5 hours. The resulting mixture was left standing to cool followed by the addition of dichloromethane-methanol (10:1) and washed with saturated aqueous sodium hydrogen carbonate solution. The organic layer was dried over anhydrous sodium sulfate, the resulting mixture was filtrated, the filtrate was concentrated under reduced pressure, and the resulting residue was purified by preparative thin layer silica gel chromatography (dichloromethane:methanol=10:1) to give the title compound (91.1 mg, 100%) as a light brown solid.

¹H-NMR (CDCl₃) δ: 0.48-0.58 (4H, m), 1.15 (6H, d, J=6.42 Hz), 1.29-1.41 (1H, m), 2.63 (2H, t, J=11.46 Hz), 3.07-3.19 (2H, m), 3.35-3.43 (2H, m), 3.83-3.90 (4H, m), 3.95 (2H, d, J=6.88 Hz), 4.21-4.36 (4H, brm), 5.55 (2H, s), 9.23 (2H, s).

Example 13

5-[8-(4-Methylpiperazin-1-yl)-6-morpholin-4-yl-9-(2,2,2-trifluoroethyl)-9H-purin-2-yl]pyrimidin-2-amine

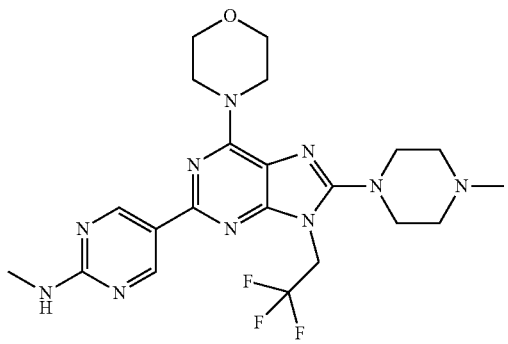

Step 1: tert-Butyl {5-[8-(4-methylpiperazin-1-yl)-6-morpholin-4-yl-9-(2,2,2-trifluoroethyl)-9H-purin-2-yl]pyrimidin-2-yl}carbamate

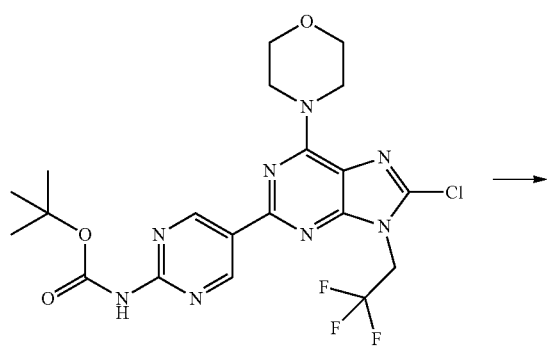

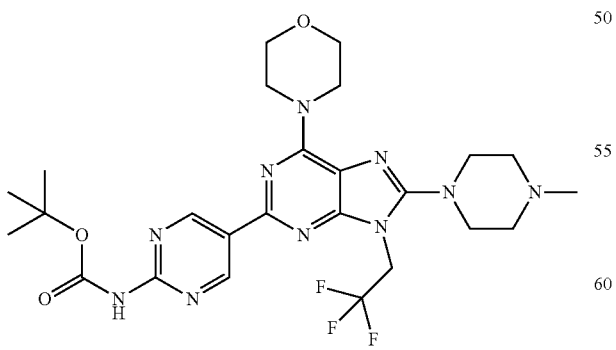

In the same way as in Step 5 of Example 1, N-methylpiperazine was used in excess and the resulting mixture was stirred at 80° C. for 3 hours to synthesize the title compound.

$^1$H-NMR (CDCl$_3$) δ: 1.56 (9H, s), 2.40 (3H, s), 2.59-2.66 (4H, m), 3.25-3.32 (4H, m), 3.81-3.88 (4H, m), 4.22-4.33 (4H, m), 4.69 (2H, q, J=8.2 Hz), 7.98 (1H, s), 9.48 (2H, s).

Step 2: 5-[8-(4-Methylpiperazin-1-yl)-6-morpholin-4-yl-9-(2,2,2-trifluoroethyl)-9H-purin-2-yl]pyrimidin-2-amine

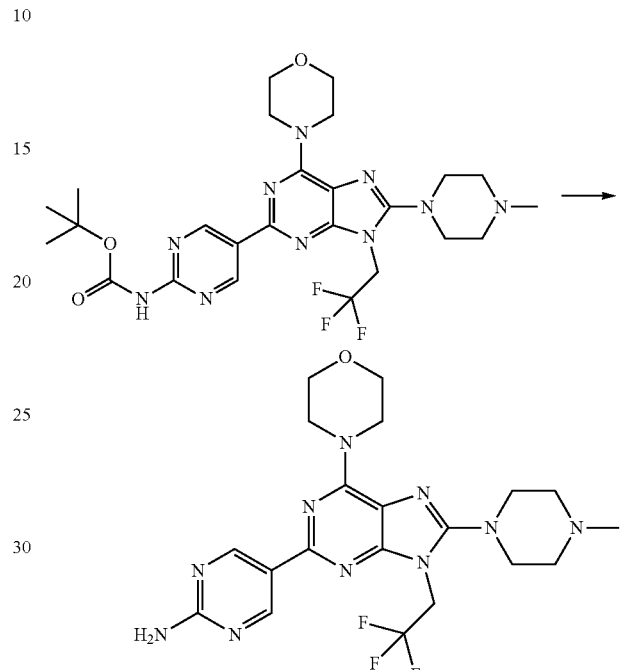

The title compound was synthesized in the same way as in Step 3 of Example 6.

$^1$H-NMR (CDCl$_3$) δ: 2.38 (3H, s), 2.57-2.64 (4H, m), 3.23-3.29 (4H, m), 3.83-3.88 (4H, m), 4.23-4.33 (4H, m), 4.69 (2H, q, J=8.3 Hz), 5.24 (2H, s), 9.22 (2H, s).

Example 14

5-[8-(cis-3,5-Dimethylpiperazin-1-yl)-6-morpholin-4-yl-9-(2,2,2-trifluoroethyl)-9H-purin-2-yl]pyrimidin-2-amine

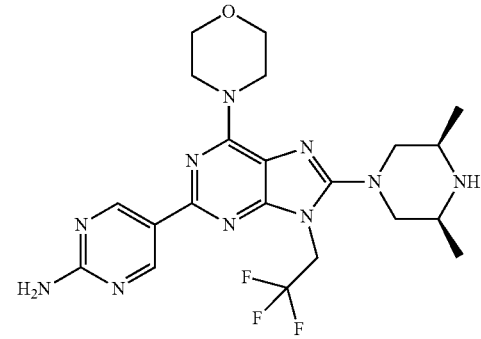

167

Step 1: tert-Butyl {5-[8-(cis-3,5-dimethylpiperazin-1-yl)-6-morpholin-4-yl-9-(2,2,2-trifluoroethyl)-9H-purin-2-yl]pyrimidin-2-yl)}carbamate

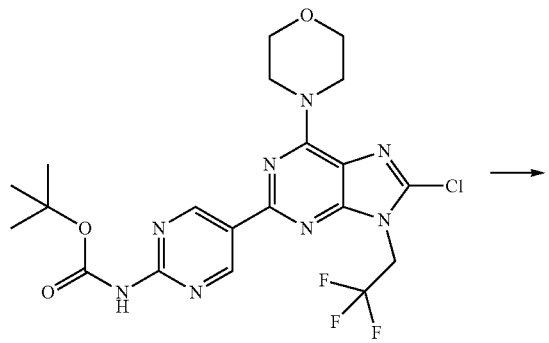

In the same way as in Step 5 of Example 1, cis-2,6-dimethylpiperazine was used in excess and the resulting mixture was stirred at 80° C. for 3 hours to synthesize the title compound.

$^1$H-NMR (CDCl$_3$) δ: 1.16 (6H, d, J=6.3 Hz), 1.56 (9H, s), 2.64-2.74 (2H, m), 3.08-3.20 (2H, m), 3.21-3.28 (2H, m), 3.82-3.88 (4H, m), 4.23-4.32 (4H, m), 4.69 (2H, q, J=8.2 Hz), 7.95 (1H, s), 9.48 (2H, s).

Step 2: {5-[8-(cis-3,5-Dimethylpiperazin-1-yl)-6-morpholin-4-yl-9-(2,2,2-trifluoroethyl)-9H-purin-2-yl]pyrimidin-2-amine

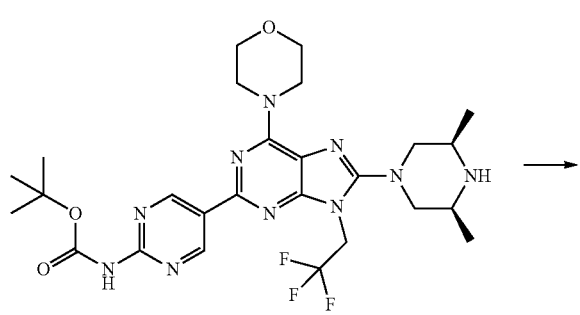

168

-continued

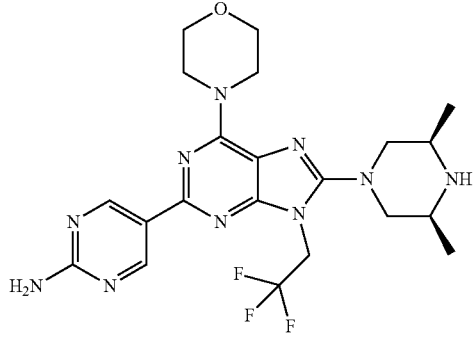

The title compound was synthesized in the same way as in Step 3 of Example 6.

$^1$H-NMR (CDCl$_3$) δ: 1.13 (6H, d, J=6.1 Hz), 2.59-2.68 (2H, m), 3.06-3.17 (2H, m), 3.19-3.26 (2H, m), 3.83-3.89 (4H, m), 4.23-4.33 (4H, m), 4.69 (2H, q, J=8.4 Hz), 5.24 (2H, s), 9.23 (2H, s).

Step 3: {5-[8-(cis-3,5-Dimethylpiperazin-1-yl)-6-morpholin-4-yl-9-(2,2,2-trifluoroethyl)-9H-purin-2-yl]pyrimidin-2-amine methanesulfonate

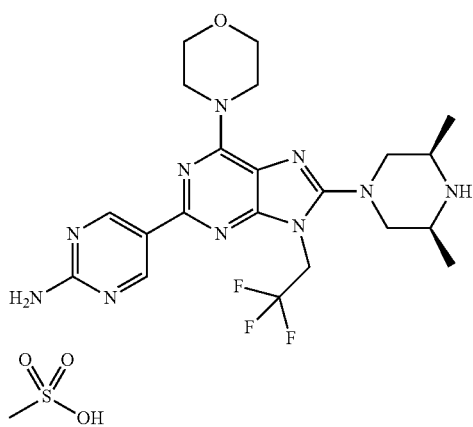

The title compound was synthesized in the same way as in Step 8 of Example 3.

$^1$H-NMR (CDCl$_3$+CD$_3$OD) δ: 1.45 (6H, d, J=6.6 Hz), 2.83 (3H, s), 3.14-3.23 (2H, m), 3.35-3.43 (3H, m), 3.56-3.67 (2H, m), 3.85-3.90 (4H, m), 4.22-4.32 (4H, m), 4.74 (2H, q, J=8.2 Hz), 9.20 (1H, s).

Example 15

5-[9-(Cyclopropylmethyl)-8-(cis-3,5-dimethylpiperazin-1-yl)-6-morpholin-4-yl-9H-purin-2-yl]-4-methylpyrimidin-2-amine

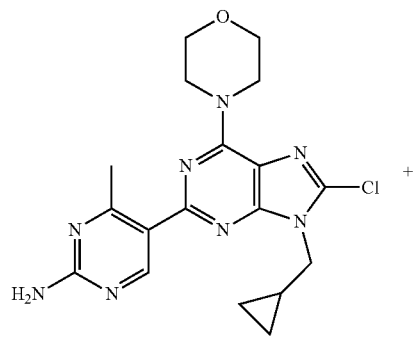

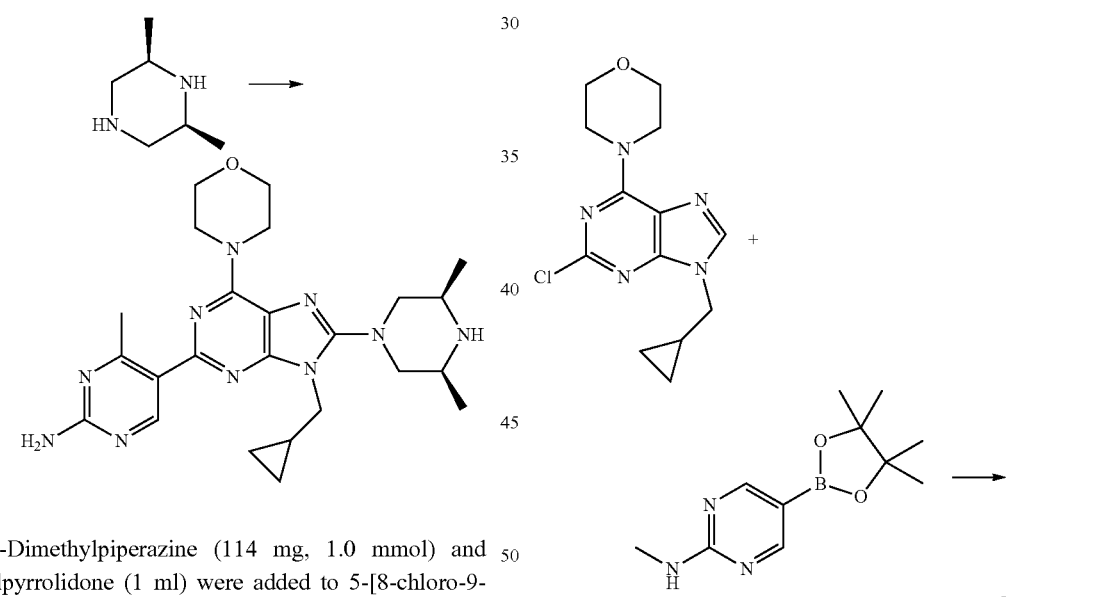

cis-2,6-Dimethylpiperazine (114 mg, 1.0 mmol) and N-methylpyrrolidone (1 ml) were added to 5-[8-chloro-9-(cyclopropylmethyl)-6-morpholin-4-yl-9H-purin-2-yl]-4-methylpyrimidin-2-amine (100 mg, 0.25 mmol) and the resulting mixture was stirred at 150° C. for 4 hours. The reaction mixture was partitioned with ethyl acetate and water and the organic layer was washed with saturated brine and dried over magnesium sulfate. The solvent was evaporated under reduced pressure and then the residue was purified by preparative HPLC (column, NOMURA Develosil Combi-RP-5; mobile phase, acetonitrile/water/formic acid) to give the title compound (90 mg, 75%) as a light brown solid.

$^1$H-NMR (DMSO-$d_6$) δ: 0.40-0.43 (2H, m), 0.45-0.49 (2H, m), 1.09 (6H, d, J=6.30 Hz), 1.31-1.37 (1H, m), 2.58-2.62 (2H, m), 2.63 (3H, s), 3.08-3.12 (2H, m), 3.38-3.44 (2H, m), 3.73-3.75 (4H, m), 3.96 (2H, d, J=6.87 Hz), 4.15 (4H, s), 6.77 (2H, s), 8.22 (1H, s), 8.78 (1H, s).

Example 16

5-{9-(Cyclopropylmethyl)-8-(cis-3,5-dimethylpiperazin-1-yl)-6-morpholin-4-yl-9H-purin-2-yl}-N-methylpyrimidin-2-amine

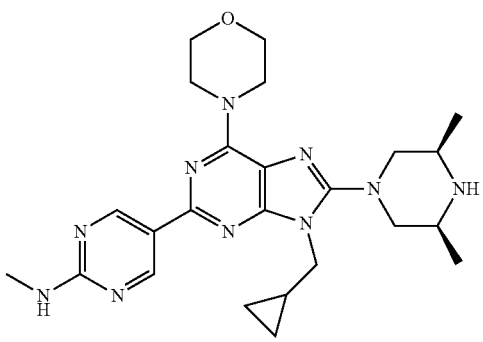

Step 1: 5-[9-(Cyclopropylmethyl)-6-morpholin-4-yl-9H-purin-2-yl]-N-methylpyrimidin-2-amine Sodium carbonate (2.40 g, 22.7 mmol) and tetrakis triphenylphosphine palladium (0.44 g, 0.38 mmol) were added to a 1,4-dioxane (44.0 ml)-water (22.0 ml) mixture solution of 2-chloro-9-(cyclopropylmethyl)-6-morpholin-4-yl-9H-purine (2.22 g, 7.56 mmol) and 2-methylaminopyrimidine-5-boronic acid pinacol ester (2.31 g, 9.82 mmol) at room temperature and the resulting mixture was heated to reflux for 3.5 hours in an argon atmosphere. The reaction mixture was left standing to cool and then poured into water and ethyl acetate was added to separate the layers. The solid precipitated in the aqueous layer was collected by filtration, washed with water, and then dried at 50° C. under reduced pressure. Meanwhile, the organic layer was dried over anhydrous sodium sulfate, the mixture was filtrated, then the filtrate was concentrated under reduced pressure, and the resulting solid was washed with dichloromethane and collected by filtration. These solids were combined to give the title compound (1.68 g, 61%) as a white solid.

$^1$H-NMR (CDCl$_3$) δ: 0.47-0.52 (2H, m), 0.63-0.69 (2H, m), 1.28-1.37 (1H, m), 3.09 (3H, d, J=5.15 Hz), 3.84-3.88 (4H, m), 4.06 (2H, d, J=7.45 Hz), 4.27-4.45 (4H, brm), 5.24-5.34 (1H, m), 7.82 (1H, s), 9.29 (2H, s).

Step 2: tert-Butyl {5-[9-(cyclopropylmethyl)-6-morpholin-4-yl-9H-purin-2-yl]pyrimidin-2-yl}methylcarbamate Step 3: tert-Butyl {5-[8-chloro-9-(cyclopropylmethyl)-6-morpholin-4-yl-9H-purin-2-yl]pyrimidin-2-yl}methylcarbamate

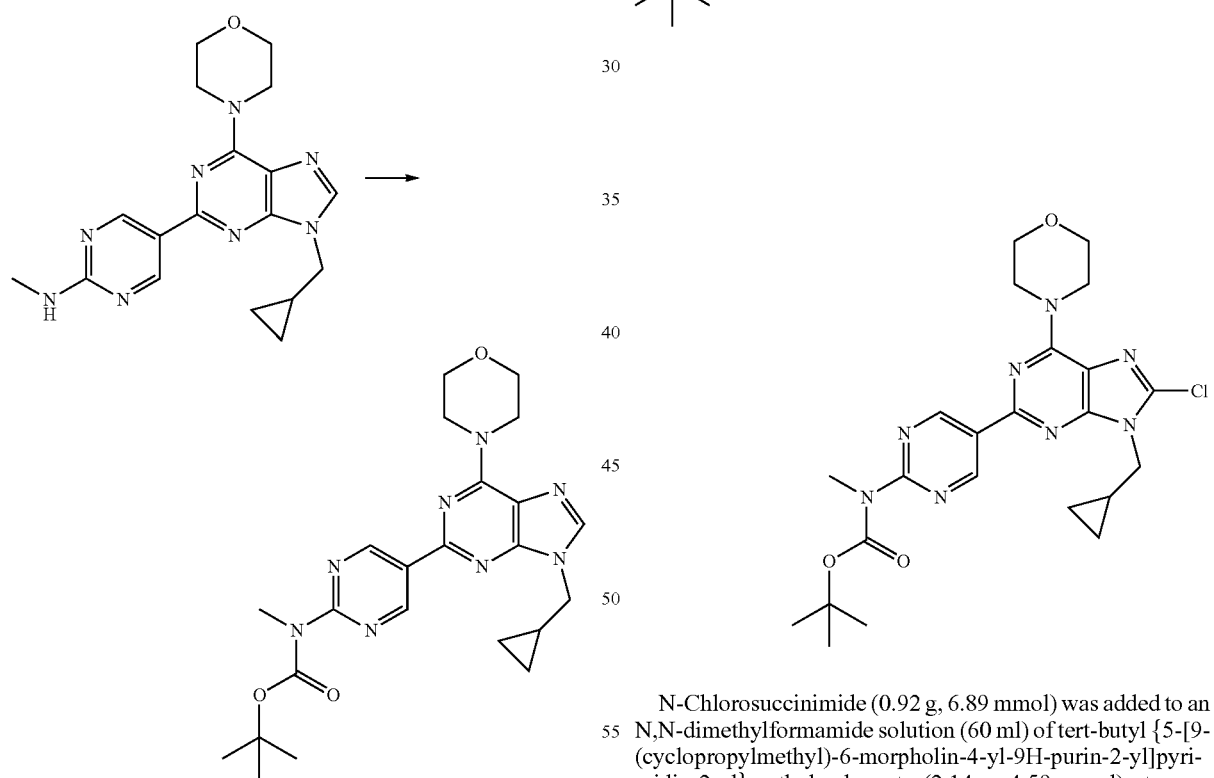

Di-tert-butyl dicarbonate (2.01 g, 9.19 mmol) and 4-dimethylaminopyridine (0.11 g, 0.92 mmol) were added to a dimethylformamide suspension (5.0 ml) of 5-[9-(cyclopropylmethyl)-6-morpholin-4-yl-9H-purin-2-yl]-N-methylpyrimidin-2-amine (1.68 g, 4.59 mmol) at room temperature. The resulting mixture was stirred at 60° C. for 3.5 hours and then the reaction mixture was poured into ethyl acetate, washed successively with 10% aqueous citric acid solution and saturated aqueous sodium hydrogen carbonate solution, and dried over anhydrous sodium sulfate. After filtration, the filtrate was concentrated under reduced pressure to give the title compound as a pale yellow white amorphous substance. This substance was used in the next step (Step 3) without being purified.

N-Chlorosuccinimide (0.92 g, 6.89 mmol) was added to an N,N-dimethylformamide solution (60 ml) of tert-butyl {5-[9-(cyclopropylmethyl)-6-morpholin-4-yl-9H-purin-2-yl]pyrimidin-2-yl}methylcarbamate (2.14 g, 4.59 mmol) at room temperature. The resulting mixture was stirred for 4.5 hours followed by the addition of N-chlorosuccinimide (0.12 g, 0.92 mmol) and the resulting mixture was further stirred for 2.5 hours. The reaction mixture was poured into ethyl acetate, washed with water, and dried over anhydrous sodium sulfate. After filtration, the filtrate was concentrated under reduced pressure and the resulting residue was purified by silica gel column chromatography (hexane:ethyl acetate=17:3 to 3:1) to give the title compound (1.29 g, 56%, two steps combined) as a colorless amorphous substance.

173

$^1$H-NMR (CDCl$_3$) δ: 0.52-0.61 (4H, m), 1.30-1.41 (1H, m), 1.56-1.59 (9H, m), 3.49-3.52 (3H, m), 3.83-3.89 (4H, m), 4.11 (2H, d, J=7.45 Hz), 4.20-4.40 (4H, brm), 9.53 (2H, s).

Step 4: 5-[8-Chloro-9-(cyclopropylmethyl)-6-morpholin-4-yl-9H-purin-2-yl]-N-methylpyrimidin-2-amine

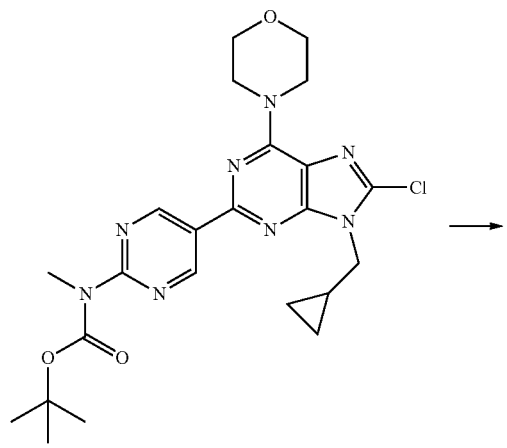

Trifluoroacetic acid (13 ml) was added to a dichloromethane solution (26 ml) of tert-butyl {5-[8-chloro-9-(cyclopropylmethyl)-6-morpholin-4-yl-9H-purin-2-yl]pyrimidin-2-yl}methylcarbamate (1.29 g, 2.57 mmol) with ice cooling and the resulting mixture was stirred at room temperature for 2 hours. The reaction mixture was concentrated, then neutralized with saturated aqueous sodium hydrogen carbonate solution, and extracted with a chloroform-ethyl acetate (5:1) mixed solvent. The organic layer was dried over anhydrous sodium sulfate and, after the reaction mixture was filtrated, the filtrate was concentrated under reduced pressure and evaporated to dryness to give the title compound (1.25 g, 100%) as a white solid.

174

$^1$H-NMR (CDCl$_3$) δ: 0.51-0.60 (4H, m), 1.29-1.39 (1H, m), 3.09 (3H, d, J=5.15 Hz), 3.82-3.88 (4H, m), 4.08 (2H, d, J=6.87 Hz), 4.15-4.42 (4H, brm), 5.47-5.68 (1H, m), 9.25 (2H, brs).

Step 5: 5-{9-(Cyclopropylmethyl)-8-(cis-3,5-dimethylpiperazin-1-yl)-6-morpholin-4-yl-9H-purin-2-yl}-N-methylpyrimidin-2-amine

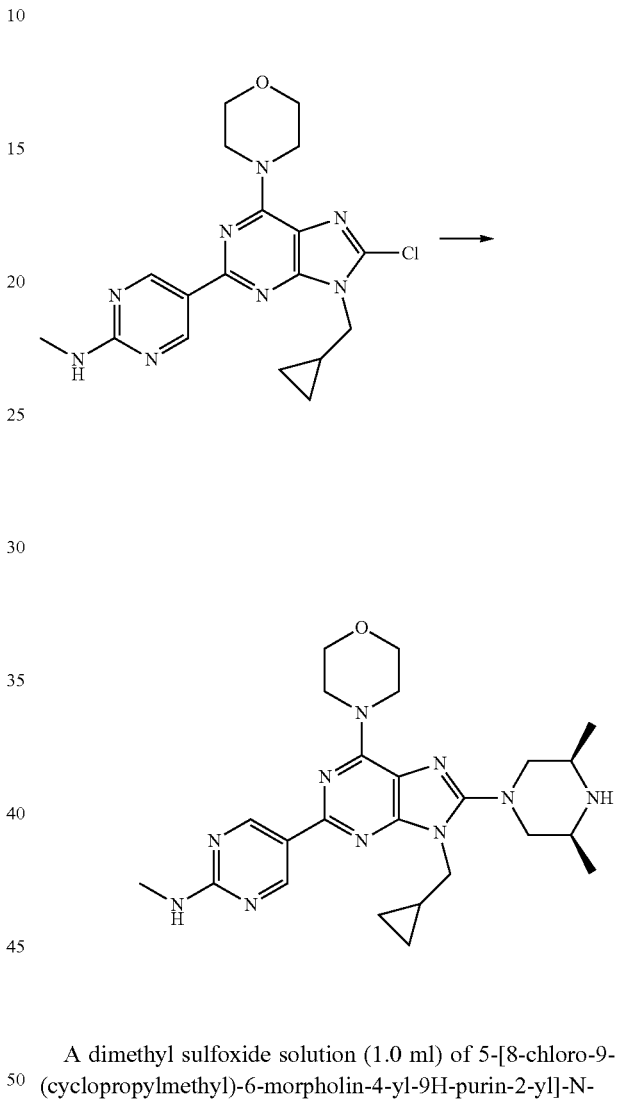

A dimethyl sulfoxide solution (1.0 ml) of 5-[8-chloro-9-(cyclopropylmethyl)-6-morpholin-4-yl-9H-purin-2-yl]-N-methylpyrimidin-2-amine (112.3 mg, 0.23 mmol) and cis-2,6-dimethylpiperazine (105.7 mg, 0.93 mmol) was heated at 140° C., stirred for 5 hours, and left standing to cool followed by the addition of dichloromethane-methanol (10:1) and the resulting mixture was washed with saturated aqueous sodium hydrogen carbonate solution. The organic layer was dried over anhydrous sodium sulfate, the mixture was filtrated, the filtrate was concentrated under reduced pressure, and the resulting residue was purified by preparative thin layer silica gel chromatography (dichloromethane:methanol=10:1) to give the title compound (98.2 mg, 89%) as a light brown solid.

$^1$H-NMR (CDCl$_3$) δ: 0.50-0.54 (4H, m), 1.14 (6H, d, J=6.30 Hz), 1.29-1.38 (1H, m), 2.58-2.67 (2H, m), 3.08 (3H, d, J=5.15 Hz), 3.09-3.17 (2H, m), 3.35-3.41 (2H, m), 3.82-

3.88 (4H, m), 3.94 (2H, d, J=6.87 Hz), 4.20-4.35 (4H, brm), 5.27-5.34 (1H, m), 9.25 (2H, s).

Example 17

5-[8-(cis-3,5-Dimethylpiperazin-1-yl)-6-morpholin-4-yl-9-(tetrahydrofuran-3-ylmethyl)-9H-purin-2-yl]pyrimidin-2-amine

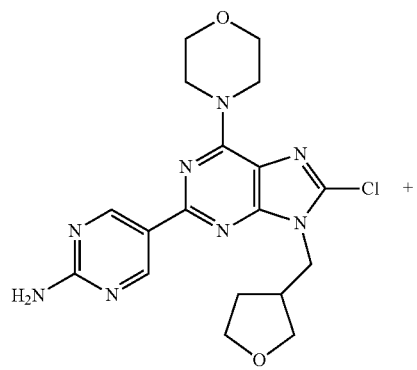

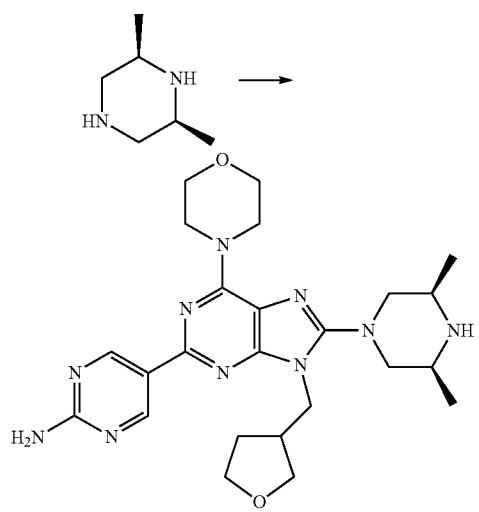

A mixture of 5-[8-chloro-6-morpholin-4-yl-9-(tetrahydrofuran-3-ylmethyl)-9H-purin-2-yl]pyrimidin-2-amine (100 mg, 0.24 mmol), cis-2,6-dimethylpiperazine (82 mg, 0.72 mmol), and dimethyl sulfoxide (800 μl) was stirred at 150° C. for 1.5 hours. The reaction mixture was cooled and then partitioned with ethyl acetate and water and the organic layer was washed twice with saturated brine and then dried over magnesium sulfate. The solvent was evaporated under reduced pressure and the residue was purified by silica gel chromatography (chloroform:methanol=9:1) to give the title compound (64 mg, 57%) as a light brown solid.

$^1$H-NMR (DMSO-$d_6$) δ: 1.01 (6H, d, J=6.30 Hz), 1.26-1.28 (1H, m), 1.52-1.58 (1H, m), 1.81-1.86 (1H, m), 2.38-2.44 (2H, m), 2.90-2.95 (3H, m), 3.29 (1H, brs), 3.52 (1H, dd, J=8.59, 5.15 Hz), 3.59-3.65 (2H, m), 3.73-3.75 (4H, m), 3.77-3.81 (1H, m), 4.09 (2H, d, J=7.45 Hz); 4.18 (4H, brs), 9.06 (2H, s).

Example 18

5-[8-(cis-3,5-Dimethylpiperazin-1-yl)-6-morpholin-4-yl-9-(tetrahydrofuran-3-ylmethyl)-9H-purin-2-yl]-N-methylpyrimidin-2-amine

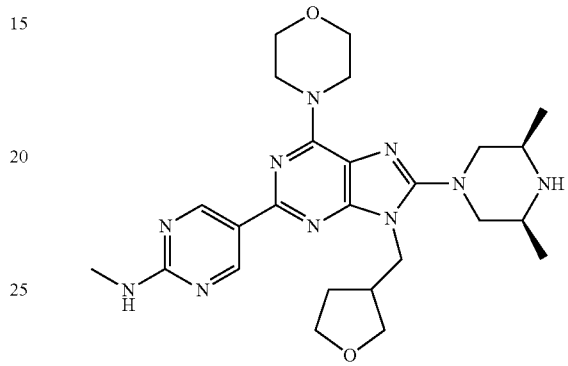

Step 1: 5-Bromo-N-methylpyrimidin-2-amine

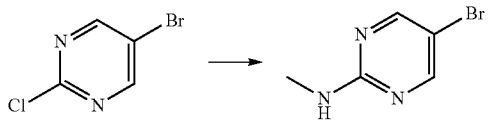

40% Aqueous methylamine solution (35 ml) and methanol (20 ml) were added to 5-bromo-2-chloropyrimidine (3 μg, 15.5 mmol) and the resulting mixture was heated to reflux for 3 days. The mixture was cooled, then the solvent was evaporated under reduced pressure, the residue was partitioned with methylene chloride and 1 M sodium hydroxide, the organic layer was dried over magnesium sulfate, and the solvent was evaporated under reduced pressure to give the title compound (3.0 g, 100%) as a white solid.

$^1$H-NMR (CDCl$_3$) δ: 2.98 (3H, d, J=5.12 Hz), 5.16 (1H, brs), 8.29 (2H, s).

Step 2: N-Methyl-5-(4,4,5,5-tetramethyl-1,3,2-dioxaborolan-2-yl)pyrimidin-2-amine

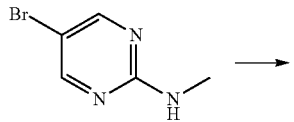

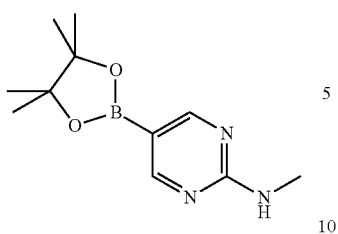

N,N-Dimethylformamide (20 ml) was added to 5-bromo-N-methylpyrimidin-2-amine (3.0 g, 16.0 mmol), bispinacolatodiboron (4.86 g, 19.2 mmol), and potassium acetate (4.7 g, 47.9 mmol) and the atmosphere in the reaction vessel was substituted with nitrogen. A 1,1'-bis(diphenylphosphino)ferrocene]palladium (II) dichloride dichloromethane complex (650 mg, 0.80 mmol) was added, the atmosphere in the reaction vessel was substituted with nitrogen again, and the resulting mixture was stirred at 80° C. for 2 hours. The reaction mixture was partitioned with ethyl acetate and saturated brine and filtrated through celite and the organic layer was washed twice with saturated brine and dried over magnesium sulfate. The solvent was evaporated under reduced pressure and the residue was purified by silica gel chromatography (hexane:ethyl acetate=8:2 to 6:4) to give the title compound (3.8 g, 100%) as a white solid.

$^1$H-NMR (CDCl$_3$) δ: 1.32 (12H, s), 3.03 (3H, d, J=5.12 Hz), 5.66 (1H, brs), 8.58 (2H, brs).

Step 3: N-Methyl-5-[6-morpholin-4-yl-9-(tetrahydrofuran-3-ylmethyl)-9H-purin-2-yl]pyrimidin-2-amine

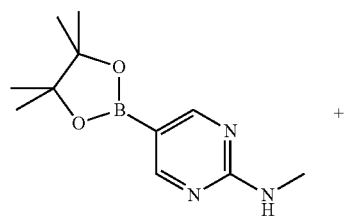

+

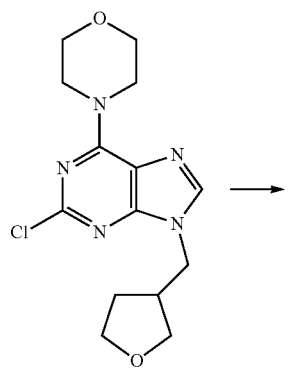

→

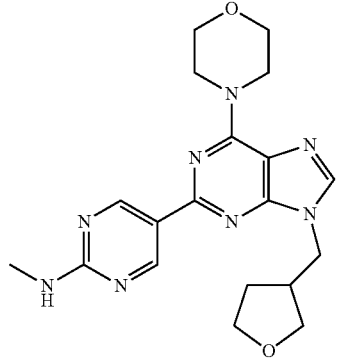

1,4-Dioxane (40 ml), water (20 ml), and sodium carbonate (2 g, 19 mmol) were added to N-methyl-5-(4,4,5,5-tetramethyl-1,3,2-dioxaborolan-2-yl)pyrimidin-2-amine (1.45 g, 6.18 mmol) and 2-chloro-6-morpholin-4-yl-9-(tetrahydrofuran-3-ylmethyl)-9H-purine (2.0 g, 6.18 mmol) and the atmosphere in the reaction vessel was substituted with nitrogen. Tetrakis triphenylphosphine palladium (0.36 g, 0.31 mmol) was added, then the atmosphere in the reaction vessel was substituted with nitrogen again, and the resulting mixture was heated to reflux for 3 hours. The reaction mixture was partitioned with ethyl acetate and water, the organic layer was dried over magnesium sulfate, and the solvent was evaporated under reduced pressure. Methylene chloride-ether was added to the residue and the insoluble matter was collected by filtration and dried to give the title compound (1.0 g, 41%) as a white solid.

$^1$H-NMR (CDCl$_3$) δ: 1.71-1.78 (1H, m), 2.02-2.08 (1H, m), 2.95-2.99 (1H, m), 3.09 (3H, d, J=5.15 Hz), 3.66 (1H, dd, J=8.88, 4.87 Hz), 3.76-3.81 (2H, m), 3.85-3.87 (4H, m), 3.94-3.99 (1H, m), 4.17 (1H, dd, J=13.75, 8.02 Hz), 4.23 (1H, dd, J=14.03, 7.73 Hz), 4.35 (4H, s), 5.29-5.32 (1H, m), 7.70 (1H, s), 9.28 (2H, s).

Step 4: tert-Butylmethyl {5-[6-morpholin-4-yl-9-(tetrahydrofuran-3-ylmethyl)-9H-purin-2-yl]pyrimidin-2-yl}carbamate

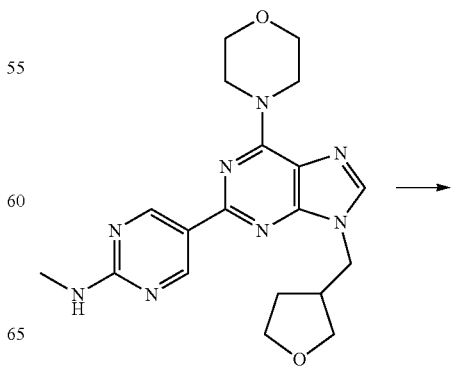

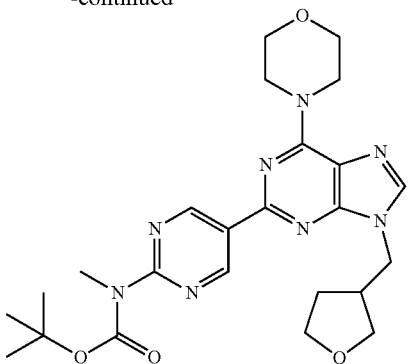

N-Methyl-5-[6-morpholin-4-yl-9-(tetrahydrofuran-3-ylmethyl)-9H-purin-2-yl]pyrimidin-2-amine (0.96 g, 2.96 mmol) was suspended in N,N-dimethylformamide (10 ml) followed by the addition of 4-dimethylaminopyridine (70 mg, 0.59 mmol) and di-tert-butyl dicarbonate (1.29 g, 5.93 mmol) and the resulting mixture was stirred at 60° C. for 2 hours. The reaction mixture was cooled and then partitioned with ethyl acetate and water and the organic layer was washed with 5% aqueous citric acid solution, water, saturated aqueous sodium bicarbonate solution, and saturated brine and dried over magnesium sulfate. The solvent was evaporated under reduced pressure to give the title compound (1.25 g, 85%) as a white solid.

$^1$H-NMR (CDCl$_3$) δ: 1.57 (9H, s), 1.69-1.78 (1H, m), 2.03-2.09 (1H, m), 2.94-3.00 (1H, m), 3.50 (3H, s), 3.64-3.67 (1H, m), 3.77-3.81 (2H, m), 3.86-3.88 (4H, m), 3.95-3.99 (1H, m), 4.19 (1H, dd, J=14.03, 7.73 Hz), 4.26 (1H, dd, J=13.75, 7.45 Hz), 4.37 (4H, brs), 7.75 (1H, s), 9.56 (2H, s).

Step 5: tert-Butyl {5-[8-chloro-6-morpholin-4-yl-9-(tetrahydrofuran-3-ylmethyl)-9H-purin-2-yl]pyrimidin-2-yl}methylcarbamate

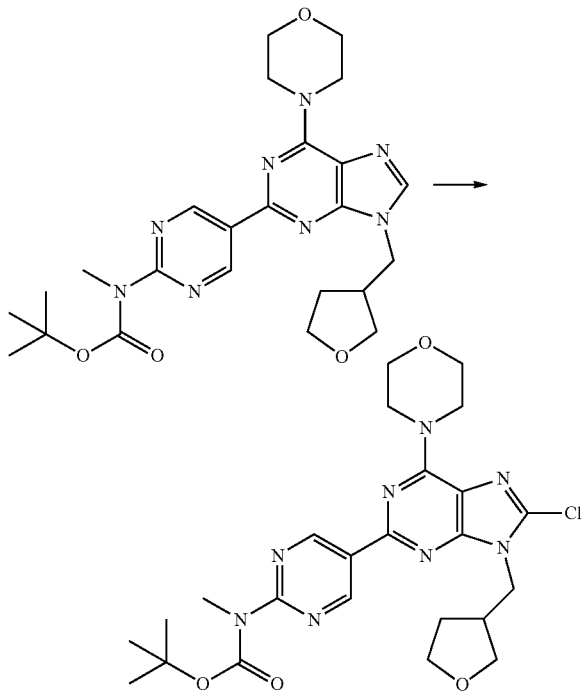

tert-Butylmethyl {5-[6-morpholin-4-yl-9-(tetrahydrofuran-3-ylmethyl)-9H-purin-2-yl]pyrimidin-2-yl}carbamate (1.25 g, 2.52 mmol) was dissolved in N,N-dimethylformamide (20 ml) followed by the addition of N-chlorosuccinimide (440 mg, 3.27 mmol) and the resulting mixture was stirred for 4 hours. The reaction mixture was partitioned with ethyl acetate and water, the organic layer was dried over magnesium sulfate, and then the solvent was evaporated under reduced pressure. The residue was purified by silica gel chromatography (hexane:ethyl acetate, 5:5 to 0:10) to give the title compound (1.35 g, 100%) as a white solid.

$^1$H-NMR (CDCl$_3$) δ: 1.57 (9H, s), 1.75-1.82 (1H, m), 1.97-2.03 (1H, m), 2.94-2.99 (1H, m), 3.50 (3H, s), 3.71 (1H, dd, J=8.88, 4.87 Hz), 3.78-3.82 (2H, m), 3.84-3.86 (4H, m), 3.98-4.03 (1H, m), 4.20-4.32 (6H, m), 9.53 (2H, s).

Step 6: 5-[8-Chloro-6-morpholin-4-yl-9-(tetrahydrofuran-3-ylmethyl)-9H-purin-2-yl]-N-methylpyrimidin-2-amine

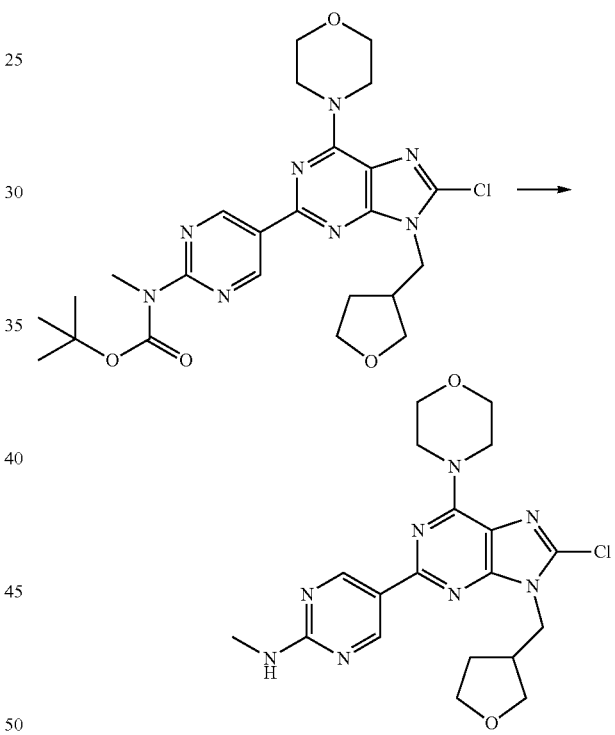

tert-Butyl {5-[8-chloro-6-morpholin-4-yl-9-(tetrahydrofuran-3-ylmethyl)-9H-purin-2-yl]pyrimidin-2-yl}methylcarbamate (1.30 g, 2.45 mmol) was dissolved in methylene chloride (5 ml) followed by the addition of trifluoroacetic acid (10 ml) with ice cooling and the resulting mixture was stirred at room temperature for 2 hours. The solvent was evaporated under reduced pressure, the residue was partitioned with chloroform and saturated aqueous sodium bicarbonate solution, the organic layer was dried over magnesium sulfate, and then the solvent was evaporated under reduced pressure to give the title compound (1.1 g, 100%) as a white solid.

$^1$H-NMR (CDCl$_3$) δ: 1.75-1.82 (1H, m), 1.96-2.03 (1H, m), 2.94-2.99 (1H, m), 3.09 (3H, d, J=5.15 Hz), 3.71 (1H, dd, J=8.88, 4.87 Hz), 3.78-3.81 (2H, m), 3.84-3.86 (4H, m), 3.98-4.02 (1H, m), 4.20 (1H, dd, J=14.32, 7.45 Hz), 4.25-4.29 (5H, m), 5.33 (1H, s), 9.25 (2H, s).

Step 7: 5-[8-(cis-3,5-Dimethylpiperazin-1-yl)-6-morpholin-4-yl-9-(tetrahydrofuran-3-ylmethyl)-9H-purin-2-yl]-N-methylpyrimidin-2-amine

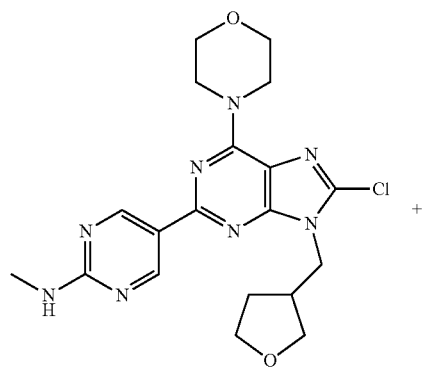

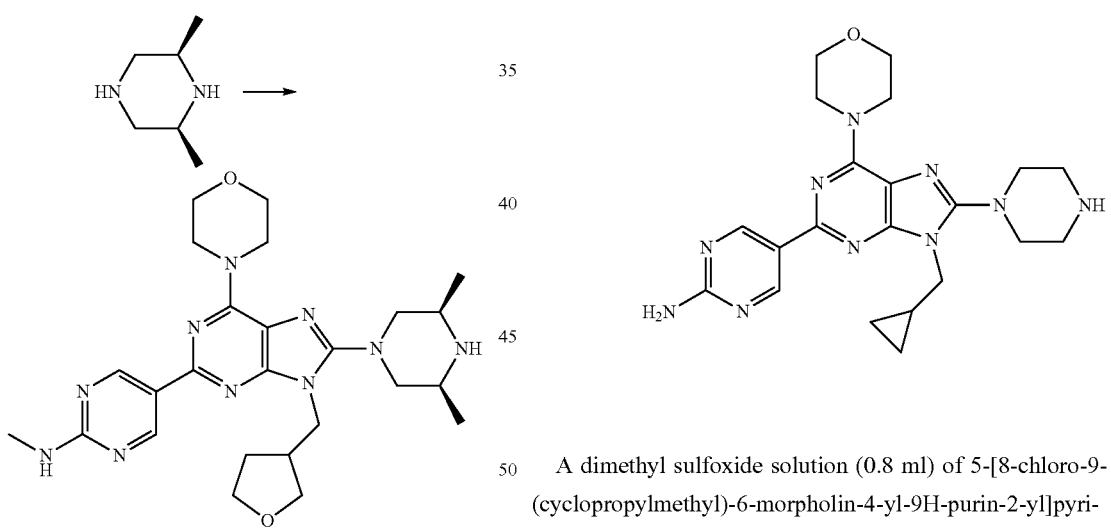

A mixture of 5-[8-chloro-6-morpholin-4-yl-9-(tetrahydrofuran-3-ylmethyl)-9H-purin-2-yl]-N-methylpyrimidin-2-amine (100 mg, 0.23 mmol), cis-2,6-dimethylpiperazine (80 mg, 0.70 mmol), and dimethyl sulfoxide (1 ml) was stirred at 150° C. for 2 hours. The mixture was purified by preparative HPLC (column, NOMURA Develosil Combi-RP-5; mobile phase, acetonitrile/water/formic acid) to give the title compound (64 mg, 54%) as a light brown solid.

¹H-NMR (CDCl₃) δ: 1.33 (6H, d, J=5.73 Hz), 1.62-1.68 (1H, m), 1.93-1.99 (1H, m), 3.02-3.09 (6H, m), 3.37-3.41 (4H, m), 3.60 (1H, dd, J=9.16, 4.58 Hz), 3.69 (1H, dd, J=8.59, 6.30 Hz), 3.76 (1H, dd, J=15.18, 8.31 Hz), 3:85-3.87 (4H, m), 3.94 (1H, dd, J=14.03, 8.31 Hz), 4.02 (1H, dd, J=13.75, 8.02 Hz), 4.09 (1H, dd, J=13.75, 7.45 Hz), 4.27 (4H, brs), 5.77-5.80 (1H, m), 8.42 (1H, s), 9.24 (2H, s).

Example 19

5-[9-(Cyclopropylmethyl)-6-morpholin-4-yl-8-piperazin-1-yl-9H-purin-2-yl]pyrimidin-2-amine

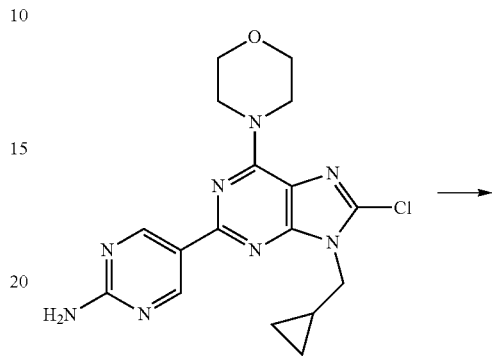

A dimethyl sulfoxide solution (0.8 ml) of 5-[8-chloro-9-(cyclopropylmethyl)-6-morpholin-4-yl-9H-purin-2-yl]pyrimidin-2-amine (78.3 mg, 0.20 mmol) and piperazine (67.6 mg, 0.78 mmol) was heated at 140° C. and stirred for 2.5 hours. The mixture was left standing to cool followed by the addition of dichloromethane-methanol (10:1) and the resulting mixture was washed with saturated aqueous sodium hydrogen carbonate solution. The organic layer was dried over anhydrous sodium sulfate, the mixture was filtrated, the filtrate was concentrated under reduced pressure, and the resulting residue was purified by preparative thin layer silica gel chromatography (dichloromethane:methanol=5:1) to give the title compound (76.5 mg, 89%) as a pale yellow solid.

1H-NMR (CDCl3) δ: 0.49-0.56 (4H, m), 1.30-1.41 (1H, m), 3.02-3.10 (4H, m), 3.21-3.28 (4H, m), 3.82-3.89 (4H, m), 3.96 (2H, d, J=6.88 Hz), 4.21-4.37 (4H, brm), 5.28 (2H, s), 9.24 (2H, s).

Example 20

5-[9-(Cyclopropylmethyl)-6,8-dimorpholin-4-yl-9H-purin-2-yl]pyrimidin-2-amine

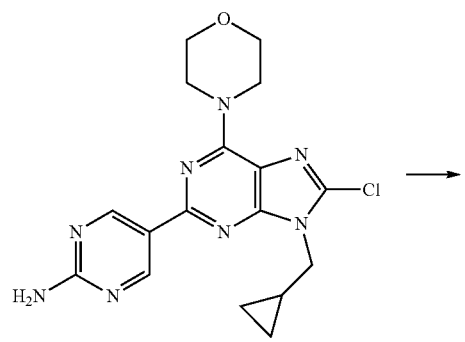

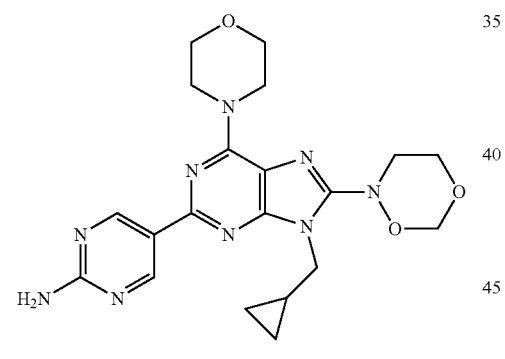

A dimethyl sulfoxide solution (1.0 ml) of 5-[8-chloro-9-(cyclopropylmethyl)-6-morpholin-4-yl-9H-purin-2-yl]pyrimidin-2-amine (75.3 mg, 0.19 mmol) and morpholine (65.8 μl, 0.75 mmol) was heated at 140° C. and stirred for 4 hours. Morpholine (32.9 μl, 0.38 mmol) was added at room temperature and the resulting mixture was further stirred at 140° C. for 2 hours. The resulting mixture was left standing to cool followed by the addition of dichloromethane-methanol (10:1) and the resulting mixture was washed with saturated aqueous sodium hydrogen carbonate solution. The organic layer was dried over anhydrous sodium sulfate, the mixture was filtrated, the filtrate was concentrated under reduced pressure, and the resulting residue was purified by preparative thin layer silica gel chromatography (dichloromethane:methanol=15:1) to give the title compound (85.9 mg, 100%) as a white solid.

1H-NMR (CDCl3) δ: 0.51-0.58 (4H, m), 1.28-1.40 (1H, m), 3.25-3.33 (4H, m), 3.83-3.91 (8H, m), 3.97 (2H, d, J=6.88 Hz), 4.20-4.38 (4H, m), 5.35 (2H, s), 9.23 (2H, s).

Example 21

N'-[2-(2-Amino-4-methylpyrimidin-5-yl)-9-(cyclopropylmethyl)-6-morpholin-4-yl-9H-purin-8-yl]-N,N-dimethylethane-1,2-diamine

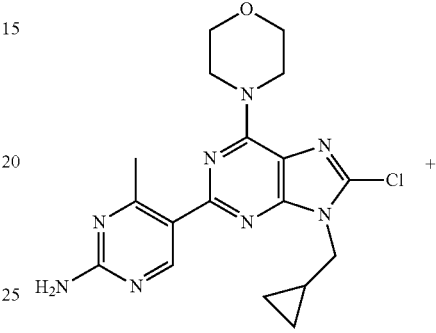

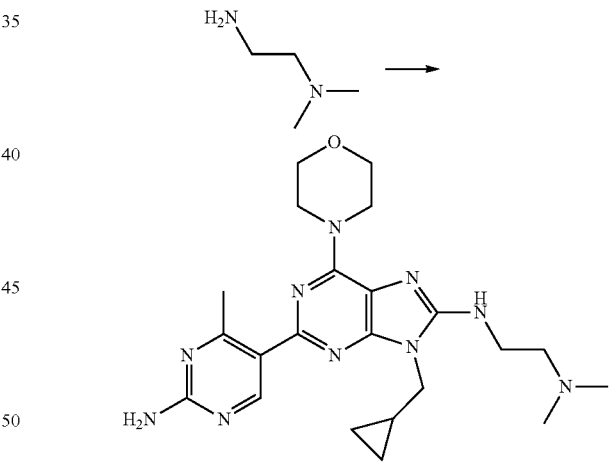

N,N-Dimethylethylenediamine (110 mg, 1.3 mmol) and dimethyl sulfoxide (700 μl) were added to 5-[8-chloro-9-(cyclopropylmethyl)-6-morpholin-4-yl-9H-purin-2-yl]-4-methylpyrimidin-2-amine (100 mg, 0.26 mmol) and the resulting mixture was stirred at 150° C. for 3 hours. The reaction mixture was partitioned with ethyl acetate and water, the organic layer was concentrated, and then the residue was purified by preparative HPLC (column, NOMURA Develosil Combi-RP-5; mobile phase, acetonitrile/water/formic acid) to give the title compound (64 mg, 52%) as a pale yellow solid.

1H-NMR (DMSO-$d_5$) δ: 0.42-0.45 (4H, m), 1.22-1.27 (1H, m), 2.25 (6H, s), 2.55 (2H, t, J=6.59 Hz), 2.62 (3H, s), 3.46

(2H, q, J=6.30 Hz), 3.70-3.72 (4H, m), 3.89 (2H, d, J=6.87 Hz), 4.08-4.10 (4H, m), 6.69 (2H, s), 6.78 (1H, t, J=5.44 Hz), 8.17 (2H, s), 8.75 (1H, s).

Example 22

2-(2-Amino-4-methylpyrimidin-5-yl)-9-(cyclopropylmethyl)-6-morpholin-4-yl-N-(2-morpholin-4-yl-ethyl)-9H-purin-8-amine

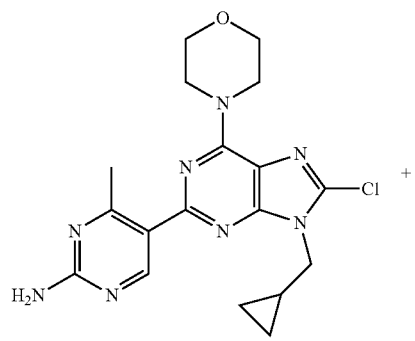

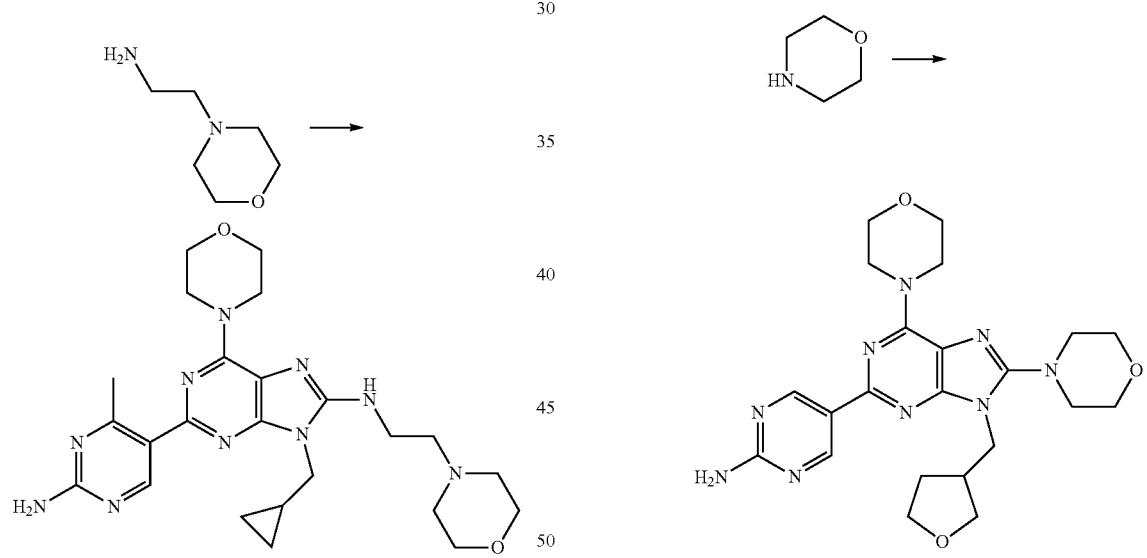

2-Morpholin-4-yl-ethylamine (162 mg, 1.25 mmol) and dimethyl sulfoxide (700 μl) were added to 5-[8-chloro-9-(cyclopropylmethyl)-6-morpholin-4-yl-9H-purin-2-yl]-4-methylpyrimidin-2-amine (100 mg, 0.25 mmol) and the resulting mixture was stirred at 150° C. for 3 hours. The reaction mixture was partitioned with ethyl acetate and water, the organic layer was concentrated, and then the residue was purified by preparative HPLC (column, NOMURA Develosil Combi-RP-5; mobile phase, acetonitrile/water/formic acid) to give the title compound (101 mg, 75%) as a pale yellow solid.

$^1$H-NMR (DMSO-$d_6$) δ: 0.41-0.47 (4H, m), 1.23-1.28 (1H, m), 2.44 (4H, brs), 2.55 (2H, t, J=6.59 Hz), 2.62 (3H, s), 3.47 (2H, q, J=6.30 Hz), 3.56 (4H, t, J=4.58 Hz), 3.71 (4H, t, J=4.58 Hz), 3.89 (2H, d, J=6.87 Hz), 4.09 (4H, t, J=4.30 Hz), 6.69 (2H, s), 6.74 (1H, t, J=5.73 Hz), 8.14 (2H, s), 8.75 (1H, s).

Example 23

5-[6,8-Dimorpholin-4-yl-9-(tetrahydrofuran-3-ylmethyl)-9H-purin-2-yl]pyrimidin-2-amine

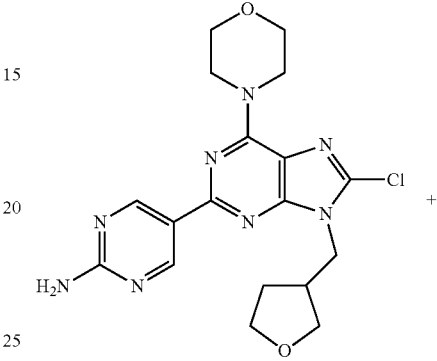

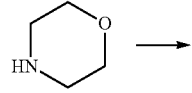

Dimethyl sulfoxide (1 ml) was added to a mixture of 5-[8-chloro-6-morpholin-4-yl-9-(tetrahydrofuran-3-ylmethyl)-9H-purin-2-yl]pyrimidin-2-amine (100 mg, 0.24 mmol) and morpholine (63 μl, 0.72 mmol) and the resulting mixture was stirred at 150° C. for 3 hours. The reaction mixture was cooled and then partitioned with chloroform and water, and the organic layer was washed again with water and then dried over magnesium sulfate. The solvent was evaporated under reduced pressure and then the residue was purified by silica gel chromatography (chloroform:methanol=10:0 to 25:1 to 20:1) to give the title compound (75 mg, 67%) as a pale yellow solid.

$^1$H-NMR (CDCl$_3$) δ: 1.64-1.70 (1H, m), 1.92-1.99 (1H, m), 3.07-3.12 (1H, m), 3.23-3.25 (4H, m), 3.64 (1H, dd, J=8.88, 4.87 Hz), 3.71-3.80 (2H, m), 3.86-3.88 (8H, m), 3.93-3.98 (1H, m), 4.07 (1H, dd, J=13.75, 7.45 Hz), 4.13 (1H, dd, J=13.75, 7.45 Hz), 4.29 (4H, brs), 5.18 (2H, brs), 9.23 (2H, s).

Example 24

5-[6,8-Dimorpholin-4-yl-9-(tetrahydrofuran-3-ylmethyl)-9H-purin-2-yl]-N-methylpyrimidin-2-amine

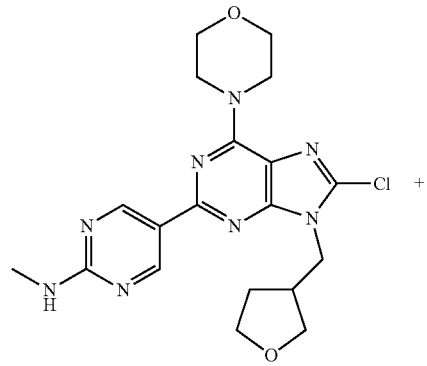

A mixture of 5-[8-chloro-6-morpholin-4-yl-9-(tetrahydrofuran-3-ylmethyl)-9H-purin-2-yl]-N-methylpyrimidin-2-amine (100 mg, 0.23 mmol), morpholine (61 µl, 0.70 mmol), and dimethyl sulfoxide (1 ml) was stirred at 150° C. for 3 hours. The mixture was purified by preparative HPLC (column, NOMURA Develosil Combi-RP-5; mobile phase, acetonitrile/water/formic acid) to give the title compound (56 mg, 50%) as a light brown solid.

¹H-NMR (CDCl₃) δ: 1.64-1.70 (1H, m), 1.91-1.98 (1H, m), 3.09-3.10 (4H, m), 3.23-3.24 (4H, m), 3.63 (1H, dd, J=8.88, 4.87 Hz), 3.71-3.79 (2H, m), 3.84-3.88 (8H, m), 3.93-3.97 (1H, m), 4.06 (1H, dd, J=13.75, 8.02 Hz), 4.12 (1H, dd, J=13.75, 7.45 Hz), 4.28 (4H, brs), 5.26-5.29 (1H, m), 9.25 (2H, s).

Example 25

N-Methyl-5-{8-[4-(methylsulfonyl)piperazin-1-yl]-6-morpholin-4-yl-9-(tetrahydrofuran-3-ylmethyl)-9H-purin-2-yl}pyrimidin-2-amine

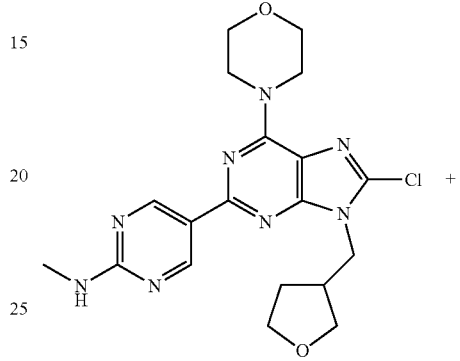

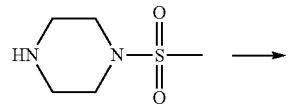

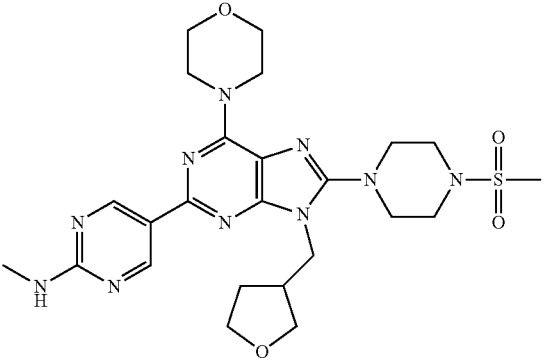

A mixture of 5-[8-chloro-6-morpholin-4-yl-9-(tetrahydrofuran-3-ylmethyl)-9H-purin-2-yl]-N-methylpyrimidin-2-amine (100 mg, 0.23 mmol), N-methanesulfonylpiperazine (114 mg, 0.70 mmol), and dimethyl sulfoxide (1 ml) was stirred at 150° C. for 4 hours. The mixture was purified by preparative HPLC (column, NOMURA Develosil Combi-RP-5; mobile phase, acetonitrile/water/formic acid) to give the title compound (32 mg, 25%) as a light brown solid.

¹H-NMR (CDCl₃) δ: 1.65-1.69 (1H, m), 1.95-1.98 (1H, m), 2.87 (3H, s), 3.08-3.11 (4H, m), 3.34-3.36 (4H, m), 3.43-3.44 (4H, m), 3.62 (1H, dd, J=8.88, 4.87 Hz), 3.70 (1H, dd, J=9.16, 6.30 Hz), 3.73-3.78 (1H, m), 3.84-3.86 (4H, m), 3.92-3.97 (1H, m), 4.03 (1H, dd, J=13.75, 7.45 Hz), 4.11 (1H, dd, J=13.75, 7.45 Hz), 4.27 (4H, brs), 5.29-5.31 (1H, m), 9.25 (2H, s).

Example 26

5-{8-(cis-3,5-Dimethylpiperazin-1-yl)-9-[(3S)-1-(methylsulfonyl)pyrrolidin-3-yl]-6-morpholin-4-yl-9H-purin-2-yl}pyrimidin-2-amine

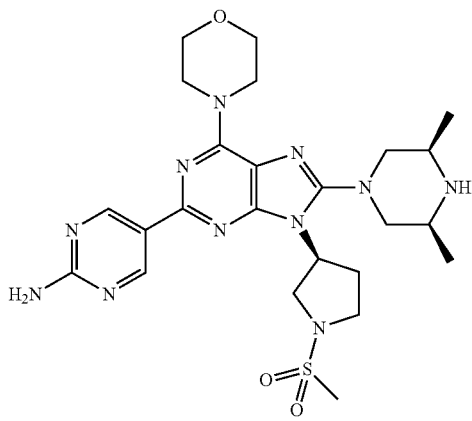

Step 1: tert-Butyl (3S)-3-(2,6-dichloro-9H-purin-9-yl)pyrrolidine-1-carboxylate

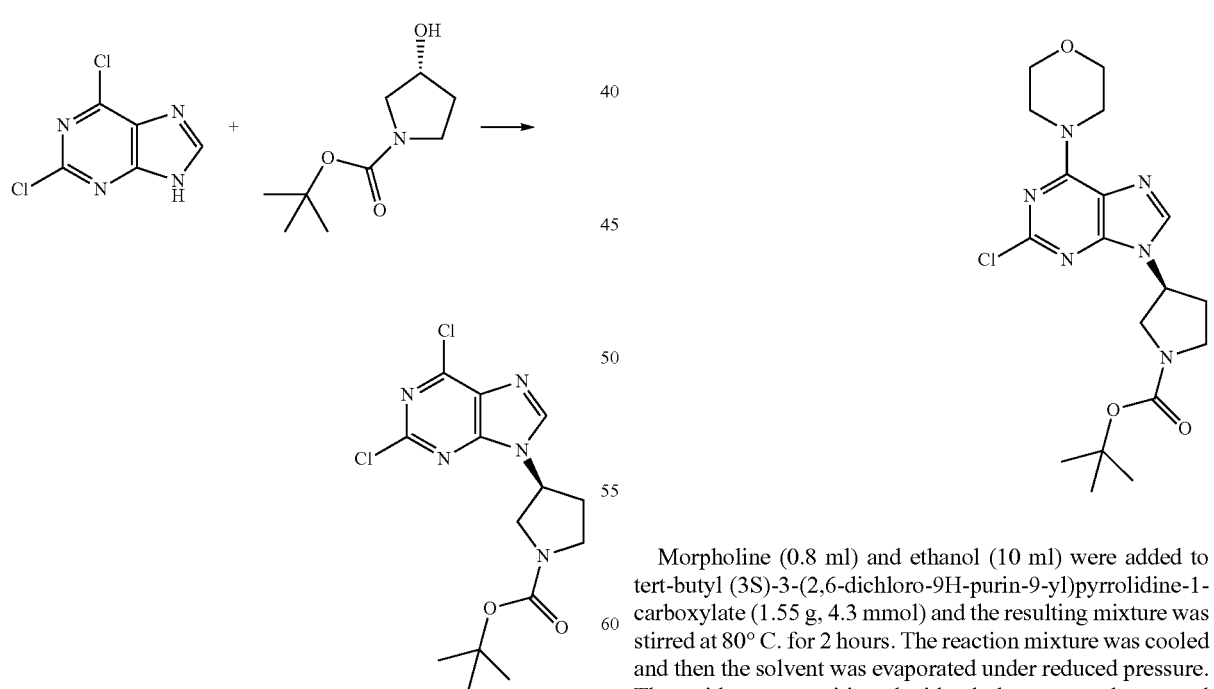

Tetrahydrofuran (200 ml) was added to 2,6-dichloropurine (6 g, 31.8 mmol), tert-butyl (3R)-3-hydroxypyrrolidine-1-carboxylate (5.94 g, 31.8 mmol), and triphenylphosphine (9.2 g, 34.9 mmol) and the resulting mixture was made uniform. Diisopropyl azodicarboxylate (6.9 ml, 35 mmol) was added with ice cooling and the resulting mixture was stirred at room temperature for 30 minutes and then heated to reflux for 1 hour. The reaction mixture was cooled, then the solvent was evaporated under reduced pressure, and the residue was purified by silica gel chromatography (hexane:ethyl acetate=7:3 to 6:4 to 5:5 to 4:6) to give the title compound (10.5 g, 92%) as a white solid.

Step 2: tert-Butyl (3S)-3-(2-chloro-6-morpholin-4-yl-9H-purin-9-yl)pyrrolidine-1-carboxylate

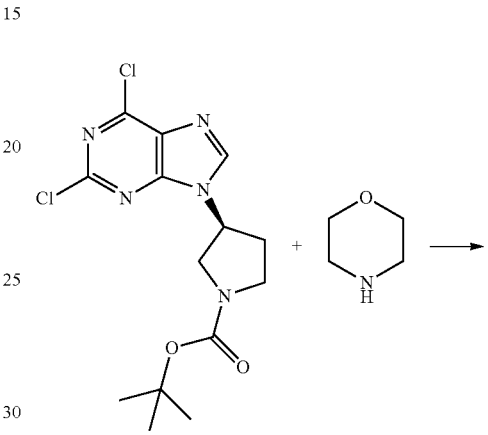

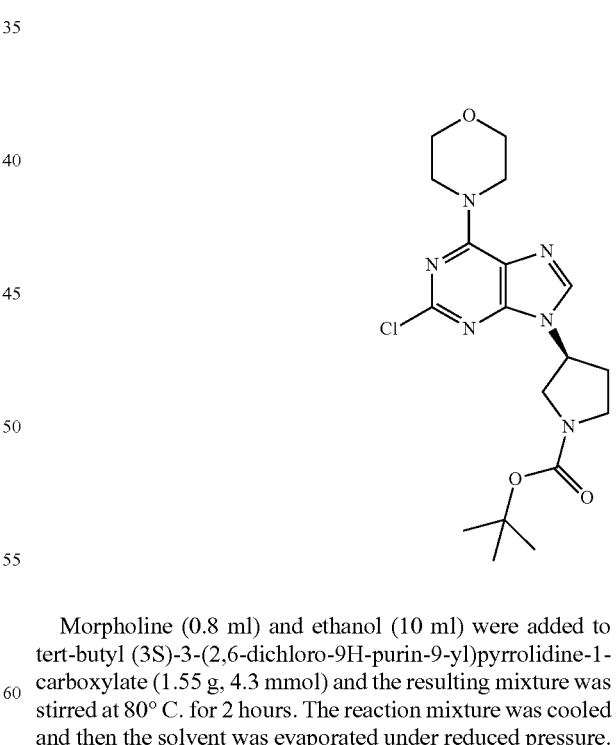

Morpholine (0.8 ml) and ethanol (10 ml) were added to tert-butyl (3S)-3-(2,6-dichloro-9H-purin-9-yl)pyrrolidine-1-carboxylate (1.55 g, 4.3 mmol) and the resulting mixture was stirred at 80° C. for 2 hours. The reaction mixture was cooled and then the solvent was evaporated under reduced pressure. The residue was partitioned with ethyl acetate and saturated aqueous sodium bicarbonate solution, the organic layer was dried over magnesium sulfate, and the solvent was evaporated under reduced pressure to give the title compound (1.76 g, 100%) as a white solid.

¹H-NMR (CDCl₃) δ: 1.48 (9H, s), 2.26-2.31 (1H, m), 2.43-2.48 (1H, m), 3.52-3.64 (3H, m), 3.82-3.83 (4H, m), 3.89 (1H, dd, J=12.03, 6.30 Hz), 4.28 (4H, brs), 5.19 (1H, s), 7.69 (1H, s).

Step 3: tert-Butyl (3S)-3-(2-{2-[bis(tert-butoxycarbonyl)amino]pyrimidin-5-yl}-6-morpholin-4-yl-9H-purin-9-yl)pyrrolidine-1-carboxylate

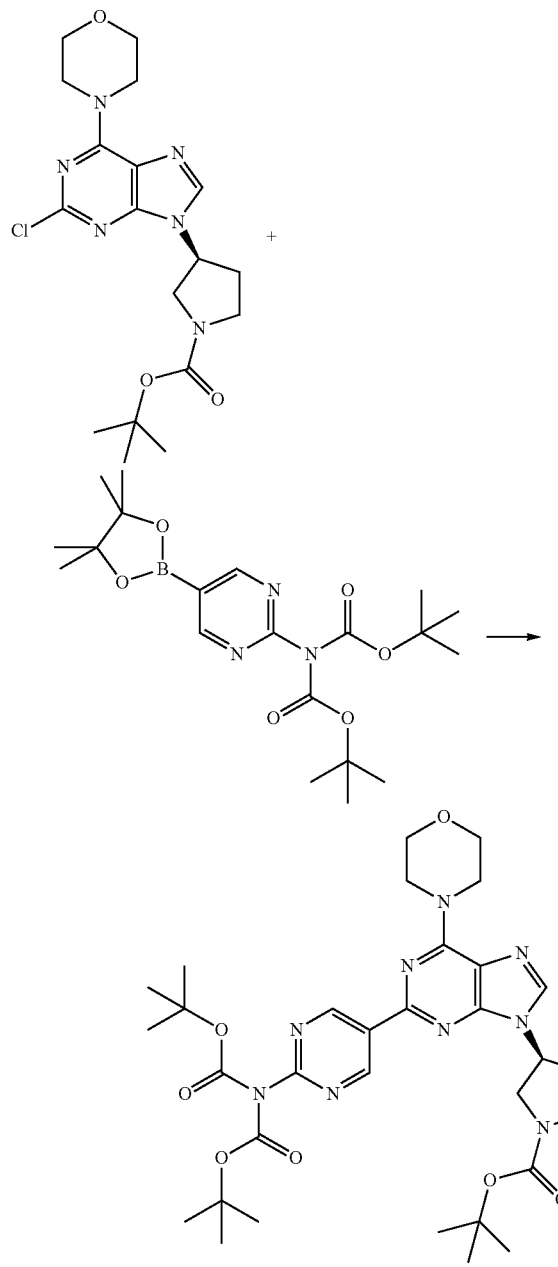

1,4-Dioxane (15 ml) and water (8 ml) were added to tert-butyl (3S)-3-(2-chloro-6-morpholin-4-yl-9H-purin-9-yl)pyrrolidine-1-carboxylate (806 mg, 1.97 mmol), di-tert-butyl [5-(4,4,5,5-tetramethyl-1,3,2-dioxaborolan-2-yl)pyrimidin-2-yl]imide dicarbonate (947 mg, 2.25 mmol), and sodium carbonate (630 mg, 6 mmol) and the atmosphere in the reaction vessel was substituted with nitrogen under stirring. Tetrakis triphenylphosphine palladium (114 mg, 0.10 mmol) was added, the atmosphere in the reaction vessel was substituted with nitrogen again, and then the resulting mixture was heated to reflux for 3 hours. The reaction mixture was partitioned with ethyl acetate and water, the organic layer was dried over magnesium sulfate, and then the solvent was evaporated under reduced pressure. The residue was dissolved in tetrahydrofuran (5 ml) followed by the addition of 4-dimethylaminopyridine (24 mg) and di-tert-butyl dicarbonate (495 mg, 2.27 mmol) and the resulting mixture was stirred at 50° C. for 2 hours. The solvent was evaporated under reduced pressure and the residue was purified by silica gel chromatography (hexane:ethyl acetate=4:6 to 2:8) to give the title compound (1.28 g, 97%) as a colorless oil.

¹H-NMR (CDCl₃) δ: 1.46-1.49 (29H, m), 2.44-2.54 (2H, m), 3.61-3.77 (3H, m), 3.85-3.90 (5H, m), 3.96-3.98 (1H, brm), 4.39 (4H, brs), 5.27 (1H, brs), 7.78 (1H, s), 9.66 (2H, s).

Step 4: tert-Butyl (3S)-3-(2-{2-[bis(tert-butoxycarbonyl)amino]pyrimidin-5-yl}-8-chloro-6-morpholin-4-yl-9H-purin-9-yl)pyrrolidine-1-carbamate

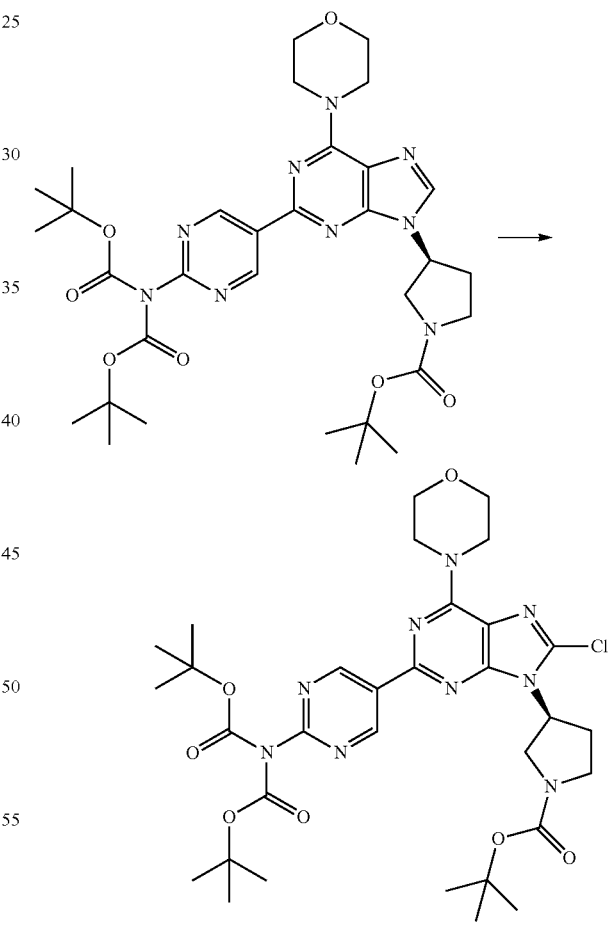

tert-Butyl (3S)-3-(2-{2-[bis(tert-butoxycarbonyl)amino]pyrimidin-5-yl}-6-morpholin-4-yl-9H-purin-9-yl)pyrrolidine-1-carboxylate (1.28 g, 1.92 mmol) was dissolved in N,N-dimethylformamide (10 ml) followed by the addition of N-chlorosuccinimide (0.38 g, 2.88 mmol) and the resulting mixture was stirred for 3 hours. The reaction mixture was partitioned with ethyl acetate and water, the organic layer was washed twice with water and then dried over magnesium sulfate, and the solvent was evaporated under reduced pressure to give the title compound (1.32 g, 98%).

Step 5: 5-{8-Chloro-9-[(3S)-1-(methylsulfonyl)pyrrolidin-3-yl]-6-morpholin-4-yl-9H-purin-2-yl}pyrimidin-2-amine

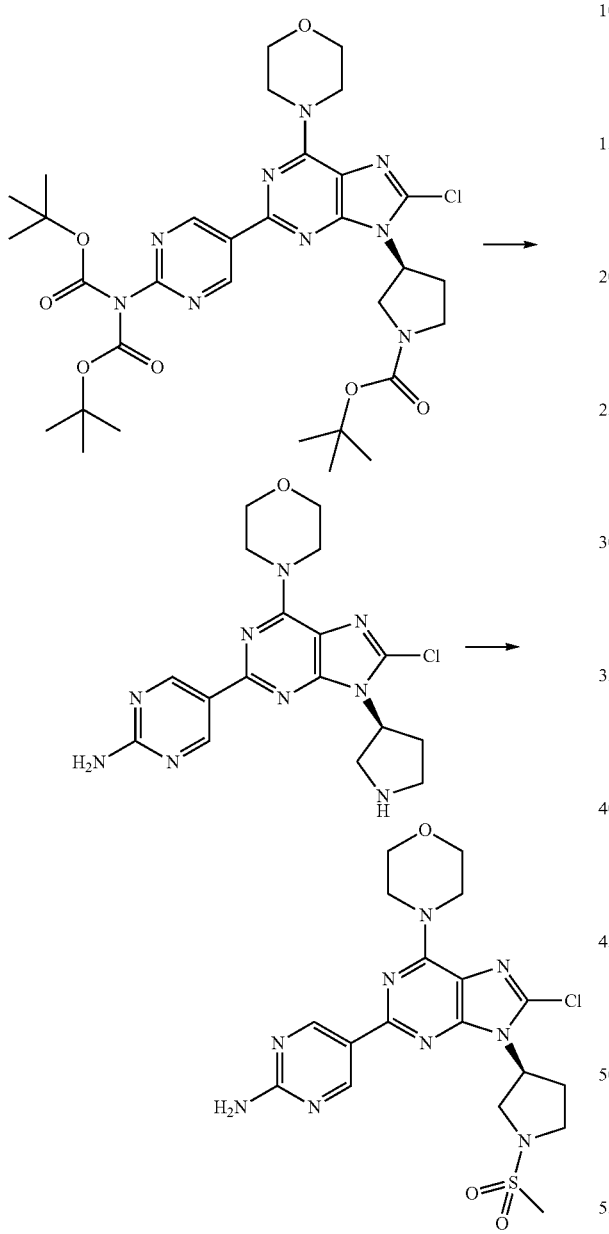

tert-Butyl (3S)-3-(2-{2-[bis(tert-butoxycarbonyl)amino]pyrimidin-5-yl}-8-chloro-6-morpholin-4-yl-9H-purin-9-yl)pyrrolidine-1-carboxylate (1.32 g, 1.88 mmol) was dissolved in methylene chloride (5 ml) followed by the addition of trifluoroacetic acid (5 ml) and the resulting mixture was stirred for 0.5 hours. The solvent was removed azeotropically with toluene and evaporated under reduced pressure. The residue was dissolved in methylene chloride followed by the addition of triethylamine (1 ml) and methanesulfonyl chloride (170 μl, 2.26 mmol) with ice cooling and the resulting mixture was stirred at room temperature for 4 hours. The reaction mixture was partitioned with ethyl acetate and water, and the solid that was not dissolved in either layer was collected by filtration, washed with ethyl acetate and water, and dried. This solid was suspended in methylene chloride, and then the insoluble matter was collected by filtration and dried to give the title compound (0.38 g, 42%) as a pale grey solid.

$^1$H-NMR (DMSO-$d_6$) δ: 2.80-2.84 (1H, m), 3.04 (3H, s), 3.47-3.52 (1H, m), 3.75-3.77 (5H, m), 3.78-3.82 (2H, m), 3.94 (1H, dd, J=10.31, 7.45 Hz), 4.24 (4H, brs), 5.35-5.41 (1H, m), 9.52 (2H, s).

Step 6: 5-{8-(cis-3,5-Dimethylpiperazin-1-yl)-9-[(3S)-1-(methylsulfonyl)pyrrolidin-3-yl]-6-morpholin-4-yl-9H-purin-2-yl}pyrimidin-2-amine

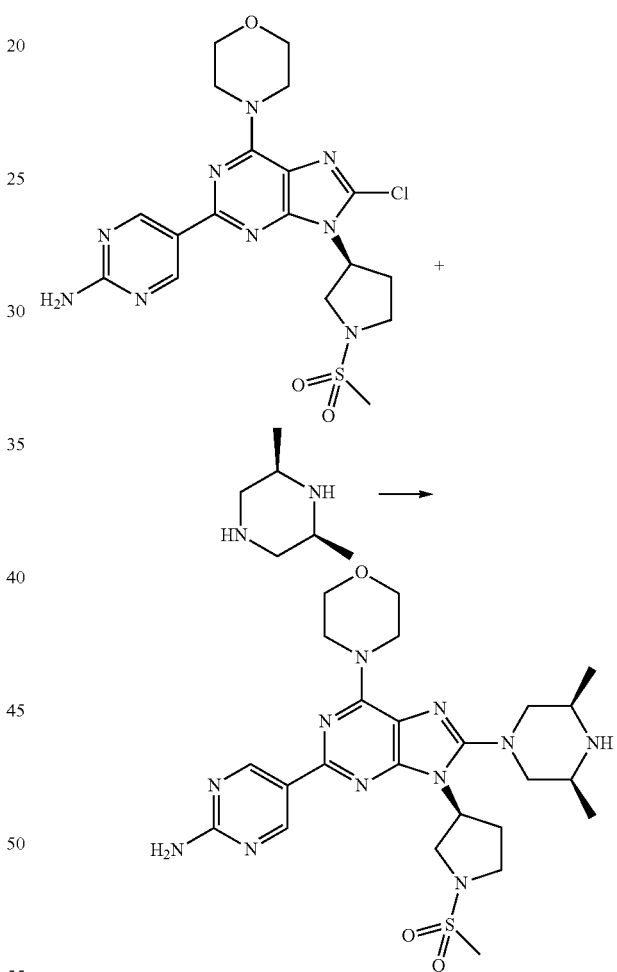

Dimethyl sulfoxide (1 ml) was added to 5-{8-chloro-9-[(3S)-1-(methylsulfonyl)pyrrolidin-3-yl]-6-morpholin-4-yl-9H-purin-2-yl}pyrimidin-2-amine (100 mg, 0.21 mmol) and cis-2,6-dimethylpiperazine (119 mg, 1.04 mmol) and the resulting mixture was stirred at 140° C. for 1 hour. The reaction mixture was partitioned with chloroform and water, the organic layer was dried over magnesium sulfate, and then the solvent was evaporated under reduced pressure. The residue was purified by silica gel chromatography (chloroform: methanol=9:1) to give the title compound (95 mg, 82%) as a light brown solid.

¹H-NMR (DMSO-d₆) δ: 0.95-0.97 (1H, m), 1.01 (6H, d, J=6.34 Hz), 2.33-2.35 (1H, m), 2.77-2.80 (1H, m), 2.99-3.03 (5H, brm), 3.03 (3H, s), 3.17-3.20 (2H, m), 3.45-3.51 (1H, m), 3.72-3.75 (4H, m), 3.79-3.81 (2H, m), 3.89-3.91 (1H, m), 4.18 (4H, brs), 5.02-5.05 (1H, m), 7.00 (2H, s), 9.05 (2H, s).

Example 27

5-{8-[4-(Methylsulfonyl)piperazin-1-yl]-9-[(3S)-1-(methylsulfonyl)pyrrolidin-3-yl]-6-morpholin-4-yl-9H-purin-2-yl}pyrimidin-2-amine

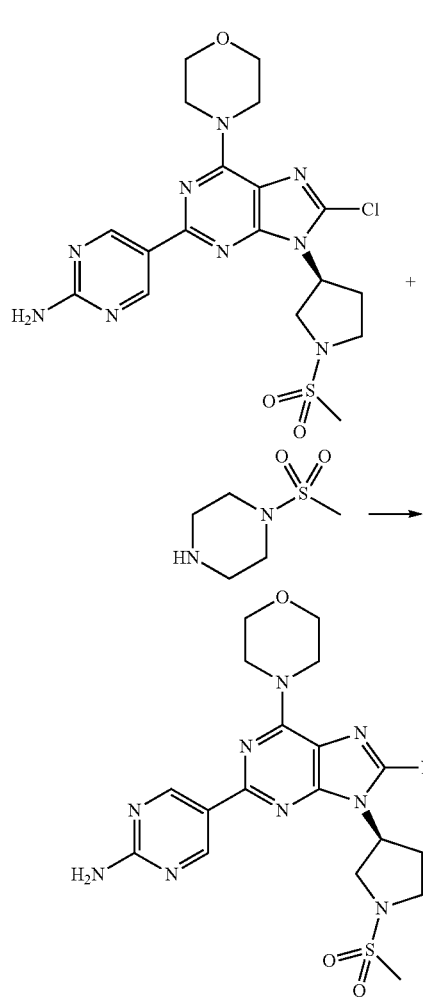

Dimethyl sulfoxide (1 ml) was added to 5-{8-chloro-9-[(3S)-1-(methylsulfonyl)pyrrolidin-3-yl]-6-morpholin-4-yl-9H-purin-2-yl}pyrimidin-2-amine (100 mg, 0.21 mmol) and N-mesylpiperazine (171 mg, 1.04 mmol) and the resulting mixture was stirred at 140° C. for 1 hour. The reaction mixture was partitioned with chloroform and water, the organic layer was dried over magnesium sulfate, and the solvent was evaporated under reduced pressure. The residue was purified by silica gel chromatography (chloroform:methanol=19:1) to give the title compound (105 mg, 83%) as a light brown solid.

¹H-NMR (DMSO-d₆) δ: 2.30-2.37 (1H, m), 2.80-2.86 (1H, m), 2.96 (3H, s), 3.04 (3H, s), 3.24-3.28 (4H, m), 3.33-3.35 (4H, m), 3.44-3.48 (1H, m), 3.72-3.83 (6H, m), 3.93 (1H, t, J=9.02 Hz), 4.20 (4H, brs), 5.01-5.09 (1H, m), 7.02 (2H, s), 9.05 (2H, s).

Example 28

N'-[2-(2-Aminopyrimidin-5-yl)-9-(cyclopropylmethyl)-6-morpholin-4-yl-9H-purin-8-yl]-N,N-dimethylethane-1,2-diamine

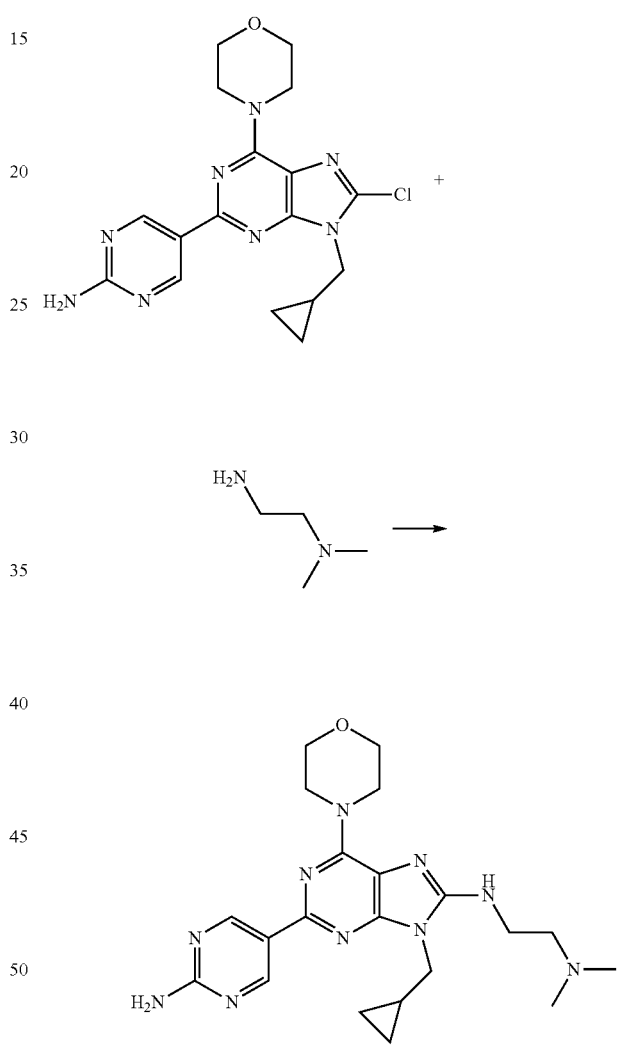

N,N-Dimethylethylenediamine (113 mg, 1.3 mmol) and dimethyl sulfoxide (1 ml) were added to 5-[8-chloro-9-(cyclopropylmethyl)-6-morpholin-4-yl-9H-purin-2-yl]pyrimidin-2-amine (100 mg, 0.26 mmol) and the resulting mixture was stirred at 150° C. for 4 hours. The reaction mixture was purified by preparative HPLC (column, NOMURA Develosil Combi-RP-5; mobile phase, acetonitrile/water/formic acid) to give the title compound (85 mg, 68%) as a pale yellow solid.

¹H-NMR (DMSO-d₆) δ: 0.44-0.47 (4H, m), 1.21-1.26 (1H, m), 2.30 (7H, s), 2.62 (2H, t, J=6.59 Hz), 3.48 (2H, q, J=6.30

Hz), 3.71-3.73 (4H, m), 3.91 (2H, d, J=6.87 Hz), 4.12-4.14 (4H, m), 6.82 (1H, t, J=5.73 Hz), 6.91 (2H, s), 8.19 (1H, s), 9.03 (2H, s).

d, J=6.87 Hz), 4.12-4.13 (4H, m), 6.73 (1H, t, J=5.73 Hz), 6.91 (2H, s), 8.14 (1H, s), 9.02 (2H, s).

Example 29

2-(2-Aminopyrimidin-5-yl)-9-(cyclopropylmethyl)-6-morpholin-4-yl-N-(2-morpholin-4-ylethyl)-9H-purin-8-amine

Example 30

2-{[2-(2-Aminopyrimidin-5-yl)-9-(cyclopropylmethyl)-6-morpholin-4-yl-9H-purin-8-yl]amino}ethanol

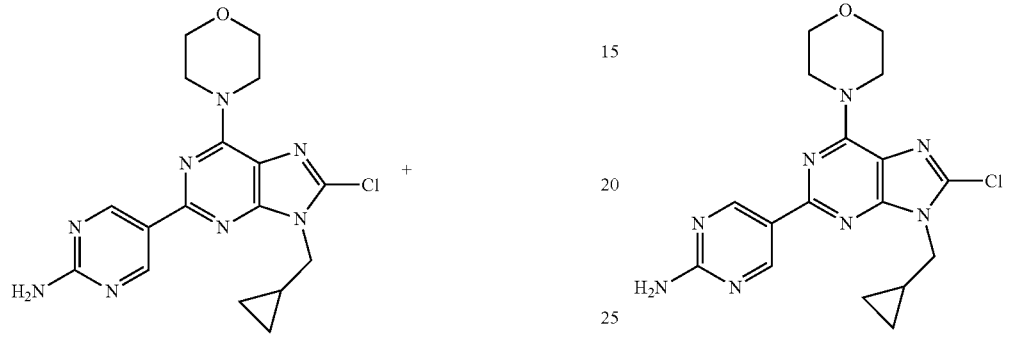

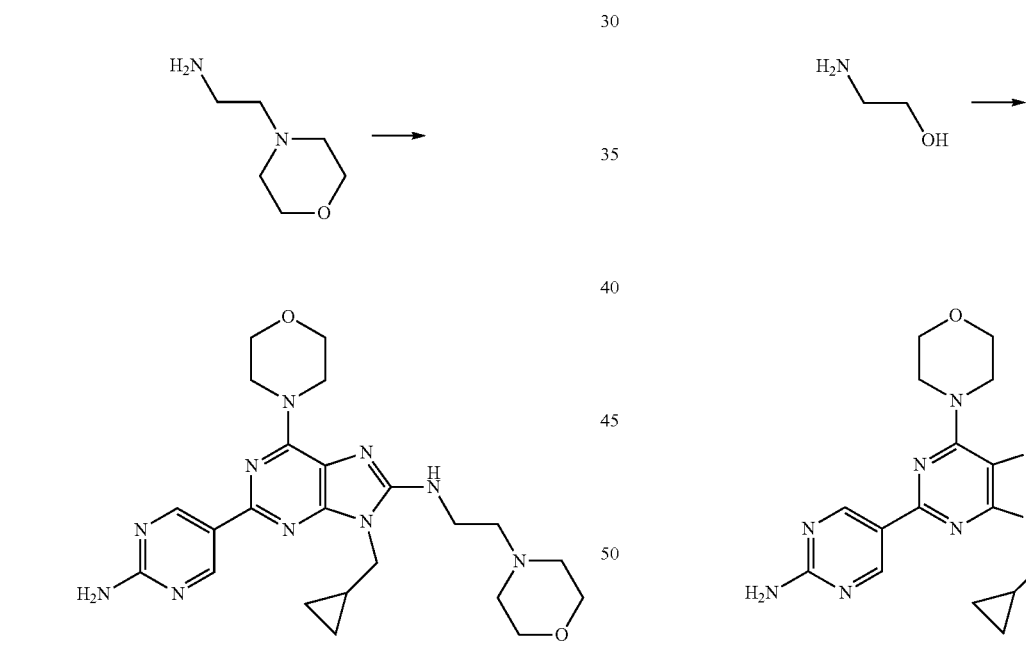

2-Morpholin-4-yl-ethylamine (168 mg, 1.29 mmol) and dimethyl sulfoxide (1 ml) were added to 5-[8-chloro-9-(cyclopropylmethyl)-6-morpholin-4-yl-9H-purin-2-yl]pyrimidin-2-amine (100 mg, 0.26 mmol) and the resulting mixture was stirred at 150° C. for 4 hours. The reaction mixture was purified by preparative HPLC (column, NOMURA Develosil Combi-RP-5; mobile phase, acetonitrile/water/formic acid) to give the title compound (85 mg, 62%) as a pale yellow solid.

$^1$H-NMR (DMSO-d$_6$) δ: 0.44-0.47 (4H, m), 1.21-1.27 (1H, m), 2.44 (4H, brs), 2.56 (2H, t, J=6.87 Hz), 3.47 (3H, q, J=6.30 Hz), 3.55-3.57 (4H, m), 3.71-3.73 (4H, m), 3.91 (2H, 2-Aminoethanol (79 mg, 1.3 mmol) and dimethyl sulfoxide (1 ml) were added to 5-[8-chloro-9-(cyclopropylmethyl)-6-morpholin-4-yl-9H-purin-2-yl]pyrimidin-2-amine (100 mg, 0.26 mmol) and the resulting mixture was stirred at 150° C. for 4 hours. The reaction mixture was purified by preparative HPLC (column, NOMURA Develosil Combi-RP-5; mobile phase, acetonitrile/water/formic acid) to give the title compound (70 mg, 66%) as a white solid.

$^1$H-NMR (DMSO-d$_6$) δ: 0.43-0.48 (4H, m), 1.23-1.28 (1H, m), 3.42 (2H, q, J=5.92 Hz), 3.61 (2H, t, J=6.01 Hz), 3.71-

3.73 (4H, m), 3.92 (2H, d, J=6.87 Hz), 4.11-4.13 (4H, m), 4.75 (1H, brs), 6.82 (1H, t, J=5.44 Hz), 6.91 (2H, s), 9.03 (2H, d, J=5.73 Hz).

Example 31

5-{9-(Cyclopropylmethyl)-6-morpholin-4-yl-8-[3-(phenylsulfonyl)pyrrolidin-1-yl]-9H-purin-2-yl}pyrimidin-2-amine

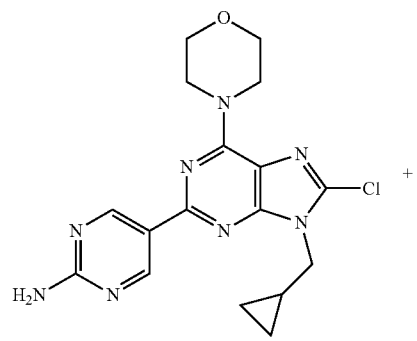

3-(Phenylsulfonyl)pyrrolidine (110 mg, 0.52 mmol) and dimethyl sulfoxide (0.8 ml) were added to 5-[8-chloro-9-(cyclopropylmethyl)-6-morpholin-4-yl-9H-purin-2-yl]pyrimidin-2-amine (80 mg, 0.21 mmol) and the resulting mixture was stirred at 150° C. for 4 hours. The reaction mixture was partitioned with ethyl acetate and water and the organic layer was washed with saturated brine and dried over magnesium sulfate. The solvent was evaporated under reduced pressure and then the residue was purified by silica gel chromatography (ethyl acetate:hexane=2:1) to give the title compound (20 mg, 17%) as a white solid.

$^1$H-NMR (CDCl$_3$) δ: 0.50 (4H, d, J=6.87 Hz), 1.18-1.23 (1H, m), 2.31-2.36 (1H, m), 2.53-2.59 (1H, m), 3.60-3.65 (1H, m), 3.72-3.76 (1H, m), 3.83-3.88 (4H, m), 3.87-3.90 (1H, m), 3.96-4.02 (1H, m), 4.04-4.07 (1H, m), 4.24 (4H, brs), 5.15 (2H, s), 7.61 (2H, t, J=7.73 Hz), 7.69-7.72 (1H, m), 7.96-7.98 (2H, m), 9.21 (2H, s).

Example 32

N-(2-{[2-(2-Amino-4-methylpyrimidin-5-yl)-9-(cyclopropylmethyl)-6-morpholin-4-yl-9H-purin-8-yl]amino}ethyl)methanesulfonamide

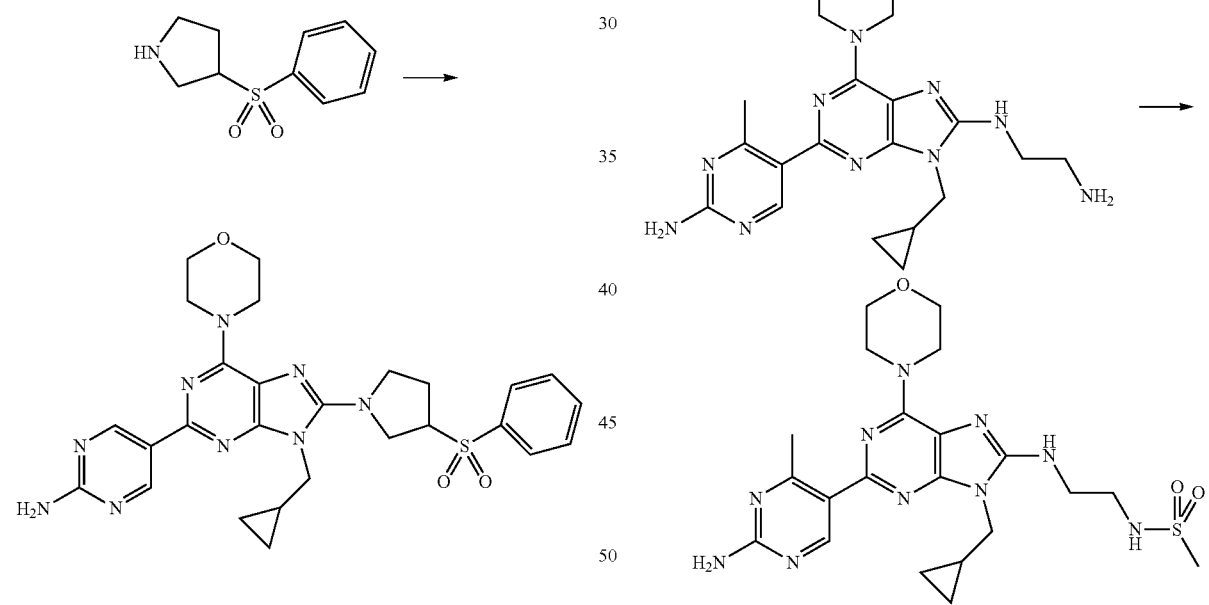

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and ethylenediamine (150 mg, 2.49 mmol) and the resulting mixture was stirred at 120° C. for 3.5 hours. The reaction mixture was partitioned with chloroform and saturated brine and the organic layer was washed with saturated brine and dried over magnesium sulfate. The solvent was concentrated under reduced pressure, then triethylamine (100 μl, 0.75 mmol) and mesyl chloride (25 μl, 0.32 mmol) were added to the residue, and the resulting mixture was stirred for 1 hour. The reaction mixture was partitioned with ethyl acetate and water and the organic layer was washed with saturated brine and dried over magnesium sulfate. The solvent was evaporated under reduced pressure and then the residue was purified by preparative HPLC (column, NOMURA Develosil Combi-RP-5; mobile phase, acetonitrile/water/formic acid) to give the title compound (57 mg, 46%) as a pale yellow solid.

¹H-NMR (CDCl₃) δ: 0.45-0.48 (2H, m), 0.59-0.63 (2H, m), 1.17-1.22 (1H, m), 2.74 (3H, s), 2.96 (3H, s), 3.47-3.49 (2H, m), 3.71-3.74 (2H, m), 3.85 (4H, t, J=4.87 Hz), 3.90 (2H, d, J=6.87 Hz), 4.17 (4H, t, J=4.58 Hz), 4.89 (1H, t, J=5.44 Hz), 5.43 (2H, s), 8.88 (1H, s).

Example 33

5-{9-(Cyclopropylmethyl)-8-[3-(dimethylamino)pyrrolidin-1-yl]-6-morpholin-4-yl-9H-purin-2-yl}-4-methylpyrimidin-2-amine

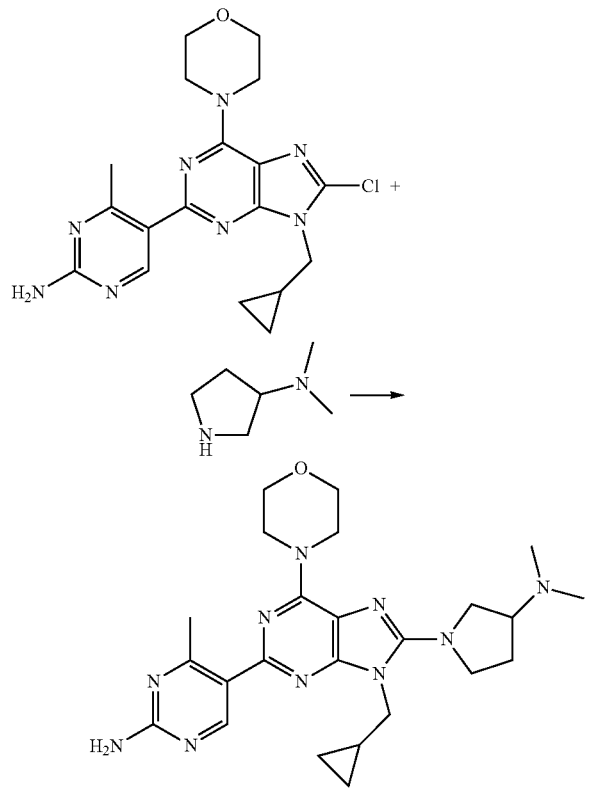

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and 3-(dimethylamino)pyrrolidine (285 mg, 2.49 mmol) and the resulting mixture was stirred at 120° C. for 3.5 hours. The reaction mixture was partitioned with chloroform and saturated brine and the organic layer was washed with saturated brine and dried over magnesium sulfate. The solvent was concentrated under reduced pressure, then methylene chloride-ether was added to the residue, and the precipitate was collected by filtration, washed with ether, and dried under reduced pressure to give the title compound (55 mg, 46%) as a pale orange solid.

¹H-NMR (CDCl₃) δ: 0.40-0.53 (4H, m), 1.24-1.29 (1H, m), 1.92-1.97 (1H, m), 2.18-2.23 (1H, m), 2.34 (6H, s), 2.73 (3H, s), 2.86-2.92 (1H, m), 3.54 (1H, t, J=8.59 Hz), 3.70-3.73 (2H, m), 3.76-3.79 (1H, m), 3.83-3.85 (4H, m), 4.02 (1H, dd, J=14.61, 6.59 Hz), 4.10 (1H, dd, J=14.89, 7.45 Hz), 4.22-4.24 (4H, m), 5.01 (2H, s), 8.90 (1H, s).

Example 34

N-{1-[2-(2-Amino-4-methylpyrimidin-5-yl)-9-(cyclopropylmethyl)-6-morpholin-4-yl-9H-purin-8-yl]pyrrolidin-3-yl}-N-methylmethanesulfonamide

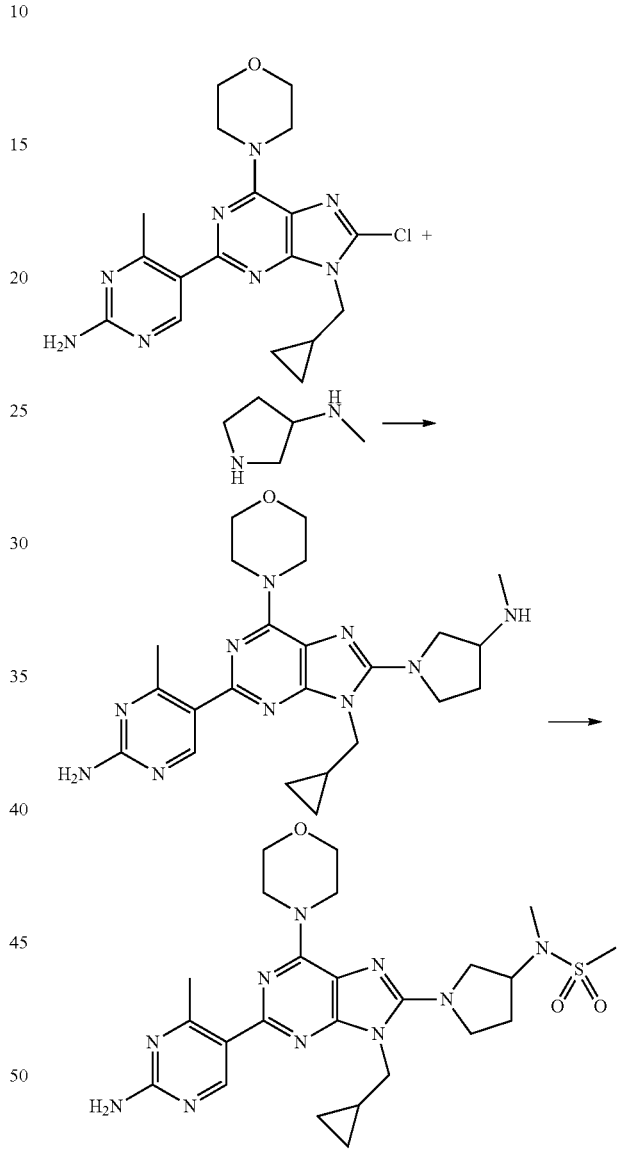

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and 3-methylaminopyrrolidine (130 mg, 1.5 mmol) and the resulting mixture was stirred at 120° C. for 0.5 hours. The reaction mixture was partitioned with chloroform and saturated brine and the organic layer was washed with saturated brine and dried over magnesium sulfate. The solvent was concentrated under reduced pressure, triethylamine (100 μl, 0.75 mmol) and mesyl chloride (60 μl, 0.75 mmol) were added to the residue, and the resulting mixture was stirred for 1 hour. The reaction mixture was partitioned with ethyl acetate (containing a small amount of tetrahydrofuran) and water and the organic layer was washed with saturated brine and dried over magnesium sulfate. The solvent was evaporated under reduced pressure and then the residue was purified by silica gel chromatography (chloroform:methanol=9:1) to give a pale yellow solid (75 mg, 50%).

$^1$H-NMR (DMSO-d$_6$) δ: 0.38-0.48 (4H, m), 1.25-1.31 (1H, m), 2.10-2.16 (1H, m), 2.18-2.24 (1H, m), 2.63 (3H, s), 2.82 (3H, s), 2.98 (3H, s), 3.55-3.60 (2H, m), 3.71-3.78 (6H, m), 4.09 (2H, d, J=7.45 Hz), 4.13 (4H, brs), 4.48-4.55 (1H, m), 6.73 (2H, s), 8.79 (1H, s).

Example 35

N-{1-[2-(2-Amino-4-methylpyrimidin-5-yl)-9-(cyclopropylmethyl)-6-morpholin-4-yl-9H-purin-8-yl]pyrrolidin-3-yl}methanesulfonamide

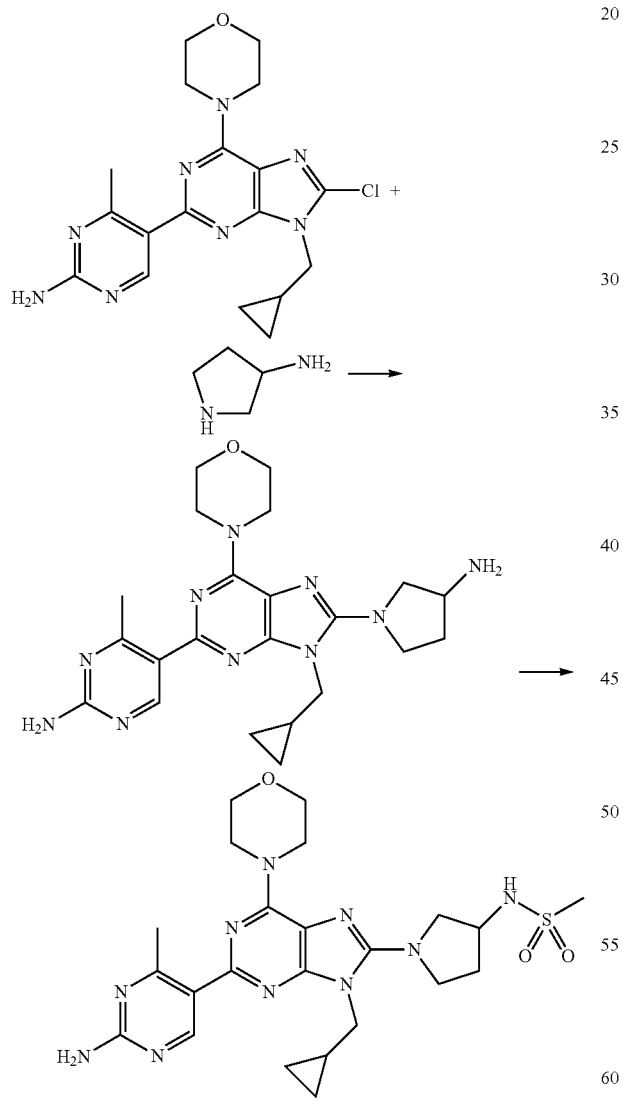

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and 3-aminopyrrolidine (130 mg, 1.5 mmol) and the resulting mixture was stirred at 120° C. for 1 hour. The reaction mixture was partitioned with chloroform and saturated brine and the organic layer was washed with saturated brine and dried over magnesium sulfate. The solvent was concentrated under reduced pressure, then triethylamine (100 µl, 0.75 mmol) and mesyl chloride (60 µl, 0.75 mmol) were added to the residue, and the resulting mixture was stirred for 1 hour. The reaction mixture was partitioned with ethyl acetate and water and the organic layer was washed with saturated brine and dried over magnesium sulfate. The solvent was evaporated under reduced pressure and then the residue was purified by preparative HPLC (column, NOMURA Develosil Combi-RP-5; mobile phase, acetonitrile/water/formic acid) to give the title compound (70 mg, 53%) as a pale yellow solid.

$^1$H-NMR (DMSO-d$_6$) δ: 0.42-0.47 (4H, m), 1.27-1.32 (1H, m), 1.94-1.99 (1H, m), 2.21-2.27 (1H, m), 2.62 (3H, s), 2.99 (3H, s), 3.50 (1H, dd, J=9.74, 5.15 Hz), 3.62-3.66 (1H, m), 3.70-3.75 (5H, m), 3.83 (1H, dd, J=10.31, 6.30 Hz), 4.04-4.07 (7H, m), 6.72 (2H, s), 7.46 (1H, d, J=6.87 Hz), 8.78 (1H, s).

Example 36

1-[2-(2-Amino-4-methylpyrimidin-5-yl)-9-(cyclopropylmethyl)-6-morpholin-4-yl-9H-purin-8-yl]piperidine-4-carboxamide

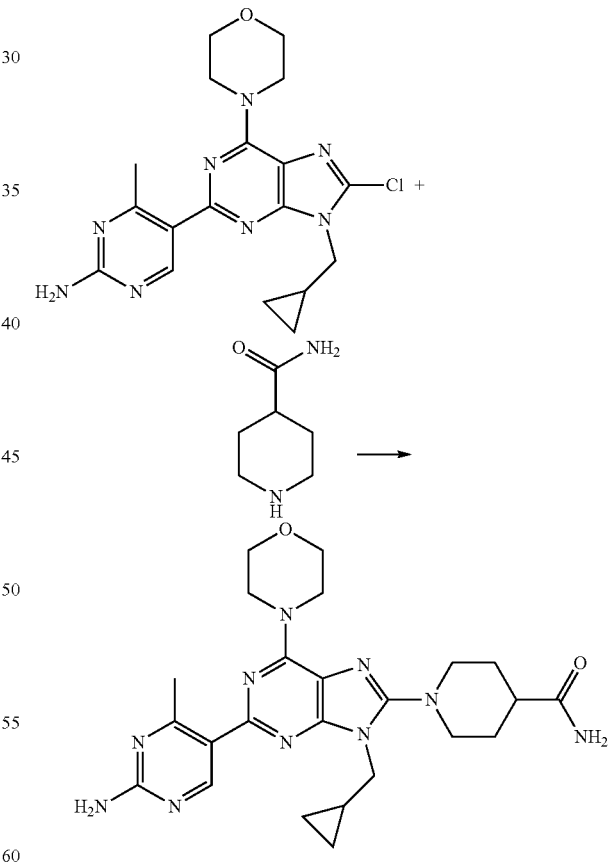

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and isonipecotamide (191 mg, 1.5 mmol) and the resulting mixture was stirred at 120° C. for 2.5 hours. The reaction mixture was left standing to cool followed by the addition of water and the insoluble matter was collected by filtration and dried to give the title compound (85 mg, 69%) as a pale yellow solid.

$^1$H-NMR (DMSO-$d_6$) δ: 0.41-0.49 (4H, m), 1.33-1.36 (1H, m), 1.72-1.84 (4H, m), 2.28-2.32 (1H, m), 2.87-2.91 (2H, m), 3.52-3.56 (2H, m), 3.72-3.74 (4H, m), 3.93 (2H, d, J=6.87 Hz), 4.15 (4H, brs), 6.75 (2H, s), 6.82 (1H, s), 7.32 (1H, s), 8.78 (1H, s).

Example 37

{1-[2-(2-Amino-4-methylpyrimidin-5-yl)-9-(cyclopropylmethyl)-6-morpholin-4-yl-9H-purin-8-yl]piperidin-4-yl}methanol

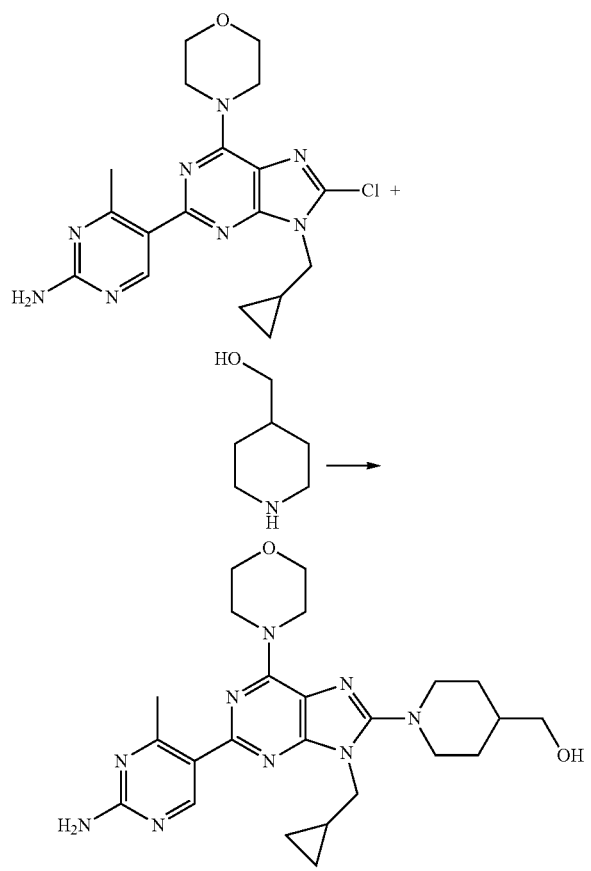

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and 4-piperidinemethanol (172 mg, 1.5 mmol) and the resulting mixture was stirred at 120° C. for 0.5 hours. The reaction mixture was partitioned with ethyl acetate and water and the organic layer was washed with saturated brine and dried over magnesium sulfate. The solvent was concentrated under reduced pressure and the residue was purified by preparative HPLC (column, NOMURA Develosil Combi-RP-5; mobile phase, acetonitrile/water/formic acid) to give the title compound (69 mg, 58%) as a pale yellow solid.

$^1$H-NMR (CDCl$_3$) δ: 0.45-0.55 (4H, m), 1.35-1.41 (1H, m), 1.47 (3H, ddd, J=24.49, 12.46, 3.58 Hz), 1.88 (2H, d, J=12.60 Hz), 2.74 (3H, s), 2.99 (2H, td, J=12.60, 2.29 Hz), 3.56-3.59 (2H, m), 3.60 (2H, d, J=6.30 Hz), 3.84-3.86 (4H, m), 3.93 (2H, d, J=6.87 Hz), 4.26 (4H, brs), 5.17 (2H, brs), 8.90 (1H, s).

Example 38

5-{9-(Cyclopropylmethyl)-8-[cis-3,5-dimethyl-4-(methylsulfonyl)piperazin-1-yl]-6-morpholin-4-yl-9H-purin-2-yl}pyrimidin-2-amine

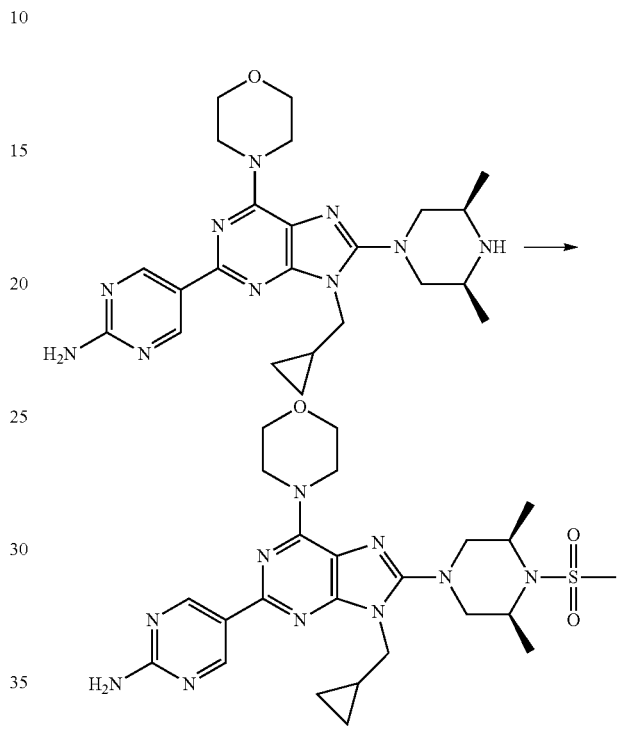

Triethylamine (127.1 μl, 0.91 mmol) and methanesulfonyl chloride (35.3 ml, 0.46 mmol) were added to a dichloromethane suspension (2.0 ml) of 5-[9-(cyclopropylmethyl)-8-(cis-3,5-dimethylpiperazin-1-yl)-6-morpholin-4-yl-9H-purin-2-yl]pyrimidin-2-amine (105.9 mg, 0.23 mmol) with ice cooling and the resulting mixture was stirred at the same temperature for 2.5 hours and at room temperature for 4 hours. Triethylamine (127.1 μl, 0.91 mmol) and methanesulfonyl chloride (35.3 ml, 0.46 mmol) were added at room temperature and the resulting mixture was stirred for 16 hours followed by the addition of dichloromethane-methanol (10:1) and washed with water. The organic layer was dried over anhydrous sodium sulfate, the mixture was filtrated, the filtrate was concentrated under reduced pressure, and the resulting residue was dissolved in 1,2-dichloroethane (2.0 ml). Triethylamine (127.1 μl, 0.91 mmol) and methanesulfonyl chloride (35.3 ml, 0.46 mmol) were added at room temperature and the resulting mixture was stirred for 19 hours followed by the addition of dichloromethane and washed with 10% aqueous citric acid solution. The organic layer was dried over anhydrous sodium sulfate, the mixture was filtrated, the filtrate was concentrated under reduced pressure, and the resulting residue was purified by preparative thin layer silica gel chromatography (dichloromethane:methanol=10:1) to give the title compound (16.3 mg, 13%) as a pale yellow solid.

$^1$H-NMR (CDCl$_3$) δ: 0.52-0.57 (4H, m), 1.33-1.42 (1H, m), 1.62 (6H, d, J=6.87 Hz), 2.94 (3H, s), 3.13 (2H, dd, J=12.03, 4.58 Hz), 3.36 (2H, d, J=12.03 Hz), 3.82-3.88 (4H, m), 4.03 (2H, d, J=7.45 Hz), 4.18-4.33 (6H, m), 5.35 (2H, s), 9.24 (2H, s).

Example 39

5-[9-(Cyclopropylmethyl)-6,8-dimorpholin-4-yl-9H-purin-2-yl]-N-methylpyrimidin-2-amine

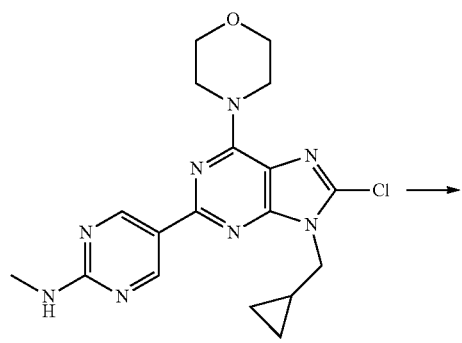

A dimethyl sulfoxide solution (1.0 ml) of 5-[8-chloro-9-(cyclopropylmethyl)-6-morpholin-4-yl-9H-purin-2-yl]-N-methylpyrimidin-2-amine (103.3 mg, 0.21 mmol) and morpholine (74.3 mg, 0.85 mmol) was heated at 140° C. and stirred for 3 hours. Morpholine (74.3 mg, 0.85 mmol) was added, the resulting mixture was further stirred for 3 hours, left standing to cool followed by the addition of dichloromethane-methanol (10:1), and the resulting mixture was washed with saturated aqueous sodium hydrogen carbonate solution. The organic layer was dried over anhydrous sodium sulfate, the mixture was filtrated, the filtrate was concentrated under reduced pressure, and the resulting residue was purified by preparative thin layer silica gel chromatography (dichloromethane:methanol=10:1) to give the title compound (87.1 mg, 91%) as a pale yellow solid.

$^1$H-NMR (CDCl$_3$) δ: 0.52-0.56 (4H, m), 1.29-1.38 (1H, m), 3.08 (3H, d, J=5.15 Hz), 3.26-3.32 (4H, m), 3.82-3.91 (8H, m), 3.96 (2H, d, J=6.87 Hz), 4.21-4.34 (4H, brm), 5.31-5.37 (1H, m), 9.25 (2H, s).

Example 40

5-[9-(Cyclopropylmethyl)-8-{4-[(dimethylamino)acetyl]piperazin-1-yl}-6-morpholin-4-yl-9H-purin-2-yl]pyrimidin-2-amine

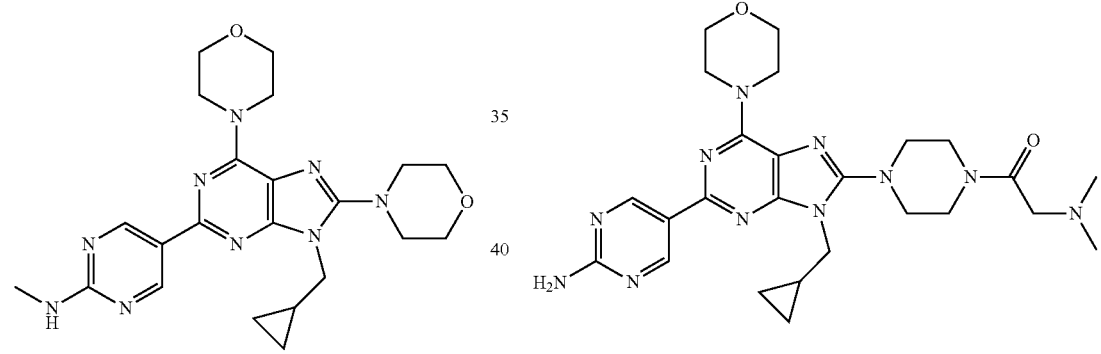

1-Hydroxybenzotriazole monohydrate (35.0 mg, 0.23 mmol), 1-(dimethylaminopropyl)-3-ethylcarbodiimide hydrochloride (65.7 mg, 0.34 mmol), and triethylamine (38.2 μl, 0.27 mmol) were added to an N,N-dimethylformamide suspension (2.0 ml) of 5-[9-(cyclopropylmethyl)-6-morpholin-4-yl-8-piperazin-1-yl-9H-purin-2-yl]pyrimidin-2-amine (99.7 mg, 0.23 mmol) and N,N-dimethylglycine hydrochloride (38.3 mg, 0.27 mmol) at room temperature. The resulting mixture was stirred for 20.5 hours and heated to 50° C. followed by the addition of triethylamine (38.2 μl, 0.27 mmol) and the resulting mixture was stirred for 6 hours. The resulting mixture was further stirred at room temperature for 17 hours and then the reaction mixture was poured into dichloromethane-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (dichloromethane:methanol=5:1) to give the title compound (84.6 mg, 71%) as a pale yellow solid.

¹H-NMR (CDCl₃) δ: 0.48-0.61 (4H, m), 1.29-1.40 (1H, m), 2.30 (6H, s), 3.17 (2H, s), 3.21-3.36 (4H, m), 3.76-3.89 (8H, m), 3.98 (2H, d, J=7.07 Hz), 4.20-4.36 (4H, brm), 5.39 (2H, s), 9.23 (2H, s).

Example 41

5-[9-(Cyclopropylmethyl)-8-{4-[(methylamino)acetyl]piperazin-1-yl}-6-morpholin-4-yl-9H-purin-2-yl]pyrimidin-2-amine

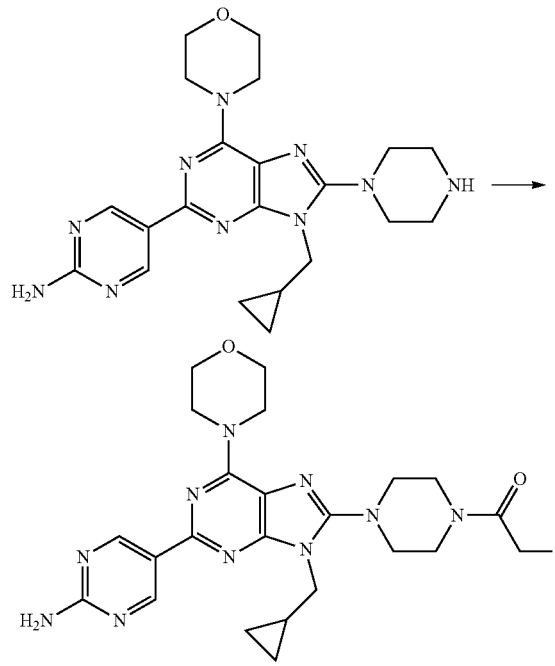

1-Hydroxybenzotriazole monohydrate (35.1 mg, 0.23 mmol), 1-(dimethylaminopropyl)-3-ethylcarbodiimide hydrochloride (65.9 mg, 0.34 mmol), and triethylamine (86.2 µl, 0.62 mmol) were added to an N,N-dimethylformamide suspension (2.0 ml) of 5-[9-(cyclopropylmethyl)-6-morpholin-4-yl-8-piperazin-1-yl-9H-purin-2-yl]pyrimidin-2-amine (100.0 mg, 0.23 mmol) and N-tert-butoxycarbonyl-N-methylglycine (52.0 mg, 0.27 mmol) at room temperature. The resulting mixture was stirred for 3 days and the reaction mixture was poured into dichloromethane-methanol (10:1), washed with saturated aqueous sodium bicarbonate solution and dried over anhydrous sodium sulfate. After filtration, the filtrate was concentrated under reduced pressure and the resulting residue was dissolved in dichloromethane (4.0 ml) followed by the addition of trifluoroacetic acid (2.0 ml) with ice cooling. The resulting mixture was stirred at room temperature for 2 hours and concentrated, dichloromethane was added to the residue, and the resulting mixture was neutralized with saturated aqueous sodium hydrogen carbonate solution. The resulting mixture was extracted with dichloromethane-methanol (10:1), dried over anhydrous sodium sulfate, and filtrated, the filtrate was concentrated under reduced pressure, and the resulting residue was purified by preparative thin layer silica gel chromatography (dichloromethane:methanol=5:1) to give the title compound (67.1 mg, 58%) as a pale yellow solid.

¹H-NMR (CD₃OD/CDCl₃=1/1) δ: 0.49-0.62 (4H, m), 1.32-1.41 (1H, m), 2.47 (3H, s), 3.26-3.39 (4H, m), 3.48 (2H, s), 3.61-3.70 (2H, m), 3.79-3.91 (6H, m), 4.01 (2H, d, J=6.87 Hz), 4.10-4.46 (4H, m), 9.19 (2H, s).

Example 42

5-{8-[4-(Aminoacetyl)piperazin-1-yl]-9-(cyclopropylmethyl)-6-morpholin-4-yl-9H-purin-2-yl}pyrimidin-2-amine

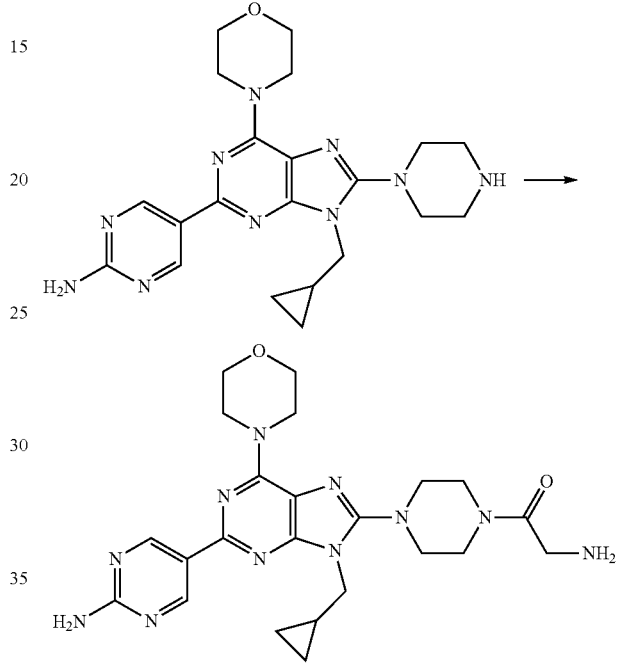

1-Hydroxybenzotriazole monohydrate (33.8 mg, 0.22 mmol), 1-(dimethylaminopropyl)-3-ethylcarbodiimide hydrochloride (63.4 mg, 0.33 mmol), and triethylamine (82.9 µl, 0.60 mmol) were added to an N,N-dimethylformamide suspension (2.0 ml) of 5-[9-(cyclopropylmethyl)-6-morpholin-4-yl-8-piperazin-1-yl-9H-purin-2-yl]pyrimidin-2-amine (96.2 mg, 0.22 mmol) and N-tert-butoxycarbonyl-glycine (46.3 mg, 0.26 mmol) at room temperature. The resulting mixture was stirred for 3 days and then the reaction mixture was poured into dichloromethane-methanol (10:1), washed with saturated aqueous sodium hydrogen carbonate solution, and dried over anhydrous sodium sulfate. After filtration, the filtrate was concentrated under reduced pressure and the resulting residue was dissolved in dichloromethane (4.0 ml) followed by the addition of trifluoroacetic acid (2.0 ml) with ice cooling. The resulting mixture was stirred at room temperature for 2 hours and the concentrated, dichloromethane was added to the residue, and the resulting mixture was neutralized with saturated aqueous sodium hydrogen carbonate solution. The resulting mixture was extracted with dichloromethane-methanol (10:1), dried over anhydrous sodium sulfate, and then filtrated, the filtrate was concentrated under reduced pressure, and the resulting residue was purified by preparative thin layer silica gel chromatography (dichloromethane:methanol=5:1) to give the title compound (19.1 mg, 18%) as a pale yellow solid.

$^1$H-NMR (CD$_3$OD/CDCl$_3$=1/1) δ: 0.50-0.62 (4H, m), 1.33-1.44 (1H, m), 3.28-3.38 (4H, m), 3.55 (2H, s), 3.61-3.69 (2H, m), 3.81-3.90 (6H, m), 4.02 (2H, d, J=6.87 Hz), 4.25-4.33 (4H, m), 9.18 (2H, s).

Example 43

5-{9-(Cyclopropylmethyl-8-[4-(methylsulfonyl)piperazin-1-yl]-6-morpholin-4-yl-9H-purin-2-yl}-N,4-dimethylpyrimidin-2-amine

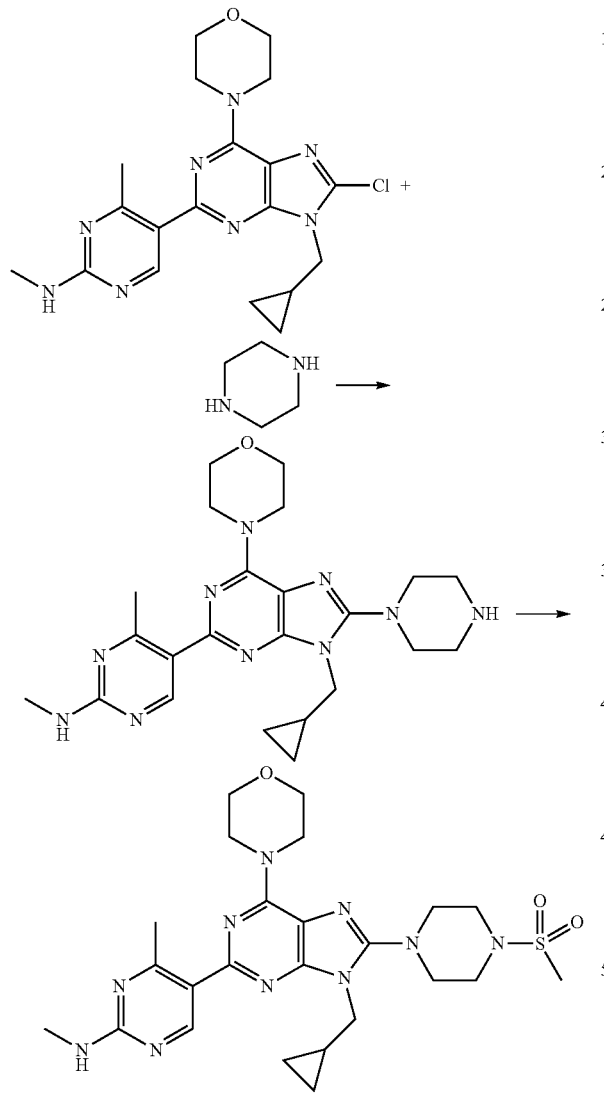

N-Methylpyrrolidone (2 ml) was added to 5-[8-chloro-9-(cyclopropylmethyl)-6-morpholin-4-yl-9H-purin-2-yl]-N,4-dimethylpyrimidin-2-amine (190 mg, 0.46 mmol) and piperazine (395 mg, 4.6 mmol) and the resulting mixture was stirred at 120° C. for 2 hours. The reaction mixture was partitioned with ethyl acetate and water, the organic layer was fractionated, and the aqueous layer extracted three times with ethyl acetate. The organic layer fractions were combined and dried over magnesium sulfate and the solvent was concentrated under reduced pressure. Triethylamine (130 μl) and mesyl chloride (50 μl) were added to the residue with ice cooling and the resulting mixture was stirred for 1 hour. The reaction mixture was partitioned with ethyl acetate and water, the organic layer was fractionated and then dried over magnesium sulfate, and the solvent was evaporated under reduced pressure. The residue was purified by preparative HPLC (column, NOMURA Develosil Combi-RP-5; mobile phase, acetonitrile/water/formic acid) to give the title compound (140 mg, 56%) as a white solid.

$^1$H-NMR (CDCl$_3$) δ: 0.47-0.55 (4H, m), 1.32-1.38 (1H, m), 2.75 (3H, s), 2.87 (3H, s), 3.06 (3H, d, J=5.1 Hz), 3.39-3.45 (8H, m), 3.83-3.85 (4H, m), 3.95 (2H, d, J=6.83 Hz), 4.24-4.27 (4H, m), 5.15-5.21 (1H, m), 9.00 (1H, s).

Example 44

5-{9-(Cyclopropylmethyl)-8-[4-(methylsulfonyl)piperazin-1-yl]-6-morpholin-4-yl-9H-purin-2-yl}-N,N,4-trimethylpyrimidin-2-amine

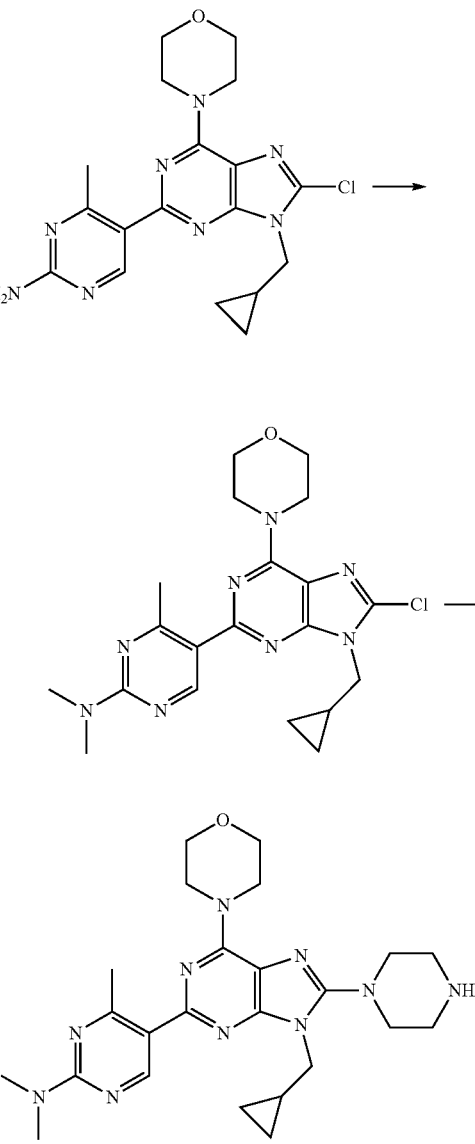

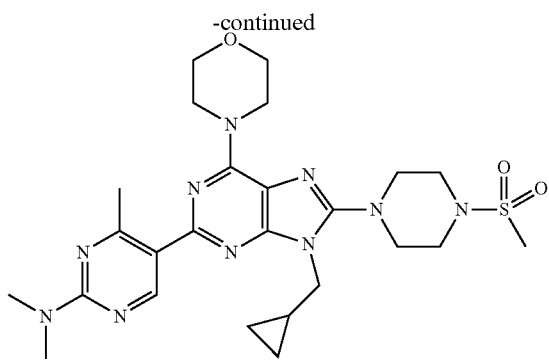

5-(8-Chloro-9-cyclopropylmethyl-6-morpholin-4-yl-9H-purin-2-yl)-4-methyl-pyrimidin-2-amine (100 mg, 0.25 mmol) was dissolved in N,N-dimethylformamide (2 ml) followed by the addition of NaH (60% oil dispersion, 20 mg, 0.5 mmol) and the resulting mixture was stirred for 5 minutes. Methyl iodide (32 µl) was added, the resulting mixture was stirred for 5 hours, then the reaction mixture was partitioned with ethyl acetate and water, the organic layer was dried over magnesium sulfate, and then the solvent was evaporated under reduced pressure. The residue was dissolved in N-methylpyrrolidone (1 ml) followed by the addition of piperazine (215 mg) and the resulting mixture was stirred at 120° C. for 2 hours. The reaction mixture was partitioned with methylene chloride and water, the organic layer was dried over magnesium sulfate, and then the solvent was evaporated under reduced pressure. Triethylamine (70 µl) and mesyl chloride (40 µl) were added to the residue, the resulting mixture was stirred for 2 hours, the reaction mixture was partitioned with ethyl acetate and water, the organic layer was dried over magnesium sulfate, and then the solvent was evaporated under reduced pressure. The residue was purified by preparative HPLC (column, NOMURA Develosil Combi-RP-5; mobile phase, acetonitrile/water/formic acid) to give the title compound (60 mg, 58%) as a light brown solid.

$^1$H-NMR (CDCl$_3$) δ: 0.47-0.55 (4H, m), 1.32-1.38 (1H, m), 2.75 (3H, s), 2.86 (3H, s), 3.25 (6H, s), 3.39-3.45 (8H, m), 3.83-3.85 (4H, m), 3.95 (2H, d, J=6.83 Hz), 4.25 (4H, brs), 9.00 (1H, s).

Example 45

4-[2-(2-Aminopyrimidin-5-yl)-9-isobutyl-6-morpholin-4-yl-9H-purin-8-yl]-N,N-dimethylpiperazine-1-carboxamide

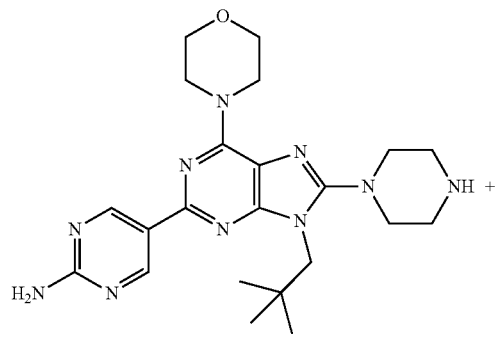

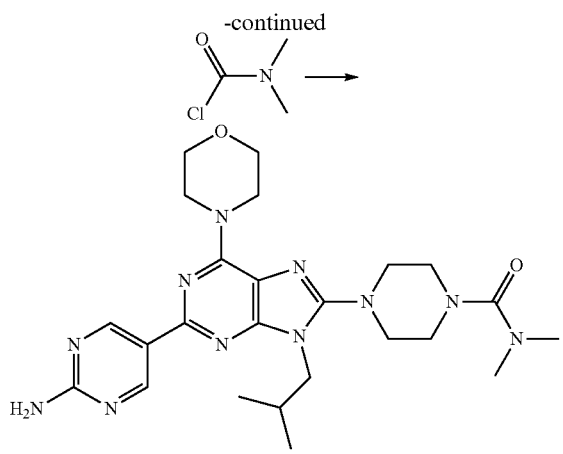

Triethylamine (64 µl) and 2-acetamide-4-dimethylcarbamoyl chloride (35 µl) were added to an N-methylpyrrolidone solution (1 ml) of 5-(9-isobutyl-6-morpholin-4-yl-8-piperazin-1-yl-9H-purin-2-yl)pyrimidin-2-ylamine (100 mg) and the resulting mixture was stirred for 24 hours. The reaction mixture was partitioned with ethyl acetate and water, the insoluble solid was collected by filtration, and then the organic layer of the filtrate was dried over magnesium sulfate. The solvent was evaporated under reduced pressure, the residue was combined with the solid separately collected by filtration followed by the addition of dimethyl sulfoxide (3 ml) and water (3 ml), the resulting mixture was stirred, and the insoluble matter was collected by filtration, washed with water, and dried to give the title compound (50 mg, 43%) as a pale yellow solid.

$^1$H-NMR (DMSO-d$_6$) δ: 0.82 (6H, d, J=6.87 Hz), 2.36-2.44 (1H, m), 2.78 (6H, s), 3.18-3.20 (4H, m), 3.25-3.26 (4H, m), 3.73-3.75 (4H, m), 3.95 (2H, d, J=7.45 Hz), 4.18 (4H, brs), 6.99 (2H, s), 9.06 (2H, s).

Example 46

5-{9-Isopropyl-8-[4-(methylsulfonyl)piperazin-1-yl]-6-morpholin-4-yl-9H-purin-2-yl}pyrimidin-2-amine

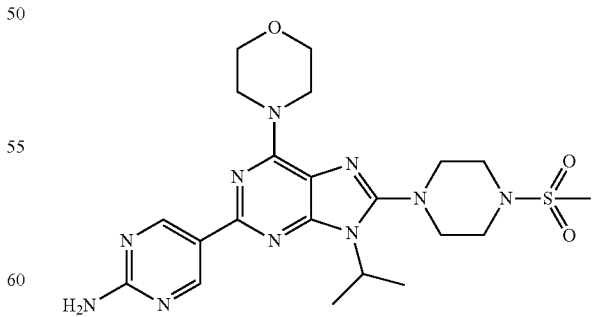

In the same way as in Step 1 of Example 1, an intermediate obtained by using isopropyl bromide was synthesized, and then the intermediate was led to the title compound by the ways in Steps 2 and after of Example 1.

¹H-NMR (CDCl₃) δ: 1.71-1.72 (6H, m), 2.89 (3H, s), 3.32-3.35 (4H, m), 3.37-3.43 (1H, m), 3.44-3.47 (4H, m), 3.84-3.87 (4H, m), 4.27-4.29 (4H, m), 9.21 (2H, s).

Example 47

1-[2-(2-Amino-4-methylpyrimidin-5-yl)-9-(cyclopropylmethyl)-6-morpholin-4-yl-9H-purin-8-yl]piperidine-4-carboxamide methanesulfonate

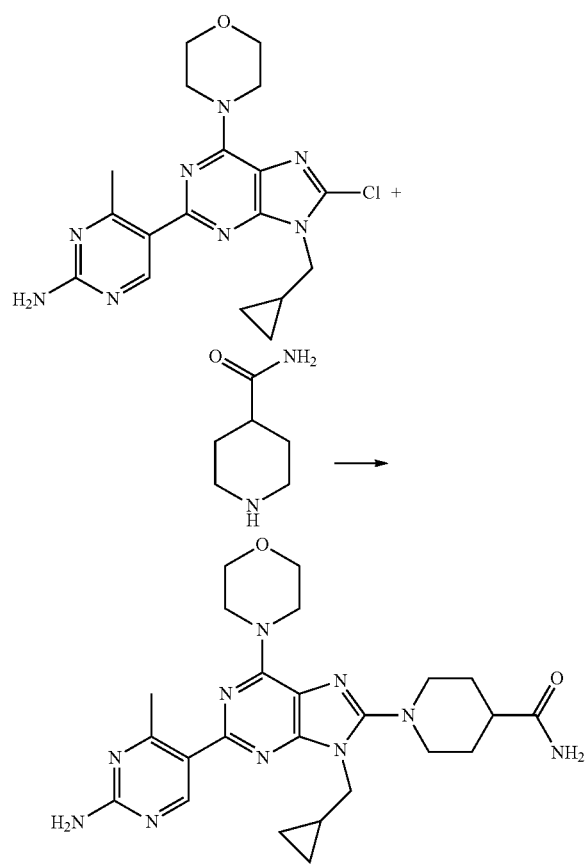

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and isonipecotamide (191 mg, 1.5 mmol) and the resulting mixture was stirred at 120° C. for 2.5 hours. The reaction mixture was left standing to cool followed by the addition of water and the insoluble matter was collected by filtration and dried to give 1-[2-(2-amino-4-methylpyrimidin-5-yl)-9-(cyclopropylmethyl)-6-morpholin-4-yl-9H-purin-8-yl]piperidine-4-carboxamide (85 mg, 69%) as a pale yellow solid.

To this compound (39.5 mg) was added chloroform (3 ml) and a solution (1 ml) of methanesulfonic acid (50 μl) in methanol (10 ml). The solvent was evaporated under reduced pressure to give the title compound (47 mg) as a yellow solid.

¹H-NMR (DMSO-d₆) δ: 0.40-0.50 (4H, m), 1.34-1.37 (1H, m), 1.70-1.77 (2H, m), 1.81-1.85 (2H, m), 2.29-2.33 (1H, m), 2.31 (3H, s), 2.76 (3H, s), 2.89-2.93 (2H, m), 3.55-3.58 (2H, m), 3.74-3.75 (4H, m), 3.95 (2H, d, J=7.4 Hz), 4.16 (4H, s), 6.82 (1H, s), 7.32 (1H, s), 8.96 (1H, s).

Example 48

{1-[2-(2-Amino-4-methylpyrimidin-5-yl)-9-(cyclopropylmethyl)-6-morpholin-4-yl-9H-purin-8-yl]piperidin-4-yl}methanol methanesulfonate

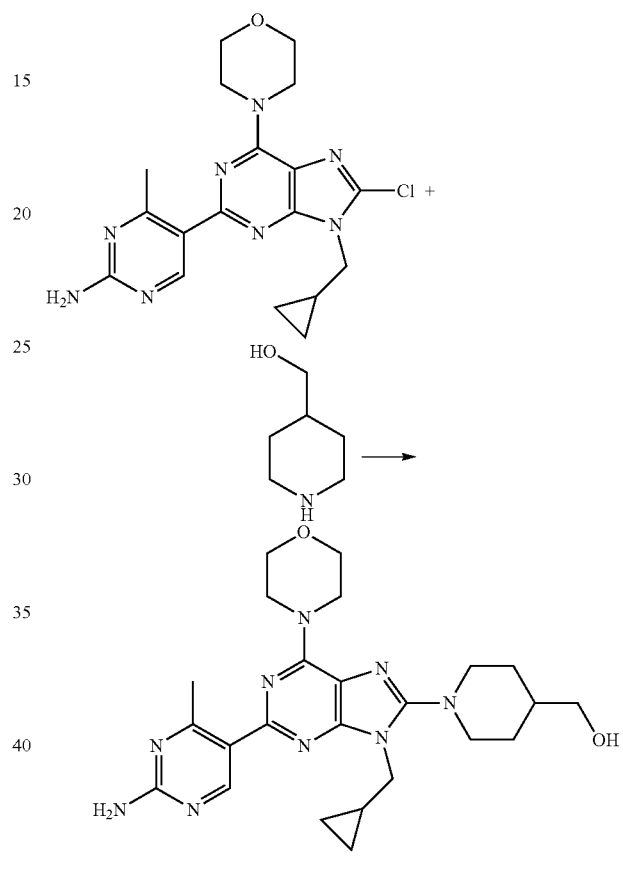

N-Methylpyrrolidone (1 ml) was added to 5-[8-chloro-9-(cyclopropylmethyl)-6-morpholin-4-yl-9H-purin-2-yl]-4-methylpyrimidin-2-amine (100 mg, 0.25 mmol) and 4-piperidinemethanol (172 mg, 1.5 mmol) and the resulting mixture was stirred at 120° C. for 0.5 hours. The reaction mixture was partitioned with ethyl acetate and water and the organic layer was washed with saturated brine and dried over magnesium sulfate. The solvent was concentrated under reduced pressure and the residue was purified by preparative HPLC (column, NOMURA Develosil Combi-RP-5; mobile phase, acetonitrile/water/formic acid) to give {1-[(2-(2-amino-4-methylpyrimidin-5-yl)-9-(cyclopropylmethyl)-6-morpholin-4-yl-9H-purin-8-yl]piperidin-4-yl}methanol (69 mg, 58%) as a pale yellow solid.

To this compound (35.2 mg) was added chloroform (3 ml) and a solution (1 ml) of methanesulfonic acid (50 μl) in methanol (10 ml). The solvent was evaporated under reduced pressure to give the title compound (40 mg) as a yellow solid.

¹H-NMR (CDCl₃) δ: 0.41-0.44 (2H, m), 0.53-0.57 (2H, m), 1.31-1.38 (1H, m), 1.48 (2H, ddd, J=24.77, 12.46, 3.87 Hz), 1.75-1.79 (2H, m), 1.90 (3H, d, J=13.17 Hz), 2.91 (3H, s), 2.98 (3H, s), 3.06 (2H, t, J=11.74 Hz), 3.61-3.63 (4H, m), 3.85-3.86 (4H, m), 3.94 (2H, d, J=6.87 Hz), 4.22 (4H, s), 9.14 (1H, br s).

Example 49

5-{9-Isobutyl-8-[4-(methylsulfonyl)-1,4-diazepan-1-yl]-6-morpholin-4-yl-9H-purin-2-yl}pyrimidin-2-amine

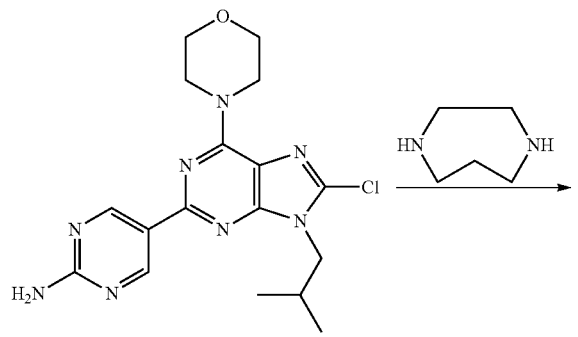

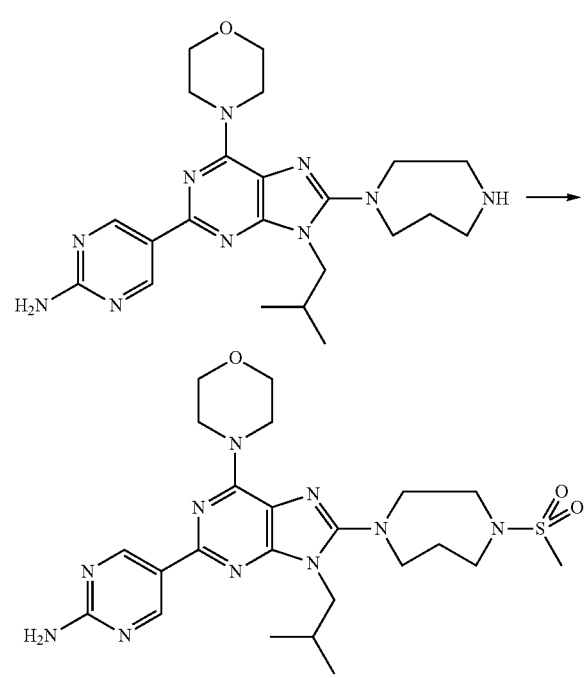

Homopiperazine (130 mg, 1.3 mmol) and N-methylpyrrolidone (1 ml) were added to 5-(8-chloro-9-isobutyl-6-morpholin-4-yl-9H-purin-2-yl)pyrimidin-2-amine (100 mg, 0.26 mmol) and the resulting mixture stirred at 120° C. for 2 hours. The reaction mixture was cooled and partitioned with methylene chloride and water, the organic layer was dried over magnesium sulfate, and the solvent was concentrated under reduced pressure. Triethylamine (110 µl) and mesyl chloride (45 µl, 0.58 mmol) were added to the resulting mixture and the resulting mixture was stirred for 0.5 hours. The reaction mixture was partitioned with ethyl acetate and water and the organic layer was dried over magnesium sulfate. The solvent was evaporated under reduced pressure and the residue was purified by preparative HPLC (column, NOMURA Develosil Combi-RP-5; mobile phase, acetonitrile/water/formic acid) to give the title compound (153 mg, 75%) as a white solid.

$^1$H-NMR (CDCl$_3$) δ: 0.87 (6H, d, J=6.87 Hz), 2.01-2.07 (2H, m), 2.31-2.39 (1H, m), 2.87 (3H, s), 3.48 (2H, t, J=6.30 Hz), 3.60-3.66 (6H, m), 3.84-3.86 (5H, m), 3.96 (2H, d, J=7.45 Hz), 4.25 (4H, br s), 5.23 (2H, s), 9.23 (2H, s).

Example 50

5-[8-(trans-2,5-Dimethylpiperazin-1-yl)-9-isobutyl-6-morpholin-4-yl-9H-purin-2-yl]pyrimidin-2-amine

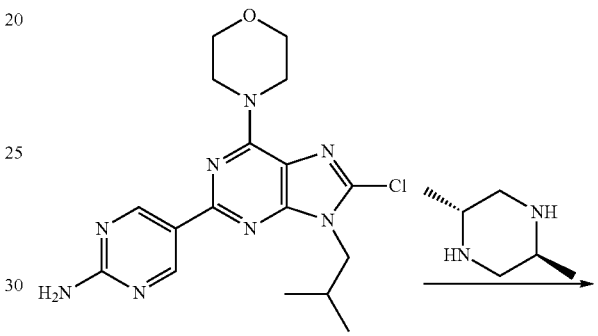

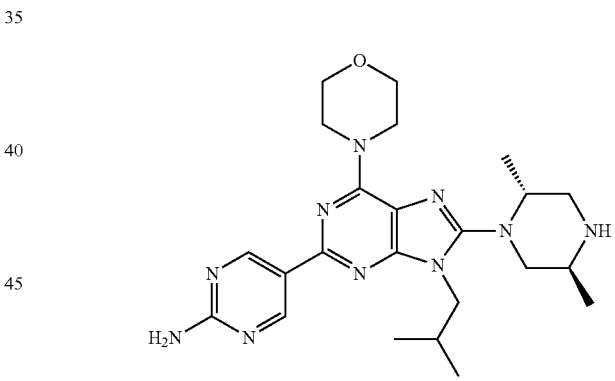

trans-2,5-Dimethylpiperazine (150 mg, 1.3 mmol) and N-methylpyrrolidone (1 ml) were added to 5-(8-chloro-9-isobutyl-6-morpholin-4-yl-9H-purin-2-yl)pyrimidin-2-amine (100 mg, 0.26 mmol) and the resulting mixture was stirred at 150° C. for 48 hours. The reaction mixture was cooled and partitioned with methylene chloride and water, the organic layer was dried over magnesium sulfate, and the solvent was concentrated under reduced pressure. The residue was purified by preparative HPLC (column, NOMURA Develosil Combi-RP-5; mobile phase, acetonitrile/water/formic acid) to give the title compound (120 mg) as a pale yellow solid.

$^1$H-NMR (DMSO-d$_6$) δ: 0.83-0.86 (6H, m), 0.88 (3H, d, J=6.30 Hz), 0.99 (3H, s), 1.00 (3H, d, J=6.30 Hz), 2.42 2.46 (1H, m), 2.55-2.60 (1H, m), 2.91-2.96 (1H, m), 2.99-3.06 (2H, m), 3.16-3.21 (1H, m), 3.74-3.76 (4H, m), 3.83 (1H, dd,

J=13.75, 7.45 Hz), 3.98 (1H, dd, J=13.75, 7.45 Hz), 4.20 (4H, br s), 7.01 (2H, s), 8.21 (1H, s), 9.07 (2H, s).

Example 51

5-{9-Isobutyl-8-[(3S)-3-methylpiperazin-1-yl]-6-morpholin-4-yl-9H-purin-2-yl}pyrimidin-2-amine

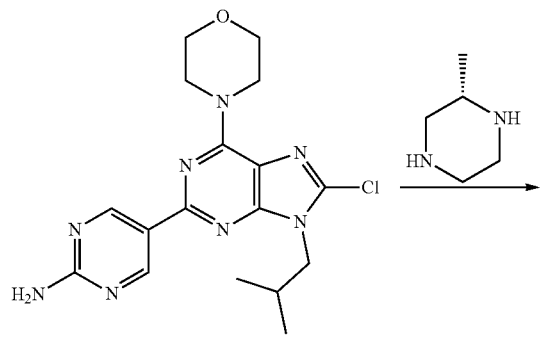

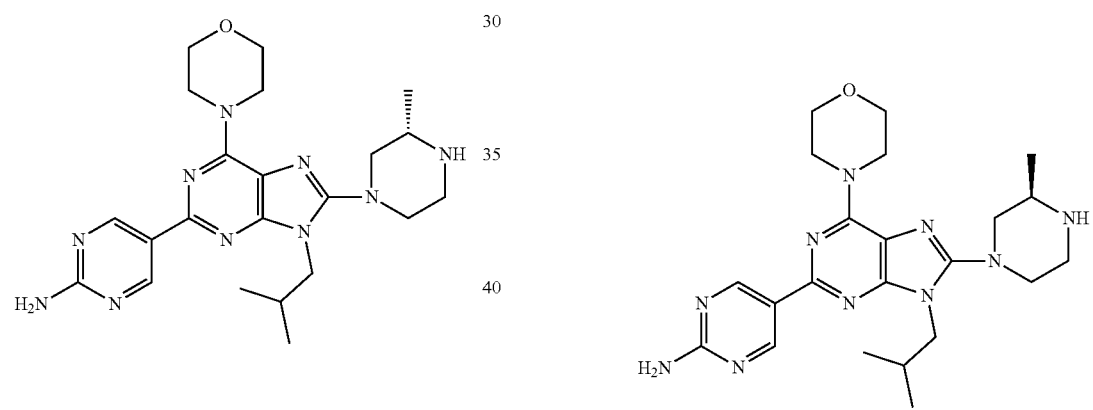

N-Methylpyrrolidone (2 ml) was added to 5-(8-chloro-9-isobutyl-6-morpholin-4-yl-9H-purin-2-yl)pyrimidin-2-amine (200 mg, 0.51 mmol) and (2S)-2-methylpiperazine (412 mg, 4.1 mmol) and the resulting mixture was stirred at 120° C. for 4 hours. The reaction mixture was purified by preparative HPLC (column, NOMURA Develosil Combi-RP-5; mobile phase, acetonitrile/water/formic acid) to give a formate of the title compound (192 mg) as a white solid.

$^1$H-NMR (DMSO-d$_6$) δ: 0.80-0.82 (6H, m), 1.06 (3H, d, J=6.30 Hz), 2.36-2.40 (1H, m), 2.59-2.63 (1H, m), 2.87-3.03 (3H, m), 3.33-3.36 (2H, m), 3.73-3.75 (4H, m), 3.88-3.98 (2H, m), 4.18 (4H, br s), 6.98 (2H, s), 8.21 (1H, s), 9.06 (2H, s).

This compound was dissolved in chloroform-methanol (9:1), washed with saturated aqueous sodium bicarbonate solution, and dried over magnesium sulfate and the solvent was evaporated under reduced pressure to give the title compound (150 mg, 64%) as a white solid.

$^1$H-NMR (CDCl$_3$) δ: 0.87-0.88 (6H, m), 1.13 (3H, d, J=6.30 Hz), 2.44-2.50 (1H, m), 2.65-2.69 (1H, m), 2.96-3.10

(4H, m), 3.32-3.36 (2H, m), 3.85-3.87 (4H, m), 3.89-3.95 (2H, m), 4.28 (4H, br s), 5.18 (2H, s), 9.24 (2H, s).

Example 52

5-{9-Isobutyl-8-[(3R)-3-methylpiperazin-1-yl]-6-morpholin-4-yl-9H-purin-2-yl}pyrimidin-2-amine

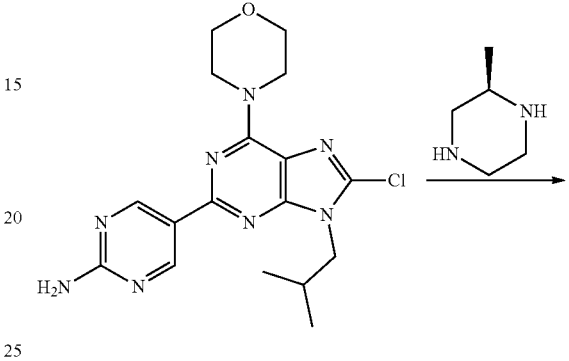

N-Methylpyrrolidone (2 ml) was added to 5-(8-chloro-9-isobutyl-6-morpholin-4-yl-9H-purin-2-yl)pyrimidin-2-amine (200 mg, 0.51 mmol) and (2R)-2-methylpiperazine (412 mg, 4.1 mmol) and the resulting mixture was stirred at 120° C. for 4 hours. The reaction mixture was purified by preparative HPLC (column, NOMURA Develosil Combi-RP-5; mobile phase, acetonitrile/water/formic acid) to give a formate of the title compound (204 mg) as a white solid.

$^1$H-NMR (DMSO-d$_6$) δ: 0.80-0.82 (6H, m), 1.06 (3H, d, J=6.30 Hz), 2.36-2.40 (1H, m), 2.59-2.63 (1H, m), 2.87-3.03 (3H, m), 3.33-3.36 (2H, m), 3.73-3.75 (4H, m), 3.88-3.98 (2H, m), 4.18 (4H, br s), 6.98 (2H, s), 8.21 (1H, s), 9.06 (2H, s).

This compound was dissolved in chloroform-methanol (9:1), washed with saturated aqueous sodium bicarbonate solution, and dried over magnesium sulfate and then the solvent was evaporated under reduced pressure to give the title compound (180 mg, 77%) as a white solid.

$^1$H-NMR (CDCl$_3$) δ: 0.87-0.88 (6H, m), 1.13 (3H, d, J=6.30 Hz), 2.44-2.50 (1H, m), 2.65-2.69 (1H, m), 2.96-3.10

(4H, m), 3.32-3.36 (2H, m), 3.85-3.87 (4H, m), 3.89-3.95 (2H, m), 4.28 (4H, br s), 5.18 (2H, s), 9.24 (2H, s).

Example 53

5-{9-Isobutyl-8-[(3S)-3-methyl-4-(methylsulfonyl)piperazin-1-yl]-6-morpholin-4-yl-9H-purin-2-yl}pyrimidin-2-amine

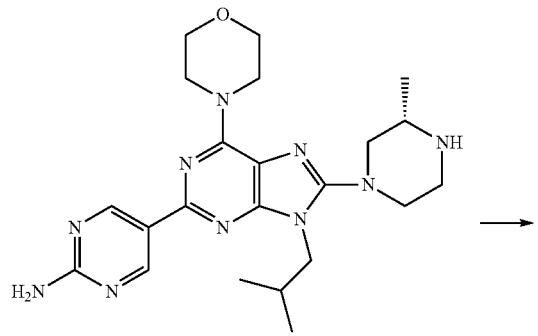

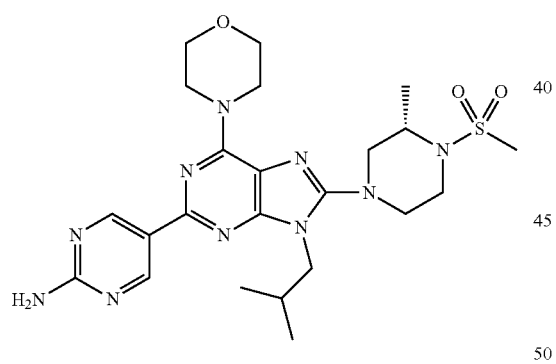

5-{9-Isobutyl-8-[(3S)-3-methylpiperazin-1-yl]-6-morpholin-4-yl-9H-purin-2-yl}pyrimidin-2-amine (140 mg, 0.32 mmol) was dissolved in tetrahydrofuran (5 ml) followed by the addition of triethylamine (68 μl) and mesyl chloride (28 μl) with ice cooling and the resulting mixture was stirred at room temperature for 30 minutes. The reaction mixture was partitioned with ethyl acetate and water, the organic layer was dried over magnesium sulfate, and the solvent was evaporated under reduced pressure. The residue was purified by silica gel chromatography (hexane:ethyl acetate=5:5 to 0:10) to give a white solid (115 g, 67%).

$^1$H-NMR (CDCl$_3$) δ: 0.87-0.90 (6H, m), 1.27-1.30 (2H, m), 1.50 (3H, d, J=6.87 Hz), 2.41-2.50 (1H, m), 2.94 (3H, s), 3.13 (1H, td, J=12.03, 3.44 Hz), 3.21-3.28 (2H, m), 3.40 (1H, d, J=12.60 Hz), 3.47 (1H, td, J=12.60, 2.86 Hz), 3.73 (1H, d,

J=13.17 Hz), 3.84-3.86 (4H, m), 3.91 (2H, d, J=8.02 Hz), 4.27 (4H, br s), 5.22 (2H, s), 9.23 (2H, s).

Example 54

5-{9-Isobutyl-8-[(3R)-3-methyl-4-(methylsulfonyl)piperazin-1-yl]-6-morpholin-4-yl-9H-purin-2-yl}pyrimidin-2-amine

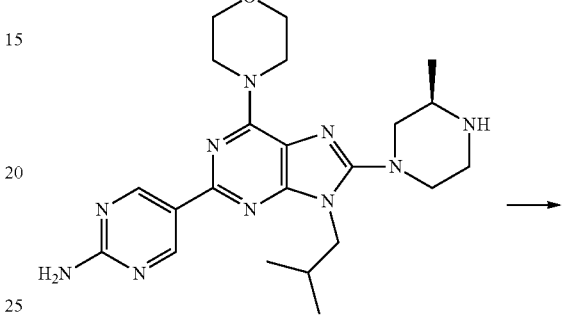

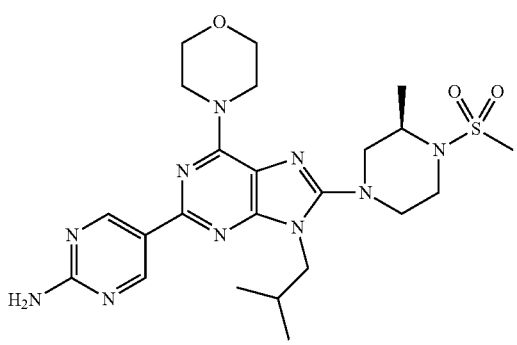

5-{9-Isobutyl-8-[(3R)-3-methylpiperazin-1-yl]-6-morpholin-4-yl-9H-purin-2-yl}pyrimidin-2-amine (140 mg, 0.32 mmol) was dissolved in tetrahydrofuran (5 ml) followed by the addition of triethylamine (68 μl) and mesyl chloride (28 μl) with ice cooling and the resulting mixture was stirred at room temperature for 30 minutes. The reaction mixture was partitioned with ethyl acetate and water, the organic layer was dried over magnesium sulfate, and the solvent was evaporated under reduced pressure. The residue was purified by silica gel chromatography (hexane:ethyl acetate=5:5 to 0:10) to give a white solid (135 mg, 62%).

$^1$H-NMR (CDCl$_3$) δ: 0.87-0.90 (6H, m), 1.27-1.30 (1H, m), 1.50 (3H, d, J=6.87 Hz), 2.41-2.50 (1H, m), 2.94 (3H, s), 3.13 (1H, td, J=12.03, 3.44 Hz), 3.21-3.28 (2H, m), 3.40 (1H, d, J=12.60 Hz), 3.47 (1H, td, J=12.60, 2.86 Hz), 3.73 (1H, d,

J=13.17 Hz), 3.84-3.86 (4H, m), 3.91 (2H, d, J=8.02 Hz), 4.27 (4H, br s), 5.22 (2H, s), 9.23 (2H, s).

Example 55

5-(8-{4-[(Dimethylamino)acetyl]piperazin-1-yl}-9-isobutyl-6-morpholin-4-yl-9H-purin-2-yl)pyrimidin-2-amine

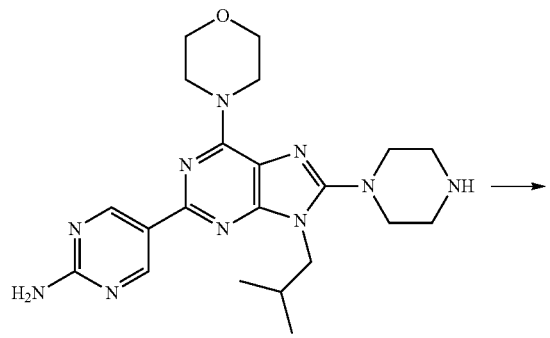

1-Hydroxybenzotriazole monohydrate (48.9 mg, 0.32 mmol), 1-(dimethylaminopropyl)-3-ethylcarbodiimide hydrochloride (91.8 mg, 0.48 mmol), and triethylamine (164.6 μl, 1.18 mmol) were added to an N,N-dimethylformamide suspension (2.0 ml) of 5-[9-(isobutyl)-6-morpholin-4-yl-8-piperazin-1-yl-9H-purin-2-yl]pyrimidin-2-amine (140.0 mg, 0.32 mmol) and N,N-dimethylglycine hydrochloride (53.5 mg, 0.38 mmol) at room temperature. The resulting mixture was stirred for 21 hour and then the reaction mixture was poured into dichloromethane-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (dichloromethane:methanol=5:1) to give the title compound (103.9 mg, 62%) as a pale yellow solid.

$^1$H-NMR (CDCl$_3$) δ: 0.89 (6H, d, J=6.87 Hz), 2.31 (6H, s), 2.43-2.53 (1H, m), 3.17 (2H, s), 3.19-3.30 (4H, m), 3.76-3.88 (8H, m), 3.92 (2H, d, J=7.45 Hz), 4.20-4.34 (4H, brm), 5.53 (2H, s), 9.24 (2H, s).

Example 56

5-{9-(Cyclopropylmethyl)-8-[4-(1H-imidazol-1-ylacetyl)piperazin-1-yl]-6-morpholin-4-yl-9H-purin-2-yl}pyrimidin-2-amine

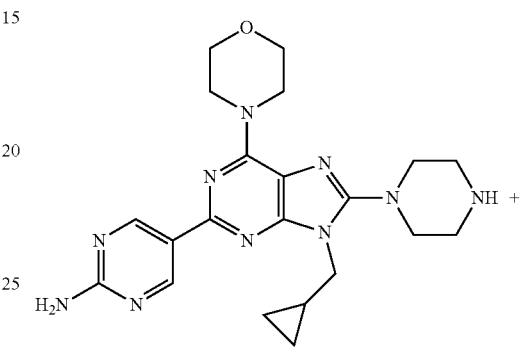

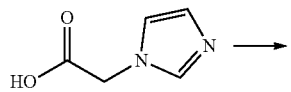

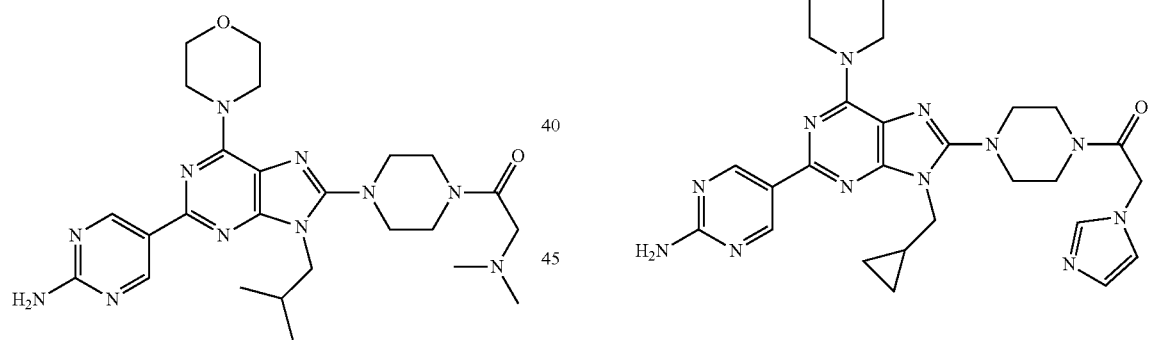

1-Hydroxybenzotriazole monohydrate (38.2 mg, 0.25 mmol), 1-(dimethylaminopropyl)-3-ethylcarbodiimide hydrochloride (71.8 mg, 0.37 mmol), and triethylamine (52.2 μl, 0.37 mmol) were added to an N,N-dimethylformamide suspension (3.0 ml) of 5-[9-(cyclopropylmethyl)-6-morpholin-4-yl-8-piperazin-1-yl-9H-purin-2-yl]pyrimidin-2-amine (109.0 mg, 0.25 mmol) and imidazol-1-ylacetic acid (37.8 mg, 0.30 mmol) at room temperature. The resulting mixture was stirred for 17.5 hours and the reaction mixture was poured into dichloromethane-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (dichloromethane:methanol=6:1) to give the title compound (108.0 mg, 79%) as a pale yellow solid.

$^1$H-NMR (CDCl$_3$) δ: 0.50-0.59 (4H, m), 1.28-1.37 (1H, m), 3.26-3.35 (4H, m), 3.63-3.70 (2H, m), 3.81-3.89 (6H, m), 3.97 (2H, d, J=6.87 Hz), 4.20-4.35 (4H, m), 4.84 (2H, s), 5.26 (2H, s), 6.97-7.00 (1H, m), 7.12-7.14 (1H, m), 7.53 (1H, s), 9.23 (2H, s).

Example 57

5-{8-[4-(Methylsulfonyl)piperidin-1-yl]-6-morpholin-4-yl-9-(2,2,2-trifluoroethyl)-9H-purin-2-yl}pyrimidin-2-amine

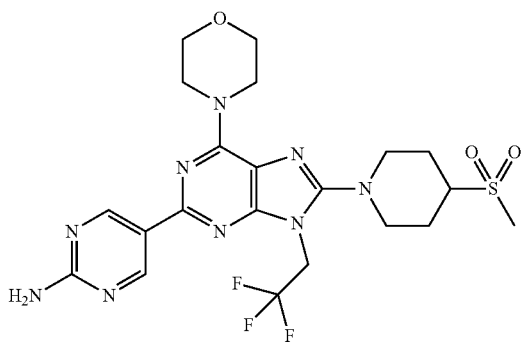

Step 1: 5-[8-Chloro-6-morpholin-4-yl-9-(2,2,2-trifluoroethyl)-9H-purin-2-yl]pyrimidin-2-amine

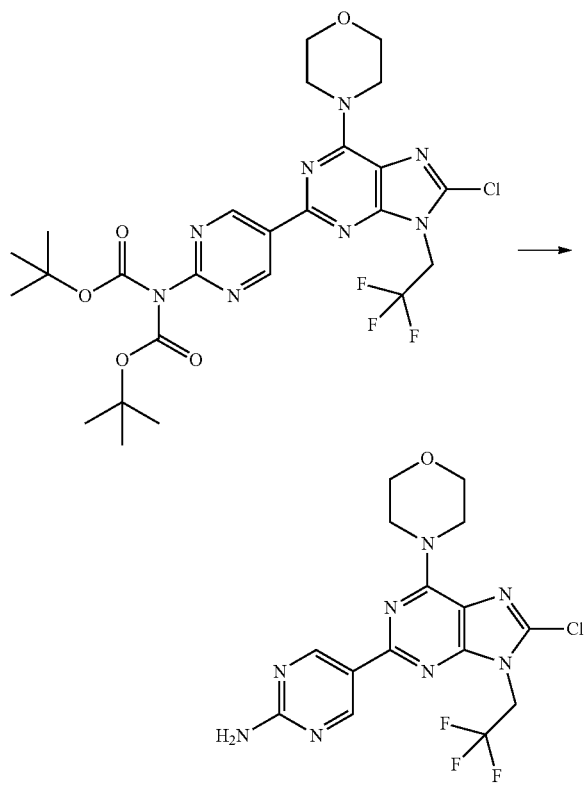

Di-tert-butyl {5-[8-chloro-6-morpholin-4-yl-9-(2,2,2-trifluoroethyl)-9H-purin-2-yl]pyrimidin-2-yl}imide dicarbonate (7 g, 11.4 mmol) was dissolved in methylene chloride (20 ml) followed by the addition of trifluoroacetic acid (20 ml) with ice cooling and the resulting mixture was stirred at room temperature for 1 hour. The solvent was evaporated under reduced pressure, then toluene was added to the residue, the resulting mixture was evaporated under reduced pressure, saturated aqueous sodium bicarbonate solution and a small amount of methanol were added to the residue, and the insoluble matter was collected by filtration, washed with water, and dried to give the title compound (4.5 g, 95%) as a colorless solid.

$^1$H-NMR (DMSO-$d_6$) δ: 3.74-3.76 (4H, m), 4.19 (4H, brs), 5.19 (2H, q, J=8.8 Hz), 7.18 (2H, brs), 9.12 (2H, s).

Step 2: 5-{8-[4-(Methylsulfonyl)piperidin-1-yl]-6-morpholin-4-yl-9-(2,2,2-trifluoroethyl)-9H-purin-2-yl}pyrimidin-2-amine

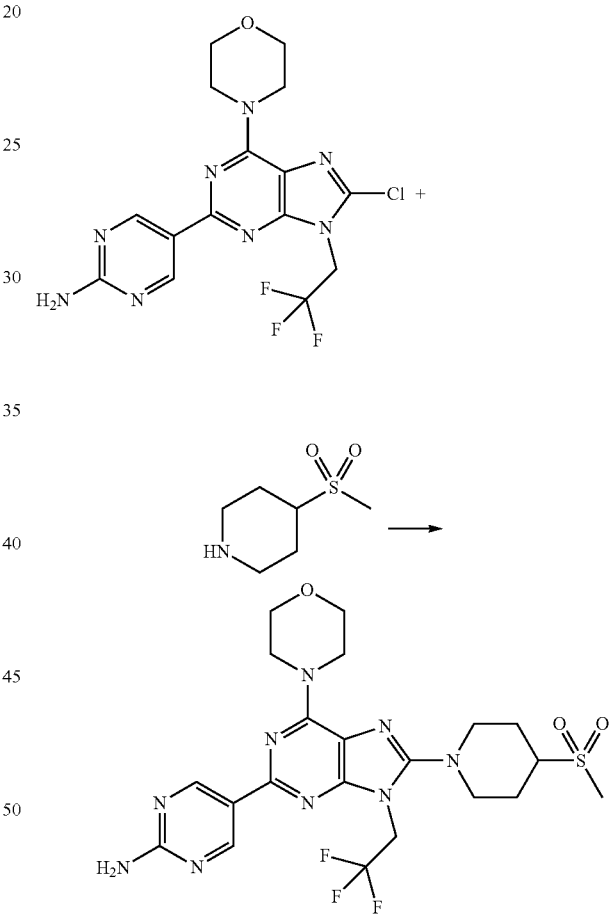

4-Methanesulfonylpiperidine hydrochloride (385 mg, 1.93 mmol), diisopropylethylamine (672 µg, 3.9 mmol), and N-methyl-2-pyrrolidone (2 ml) were added to 5-[8-chloro-6-morpholin-4-yl-9-(2,2,2-trifluoroethyl)-9H-purin-2-yl]pyrimidin-2-amine (200 mg, 0.48 mmol) and the resulting mixture was stirred at 100° C. for 12 hours. The reaction mixture was partitioned with ethyl acetate and water, the organic layer was dried over magnesium sulfate, and then the solvent was evaporated under reduced pressure. The residue was purified by silica gel chromatography (chloroform:methanol=20:1) to give the title compound (81 mg, 33%) as a pale yellow solid.

$^1$H-NMR (DMSO-$d_6$) δ: 1.79-1.87 (2H, m), 2.09-2.13 (2H, m), 2.95-3.00 (5H, m), 3.32-3.36 (1H, m), 3.58-3.60 (2H, m), 3.74-3.76 (4H, m), 4.19 (4H, brs), 5.02 (2H, q, J=8.8 Hz), 7.05 (2H, s), 9.09 (2H, s).

Example 58

5-{8-[(3S)-3-Methylpiperazin-1-yl]-6-morpholin-4-yl-9-(2,2,2-trifluoroethyl)-9H-purin-2-yl}pyrimidin-2-amine

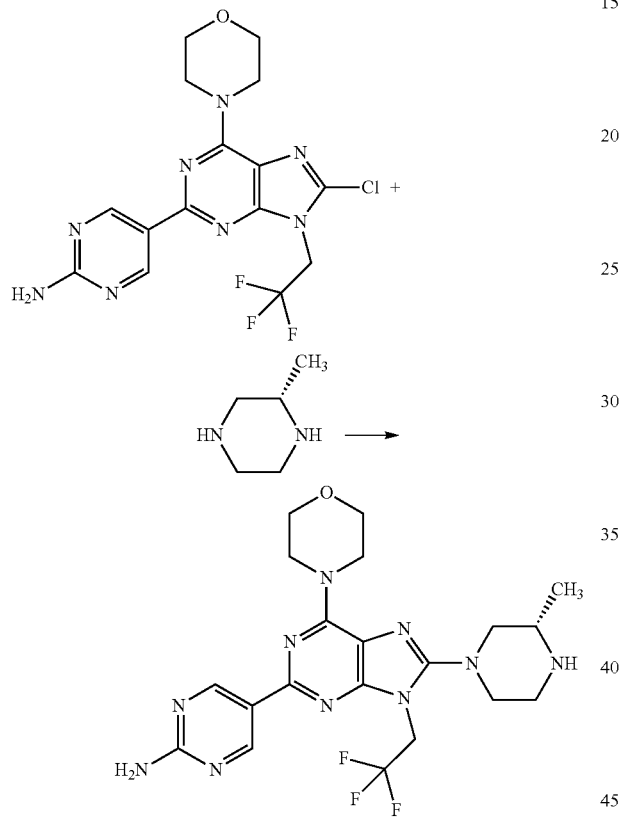

An N-methyl-2-pyrrolidone suspension (10 ml) of 5-[8-chloro-6-morpholin-4-yl-9-(2,2,2-trifluoroethyl)-9H-purin-2-yl]pyrimidin-2-amine (1.02 g, 2.46 mmol) and (2S)-2-methylpiperazine (1.23 g, 12.3 mmol) was heated at 120° C. to dissolve and then the resulting mixture was stirred at 100° C. for 5 hours. The resulting mixture was left standing to cool, poured into methylene chloride-methanol (10:1), and washed with saturated aqueous sodium hydrogen carbonate solution. The organic layer was dried over anhydrous sodium sulfate, the mixture was filtrated, the filtrate was concentrated under reduced pressure, and the resulting solid was washed with a small amount of methylene chloride and collected by filtration to give the title compound (362.9 mg). The filtrate was concentrated under reduced pressure and the resulting residue was purified by medium pressure silica gel column chromatography (methylene chloride:methanol=32:1 to 7:1) to give the title compound (623.8 mg). These lots were combined to give the title compound (986.7 mg, 84%) as a pale yellow solid.

$^1$H-NMR (CDCl$_3$) δ: 1.12 (3H, d, J=6.87 Hz), 2.71 (1H, dd, J=12.03, 10.31 Hz), 2.99-3.13 (4H, m), 3.20-3.28 (2H, m), 3.83-3.89 (4H, m), 4.22-4.35 (4H, brm), 4.63-4.76 (2H, m), 5.19 (2H, s), 9.23 (2H, s).

Example 59

5-{8-[(3R)-3-Methylpiperazin-1-yl]-6-morpholin-4-yl-9-(2,2,2-trifluoroethyl)-9H-purin-2-yl}pyrimidin-2-amine

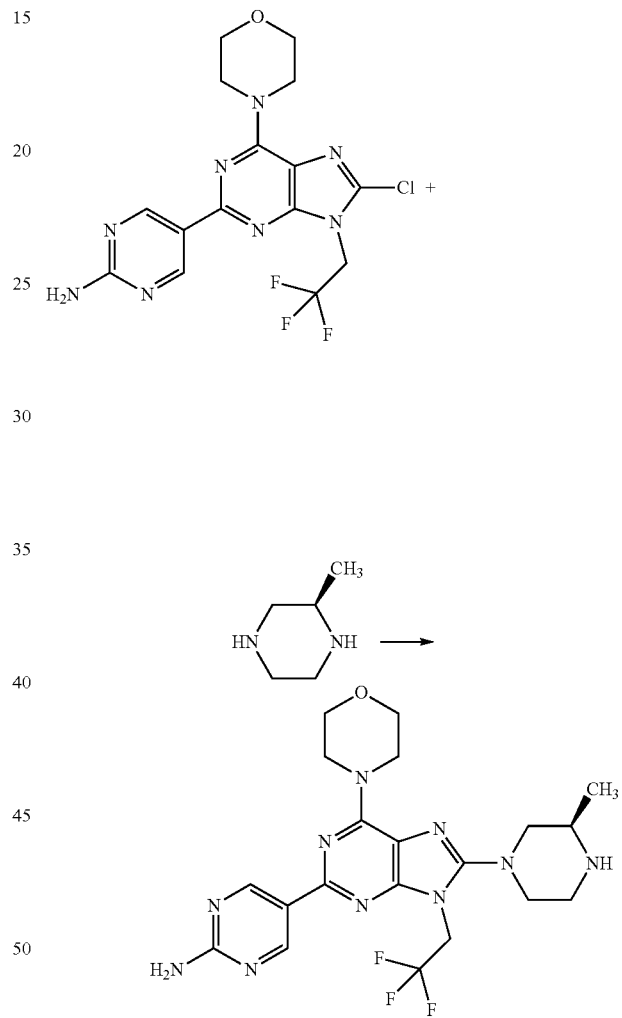

An N-methyl-2-pyrrolidone suspension (24 ml) of 5-[8-chloro-6-morpholin-4-yl-9-(2,2,2-trifluoroethyl)-9H-purin-2-yl]pyrimidin-2-amine (2.42 g, 5.82 mmol) and (2R)-2-methylpiperazine (2.92 g, 29.1 mmol) was heated at 120° C. to dissolve and the resulting mixture was stirred at 100° C. for 6 hours. The resulting mixture was left standing to cool, then poured into methylene chloride-methanol (10:1), and washed with water. The organic layer was dried over anhydrous sodium sulfate, the mixture was filtrated, the filtrate was concentrated under reduced pressure, and the resulting residue was purified by medium pressure silica gel column chromatography (methylene chloride:methanol=32:1 to 9:1) to give the title compound (2.51 g, 90%) as a pale yellow solid.

$^1$H-NMR (CDCl$_3$) δ: 1.13 (3H, d, J=6.30 Hz), 2.71 (1H, dd, J=11.74, 10.02 Hz), 3.00-3.13 (4H, m), 3.20-3.27 (2H, m), 3.82-3.88 (4H, m), 4.21-4.35 (4H, brm), 4.64-4.75 (2H, m), 5.18 (2H, s), 9.23 (2H, s).

Example 60
5-{8-[(3R)-4-Acetyl-3-methylpiperazin-1-yl]-6-morpholin-4-yl-9-(2,2,2-trifluoroethyl)-9H-purin-2-yl}pyrimidin-2-amine

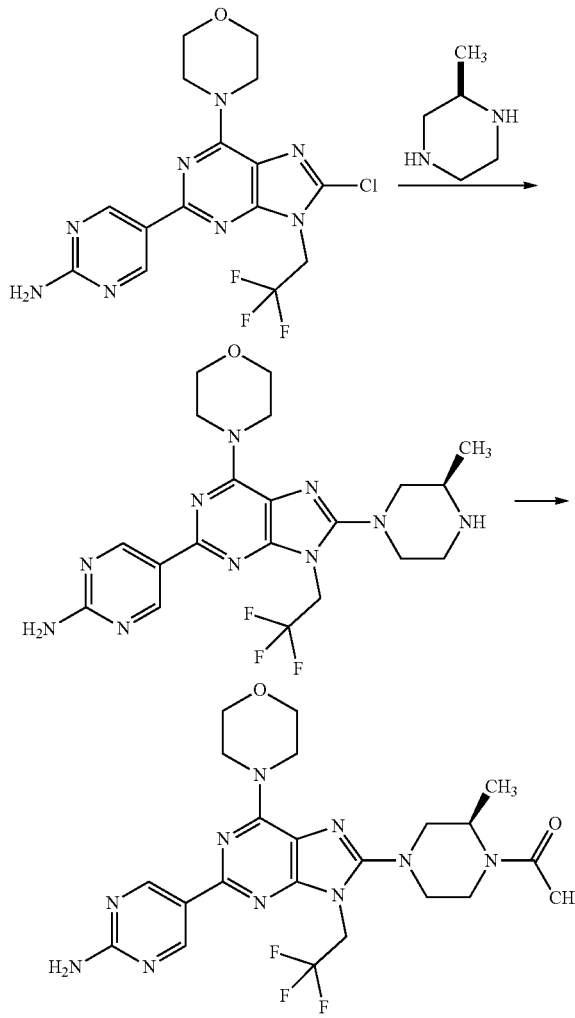

(2R)-2-Methylpiperazine (241 mg, 2.41 mmol) and N-methyl-2-pyrrolidone (2 ml) were added to 5-[8-chloro-6-morpholin-4-yl-9-(2,2,2-trifluoroethyl)-9H-purin-2-yl]pyrimidin-2-amine (200 mg, 0.48 mmol) and the resulting mixture was stirred at 100° C. for 2 hours. The reaction mixture was partitioned with chloroform and water, the organic layer was dried over magnesium sulfate, and the solvent was concentrated under reduced pressure. Acetic anhydride (68 μl) and triethylamine (200 μl) were added to the residue with ice cooling and the resulting mixture was stirred for 1 hour and partitioned with ethyl acetate and saturated aqueous sodium bicarbonate solution. The organic layer was dried over magnesium sulfate, then the solvent was evaporated under reduced pressure, and the residue was purified by silica gel chromatography (chloroform:methanol=20:1) to give the title compound (127 mg, 52%) as a colorless solid.

$^1$H-NMR (DMSO-d$_6$, 140° C.) δ: 1.29 (3H, d, J=6.9 Hz), 2.03 (3H, s), 2.90-2.97 (1H, m), 3.11-3.20 (1H, m), 3.28-3.35 (2H, m), 3.43-3.46 (1H, m), 3.73-3.76 (4H, m), 3.99-4.04 (1H, m), 4.17-4.19 (4H, m), 4.43-4.51 (1H, m), 4.90-5.01 (2H, m), 6.44 (2H, brs), 9.06 (2H, s).

5-{8-[(3R)-4-acetyl-3-methylpiperazin-1-yl]-6-morpholin-4-yl-9-(2,2,2-trifluoroethyl)-9H-purin-2-yl}pyrimidin-2-amine methanesulfonate

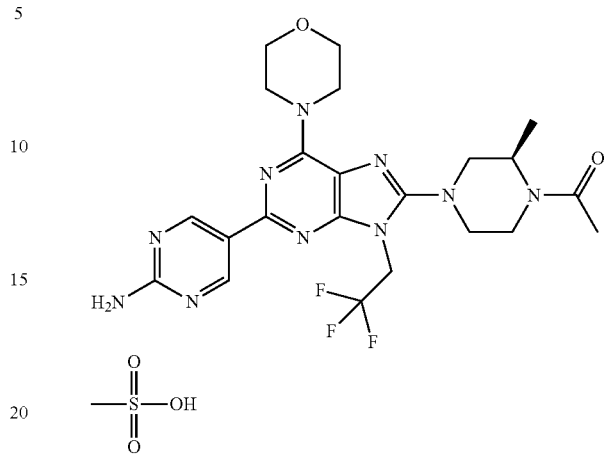

To a solution of 5-{8-[(3R)-4-acetyl-3-methylpiperazin-1-yl]-6-morpholin-4-yl-9-(2,2,2-trifluoroethyl)-9H-purin-2-yl}pyrimidin-2-amine (100.4 mg, 0.18 mmol) in methanol/dichloromethane solution (2/3, 3.5 ml) was added methanesulfonic acid (11.9 μl, 0.18 mmol) at room temperature, and the mixture was stirred for 10 minutes. Then the solvent was removed in reduced pressure, and the resultant solid was dried to give 5-{8-[(3R)-4-acetyl-3-methylpiperazin-1-yl]-6-morpholin-4-yl-9-(2,2,2-trifluoroethyl)-9H-purin-2-yl}pyrimidin-2-amine methanesulfonate (107.1 mg) as a yellow solid.

$^1$H-NMR (CDCl$_3$/CD$_3$OD=10/1) δ: 1.35-1.51 (3H, m), 2.13-2.19 (3H, m), 2.91 (3H, s), 2.95-3.40 (4H, m), 3.59-3.79 (1H, m), 3.81-3.90 (4H, m), 4.11-4.60 (5H, m), 4.68-4.96 (3H, m), 9.34 (2H, s).

5-{8-[(3R)-4-acetyl-3-methylpiperazin-1-yl]-6-morpholin-4-yl-9-(2,2,2-trifluoroethyl)-9H-purin-2-yl}pyrimidin-2-amine sulfate

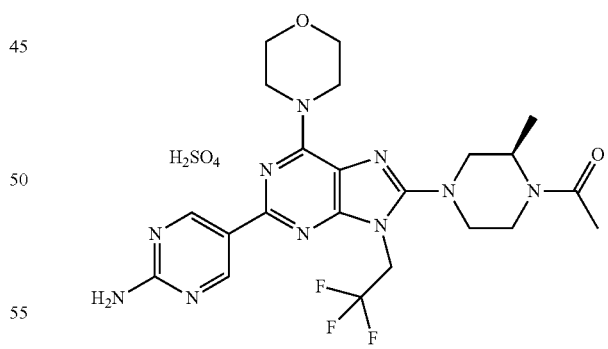

To a suspension of 5-{8-[(3R)-4-acetyl-3-methylpiperazin-1-yl]-6-morpholin-4-yl-9-(2,2,2-trifluoroethyl)-9H-purin-2-yl}pyrimidin-2-amine (101 mg, 0.194 mmol) in 10% aqueous ethanol solution (2 ml) was added 98% sulfuric acid (0.012 mL, 0.213 mmol) at room temperature, and the mixture was stirred for 30 minutes. The insoluble solid was collected and dried to give 5-{8-[(3R)-4-acetyl-3-methylpiperazin-1-yl]-6-morpholin-4-yl-9-(2,2,2-trifluoroethyl)-9H-purin-2-yl}pyrimidin-2-amine sulfate (89 mg) as a yellow solid.

¹H-NMR (DMSO-d₆, 80° C.) δ: 1.29 (3H, d, J=6.6 Hz), 2.04 (3H, s), 2.85-2.94 (1H, m), 3.06-3.12 (1H, m), 3.28-3.33 (1H, m), 3.43-3.48 (1H, m), 3.73-3.76 (4H, m), 4.17-4.21 (4H, m), 4.94-5.07 (2H, m), 9.11 (2H, s).

5-{8-[(3R)-4-acetyl-3-methylpiperazin-1-yl]-6-morpholin-4-yl-9-(2,2,2-trifluoroethyl)-9H-purin-2-yl}pyrimidin-2-amine p-toluenesulfonate

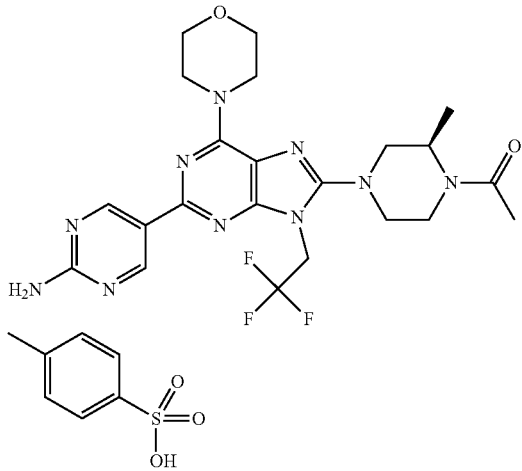

To a suspension of 5-{8-[(3R)-4-acetyl-3-methylpiperazin-1-yl]-6-morpholin-4-yl-9-(2,2,2-trifluoroethyl)-9H-purin-2-yl}pyrimidin-2-amine (137 mg, 0.263 mmol) in 10% aqueous ethanol solution (2 ml) was added p-toluenesulfonic acid mono hydrate (55.2 mg, 0.290 mmol) at 50° C., and the mixture was allowed to be cooled down to room temperature, and was stirred for 3 days. The solid precipitated out was collected and dried to give 5-{8-[(3R)-4-acetyl-3-methylpiperazin-1-yl]-6-morpholin-4-yl-9-(2,2,2-trifluoroethyl)-9H-purin-2-yl}pyrimidin-2-amine p-toluenesulfonate (94 mg) as a yellow solid.

¹H-NMR (DMSO-d₆, 80° C.) δ: 1.29 (3H, d, J=5.95 Hz), 2.04 (3H, s), 2.29 (3H, s), 2.82-2.97 (1H, m), 3.04-3.15 (1H, m), 3.28-3.35 (1H, m), 3.43-3.51 (1H, m), 3.72-3.77 (4H, m), 4.17-4.23 (4H, m), 4.93-5.12 (2H, m), 7.09 (2H, d, J=7.80 Hz), 7.50 (2H, d, J=7.80 Hz), 9.16 (2H, s).

5-{8-[(3R)-4-acetyl-3-methylpiperazin-1-yl]-6-morpholin-4-yl-9-(2,2,2-trifluoroethyl)-9H-purin-2-yl}pyrimidin-2-amine benzenesulfonate

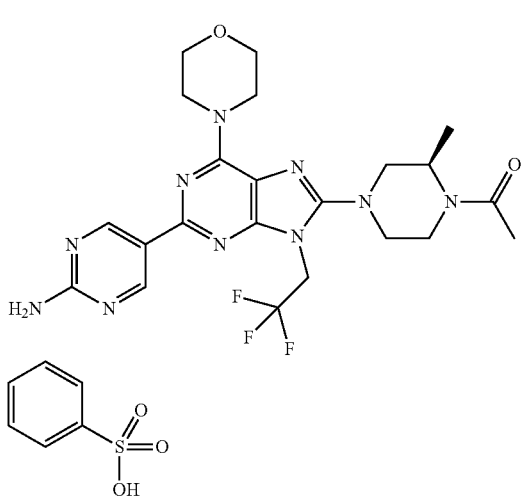

To a suspension of 5-{8-[(3R)-4-acetyl-3-methylpiperazin-1-yl]-6-morpholin-4-yl-9-(2,2,2-trifluoroethyl)-9H-purin-2-yl}pyrimidin-2-amine (126 mg, 0.242 mmol) in 10% aqueous ethanol solution (5 ml) was added benzenesulfonic acid mono hydrate (46.8 mg, 0.266 mmol) at 50° C., and the mixture was allowed to be cooled down to room temperature, and stirred for 15 hr. The solid precipitated out was collected and dried to give 5-{8-[(3R)-4-acetyl-3-methylpiperazin-1-yl]-6-morpholin-4-yl-9-(2,2,2-trifluoroethyl)-9H-purin-2-yl}pyrimidin-2-amine benzenesulfonate (110 mg) as a yellow solid.

¹H-NMR (DMSO-d₆, 80° C.) δ: 1.24-1.33 (3H, m), 2.04 (3H, s), 2.84-2.95 (1H, m), 3.04-3.14 (1H, m), 3.30-3.35 (1H, m), 3.44-3.51 (1H, m), 3.72-3.78 (4H, m), 4.17-4.23 (4H, m), 4.97-5.09 (2H, m), 7.26-7.31 (3H, m), 7.60-7.66 (2H, m), 9.17 (2H, s).

Example 61

5-{8-[(3R)-3-Methyl-4-(methylsulfonyl)piperazin-1-yl]-6-morpholin-4-yl-9-(2,2,2-trifluoroethyl)-9H-purin-2-yl}pyrimidin-2-amine

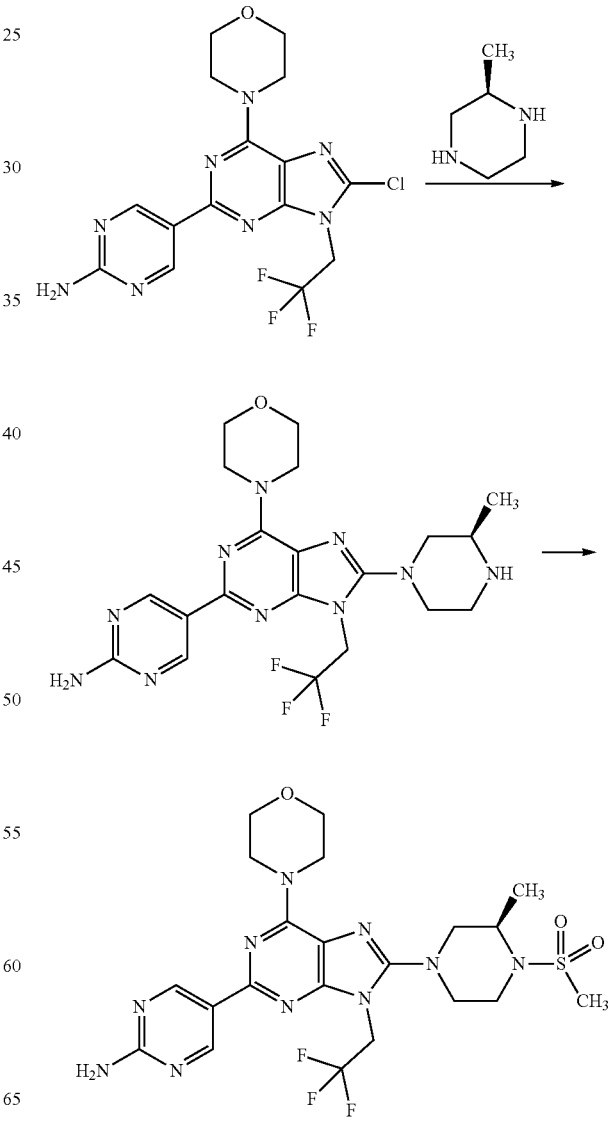

(2R)-2-Methylpiperazine (241 mg, 2.41 mmol) and N-methyl-2-pyrrolidone (2 ml) were added to 5-[8-chloro-6-morpholin-4-yl-9-(2,2,2-trifluoroethyl)-9H-purin-2-yl]pyrimidin-2-amine (200 mg, 0.48 mmol) and the resulting mixture was stirred at 100° C. for 2 hours. The reaction mixture was partitioned with chloroform and water, the organic layer was dried over magnesium sulfate, and then the solvent was concentrated under reduced pressure. Mesyl chloride (45 μl) and triethylamine (135 μl) were added to the residue with ice cooling and the resulting mixture was stirred for 20 minutes and then partitioned with ethyl acetate and saturated aqueous sodium bicarbonate solution. The organic layer was dried over magnesium sulfate, then the solvent was evaporated under reduced pressure, and the residue was purified by silica gel chromatography (chloroform:methanol=20:1) to give the title compound (204 mg, 76%) as a colorless solid.

¹H-NMR (CDCl₃) δ: 1.50 (3H, d, J=6.9 Hz), 2.94 (3H, s), 3.14-3.19 (2H, m), 3.27-3.32 (2H, m), 3.44-3.49 (1H, m), 3.71-3.75 (1H, m), 3.84-3.86 (4H, m), 4.25-4.30 (5H, m), 4.69-4.74 (2H, m), 5.24-5.26 (2H, m), 9.23 (2H, s).

Example 62

5-{8-[(3S)-3-Methyl-4-(methylsulfonyl)piperazin-1-yl]-6-morpholin-4-yl-9-(2,2,2-trifluoroethyl)-9H-purin-2-yl}pyrimidin-2-amine

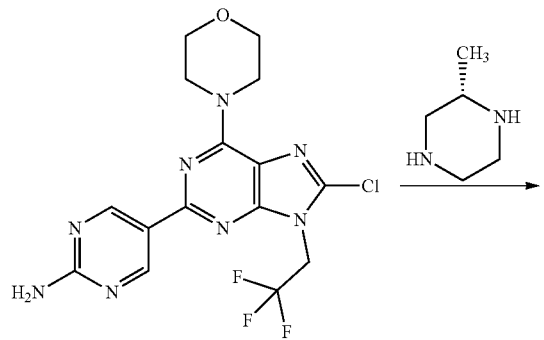

-continued

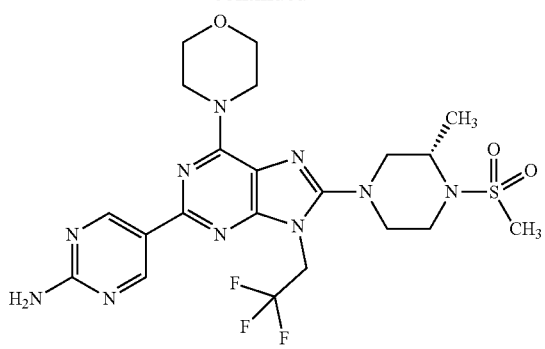

(2S)-2-Methylpiperazine (480 mg) and N-methyl-2-pyrrolidone (4 ml) were added to 5-[8-chloro-6-morpholin-4-yl-9-(2,2,2-trifluoroethyl)-9H-purin-2-yl]pyrimidin-2-amine (400 mg, 0.96 mmol) and the resulting mixture was stirred at 100° C. for 2 hours. The reaction mixture was partitioned with chloroform and water, the organic layer was dried over magnesium sulfate, and then the solvent was concentrated under reduced pressure.

Triethylamine (135 μl) and mesyl chloride (45 μl) were added to a half amount of the residue with ice cooling and the resulting mixture was stirred for 20 minutes. The reaction mixture was partitioned with ethyl acetate and saturated aqueous sodium bicarbonate solution, the organic layer was dried over magnesium sulfate, and then the solvent was evaporated under reduced pressure. The residue was purified by silica gel chromatography (chloroform:methanol=20:1) to give the title compound (127 mg) as a colorless solid.

¹H-NMR (CDCl₃) δ: 1.50 (3H, d, J=6.9 Hz), 2.94 (3H, s), 3.14-3.19 (2H, m), 3.27-3.32 (2H, m), 3.44-3.49 (1H, m), 3.71-3.76 (1H, m), 3.84-3.86 (4H, m), 4.25-4.30 (5H, m), 4.69-4.74 (2H, m), 5.24-5.26 (2H, m), 9.23 (2H, s).

Example 63

5-{8-[(3S)-4-Acetyl-3-methylpiperazin-1-yl]-6-morpholin-4-yl-9-(2,2,2-trifluoroethyl)-9H-purin-2-yl}pyrimidin-2-amine

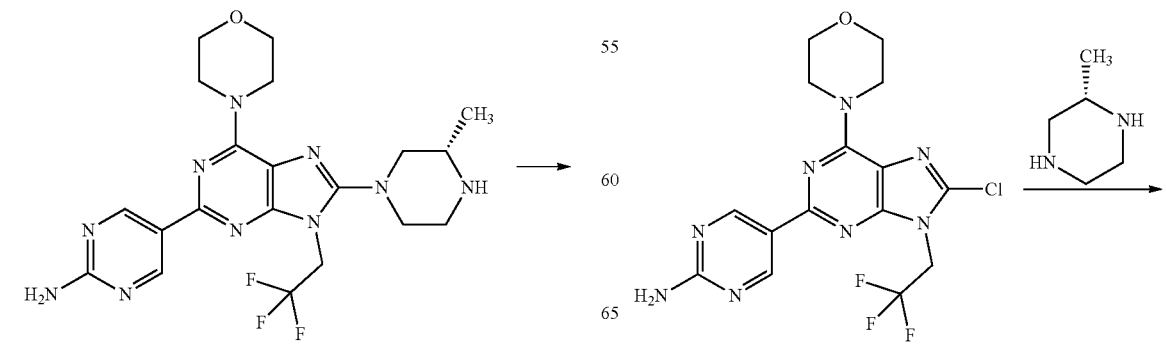

235
-continued

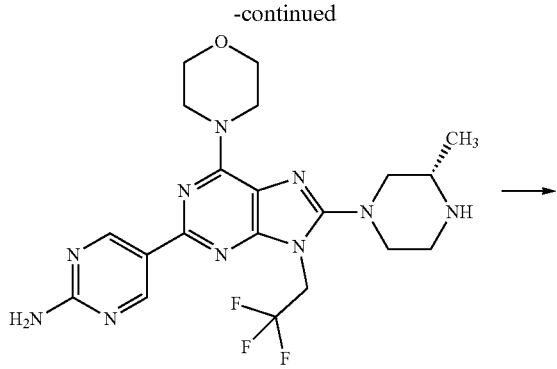

→

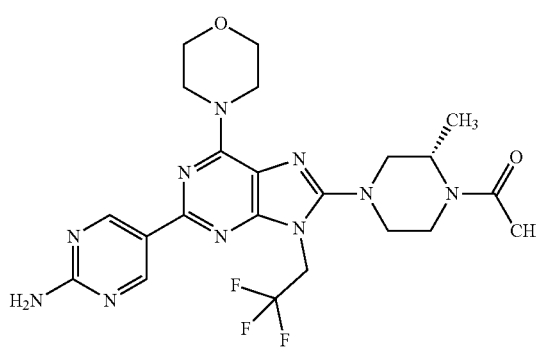

(2S)-2-Methylpiperazine (480 mg) and N-methyl-2-pyrrolidone (4 ml) were added to 5-[8-chloro-6-morpholin-4-yl-9-(2,2,2-trifluoroethyl)-9H-purin-2-yl]pyrimidin-2-amine (400 mg, 0.96 mmol) and the resulting mixture was stirred at 100° C. for 2 hours. The reaction mixture was partitioned with chloroform and water, the organic layer was dried over magnesium sulfate, and then the solvent was concentrated under reduced pressure.

Triethylamine (135 μl) and acetic anhydride (45 μl) were added to a half amount of the residue with ice cooling and the resulting mixture was stirred for 20 minutes. The reaction mixture was partitioned with ethyl acetate and saturated aqueous sodium bicarbonate solution, the organic layer was dried over magnesium sulfate, and then the solvent was evaporated under reduced pressure. The residue was purified by silica gel chromatography (chloroform:methanol=20:1) to give the title compound (125 mg) as a colorless solid.

$^1$H-NMR (DMSO-d$_6$, 140° C.) δ: 1.29 (3H, d, J=6.9 Hz), 2.03 (3H, s), 2.90-2.97 (1H, m), 3.10-3.14 (1H, m), 3.27-3.34 (2H, m), 3.43-3.46 (1H, m), 3.73-3.76 (4H, m), 4.00-4.03 (1H, m), 4.17-4.19 (4H, m), 4.43-4.51 (2H, m), 4.90-5.01 (2H, m), 6.45 (2H, brs), 9.06 (2H, s).

236

5-{8-[(3S)-4-Acetyl-3-methylpiperazin-1-yl]-6-morpholin-4-yl-9-(2,2,2-trifluoroethyl)-9H-purin-2-yl}pyrimidin-2-amine methanesulfonate

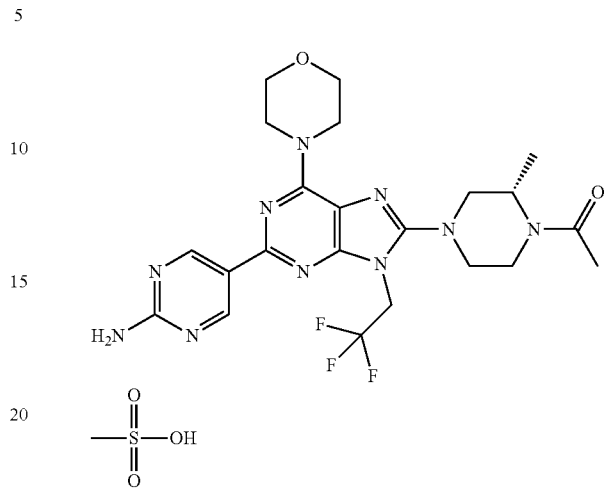

To a solution of 5-{8-[(3S)-4-acetyl-3-methylpiperazin-1-yl]-6-morpholin-4-yl-9-(2,2,2-trifluoroethyl)-9H-purin-2-yl}pyrimidin-2-amine (33.2 mg, 0.06 mmol) in methanol/dichloromethane solution (1/1, 1 ml) was added methanesulfonic acid (3.9 μl, 0.06 mmol) at room temperature, and the mixture was stirred for 3 hr. Then the solvent was removed in reduced pressure, and the resultant solid was dried to give 5-{8-[(3S)-4-acetyl-3-methylpiperazin-1-yl]-6-morpholin-4-yl-9-(2,2,2-trifluoroethyl)-9H-purin-2-yl}pyrimidin-2-amine methanesulfonate (31.4 mg) as a yellow solid.

$^1$H-NMR (DMSO-d$_6$, 80° C.) δ: 1.25-1.33 (3H, m), 2.04 (3H, s), 2.43 (3H, s), 2.82-2.97 (1H, m), 3.04-3.15 (1H, m), 3.29-3.35 (1H, m), 3.44-3.51 (1H, m), 3.72-3.78 (4H, m), 4.17-4.23 (4H, m), 4.94-5.12 (2H, m), 9.19 (2H, s).

5-{8-[(3S)-4-Acetyl-3-methylpiperazin-1-yl]-6-morpholin-4-yl-9-(2,2,2-trifluoroethyl)-9H-purin-2-yl}pyrimidin-2-amine sulfate

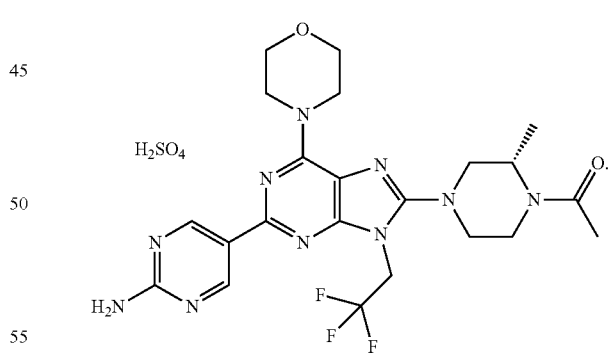

To a suspension of 5-{8-[(3S)-4-acetyl-3-methylpiperazin-1-yl]-6-morpholin-4-yl-9-(2,2,2-trifluoroethyl)-9H-purin-2-yl}pyrimidin-2-amine (48.7 mg, 0.09 mmol) in 10% aqueous ethanol solution (1 ml) was added 98% sulfuric acid (5.44 μL, 0.09 mmol) at room temperature, and the mixture was heated up to 50° C., then allowed to be cooled down to r.t., and stirred for 5 hr. The solid precipitated out was collected and dried to give 5-{8-[(3S)-4-acetyl-3-methylpiperazin-1-yl]-6-morpholin-4-yl-9-(2,2,2-trifluoroethyl)-9H-purin-2-yl}pyrimidin-2-amine sulfate (48.9 mg) as a yellow solid.

¹H-NMR (DMSO-d₆, 80° C.) δ: 1.29 (3H, d, J=6.0 Hz), 2.04 (3H, s), 2.85-2.97 (1H, m), 3.04-3.14 (1H, m), 3.28-3.34 (1H, m), 3.43-3.50 (1H, m), 3.72-3.77 (4H, m), 4.16-4.22 (4H, m), 4.94-5.09 (2H, m), 9.14 (2H, s).

5-{8-[(3S)-4-Acetyl-3-methylpiperazin-1-yl]-6-morpholin-4-yl-9-(2,2,2-trifluoroethyl)-9H-purin-2-yl}pyrimidin-2-amine p-toluenesulfonate

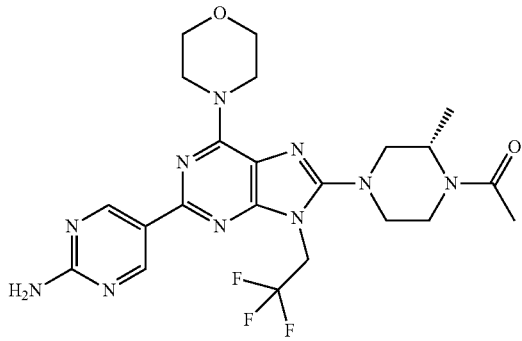

To a suspension of 5-{8-[(3S)-4-acetyl-3-methylpiperazin-1-yl]-6-morpholin-4-yl-9-(2,2,2-trifluoroethyl)-9H-purin-2-yl}pyrimidin-2-amine (56.3 mg, 0.11 mmol) in 10% aqueous ethanol solution (0.5 ml) was added p-toluenesulfonic acid mono hydrate (22.6 mg, 0.12 mmol) at 50° C., and the mixture was cooled down to room temperature, and was then stirred under ice-cooling for 2 hr. The solid precipitated out was collected and dried to give 5-{8-[(3S)-4-acetyl-3-methylpiperazin-1-yl]-6-morpholin-4-yl-9-(2,2,2-trifluoroethyl)-9H-purin-2-yl}pyrimidin-2-amine p-toluenesulfonate (55.1 mg) as a yellow solid.

¹H-NMR (DMSO-d₆, 80° C.) δ: 1.29 (3H, d, J=6.41 Hz), 2.04 (3H, s), 2.28 (3H, s), 2.81-2.96 (1H, m), 3.03-3.14 (1H, m), 3.27-3.34 (1H, m), 3.42-3.50 (1H, m), 3.71-3.78 (4H, m), 4.16-4.22 (4H, m), 4.92-5.10 (2H, m), 7.09 (2H, d, J=7.8 Hz), 7.49 (2H, d, J=7.8 Hz), 9.12 (2H,S).

5-{8-[(3S)-4-Acetyl-3-methylpiperazin-1-yl]-6-morpholin-4-yl-9-(2,2,2-trifluoroethyl)-9H-purin-2-yl}pyrimidin-2-amine benzensulfonate

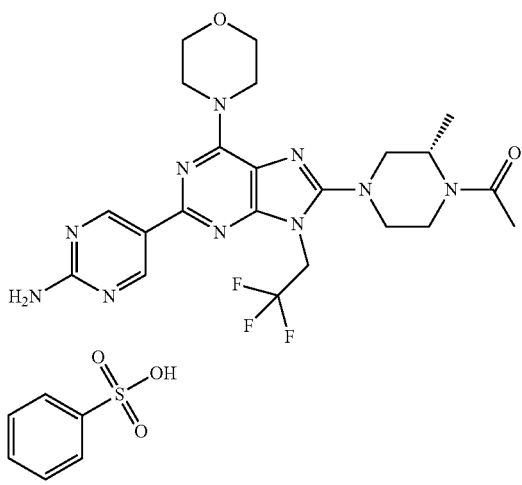

To a suspension of 5-{8-[(3S)-4-acetyl-3-methylpiperazin-1-yl]-6-morpholin-4-yl-9-(2,2,2-trifluoroethyl)-9H-purin-2-yl}pyrimidin-2-amine (53.8 mg, 0.1 mmol) in 10% aqueous ethanol solution (0.6 ml) was added benzenesulfonic acid mono hydrate (20.0 mg, 0.11 mmol) at 50° C., and the mixture was cooled down to room temperature, and was stirred for 5 hr. The solid precipitated out was collected and dried to give 5-{8-[(3S)-4-acetyl-3-methylpiperazin-1-yl]-6-morpholin-4-yl-9-(2,2,2-trifluoroethyl)-9H-purin-2-yl}pyrimidin-2-amine benzenesulfonate (52.4 mg) as a yellow solid.

¹H-NMR (DMSO-d₆, 80° C.) δ: 1.29 (3H, d, J=6.41 Hz), 2.04 (3H, s), 2.82-2.95 (1H, m), 3.04-3.14 (1H, m), 3.27-3.34 (1H, m), 3.42-3.49 (1H, m), 3.72-3.77 (4H, m), 4.16-4.22 (4H, m), 4.94-5.08 (2H, m), 7.25-7.32 (3H, m), 7.59-7.64 (2H, m), 9.12 (2H, s).

Example 64

5-{9-(2,2-Difluoro-ethyl)-8-[4-(methylsulfonyl)piperazin-1-yl]-6-morpholin-4-yl-9H-purin-2-yl}pyrimidin-2-amine

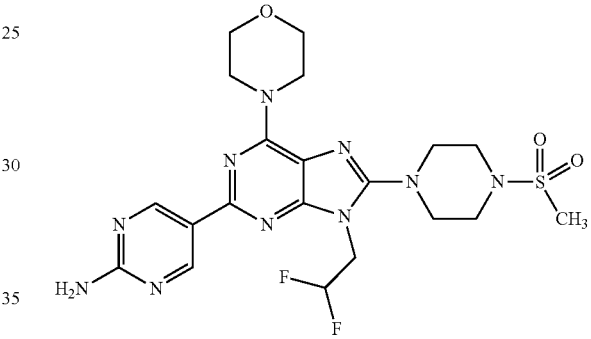

In the same way as in Step 1 of Example 1, the intermediate obtained by using 2,2-difluoro-ethyl p-toluenesulfonate was synthesized, and then the intermediate was led to the title compound by the ways in Steps 2 and after of Example 1.

¹H-NMR (CDCl₃) δ: 2.87 (3H, s), 3.36-3.39 (4H, m), 3.43-3.46 (4H, m), 3.84-3.86 (4H, m), 4.28 (4H, s), 4.37 (2H, td, J=12.8, 4.7 Hz), 5.35 (2H, s), 6.55 (1H, tt, J=56.2, 4.8 Hz), 9.21 (2H, s).

Example 65

1-{4-[2-(2-Aminopyrimidin-5-yl)-6-morpholin-4-yl-9-(2,2,2-trifluoroethyl)-9H-purin-8-yl]piperazin-1-yl}-1-oxoacetone

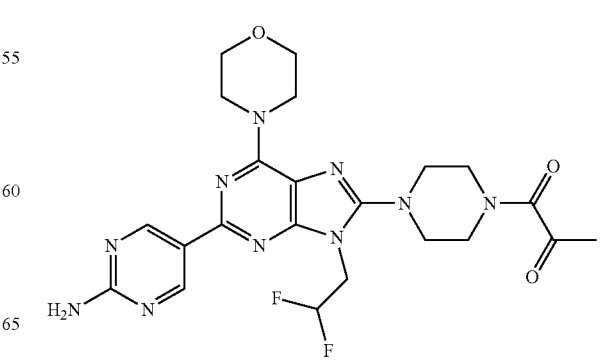

Step 1: tert-Butyl {5-[6-morpholin-4-yl-8-(4-piru-voylpiperazin-1-yl)-9-(2,2,2-trifluoroethyl)-9H-purin-2-yl]pyrimidin-2-yl}carbamate

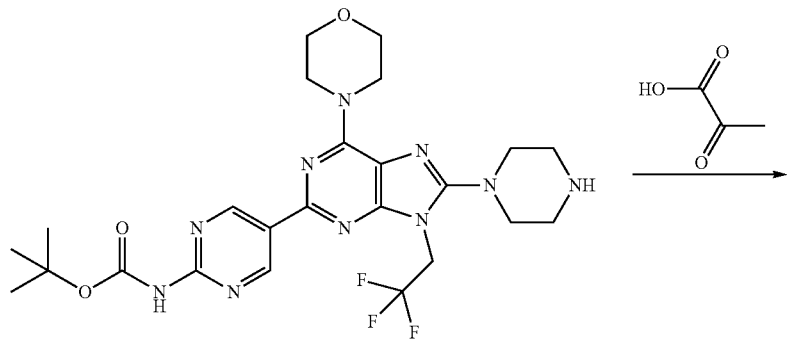

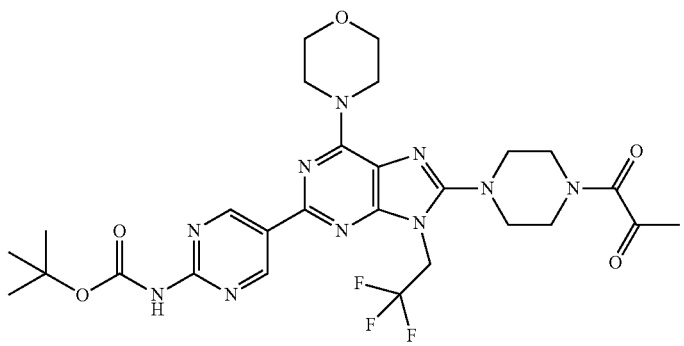

2-oxo-Propionic acid (26 mg, 0.29 mmol), hydroxybenzotriazole hydrate (45 mg, 0.29 mmol), and tetrahydrofuran (5 ml) were added to tert-butyl {5-[6-morpholin-4-yl-8-piperazin-1-yl-9-(2,2,2-trifluoroethyl)-9H-purin-2-yl]pyrimidin-2-yl}carbamate (150 mg, 0.27 mmol). 1-Ethyl-3-(3-dimethylaminopropyl)-carbodiimide hydrochloride (56 mg; 0.29 mmol) and triethylamine (74 µl, 0.53 mmol) were added and the resulting mixture was stirred for 18 hours. The reaction mixture was partitioned with ethyl acetate and water and the organic layer was washed with saturated aqueous sodium bicarbonate solution and dried over magnesium sulfate. The solvent was evaporated under reduced pressure and then the residue was purified by silica gel chromatography (ethyl acetate) to give the title compound (91 mg, 54%) as a colorless solid.

$^1$H-NMR (CDCl$_3$) δ: 1.56 (9H, s), 2.48 (3H, s), 3.25-3.27 (4H, m), 3.71-3.73 (2H, m), 3.84-3:86 (6H, m), 4.28 (4H, brs), 4.72 (2H, q, J=8.3 Hz), 7.90 (1H, s), 9.48 (2H, s).

Step 2: 1-{4-[2-(2-Aminopyrimidin-5-yl)-6-morpholin-4-yl-9-(2,2,2-trifluoroethyl)-9H-purin-8-yl]piperazin-1-yl}-1-oxoacetone

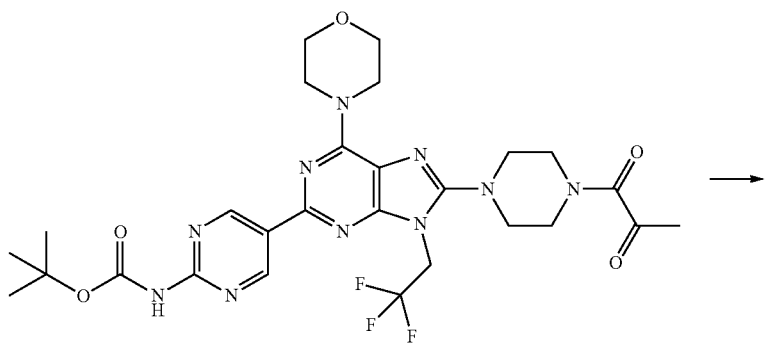

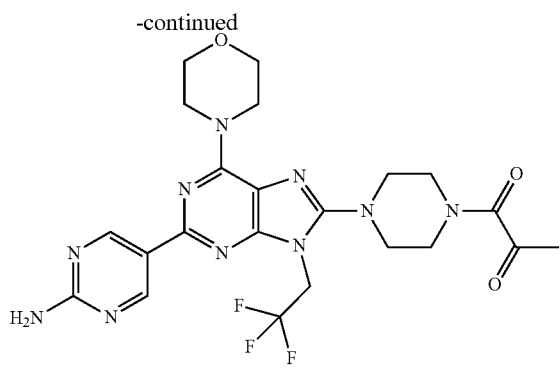

Trifluoroacetic acid (5 ml) was added to tert-butyl {5-[6-morpholin-4-yl-8-(4-piruvoylpiperazin-1-yl)-9-(2,2,2-trifluoroethyl)-9H-purin-2-yl]pyrimidin-2-yl}carbamate (91 mg, 0.14 mmol) and the resulting mixture was stirred for 30 minutes. Toluene was added and the solvent was evaporated under reduced pressure. The residue was partitioned with ethyl acetate and saturated aqueous sodium bicarbonate solution, the organic layer was dried over magnesium sulfate, and then the solvent was evaporated under reduced pressure. The residue was purified by silica gel chromatography (chloroform:methanol=19:1) followed by the addition of 4 M hydrochloric acid-1,4-dioxane (3 ml) and the solvent was evaporated under reduced pressure and dried to give the title compound (70 mg, 76%) as a yellow solid.

$^1$H-NMR (CD$_3$OD) δ: 2.43 (3H, s), 3.28-3.30 (4H, m), 3.68-3.70 (2H, m), 3.80-3.83 (6H, m), 4.30 (4H, brs), 4.99 (2H, q, J=8.6 Hz), 9.37 (2H, s).

Example 66

2-{4-[2-(2-Aminopyrimidin-5-yl)-6-morpholin-4-yl-9-(2,2,2-trifluoroethyl)-9H-purin-8-yl]piperazin-1-yl}-N,N-dimethyl-2-oxoacetamide

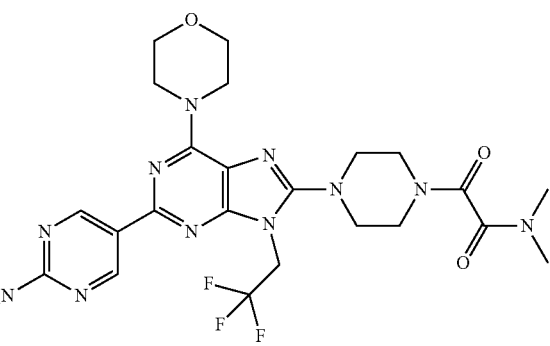

Step 1: tert-Butyl {5-[8-{4-[(dimethylamino)(oxo)acetyl]piperazin-1-yl}-6-morpholin-4-yl-9-(2,2,2-trifluoroethyl)-9H-purin-2-yl]pyrimidin-2-yl}carbamate

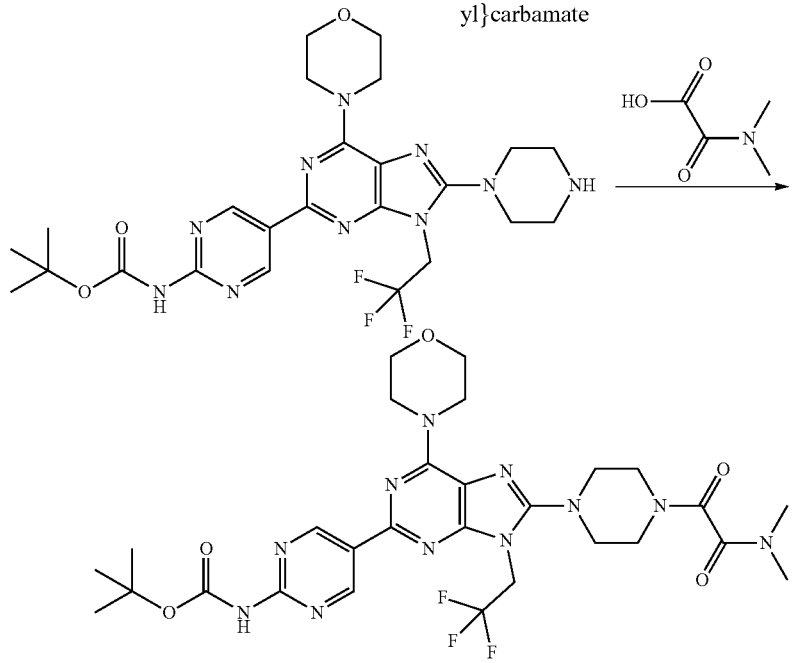

N,N-Dimethyl-oxalamic acid (34 mg, 0.29 mmol), hydroxybenzotriazole hydrate (45 mg, 0.29 mmol), and tetrahydrofuran (5 ml) were added to tert-butyl {5-[6-morpholin-4-yl-8-piperazin-1-yl-9-(2,2,2-trifluoroethyl)-9H-purin-2-yl]pyrimidin-2-yl}carbamate (150 mg, 0.27 mmol). 1-Ethyl-3-(3-dimethylaminopropyl)-carbodiimide hydrochloride (56 mg, 0.29 mmol) and triethylamine (74 μl, 0.53 mmol) were added and the resulting mixture was stirred for 18 hours. The reaction mixture was partitioned with ethyl acetate and water and the organic layer was washed with saturated aqueous sodium bicarbonate solution and dried over magnesium sulfate. The solvent was evaporated under reduced pressure and then the residue was purified by silica gel chromatography (chloroform:methanol=19:1) to give the title compound (148 mg, 84%) as a white solid.

$^1$H-NMR (CDCl$_3$) δ: 1.56 (9H, s), 3.03 (3H, s), 3.07 (3H, s), 3.25-3.29 (4H, m), 3.61-3.62 (2H, m), 3.84-3.87 (6H, m), 4.27 (4H, brs), 4.72 (2H, q, J=8.4 Hz), 8.07 (1H, s), 9.49 (2H, s).

Step 2: 2-{4-[(2-(2-Aminopyrimidin-5-yl)-6-morpholin-4-yl-9-(2,2,2-trifluoroethyl)-9H-purin-8-yl]piperazin-1-yl}-N,N-dimethyl-2-oxoacetamide

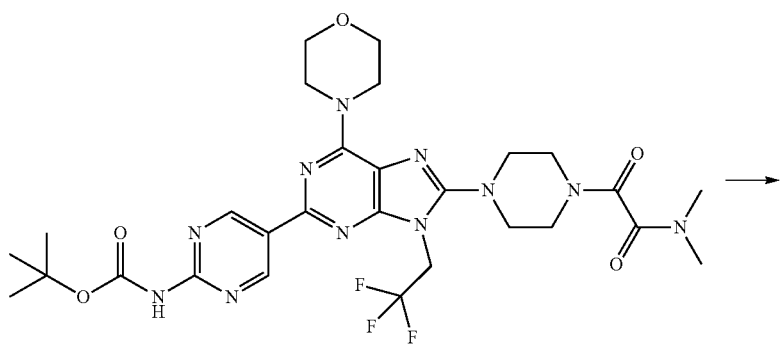

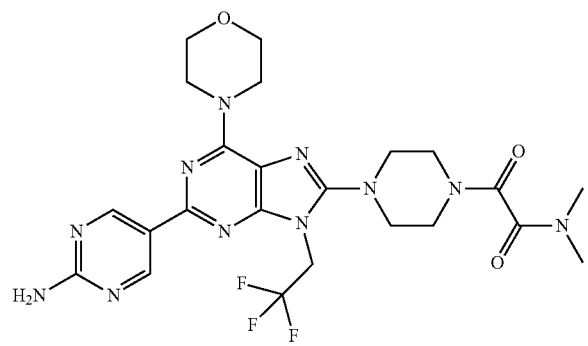

Trifluoroacetic acid (5 ml) was added to tert-butyl {5-[8-{4-[(dimethylamino)(oxo)acetyl]piperazin-1-yl}-6-morpholin-4-yl-9-(2,2,2-trifluoroethyl)-9H-purin-2-yl]pyrimidin-2-yl}carbamate (148 mg, 0.22 mmol) and the resulting mixture was stirred for 30 minutes. Toluene was added and the solvent was evaporated under reduced pressure. Hydrochloric acid-methanol was added to the residue and the solvent was evaporated and dried to give the title compound (118 mg, 88%) as a yellow solid.

$^1$H-NMR (CD$_3$OD) δ: 3.05 (3H, s), 3.09 (3H, s), 3.31-3.34 (OH, m), 3.61-3.64 (1H, m), 3.87-3.89 (8H, m), 4.32 (2H, brs), 4.87 (2H, q, J=8.4 Hz), 7.56 (2H, s), 9.38 (2H, s).

Example 67

2-{4-[2-(2-Aminopyrimidin-5-yl)-6-morpholin-4-yl-9-(2,2,2-trifluoroethyl)-9H-purin-8-yl]piperazin-1-yl}-2-oxoethanol

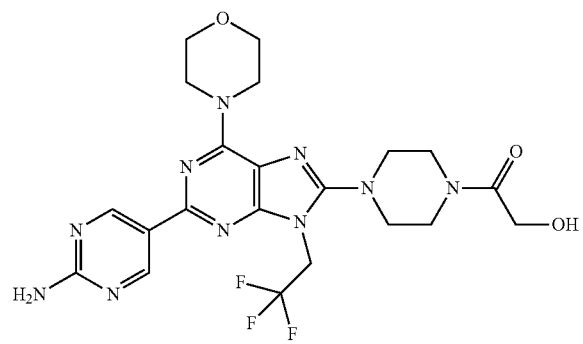

Step 1: 5-[6-Morpholin-4-yl-8-piperazin-1-yl-9-(2,2,2-trifluoroethyl)-9H-purin-2-yl]pyrimidin-2-amine trifluoroacetate

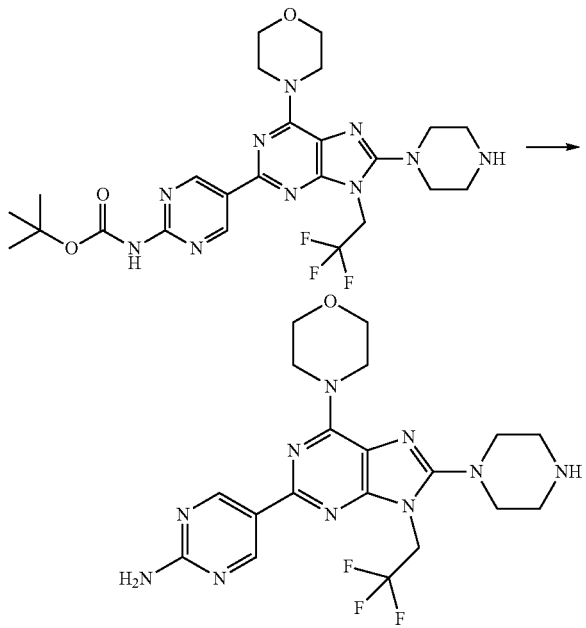

tert-Butyl {5-[6-morpholin-4-yl-8-piperazin-1-yl-9-(2,2,2-trifluoroethyl)-9H-purin-2-yl]pyrimidin-2-yl}carbamate (1.18 g, 2.09 mmol) was dissolved in methylene chloride (10 ml) followed by the addition of trifluoroacetic acid (10 ml) with ice cooling and the resulting mixture was stirred at room temperature for 2 hours. The solvent was evaporated under reduced pressure followed by the addition of toluene and evaporated again under reduced pressure to give the title compound (1.5 g, 100%) as a yellow solid.

$^1$H-NMR (DMSO-d$_6$) δ: 3.29-3.31 (4H, m), 3.36-3.38 (4H, m), 3.74-3.76 (4H, m), 4.20 (4H, brs), 5.09 (2H, q, J=9.0 Hz), 8.81 (2H, brs), 9.13 (2H, s).

Step 2: 2-{4-[2-(2-Aminopyrimidin-5-yl)-6-morpholin-4-yl-9-(2,2,2-trifluoroethyl)-9H-purin-8-yl]piperazin-1-yl}-2-oxoethanol

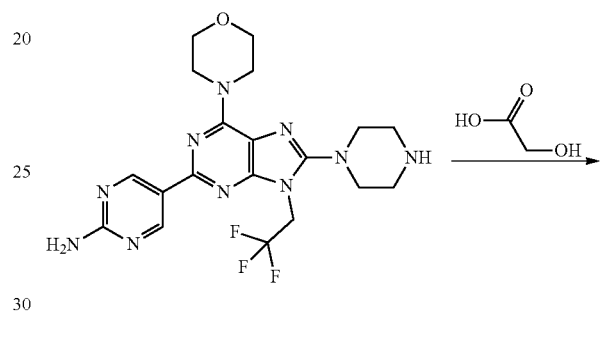

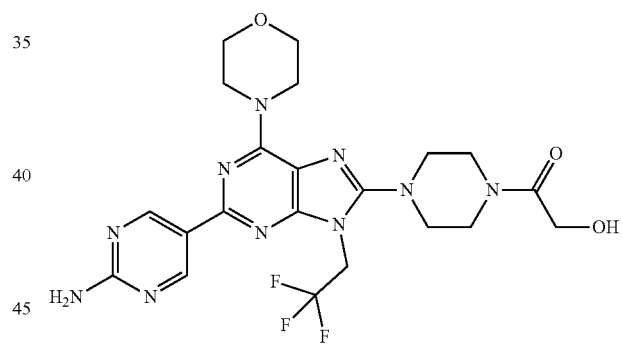

2-Hydroxyacetic acid (15 mg, 0.19 mmol), hydroxybenzotriazole hydrate (37 mg, 0.19 mmol), 1-ethyl-3-(3-dimethylaminopropyl)-carbodiimide hydrochloride (37 mg, 0.19 mmol), dimethylformamide (3 ml), and triethylamine (100 μl) were added to 5-[6-morpholin-4-yl-8-piperazin-1-yl-9-(2,2,2-trifluoroethyl)-9H-purin-2-yl]pyrimidin-2-amine trifluoroacetate (120 mg, 0.17 mmol) and the resulting mixture was stirred for 4 hours. The reaction mixture was partitioned with ethyl acetate and water, the organic layer was washed with saturated aqueous sodium bicarbonate solution and dried over magnesium sulfate, and then the solvent was evaporated under reduced pressure. The residue was purified by silica gel chromatography (chloroform:methanol=19:1) to give the title compound (70 mg) as a colorless solid.

4 M Hydrochloric acid-1,4-dioxane was added to this compound and the solvent was evaporated under reduced pressure and dried to give a hydrochloride of the title compound (75 mg, 77%) as a yellow solid.

¹H-NMR (DMSO-d₆) δ: 3.16-3.21 (4H, m), 3.51-3.53 (2H, m), 3.63-3.66 (2H, m), 3.74-3.76 (4H, m), 4.14 (2H, s), 4.19 (4H, brs), 5.08 (2H, q, J=9.0 Hz), 7.45 (2H, brs), 9.16 (2H, s).

Example 68

(2S)-1-{4-[2-(2-Aminopyrimidin-5-yl)-6-morpholin-4-yl-9-(2,2,2-trifluoroethyl)-9H-purin-8-yl]piperazin-1-yl}-1-oxopropan-2-ol

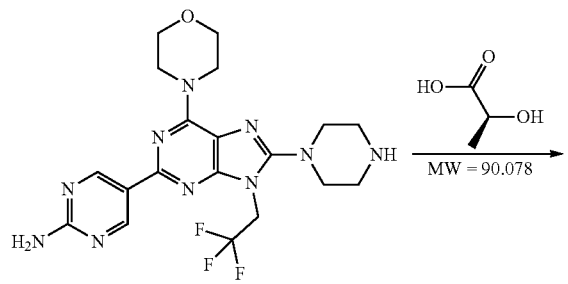

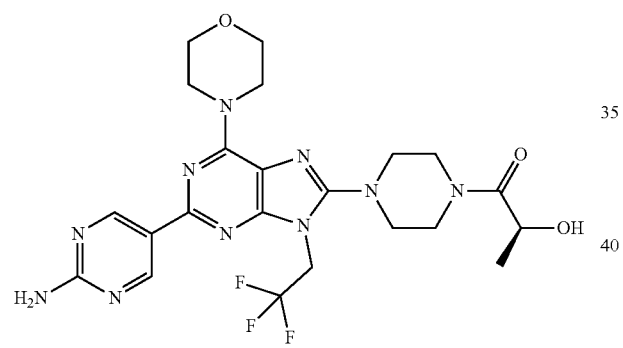

L-Lactic acid (17 mg, 0.19 mmol), hydroxybenzotriazole hydrate (37 mg, 0.19 mmol), 1-ethyl-3-(3-dimethylaminopropyl)-carbodiimide hydrochloride (37 mg, 0.19 mmol), dimethylformamide (3 ml), and triethylamine (100 μl) were added to 5-[6-morpholin-4-yl-8-piperazin-1-yl-9-(2,2,2-trifluoroethyl)-9H-purin-2-yl]pyrimidin-2-amine trifluoroacetate (120 mg, 0.17 mmol) and the resulting mixture was stirred for 5 hours. The reaction mixture was partitioned with ethyl acetate and water, the organic layer was washed with saturated aqueous sodium bicarbonate solution and dried over magnesium sulfate, and then the solvent was evaporated under reduced pressure. The residue was purified by silica gel chromatography (chloroform:methanol=19:1) to give the title compound as a colorless solid.

4 M Hydrochloric acid-1,4-dioxane was added to this compound and the solvent was evaporated under reduced pressure and dried to give a hydrochloride of the title compound (77 mg, 78%) as a yellow solid.

¹H-NMR (DMSO-d₆) δ: 1.21 (3H, d, J=6.9 Hz), 3.13-3.24 (4H, m), 3.57-3.76 (8H, m), 4.17-4.23 (4H, m), 4.47 (1H, q, J=6.5 Hz), 5.11 (2H, q, J=8.8 Hz), 9.26 (2H, s).

Example 69

(2S)-4-{4-[2-(2-Aminopyrimidin-5-yl)-6-morpholin-4-yl-9-(2,2,2-trifluoroethyl)-9H-purin-8-yl]piperazin-1-yl}-4-oxobutan-2-ol

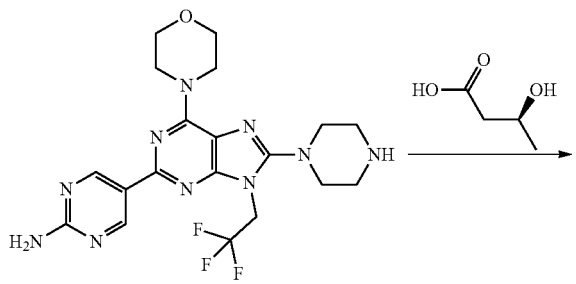

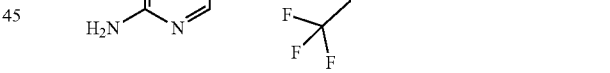

(S)-3-hydroxybutanoic acid (39 mg, 0.38 mmol), hydroxybenzotriazole hydrate (58 mg, 0.38 mmol), 1-ethyl-3-(3-dimethylaminopropyl)-carbodiimide hydrochloride (72 mg, 0.38 mmol), dimethylformamide (5 ml), and triethylamine (161 μl) were added to 5-[6-morpholin-4-yl-8-piperazin-1-yl-9-(2,2,2-trifluoroethyl)-9H-purin-2-yl]pyrimidin-2-amine trifluoroacetate (200 mg, 0.29 mmol) and the resulting mixture was stirred for 15 hours. The reaction mixture was partitioned with ethyl acetate and saturated aqueous sodium bicarbonate solution, the organic layer was dried over magnesium sulfate, and then the solvent was evaporated under reduced pressure. The residue was purified by silica gel chromatography (chloroform:methanol=19:1) to give the title compound (80 mg, 50%) as a white solid.

¹H-NMR (CDCl₃) δ: 1.26 (3H, d, J=6.3 Hz), 2.38 (1H, dd, J=16.3, 9.5 Hz), 2.53 (1H, dd, J=16.6, 2.3 Hz), 3.17-3.24 (4H, m), 3.63-3.80 (4H, m), 3.84-3.89 (5H, m), 4.27 (4H, brs), 4.73 (2H, q, J=8.4 Hz), 9.23 (2H, s).

Example 70

(2R)-4-{4-[2-(2-Aminopyrimidin-5-yl)-6-morpholin-4-yl-9-(2,2,2-trifluoroethyl)-9H-purin-8-yl]piperazin-1-yl}-4-oxobutan-2-ol

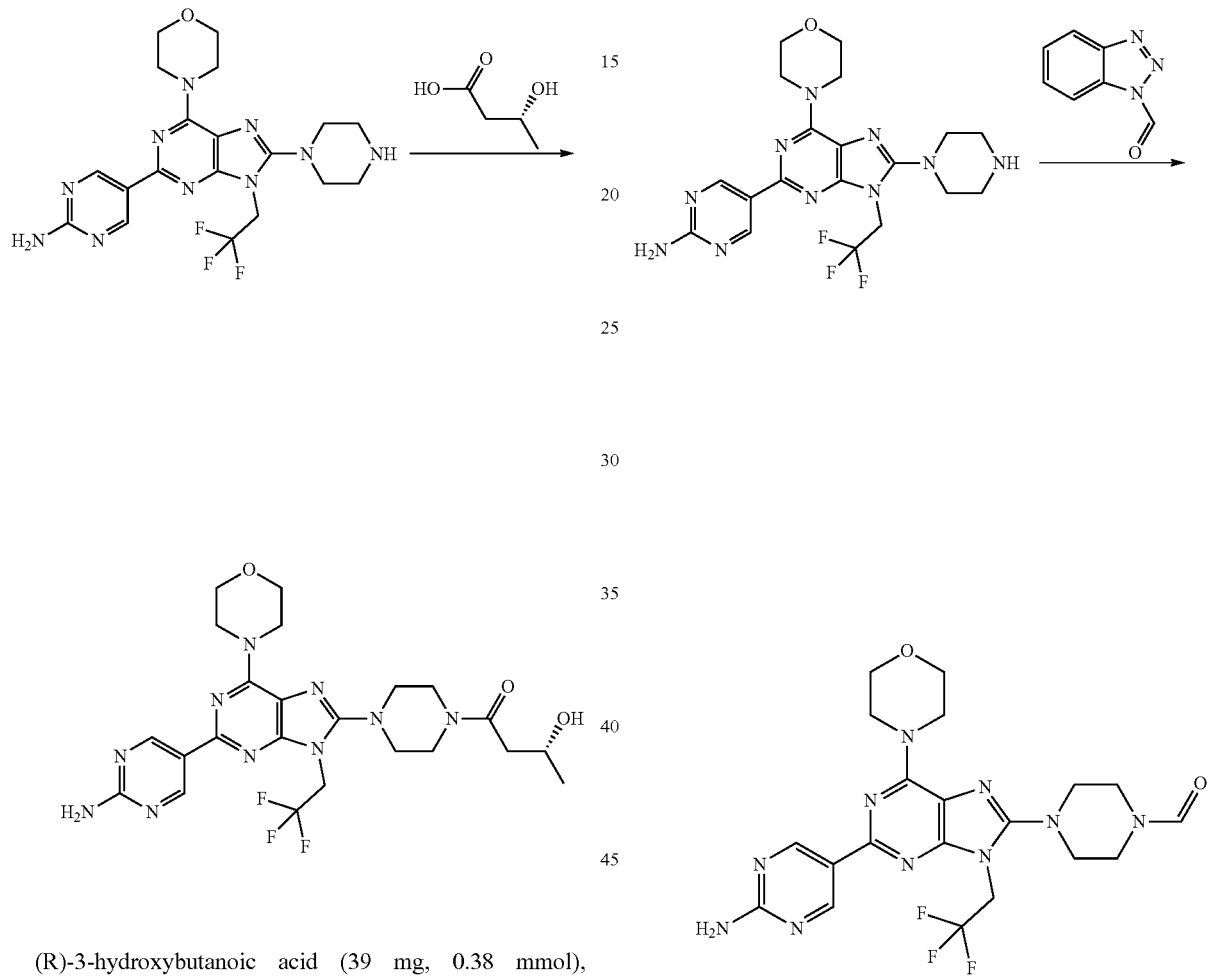

(R)-3-hydroxybutanoic acid (39 mg, 0.38 mmol), hydroxybenzotriazole hydrate (58 mg, 0.38 mmol), 1-ethyl-3-(3-dimethylaminopropyl)-carbodiimide hydrochloride (72 mg, 0.38 mmol), dimethylformamide (5 ml), triethylamine (161 µl) were added to 5-[6-morpholin-4-yl-8-piperazin-1-yl-9-(2,2,2-trifluoroethyl)-9H-purin-2-yl]pyrimidin-2-amine trifluoroacetate (200 mg, 0.29 mmol) and the resulting mixture was stirred for 15 hours. The reaction mixture was partitioned with ethyl acetate and saturated aqueous sodium bicarbonate solution, the organic layer was dried over magnesium sulfate, and then the solvent was evaporated under reduced pressure. The residue was purified by silica gel chromatography (chloroform:methanol=19:1) to give the title compound (77 mg, 48%) as a colorless solid.

$^1$H-NMR (CDCl$_3$) δ: 1.26 (3H, d, J=6.3 Hz), 2.38 (1H, dd, J=16.3, 9.5 Hz), 2.53 (1H, dd, J=16.6, 2.3 Hz), 3.17-3.24 (4H, m), 3.63-3.80 (4H, m), 3.84-3.89 (5H, m), 4.27 (4H, brs), 4.73 (2H, q, J=8.4 Hz), 5.28-5.30 (2H, m), 9.23 (2H, s).

Example 71

4-[2-(2-Aminopyrimidin-5-yl)-6-morpholin-4-yl-9-(2,2,2-trifluoroethyl)-9H-purin-8-yl]piperazine-1-carboaldehyde Benzotriazole-1-carboaldehyde (55 mg, 0.38 mmol) was dissolved in tetrahydrofuran (10 ml) followed by the addition of 5-[6-morpholin-4-yl-8-piperazin-1-yl-9-(2,2,2-trifluoroethyl)-9H-purin-2-yl]pyrimidin-2-amine trifluoroacetate (200 mg, 0.29 mmol). The resulting mixture was stirred for 20 minutes and the reaction mixture was diluted with ethyl acetate, washed with 1 M sodium hydroxide and saturated brine, and dried over magnesium sulfate. The solvent was evaporated under reduced pressure and the residue was purified by silica gel chromatography (chloroform:methanol=19:1) to give a white solid (80 mg, 56%).

¹H-NMR (CDCl₃) δ: 3.17-3.19 (2H, m), 3.23-3.25 (2H, m), 3.58-3.59 (2H, m), 3.75-3.77 (2H, m), 3.84-3.86 (4H, m), 4.28 (4H, s), 4.73 (2H, q, J=8.4 Hz), 5.20-5.23 (2H, m), 8.13 (1H, s), 9.23 (2H, s).

Example 72

N-{(3R)-1-[2-(2-Amino-4-methylpyrimidin-5-yl)-9-(cyclopropylmethyl)-6-morpholin-4-yl-9H-purin-8-yl]pyrrolidin-3-yl}methanesulfonamide

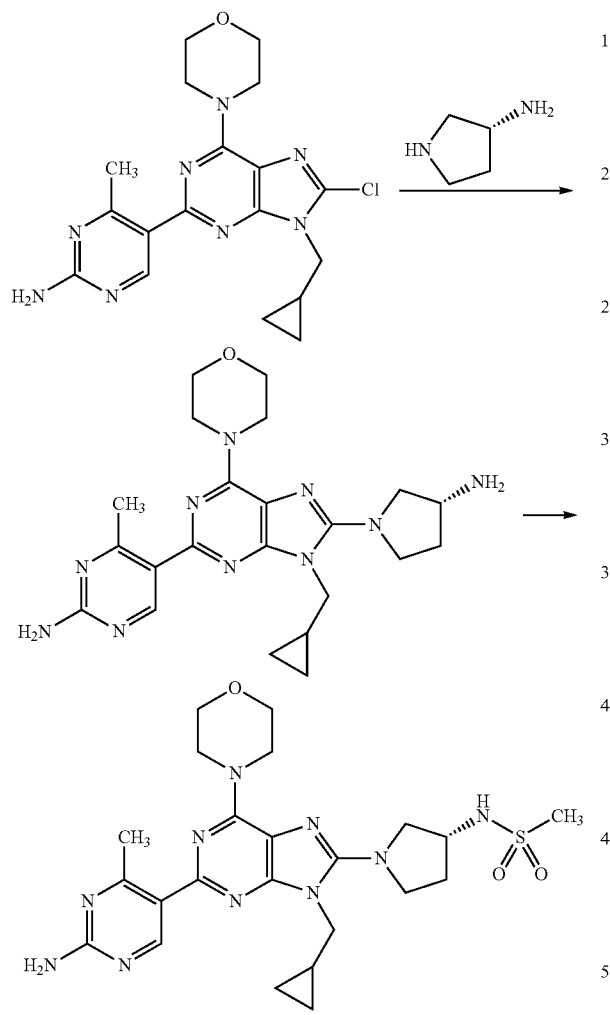

N-Methyl-2-pyrrolidone (3 ml) was added to 5-[8-chloro-9-(cyclopropylmethyl)-6-morpholin-4-yl-9H-purin-2-yl]-4-methylpyrimidin-2-amine (300 mg, 0.75 mmol), and (3R)-aminopyrrolidine (516 mg) and the resulting mixture was stirred at 140° C. for 1 hour. The reaction mixture was cooled, then diluted with methylene chloride, washed with water, and dried over magnesium sulfate. The solvent was concentrated under reduced pressure followed by the addition of triethylamine (261 µl), mesyl chloride (70 µl) was added with ice cooling, and the resulting mixture was stirred at room temperature for 30 minutes. Mesyl chloride (25 µl) was further added with ice cooling and the resulting mixture was stirred at room temperature for 30 minutes and partitioned with ethyl acetate and water. The organic layer was washed three times with water and then dried over magnesium sulfate and the solvent was evaporated under reduced pressure. The residue was purified by silica gel chromatography (chloroform:methanol=20:1) to give a light brown solid (355 mg, 90%).

¹H-NMR (CDCl₃) δ: 0.45-0.54 (4H, m), 1.26-1.29 (1H, m), 2.10-2.16 (1H, m), 2.33-2.40 (1H, m), 2.72 (3H, s), 3.04 (3H, s), 3.60-3.79 (3H, m), 3.82-3.84 (4H, m), 3.93-4.04 (2H, m), 4.17-4.24 (5H, m), 5.17-5.20 (2H, m), 5.88 (1H, d, J=8.0 Hz), 8.88 (1H, s).

This compound was dissolved in chloroform (10 ml)-methanol (10 ml) followed by the addition of methanesulfonic acid (43 µl) with ice cooling and then the solvent was evaporated under reduced pressure to give methanesulfonate (450 mg) as a yellow solid.

¹H-NMR (DMSO-d₆) δ: 0.40-0.49 (4H, m), 1.26-1.32 (1H, m), 1.93-2.00 (1H, m), 2.21-2.27 (1H, m), 2.34 (3H, s), 2.81 (3H, s), 3.00 (3H, s), 3.52 (1H, dd, J=10.3, 5.2 Hz), 3.64-3.69 (1H, m), 3.72-3.76 (5H, m), 3.85 (1H, dd, J=9.7, 6.3 Hz), 4.05-4.14 (7H, m), 7.47 (1H, d, J=6.3 Hz), 8.10 (1H, brs), 9.03 (1H, s).

Example 73

N-{(3S)-1-[2-(2-Amino-4-methylpyrimidin-5-yl)-9-(cyclopropylmethyl)-6-morpholin-4-yl-9H-purin-8-yl]pyrrolidin-3-yl}methanesulfonamide

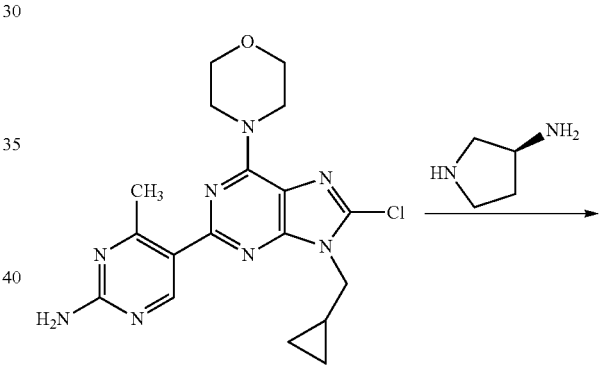

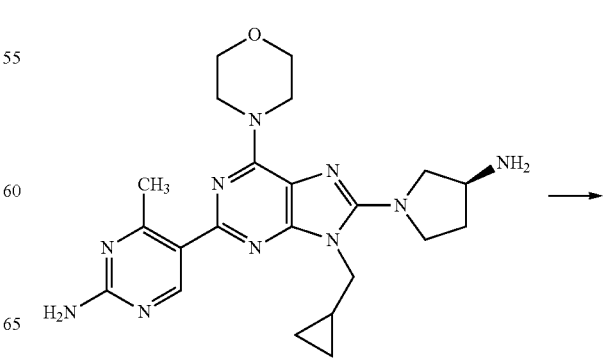

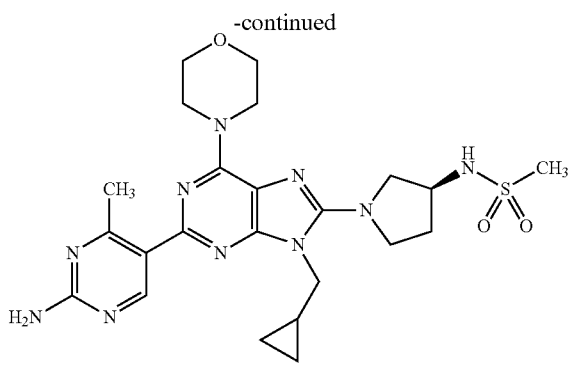

N-Methyl-2-pyrrolidone (3 ml) was added to 5-[8-chloro-9-(cyclopropylmethyl)-6-morpholin-4-yl-9H-purin-2-yl]-4-methylpyrimidin-2-amine (300 mg, 0.75 mmol) and (3S)-aminopyrrolidine (516 mg) and the resulting mixture was stirred at 140° C. for 1 hour. The reaction mixture was cooled and then diluted with methylene chloride, washed with water, and dried over magnesium sulfate. The solvent was concentrated under reduced pressure followed by the addition of triethylamine (261 μl), mesyl chloride (70 μl) was added with ice cooling, and the resulting mixture was stirred at room temperature for 30 minutes. Mesyl chloride (25 μl) was further added with ice cooling and then the resulting mixture was stirred at room temperature for 30 minutes and partitioned with ethyl acetate and water. The organic layer was washed three times with water and dried over magnesium sulfate and the solvent was evaporated under reduced pressure. The residue was purified by silica gel chromatography (chloroform:methanol=20:1) to give the title compound (328 mg) as a pale yellow solid.

This compound was dissolved in chloroform (10 ml)-methanol (10 ml) followed by the addition of methanesulfonic acid (40 μl) with ice cooling and then the solvent was evaporated under reduced pressure to give methanesulfonate (370 mg, 79%) as a yellow solid.

$^1$H-NMR (DMSO-d$_6$) δ: 0.40-0.49 (4H, m), 1.26-1.32 (1H, m), 1.93-2.00 (1H, m), 2.21-2.27 (1H, m), 2.34 (3H, s), 2.81 (3H, s), 3.00 (3H, s), 3.52 (1H, dd, J=10.3, 5.2 Hz), 3.64-3.69 (1H, m), 3.72-3.76 (5H, m), 3.85 (1H, dd, J=9.7, 6.3 Hz), 4.05-4.14 (7H, m), 7.47 (1H, d, J=6.3 Hz), 8.06 (1H, brs), 9.03 (1H, s).

Example 74

5-{8-[(3S)-3-Ethylpiperazin-1-yl]-6-morpholin-4-yl-9-(2,2,2-trifluoroethyl)-9H-purin-2-yl}pyrimidin-2-amine

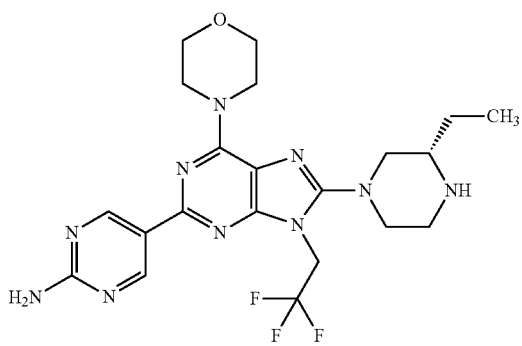

Step 1: 2-(S)-Ethylpiperazine 2 hydrochloride

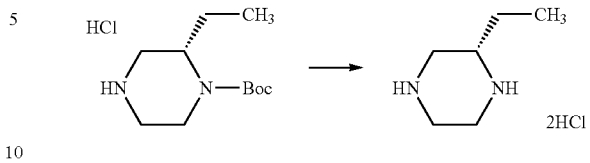

Concentrated hydrochloric acid (3 ml) was added to 2-(S)-ethyl-1-tert-butoxycarbonylpiperazine (986 mg, 4.27 mmol) and the resulting mixture was stirred for 20 minutes and then concentrated under reduced pressure, and the solvent was removed azeotropically with ethanol. The resulting solid was washed with 2-propanol to give the title compound (694 mg) as a colorless solid. This compound was used in the next step without being purified.

Step 2: 5-{8-[(3S)-3-Ethylpiperazin-1-yl]-6-morpholin-4-yl-9-(2,2,2-trifluoroethyl)-9H-purin-2-yl}pyrimidin-2-amine

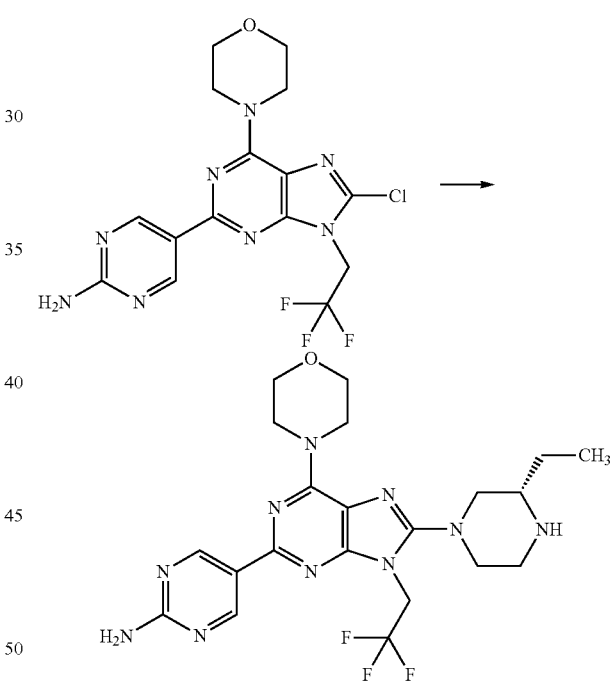

Diisopropylethylamine (1.48 ml, 8.49 mmol) was added to an N-methyl-2-pyrrolidone suspension (4 ml) of 2-(S)-ethylpiperazine 2 hydrochloride (529 mg, 2.83 mmol) and 2-(2-aminopyrimidin-5-yl)-8-chloro-6-(morpholin-4-yl)-9-(2,2,2-trifluoroethyl)-9H-purine (391 mg, 0.94 mmol) and the resulting mixture was stirred at 100° C. for 4 days. Water was added to the reaction mixture and the resulting mixture was extracted twice with ethyl acetate. The organic layers were combined, washed with water and saturated brine, and dried over anhydrous sodium sulfate, the mixture was filtrated, the filtrate was concentrated under reduced pressure, and the resulting residue was purified by silica gel chromatography (chloroform:methanol=97:3 to 90:10) to give the title compound (379 mg) as a pale yellow solid.

¹H-NMR (CDCl₃) δ: 0.98 (3H, t, J=7.45 Hz), 1.42-1.50 (2H, m), 2.71 (1H, t, J=10.86 Hz), 2.80-2.84 (1H, m), 3.05-3.13 (3H, m), 3.26-3.30 (2H, m), 3.84-3.88 (4H, m), 4.27-4.30 (4H, m), 4.69 (2H, q, J=8.38 Hz), 5.21 (2H, brs), 9.24 (2H, brs).

Example 75

5-{8-[(3S)-4-Acetyl-3-ethylpiperazin-1-yl]-6-morpholin-4-yl-9-(2,2,2-trifluoroethyl)-9H-purin-2-yl}pyrimidin-2-amine

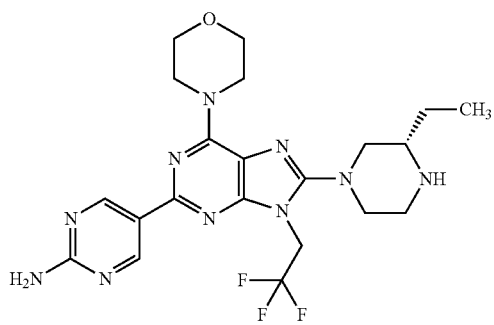

Acetic anhydride (0.035 ml, 0.38 mmol) was added dropwise to a methylene chloride solution (6 ml) of 5-{8-[(3S)-3-ethylpiperazin-1-yl]-6-morpholin-4-yl-9-(2,2,2-trifluoroethyl)-9H-purin-2-yl}pyrimidin-2-amine (123 mg, 0.25 mmol) and triethylamine (0.069 ml, 0.50 mmol) with ice cooling and the resulting mixture was stirred at room temperature for 1.5 hours. The resulting mixture was partitioned with ethyl acetate and saturated aqueous ammonium chloride solution and the organic layer was washed with saturated brine and dried over anhydrous sodium sulfate, the mixture was filtrated, the filtrate was concentrated under reduced pressure, and the resulting residue was purified by preparative thin layer silica gel chromatography (chloroform:methanol=95:5) to give the title compound (92 mg) as a pale yellow solid.

¹H-NMR (CDCl₃) δ: 0.92-1.00 (3H, m), 1.76-1.91 (2H, m), 2.16 (3H, s), 2.98-3.12 (2H, m), 3.25-3.30 (2H, m), 3.51-3.74 (2H, m) 3.84-3.86 (4H, m), 4.28-3.32 (4H, m), 4.64-4.80 (3H, m), 5.21 (2H, brs), 9.23 (2H, s).

¹H-NMR (DMSO-d₆, 100° C.) δ: 0.85 (3H, t, J=7.33 Hz), 1.71-1.90 (2H, m), 2.05 (3H, s), 2.81-2.99 (2H, m), 3.34-3.48 (2H, m), 3.73-3.76 (4H, m), 4.17-4.19 (4H, m), 4.92-5.01 (2H, m), 6.66 (2H, brs), 9.07 (2H, s).

Example 76

5-{8-[(3S)-3-Ethyl-4-(methylsulfonyl)piperazin-1-yl]-6-morpholin-4-yl-9-(2,2,2-trifluoroethyl)-9H-purin-2-yl}pyrimidin-2-amine

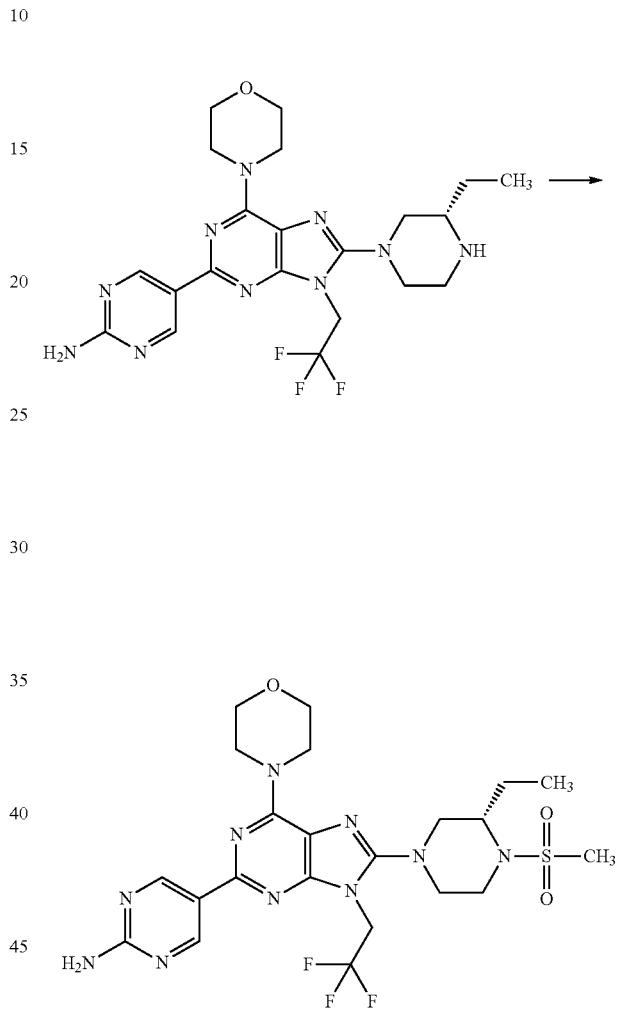

Methanesulfonyl chloride (0.022 ml, 0.28 mmol) was added dropwise to a methylene chloride solution (6 ml) of 5-{8-[(3S)-3-ethylpiperazin-1-yl]-6-morpholin-4-yl-9-(2,2,2-trifluoroethyl)-9H-purin-2-yl}pyrimidin-2-amine (107 mg, 0.22 mmol) and triethylamine (0.061 ml, 0.44 mmol) with ice cooling and the resulting mixture was stirred at the same temperature for 2 hours. The resulting mixture was partitioned with ethyl acetate and saturated aqueous ammonium chloride solution and the organic layer was washed with saturated brine and dried over anhydrous sodium sulfate, the mixture was filtrated, the filtrate was concentrated under reduced pressure, and the resulting residue was purified by preparative thin layer silica gel chromatography (chloroform:methanol=95:5) to give the title compound (86 mg) as a pale yellow solid.

¹H-NMR (CDCl₃) δ: 1.01 (3H, t, J=7.45 Hz), 1.81-1.89 (1H, m), 1.98-2.05 (1H, m), 2.98 (3H, s), 3.14 (1H, td, J=12.21, 3.17 Hz), 3.21-3.26 (3H, m), 3.39-3.46 (1H, m), 3.83 (5H, m), 3.96 (1H, t, J=7.57 Hz), 4.28 (4H, brs), 4.71 (2H, q, J=8.30 Hz), 5.21 (2H, brs), 9.23 (2H, s).

Example 77

(2S)-1-{(2S)-4-[2-(2-Aminopyrimidin-5-yl)-6-morpholin-4-yl-9-(2,2,2-trifluoroethyl)-9H-purin-8-yl]-2-ethylpiperazin-1-yl}-1-oxopropan-2-ol

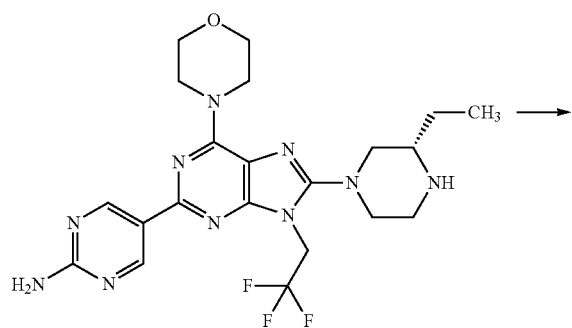

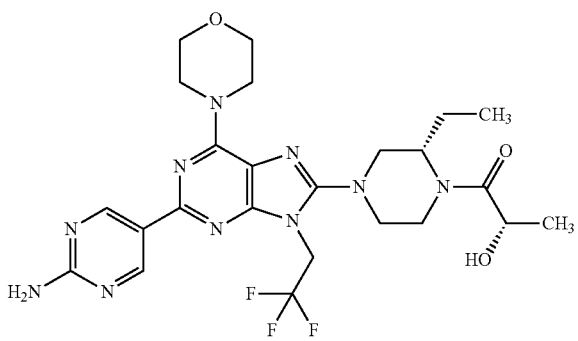

1-Ethyl-3-(3-dimethylaminopropyl)-carbodiimide hydrochloride (80 mg, 0.42 mmol) was added to an N,N-dimethylformamide solution (5 ml) of 5-{8-[(3S)-3-ethylpiperazin-1-yl]-6-morpholin-4-yl-9-(2,2,2-trifluoroethyl)-9H-purin-2-yl}pyrimidin-2-amine (136 mg, 0.28 mmol), triethylamine (0.096 ml, 0.69 mmol), L-lactic acid (30 mg, 0.33 mmol), and 1-hydroxybenzotriazole (47 mg, 0.30 mmol) and the resulting mixture was stirred at room temperature for 16 hours. The resulting mixture was partitioned with ethyl acetate and saturated aqueous ammonium chloride solution and the organic layer washed with water and saturated brine and dried over anhydrous sodium sulfate, the mixture was filtrated, the filtrate was concentrated under reduced pressure, and the resulting residue was purified by preparative thin layer silica gel chromatography (chloroform:methanol=95:10) to give the title compound (31 mg) as a pale yellow solid.

$^1$H-NMR (CDCl$_3$) δ: 0.94-1.02 (3H, m), 1.40-1.51 (3H, m), 1.75-2.03 (2H, m), 3.01-3.34 (4H, m), 3.50-3.86 (7H, m), 4.27-4.54 (5H, m), 4.63-4.80 (3H, m), 5.24 (2H, brs), 9.23 (2H, s).

$^1$H-NMR (DMSO-d$_6$, 60° C.) δ: 0.85 (3H, t, J=7.57 Hz), 1.24 (3H, d, J=6.59 Hz), 1.69-1.93 (2H, m), 2.72-3.12 (2H, m), 3.28-3.57 (3H, m), 3.68-3.82 (5H, m), 3.96-4.55 (8H, m), 4.79-5.22 (3H, m), 6.84 (2H, s), 9.08 (2H, s).

Example 78

5-{8-[(3R)-3-Ethylpiperazin-1-yl]-6-morpholin-4-yl-9-(2,2,2-trifluoroethyl)-9H-purin-2-yl}pyrimidin-2-amine

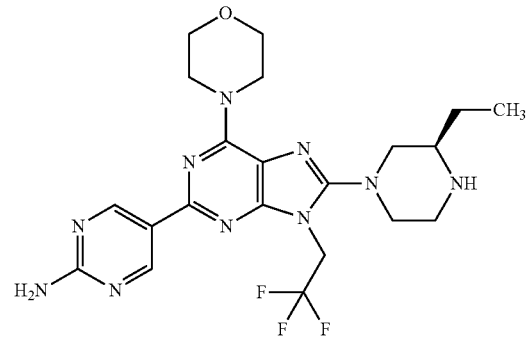

Step 1: 2-(R)-Ethylpiperazine 2 hydrochloride

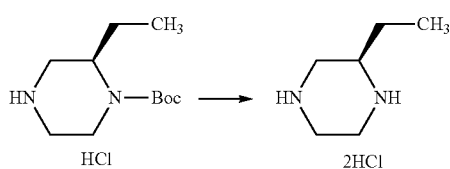

Concentrated hydrochloric acid (3 ml) was added to 2-(R)-ethyl-1-tert-butoxycarbonylpiperazine (918 mg, 3.66 mmol), the resulting mixture was stirred for 20 minutes and concentrated under reduced pressure, the solvent was removed azeotropically with ethanol, and the resulting solid was washed with 2-propanol to give the title compound (751 mg) as a colorless solid. This compound was used in the next step without being purified.

Step 2: 5-{8-[(3R)-3-Ethylpiperazin-1-yl]-6-morpholin-4-yl-9-(2,2,2-trifluoroethyl)-9H-purin-2-yl}pyrimidin-2-amine

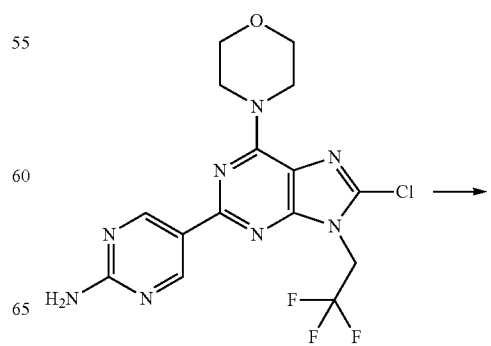

-continued

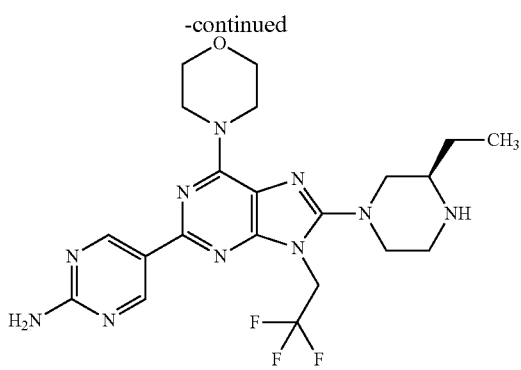

Diisopropylethylamine (1.91 ml, 10.98 mmol) was added to an N-methyl-2-pyrrolidone suspension (5 ml) of 2-(R)-ethylpiperazine-2-hydrochloride (751 mg) and 2-(2-aminopyrimidin-5-yl)-8-chloro-6-(morpholin-4-yl)-9-(2,2,2-trifluoroethyl)-9H-purine (506 mg, 1.22 mmol) and the resulting mixture was heated at 100° C. and stirred for 5 days. Water was added to the reaction mixture and the resulting mixture was extracted twice with ethyl acetate. The organic layers were combined, washed with water and saturated brine, and dried over anhydrous sodium sulfate, the mixture was filtrated, the filtrate was concentrated under reduced pressure, and the resulting residue was purified by silica gel chromatography (chloroform:methanol=97:3 to 90:10) to give the title compound (562 mg) as a pale yellow solid.

$^1$H-NMR (CDCl$_3$) δ: 0.98 (3H, t, J=7.45 Hz), 1.42-1.50 (2H, m), 2.71 (1H, t, J=10.86 Hz), 2.80-2.84 (1H, m), 3.05-3.13 (3H, m), 3.26-3.30 (2H, m), 3.86 (4H, m), 4.27-4.30 (4H, m), 4.69 (2H, q, J=8.38 Hz), 5.21 (2H, brs), 9.24 (2H, s).

Example 79

(2S)-1-{(2R)-4-[(2-(2-Aminopyrimidin-5-yl)-6-morpholin-4-yl-9-(2,2,2-trifluoroethyl)-9H-purin-8-yl]-2-ethylpiperazin-1-yl}-1-oxopropan-2-ol

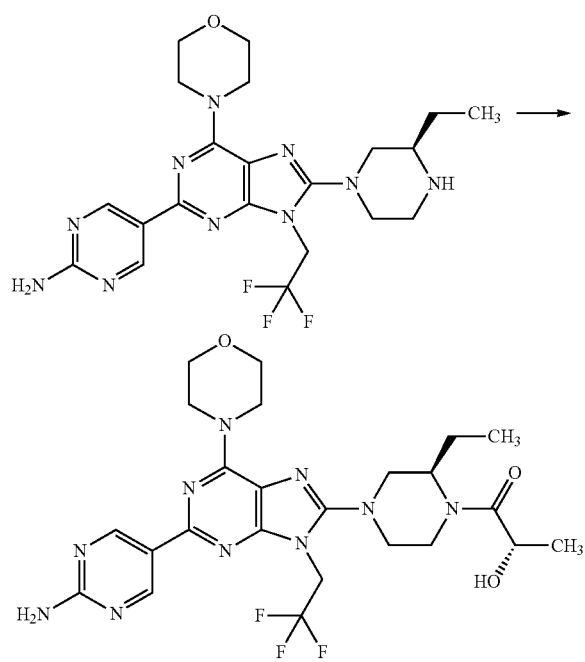

1-Ethyl-3-(3-dimethylaminopropyl)-carbodiimide hydrochloride (72.4 mg, 0.38 mmol) was added to an N,N-dimethylformamide solution (5 ml) of 5-{8-[(3R)-3-ethylpiperazin-1-yl]-6-morpholin-4-yl-9-(2,2,2-trifluoroethyl)-9H-purin-2-yl}pyrimidin-2-amine (124 mg, 0.25 mmol), triethylamine (0.087 ml, 0.63 mmol), L-lactic acid (27.2 mg, 0.30 mmol), and 1-hydroxybenzotriazole (42.6 mg, 0.28 mmol), the resulting mixture was stirred at room temperature for 17 hours followed by the addition of 1-ethyl-3-(3-dimethylaminopropyl)-carbodiimide hydrochloride (72.4 mg, 0.38 mmol), and the resulting mixture was stirred at 40° C. for 8 hours. The resulting mixture was partitioned with ethyl acetate and water and the organic layer was washed with water and saturated brine and dried over anhydrous sodium sulfate, the mixture was filtrated, the filtrate was concentrated under reduced pressure, and the resulting residue was purified by preparative thin layer silica gel chromatography (chloroform:methanol=90:10) to give the title compound (38.9 mg) as a pale yellow solid.

$^1$H-NMR (CDCl$_3$) δ: 0.89-1.02 (3H, m), 1.40-1.51 (3H, m), 1.49-1.69 (2H, m), 3.17-3.31 (4H, m), 3.61-3.89 (7H, m), 4.25-4.38 (4H, m), 4.50-4.58 (1H, m), 4.67-4.79 (3H, m), 5.19 (2H, s), 9.23 (2H, s).

$^1$H-NMR (DMSO-d$_6$, 60° C.) δ: 0.81-0.83 (3H, m), 1.18-1.23 (3H, m), 1.62-1.93 (2H, m), 2.66-3.17 (3H, m), 3.36-3.49 (3H, m), 3.73-3.75 (4H, m), 3.89-4.31 (4H, m), 4.48-4.74 (3H, m), 4.95-5.08 (2H, m), 6.87 (2H, s), 9.08 (2H, s)

Example 80

4-{4-[2-(2-Aminopyrimidin-5-yl)-9-isobutyl-6-morpholin-4-yl-9H-purin-8-yl]piperazin-1-yl}-2-methyl-4-oxobutan-2-ol

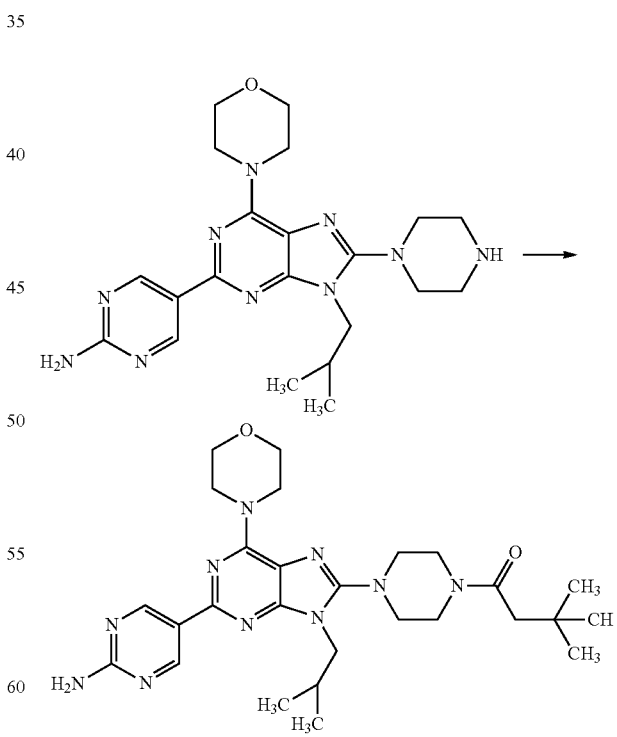

5-(9-Isobutyl-6-morpholin-4-yl-8-piperazin-1-yl-9H-purin-2-yl)pyrimidin-2-amine (150 mg, 0.33 mmol), 1-ethyl-3-(3-dimethylaminopropyl)-carbodiimide hydrochloride (128 mg, 0.67 mmol), 1-hydroxybenzotriazole (45 mg, 0.33 mmol), and 3-hydroxy-3-methylbutanoic acid (79 mg, 0.67 mmol) were dissolved in dimethylformamide (5 ml) and the resulting mixture was stirred for 16 hours. The solvent was evaporated under reduced pressure and the residue was purified by preparative HPLC (column, NOMURA Develosil Combi-RP-5; mobile phase, acetonitrile/water/formic acid) to give the title compound (120 mg, 67%) as a white solid.

$^1$H-NMR (CDCl$_3$) δ: 0.88 (3H, s), 0.90 (3H, s), 1.32 (6H, s), 2.46-2.50 (3H, m), 3.22-3.27 (4H, m), 3.66-3.67 (2H, m), 3.82-3.87 (6H, m), 3.92 (2H, d, J=7.6 Hz), 4.28 (4H, brs), 4.99 (1H, s), 5.23 (2H, s), 9.24 (2H, s).

Example 81

(2R)-4-{4-[2-(2-Aminopyrimidin-5-yl)-9-isobutyl-6-morpholin-4-yl-9H-purin-8-yl]piperazin-1-yl}-4-oxobutan-2-ol

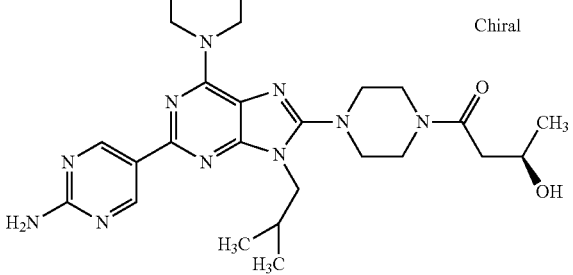

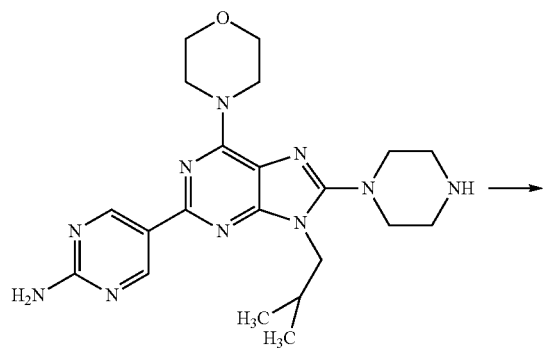

5-(9-Isobutyl-6-morpholin-4-yl-8-piperazin-1-yl-9H-purin-2-yl)pyrimidin-2-amine (150 mg, 0.33 mmol), 1-ethyl-3-(3-dimethylaminopropyl)-carbodiimide hydrochloride (128 mg, 0.67 mmol), 1-hydroxybenzotriazole (45 mg, 0.33 mmol), and (R)-3-hydroxybutyric acid (70 mg, 0.67 mmol) were dissolved in dimethylformamide (5 ml) and the resulting mixture was stirred for 16 hours. The solvent was evaporated under reduced pressure and then the residue was purified by preparative HPLC (column, NOMURA Develosil Combi-RP-5; mobile phase, acetonitrile/water/formic acid) to give the title compound (62 mg, 36%) as a white solid.

$^1$H-NMR (CDCl$_3$) δ: 0.89 (6H, d, J=6.59 Hz), 1.26 (3H, d, J=6.35 Hz), 2.34-2.57 (3H, m), 3.18-3.24 (2H, m), 3.24-3.30 (2H, m), 3.61-3.67 (2H, m), 3.74-3.88 (6H, m), 3.92 (2H, d, J=7.32 Hz), 4.21-4.33 (5H, m), 5.24 (2H, s), 9.24 (2H, s).

Example 82

(2S)-4-{4-[2-(2-Aminopyrimidin-5-yl)-9-isobutyl-6-morpholin-4-yl-9H-purin-8-yl]piperazin-1-yl}-4-oxobutan-2-ol

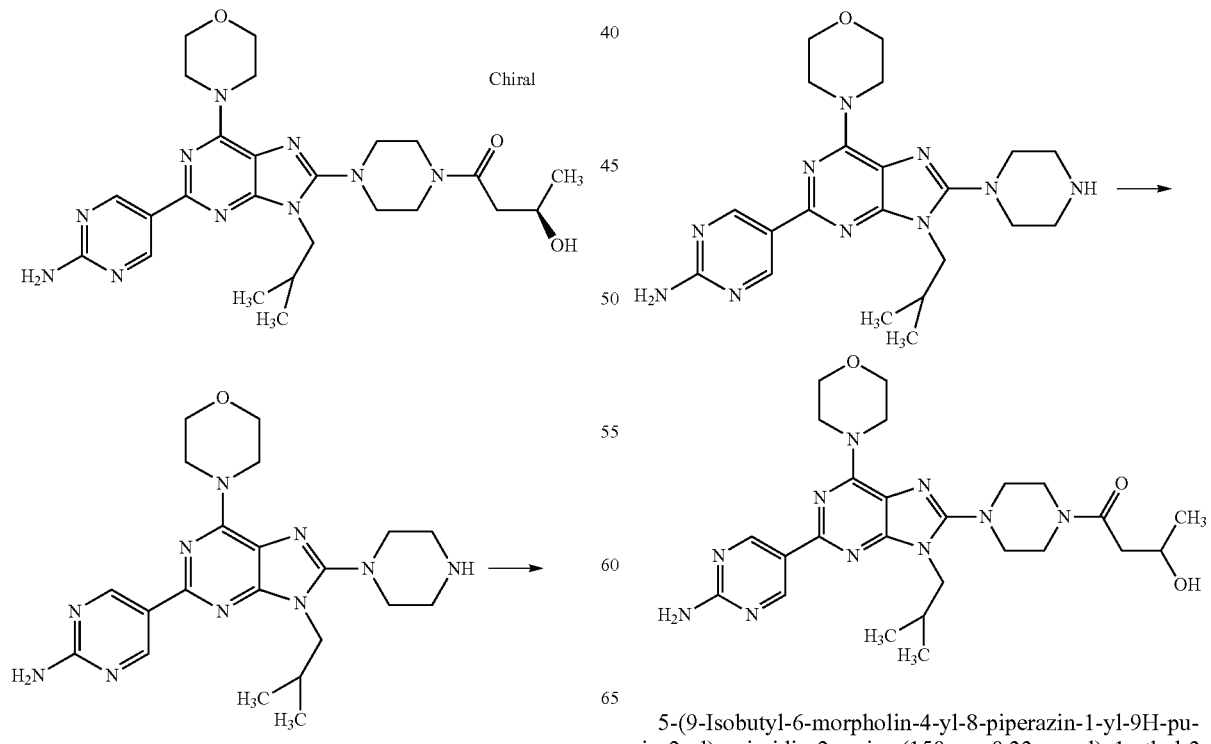

5-(9-Isobutyl-6-morpholin-4-yl-8-piperazin-1-yl-9H-purin-2-yl)pyrimidin-2-amine (150 mg, 0.33 mmol), 1-ethyl-3-

(3-dimethylaminopropyl)-carbodiimide hydrochloride (128 mg, 0.67 mmol), 1-hydroxybenzotriazole (45 mg, 0.33 mmol), and (S)-3-hydroxybutyric acid (70 mg, 0.67 mmol) were dissolved in dimethylformamide (5 ml) and the resulting mixture was stirred for 16 hours. The solvent was evaporated under reduced pressure and then the residue was purified by preparative HPLC (column, NOMURA Develosil Combi-RP-5; mobile phase, acetonitrile/water/formic acid) to give the title compound (97 mg, 56%) as a white solid.

$^1$H-NMR (CDCl$_3$) δ: 0.88 (3H, s), 0.90 (3H, s), 1.26 (3H, d, J=6.3 Hz), 2.35-2.56 (3H, m), 3.21 (2H, t, J=5.0 Hz), 3.26 (2H, t, J=5.0 Hz), 3.64 (2H, t, J=5.0 Hz), 3.81-3.85 (6H, m), 3.92 (2H, d, J=7.6 Hz), 4.25-4.28 (5H, m), 5.22 (2H, s), 9.24 (2H, s).

Example 83

(2R)-4-{(2S)-4-[2-(2-Aminopyrimidin-5-yl)-9-isobutyl-6-morpholin-4-yl-9H-purin-8-yl]-2-methylpiperazin-1-yl}-4-oxobutan-2-ol

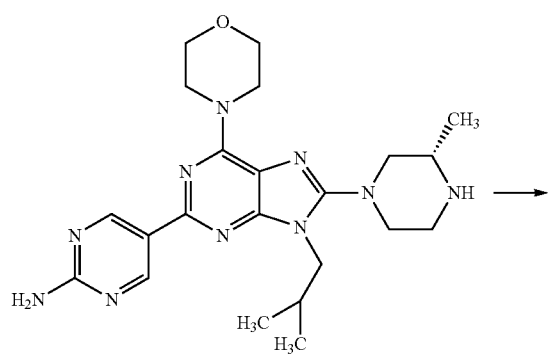

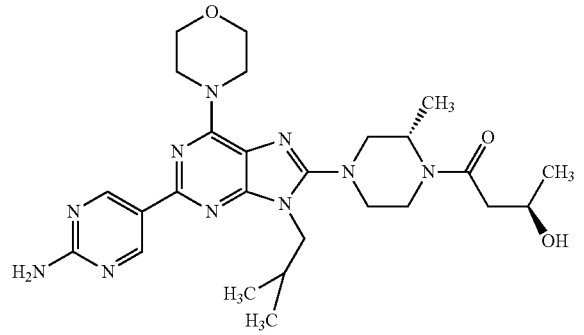

5-{9-Isobutyl-8-[(3S)-3-methylpiperazin-1-yl]-6-morpholin-4-yl-9H-purin-2-yl}pyrimidin-2-amine (150 mg, 0.33 mmol), dicyclohexylcarbodiimide (103 mg, 0.5 mmol), 1-hydroxybenzotriazole (45 mg, 0.33 mmol), and (R)-3-hydroxybutyric acid (70 mg, 0.67 mmol) were dissolved in dimethylformamide (5 ml) and the resulting mixture was stirred at 40° C. for 16 hours. The solvent was evaporated under reduced pressure and then the residue was purified by preparative HPLC (column, NOMURA Develosil Combi-RP-5; mobile phase, acetonitrile/water/formic acid) to give the title compound (50 mg, 28%) as a white solid.

$^1$H-NMR (CDCl$_3$) δ: 0.90 (6H, t, J=6.6 Hz), 1.24-1.27 (3H, m), 1.39 (1.5H, d, J=6.8 Hz), 1.47 (1.5H, d, J=6.8 Hz), 2.27-2.57 (4H, m), 3.01-3.15 (3H, m), 3.29 (1H, d, J=12.2 Hz), 3.42 (1H, d, J=12.2 Hz), 3.54-3.56 (0.5H, m), 3.69-3.71 (0.5H, m), 3.84-3.96 (6H, m), 4.18-4.27 (6H, m), 4.58-4.61 (0.5H, m), 4.92-4.95 (0.5H, m), 5.67 (2H, s), 9.22 (2H, s).

Example 84

(2R)-4-{(2R)-4-[2-(2-Aminopyrimidin-5-yl)-9-isobutyl-6-morpholin-4-yl-9H-purin-8-yl]-2-methylpiperazin-1-yl}-4-oxobutan-2-ol

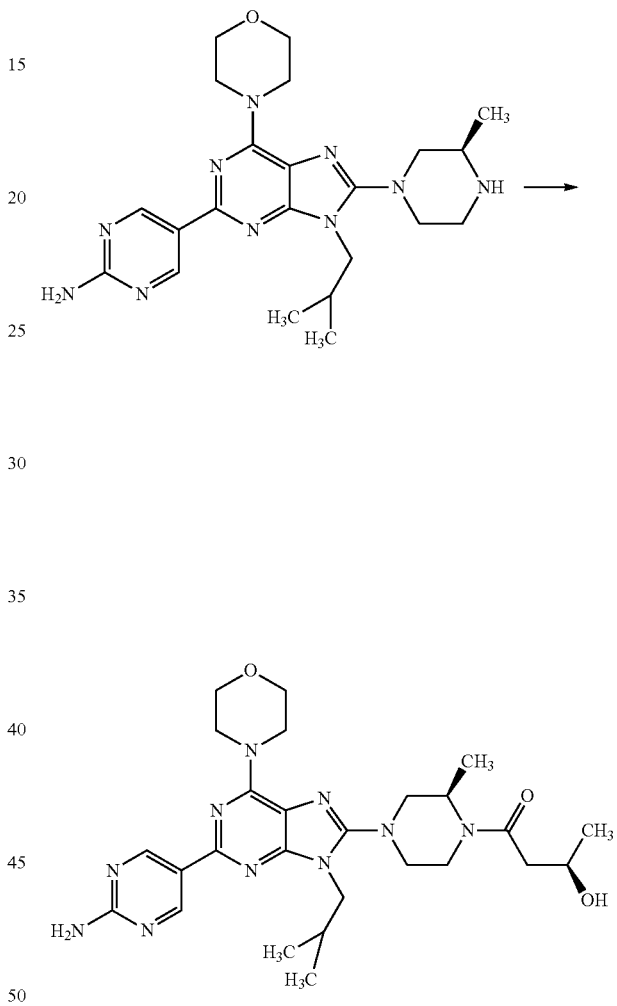

5-{9-Isobutyl-8-[(3R)-3-methylpiperazin-1-yl]-6-morpholin-4-yl-9H-purin-2-yl}pyrimidin-2-amine (150 mg, 0.33 mmol), dicyclohexylcarbodiimide (103 mg, 0.5 mmol), 1-hydroxybenzotriazole (45 mg, 0.33 mmol), and (R)-3-hydroxybutyric acid (70 mg, 0.67 mmol) were dissolved in dimethylformamide (5 ml) and the resulting mixture was stirred at 40° C. for 16 hours. The solvent was evaporated under reduced pressure and then the residue was purified by preparative HPLC (column, NOMURA Develosil Combi-RP-5; mobile phase, acetonitrile/water/formic acid) to give the title compound (90 mg, 50%) as a white solid.

$^1$H-NMR (CDCl$_3$) δ: 0.90 (6H, t, J=6.6 Hz), 1.24-1.27 (3H, m), 1.40 (1.5H, d, J=6.8 Hz), 1.48 (1.5H, d, 6.8 Hz), 2.32-2.64 (4H, m), 2.96-3.20 (3H, m), 3.27 (1H, d, J=12.2 Hz), 3.42 (1H, d, J=12.2 Hz), 3.54-3.56 (0.5H, m), 3.69-3.71 (0.5H, m), 3.84-3.96 (6H, m), 4.18-4.27 (6H, m), 4.58-4.61 (0.5H, m), 4.92-4.95 (0.5H, m), 5.64 (2H, s), 9.22 (2H, s).

Example 85

(2S)-4-{(2S)-4-[2-(2-Aminopyrimidin-5-yl)-9-isobutyl-6-morpholin-4-yl-9H-purin-8-yl]-2-methylpiperazin-1-yl}-4-oxobutan-2-ol

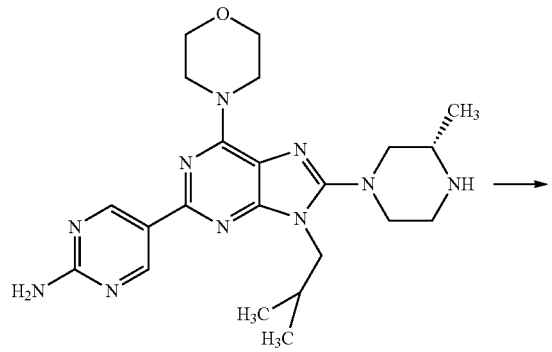

(0.5H, m), 3.84-3.96 (6H, m), 4.18-4.27 (6H, m), 4.58-4.61 (0.5H, m), 4.92-4.95 (0.5H, m), 5.49 (2H, s), 9.23 (2H, s).

Example 86

(2S)-4-{(2R)-4-[2-(2-Aminopyrimidin-5-yl)-9-isobutyl-6-morpholin-4-yl-9H-purin-8-yl]-2-methylpiperazin-1-yl}-4-oxobutan-2-ol

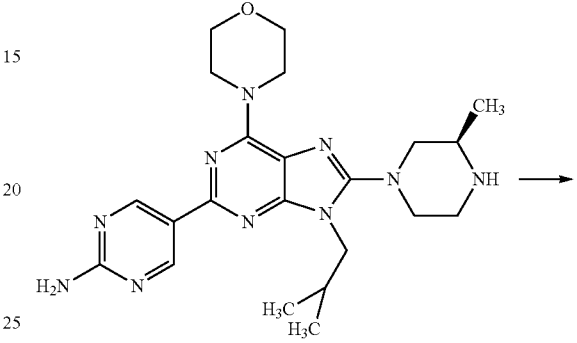

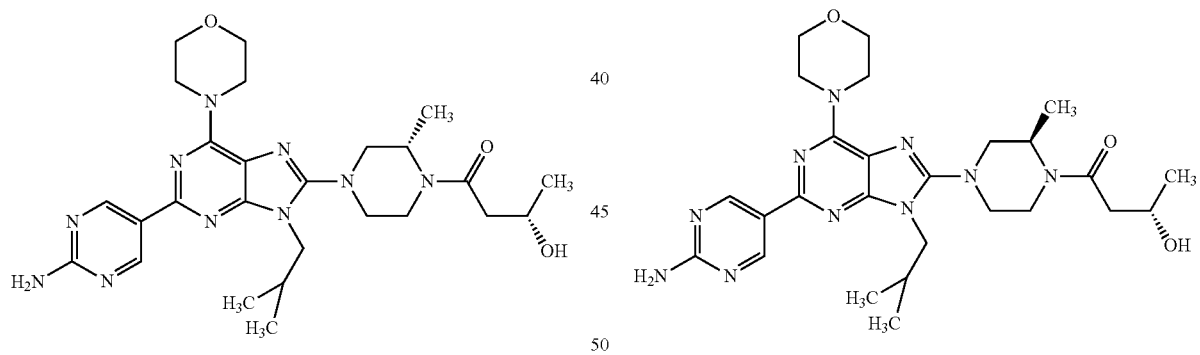

5-{9-Isobutyl-8-[(3S)-3-methylpiperazin-1-yl]-6-morpholin-4-yl-9H-purin-2-yl}pyrimidin-2-amine (230 mg, 0.5 mmol), dicyclohexylcarbodiimide (160 mg, 0.77 mmol), 1-hydroxybenzotriazole (70 mg, 0.51 mmol), and (S)-3-hydroxybutyric acid (107 mg, 1.0 mmol) were dissolved in dimethylformamide (5 ml) and the resulting mixture was stirred at 40° C. for 16 hours. The solvent was evaporated under reduced pressure and then the residue was purified by preparative HPLC (column, NOMURA Develosil Combi-RP-5; mobile phase, acetonitrile/water/formic acid) to give the title compound (131 mg, 48%) as a white solid.

$^1$H-NMR (CDCl$_3$) δ: 0.90 (6H, t, J=6.6 Hz), 1.24-1.27 (3H, m), 1.40 (1.5H, d, J=6.8 Hz), 1.48 (1.5H, d, J=6.8 Hz), 2.28-2.64 (4H, m), 3.01-3.15 (3H, m), 3.27 (1H, d, J=12.2 Hz), 3.42 (1H, d, J=12.2 Hz), 3.54-3.56 (0.5H, m), 3.72-3.74

5-{9-Isobutyl-8-[(3R)-3-methylpiperazin-1-yl]-6-morpholin-4-yl-9H-purin-2-yl}pyrimidin-2-amine (230 mg, 0.5 mmol), dicyclohexylcarbodiimide (160 mg, 0.77 mmol), 1-hydroxybenzotriazole (70 mg, 0.51 mmol), and (S)-3-hydroxybutyric acid (107 mg, 1.0 mmol) were dissolved in dimethylformamide (5 ml) and the resulting mixture was stirred at 40° C. for 16 hours. The solvent was evaporated under reduced pressure and then the residue was purified by preparative HPLC (column, NOMURA Develosil Combi-RP-5; mobile phase, acetonitrile/water/formic acid) to give the title compound (167 mg, 61%) as a white solid.

$^1$H-NMR (CDCl$_3$) δ: 0.90 (6H, t, J=6.6 Hz), 1.24-1.27 (3H, m), 1.39 (1.5H, d, J=6.8 Hz), 1.47 (1.5H, d, J=6.8 Hz)/2.27-2.57 (4H, m), 2.96-3.20 (3H, m), 3.29 (1H, d, J=12.2 Hz), 3.42 (1H, d, J=12.2 Hz), 3.54-3.56 (0.5H, m), 3.71-3.74

(0.5H, m), 3.84-3.96 (6H, m), 4.18-4.27 (6H, m), 4.58-4.61 (0.5H, m), 4.92-4.95 (0.5H, m), 5.50 (2H, s), 9.22 (2H, s).

Example 87

N,N-Dimethyl-2-[(2R)-2-methyl-4-{2-[2-(methylamino)pyrimidin-5-yl]-6-morpholin-4-yl-9-(2,2,2-trifluoroethyl)-9H-purin-8-yl}piperazin-1-yl]acetamide

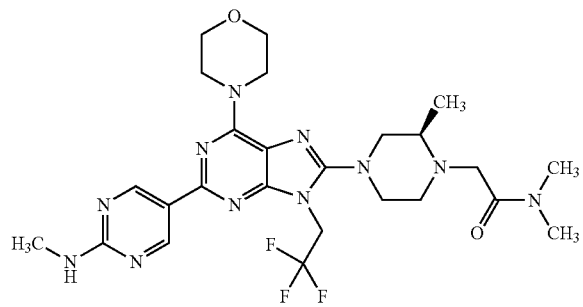

$^1$H-NMR (CDCl$_3$) δ: 1.16 (3H, d, J=6.1 Hz), 2.76 (1H, s), 2.92-2.94 (3H, m), 2.97 (3H, s), 3.08 (3H, d, J=7.0 Hz), 3.13 (3H, s), 3.18-3.25 (4H, m), 3.63 (0.5H, s), 3.67 (0.5H, s), 3.84 (4H, t, J=4.8 Hz), 4.27 (4H, brs), 4.64-4.71 (2H, m), 5.30-5.31 (1H, m), 9.25 (2H, s).

Example 88

(2S)-1-{4-[2-(2-Aminopyrimidin-5-yl)-9-(cyclopropylmethyl)-6-morpholin-4-yl-9H-purin-8-yl]piperazin-1-yl}-1-oxopropan-2-ol

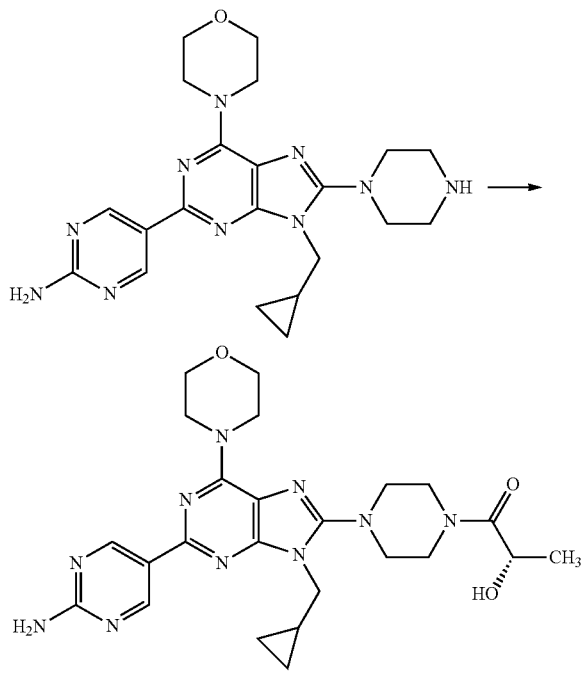

L-Lactic acid (25.2 μl, 0.29 mmol), 1-hydroxybenzotriazole monohydrate (36.7 mg, 0.24 mmol), 1-ethyl-3-(3-dimethylaminopropyl)-carbodiimide hydrochloride (68.8 mg, 0.36 mmol), and triethylamine (50.1 μl, 0.36 mmol) were added to an N,N-dimethylformamide suspension (2.0 ml) of 5-[9-(cyclopropylmethyl)-6-morpholin-4-yl-8-piperazin-1-yl-9H-purin-2-yl]pyrimidin-2-amine (104.5 mg, 0.24 mmol) at room temperature. The resulting mixture was stirred for 17 hours and then the reaction mixture was poured into methylene chloride-methanol (10:1), washed with saturated aqueous sodium hydrogencarbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (80.1 mg, 66%) as a pale yellow solid.

$^1$H-NMR (CDCl$_3$) δ: 0.50-0.59 (4H, m), 1.30-1.37 (1H, m), 1.39 (3H, d, J=6.87 Hz), 1.93-2.11 (1H, m), 3.24-3.37 (4H, m), 3.60-3.67 (2H, m), 3.81-3.93 (6H, m), 3.98 (2H, d, J=7.45 Hz), 4.22-4.33 (4H, brm), 4.49-4.57 (1H, m), 5.50 (2H, s), 9.23 (2H, s).

Example 89

2-{4-[2-(2-Aminopyrimidin-5-yl)-9-isobutyl-6-morpholin-4-yl-9H-purin-8-yl]piperazin-1-yl}-2-oxoethanol

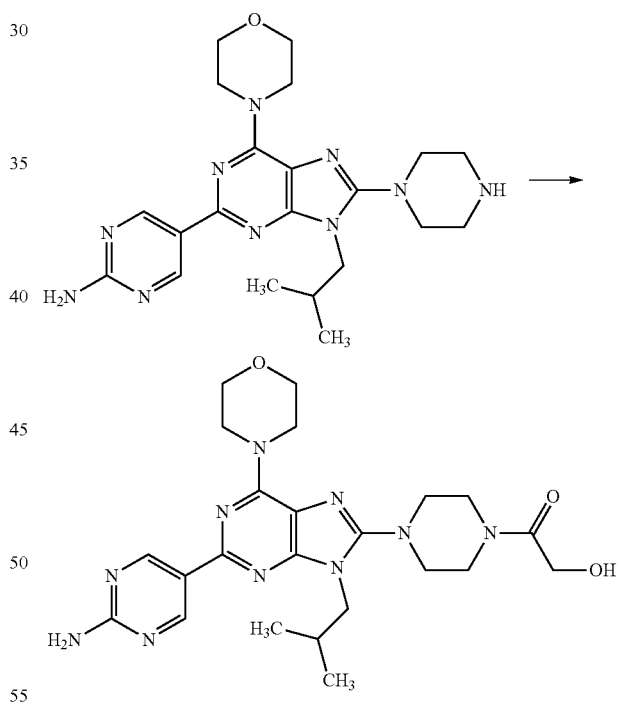

1-Hydroxybenzotriazole monohydrate (37.9 mg, 0.25 mmol), 1-ethyl-3-(3-dimethylaminopropyl)-carbodiimide hydrochloride (71.2 mg, 0.37 mmol), and triethylamine (51.7 μl, 0.37 mmol) were added to an N,N-dimethylformamide suspension (2.0 ml) of 5-[9-(isobutyl)-6-morpholin-4-yl-8-piperazin-1-yl-9H-purin-2-yl]pyrimidin-2-amine (108.5 mg, 0.25 mmol) and glycolic acid (22.6 mg, 0.30 mmol) at room temperature. The resulting mixture was stirred for 21 hours and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (89.2 mg, 73%) as a pale yellow solid.

$^1$H-NMR (CDCl$_3$) δ: 0.89 (6H, d, J=6.88 Hz), 2.41-2.53 (1H, m), 3.21-3.32 (4H, m), 3.44-3.52 (2H, m), 3.65-3.76 (1H, m), 3.82-3.89 (6H, m), 3.92 (2H, d, J=7.34 Hz), 4.20-4.33 (6H, m), 5.38 (2H, s), 9.23 (2H, s).

Example 90

4-[2-(2-Aminopyrimidin-5-yl)-9-isobutyl-6-morpholin-4-yl-9H-purin-8-yl]piperazine-1-carboaldehyde

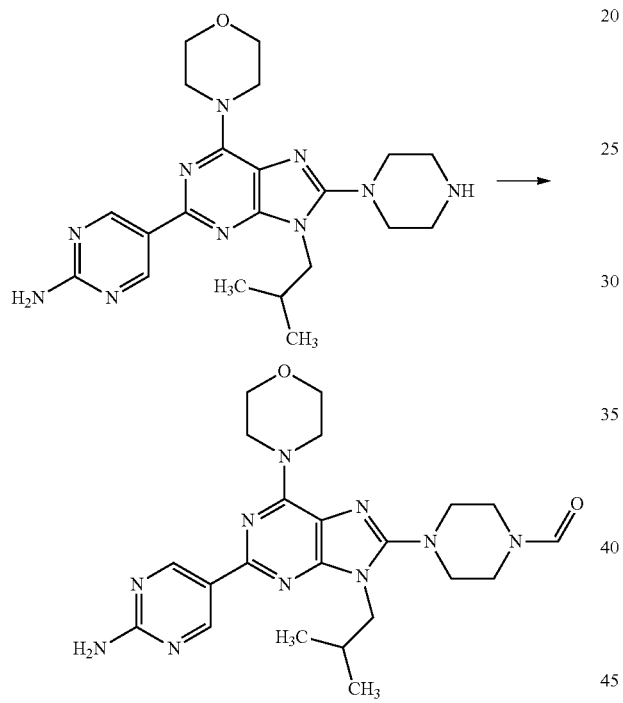

5-[9-(Isobutyl)-6-morpholin-4-yl-8-piperazin-1-yl-9H-purin-2-yl]pyrimidin-2-amine (129.8 mg, 0.30 mmol) was added to a tetrahydrofuran solution (7.0 ml) of 1H-benzotriazole-1-carboxyaldehyde (48.4 mg, 0.30 mmol) at room temperature and the resulting mixture was stirred for 75 minutes. Methylene chloride was added to the reaction mixture and the resulting mixture was poured into 2 N aqueous sodium hydroxide solution and extracted with methylene chloride-methanol (10:1). The organic layer was dried over anhydrous sodium sulfate, the mixture was filtrated, the filtrate was concentrated under reduced pressure, and the resulting residue was purified by medium pressure silica gel column chromatography (methylene chloride:methanol=49:1 to 32:1) to give the title compound (103.4 mg, 75%) as a pale yellow solid.

$^1$H-NMR (CDCl$_3$) δ: 0.89 (6H, d, J=6.88 Hz), 2.42-2.54 (1H, m), 3.18-3.24 (2H, m), 3.25-3.31 (2H, m), 3.54-3.61 (2H, m), 3.71-3.78 (2H, m), 3.82-3.88 (4H, m), 3.92 (2H, d, J=7.34 Hz), 4.20-4.35 (4H, brm), 5.32 (2H, s), 8.13 (1H, s), 9.24 (2H, s).

Example 91

5-{9-(Cyclopropylmethyl)-8-[(3S)-3-methylpiperazin-1-yl]-6-morpholin-4-yl-9H-purin-2-yl}pyrimidin-2-amine

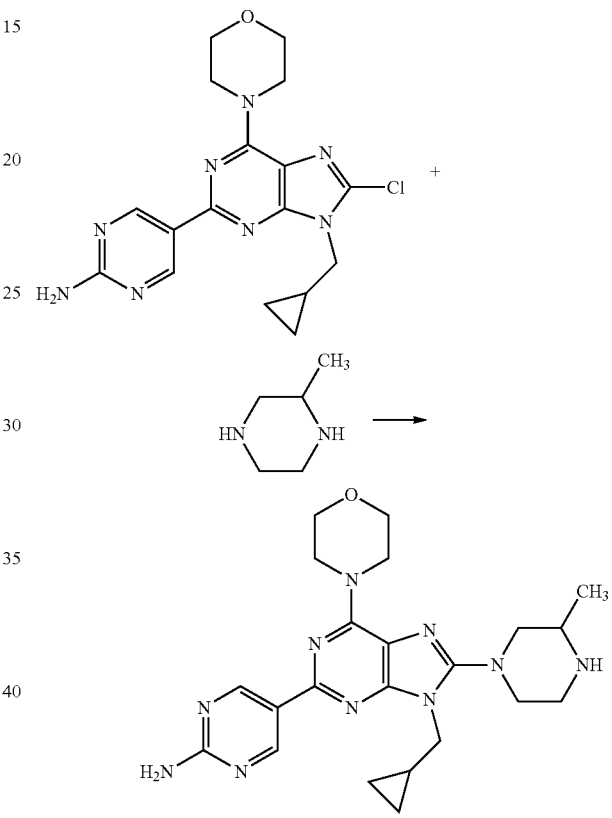

A dimethyl sulfoxide suspension (5 ml) of 5-[8-chloro-9-(cyclopropylmethyl)-6-morpholin-4-yl-9H-purin-2-yl]pyrimidin-2-amine (476.1 mg, 1.23 mmol) and (2S)-2-methylpiperazine (616.4 mg, 6.15 mmol) was heated at 100° C. to dissolve and the resulting mixture was stirred at 85° C. for 18.5 hours. (2S)-2-Methylpiperazine (123.3 mg, 1.23 mmol) was added and the resulting mixture was further stirred at 85° C. for 5.5 hours, left standing to cool, poured into methylene chloride-methanol (10:1), and washed with saturated aqueous sodium hydrogen carbonate solution. The organic layer was dried over anhydrous sodium sulfate, the mixture was filtrated, the filtrate was concentrated under reduced pressure, and the resulting residue was purified by medium pressure silica gel column chromatography (methylene chloride:methanol=32:1 to 9:1) to give the title compound (516.0 mg, 93%) as a pale yellow solid.

$^1$H-NMR (CDCl$_3$) δ: 0.48-0.57 (4H, m), 1.15 (3H, d, J=6.87 Hz), 1.31-1.41 (1H, m), 2.71 (1H, t, J=11.17 Hz), 2.98-3.15 (4H, m), 3.36-3.45 (2H, m), 3.83-3.89 (4H, m), 3.90-4.02 (2H, m), 4.18-4.41 (4H, brm), 5.60 (2H, brs), 9.24 (2H, s).

Example 92

(2S)-1-{(2S)-4-[2-(2-Aminopyrimidin-5-yl)-9-(cyclopropylmethyl)-6-morpholin-4-yl-9H-purin-8-yl]-2-methylpiperazin-1-yl}-1-oxopropan-2-ol

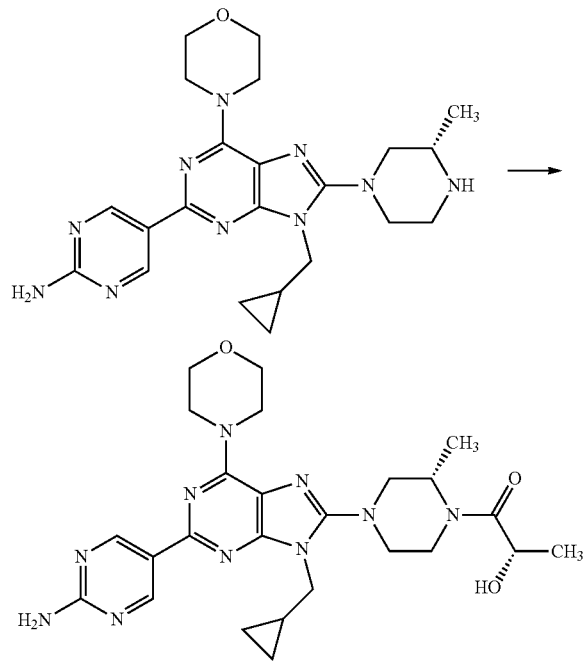

L-Lactic acid (27.1 μl, 0.31 mmol), 1-hydroxybenzotriazole monohydrate (39.3 mg, 0.26 mmol), 1-ethyl-3-(3-dimethylaminopropyl)-carbodiimide hydrochloride (73.8 mg, 0.38 mmol), and triethylamine (53.6 μl, 0.38 mmol) were added to an N,N-dimethylformamide solution (2.0 ml) of 5-{9-(cyclopropylmethyl)-8-[(3S)-3-methylpiperazin-1-yl]-6-morpholin-4-yl-9H-purin-2-yl}pyrimidin-2-amine (115.6 mg, 0.26 mmol) at room temperature. The resulting mixture was stirred for 20 hours followed by the addition of L-lactic acid (27.1 μl, 0.31 mmol), 1-ethyl-3-(3-dimethylaminopropyl)-carbodiimide hydrochloride (73.8 mg, 0.38 mmol), and triethylamine (53.6 μl, 0.38 mmol) and the resulting mixture was stirred for 3 days. L-Lactic acid (27.1 μl, 0.31 mmol), 1-ethyl-3-(3-dimethylaminopropyl)-carbodiimide hydrochloride (73.8 mg, 0.38 mmol), and triethylamine (53.6 μl, 0.38 mmol) were further added, the resulting mixture was stirred for 2 days, and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (double development with methylene chloride:methanol=15:1) to give the title compound (89.7 mg, 67%) as a pale yellow solid.

$^1$H-NMR (DMSO-$d_6$, 80° C.) δ: 0.45-0.53 (4H, m), 1.24 (3H, d, J=6.41 Hz), 1.30-1.44 (4H, m), 2.85-2.95 (1H, m), 3.02-3.13 (1H, m), 3.29-3.45 (2H, m), 3.47-3.55 (1H, m), 3.70-3.77 (4H, m), 4.02 (2H, d, J=6.87 Hz), 4.06-4.26 (5H, m), 4.39-4.48 (1H, m), 4.56-4.67 (1H, m), 4.73-4.83 (1H, m), 6.70 (2H, s), 9.06 (2H, s).

Example 93

(2R)-1-{4-[(2-(2-Aminopyrimidin-5-yl)-9-isobutyl-6-morpholin-4-yl-9H-purin-8-yl]piperazin-1-yl}-1-oxopropan-2-ol

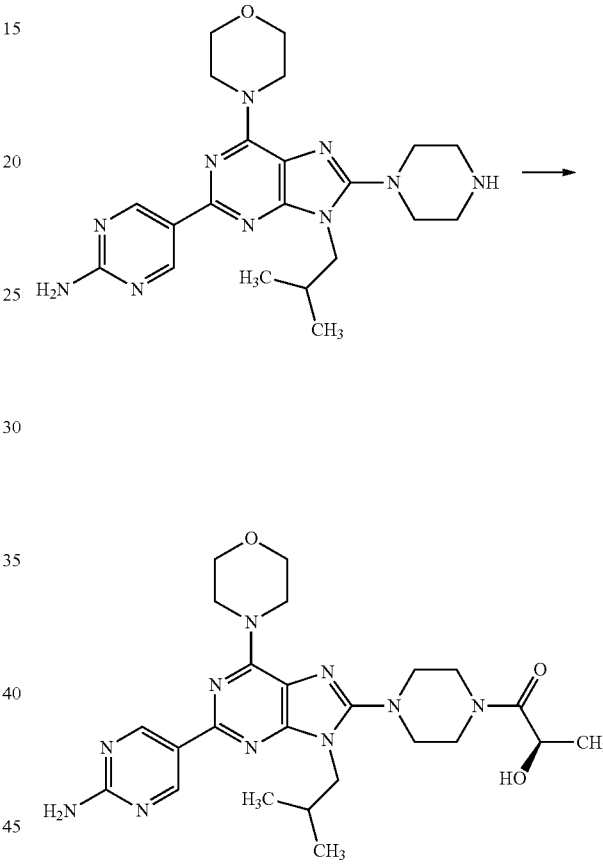

D-Lactic acid (26.3 mg, 0.29 mmol), 1-hydroxybenzotriazole monohydrate (37.2 mg, 0.24 mmol), 1-ethyl-3-(3-dimethylaminopropyl)-carbodiimide hydrochloride (69.8 mg, 0.36 mmol), and triethylamine (50.8 μl, 0.36 mmol) were added to an N,N-dimethylformamide suspension (2.0 ml) of 5-[9-(isobutyl)-6-morpholin-4-yl-8-piperazin-1-yl-9H-purin-2-yl]pyrimidin-2-amine (106.5 mg, 0.24 mmol) at room temperature. The resulting mixture was stirred for 4 days and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (89.9 mg, 73%) as a pale yellow solid.

$^1$H-NMR (CDCl$_3$) δ: 0.89 (6H, d, J=6.87 Hz), 1.39 (3H, d, J=6.87 Hz), 2.42-2.53 (1H, m), 3.19-3.34 (4H, m), 3.57-3.65

(2H, m), 3.79-3.98 (9H, m), 4.21-4.34 (4H, brm), 4.47-4.57 (1H, m), 5.46 (2H, s), 9.24 (2H, s).

Example 94

5-{9-(Cyclopropylmethyl)-8-[(3R)-3-methylpiperazin-1-yl]-6-morpholin-4-yl-9H-purin-2-yl}pyrimidin-2-amine

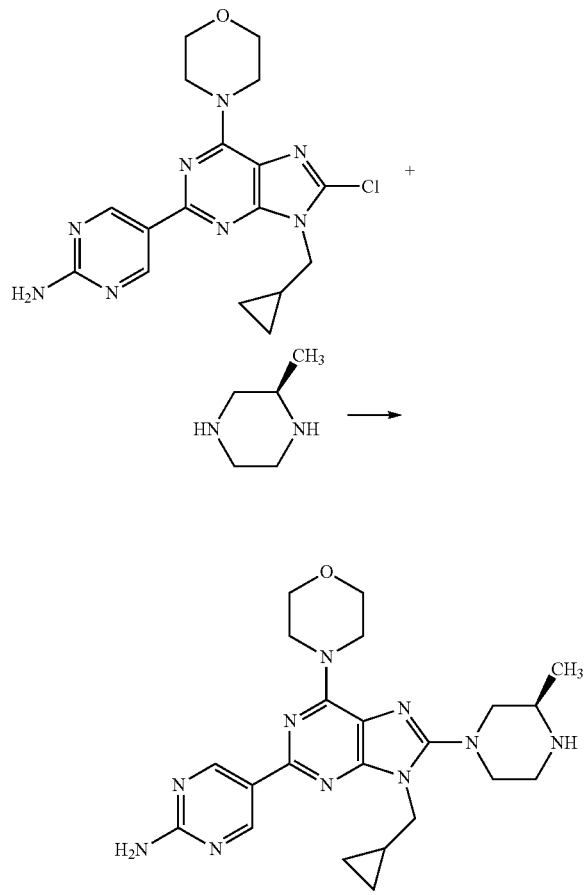

A dimethyl sulfoxide suspension (5 ml) 5-[8-chloro-9-(cyclopropylmethyl)-6-morpholin-4-yl-9H-purin-2-yl]pyrimidin-2-amine (502.6 mg, 1.30 mmol) and (2R)-2-methylpiperazine (650.7 mg, 6.50 mmol) was heated to dissolve at 100° C. and then the resulting mixture was stirred at 85° C. for 18.5 hours. (2R)-2-Methylpiperazine (130.1 mg, 1.30 mmol) was added and the resulting mixture was further stirred at 85° C. for 5.5 hours and then left standing to cool, poured into methylene chloride-methanol (10:1), and washed with saturated aqueous sodium hydrogen carbonate solution. The organic layer was dried over anhydrous sodium sulfate, the mixture was filtrated, the filtrate was concentrated under reduced pressure, and the resulting residue was purified by medium pressure silica gel column chromatography (methylene chloride:methanol=32:1 to 9:1) to give the title compound (556.6 mg, 95%) as a pale yellow solid.

$^1$H-NMR (CDCl$_3$) δ: 0.48-0.57 (4H, m), 1.11-1.17 (3H, m), 1.30-1.40 (1H, m), 2.70 (1H, t, J=11.17 Hz), 2.97-3.14 (4H, m), 3.35-3.45 (2H, m), 3.82-3.89 (4H, m), 3.89-4.02 (2H, m), 4.17-4.40 (4H, m), 5.37-5.59 (2H, brm), 9.23 (2H, s).

Example 95

(2S)-1-{(2R)-4-[2-(2-Aminopyrimidin-5-yl)-9-(cyclopropylmethyl)-6-morpholin-4-yl-9H-purin-8-yl]-2-methylpiperazin-1-yl}-1-oxopropan-2-ol

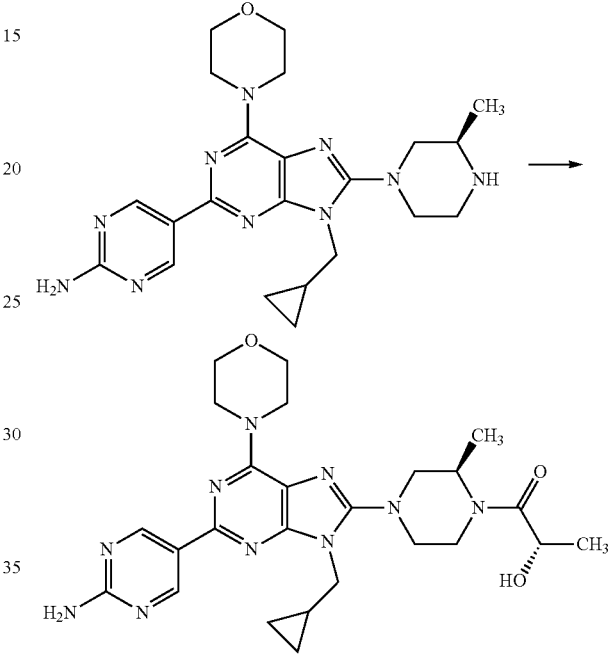

L-Lactic acid (26.8 μl, 0.30 mmol), 1-hydroxybenzotriazole monohydrate (38.9 mg, 0.25 mmol), 1-ethyl-3-(3-dimethylaminopropyl)-carbodiimide hydrochloride (73.0 mg, 0.38 mmol), and triethylamine (53.0 μl, 0.38 mmol) were added to an N,N-dimethylformamide solution (2.0 ml) of 5-{9-(cyclopropylmethyl)-8-[(3R)-3-methylpiperazin-1-yl]-6-morpholin-4-yl-9H-purin-2-yl}pyrimidin-2-amine (114.3 mg, 0.25 mmol) at room temperature. The resulting mixture was stirred for 20 hours followed by the addition of L-lactic acid (26.8 μl, 0.30 mmol), 1-ethyl-3-(3-dimethylaminopropyl)-carbodiimide hydrochloride (73.0 mg, 0.38 mmol), and triethylamine (53.0 μl, 0.38 mmol) and the resulting mixture was stirred for 3 days. L-Lactic acid (26.8 μl, 0.30 mmol), 1-ethyl-3-(3-dimethylaminopropyl)-carbodiimide hydrochloride (73.0 mg, 0.38 mmol), and triethylamine (53.0 μl, 0.38 mmol) were further added, the resulting mixture was stirred for 2 days, and the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (54.3 mg, 41%) as a pale yellow solid.

$^1$H-NMR (DMSO-d$_6$, 80° C.) δ: 0.45-0.53 (4H, m), 1.19-1.50 (7H, m), 2.83-2.99 (1H, m), 3.01-3.13 (1H, m), 3.26-3.47 (2H, m), 3.47-3.56 (1H, m), 3.70-3.77 (4H, m), 4.02 (2H, d, J=6.87 Hz), 4.11-4.26 (5H, m), 4.41-4.50 (1H, m), 4.52-4.73 (2H, brm), 6.70 (2H, s), 9.06 (2H, s).

Example 96

5-{8-[(3S)-4-Acetyl-3-methylpiperazin-1-yl]-9-(cyclopropylmethyl)-6-morpholin-4-yl-9H-purin-2-yl}pyrimidin-2-amine

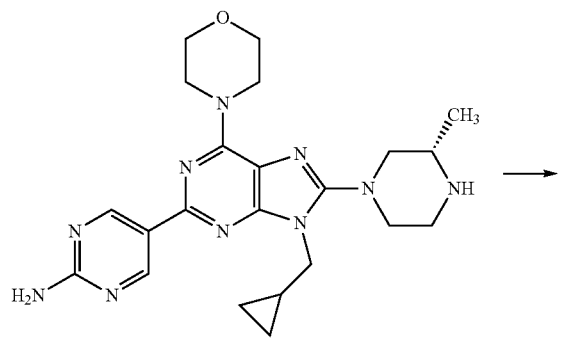

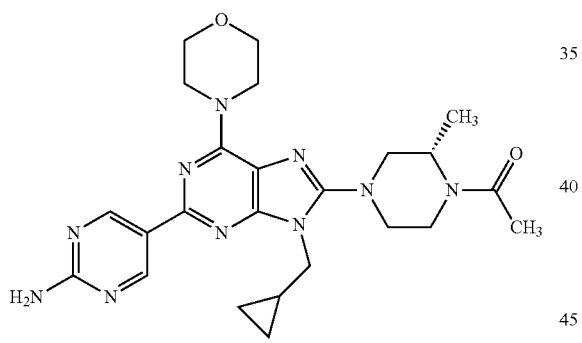

Triethylamine (80.3 μl, 0.58 mmol) was added to a methylene chloride solution (3.0 ml) of 5-{9-(cyclopropylmethyl)-8-[(3S)-3-methylpiperazin-1-yl]-6-morpholin-4-yl-9H-purin-2-yl}pyrimidin-2-amine (108.1 mg, 0.24 mmol) at room temperature followed by the addition of acetic anhydride (27.2 μl, 0.29 mmol) with ice cooling. The resulting mixture was stirred at room temperature for 2 hours and then the reaction mixture was poured into methylene chloride-methanol (10:1), washed with water, and dried over anhydrous sodium sulfate. After filtration, the filtrate was concentrated under reduced pressure and the resulting residue was purified by medium pressure silica gel column chromatography (methylene chloride:methanol=49:1 to 19:1) to give the title compound (115.8 mg, 98%) as a pale yellow solid.

$^1$H-NMR (CDCl$_3$) δ: 0.47-0.62 (4H, m), 1.31-1.53 (4H, m), 2.12-2.20 (3H, m), 2.91-3.28 (2.5H, m), 3.29-3.40 (1H, m), 3.44-3.53 (1H, m), 3.57-3.77 (1H, m), 3.81-3.89 (4H, m), 3.89-4.10 (2H, m), 4.11-4.21 (0.5H, m), 4.21-4.35 (4H, m), 4.52-4.64 (0.5H, m), 4.87-5.00 (0.5H, m), 5.48 (2H, s), 9.23 (2H, s).

Example 97

5-{8-[(3R)-4-Acetyl-3-methylpiperazin-1-yl]-9-(cyclopropylmethyl)-6-morpholin-4-yl-9H-purin-2-yl}pyrimidin-2-amine

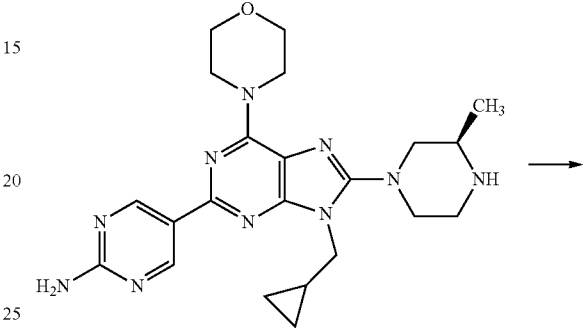

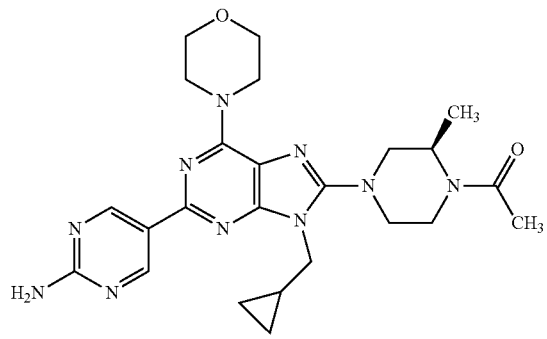

Triethylamine (77.3 μl, 0.55 mmol) was added to a methylene chloride solution (3.0 ml) of 5-{9-(cyclopropylmethyl)-8-[(3R)-3-methylpiperazin-1-yl]-6-morpholin-4-yl-9H-purin-2-yl}pyrimidin-2-amine (104.1 mg, 0.23 mmol) at room temperature followed by the addition of acetic anhydride (26.2 μl, 0.28 mmol) with ice cooling. The resulting mixture was stirred at room temperature for 95 minutes and the reaction mixture was poured into methylene chloride-methanol (10:1), washed with water, and dried over anhydrous sodium sulfate. After filtration, the filtrate was concentrated under reduced pressure and the resulting residue was purified by medium pressure silica gel column chromatography (methylene chloride:methanol=32:1 to 16:1) to give the title compound (114.3 mg, 100%) as a pale yellow solid.

$^1$H-NMR (CDCl$_3$) δ: 0.49-0.60 (4H, m), 1.31-1.51 (4H, m), 2.11-2.20 (3H, m), 2.91-3.28 (2.5H, m), 3.29-3.39 (1H, m), 3.45-3.52 (1H, m), 3.58-3.77 (1H, m), 3.81-3.89 (4H, m), 3.89-4.10 (2H, m), 4.10-4.20 (0.5H, m), 4.21-4.36 (4H, m), 4.53-4.63 (0.5H, m), 4.89-4.99 (0.5H, m), 5.42 (2H, s), 9.23 (2H, s).

Example 98

5-{8-[4-Acetyl-cis-3,5-dimethylpiperazin-1-yl]-9-(cyclopropylmethyl)-6-morpholin-4-yl-9H-purin-2-yl}pyrimidin-2-amine

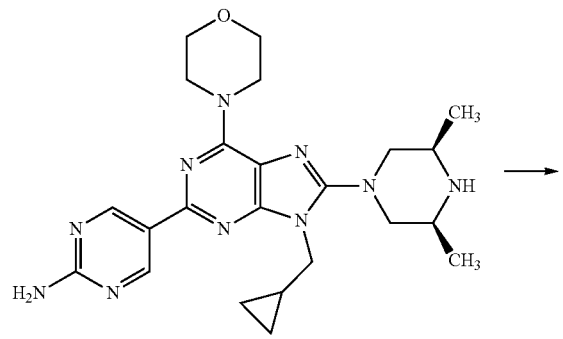

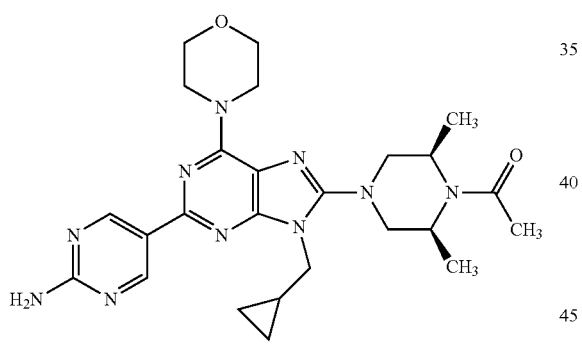

Triethylamine (73.7 µl, 0.53 mmol) was added to a methylene chloride (10 ml)-dimethylformamide (1.5 ml) mixture solution of 5-{9-(cyclopropylmethyl)-8-[cis-3,5-dimethylpiperazin-1-yl]-6-morpholin-4-yl-9H-purin-2-yl}pyrimidin-2-amine (102.3 mg, 0.22 mmol) at room temperature followed by the addition of acetic anhydride (24.9 µl, 0.26 mmol) with ice cooling. The resulting mixture was stirred at room temperature for 3 days followed by the addition of acetic anhydride (6.2 µl, 0.07 mmol) and the resulting mixture was further stirred for 3 days. The reaction mixture was poured into methylene chloride-methanol (10:1) and the resulting mixture was washed with saturated aqueous sodium hydrogen carbonate solution and dried over anhydrous sodium sulfate. After filtration, the filtrate was concentrated under reduced pressure and the resulting residue was purified by preparative thin layer silica gel chromatography (methylene chloride:methanol=10:1) to 0.10 give the title compound (107.7 mg, 97%) as a pale yellow solid.

$^1$H-NMR (CDCl$_3$) δ: 0.50-0.60 (4H, m), 1.33-1.60 (7H, m), 2.18 (3H, s), 2.93-3.26 (2H, brm), 3.33-3.43 (2H, m), 3.77-3.93 (4H, m), 3.97-4.18 (3H, brm), 4.19-4.37 (4H, brm), 4.59-4.97 (1H, brm), 5.31 (2H, s), 9.24 (2H, s).

Example 99

5-{8-[(3R)-4-Acetyl-3-methylpiperazin-1-yl]-9-isobutyl-6-morpholin-4-yl-9H-purin-2-yl}pyrimidin-2-amine

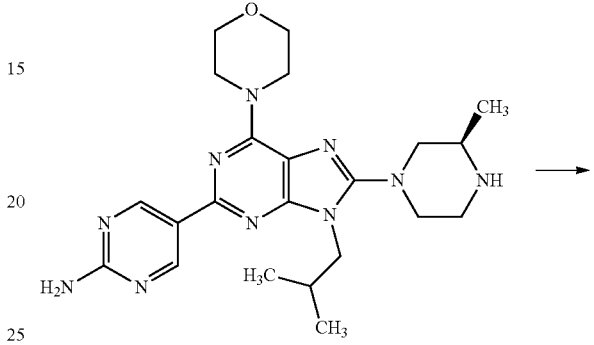

Triethylamine (79.9 µl, 0.57 mmol) was added to a methylene chloride solution (3.0 ml) of 5-{9-isobutyl-8-[(3R)-3-methylpiperazin-1-yl]-6-morpholin-4-yl-9H-purin-2-yl}pyrimidin-2-amine (108.1 mg, 0.24 mmol) at room temperature followed by the addition of acetic anhydride (27.1 µl, 0.29 mmol) with ice cooling. The resulting mixture was stirred at room temperature for 1 hour and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (110.9 mg, 94%) as a pale yellow solid.

$^1$H-NMR (CDCl$_3$) δ: 0.84-0.95 (6H, m), 1.33-1.52 (3H, m), 2.10-2.20 (3H, m), 2.42-2.52 (1H, m), 2.89-3.34 (3.5H, m), 3.37-3.45 (1H, m), 3.56-3.76 (1H, m), 3.80-4.01 (6H, m), 4.10-4.20 (0.5H, m), 4.20-4.35 (4H, m), 4.52-4.62 (0.5H, m), 4.88-4.98 (0.5H, m), 5.40 (2H, s), 9.24 (2H, s).

Example 100

(2R)-4-[2-(2-Aminopyrimidin-5-yl)-9-isobutyl-6-morpholin-4-yl-9H-purin-8-yl]-2-methylpiperazine-1-carboaldehyde

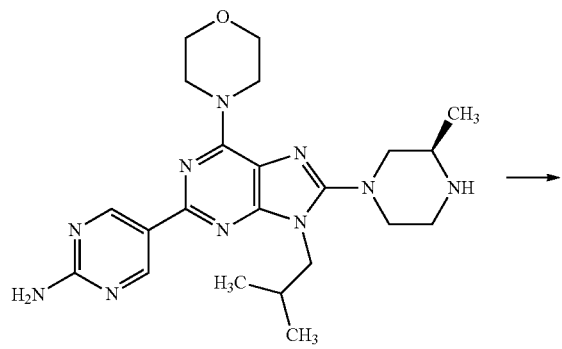

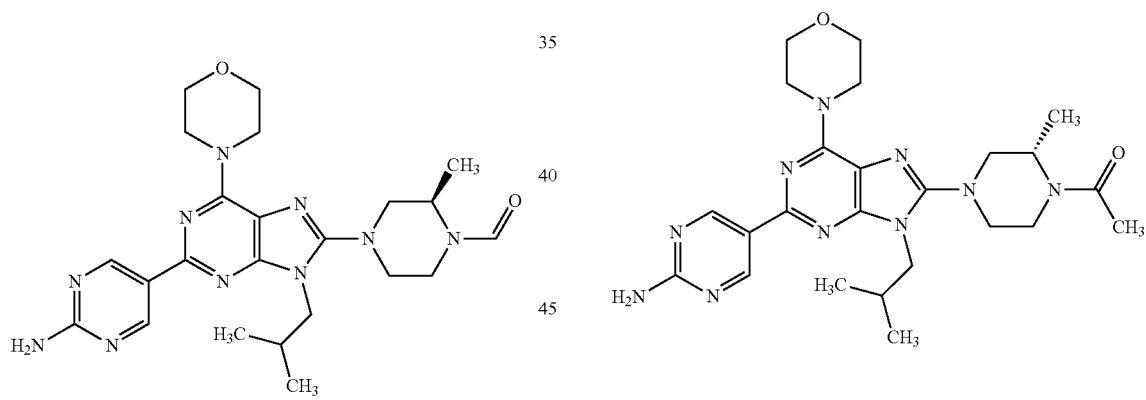

5-{9-Isobutyl-8-[(3R)-3-methylpiperazin-1-yl]-6-morpholin-4-yl-9H-purin-2-yl}pyrimidin-2-amine (109.5 mg, 0.24 mmol) was added to a tetrahydrofuran solution (7.0 ml) of 1H-benzotriazole-1-carboxyaldehyde (39.6 mg, 0.24 mmol) at room temperature and the resulting mixture was stirred for 70 minutes. Methylene chloride was added to the reaction mixture and the resulting mixture was poured into a 2 N aqueous sodium hydroxide solution and extracted with methylene chloride. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (107.9 mg, 93%) as a pale yellow solid.

$^1$H-NMR (CDCl$_3$) δ: 0.86-0.95 (6H, m), 1.44 (1.5H, d, J=6.88 Hz), 1.51 (1.5H, d, J=6.88 Hz), 2.40-2.55 (1H, m), 2.97-3.12 (1.5H, m), 3.18-3.55 (4H, m), 3.59-3.69 (0.5H, m), 3.82-4.00 (6H, m), 4.16-4.37 (4.5H, m), 4.66-4.83 (0.5H, m), 5.39 (2H, s), 8.07 (0.5H, s), 8.19 (0.5H, s), 9.24 (2H, s).

Example 101

5-{8-[(3S)-4-Acetyl-3-methylpiperazin-1-yl]-9-isobutyl-6-morpholin-4-yl-9H-purin-2-yl}pyrimidin-2-amine

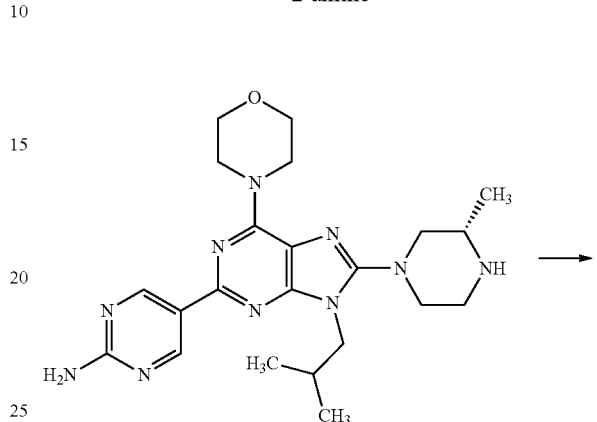

Triethylamine (86.3 μl, 0.62 mmol) was added to a methylene chloride solution (3.0 ml) of 5-{9-isobutyl-8-[(3S)-3-methylpiperazin-1-yl]-6-morpholin-4-yl-9H-purin-2-yl}pyrimidin-2-amine (116.8 mg, 0.26 mmol) at room temperature followed by the addition of acetic anhydride (29.2 μl, 0.31 mmol) with ice cooling. The resulting mixture was stirred at room temperature for 70 minutes and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (107.1 mg, 84%) as a pale yellow solid.

$^1$H-NMR (DMSO-d$_6$, 140° C.) δ: 0.88 (6H, d, J=6.87 Hz), 1.31 (3H, d, J=6.87 Hz), 2.03 (3H, s), 2.36-2.47 (1H, m), 2.87-2.97 (1H, m), 3.04-3.11 (1H, m), 3.24-3.36 (2H, m), 3.42-3.50 (1H, m), 3.71-3.77 (4H, m), 3.94-4.07 (3H, m), 4.15-4.20 (4H, m), 4.42-4.53 (1H, m), 6.38 (2H, s), 9.05 (2H, s).

Example 102

(2S)-4-[2-(2-Aminopyrimidin-5-yl)-9-isobutyl-6-morpholin-4-yl-9H-purin-8-yl]-2-methylpiperazine-1-carboaldehyde

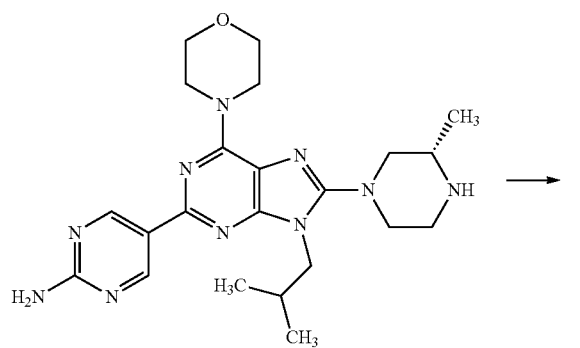

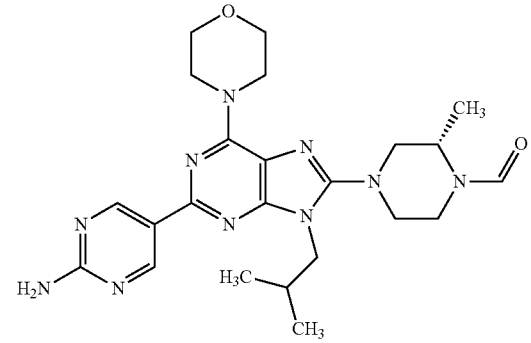

5-{9-Isobutyl-8-[(3S)-3-methylpiperazin-1-yl]-6-morpholin-4-yl-9H-purin-2-yl}pyrimidin-2-amine (123.4 mg, 0.27 mmol) was added to a tetrahydrofuran solution (7.0 ml) of 1H-benzotriazole-1-carboxyaldehyde (44.6 mg, 0.27 mmol) at room temperature and the resulting mixture was stirred for 35 minutes. Methylene chloride was added to the reaction mixture and then the resulting mixture was poured into a 2 N aqueous sodium hydroxide solution and extracted with methylene chloride. The organic layer was dried over anhydrous sodium sulfate, the mixture was filtered, the filtrate was concentrated under reduced pressure, and the resulting residue was purified by preparative thin layer silica gel chromatography (methylene chloride:methanol=10:1) to give the title compound (98.3 mg, 75%) as a pale yellow solid.

$^1$H-NMR (CDCl$_3$) δ: 0.87-0.93 (6H, m), 1.44 (1.5H, d, J=6.87 Hz), 1.51 (1.5H, d, J=6.87 Hz), 2.42-2.52 (1H, m), 2.98-3.11 (1.5H, m), 3.19-3.55 (4H, m), 3.60-3.68 (0.5H, m), 3.82-4.00 (6H, m), 4.17-4.33 (4.5H, m), 4.69-4.81 (0.5H, m), 5.42 (2H, s), 8.07 (0.5H, s), 8.19 (0.5H, s), 9.24 (2H, s).

Example 103

(2S)-1-{(2R)-4-[2-(2-Aminopyrimidin-5-yl)-9-isobutyl-6-morpholin-4-yl-9H-purin-8-yl]-2-methylpiperazin-1-yl}-1-oxopropan-2-ol

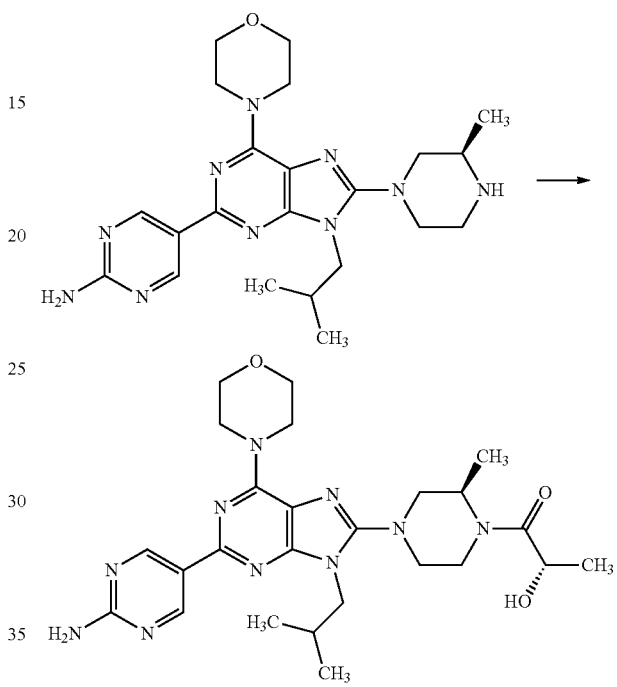

L-Lactic acid (25.9 μl, 0.29 mmol), 1-hydroxybenzotriazole monohydrate (37.6 mg, 0.25 mmol), 1-ethyl-3-(3-dimethylaminopropyl)-carbodiimide hydrochloride (70.5 mg, 0.37 mmol), and triethylamine (51.3 μl, 0.37 mmol) were added to an N,N-dimethylformamide solution (2.0 ml) of 5-{9-isobutyl-8-[(3R)-3-methylpiperazin-1-yl]-6-morpholin-4-yl-9H-purin-2-yl}pyrimidin-2-amine (111.0 mg, 0.25 mmol) at room temperature. The resulting mixture was stirred for 2 days followed by the addition of L-lactic acid (25.9 μl, 0.29 mmol), 1-ethyl-3-(3-dimethylaminopropyl)-carbodiimide hydrochloride (70.5 mg, 0.37 mmol), and triethylamine (51.3 μl, 0.37 mmol). The resulting mixture was stirred for 25 hours and the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was dissolved in methylene chloride (3.0 ml) followed by the addition of L-lactic acid (25.9 μl, 0.29 mmol), 1-hydroxybenzotriazole monohydrate (37.6 mg, 0.25 mmol), 1-ethyl-3-(3-dimethylaminopropyl)-carbodiimide hydrochloride (70.5 mg, 0.37 mmol), and triethylamine (51.3 μl, 0.37 mmol) at room temperature. The resulting mixture was stirred for 18 hours and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (64.8 mg, 50%) as a pale yellow solid.

¹H-NMR (DMSO-d₆, 140° C.) δ: 0.88 (6H, d, J=6.87 Hz), 1.24 (3H, d, J=5.95 Hz), 1.33 (3H, d, J=6.41 Hz), 2.36-2.47 (1H, m), 2.89-3.00 (1H, m), 3.04-3.13 (1H, m), 3.30-3.41 (2H, m), 3.43-3.51 (1H, m), 3.71-3.77 (4H, m), 3.97 (2H, d, J=7.33 Hz), 4.06-4.15 (1H, m), 4.15-4.20 (4H, m), 4.39-4.50 (2H, m), 4.53-4.64 (1H, m), 6.38 (2H, s), 9.05 (2H, s).

Example 104

(2S)-1-{(2S)-4-[2-(2-Aminopyrimidin-5-yl)-9-isobutyl-6-morpholin-4-yl-9H-purin-8-yl]-2-methylpiperazin-1-yl}-1-oxopropan-2-ol

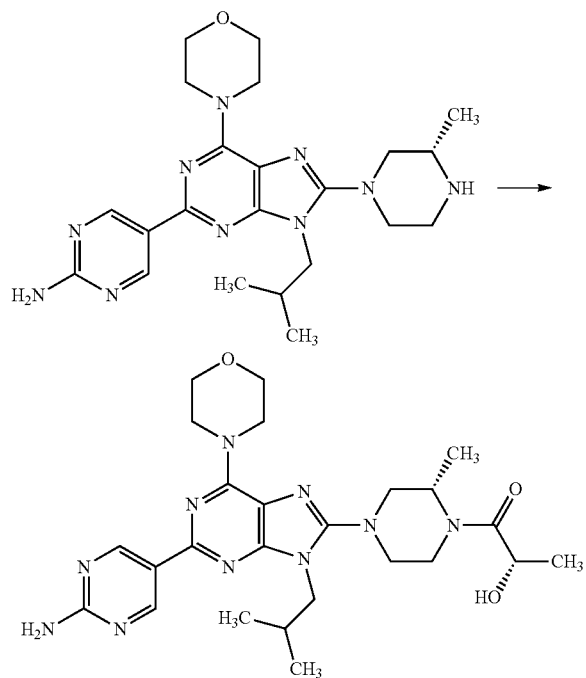

L-Lactic acid (29.6 µl, 0.34 mmol), 1-hydroxybenzotriazole monohydrate (43.0 mg, 0.28 mmol), 1-ethyl-3-(3-dimethylaminopropyl)-carbodiimide hydrochloride (80.8 mg, 0.42 mmol), and triethylamine (58.8 µl, 0.42 mmol) were added to an N,N-dimethylformamide solution (3.0 ml) of 5-{9-isobutyl-8-[(3S)-3-methylpiperazin-1-yl]-6-morpholin-4-yl-9H-purin-2-yl}pyrimidin-2-amine (127.2 mg, 0.28 mmol) at room temperature. The resulting mixture was stirred for 1 day followed by the addition of L-lactic acid (29.6 µl, 0.34 mmol), 1-ethyl-3-(3-dimethylaminopropyl)-carbodiimide hydrochloride (80.8 mg, 0.42 mmol), triethylamine (58.8 µl, 0.42 mmol), and methylene chloride (3.0 ml). The resulting mixture was stirred for 1 day and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (77.9 mg, 53%) as a pale yellow solid.

¹H-NMR (DMSO-d₆, 140° C.) δ: 0.88 (6H, d, J=6.87 Hz), 1.26 (3H, d, J=6.41 Hz), 1.34 (3H, d, J=6.41 Hz), 2.35-2.47 (1H, m), 2.87-2.98 (1H, m), 3.03-3.11 (1H, m), 3.29-3.41 (2H, m), 3.42-3.51 (1H, m), 3.70-3.77 (4H, m), 3.97 (2H, d, J=7.33 Hz), 4.08-4.20 (5H, m), 4.39-4.48 (1H, m), 4.48-4.55 (1H, m), 4.56-4.64 (1H, m), 6.38 (2H, s), 9.05 (2H, s).

Example 105

N-Methyl-5-{8-[(3S)-3-methyl-4-(methylsulfonyl)piperazin-1-yl]-6-morpholin-4-yl-9-(2,2,2-trifluoroethyl)-9H-purin-2-yl}pyrimidin-2-amine

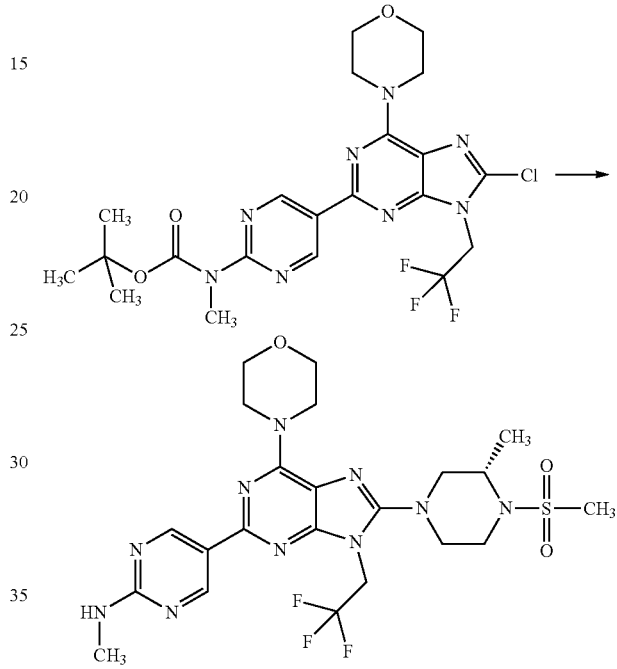

An N-methyl-2-pyrrolidone (2 ml) solution of tert-butyl {5-[8-chloro-6-morpholin-4-yl-9-(2,2,2-trifluoroethyl)-9H-purin-2-yl]pyrimidin-2-yl}methylcarbamate (153 mg, 0.29 mmol) and (S)-2-methylpiperazine (145 mg, 1.45 mmol) was stirred at 90° C. for 3 hours. The reaction mixture was returned to room temperature. The reaction mixture was purified by flash silica gel column chromatography (chloroform:methanol=19:1).

A methylene chloride (5 ml) solution of the resulting residue, methanesulfonyl chloride (45 µl, 0.58 mmol), and triethylamine (88 µl, 0.64 mmol) was stirred at room temperature for 1 hour and concentrated under reduced pressure. The residue was purified by preparative thin layer chromatography (hexane:ethyl acetate=1:2).

A methylene chloride (3 ml) solution of the resulting residue and trifluoroacetic acid (1 ml) was stirred at room temperature for 2 hours and concentrated under reduced pressure. Chloroform and saturated aqueous sodium hydrogen carbonate solution to the residue and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=19:1) to give a solid. Ether was added to the resulting solid and the solid was collected by filtration and dried to give the title compound (94 mg, 57%) as a powder.

¹H-NMR (CDCl₃) δ: 1.49 (3H, d, J=6.8 Hz), 2.94 (3H, s), 3.07-3.10 (3H, m), 3.12-3.21 (2H, m), 3.25-3.33 (2H, m), 3.42-3.51 (1H, m), 3.70-3.78 (1H, m), 3.82-3.87 (4H, m), 4.21-4.32 (5H, m), 4.71 (2H, q, J=8.3 Hz), 5.26-5.33 (1H, m), 9.25 (2H, s).

Example 106

N-Methyl-5-{8-[(3R)-3-methyl-4-(methylsulfonyl)piperazin-1-yl]-6-morpholin-4-yl-9-(2,2,2-trifluoroethyl)-9H-purin-2-yl}pyrimidin-2-amine

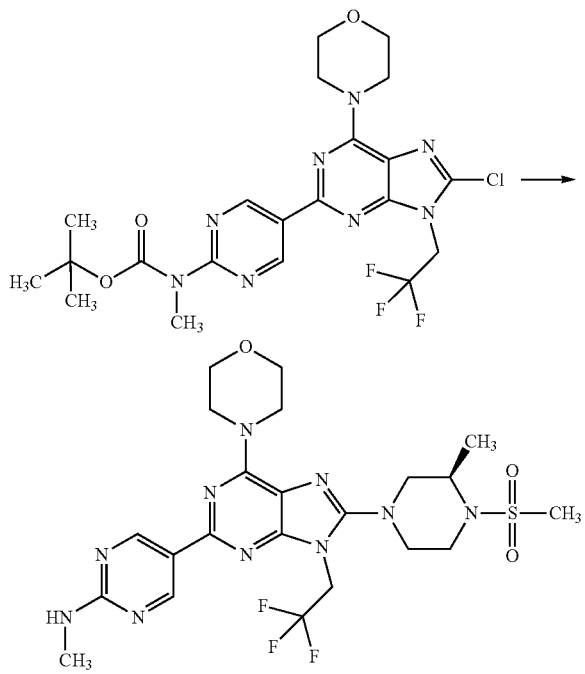

An N-methyl-2-pyrrolidone (2 ml) solution of tert-butyl {5-[8-chloro-6-morpholin-4-yl-9-(2,2,2-trifluoroethyl)-9H-purin-2-yl]pyrimidin-2-yl}methylcarbamate (154 mg, 0.29 mmol) and (R)-2-methylpiperazine (145 mg, 1.46 mmol) was stirred at 90° C. for 3 hours. The reaction mixture was returned to room temperature. The reaction mixture was purified by flash silica gel column chromatography (chloroform:methanol=9:1).

A methylene chloride (5 ml) solution the resulting residue, methanesulfonyl chloride (45 μl, 0.58 mmol), and triethylamine (89 μl, 0.64 mmol) was stirred at room temperature for 2 hours and concentrated under reduced pressure. The residue was purified by flash silica gel column chromatography (chloroform:methanol=97:3).

A methylene chloride (3 ml) solution of the resulting residue and trifluoroacetic acid (1 ml) was stirred at room temperature for 3 hours and concentrated under reduced pressure. Chloroform and saturated aqueous sodium hydrogen carbonate solution were added to the residue and the resulting mixture was extracted with chloroform. The organic layer was dried over anhydrous magnesium sulfate and, after filtration, the filtrate was concentrated under reduced pressure. The residue was purified by flash silica gel column chromatography (5% methanol:methylene chloride) to obtain a solid. Ether was added to the resulting solid and the solid was collected by filtration and dried to give the title compound (94 mg, 57%) as a powder.

¹H-NMR (CDCl₃) δ: 1.49 (3H, d, J=6.8 Hz), 2.94 (3H, s), 3.07-3.10 (3H, m), 3.12-3.21 (2H, m), 3.25-3.33 (2H, m), 3.42-3.51 (1H, m), 3.70-3.78 (1H, m), 3.82-3.87 (4H, m), 4.21-4.32 (5H, m), 4.71 (2H, q, J=8.3 Hz), 5.26-5.33 (1H, m), 9.25 (2H, s).

Example 107

5-{8-[(3S)-4-Acetyl-3-methylpiperazin-1-yl]-6-morpholin-4-yl-9-(2,2,2-trifluoroethyl)-9H-purin-2-yl}-N-methylpyrimidin-2-amine

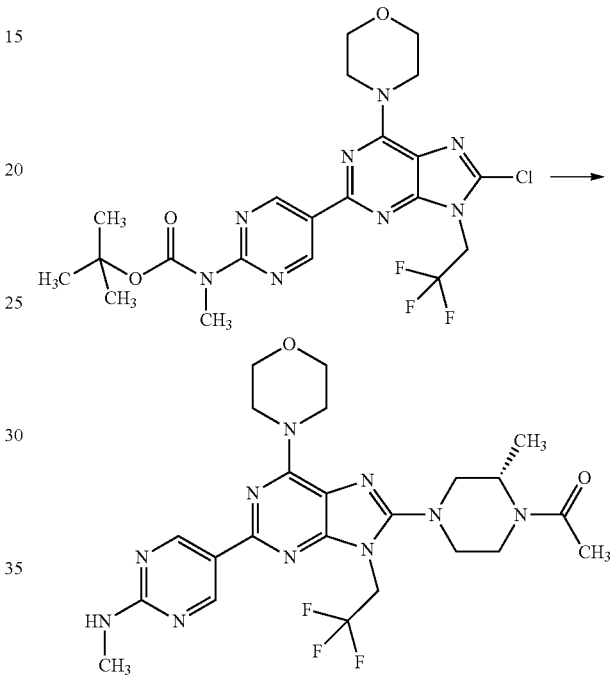

An N-methyl-2-pyrrolidinone (2 ml) solution of tert-butyl {5-[8-chloro-6-morpholin-4-yl-9-(2,2,2-trifluoroethyl)-9H-purin-2-yl]pyrimidin-2-yl}methylcarbamate (152 mg, 0.29 mmol) and (S)-2-methylpiperazine (144 mg, 1.44 mmol) was stirred at 90° C. for 3 hours. The reaction mixture was returned to room temperature. The reaction mixture was purified by flash silica gel column chromatography (10% methanol:chloroform).

A methylene chloride (5 ml) solution of the resulting residue, acetic anhydride (54 μl, 0.57 mmol), and triethylamine (80 μl, 0.57 mmol) was stirred at room temperature for 1 hour and concentrated under reduced pressure. The residue was purified by flash silica gel column chromatography (3% methanol:chloroform).

A methylene chloride (3 ml) solution of the resulting residue and trifluoroacetic acid (1 ml) was stirred at room temperature for 3 hours and concentrated under reduced pressure. Chloroform and saturated aqueous sodium hydrogen carbonate solution were added to the residue and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=95:5) to give a solid. Ether was added to the resulting solid and the solid was collected by filtration and dried to give the title compound (77 mg, 50%) as a powder.

¹H-NMR (DMSO-d₆, 140° C.) δ: 1.30 (3H, d, J=6.9 Hz), 2.03 (3H, s), 2.89-2.98 (4H, m), 3.09-3.16 (1H, m), 3.26-3.37 (2H, m), 3.40-3.48 (1H, m), 3.72-3.77 (4H, m), 3.95-4.06 (1H, m), 4.15-4.20 (4H, m), 4.47 (1H, brs), 4.88-5.02 (2H, m), 6.88 (1H, brs), 9.09 (2H, s).

Example 108

5-{8-[(3R)-4-Acetyl-3-methylpiperazin-1-yl]-6-morpholin-4-yl-9-(2,2,2-trifluoroethyl)-9H-purin-2-yl}-N-methylpyrimidin-2-amine

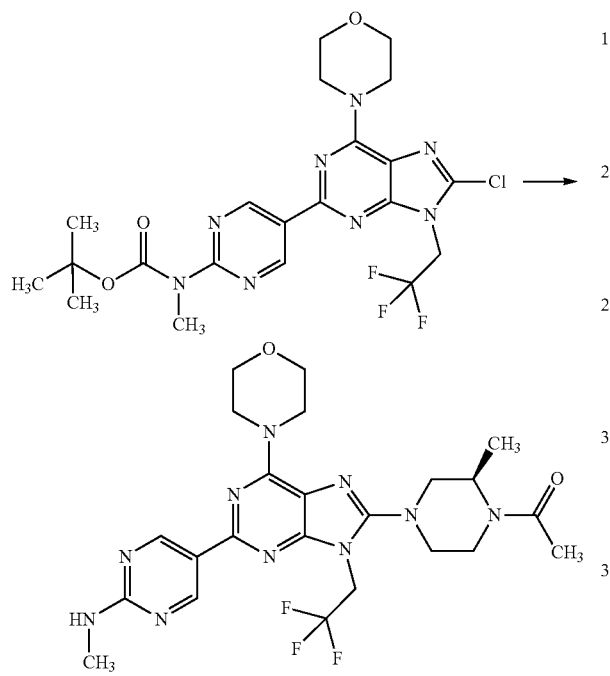

An N-methyl-2-pyrrolidinone (2 ml) solution of tert-butyl {5-[8-chloro-6-morpholin-4-yl-9-(2,2,2-trifluoroethyl)-9H-purin-2-yl]pyrimidin-2-yl}methylcarbamate (154 mg, 0.29 mmol) and (R)-2-methylpiperazine (145 mg, 1.46 mmol) was stirred at 90° C. for 3 hours. The reaction mixture was returned to room temperature. The reaction mixture was purified by flash silica gel column chromatography (chloroform:methanol=95:5).

A methylene chloride (5 ml) solution of the resulting residue, acetic anhydride (55 μl, 0.58 mmol), and triethylamine (89 μl, 0.64 mmol) was stirred at room temperature for 1 hour and concentrated under reduced pressure. The residue was purified by flash silica gel column chromatography (chloroform:methanol=95:5).

A methylene chloride (3 ml) solution of the resulting residue and trifluoroacetic acid (1 ml) was stirred at room temperature for 22 hours and concentrated under reduced pressure. Chloroform and saturated aqueous sodium hydrogen carbonate solution were added to the residue and the resulting mixture was extracted with chloroform. The organic layer was dried with anhydrous magnesium sulfate and, after filtration, the filtrate was concentrated under reduced pressure. The residue was purified by flash silica gel column chromatography (methylene chloride:methanol=95:5) to give a solid. Ether was added to the resulting solid and the solid was collected by filtration and dried to give the title compound (90 mg, 58%) as a powder.

¹H-NMR (DMSO-d₆, 140° C.) δ: 1.30 (3H, d, J=6.4 Hz), 2.03 (3H, s), 2.89-2.98 (4H, m), 3.09-3.16 (1H, m), 3.26-3.36 (2H, m), 3.41-3.48 (1H, m), 3.72-3.77 (4H, m), 3.96-4.07 (1H, m), 4.15-4.21 (4H, m), 4.47 (1H, brs), 4.89-5.02 (2H, m), 6.88 (1H, brs), 9.09 (2H, s).

Example 109

(2S)-1-{(2S)-4-[2-(2-Aminopyrimidin-5-yl)-6-morpholin-4-yl-9-(2,2,2-trifluoroethyl)-9H-purin-8-yl]-2-methylpiperazin-1-yl}-1-oxopropan-2-ol

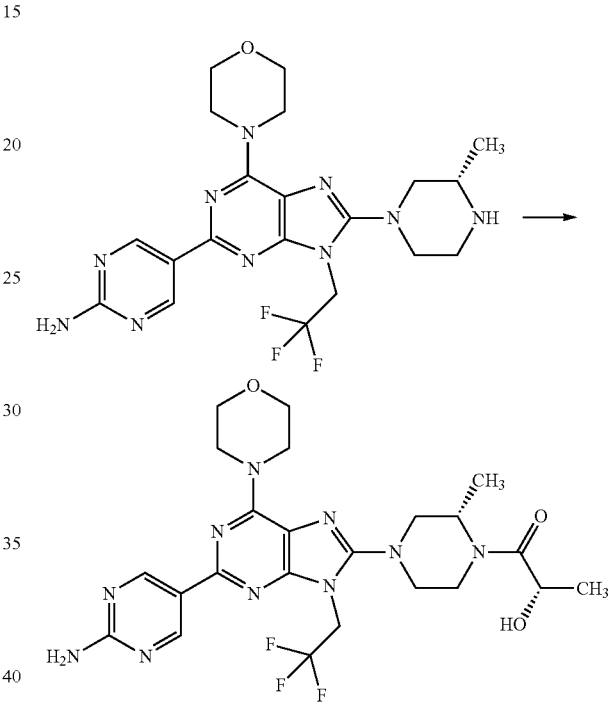

L-Lactic acid (48.7 μl, 0.55 mmol), 1-hydroxybenzotriazole monohydrate (42.5 mg, 0.28 mmol), 1-(dimethylaminopropyl)-3-ethylcarbodiimide hydrochloride (106.3 mg, 0.55 mmol), and triethylamine (77.3 μl, 0.55 mmol) were added to a methylene chloride (3.0 ml)-N,N-dimethylformamide (3.0 ml) mixture solution of 5-{8-[(3S)-3-methylpiperazin-1-yl]-6-morpholin-4-yl-9-(2,2,2-trifluoroethyl)-9H-purin-2-yl}pyrimidin-2-amine (132.7 mg, 0.28 mmol) at room temperature. The resulting mixture was stirred for 5 days followed by the addition of L-lactic acid (48.7 μl, 0.55 mmol), 1-ethyl-3-(3-dimethylaminopropyl)-carbodiimide hydrochloride (106.3 mg, 0.55 mmol), and triethylamine (77.3 μl, 0.55 mmol). The resulting mixture was stirred for 1 day and the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (72.4 mg, 47%) as a pale yellow solid.

¹H-NMR (DMSO-d₆, 140° C.) δ: 1.26 (3H, d, J=5.95 Hz), 1.33 (3H, d, J=6.41 Hz), 2.89-2.99 (1H, m), 3.09-3.17 (1H, m), 3.26-3.49 (3H, m), 3.72-3.77 (4H, m), 4.09-4.21 (5H, m), 4.39-4.48 (1H, m), 4.49-4.56 (1H, m), 4.56-4.64 (1H, m), 4.89-5.04 (2H, m), 6.44 (2H, s), 9.06 (2H, s).

Example 110

(2S)-1-{(2R)-4-[2-(2-Aminopyrimidin-5-yl)-6-morpholin-4-yl-9-(2,2,2-trifluoroethyl)-9H-purin-8-yl]-2-methylpiperazin-1-yl}-1-oxopropan-2-ol

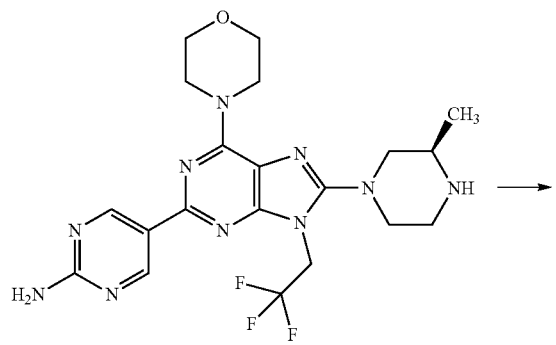

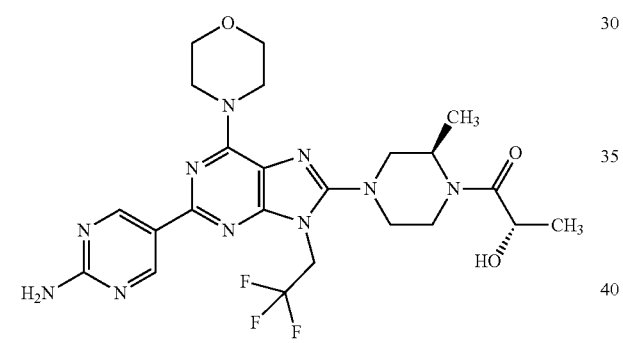

L-Lactic acid (48.2 μl, 0.55 mmol), 1-hydroxybenzotriazole monohydrate (42.0 mg, 0.27 mmol), 1-(dimethylaminopropyl)-3-ethylcarbodiimide hydrochloride (105.1 mg, 0.55 mmol), and triethylamine (76.4 μl, 0.55 mmol) were added to a methylene chloride (3.0 ml)-N,N-dimethylformamide (3.0 ml) mixture solution of 5-{8-[(3R)-3-methylpiperazin-1-yl]-6-morpholin-4-yl-9-(2,2,2-trifluoroethyl)-9H-purin-2-yl}pyrimidin-2-amine (131.1 mg, 0.27 mmol) at room temperature. The resulting mixture was stirred for 5 days followed by the addition of L-lactic acid (48.2 μl, 0.55 mmol), 1-ethyl-3-(3-dimethylaminopropyl)-carbodiimide hydrochloride (105.1 mg, 0.55 mmol), and triethylamine (76.4 μl, 0.55 mmol). The resulting mixture was stirred for 1 day and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (53.9 mg, 36%) as a pale yellow solid.

$^1$H-NMR (DMSO-d$_6$, 140° C.) δ: 1.24 (3H, d, J=5.95 Hz), 1.32 (3H, d, J=6.87 Hz), 2.90-3.01 (1H, m), 3.09-3.18 (1H, m), 3.27-3.50 (3H, m), 3.72-3.78 (4H, m), 4.05-4.14 (1H, m), 4.15-4.21 (4H, m), 4.39-4.50 (2H, m), 4.53-4.64 (1H, m), 4.89-5.04 (2H, m), 6.44 (2H, s), 9.06 (2H, s).

Example 111

(2S)-4-[2-(2-Aminopyrimidin-5-yl)-6-morpholin-4-yl-9-(2,2,2-trifluoroethyl)-9H-purin-8-yl]-2-methylpiperazine-1-carboaldehyde

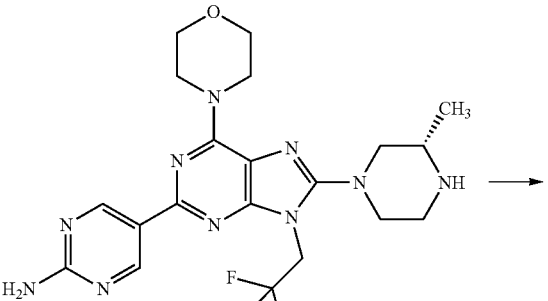

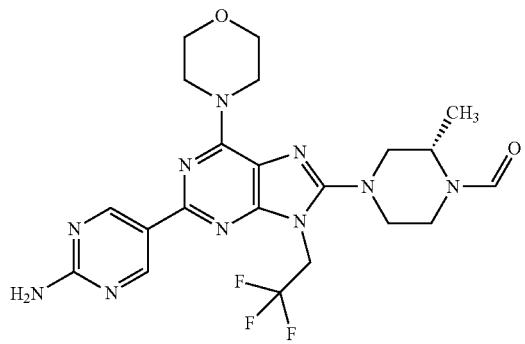

5-{8-[(3S)-3-Methylpiperazin-1-yl]-6-morpholin-4-yl-9-(2,2,2-trifluoroethyl)-9H-purin-2-yl}pyrimidin-2-amine (107.1 mg, 0.22 mmol) was added to a tetrahydrofuran solution (5.0 ml) of 1H-benzotriazole-1-carboxyaldehyde (36.6 mg, 0.22 mmol) at room temperature and the resulting mixture was stirred for 45 minutes. The reaction mixture was poured into a 2 N aqueous sodium hydroxide solution and the resulting mixture was extracted with methylene chloride. The organic layer was dried over anhydrous sodium sulfate, the mixture was filtered, the filtrate was concentrated under reduced pressure, and the resulting residue was purified by preparative thin layer silica gel chromatography (methylene chloride:methanol=10:1) to give the title compound (100.2 mg, 88%) as a pale yellow solid.

$^1$H-NMR (CDCl$_3$) δ: 1.43 (1.5H, d, J=6.87 Hz), 1.51 (1.5H, d, J=6.87 Hz), 3.01-3.31 (3.5H, m), 3.33-3.42 (1H, m), 3.47-3.55 (0.5H, m), 3.61-3.69 (0.5H, m), 3.82-3.87 (4H, m), 3.91-3.98 (0.5H, m), 4.17-4.36 (4.5H, m), 4.66-4.83 (2.5H, m), 5.30 (2H, s), 8.07 (0.5H, s), 8.19 (0.5H, s), 9.23 (2H, s).

Example 112

(2R)-4-[2-(2-Aminopyrimidin-5-yl)-6-morpholin-4-yl-9-(2,2,2-trifluoroethyl)-9H-purin-8-yl]-2-methylpiperazine-1-carboaldehyde

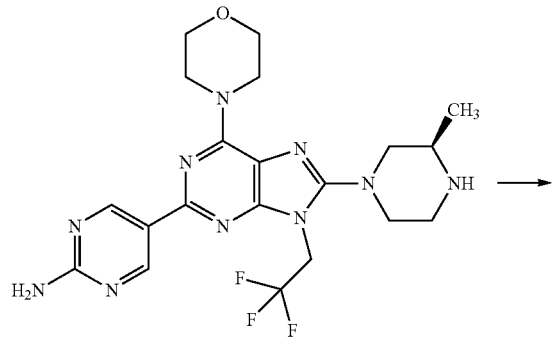

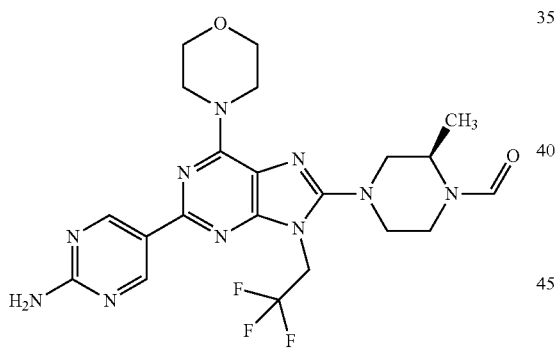

5-{8-[(3R)-3-Methylpiperazin-1-yl]-6-morpholin-4-yl-9-(2,2,2-trifluoroethyl)-9H-purin-2-yl}pyrimidin-2-amine (101.9 mg, 0.21 mmol) was added to a tetrahydrofuran solution (5.0 ml) of 1H-benzotriazole-1-carboxyaldehyde (34.8 mg, 0.21 mmol) at room temperature and the resulting mixture was stirred for 105 minutes. The reaction mixture was poured into a 2 N aqueous sodium hydroxide solution and the resulting mixture was extracted with methylene chloride. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (96.8 mg, 90%) as a pale yellow solid.

$^1$H-NMR (CDCl$_3$) δ: 1.43 (1.5H, d, J=6.87 Hz), 1.51 (1.5H, d, J=6.87 Hz), 3.01-3.31 (3.5H, m), 3.33-3.42 (1H, m), 3.48-3.55 (0.5H, m), 3.61-3.69 (0.5H, m), 3.83-3.87 (4H, m), 3.91-3.98 (0.5H, m), 4.17-4.35 (4.5H, m), 4.66-4.82 (2.5H, m), 5.30 (2H, s), 8.07 (0.5H, s), 8.19 (0.5H, s), 9.23 (2H, s).

Example 113

(2R)-1-{(2S)-4-[2-(2-Aminopyrimidin-5-yl)-9-(cyclopropylmethyl)-6-morpholin-4-yl-9H-purin-8-yl]-2-methylpiperazin-1-yl}-1-oxopropan-2-ol

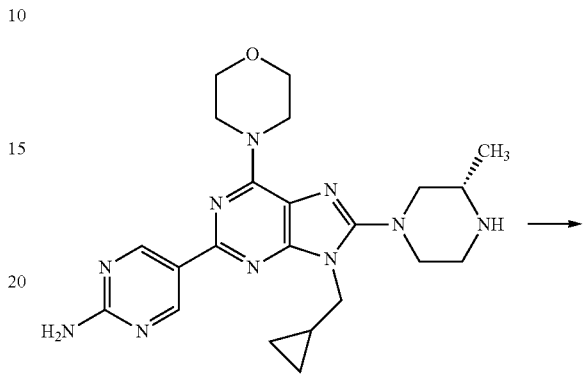

1-Hydroxybenzotriazole (31:3 mg, 0.23 mmol), N,N'-dicyclohexylcarbodiimide (71.6 mg, 0.35 mmol), and triethylamine (64.5 μl, 0.46 mmol) were added to an N,N-dimethylformamide solution (3.0 ml) of 5-{9-(cyclopropylmethyl)-8-[(3S)-3-methylpiperazin-1-yl]-6-morpholin-4-yl-9H-purin-2-yl}pyrimidin-2-amine (115.6 mg, 0.26 mmol) and D-lactic acid (25.3 mg, 0.28 mmol) at room temperature. The resulting mixture was stirred for 18.5 hours followed by the addition of N,N'-dicyclohexylcarbodiimide (71.6 mg, 0.35 mmol) and the resulting mixture was stirred at 40° C. for 22 hours. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (68.7 mg, 57%) as a pale yellow solid.

$^1$H-NMR (DMSO-d$_6$, 140° C.) δ: 0.44-0.55 (4H, m), 1.24 (3H, d, J=6.41 Hz), 1.31-1.43 (4H, m), 2.91-3.02 (1H, m), 3.08-3.15 (1H, m), 3.32-3.43 (2H, m), 3.48-3.56 (1H, m), 3.71-3.77 (4H, m), 4.03 (2H, d, J=6.87 Hz), 4.06-4.15 (1H, m), 4.15-4.21 (4H, m), 4.39-4:50 (2H, m), 4.54-4.64 (1H, m), 6.39 (2H, s), 9.05 (2H, s).

Example 114

(2R)-1-{(2R)-4-[2-(2-Aminopyrimidin-5-yl)-9-(cyclopropylmethyl)-6-morpholin-4-yl-9H-purin-8-yl]-2-methylpiperazin-1-yl}-1-oxopropan-2-ol

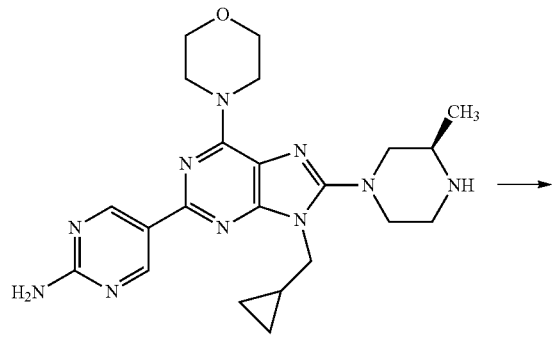

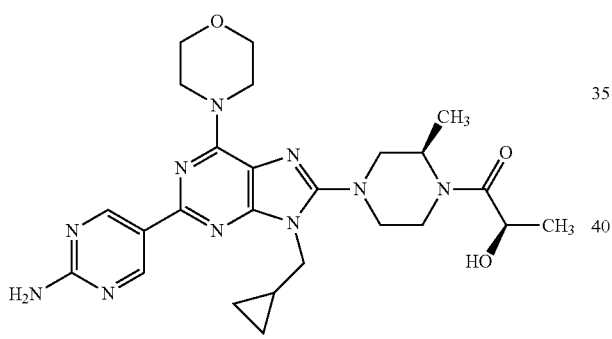

1-Hydroxybenzotriazole (33.2 mg, 0.25 mmol), N,N'-dicyclohexylcarbodiimide (76.1 mg, 0.37 mmol), and triethylamine (102.8 μl, 0.75 mmol) were added to an N,N-dimethylformamide (3.0 ml)-methylene chloride (3.0 ml) mixture solution of 5-{9-(cyclopropylmethyl)-8-[(3R)-3-methylpiperazin-1-yl]-6-morpholin-4-yl-9H-purin-2-yl}pyrimidin-2-amine (110.8 mg, 0.25 mmol) and D-lactic acid (26.9 mg, 0.30 mmol) at room temperature. The resulting mixture was stirred for 18.5 hours followed by the addition of N,N'-dicyclohexylcarbodiimide (76.1 mg, 0.37 mmol) and the resulting mixture stirred at 40° C. for 22 hours. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (98.1 mg, 76%) as a pale yellow solid.

$^1$H-NMR (DMSO-$d_6$, 140° C.) δ: 0.43-0.55 (4H, m), 1.26 (3H, d, J=6.41 Hz), 1.31-1.44 (4H, m), 2.89-3.00 (1H, m), 3.07-3.15 (1H, m), 3.32-3.44 (2H, m), 3.47-3.56 (1H, m), 3.70-3.77 (4H, m), 4.00-4.06 (2H, m), 4.08-4.21 (5H, m), 4.39-4.65 (3H, m), 6.39 (2H, s), 9.05 (2H, s).

Example 115

5-[8-(4-Acetyl-cis-3,5-dimethylpiperazin-1-yl)-6-morpholin-4-yl-9-(2,2,2-trifluoroethyl)-9H-purin-2-yl]pyrimidin-2-amine

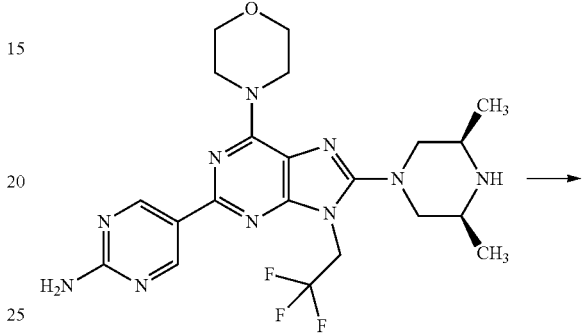

Triethylamine (73.8 μl, 0.53 mmol) was added to a methylene chloride solution (9.0 ml) of 5-[8-(cis-3,5-dimethylpiperazin-1-yl)-6-morpholin-4-yl-9-(2,2,2-trifluoroethyl)-9H-purin-2-yl]pyrimidin-2-amine (108.7 mg, 0.22 mmol) at room temperature followed by the addition of acetic anhydride (25.0 μl, 0.26 mmol) with ice cooling. The resulting mixture was stirred at room temperature for 3 days followed by the addition of acetic anhydride (8.3 μl, 0.09 mmol) and the resulting mixture was stirred for 1 day. Acetic anhydride (4.2 μl, 0.04 mmol) was further added to the resulting mixture, the resulting mixture was stirred for 1 day, and the reaction mixture was poured into methylene chloride, washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (109.8 mg, 93%) as a pale yellow solid.

¹H-NMR (CDCl₃) δ: 1.49 (6H, brs), 2.18 (3H, s), 3.05-3.31 (4H, m), 3.81-3.89 (4H, m), 4.14-4.41 (5H, m), 4.68-4.89 (3H, m), 5.30 (2H, s), 9.23 (2H, s).

Example 116

4-[2-(2-Aminopyrimidin-5-yl)-6-morpholin-4-yl-9-(2,2,2-trifluoroethyl)-9H-purin-8-yl]-cis-2,6-dimethylpiperazine-1-carboaldehyde

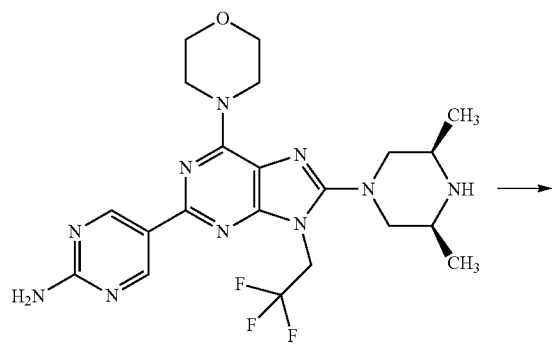

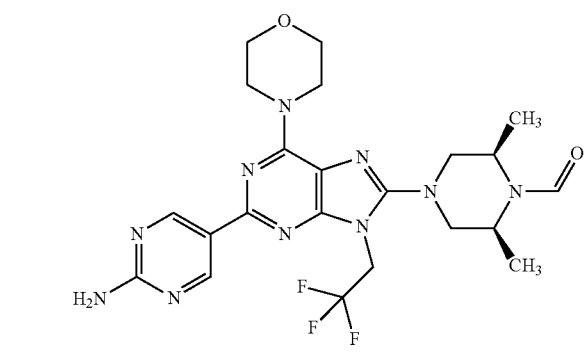

5-[8-(cis-3,5-Dimethylpiperazin-1-yl)-6-morpholin-4-yl-9-(2,2,2-trifluoroethyl)-9H-purin-2-yl]pyrimidin-2-amine (101.7 mg, 0.21 mmol) were added to a tetrahydrofuran solution (5.0 ml) of 1H-benzotriazole-1-carboxyaldehyde (33.8 mg, 0.21 mmol) at room temperature and the resulting mixture was stirred for 1 day. 1H-Benzotriazole-1-carboxyaldehyde (5.1 mg, 0.03 mmol) was added, the resulting mixture was further stirred for 1 day, and then the reaction mixture was poured into methylene chloride and washed with a 2 N aqueous sodium hydroxide solution. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (98.0 mg, 91%) as a pale yellow solid.

¹H-NMR (CDCl₃) δ: 1.50 (3H, d, J=6.87 Hz), 1.56 (3H, d, J=6.87 Hz), 3.10 (1H, dd, J=12.31, 4.30 Hz), 3.19-3.32 (3H, m), 3.82-3.88 (4H, m), 3.92-4.00 (1H, m), 4.20-4.36 (4H, brm), 4.62-4.70 (1H, m), 4.70-4.86 (2H, m), 5.25 (2H, s), 8.15 (1H, s), 9.23 (2H, s).

Example 117

5-[6-Morpholin-4-yl-8-(4-propionylpiperazin-1-yl)-9-(2,2,2-trifluoroethyl)-9H-purin-2-yl]pyrimidin-2-amine

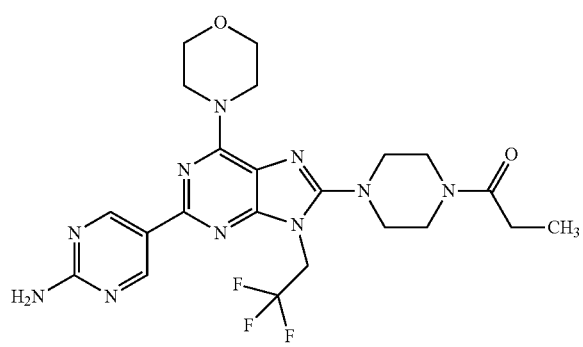

The title compound was synthesized in the same way as in Example 9 using propionyl chloride as an acylating agent.

¹H-NMR (CDCl₃) δ: 1.20 (4H, t, J=7.4 Hz), 2.41 (2H, q, J=7.4 Hz), 3.16-3.23 (4H, m), 3.65-3.67 (2H, m), 3.81-3.86 (6H, m), 4.28 (4H, brs), 4.73 (2H, q, J=8.3 Hz), 5.34 (2H, s), 9.23 (2H, s).

Example 118

5-[8-(4,7-Diazaspiro[2.5]oct-7-yl)-6-morpholin-4-yl-9-(2,2,2-trifluoroethyl)-9H-purin-2-yl]pyrimidin-2-amine

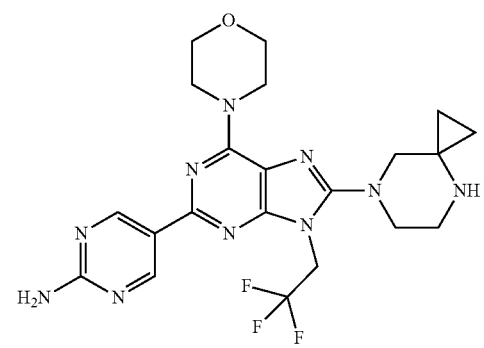

Step 1: Ethyl-N-benzyl-N-[(1-{[(benzyloxy)carbonyl]amino}cyclopropyl)carbonyl]glycinate

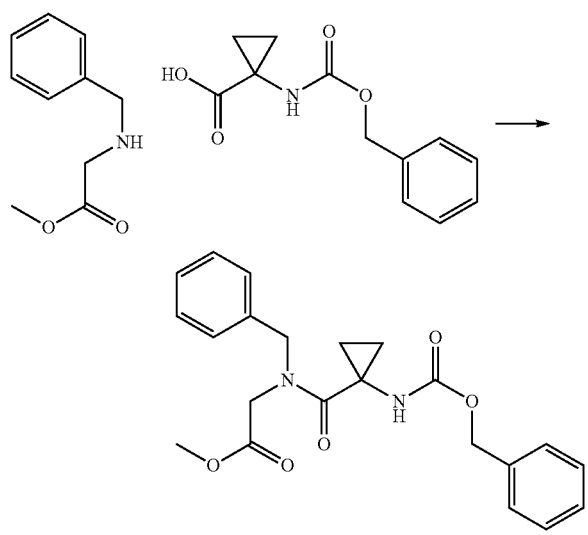

1-(3-Dimethylaminopropyl)-3-ethylcarbodiimide hydrochloride (21.0 g, 110 mmol) and 1-hydroxybenzotriazole (2.70 g, 20 mmol) were added to a methylene chloride (235 ml) solution of 1-{[(benzyloxy)carbonyl]amino}cyclopropane carboxylic acid (23.5 g, 100 mmol) and ethyl N-benzyl glycinate (19.3 g, 100 mmol) with ice cooling and the resulting mixture was stirred at room temperature for 24 hours. The solvent was concentrated under reduced pressure, then diluted with ethyl acetate, washed successively with 1 N aqueous hydrochloric acid solution, saturated aqueous sodium bicarbonate solution, and saturated brine, and dried over anhydrous sodium sulfate. The solvent was evaporated under reduced pressure and the resulting residue was purified by silica gel column chromatography (n-hexane: ethyl acetate=2:1) to give the title compound (35.7 g, 87%) as a colorless solid.

$^1$H-NMR (CDCl$_3$) δ: 1.13 (2H, br), 1.22 (3H, t, J=7.4 Hz), 1.25 (2H, br), 1.66 (2H, s), 3.91 (1H, br), 4.12 (2H, q, J=7.4 Hz), 4.91 (2H, brs), 5.36 (2H, brs), 7.19-7.31 (10H, m).

Step 2: 7-Benzyl-4,7-diazaspiro[2.5]octane-5,8-dione

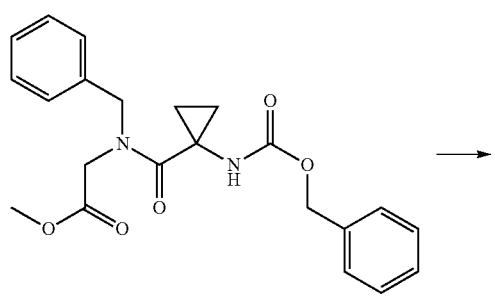

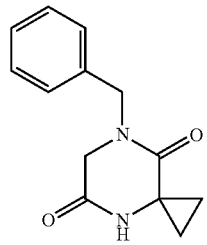

5% Palladium carbon (3.6 g) was added to an ethanol (700 ml) solution of the compound (35.5 g, 86.5 mmol) obtained in Step 1 above and contact reduction was performed for 2 hours in a hydrogen atmosphere. The catalyst was filtrated through celite, the filtrate was concentrated under reduced pressure, and the resulting residue was purified by silica gel column chromatography (n-hexane:ethyl acetate=1:1) to give the title compound (20 g, 100%) as a colorless solid.

$^1$H-NMR (CDCl$_3$) δ: 0.93-1.00 (2H, m), 1.55-1.59 (2H, m), 3.91 (2H, s), 4.60 (2H, s), 7.25-7.37 (5H, m), 7.86 (1H, brs).

Step 3: 7-Benzyl-4,7-diazaspiro[2.5]octane

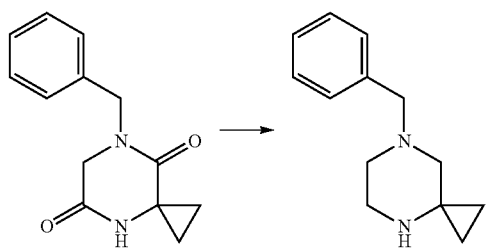

A borane-tetrahydrofuran complex (0.93 M tetrahydrofuran solution) (375 ml, 0.35 mol) was added to a tetrahydrofuran (200 ml) solution of the compound (20 g, 86.8 mmol) obtained in Step 2 above with ice cooling and then the resulting mixture was heated to reflux for 19 hours. Methanol (130 ml) was added to the reaction mixture with ice cooling, the resulting mixture was stirred for 60 minutes, and the solvent was concentrated under reduced pressure. Ethanol (450 ml), water (150 ml), and triethylamine (150 ml) were added to the resulting residue, the resulting mixture was heated to reflux for 2 hours, and then the solvent was concentrated under reduced pressure. The resulting residue was diluted with ethyl acetate, washed successively with saturated aqueous sodium bicarbonate solution and saturated brine, and then dried over anhydrous sodium sulfate. The solvent was evaporated under reduced pressure and the resulting residue was purified by silica gel column chromatography (chloroform:methanol=10:1) to give the title compound (10.4 g, 59%) as a colorless oil.

$^1$H-NMR (CDCl$_3$) δ: 0.41-0.44 (2H, m), 0.57-0.60 (2H, m), 1.49 (1H, br), 2.22 (2H, s), 2.45 (2H, brs), 2.97 (2H, t, J=4.9 Hz), 3.50 (2H, s), 7.22-7.32 (5H, m).

Step 4: 7-Benzyl-4-(trifluoroacetyl)-4,7-diazaspiro[2.5]octane

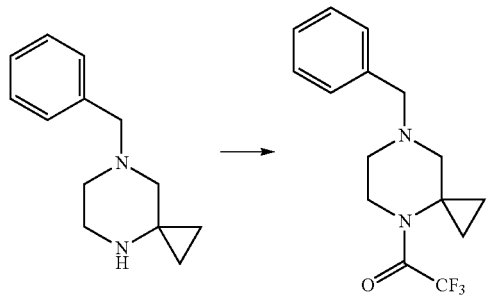

Anhydrous trifluoroacetic acid (8.50 ml, 61.1 mmol) was added dropwise to a methylene chloride (200 ml) solution of the compound (10.3 g, 50.9 mmol) obtained in Step 3 above and triethylamine (17 ml, 122 mmol) with ice cooling and the resulting mixture was stirred at the same temperature for 1 hour. Saturated aqueous sodium bicarbonate solution was added to the reaction mixture, the resulting mixture was diluted with chloroform, washed with saturated brine, and dried over anhydrous sodium sulfate. The solvent was evaporated under reduced pressure to give the title compound (15.5 g, 100%) as a colorless oil.

MS (ESI) m/z: 299 [(M+H)$^+$].

Step 5: 4-(Trifluoroacetyl)-4,7-diazaspiro[2.5]octane hydrochloride

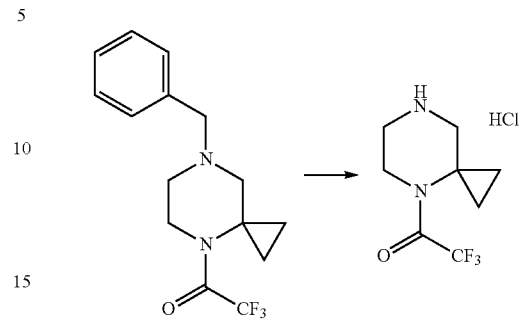

1 N Hydrochloric acid-ethanol (105 ml, 105 mmol) and 5% palladium carbon (3 g) were added to an ethanol (250 ml) solution of the compound (15.5 g, 51 mmol) obtained in Step 4 above and contact reduction was performed for 15 hours in a hydrogen atmosphere. The catalyst was filtrated through celite, then the filtrate was concentrated under reduced pressure, an ethanol-diethyl ether mixed solvent was added to the resulting residue, and the precipitated solid was collected by filtration to give the title compound (10.3 g, 83%) as a colorless solid.

$^1$H-NMR (DMSO-d$_6$, 80° C.) δ: 1.18 (4H, s), 3.16 (2H, s), 3.25 (2H, t, J=5.1 Hz), 3.89 (2H, brs), 9.71 (2H, br).

MS (ESI) m/z: 209 [(M+H)$^+$].

Step 6: 5-[8-(4,7-Diazaspiro[2.5]oct-7-yl)-6-morpholin-4-yl-9-(2,2,2-trifluoroethyl)-9H-purin-2-yl]pyrimidin-2-amine

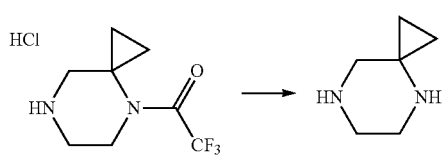

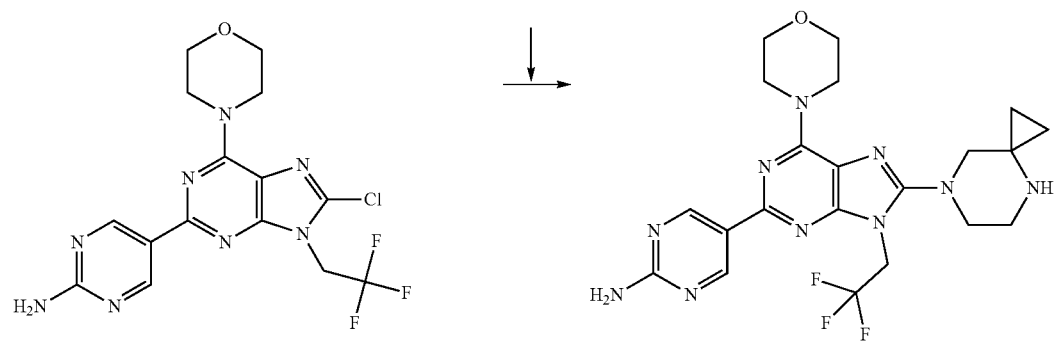

Potassium carbonate (1.19 g, 8.58 mmol) was added to a methanol solution (10 ml) of 4-(trifluoroacetyl)-4,7-diazaspiro[2.5]octane hydrochloride (1.0 g, 4.09 mmol) at room temperature and the resulting mixture was stirred at 50° C. for 16 hours. The resulting mixture was left standing to cool, then potassium carbonate was removed by filtration, and the filtrate was concentrated to give crude 4,7-diazaspiro[2.5]octane. This compound was added to an N-methyl-2-pyrrolidone suspension of 5-[8-chloro-6-morpholin-4-yl-9-(2,2,2-trifluoroethyl)-9H-purin-2-yl]pyrimidin-2-amine (277.4 mg, 0.67 mmol) and dissolved at 120° C. followed by the addition of diisopropylethylamine (1.16 ml, 6.69 mmol) and the resulting mixture was stirred at 100° C. for 4 days. The resulting mixture was left standing to cool, then poured into methylene chloride-methanol (10:1), and washed with saturated aqueous sodium hydrogen carbonate solution. The organic layer was dried over anhydrous sodium sulfate, the mixture was filtrated, the filtrate was concentrated under reduced pressure, and the resulting residue was purified by medium pressure silica gel column chromatography (methylene chloride:methanol=24:1 to 12:1) to give the title compound (83.3 mg, 26%) as a brown amorphous solid.

$^1$H-NMR (CDCl$_3$) δ: 0.56-0.60 (2H, m), 0.71-0.75 (2H, m), 3.04 (2H, s), 3.11-3.19 (4H, m), 3.82-3.89 (4H, m), 4.21-4.35 (4H, m), 4.70 (2H, q, J=8.40 Hz), 5.31 (2H, s), 9.23 (2H, s).

Example 119

5-[8-(4-Acetyl-4,7-diazaspiro[2.5]oct-7-yl)-6-morpholin-4-yl-9-(2,2,2-trifluoroethyl)-9H-purin-2-yl]pyrimidin-2-amine

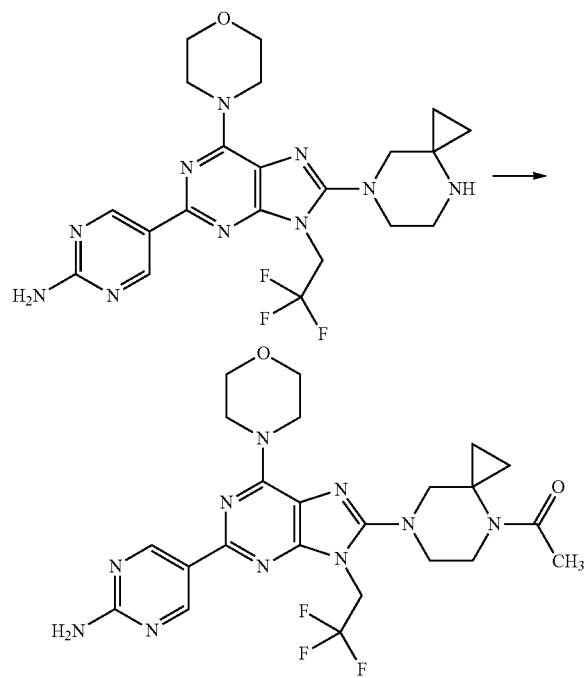

Triethylamine (56.8 μl, 0.41 mmol) and acetic anhydride (19.2 μl, 0.20 mmol) were added to a methylene chloride solution (3.0 ml) of 5-[8-(4,7-diazaspiro[2.5]oct-7-yl)-6-morpholin-4-yl-9-(2,2,2-trifluoroethyl)-9H-purin-2-yl]pyrimidin-2-amine (83.3 mg, 0.17 mmol) at room temperature. The resulting mixture was stirred at room temperature for 2 hours and then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (44.0 mg, 49%) as a light brown solid.

$^1$H-NMR (DMSO-d$_6$, 140° C.) δ: 0.92-1.00 (2H, m), 1.03-1.10 (2H, m), 2.09 (3H, s), 3.09-3.14 (2H, m), 3.20-3.27 (2H, m), 3.71-3.82 (6H, m), 4.14-4.22 (4H, m), 4.87-4.99 (2H, m), 6.43 (2H, s), 9.05 (2H, s).

Example 120

2-{4-[(2-(2-Aminopyrimidin-5-yl)-6-morpholin-4-yl-9-(2,2,2-trifluoroethyl)-9H-purin-8-yl]-cis-2,6-dimethylpiperazin-1-yl}-2-oxoethanol Triethylamine (57.8 μl, 0.41 mmol) and acetoxyacetyl chloride (23.0 μl, 0.21 mmol) were added to a methylene chloride solution (3.0 ml) of 5-[8-(cis-3,5-dimethylpiperazin-1-yl)-6-morpholin-4-yl-9-(2,2,2-trifluoroethyl)-9H-purin-2-yl]pyrimidin-2-amine (92.9 mg, 0.19 mmol) with ice cooling. The resulting mixture was stirred at room temperature for 25 hours followed by the addition of triethylamine (15.8 μl, 0.11 mmol) and acetoxyacetyl chloride (6.3 μl, 0.06 mmol) and the resulting mixture was stirred for 17 hours. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure, a 25% by weight sodium methoxide-methanol solution (86.3 μl, 0.38 mmol) was added to a methanol (9.0 ml) suspension of the resulting residue, and the resulting mixture was stirred at room temperature for 5.5 hours. Tetrahydrofuran (3.0 ml) was added, the resulting mixture was stirred at 40° C. for 16.5 hours, then methanol was concentrated to a half amount under reduced pressure, the resulting mixture was poured into methylene chloride, and the resulting mixture was washed with saturated aqueous sodium hydrogen carbonate solution. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (82.6 mg, 80%) as a pale yellow solid.

$^1$H-NMR (CDCl$_3$) δ: 1.48-1.59 (6H, m), 3.08-3.31 (4H, m), 3.71-3.90 (6H, m), 4.10-4.42 (6H, brm), 4.64-4.92 (3H, brm), 5.40 (2H, s), 9.23 (2H, s).

Example 121

5-[8-(3,3-Dimethylpiperazin-1-yl)-6-morpholin-4-yl-9-(2,2,2-trifluoroethyl)-9H-purin-2-yl]pyrimidin-2-amine

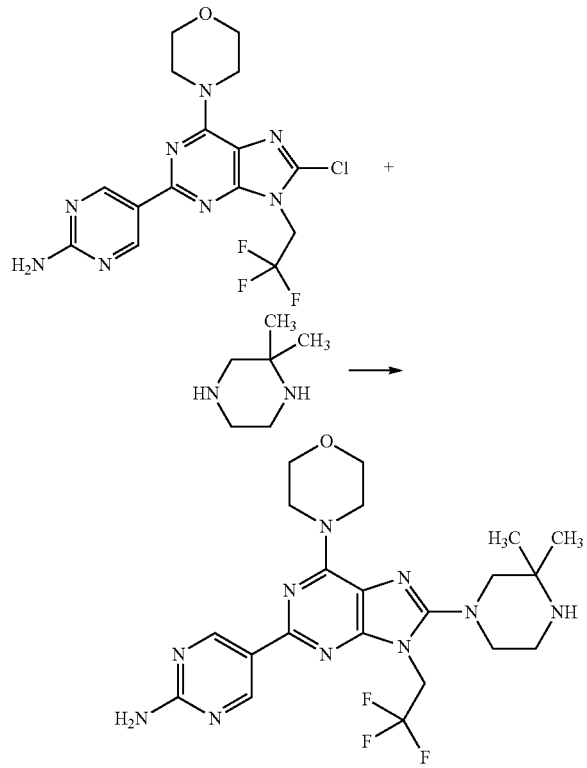

An N-methyl-2-pyrrolidone suspension (5.0 ml) of 5-[8-chloro-6-morpholin-4-yl-9-(2,2,2-trifluoroethyl)-9H-purin-2-yl]pyrimidin-2-amine (492.8 mg, 1.19 mmol) and 2,2-dimethylpiperazine (JMC, 1995, Vol. 38, No. 22, 4389) (571.3 mg, 4.75 mmol) was heated at 120° C. to dissolve and the resulting mixture was stirred at 100° C. for 12 hours. The resulting mixture was left standing to cool, poured into methylene chloride-methanol (10:1), and washed with saturated aqueous sodium hydrogen carbonate solution. The organic layer was dried over anhydrous sodium sulfate, the mixture was filtrated, the filtrate was concentrated under reduced pressure, and the resulting residue was purified by medium pressure silica gel column chromatography (methylene chloride:methanol=49:1 to 13:1) to give the title compound (554.4 mg, 95%) as a pale yellow solid.

$^1$H-NMR (CD$_3$OD/CDCl$_3$=1/1) δ: 1.29 (6H, s), 2.97 (2H, s), 3.06-3.11 (2H, m), 3.12-3.18 (2H, m), 3.84-3.91 (4H, m), 4.25-4.34 (4H, m), 4.82 (2H, q, J=8.40 Hz), 9.17 (2H, s).

Example 122

5-[8-(4-Acetyl-3,3-dimethylpiperazin-1-yl)-6-morpholin-4-yl-9-(2,2,2-trifluoroethyl)-9H-purin-2-yl]pyrimidin-2-amine

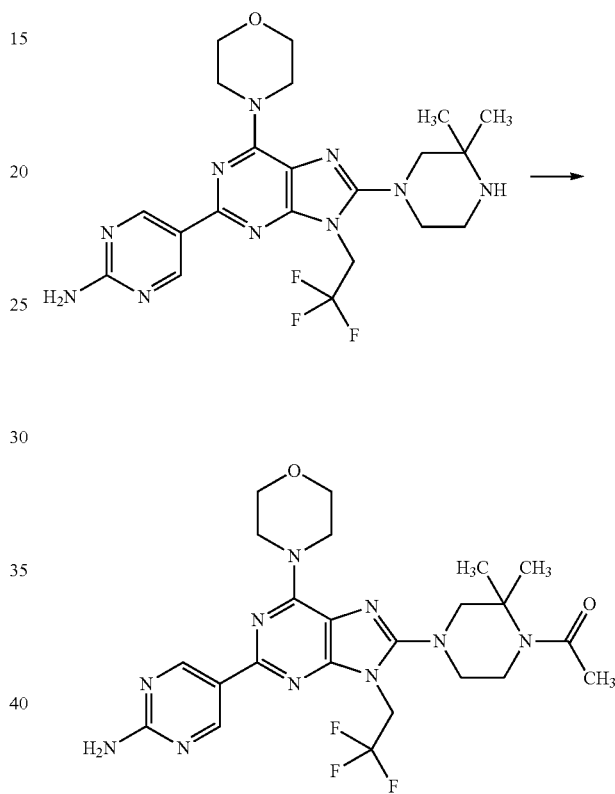

Triethylamine (72.8 μl, 0.52 mmol) and acetic anhydride (24.6 μl, 0.26 mmol) were added to a methylene chloride solution (3.0 ml) of 5-[8-(3,3-dimethylpiperazin-1-yl)-6-morpholin-4-yl-9-(2,2,2-trifluoroethyl)-9H-purin-2-yl]pyrimidin-2-amine (107.2 mg, 0.22 mmol) with ice cooling. The resulting mixture was stirred at room temperature for 2 hours followed by the addition of acetic anhydride (4.1 μl, 0.04 mmol) with ice cooling and the resulting mixture was stirred at room temperature for 4.5 hours. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure and the resulting residue was purified by preparative thin layer silica gel chromatography (methylene chloride:methanol=10:1) to give the title compound (102.6 mg, 88%) as a pale yellow solid.

$^1$H-NMR (CDCl$_3$) δ: 1.58 (6H, s), 2.13 (3H, s), 3.18 (2H, s), 3.46 (2H, t, J=5.44 Hz), 3.68 (2H, t, J=5.44 Hz), 3.84-3.88 (4H, m), 4.22-4.33 (4H, brm), 4.76 (2H, q, J=8.21 Hz), 5.27 (2H, s), 9.23 (2H, s).

Example 123

2-{4-[(2-(2-Aminopyrimidin-5-yl)-6-morpholin-4-yl-9-(2,2,2-trifluoroethyl)-9H-purin-8-yl]-2,2-dimethylpiperazin-1-yl}-2-oxoethanol

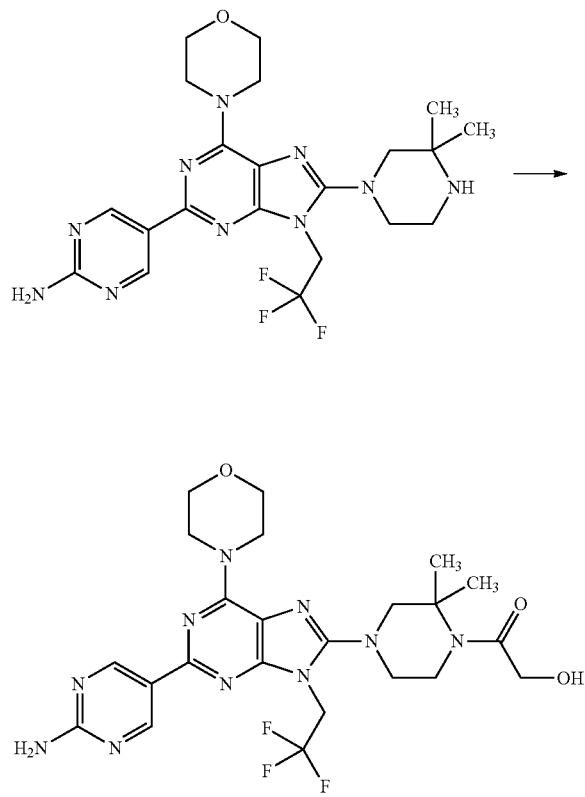

Triethylamine (63.1 μl, 0.45 mmol) was added to a methylene chloride solution (3.0 ml) of 5-[8-(3,3-dimethylpiperazin-1-yl)-6-morpholin-4-yl-9-(2,2,2-trifluoroethyl)-9H-purin-2-yl]pyrimidin-2-amine (101.3 mg, 0.21 mmol) at room temperature followed by the addition of acetoxyacetyl chloride (27.4 μl, 0.25 mmol) with ice cooling. The resulting mixture was stirred at room temperature for 1 hour followed by the addition of triethylamine (17.2 μl, 0.13 mmol) and acetoxyacetyl chloride (6.8 μl, 0.06 mmol) with ice cooling and the resulting mixture was further stirred at room temperature for 16 hours. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure, a 25% by weight sodium methoxide-methanol solution (94.1 μl, 0.41 mmol) was added to a methanol-tetrahydrofuran (3:1) mixture solution (8.0 ml) of the resulting residue, and the resulting mixture was stirred at room temperature for 17 hours. The reaction mixture was poured into methylene chloride and washed with water and the organic layer was dried over anhydrous sodium sulfate. After filtration, the filtrate was concentrated under reduced pressure and the resulting residue was purified by preparative thin layer silica gel chromatography (methylene chloride:methanol=10:1) to give the title compound (94.2 mg, 83%) as a pale yellow solid.

¹H-NMR (CDCl₃/CD₃OD=10/1) δ: 1.62 (6H, s), 3.24 (2H, s), 3.36-3.54 (4H, m), 3.83-3.91 (4H, m), 4.11-4.15 (2H, m), 4.21-4.33 (4H, brm), 4.74-4.85 (2H, m), 9.19 (2H, s).

Example 124

1-{4-[2-(2-Aminopyrimidin-5-yl)-6-morpholin-4-yl-9-(2,2,2-trifluoroethyl)-9H-purin-8-yl]-cis-2,6-dimethylpiperazin-1-yl}-1-oxopropan-2-ol

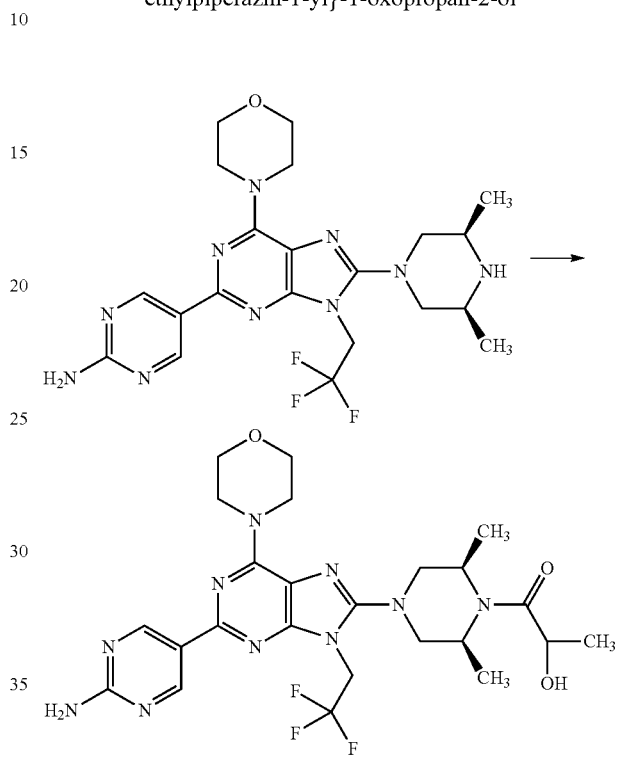

Triethylamine (70.2 μl, 0.50 mmol) and (S)-(−)-2-acetoxypropionyl chloride (32.9 μl, 0.25 mmol) were added to a methylene chloride suspension (7.0 ml) of 5-[8-(cis-3,5-dimethylpiperazin-1-yl)-6-morpholin-4-yl-9-(2,2,2-trifluoroethyl)-9H-purin-2-yl]pyrimidin-2-amine (112.7 mg, 0.23 mmol) with ice cooling. The resulting mixture was stirred at room temperature for 3 hours followed by the addition of (S)-(−)-2-acetoxypropionyl chloride (9.0 μl, 0.07 mmol) with ice cooling and the resulting mixture was stirred at room temperature for 1 day. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure, the resulting residue was dissolved in methylene chloride (7.0 ml) followed by the addition of triethylamine (140.3 μl, 1.01 mmol) and (S)-(−)-2-acetoxypropionyl chloride (65.7 μl, 0.50 mmol) with ice cooling, and the resulting mixture was stirred at room temperature for 1 day. The reaction mixture was poured into methylene chloride-methanol (10:1), washed with saturated aqueous sodium hydrogen carbonate solution, and dried over anhydrous sodium sulfate. After filtration, the filtrate was concentrated under reduced pressure, a 25% by weight sodium methoxide-methanol solution (157.0 μl, 0.69 mmol) was added to a methanol (6.0 ml) solution of the resulting residue, and the resulting mixture was stirred at 50° C. for 22 hours. The resulting mixture was left standing to cool and then the reaction mixture was poured into methylene chloride and washed with saturated brine. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (132.6 mg, 96%) as a pale yellow solid.

$^1$H-NMR (CDCl$_3$) δ: 1.38-1.44 (3H, m), 1.52 (3H, d, J=6.88 Hz), 1.55-1.61 (3H, m), 3.10-3.31 (4H, m), 3.79 (1H, d, J=8.25 Hz), 3.82-3.89 (4H, m), 3.95-4.05 (1H, m), 4.09-4.37 (4H, brm), 4.38-4.49 (1H, m), 4.66-4.90 (3H, m), 5.26 (2H, s), 9.24 (2H, s).

Example 125

2-{(2S)-4-[2-(2-Aminopyrimidin-5-yl)-6-morpholin-4-yl-9-(2,2,2-trifluoroethyl)-9H-purin-8-yl]-2-methylpiperazin-1-yl}-2-oxoethanol

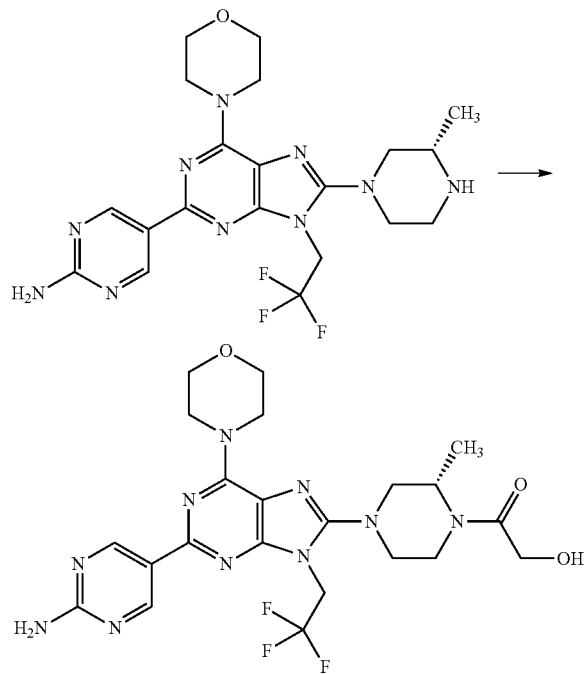

Triethylamine (55.8 μl, 0.40 mmol) was added to a methylene chloride suspension (3.0 ml) of 5-{8-[(3S)-3-methylpiperazin-1-yl]-6-morpholin-4-yl-9-(2,2,2-trifluoroethyl)-9H-purin-2-yl}pyrimidin-2-amine (87.1 mg, 0.18 mmol) at room temperature followed by the addition of acetoxyacetyl chloride (24.2 μl, 0.22 mmol) with ice cooling. The resulting mixture was stirred at room temperature for 90 minutes, then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure, a 25% by weight sodium methoxide-methanol solution (83.3 μl, 0.36 mmol) was added to a methanol-tetrahydrofuran (1:1) mixture solution (12.0 ml) of the resulting white solid, and the resulting mixture was stirred at room temperature for 25.5 hours. The reaction mixture was poured into methylene chloride and washed with saturated brine. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (85.0 mg, 87%) as a pale yellow solid.

$^1$H-NMR (DMSO-d$_6$, 80° C.) δ: 1.31 (3H, d, J=6.87 Hz), 2.84-2.97 (1H, m), 3.03-3.14 (1H, m), 3.24-3.41 (2H, brm), 3.41-3.50 (1H, m), 3.70-3.78 (4H, m), 3.84-4.04 (1H, brm), 4.13 (2H, d, J=5.04 Hz), 4.15-4.22 (4H, m), 4.31-4.55 (2H, brm), 4.90-5.10 (2H, m), 6.76 (2H, s), 9.07 (2H, s).

Example 126

2-{(2R)-4-[2-(2-Aminopyrimidin-5-yl)-6-morpholin-4-yl-9-(2,2,2-trifluoroethyl)-9H-purin-8-yl]-2-methylpiperazin-1-yl}-2-oxoethanol

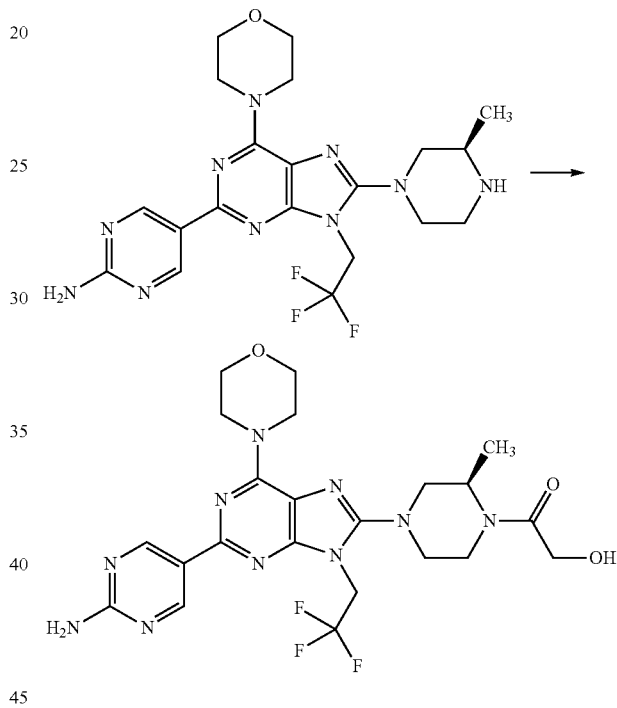

Triethylamine (55.9 μl, 0.40 mmol) was added to a methylene chloride suspension (3.0 ml) of 5-{8-[(3R)-3-methylpiperazin-1-yl]-6-morpholin-4-yl-9-(2,2,2-trifluoroethyl)-9H-purin-2-yl}pyrimidin-2-amine (87.2 mg, 0.18 mmol) at room temperature followed by the addition of acetoxyacetyl chloride (24.2 μl, 0.22 mmol) with ice cooling. The resulting mixture was stirred at room temperature for 1 hour, then the reaction mixture was poured into methylene chloride-methanol (10:1), washed with saturated aqueous sodium hydrogen carbonate solution, and dried over anhydrous sodium sulfate. After filtration, the filtrate was concentrated under reduced pressure, a 25% by weight sodium methoxide-methanol solution (83.3 μl, 0.36 mmol) was added to a methanol-tetrahydrofuran (1:1) mixture solution (12.0 ml) of the resulting white solid, and the resulting mixture was stirred at room temperature for 24 hours. The reaction mixture was poured into methylene chloride and washed with saturated brine. The organic layer was dried over anhydrous sodium sulfate, the mixture was filtrated, the filtrate was concentrated under reduced pressure, and the resulting residue was purified by preparative thin layer silica gel chromatography (methylene chloride:methanol=10:1) to give the title compound (85.2 mg, 87%) as a pale yellow solid.

¹H-NMR (DMSO-d₆: 80° C.) δ: 1.31 (3H, d, J=6.41 Hz), 2.84-2.96 (1H, m), 3.05-3.14 (1H, m), 3.25-3.40 (2H, brm), 3.41-3.50 (1H, m), 3.71-3.77 (4H, m), 3.82-4.06 (1H, brm), 4.10-4.15 (2H, m), 4.15-4.21 (4H, m), 4.32-4.55 (2H, brm), 4.90-5.10 (2H, m), 6.76 (2H, s), 9.07 (2H, s).

Example 127

5-{6-[(3S)-3-Methylmorpholin-4-yl]-8-[4-(methylsulfonyl)piperazin-1-yl]-9-(2,2,2-trifluoroethyl)-9H-purin-2-yl}pyrimidin-2-amine

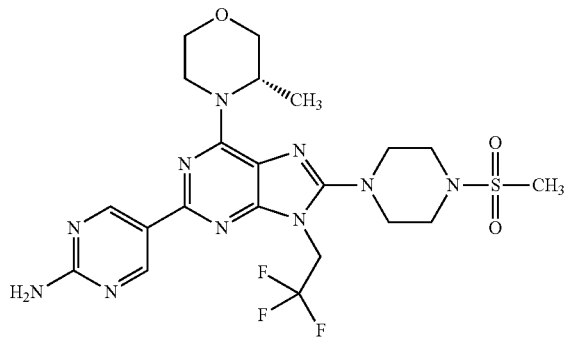

Step 1: 2-Chloro-6-[(3S)-3-methylmorpholin-4-yl]-9H-purine

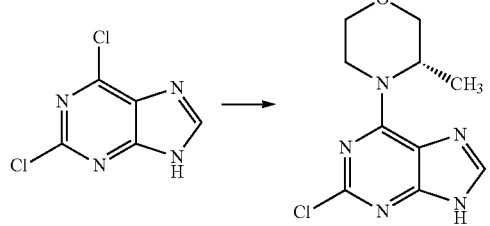

An ethanol (5 ml) solution of 2,6-dichloro-9H-purine (187 mg, 0.99 mmol), (S)-3-methyl-morpholine (100 mg, 0.99 mmol), and N,N-diisopropylethylamine (252 μl, 1.48 mmol) was heated to reflux for 15 hours. The reaction mixture was returned to room temperature and concentrated under reduced pressure. The residue was purified by flash silica gel column chromatography (methylene chloride:methanol=98:2 to 97:3) to give the title compound (132 mg, 53%) as a solid.

ESI-MS (m/z): 254 (M+1)⁺.

Step 2: 2-Chloro-6-[(3S)-3-methylmorpholin-4-yl]-9-(2,2,2-trifluoroethyl)-9H-purine

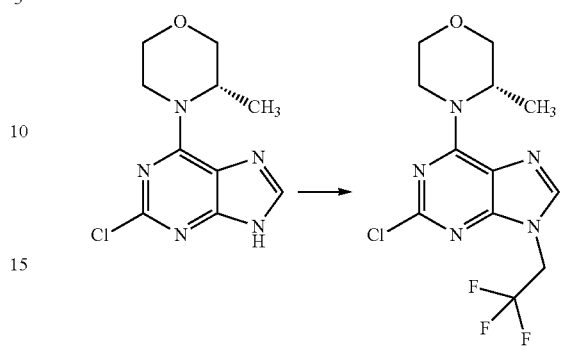

2,2,2-Trifluoroethyltrifluoromethyl sulfonate (83 μl, 0.57 mmol) was added to an N,N-dimethylformamide (5 ml) suspension of 2-chloro-6-[(3S)-3-methylmorpholin-4-yl]-9H-purine (132 mg, 0.52 mmol) and potassium carbonate (86 mg, 0.62 mmol) with ice cooling. The reaction mixture was stirred at 50° C. for 2 hours and returned to room temperature. Water was added to the reaction mixture and the resulting mixture was extracted with ethyl acetate. The organic layer was washed with saturated brine and dried over anhydrous magnesium sulfate and, after filtration, the filtrate was concentrated under reduced pressure. The residue was purified by flash silica gel column chromatography (30% ethyl acetate: hexane) to give the title compound (133 mg, 76%) as a solid.

ESI-MS (m/z): 336 (M+1)⁺.

Step 3: 5-{6-[(3S)-3-Methylmorpholin-4-yl]-9-(2,2,2-trifluoroethyl)-9H-purin-2-yl}pyrimidin-2-amine

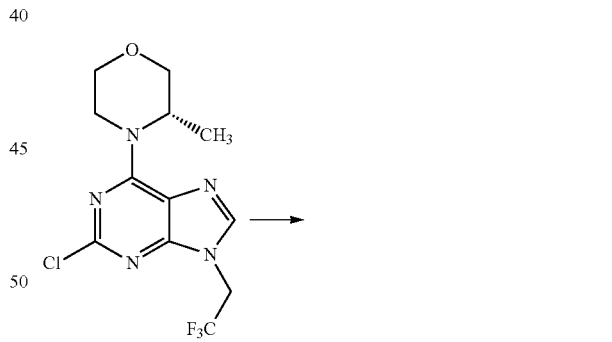

Tetrakis triphenylphosphine (62 mg, 0.05 mmol) was added to a dioxane (5 ml)-water (1 ml) suspension of 2-chloro-6-[(3S)-3-methylmorpholin-4-yl]-9-(2,2,2-trifluoroethyl)-9H-purine (361 mg, 1.08 mmol), 5-(4,4,5,5-tetramethyl-1,3,2-dioxaborolan-2-yl)pyrimidin-2-amine (261 mg, 1.18 mmol), and sodium carbonate (342 mg, 3.23 mmol). The reaction mixture was heated to reflux for 2.5 hours and returned to room temperature. Water was added to the reaction mixture and the resulting mixture was extracted with 10% methanol-chloroform. The organic layer was dried over anhydrous magnesium sulfate and, after filtration, the filtrate was concentrated under reduced pressure. The residue was purified by silica gel column chromatography (chloroform to chloroform:methanol=15:1) to give a solid. The resulting solid was washed with 50% ethyl acetate-hexane and dried to give the title compound (423 mg) as a powder.

ESI-MS (m/z): 395 (M+1)$^+$.

$^1$H-NMR (CDCl$_3$) δ: 1.45 (3H, d, J=6.8 Hz), 3.47-3.89 (4H, m), 4.03-4.11 (1H, m), 4.84 (2H, q, J=8.5 Hz), 5.00-5.61 (4H, m), 7.80 (1H, s), 9.26 (2H, s).

Step 4: Di-tert-butyl (5-{6-[(3S)-3-methylmorpholin-4-yl]-9-(2,2,2-trifluoroethyl)-9H-purin-2-yl}pyrimidin-2-yl)imidedicarbamate

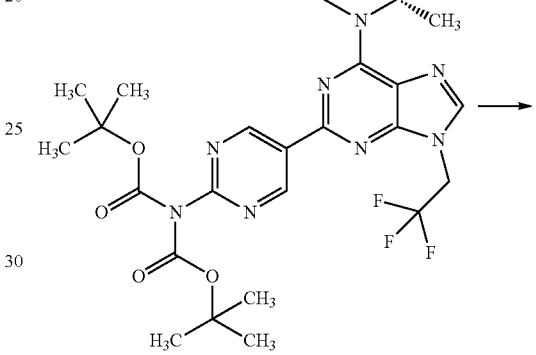

An N,N-dimethylformamide (4 ml) solution of tert-butyl dicarbonate (1.17 g, 5.36 mmol) was added to an N,N-dimethylformamide (4 ml) solution of 5-{6-[(3S)-3-methylmorpholin-4-yl]-9-(2,2,2-trifluoroethyl)-9H-purin-2-yl}pyrimidin-2-amine (423 mg, 1.07 mmol) and 4-dimethylaminopyridine (26 mg, 0.21 mmol). The reaction mixture was stirred at room temperature for 17 hours. Ethyl acetate was added to the reaction mixture and the resulting mixture was washed with water and saturated brine. The organic layer was dried over anhydrous magnesium sulfate and, after filtration, the filtrate was concentrated under reduced pressure. The residue was purified by flash silica gel column chromatography (ethyl acetate:hexane=1:1) to give the title compound (606 mg, 95%) as an amorphous substance.

ESI-MS (m/z): 595 (M+1)$^+$.

$^1$H-NMR (CDCl$_3$) δ: 1.45-1.50 (21H, m), 3.51-3.90 (4H, m), 4.04-4.12 (1H, m), 4.87 (2H, q, J=8.6 Hz), 5.01-5.65 (2H, m), 7.87 (1H, s), 9.65 (2H, s).

Step 5: Di-tert-butyl (5-{8-chloro-6-[(3S)-3-methylmorpholin-4-yl]-9-(2,2,2-trifluoroethyl)-9H-purin-2-yl}pyrimidin-2-yl)imidedicarbamate

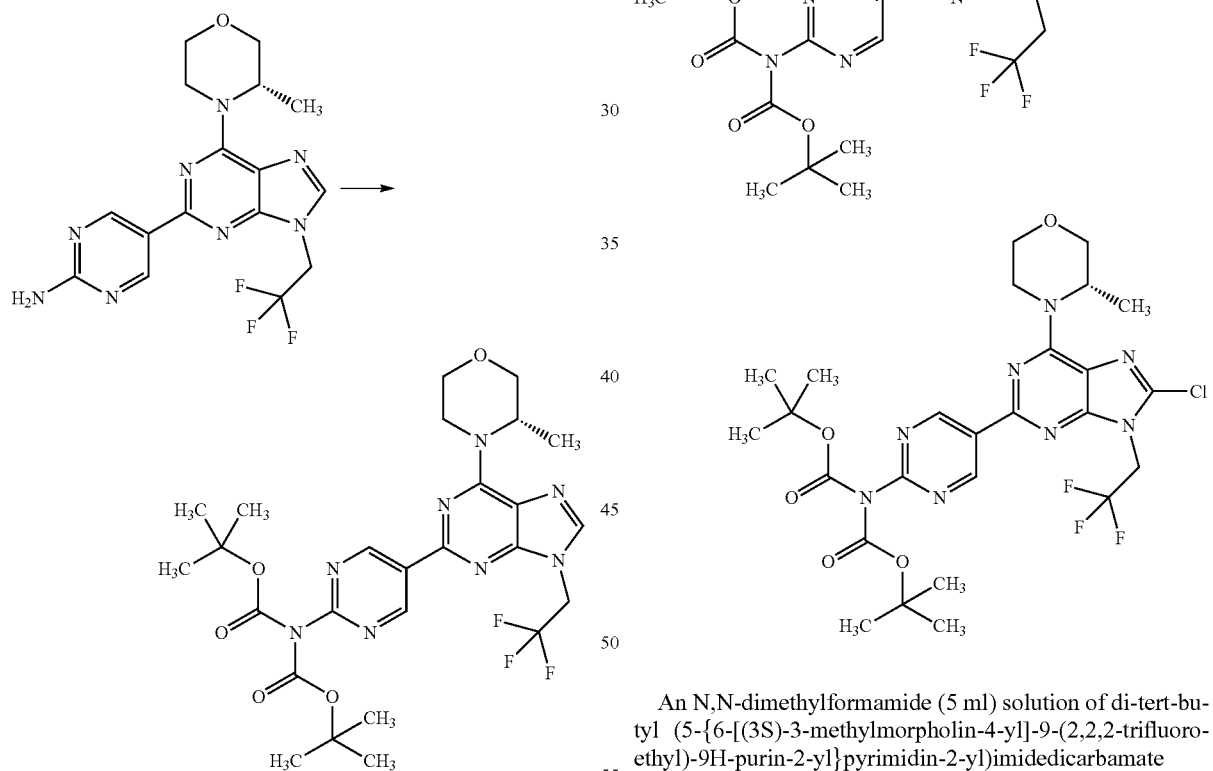

An N,N-dimethylformamide (5 ml) solution of di-tert-butyl (5-{6-[(3S)-3-methylmorpholin-4-yl]-9-(2,2,2-trifluoroethyl)-9H-purin-2-yl}pyrimidin-2-yl)imidedicarbamate (606 mg, 1.02 mmol) and N-chlorosuccinimide (177 mg, 1.32 mmol) was stirred at 50° C. for 1 hour. N-chlorosuccinimide (136 mg, 1.02 mmol) was added to the reaction solution and the resulting mixture was stirred at 50° C. for 1 hour and returned to room temperature. Ethyl acetate was added to the reaction solution and the resulting mixture was washed with water and saturated brine. The organic layer was dried over anhydrous magnesium sulfate and, after filtration, the filtrate was concentrated under reduced pressure. The residue was purified by flash silica gel column chromatography (hexane:ethyl acetate=8:2) to give the title compound (306 mg, 48%) as a solid.

¹H-NMR (CDCl₃) δ: 1.46 (3H, d, J=6.8 Hz), 1.49 (18H, s), 3.50-3.89 (4H, m), 4.04-4.11 (1H, m), 4.86 (2H, q, J=8.0 Hz), 4.93-5.48 (2H, m), 9.62 (2H, s).

Step 6: tert-Butyl (5-{6-[(3S)-3-methylmorpholin-4-yl]-8-[4-(methylsulfonyl)piperazin-1-yl]-9-(2,2,2-trifluoroethyl)-9H-purin-2-yl}pyrimidin-2-yl)carbamate

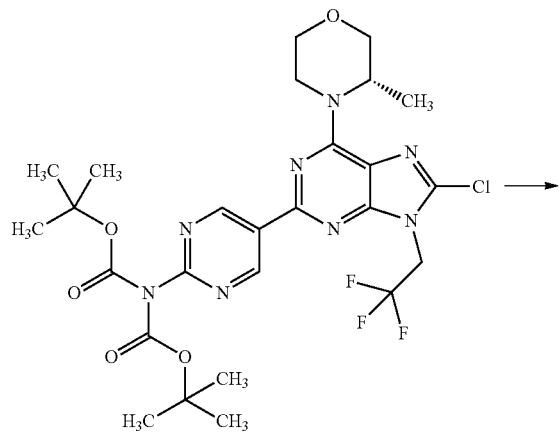

A dimethyl sulfoxide (2 ml) solution of di-tert-butyl (5-{8-chloro-6-[(3S)-3-methylmorpholin-4-yl]-9-(2,2,2-trifluoroethyl)-9H-purin-2-yl}pyrimidin-2-yl)imidedicarbamate (306 mg, 0.49 mmol) and piperazine (210 mg, 2.43 mmol) was stirred at 80° C. for 3 hours. The reaction mixture was returned to room temperature followed by the addition of ethyl acetate and the resulting mixture was washed with saturated brine. The organic layer was dried over anhydrous magnesium sulfate and, after filtration, the filtrate was concentrated under reduced pressure. The residue was purified by flash silica gel column chromatography (7 N ammonia-methanol solution:methylene chloride=97:3).

Methanesulfonyl chloride (57 μl, 0.74 mmol) was added to a methylene chloride (5 ml) solution of the resulting residue, triethylamine (122 μl, 0.88 mmol), and a catalytic amount of 4-dimethylaminopyridine with ice cooling. The reaction solution was stirred at room temperature for 16 hours and concentrated under reduced pressure. The residue was purified by flash silica gel column chromatography (methylene chloride:ethyl acetate=6:4) to give the title compound (199 mg, 62%).

¹H-NMR (CDCl₃) δ: 1.41 (3H, d, J=6.8 Hz), 1.56 (9H, s), 2.87 (3H, s), 3.30-3.36 (4H, m), 3.41-3.53 (5H, m), 3.62-3.72 (1H, m), 3.78-3.87 (2H, m), 4.02-4.09 (1H, m), 4.71 (2H, q, J=8.3 Hz), 5.00-5.40 (2H, m), 7.79 (1H, s), 9.48 (2H, s).

Step 7: 5-{6-[(3S)-3-Methylmorpholin-4-yl]-8-[4-(methylsulfonyl)piperazin-1-yl]-9-(2,2,2-trifluoroethyl)-9H-purin-2-yl}pyrimidin-2-amine

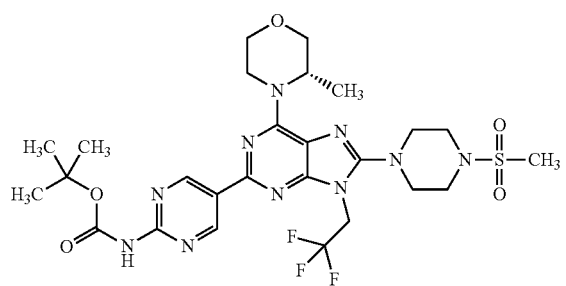

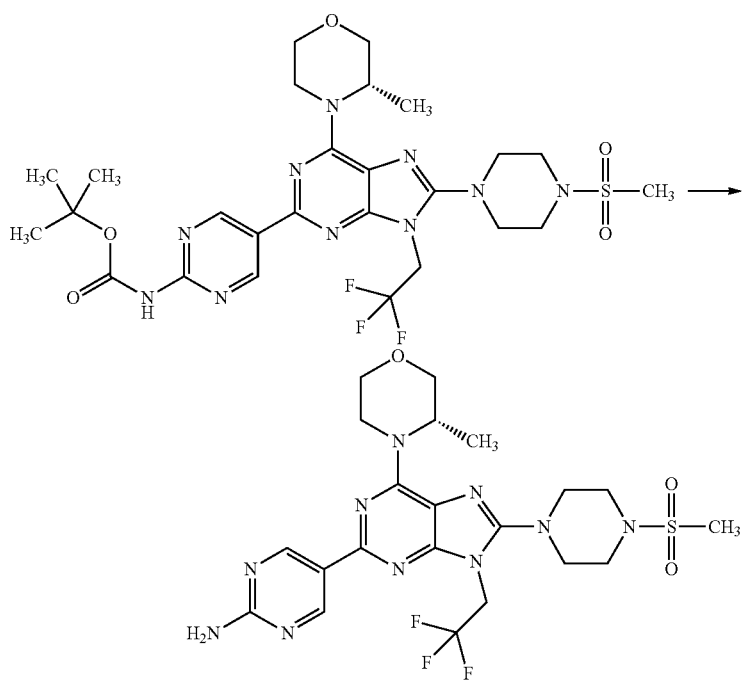

A methylene chloride (5 ml) solution of tert-butyl (5-{6-[(3S)-3-methylmorpholin-4-yl]-8-[4-(methylsulfonyl)piperazin-1-yl]-9-(2,2,2-trifluoroethyl)-9H-purin-2-yl}pyrimidin-2-yl)carbamate (199 mg, 0.30 mmol) and trifluoroacetic acid (1 ml) was stirred at room temperature for 1.5 hours and concentrated under reduced pressure. Chloroform and saturated aqueous sodium hydrogen carbonate solution were added to the residue and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=96:4) to give a solid. The resulting solid was washed with ether-hexane and dried to give the title compound (140 mg, 83%) as a powder.

ESI-MS (m/z): 557 (M+1)$^+$.

$^1$H-NMR (CDCl$_3$) δ: 1.41 (3H, d, J=6.8 Hz), 2.87 (3H, s), 3.29-3.35 (4H, m), 3.41-3.55 (5H, m), 3.63-3.72 (1H, m), 3.79-3.87 (2H, m), 4.02-4.09 (1H, m), 4.71 (2H, q, J=8.4 Hz), 4.98-5.16 (1H, m), 5.22 (2H, s), 5.29-5.43 (1H, m), 9.23 (2H, s).

Example 128

5-{8-(4-acetylpiperazin-1-yl)-9-(cyclopropylmethyl)-6-[(3S)-3-methylmorpholin-4-yl]-9H-purin-2-yl}-4-methylpyrimidin-2-amine

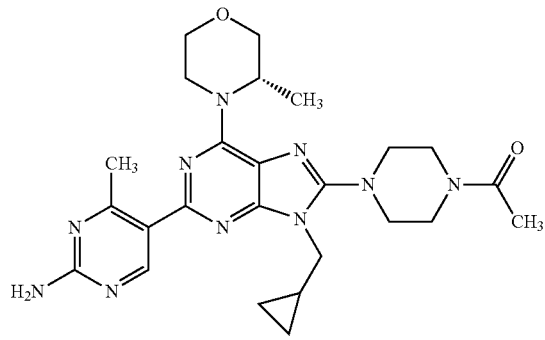

Step 1: 2-Chloro-9-(cyclopropylmethyl)-6-[(3S)-3-methylmorpholin-4-yl]-9H-purine

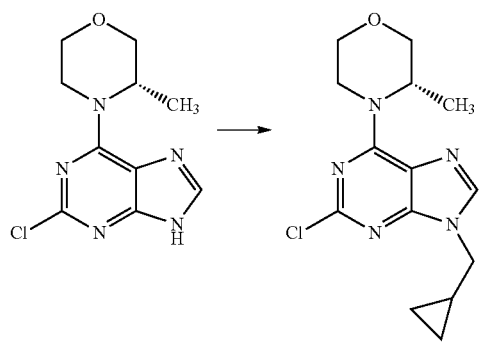

Diisopropyl azodicarboxylate (1.9 M toluene solution, 1.3 ml) was added to a tetrahydrofuran (20 ml) solution of 2-chloro-9-(cyclopropylmethyl)-6-[(3S)-3-methylmorpholin-4-yl]-9H-purine (522 mg, 2.06 mmol), cyclopropylmethanol (163 mg, 2.26 mmol), and triphenylphosphine (648 mg, 2.47 mmol) with ice cooling. The reaction mixture was stirred at room temperature for 16 hours. Ethyl acetate was added to the reaction mixture and the resulting mixture was washed with water and saturated brine. The organic layer was dried over anhydrous magnesium sulfate and, after filtration, the filtrate was concentrated under reduced pressure. The residue was purified by flash silica gel column chromatography (hexane:ethyl acetate=7:3). The resulting residue was purified by flash silica gel column chromatography (hexane:acetone=4:1) to give the title compound (516 mg, 82%).

ESI-MS (m/z): 307 (M+1)$^+$.

$^1$H-NMR (CDCl$_3$) δ: 0.40-0.46 (2H, m), 0.63-0.70 (2H, m), 1.23-1.37 (1H, m), 1.43 (3H, d, J=6.8 Hz), 3.42-3.68 (2H, m), 3.75-3.84 (2H, m), 3.97-4.05 (3H, m), 4.93-5.64 (2H, m), 7.82 (1H, s).

Step 2: Di-tert-butyl (5-{9-(cyclopropylmethyl)-6-[(3S)-3-methylmorpholin-4-yl]-9H-purin-2-yl}-4-methylpyrimidin-2-yl)imidedicarbonate

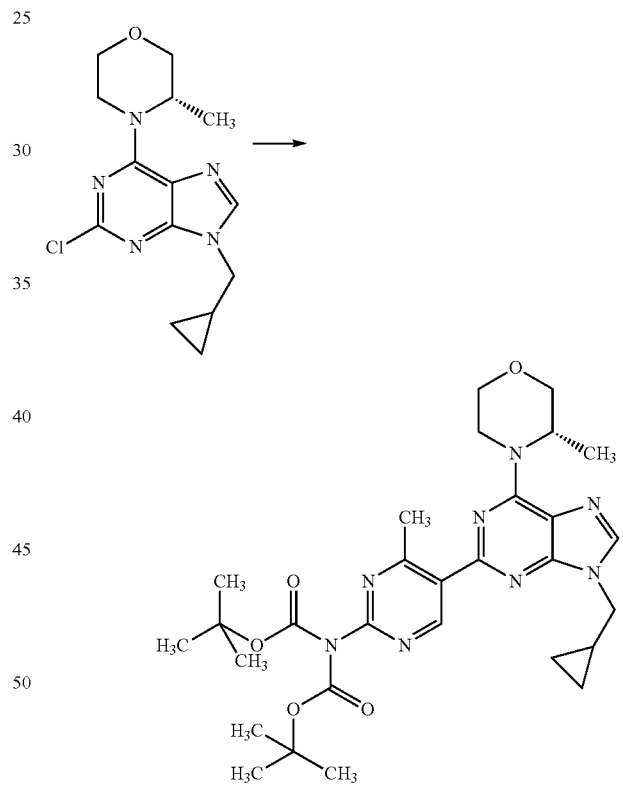

A dioxane (5 ml)-water (1 ml) suspension of 2-chloro-9-(cyclopropylmethyl)-6-[(3S)-3-methylmorpholin-4-yl]-9H-purine (248 mg, 0.81 mmol), di-tert-butyl [4-methyl-5-(4,4,5,5-tetramethyl-1,3,2-dioxaborolan-2-yl)pyrimidin-2-yl] imide dicarbonate (178 mg, 0.81 mmol), tetrakis triphenylphosphine palladium (93 mg, 0.08 mmol), and sodium carbonate (256 mg, 2.42 mmol) was heated to reflux for 3 hours and returned to room temperature. Water was added to the reaction mixture and the resulting mixture was extracted with chloroform. The organic layer was dried over anhydrous magnesium sulfate and, after filtration, the filtrate was concentrated under reduced pressure. The residue was purified by flash silica gel column chromatography (ethyl acetate:hexane=1:1) to give the title compound (426 mg, 84%) as an amorphous substance.

$^1$H-NMR (CDCl$_3$) δ: 0.44-0.50 (2H, m), 0.65-0.71 (2H, m), 1.30-1.39 (1H, m), 1.45 (3H, d, J=6.8 Hz), 1.49 (18H, s), 2.92 (3H, s), 3.46-3.73 (2H, m), 3.79-3.88 (2H, m), 4.03-4.10 (3H, m), 5.06-5.69 (2H, s), 7.90 (1H, s), 9.33 (1H, s).

Step 3: Di-tert-butyl (5-{8-chloro-9-(cyclopropylmethyl)-6-[(3S)-3-methylmorpholin-4-yl]-9H-purin-2-yl}-4-methylpyrimidin-2-yl)imide dicarbonate

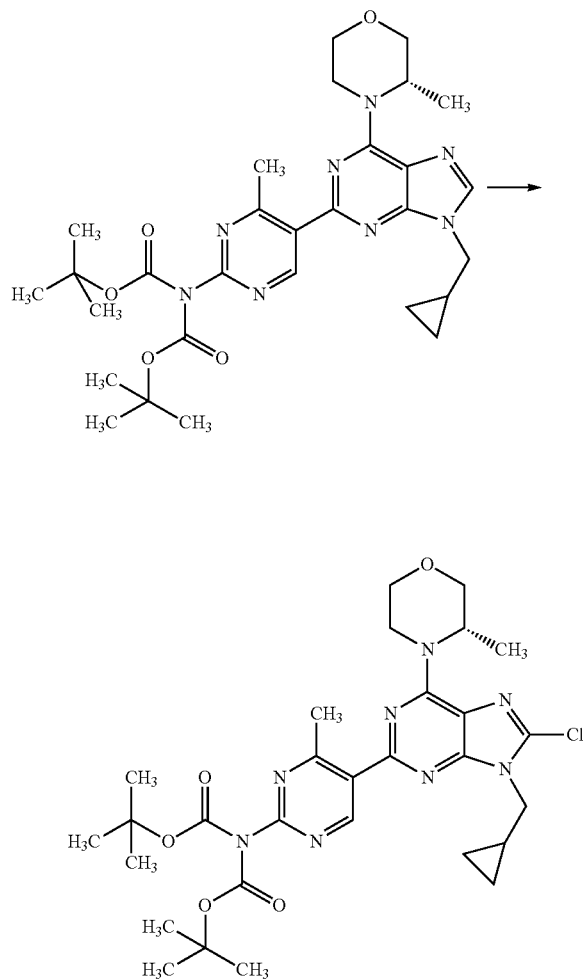

An N,N-dimethylformamide (5 ml) solution of di-tert-butyl (5-{9-(cyclopropylmethyl)-6-[(3S)-3-methylmorpholin-4-yl]-9H-purin-2-yl}-4-methylpyrimidin-2-yl)imidedicarbonate (426 mg, 0.73 mmol) and N-chlorosuccinimide (118 mg, 0.88 mmol) was stirred at room temperature for 4 hours. Ethyl acetate was added to the reaction mixture and the resulting mixture was washed with water and saturated brine. The organic layer was dried over anhydrous magnesium sulfate and, after filtration, the filtrate was concentrated under reduced pressure. The residue was purified by flash silica gel column chromatography (hexane:ethyl acetate=7:3) to give the title compound (344 mg, 76%) as an amorphous substance.

$^1$H-NMR (CDCl$_3$) δ: 0.49-0.62 (4H, m), 1.32-1.41 (1H, m), 1.44 (3H, d,=6.8 Hz), 1.50 (18H, s), 2.90 (3H, s), 3.43-3.71 (2H, m), 3.77-3.86 (2H, m), 4.02-4.13 (3H, m), 4.99-5.47 (2H, s), 9.31 (1H, s).

Step 4: 5-{8-(4-acetylpiperazin-1-yl)-9-(cyclopropylmethyl)-6-[(3S)-3-methylmorpholin-4-yl]-9H-purin-2-yl}-4-methylpyrimidin-2-amine

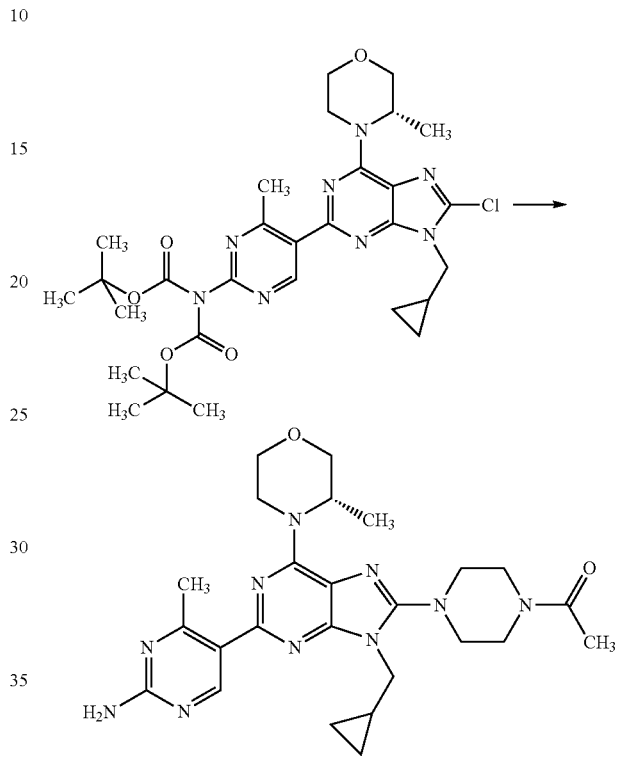

A methylene chloride (3 ml) solution of di-tert-butyl (5-[8-chloro-9-(cyclopropylmethyl)-6-[(3S)-3-methylmorpholin-4-yl]-9H-purin-2-yl]-4-methylpyrimidin-2-yl)imidedicarbonate (344 mg, 0.56 mmol) and trifluoroacetic acid (1 ml) was stirred at room temperature for 2 hours and concentrated under reduced pressure. Chloroform and saturated aqueous sodium hydrogen carbonate solution were added to the residue and the resulting mixture was extracted with chloroform. The organic layer was dried over anhydrous magnesium sulfate and, after filtration, the filtrate was concentrated under reduced pressure.

An N-methyl-2-pyrrolidone (2 ml) solution of the resulting residue and 1-acetylpiperazine (717 mg, 5.59 mmol) was stirred at 120° C. for 16 hours. The reaction mixture was returned to room temperature followed by the addition of methylene chloride and saturated aqueous sodium hydrogen carbonate solution and the resulting mixture was extracted with ethyl acetate. The organic layer was dried over anhydrous magnesium sulfate and, after filtration, the filtrate was concentrated under reduced pressure. The residue was purified by flash silica gel column chromatography (methylene chloride:methanol=95:5). The resulting residue was purified by flash NH silica gel column chromatography (ethyl acetate) to give a solid. The resulting solid was washed with hexane and dried to give the title compound (79 mg, 28%) as a powder.

$^1$H-NMR (CDCl$_3$) δ: 0.46-0.59 (4H, m), 1.32-1.42 (4H, m), 2.16 (3H, s), 2.74 (3H, s), 3.21-3.33 (4H, m), 3.43-3.55

(1H, m), 3.62-3.71 (3H, m), 3.78-3.84 (4H, m), 3.97 (2H, d, J=7.1 Hz), 4.00-4.06 (1H, m), 5.02-5.12 (3H, m), 5.27-5.43 (1H, m), 8.92 (1H, s).

Example 129

5-{8-(4-Acetylpiperazin-1-yl)-9-isobutyl-6-[(3S)-3-methylmorpholin-4-yl]-9H-purin-2-yl}pyrimidin-2-amine

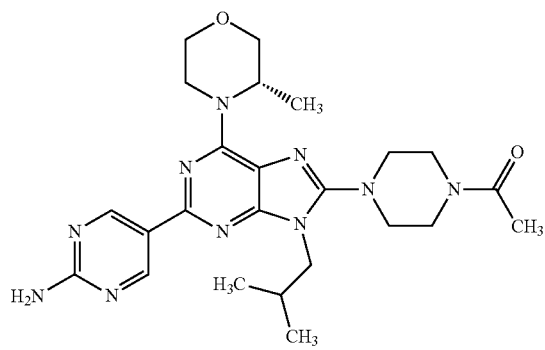

Step 1: 2-Chloro-9-isobutyl-6-[(3S)-3-methylmorpholin-4-yl]-9H-purine

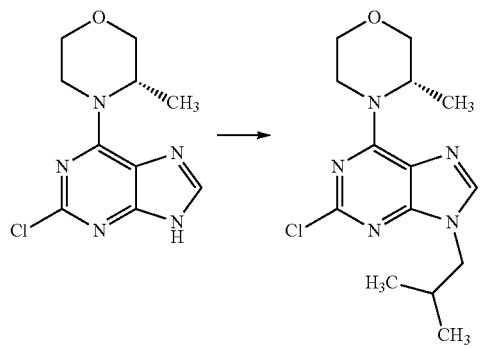

An N,N-dimethylformamide (5 ml) suspension of 2-chloro-6-((S)-3-methylmorpholin-4-yl)-9H-purine (839 mg, 3.31 mmol), 1-iodo-2-methylpropane (730 mg, 3.97 mmol), and potassium carbonate (594 mg, 4.30 mmol) was stirred at 50° C. for 4 hours. The reaction mixture was returned to room temperature. Ethyl acetate was added to the reaction mixture and the resulting mixture was washed with water and saturated brine. The organic layer was dried over anhydrous magnesium sulfate and, after filtration, the filtrate was concentrated under reduced pressure. The residue was purified by flash silica gel column chromatography (hexane:ethyl acetate=7:3) to give the title compound (868 mg, 85%) as an amorphous substance.

$^1$H-NMR (CDCl$_3$) δ: 0.94 (6H, d, J=7.1 Hz), 1.43 (3H, d, J=6.8 Hz), 2.18-2.31 (1H, m), 3.40-3.68 (2H, m), 3.75-3.84 (2H, m), 3.92-4.05 (3H, m), 4.91-5.65 (2H, m), 7.66 (1H, s).

Step 2: 5-{9-Isobutyl-6-[(3S)-3-methylmorpholin-4-yl]-9H-purin-2-yl}pyrimidin-2-amine

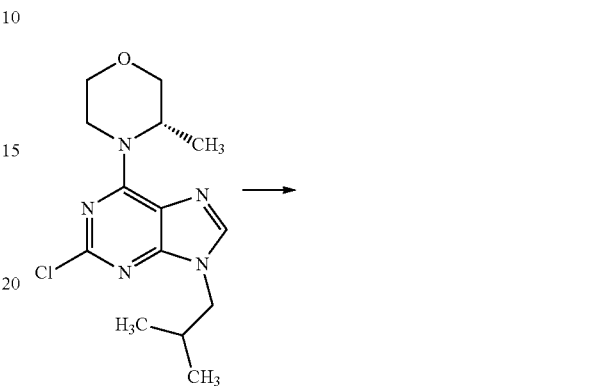

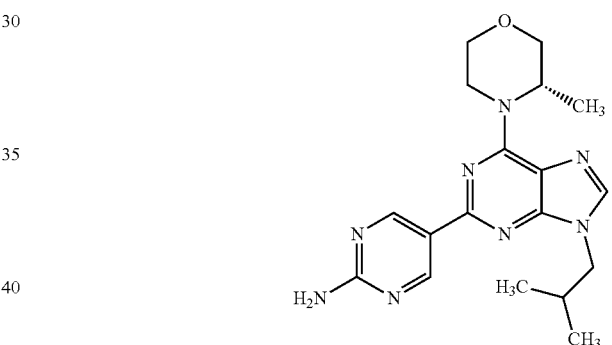

A dioxane (5 ml)-water (1 ml) suspension of 2-chloro-9-isobutyl-6-[(3S)-3-methylmorpholin-4-yl]-9H-purine (317 mg, 1.02 mmol), 5-(4,4,5,5-tetramethyl-1,3,2-dioxaborolan-2-yl)pyrimidin-2-amine (226 mg, 1.02 mmol), sodium carbonate (325 mg, 3.07 mmol), and tetrakis triphenylphosphine palladium (118 mg, 0.10 mmol) was heated to reflux for 2.5 hours. The reaction mixture was returned to room temperature. Water was added to the reaction mixture and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=96:4). The residue was purified by flash silica gel column chromatography (ethyl acetate) to give the title compound (287 mg, 76%) as a solid.

$^1$H-NMR (CDCl$_3$) δ: 0.97 (6H, d, J=6.6 Hz), 1.45 (3H, d, J=6.8 Hz), 2.24-2.35 (1H, m), 3.47-3.74 (2H, m), 3.83-3.86 (2H, m), 4.00-4.10 (3H, m), 5.14-5.26 (3H, m), 5.39-5.62 (1H, m), 7.69 (1H, s), 9.27 (2H, s).

Step 3: Di-tert-butyl (5-{8-chloro-9-isobutyl-6-[(3S)-3-methylmorpholin-4-yl]-9H-purin-2-yl}pyrimidin-2-yl)imidedicarbonate

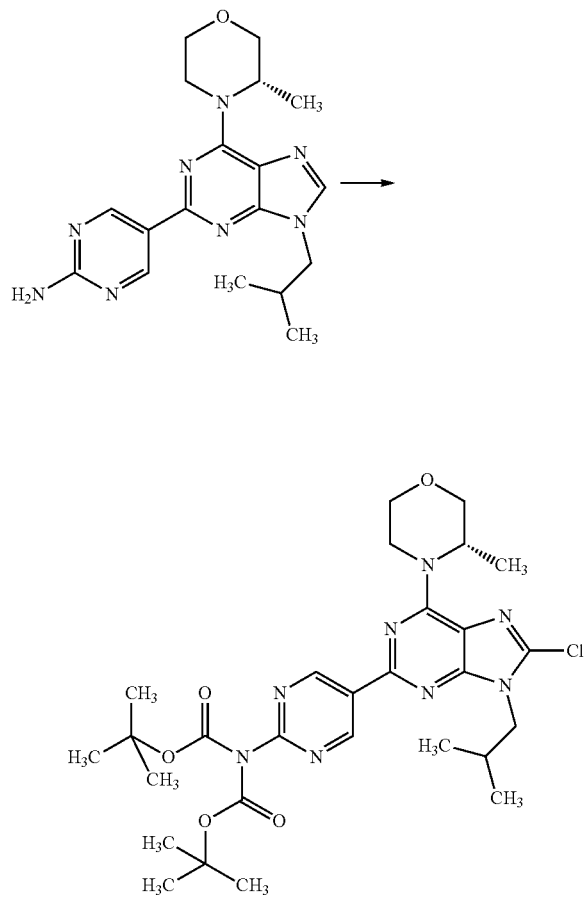

An N,N-dimethylformamide (5 ml) solution of 5-{9-isobutyl-6-[(3S)-3-methylmorpholin-4-yl]-9H-purin-2-yl}pyrimidin-2-amine (287 mg, 0.78 mmol), di-tert-butyl dicarbonate (850 mg, 3.89 mmol), and 4-dimethylaminopyridine (19 mg, 0.16 mmol) was stirred at room temperature for 15 hours. Ethyl acetate was added to the reaction mixture and the resulting mixture was washed with water and saturated brine. The organic layer was dried over anhydrous magnesium sulfate and, after filtration, the filtrate was concentrated under reduced pressure. The residue was purified by flash silica gel column chromatography (ethyl acetate:hexane=1:1).

An N,N-dimethylformamide (5 ml) solution of the resulting residue and N-chlorosuccinimide (109 mg, 0.81 mmol) was stirred at room temperature for 5 hours. N-chlorosuccinimide (50 mg) was added to the reaction mixture and the resulting mixture was stirred at room temperature for 21 hours. Ethyl acetate was added to the reaction mixture and the resulting mixture was washed with water and saturated brine. The organic layer was dried over anhydrous magnesium sulfate and, after filtration, the filtrate was concentrated under reduced pressure. The residue was purified by flash silica gel column chromatography (hexane:ethyl acetate=7:3) to give the title compound (290 mg) as an amorphous substance.

$^1$H-NMR (CDCl$_3$) δ: 0.99 (6H, d, J=6.8 Hz), 1.45 (3H, d, J=6.8 Hz), 1.49 (18H, s), 2.32-2.41 (1H, m), 3.47-3.72 (2H, m), 3.79-3.89 (2H, m), 4.02-4.11 (3H, m), 4.99-5.48 (2H, m), 9.64 (2H, s).

Step 4: 5-{8-(4-Acetylpiperazin-1-yl)-9-isobutyl-6-[(3S)-3-methylmorpholin-4-yl]-9H-purin-2-yl}pyrimidin-2-amine

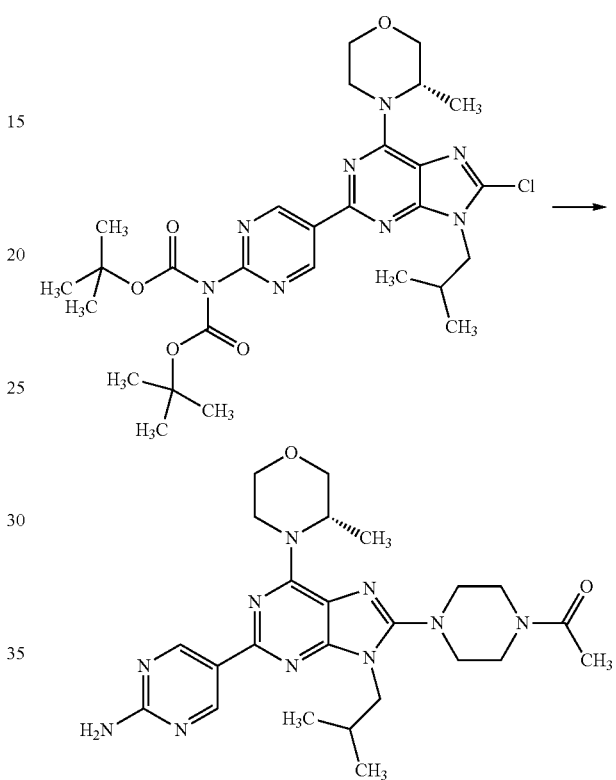

A methylene chloride (3 ml) solution of di-tert-butyl (5-{8-chloro-9-isobutyl-6-[(3S)-3-methylmorpholin-4-yl]-9H-purin-2-yl}pyrimidin-2-yl)imidedicarbonate (290 mg, 0.48 mmol) and trifluoroacetic acid (1 ml) was stirred at room temperature for 2 hours and concentrated under reduced pressure. Chloroform and saturated aqueous sodium hydrogen carbonate solution were added to the residue and the resulting mixture was extracted with chloroform. The organic layer was dried over anhydrous magnesium sulfate and, after filtration, the filtrate was concentrated under reduced pressure.

An N-methyl-2-pyrrolidone (2 ml) solution of the resulting residue and 1-acetylpiperazine (616 mg, 0.48 mmol) was stirred at 150° C. for 2 hours. The reaction mixture was returned to room temperature. The reaction mixture was purified by flash silica gel column chromatography (5% methanol:chloroform). The residue was purified by flash NH silica gel column chromatography (ethyl acetate) to give a solid. The solid was dissolved in ethyl acetate and the resulting mixture was washed with water and saturated brine. The organic layer was dried over anhydrous magnesium sulfate and, after filtration, the filtrate was concentrated under reduced pressure to give a solid. Ether was added to the resulting solids and the solid was collected by filtration and dried to give the title compound (160 mg) as a powder.

$^1$H-NMR (CDCl$_3$) δ: 0.89 (6H, d, J=6.6 Hz), 1.40 (3H, d, J=6.8 Hz), 2.16 (3H, s), 2.42-2.54 (1H, m), 3.16-3.29 (4H, m), 3.44-3.54 (1H, m), 3.61-3.72 (3H, m), 3.76-3.85 (4H, m), 3.92 (2H, d, J=7.6 Hz), 4.04 (1H, dd, J=11.4, 3.1 Hz), 5.03-5.20 (3H, m), 5.31-5.44 (1H, m), 9.24 (2H, s).

Example 130

2-(4-{2-(2-Aminopyrimidin-5-yl)-9-isobutyl-6-[(3S)-3-methylmorpholin-4-yl]-9H-purin-8-yl}piperazin-1-yl)-2-oxoethanol

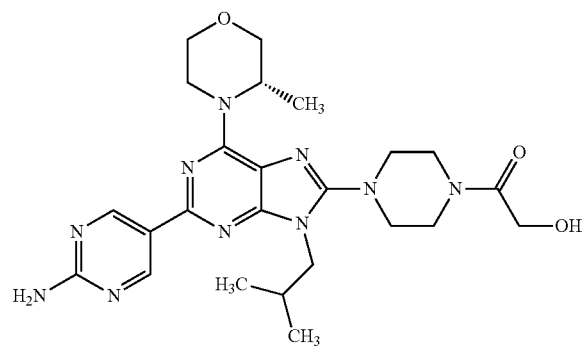

Step 1: 5-{8-Chloro-9-isobutyl-6-[(3S)-3-methyl-morpholin-4-yl]-9H-purin-2-yl}pyrimidin-2-amine

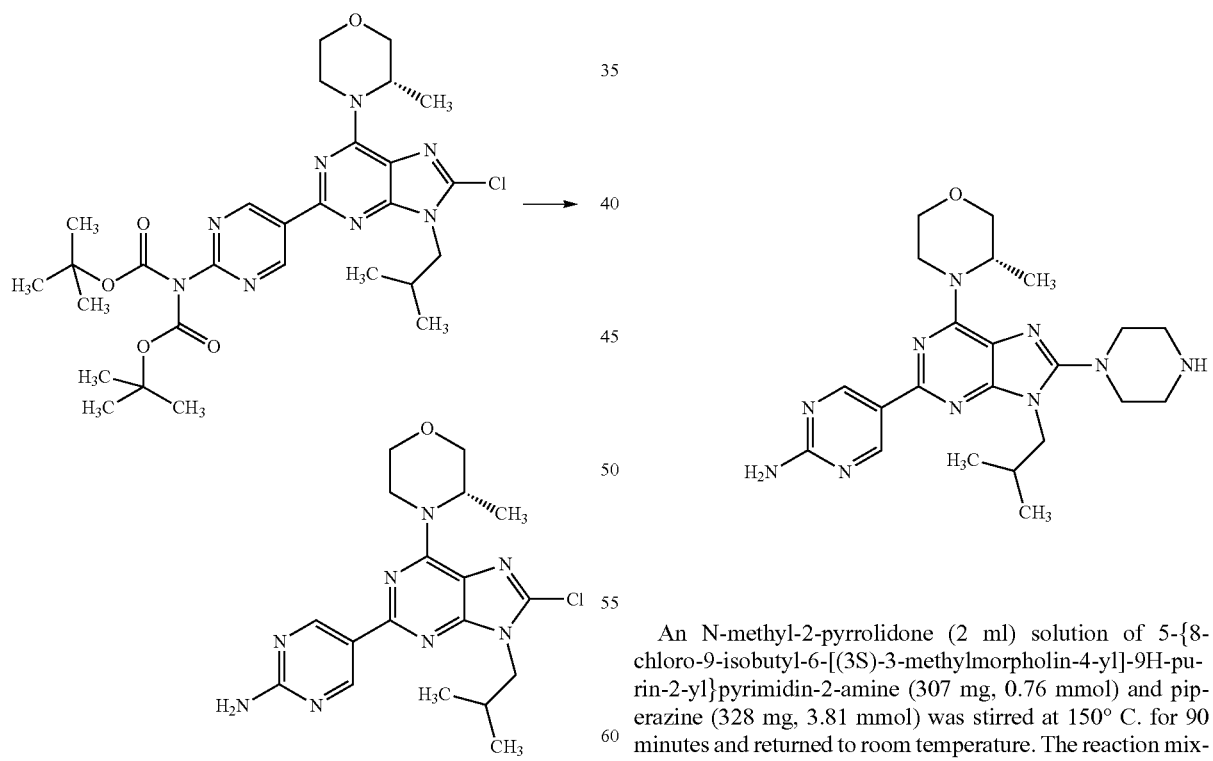

A methylene chloride (10 ml) solution of di-tert-butyl (5-{8-chloro-9-isobutyl-6-[(3S)-3-methylmorpholin-4-yl]-9H-purin-2-yl}pyrimidin-2-yl)21imidedicarbonate (1.22 g, 2.02 mmol) and trifluoroacetic acid (2 ml) was stirred at room temperature for 16 hours and concentrated under reduced pressure. Chloroform and saturated aqueous sodium hydrogen carbonate solution were added to the residue and the resulting mixture was extracted with chloroform. The organic layer was dried over anhydrous magnesium sulfate and, after filtration, the filtrate was concentrated under reduced pressure to give the title compound (934 mg) as a solid.

ESI-MSm/z: 403 (M+1)$^+$.

Step 2: 5-{9-Isobutyl-6-[(3S)-3-methylmorpholin-4-yl]-8-piperazin-1-yl-9H-purin-2-yl}pyrimidin-2-amine

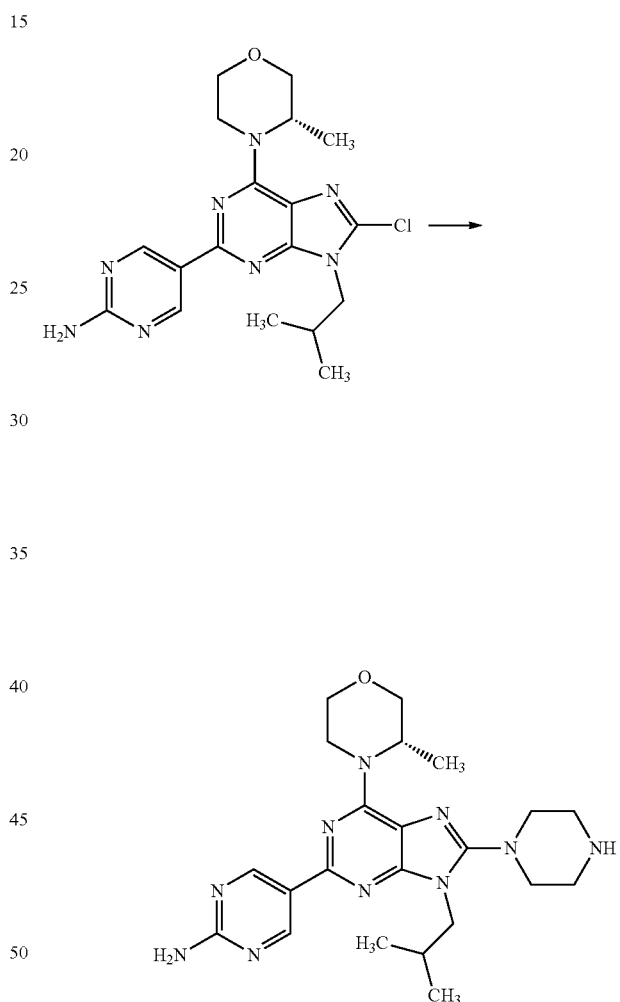

An N-methyl-2-pyrrolidone (2 ml) solution of 5-{8-chloro-9-isobutyl-6-[(3S)-3-methylmorpholin-4-yl]-9H-purin-2-yl}pyrimidin-2-amine (307 mg, 0.76 mmol) and piperazine (328 mg, 3.81 mmol) was stirred at 150° C. for 90 minutes and returned to room temperature. The reaction mixture was purified by flash silica gel column chromatography (chloroform:methanol=95:5 to 85:15) to give the title compound (245 mg, 71%) as a solid.

$^1$H-NMR (CDCl$_3$) δ: 0.88 (6H, d, J=5.9 Hz), 1.40 (3H, d, J=6.8 Hz), 2.42-2.53 (1H, m), 3.02-3.08 (4H, m), 3.18-3.24 (4H, m), 3.45-3.55 (1H, m), 3.64-3.74 (1H, m), 3.80-3.88

(2H, m), 3.91 (2H, d, J=7.3 Hz), 4.00-4.08 (1H, m), 5.07-5.18 (3H, m), 5.32-5.47 (1H, m), 9.24 (2H, s).

Step 3: 2-(4-{2-(2-Aminopyrimidin-5-yl)-9-isobutyl-6-[(3S)-3-methylmorpholin-4-yl]-9H-purin-8-yl}piperazin-1-yl)-2-oxoethanol

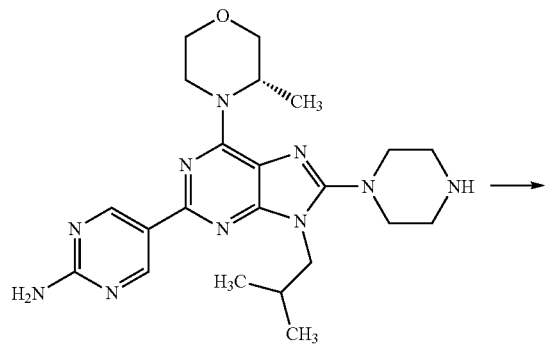

A methylene chloride (5 ml) solution of 5-{9-isobutyl-6-[(3S)-3-methylmorpholin-4-yl]-8-piperazin-1-yl-9H-purin-2-yl}pyrimidin-2-amine (126 mg, 0.28 mmol), hydroxyacetic acid (25 mg, 0.33 mmol), 1-hydroxybenzotriazole (37 mg, 0.28 mmol), 1-ethyl-3-(3-dimethylaminopropyl)carbodiimide hydrochloride (64 mg, 0.33 mmol), and triethylamine (58 μl, 0.42 mmol) was stirred at room temperature for 2 days. Chloroform and saturated aqueous sodium hydrogen carbonate solution were added to the reaction mixture and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=96:4) to give a solid. Ether was added to the resulting solid and the solid was collected by filtration and dried to give the title compound (110 mg, 77%) as a powder.

$^1$H-NMR (CDCl$_3$) δ: 0.89 (6H, d, J=6.8 Hz), 1.40 (3H, d, J=6.8 Hz), 2.41-2.53 (1H, m), 3.21-3.30 (4H, m), 3.43-3.54 (3H, m), 3.58-3.72 (2H, m), 3.80-3.88 (4H, m), 3.91 (2H, d, J=7.6 Hz), 3.99-4.07 (1H, m), 4.23 (2H, d, J=4.6 Hz), 5.04-5.22 (3H, m), 5.29-5.43 (1H, m), 9.24 (2H, s).

Example 131

(2S)-1-(4-{2-(2-Aminopyrimidin-5-yl)-9-isobutyl-6-[(3S)-3-methylmorpholin-4-yl]-9H-purin-8-yl}piperazin-1-yl)-1-oxopropan-2-ol

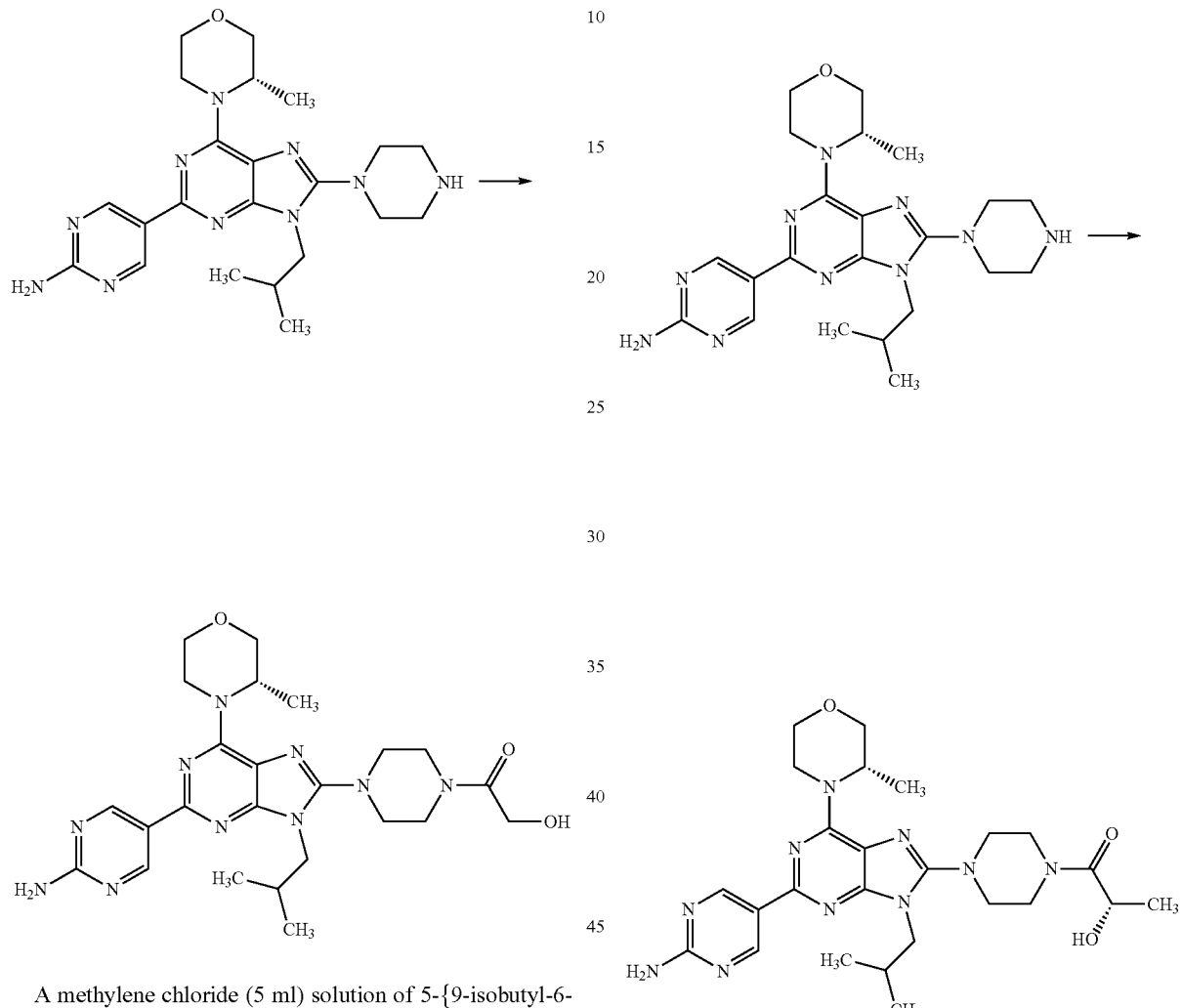

A methylene chloride (5 ml) solution of 5-{9-isobutyl-6-[(3S)-3-methylmorpholin-4-yl]-8-piperazin-1-yl-9H-purin-2-yl}pyrimidin-2-amine (119 mg, 0.26 mmol), (S)-2-hydroxypropionic acid (28 mg, 0.32 mmol), 1-hydroxybenzotriazole (35 mg, 0.26 mmol), 1-ethyl-3-(3-dimethylaminopropyl)carbodiimide hydrochloride (60 mg, 0.32 mmol), and triethylamine (55 μl, 0.39 mmol) was stirred at room temperature for 2 days. Chloroform and saturated aqueous sodium hydrogen carbonate solution were added to the reaction mixture and the resulting mixture was extracted with chloroform. The organic layer was dried over anhydrous magnesium sulfate and, after filtration, the filtrate was concentrated under reduced pressure. The residue was purified by flash silica gel column chromatography (chloroform:methanol=96:4) to give a solid. The resulting solid was purified by flash NH silica gel column chromatography (methylene chloride:methanol=99:1) to give the title compound (63 mg, 46%) as a solid.

¹H-NMR (CDCl₃) δ: 0.90 (6H, d, J=6.6 Hz), 1.36-1.42 (6H, m), 2.41-2.52 (1H, m), 3.20-3.31 (3H, m), 3.43-3.94 (11H, m), 4.00-4.07 (1H, m), 4.47-4.55 (1H, m), 5.04-5.42 (4H, m), 9.24 (2H, s).

Example 132

4-{2-(2-Aminopyrimidin-5-yl)-9-isobutyl-6-[(3S)-3-methylmorpholin-4-yl]-9H-purin-8-yl}piperazine-1-carboaldehyde

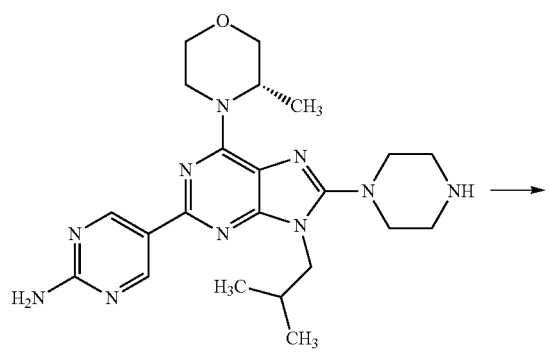

A tetrahydrofuran (3 ml) solution of 5-{9-isobutyl-6-[(3S)-3-methylmorpholin-4-yl]-8-piperazin-1-yl-9H-purin-2-yl}pyrimidin-2-amine (103 mg, 0.23 mmol) and 1H-benzotriazole-1-carboaldehyde (37 mg, 0.25 mmol) was stirred at room temperature for 16 hours. Chloroform and 2 N aqueous sodium hydroxide solution were added to the reaction mixture and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=95:5) to give a solid. Ether was added to the resulting solid and the solid was collected by filtration and dried to give the title compound (86 mg, 79%) as a powder.

¹H-NMR (CDCl₃) δ: 0.89 (6H, d, J=6.8 Hz), 1.40 (3H, d, J=6.8 Hz), 2.41-2.54 (1H, m), 3.18-3.30 (4H, m), 3.43-3.78 (6H, m), 3.80-3.85 (2H, m), 3.92 (2H, d, J=7.3 Hz), 4.00-4.08 (1H, m), 5.03-5.20 (3H, m), 5.29-5.45 (1H, m), 8.12 (1H, s), 9.24 (2H, s).

Example 133

(2S)-4-(4-[2-(2-Aminopyrimidin-5-yl)-9-isobutyl-6-[(3S)-3-methylmorpholin-4-yl]-9H-purin-8-yl]piperazin-1-yl)-4-oxobutan-2-ol

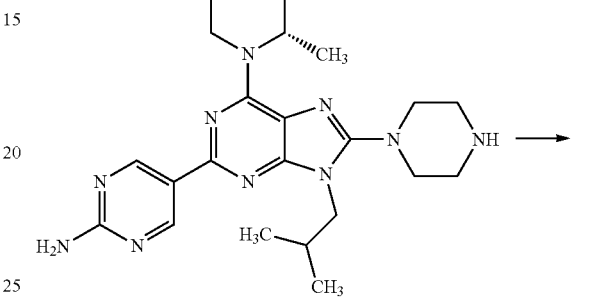

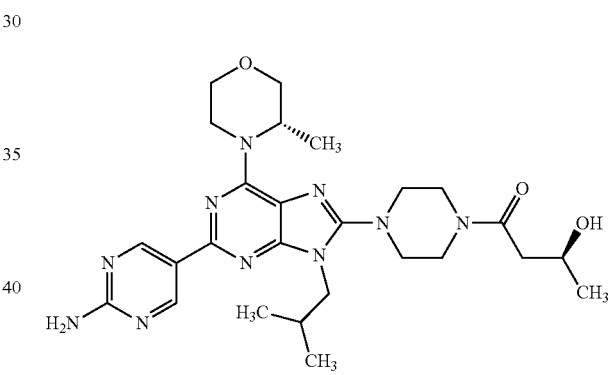

A methylene chloride (3 ml) solution of 5-{9-isobutyl-6-[(3S)-3-methylmorpholin-4-yl]-8-piperazin-1-yl-9H-purin-2-yl}pyrimidin-2-amine (94 mg, 0.21 mmol), (3S)-3-hydroxybutanoic acid (24 mg, 0.23 mmol), 1-hydroxybenzotriazole (28 mg, 0.21 mmol), 1-ethyl-3-(3-dimethylaminopropyl)carbodiimide hydrochloride (60 mg, 0.31 mmol), and triethylamine (44 μl, 0.31 mmol) was stirred at room temperature for 21 hour. Chloroform and saturated aqueous sodium hydrogen carbonate solution were added to the reaction mixture and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=95:5) to give an amorphous substance. Ethyl acetate-hexane was added to the resulting amorphous substance, the resulting mixture was solidified, and the solid was collected by filtration and dried to give the title compound (91 mg, 81%) as a powder.

¹H-NMR (CDCl₃) δ: 0.89 (6H, d, J=6.8 Hz), 1.26 (3H, d, J=6.3 Hz), 1.40 (3H, d, J=6.8 Hz), 2.33-2.58 (3H, m), 3.16-3.29 (4H, m), 3.42-3.55 (1H, m), 3.59-3.72 (3H, m), 3.75-

3.87 (4H, m), 3.99-4.13 (2H, m), 4.21-4.31 (2H, m), 5.03-5.21 (3H, m), 5.29-5.45 (1H, m), 9.24 (2H, s).

Example 134

5-[8-(4-Acetylpiperazin-1-yl)-6-morpholin-4-yl-9-(2,2,2-trifluoroethyl)-9H-purin-2-yl]-N-methylpyrimidin-2-amine

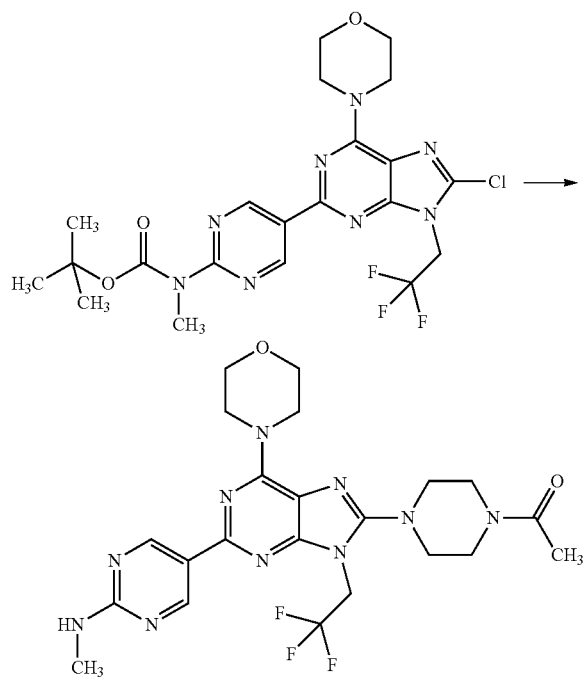

An N-methyl-2-pyrrolidone (2 ml) solution of tert-butyl {5-[8-chloro-6-morpholin-4-yl-9-(2,2,2-trifluoroethyl)-9H-purin-2-yl]pyrimidin-2-yl}methylcarbamate (157 mg, 0.30 mmol) and piperazine (128 mg, 1.48 mmol) was stirred at 90° C. for 2 hours. The reaction mixture was returned to room temperature. The reaction mixture was purified by flash silica gel column chromatography (ethyl acetate:methanol=98:2 to chloroform:methanol=90:10).

A methylene chloride (5 ml) solution of the residue, acetic anhydride (56 µl, 0.59 mmol), and triethylamine (91 µl, 0.65 mmol) was stirred at room temperature for 16 hours and concentrated under reduced pressure. Ethyl acetate was added to the residue and the resulting mixture was washed with saturated aqueous sodium hydrogen carbonate solution and saturated brine. The organic layer was dried over anhydrous magnesium sulfate and, after filtration, the filtrate was concentrated under reduced pressure. The residue was purified by flash silica gel column chromatography (methylene chloride:methanol=96:4).

A methylene chloride (3 ml) solution of the residue and trifluoroacetic acid (1 ml) was stirred at room temperature for 3 hours. Saturated aqueous sodium hydrogen carbonate solution was added to the residue and the resulting mixture was extracted with chloroform. The organic layer was dried over anhydrous magnesium sulfate and, after filtration, the filtrate was concentrated under reduced pressure. The residue was purified by flash silica gel column chromatography (methylene chloride:methanol=97:3 to 95:5) to give a solid. Ether was added to the resulting solid and the solid was collected by filtration and dried to give the title compound (87 mg, 56%) as a powder.

$^1$H-NMR (CDCl$_3$) δ: 2.16 (3H, s), 3.08 (3H, d, J=4.9 Hz), 3.13-3.26 (4H, m), 3.62-3.69 (2H, m), 3.77-3.87 (6H, m), 4.21-4.32 (4H, m), 4.71 (2H, q, J=8.3 Hz), 5.25-5.33 (1H, m), 9.25 (2H, s).

FORMULATION EXAMPLES

Formulation Example 1

Powder

A powder can be obtained by mixing 5 g of an Example compound, 895 g of lactose, and 100 g of maize starch using a blender.

Formulation Example 2

Granule 5 g of an Example compound, 895 g of lactose, and 100 g of low-substituted hydroxypropylcellulose are mixed followed by the addition of 300 g of 10% aqueous hydroxypropylcellulose solution and the resulting mixture is kneaded together. A granule can be obtained by granulating this mixture using an extruding granulating machine and drying the product.

Formulation Example 3

Tablet

A tablet can be obtained by mixing 5 g of an Example compound, 90 g of lactose, 34 g of maize starch, 20 g of crystalline cellulose, and 1 g of magnesium stearate using a blender and tableting the resulting mixture with a tableting machine.

Test Example 1

PI3K Kinase Activity Inhibition Assay

PI3Kα kinase activity was determined in the presence and absence of a test compound. The test compound was dissolved in DMSO and diluted serially with an ATP solution (30 µm ATP, 50 mM HEPES, pH 7.4, 50 mM NaCl, 0.05% CHAPS, 10 mM MgCl$_2$, and 5 mM dithiothreitol [DTT]). First, 7 µl each of the serially diluted test compound solutions was added to each well of a black 384-well plate. Subsequently, 7 µl of a phosphatidylinositol 4,5-bisphosphate (PIP$_2$) solution (45 µm PIP$_2$, 50 mM HEPES, pH 7.4, 50 mM NaCl, 0.05% CHAPS, 10 mM MgCl$_2$, and 5 mM DTT) was added to each well of the 384-well plate. Finally, 7 µl of a solution containing PI3Kα (50 nM PI3Kα, 50 mM HEPES, pH 7.4, 50 mM NaCl, 0.05% CHAPS, 10 mM MgCl$_2$, and 5 mM DTT) was added to each well of the 384-well plate to initiate a reaction. The mixture was reacted at room temperature for 2 hours and then 21 µl of the Kinase-Glo Plusreagent (Promega) was, added to each well of the 384-well plate to terminate the reaction. After the termination of the reaction, the solution was left standing for 15 minutes and then luminescence was measured with ARVO (PerkinElmer Co., Ltd.) to detect ATP remaining in the reaction solution.

The amount of ATP consumed in the reaction was obtained for each well and used as an indicator of PI3Kα kinase activity. The PI3Kα kinase activity in wells not containing the test compound was calculated by the following formula (1). Furthermore, the PI3Kα kinase activity in wells containing the test compound was calculated by the following formula (2). The PI3Kα inhibitory activity (%) of the test compound was calculated by the following formula (3).

PI3Kα kinase activity in wells not containing the test compound=$B-C$ (1)

PI3Kα kinase activity in wells containing the test compound=$B-P$ (2)

PI3Kα inhibitory activity (%) of test compound=$100-100\times[(B-P)/(B-C)]$ (3)

B: Measured value in wells not containing PI3Kα or the test compound
C: Measured value in wells containing PI3Kα and not containing the test compound
P: Measured value in wells containing PI3Kα and the test compound Furthermore, an optimal curve was calculated with Graph Pad Prism 4 using concentrations of the serially diluted test compound solutions and PI3Kα inhibitory activity (%) at each concentration to obtain the concentration showing 50% inhibition as the IC50 value of PI3Kα inhibitory activity.

The values of $IC_{50}$ against PI3K of the compounds of Examples 3, 6 to 8, 10, 13 to 14, 31, 36, 39, 41 to 42, 49, 52, 55 to 63, 65 to 67, 69, 71 to 73, 75 to 77, 79 to 81, 84 to 89, 91, 93 to 94, 96, 98, 100, 102, 105 to 107, 109 to 112, 114 to 117, 119 to 120, 122, 125 to 127, 132, and 133 to 134 were lower than 10 nM, those of the compounds of Examples 1 to 2, 4 to 5, 9, 11 to 12, 19 to 22, 28 to 30, 34 to 35, 37 to 38, 40, 43, 47 to 48, 50 to 51, 53 to 54, 64, 68, 70, 82 to 83, 90, 92, 95, 97, 99, 101, 103 to 104, 108, 113, 123 to 124, and 128 to 131 were 10 nM or higher and lower than 20 nM, and those of the compounds of Examples 5, 12, 15 to 17, 23, 25 to 27, 32, 33, 45, and 46 were 20 nM or higher and lower than 50 nM, and those of the compounds of Examples 18 and 24 were 50 nM or higher and lower than 100 nM.

Test Example 2 mTOR Kinase Activity Inhibition Assay

The mTOR kinase activity was determined in the presence and absence of a test compound. A substrate peptide is phosphorylated by mTOR kinase activity. A complex of streptavidin-XL665 and anti-phosphorylated S6K (Thr389) antibody-anti-mouse IgG-cryptate binds to this phosphorylated peptide. At this time, irradiation of excitation light induces transfer of fluorescence resonance energy from the excited cryptate to XL665, emitting fluorescence at 665 nm. Utilizing this principle, mTOR kinase activity was detected. When the mTOR inhibitor is present, phosphorylation of a substrate peptide is inhibited, and the biding of the above-mentioned complex to the substrate peptide is inhibited. As a result, transfer of fluorescence resonance energy does not occur, and fluorescence at 665 nm is attenuated.

(1) Preparation of Samples and Enzymatic Reaction

A His tag was introduced into the N terminus end of the 1362 to 2549 amino acid portion on the C terminus side of human mTOR, and a cell line was prepared, so that His-tagged mTOR should be constantly expressed in a HEK293 cell. A cell lysate was prepared from this HEK293 cell which constantly expressed His-tagged mTOR (1362C), and a crude product of His-tagged mTOR (1362C) was obtained by a usual method utilizing His tag.

Subsequently, an mTOR enzyme solution was prepared which contained the above-mentioned His-tagged mTOR (1362C) enzyme and 8 µg/ml biotinylated peptide (Biotin-Ahx-KKANQVFLGFTYVAPSVLESVKE-amide [Sigma]), as well as 50 mM HEPES (pH 7.5), 20 mM $MnCl_2$, 1 mg/ml BSA, a suitable amount of protease inhibitor cocktail (Complete EDTA free, Roche Ltd.), 100 ng/ml calyculin A, and 4 µg/ml cantharidin as other components.

The test compound was dissolved in dimethyl sulfoxide (DMSO) and serially diluted with 20 µm ATP solution (50 mM HEPES (pH 7.5), 20 µM ATP) to obtain concentrations required for the assay. 5 µl of this compound solution was added to each well of a 384-well small volume white plate manufactured by Greiner Bio-One Co., Ltd.

5 µl of the mTOR enzyme solution was added to the above-mentioned well containing the test compound and the resulting mixture was left standing for 3 hours room temperature to proceed an enzymatic reaction.

The same procedure was performed using a solution obtained by dissolving DMSO in 20 µM ATP solution as a positive control and a solution obtained by dissolving DMSO in 50 mM HEPES buffer (pH 7.5) as a negative control.

(2) Detection of Enzymatic Reaction

After the enzymatic reaction, 5 µl each of an europium solution (a solution obtained by dissolving anti-mouse IgG-cryptate [SCETI Medical Labo K.K.] and anti-phosphorylation S6K [Thr389] antibody [Cell Signaling Technology Inc.] in 50 mM HEPES [pH 7.5], 100 mM EDTA, and 1.5 mg/ml BSA) and an XL665 solution (a solution obtained by dissolving Streptavidin-XL 665 [SCETI Medical Labo K.K.] in 50 mM HEPES [pH 7.5], 100 mM EDTA, 0.8 M KF, and 1.5 mg/ml BSA) were added in this order and mixed and the resulting mixture was left standing overnight at 4° C. On the following day, the mixture was returned to room temperature and then irradiated with 337-nm excitation light and fluorescence at 620 and 665 nm was measured with RUBYstar (BMG LABTECH JAPAN Ltd.).

mTOR inhibitory activity (%) was calculated using the ratio calculated from the measured values as an indicator of enzyme activity. Here, the ratio was calculated by the following formula (1).

Ratio=$10,000\times$fluorescence at 665 nm/fluorescence at 620 nm (1)

mTOR enzyme inhibitory activity (%) was calculated by the following formula (2).

mTOR enzyme inhibitory activity (%)=$100\times[(P-S)/(P-N)]$ (2)

P: Ratio in positive control well
N: Ratio in negative control well
S: Ratio in well containing the test compound Furthermore, an optimal curve was created using the concentrations of the serially diluted test compound solutions and mTOR enzyme inhibitory activity (%) at each concentration to obtain the concentration showing 50% inhibition as the IC50 value of mTOR enzyme inhibitory activity.

The values of $IC_{50}$ against mTOR of the compounds of Examples 8 to 9, 11, 57, 60, 62 to 71, 75 to 76, 79, 83, 85, 96, 98, 101 to 102, 105 to 113, 115 to 117, 120, 122 to 127, 130, and 134 were lower than 10 nM, and those of the compounds of Examples 1 to 3, 5, 10, 13 to 14, 38, 49, 51, 53, 56, 58 to 59, 61, 77, 80 to 82, 84, 86 to 87, 89 to 95, 97, 99 to 100, 103 to 104, 114, 119, 129, and 131 to 132 were 10 nM or higher and lower than 30 nM, and those of the compounds of Examples 4, 16, 19 to 20, 23, 25, 27, 30 to 31, 39, 41 to 42, 45 to 46, 50, 52, 54 to 55, and 88 were 30 nM or higher and lower than 100 nM, and those of the compounds of Examples 6, 7, 15, 17, 18, 24, 26, 28, 29, 34, 36, 37, 40, 43, 47, 48, and 128 were 100 nM or higher and lower than 500 nM, and those of the compounds of Examples 21, 22, 32, 33, 35, 44, 72, and 73 were 500 nM or higher.

Test Example 3

In Vitro Test Compound Assay: Cell Growth Inhibition Test

After a cultured cancer cell strain was treated with a test compound for a predetermined period, a cell growth inhibition test was performed by measuring the living cell count by the 3-(4,5-dimethylthiazol-2-yl)-2,5-diphenyltetrazolium-bromide (MTT) method.

Human endometrial cancer cell strain AN3CA, human ovary cancer cell strain IGROV1, and human colon cancer cell strain HT29 were seeded in a 96-well plate at 5000, 1000, and 5000 cells, respectively, per well. On the following day of seeding, a test compound having a predetermined concentration was added and the culture was continued at 37° C. in 5% $CO_2$ for 3 days. On the final day of culture, an MTT reaction solution was added and the resulting mixture was reacted for 4 hours to form formazan by dehydrogenases contained in living cells. Subsequently, the culture broth was removed, DMSO was added to solubilize formazan, and the amount of produced formazan was determined by measuring absorbance at 540 nm using a microplate reader.

Since correlations of the amount of produced formazan and the living cell count had been confirmed, the cell growth rate was calculated by the following formula.

Cell growth rate ($T/C$ %) after addition of test compound=100×[($B-C$)/($A-C$)]

A: Absorbance of well not containing test compound (final culture day)
B: Absorbance of well containing test compound (final culture day)
C: Absorbance of well immediately before addition of test compound (following day of cell seeding)

Furthermore, the cell growth rate at each concentration of serially diluted test compound solutions was obtained, and the concentration of the test compound resulting in a 50% growth rate was obtained as the GI50 value from two concentrations including 50% therebetween and the growth rates were selected.

The compounds of Examples 1 to 43, 45 to 73, 75 to 77, 79 to 117, 119 to 120, and 122 to 134 in the present application exhibited anti-cell effect against human endometrial cancer cell strain AN3CA, human ovary cancer cell strain IGROV1, and human colon cancer cell strain HT29 at concentrations of 5 μm or lower.

Test Example 4

In Vivo Test Compound Assay: Akt and S6 Phosphorylation Inhibition Assay in Xenograft A tumor section was prepared from a human endometrial cancer cell strain AN3CA tumor mass formed in a female nude mouse as subcutaneously transplanted tumor and a xenograft model was prepared by subcutaneously transplanting the tumor to a female nude mouse. The test compound at a predetermined concentration was orally administered. After a predetermined time, the anesthetized mouse was exsanguinated to death, and a tumor mass was isolated. The tumor mass was crushed using a lysis buffer containing inhibitors of proteases and dephosphorylating enzymes (Cell Signaling Technology, Inc.) and the supernatant was separated by centrifugation to obtain a tumor extract. The protein content of the tumor extract was measured using DC Protein Assay Kit (Bio-Rad Laboratories, Inc.) and phosphorylation conditions of Akt (threonine 308) and S6 (serine 235 and 236) were analyzed by a usual technique of western blotting using tumor extracts containing the same amount of protein. The primary antibody and the secondary antibody used for detecting each molecule were rabbit anti-phospho-Akt(T308) antibody and HRP-labeled goat anti-rabbit IgG antibody or mouse anti-phospho-S6(S235/236) antibody and HRP-labeled sheep anti-mouse IgG antibody.

The signal intensity detected using an image analyzer Typhoon 9400 (GE Healthcare) was quantified, and the phosphorylation inhibition rate (%) was calculated by the following formula.

Phosphorylation inhibitory activity (%) of Akt and S6 after treatment with test compound=100−100×($B/A$)

A: Signal intensity derived from phosphorylated protein in tumor mass isolated from mouse untreated with test compound
B: Signal intensity derived from phosphorylated protein in tumor mass isolated from mouse treated with test compound The compounds of Examples 3, 6, 8, 60 to 61, 63, 68 to 71, 75 to 77, 79, 81 to 90, 92 to 93, 95 to 96, 100 to 104, 106 to 116, 131 to 133 in the present application exhibited more than 60% inhibition of the Akt phosphorylation at the dose of 10 mg/kg after 6 hr from the dosing in the xenograft.

The compounds of Examples 53 to 54, 57, 62, 64 to 67, 80, 97 to 99, 105, 117, 119, 128, 130, 134 in the present application exhibited 30% to 60% inhibition of the Akt phosphorylation at the dose of 10 mg/kg after 6 hr from the dosing in the xenograft.

The compounds of Examples 3, 8, 57, 60 to 65, 68 to 71, 75 to 77, 79 to 86, 90, 92 to 93, 96, 98, 100 to 116, 119, 130 to 134 in the present application exhibited more than 90% inhibition of the S6 phosphorylation at the dose of 10 mg/kg after 6 hr from the dosing in the xenograft.

The compounds of Examples 66 to 67, 88 to 89, 95, 97, 117, 129 in the present application exhibited 70% to 90% inhibition of the S6 phosphorylation at the dose of 10 mg/kg after 6 hr from the dosing in the xenograft.

Test Example 5

In Vivo Test Compound Assay: Anti-Tumor Effect Assay Using Mouse Subcutaneous Transplantation Model A tumor section was prepared from a human endometrial cancer cell strain AN3CA tumor mass formed in a female nude mouse as a subcutaneously transplanted tumor and then a xenograft model was prepared by transplanting the tumor section into female nude mouse. Tumor-bearing mice having an estimated tumor volume (long diameter×short diameter× short diameter/2) of 80 to 200 $mm^3$ were divided, so that there should be no significant difference in the mean estimated tumor volume and body weight as compared with the negative control group to perform a test. The test compound was orally administered at a predetermined dose for 8 consecutive days. On the following day of the final administration day, tumor-bearing mice were anesthetized and exsanguinated to death and a tumor mass was isolated to measure tumor weight (the compounds of Examples 1, 3, 6, 8, 11, 12, and 14). Furthermore, as a similar test, the test compound was orally administered for 5 consecutive days, animals were sacrificed on the final administration day, and tumor weight was measured (the compounds of Examples 60, 63, 75, 77, 79, 89, 92, 107, 108, 109, 110, and 127).

In all the tests, anti-tumor effect was calculated by the following formula.

{1−(tumor weight in compound treatment group/tumor weight in negative control group)}×100

The results are shown in Table 19.

| | Dose (mg/kg/day) | Anti-tumor effect (tumor growth inhibition rate) |
|---|---|---|
| Compound of Example 1 | 10 | 92 |
| | 5 | 79 |
| Compound of Example 2 | 10 | 70 |
| | 5 | 44 |
| Compound of Example 3 | 10 | 86 |
| | 5 | 75 |
| Compound of Example 6 | 10 | 69 |
| | 5 | 66 |
| Compound of Example 8 | 5 | 93 |
| | 2.5 | 72 |
| Compound of Example 10 | 20 | 73 |
| | 10 | 39 |
| Compound of Example 11 | 5 | 85 |
| | 2.5 | 68 |
| Compound of Example 12 | 20 | 71 |
| | 10 | 61 |
| Compound of Example 14 | 10 | 82 |
| | 5 | 64 |
| Compound of Example 53 | 10 | 68 |
| | 5 | 45 |
| Compound of Example 54 | 20 | 82 |
| | 10 | 74 |
| Compound of Example 55 | 20 | 59 |
| | 10 | 32 |
| Compound of Example 60 | 6 | 89 |
| | 1.5 | 64 |
| Compound of Example 63 | 3.5 | 88 |
| | 0.875 | 52 |
| Compound of Example 75 | 7.5 | 77 |
| | 1.875 | 44 |
| Compound of Example 77 | 15 | 84 |
| | 3.75 | 47 |
| Compound of Example 79 | 10 | 59 |
| | 2.5 | 27 |
| Compound of Example 81 | 10 | 74 |
| | 5 | 37 |
| Compound of Example 88 | 10 | 54 |
| | 5 | 30 |
| Compound of Example 89 | 10 | 69 |
| | 5 | 56 |
| Compound of Example 90 | 10 | 80 |
| | 5 | 40 |
| Compound of Example 92 | 10 | 61 |
| | 5 | 52 |
| Compound of Example 93 | 5 | 54 |
| | 2.5 | 42 |
| Compound of Example 95 | 10 | 62 |
| | 5 | 44 |
| Compound of Example 100 | 5 | 62 |
| | 2.5 | 53 |
| Compound of Example 101 | 5 | 69 |
| | 2.5 | 42 |
| Compound of Example 102 | 5 | 64 |
| | 2.5 | 54 |
| Compound of Example 107 | 5 | 76 |
| | 1.25 | 46 |
| Compound of Example 108 | 10 | 82 |
| | 2.5 | 53 |

-continued

| | Dose (mg/kg/day) | Anti-tumor effect (tumor growth inhibition rate) |
|---|---|---|
| Compound of Example 109 | 7.5 | 80 |
| | 1.875 | 42 |
| Compound of Example 110 | 7.5 | 73 |
| | 1.875 | 43 |
| Compound of Example 127 | 10 | 79 |
| | 5 | 69 |

What is claimed is:

1. A medicament comprising of a compound represented by the formula:

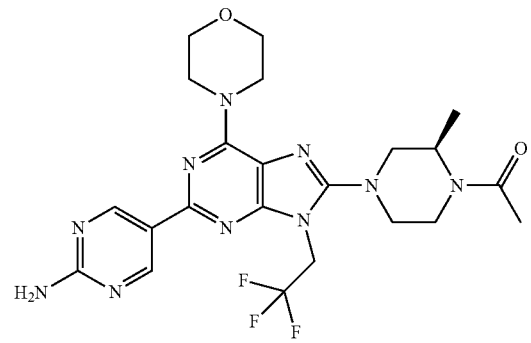

or a pharmaceutically acceptable salt thereof as an active ingredient.

2. A pharmaceutical composition comprising a compound represented by the formula:

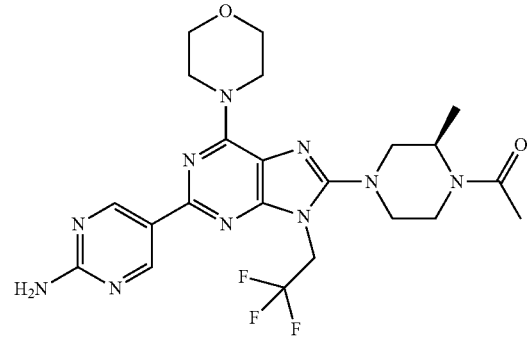

or a pharmaceutically acceptable salt thereof, and a pharmaceutically acceptable carrier.

3. A method for inhibiting phosphatidylinositol 3-kinase (PI3K) in a subject, comprising administering to a subject in need thereof an effective amount of a compound represented by the formula:

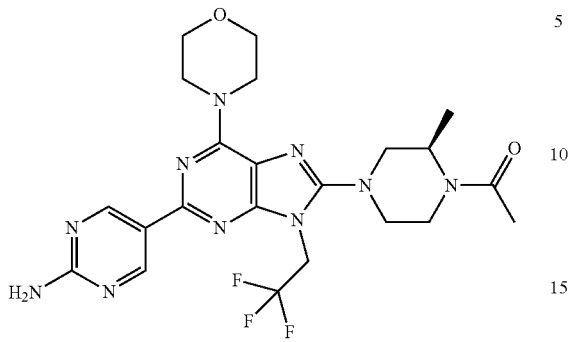

or a pharmaceutically acceptable salt thereof.

4. The method of claim 3, wherein the subject is a human.

5. A method for inhibiting the mammalian target of rapamycin (mTOR) in a subject, comprising administering to a subject in need thereof an effective amount of a compound represented by the formula:

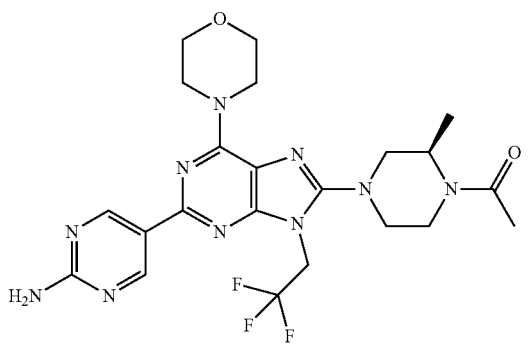

or a pharmaceutically acceptable salt thereof.

6. The method of claim 5, wherein the subject is a human.

7. A method for inhibiting phosphatidylinositol 3-kinase (PI3K) and the mammalian target of rapamycin (mTOR) in a subject, comprising administering to a subject in need thereof an effective amount of a compound represented by the formula:

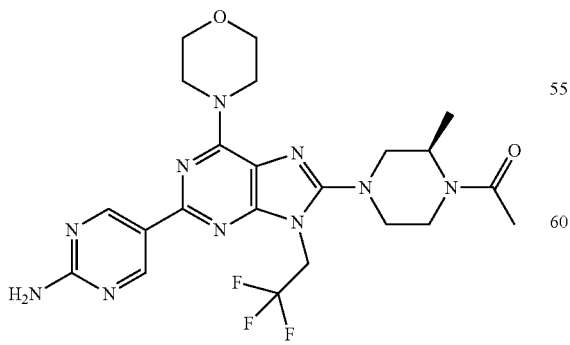

or a pharmaceutically acceptable salt thereof.

8. The method of claim 7, wherein the subject is a human.

9. A method for treating a tumor, comprising administering to a subject in need thereof an effective amount of a compound represented by the formula:

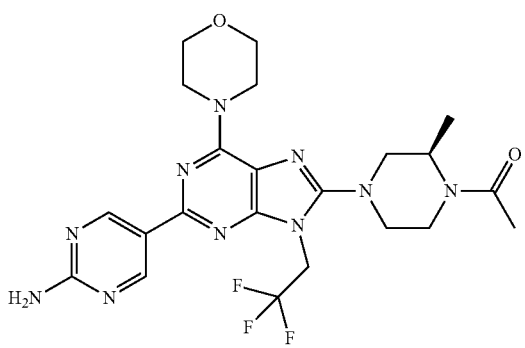

or a pharmaceutically acceptable salt thereof, wherein the tumor is selected from the following group: ovary cancer, colon cancer, and endometrial cancer.

10. The method of claim 9, wherein the subject is a human.

11. The method of claim 10, wherein the tumor is ovary cancer.

12. The method of claim 10, wherein the tumor is colon cancer.

13. The method of claim 10, wherein the tumor is endometrial cancer.

14. A method for treating a cancer treatable by inhibiting phosphatidylinositol 3-kinase (PI3K), comprising administering to a human subject in need thereof an effective amount of a compound represented by the formula:

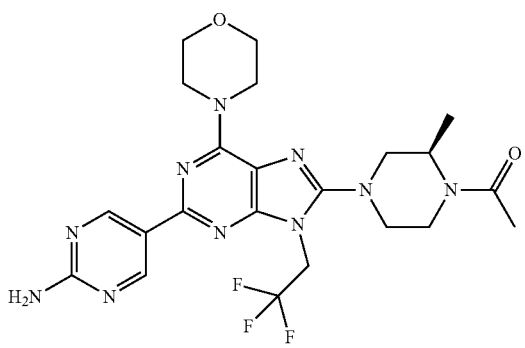

or a pharmaceutically acceptable salt thereof.

15. A method for treating a cancer treatable by inhibiting the mammalian target of rapamycin (mTOR), comprising administering to a human subject in need thereof an effective amount of a compound represented by the formula:

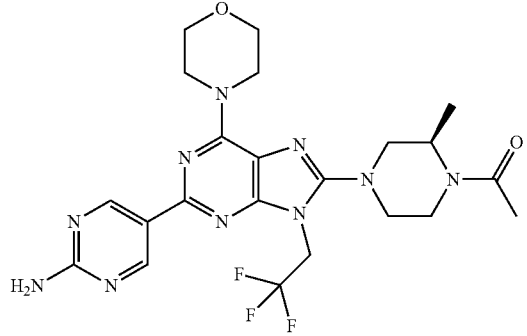

or a pharmaceutically acceptable salt thereof.

16. A method for treating a cancer treatable by inhibiting phosphatidylinositol 3-kinase (PI3K) and the mammalian target of rapamycin (mTOR), comprising administering to a human subject in need thereof an effective amount of a compound represented by the formula:

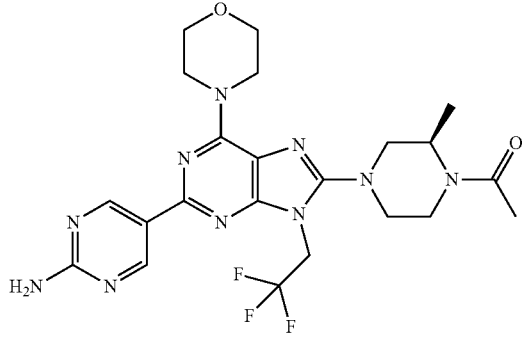

or a pharmaceutically acceptable salt thereof.

* * * * *